(12) United States Patent
Murgolo et al.

(10) Patent No.: US 9,181,632 B1
(45) Date of Patent: Nov. 10, 2015

(54) C.DIFFICILE TOXIN B CROP DOMAIN PEPTIDES, ANTIBODIES AND COMPLEXES THEREOF

(71) Applicant: Merck Sharp & Dohme Corp., Rahway, NJ (US)

(72) Inventors: Nicholas Murgolo, Millington, NJ (US); Lorraine Hernandez, Warren, NJ (US); Payal Sheth, Somerset, NJ (US); Corey Strickland, Martinsville, NJ (US); Peter Orth, Bronxville, NY (US); Alex Therien, Fanwood, NJ (US); Paul Reichert, Montville, NJ (US); Li Xiao, Cranbury, NJ (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 0 days.

(21) Appl. No.: 14/479,735

(22) Filed: Sep. 8, 2014

Related U.S. Application Data

(60) Provisional application No. 61/875,266, filed on Sep. 9, 2013.

(51) Int. Cl.
| | |
|---|---|
| *C30B 29/58* | (2006.01) |
| *C07K 16/12* | (2006.01) |
| *C12N 9/10* | (2006.01) |
| *C30B 7/04* | (2006.01) |

(52) U.S. Cl.
CPC ............. *C30B 29/58* (2013.01); *C07K 16/1282* (2013.01); *C12N 9/1051* (2013.01); *C30B 7/04* (2013.01); *C07K 2299/00* (2013.01); *C07K 2317/55* (2013.01)

(58) Field of Classification Search
None
See application file for complete search history.

(56) References Cited

U.S. PATENT DOCUMENTS

| | | |
|---|---|---|
| 7,625,559 B2 | 12/2009 | Ambrosino et al. |
| 8,236,311 B2 | 8/2012 | Ambrosino et al. |
| 8,257,709 B2 | 9/2012 | Ambrosino et al. |
| 8,609,111 B2 | 12/2013 | Ambrosino et al. |

FOREIGN PATENT DOCUMENTS

| | | |
|---|---|---|
| WO | WO2006/121422 | 11/2006 |
| WO | WO2013/130981 | 9/2013 |

OTHER PUBLICATIONS

Orth P, Xiao L, Hernandez LD, Reichert P, Sheth PR, Beaumont M, Yang X, Murgolo N, Ermakov G, DiNunzio E, Racine F, Karczewski J, Secore S, Ingram RN, Mayhood T, Strickland C, Therien AG. Mechanism of Action and Epitopes of *Clostridium difficile* B-neutralizing Antibody Bezlotoxumab Revealed by X-ray Crystallography. J Biol Chem. Jun. 27, 2014;289 (26):18008-21. doi: 10.1074/jbc.M114.560748. Epub May 12, 2014.

*Primary Examiner* — Suzanne M Noakes

(57) ABSTRACT

The present invention provides polypeptide domains of *C. difficile* toxin B (B1, B2, B3, B4) and complexes between the polypeptides and antibodies that bind specifically for the polypeptide. Methods of using the polypeptides to generate antibodies are also provided.

4 Claims, 4 Drawing Sheets

SEQUENCE LISTING

<160> NUMBER OF SEQ ID NOS: 14

<210> SEQ ID NO 1
<211> LENGTH: 2366
<212> TYPE: PRT
<213> ORGANISM: Clostridium difficile

<400> SEQUENCE: 1

```
Met Ser Leu Val Asn Arg Lys Gln Leu Glu Lys Met Ala Asn Val Arg
1               5                   10                  15

Phe Arg Thr Gln Glu Asp Glu Tyr Val Ala Ile Leu Asp Ala Leu Glu
            20                  25                  30

Glu Tyr His Asn Met Ser Glu Asn Thr Val Val Glu Lys Tyr Leu Lys
        35                  40                  45

Leu Lys Asp Ile Asn Ser Leu Thr Asp Ile Tyr Ile Asp Thr Tyr Lys
    50                  55                  60

Lys Ser Gly Arg Asn Lys Ala Leu Lys Lys Phe Lys Glu Tyr Leu Val
65                  70                  75                  80

Thr Glu Val Leu Glu Leu Lys Asn Asn Asn Leu Thr Pro Val Glu Lys
                85                  90                  95

Asn Leu His Phe Val Trp Ile Gly Gly Gln Ile Asn Asp Thr Ala Ile
            100                 105                 110

Asn Tyr Ile Asn Gln Trp Lys Asp Val Asn Ser Asp Tyr Asn Val Asn
        115                 120                 125

Val Phe Tyr Asp Ser Asn Ala Phe Leu Ile Asn Thr Leu Lys Lys Thr
    130                 135                 140

Val Val Glu Ser Ala Ile Asn Asp Thr Leu Glu Ser Phe Arg Glu Asn
145                 150                 155                 160

Leu Asn Asp Pro Arg Phe Asp Tyr Asn Lys Phe Phe Arg Lys Arg Met
                165                 170                 175

Glu Ile Ile Tyr Asp Lys Gln Lys Asn Phe Ile Asn Tyr Tyr Lys Ala
            180                 185                 190

Gln Arg Glu Glu Asn Pro Glu Leu Ile Ile Asp Asp Ile Val Lys Thr
        195                 200                 205

Tyr Leu Ser Asn Glu Tyr Ser Lys Glu Ile Asp Glu Leu Asn Thr Tyr
    210                 215                 220

Ile Glu Glu Ser Leu Asn Lys Ile Thr Gln Asn Ser Gly Asn Asp Val
225                 230                 235                 240

Arg Asn Phe Glu Glu Phe Lys Asn Gly Glu Ser Phe Asn Leu Tyr Glu
                245                 250                 255

Gln Glu Leu Val Glu Arg Trp Asn Leu Ala Ala Ala Ser Asp Ile Leu
            260                 265                 270

Arg Ile Ser Ala Leu Lys Glu Ile Gly Gly Met Tyr Leu Asp Val Asp
        275                 280                 285

Met Leu Pro Gly Ile Gln Pro Asp Leu Phe Glu Ser Ile Glu Lys Pro
    290                 295                 300

Ser Ser Val Thr Val Asp Phe Trp Glu Met Thr Lys Leu Glu Ala Ile
305                 310                 315                 320

Met Lys Tyr Lys Glu Tyr Ile Pro Glu Tyr Thr Ser Glu His Phe Asp
                325                 330                 335

Met Leu Asp Glu Glu Val Gln Ser Ser Phe Glu Ser Val Leu Ala Ser
            340                 345                 350

Lys Ser Asp Lys Ser Glu Ile Phe Ser Ser Leu Gly Asp Met Glu Ala
        355                 360                 365
```

```
Ser Pro Leu Glu Val Lys Ile Ala Phe Asn Ser Lys Gly Ile Ile Asn
    370                 375                 380

Gln Gly Leu Ile Ser Val Lys Asp Ser Tyr Cys Ser Asn Leu Ile Val
385                 390                 395                 400

Lys Gln Ile Glu Asn Arg Tyr Lys Ile Leu Asn Asn Ser Leu Asn Pro
                405                 410                 415

Ala Ile Ser Glu Asp Asn Asp Phe Asn Thr Thr Thr Asn Thr Phe Ile
                420                 425                 430

Asp Ser Ile Met Ala Glu Ala Asn Ala Asp Asn Gly Arg Phe Met Met
            435                 440                 445

Glu Leu Gly Lys Tyr Leu Arg Val Gly Phe Phe Pro Asp Val Lys Thr
450                 455                 460

Thr Ile Asn Leu Ser Gly Pro Glu Ala Tyr Ala Ala Tyr Gln Asp
465                 470                 475                 480

Leu Leu Met Phe Lys Glu Gly Ser Met Asn Ile His Leu Ile Glu Ala
                485                 490                 495

Asp Leu Arg Asn Phe Glu Ile Ser Lys Thr Asn Ile Ser Gln Ser Thr
                500                 505                 510

Glu Gln Glu Met Ala Ser Leu Trp Ser Phe Asp Asp Ala Arg Ala Lys
            515                 520                 525

Ala Gln Phe Glu Glu Tyr Lys Arg Asn Tyr Phe Glu Gly Ser Leu Gly
530                 535                 540

Glu Asp Asp Asn Leu Asp Phe Ser Gln Asn Ile Val Val Asp Lys Glu
545                 550                 555                 560

Tyr Leu Leu Glu Lys Ile Ser Ser Leu Ala Arg Ser Ser Glu Arg Gly
                565                 570                 575

Tyr Ile His Tyr Ile Val Gln Leu Gln Gly Asp Lys Ile Ser Tyr Glu
            580                 585                 590

Ala Ala Cys Asn Leu Phe Ala Lys Thr Pro Tyr Asp Ser Val Leu Phe
            595                 600                 605

Gln Lys Asn Ile Glu Asp Ser Glu Ile Ala Tyr Tyr Tyr Asn Pro Gly
    610                 615                 620

Asp Gly Glu Ile Gln Glu Ile Asp Lys Tyr Lys Ile Pro Ser Ile Ile
625                 630                 635                 640

Ser Asp Arg Pro Lys Ile Lys Leu Thr Phe Ile Gly His Gly Lys Asp
                645                 650                 655

Glu Phe Asn Thr Asp Ile Phe Ala Gly Phe Asp Val Asp Ser Leu Ser
                660                 665                 670

Thr Glu Ile Glu Ala Ala Ile Asp Leu Ala Lys Glu Asp Ile Ser Pro
            675                 680                 685

Lys Ser Ile Glu Ile Asn Leu Leu Gly Cys Asn Met Phe Ser Tyr Ser
    690                 695                 700

Ile Asn Val Glu Glu Thr Tyr Pro Gly Lys Leu Leu Leu Lys Val Lys
705                 710                 715                 720

Asp Lys Ile Ser Glu Leu Met Pro Ser Ile Ser Gln Asp Ser Ile Ile
                725                 730                 735

Val Ser Ala Asn Gln Tyr Glu Val Arg Ile Asn Ser Glu Gly Arg Arg
                740                 745                 750

Glu Leu Leu Asp His Ser Gly Glu Trp Ile Asn Lys Glu Glu Ser Ile
            755                 760                 765

Ile Lys Asp Ile Ser Ser Lys Glu Tyr Ile Ser Phe Asn Pro Lys Glu
    770                 775                 780

Asn Lys Ile Thr Val Lys Ser Lys Asn Leu Pro Glu Leu Ser Thr Leu
```

```
            785                 790                 795                 800
Leu Gln Glu Ile Arg Asn Asn Ser Asn Ser Ser Asp Ile Glu Leu Glu
                    805                 810                 815
Glu Lys Val Met Leu Thr Glu Cys Glu Ile Asn Val Ile Ser Asn Ile
                    820                 825                 830
Asp Thr Gln Ile Val Glu Arg Ile Glu Ala Lys Asn Leu Thr
                    835                 840                 845
Ser Asp Ser Ile Asn Tyr Ile Lys Asp Glu Phe Lys Leu Ile Glu Ser
    850                 855                 860
Ile Ser Asp Ala Leu Cys Asp Leu Lys Gln Gln Asn Glu Leu Glu Asp
865                 870                 875                 880
Ser His Phe Ile Ser Phe Glu Asp Ile Ser Glu Thr Asp Glu Gly Phe
                    885                 890                 895
Ser Ile Arg Phe Ile Asn Lys Glu Thr Gly Glu Ser Ile Phe Val Glu
                    900                 905                 910
Thr Glu Lys Thr Ile Phe Ser Glu Tyr Ala Asn His Ile Thr Glu Glu
                    915                 920                 925
Ile Ser Lys Ile Lys Gly Thr Ile Phe Asp Thr Val Asn Gly Lys Leu
    930                 935                 940
Val Lys Lys Val Asn Leu Asp Thr Thr His Glu Val Asn Thr Leu Asn
945                 950                 955                 960
Ala Ala Phe Phe Ile Gln Ser Leu Ile Glu Tyr Asn Ser Ser Lys Glu
                    965                 970                 975
Ser Leu Ser Asn Leu Ser Val Ala Met Lys Val Gln Val Tyr Ala Gln
                    980                 985                 990
Leu Phe Ser Thr Gly Leu Asn Thr Ile Thr Asp Ala Ala Lys Val Val
                    995                1000                1005
Glu Leu Val Ser Thr Ala Leu Asp Glu Thr Ile Asp Leu Leu Pro
    1010                1015                1020
Thr Leu Ser Glu Gly Leu Pro Ile Ile Ala Thr Ile Ile Asp Gly
    1025                1030                1035
Val Ser Leu Gly Ala Ala Ile Lys Glu Leu Ser Glu Thr Ser Asp
    1040                1045                1050
Pro Leu Leu Arg Gln Glu Ile Glu Ala Lys Ile Gly Ile Met Ala
    1055                1060                1065
Val Asn Leu Thr Thr Ala Thr Thr Ala Ile Ile Thr Ser Ser Leu
    1070                1075                1080
Gly Ile Ala Ser Gly Phe Ser Ile Leu Leu Val Pro Leu Ala Gly
    1085                1090                1095
Ile Ser Ala Gly Ile Pro Ser Leu Val Asn Asn Glu Leu Val Leu
    1100                1105                1110
Arg Asp Lys Ala Thr Lys Val Val Asp Tyr Phe Lys His Val Ser
    1115                1120                1125
Leu Val Glu Thr Glu Gly Val Phe Thr Leu Leu Asp Asp Lys Ile
    1130                1135                1140
Met Met Pro Gln Asp Asp Leu Val Ile Ser Glu Ile Asp Phe Asn
    1145                1150                1155
Asn Asn Ser Ile Val Leu Gly Lys Cys Glu Ile Trp Arg Met Glu
    1160                1165                1170
Gly Gly Ser Gly His Thr Val Thr Asp Asp Ile Asp His Phe Phe
    1175                1180                1185
Ser Ala Pro Ser Ile Thr Tyr Arg Glu Pro His Leu Ser Ile Tyr
    1190                1195                1200
```

```
Asp Val Leu Glu Val Gln Lys Glu Leu Asp Leu Ser Lys Asp
1205                 1210                1215

Leu Met Val Leu Pro Asn Ala Pro Asn Arg Val Phe Ala Trp Glu
1220                 1225                1230

Thr Gly Trp Thr Pro Gly Leu Arg Ser Leu Glu Asn Asp Gly Thr
1235                 1240                1245

Lys Leu Leu Asp Arg Ile Arg Asp Asn Tyr Glu Gly Glu Phe Tyr
1250                 1255                1260

Trp Arg Tyr Phe Ala Phe Ile Ala Asp Ala Leu Ile Thr Thr Leu
1265                 1270                1275

Lys Pro Arg Tyr Glu Asp Thr Asn Ile Arg Ile Asn Leu Asp Ser
1280                 1285                1290

Asn Thr Arg Ser Phe Ile Val Pro Ile Ile Thr Thr Glu Tyr Ile
1295                 1300                1305

Arg Glu Lys Leu Ser Tyr Ser Phe Tyr Gly Ser Gly Gly Thr Tyr
1310                 1315                1320

Ala Leu Ser Leu Ser Gln Tyr Asn Met Gly Ile Asn Ile Glu Leu
1325                 1330                1335

Ser Glu Ser Asp Val Trp Ile Ile Asp Val Asp Asn Val Val Arg
1340                 1345                1350

Asp Val Thr Ile Glu Ser Asp Lys Ile Lys Lys Gly Asp Leu Ile
1355                 1360                1365

Glu Gly Ile Leu Ser Thr Leu Ser Ile Glu Glu Asn Lys Ile Ile
1370                 1375                1380

Leu Asn Ser His Glu Ile Asn Phe Ser Gly Glu Val Asn Gly Ser
1385                 1390                1395

Asn Gly Phe Val Ser Leu Thr Phe Ser Ile Leu Glu Gly Ile Asn
1400                 1405                1410

Ala Ile Ile Glu Val Asp Leu Leu Ser Lys Ser Tyr Lys Leu Leu
1415                 1420                1425

Ile Ser Gly Glu Leu Lys Ile Leu Met Leu Asn Ser Asn His Ile
1430                 1435                1440

Gln Gln Lys Ile Asp Tyr Ile Gly Phe Asn Ser Glu Leu Gln Lys
1445                 1450                1455

Asn Ile Pro Tyr Ser Phe Val Asp Ser Glu Gly Lys Glu Asn Gly
1460                 1465                1470

Phe Ile Asn Gly Ser Thr Lys Glu Gly Leu Phe Val Ser Glu Leu
1475                 1480                1485

Pro Asp Val Val Leu Ile Ser Lys Val Tyr Met Asp Asp Ser Lys
1490                 1495                1500

Pro Ser Phe Gly Tyr Tyr Ser Asn Asn Leu Lys Asp Val Lys Val
1505                 1510                1515

Ile Thr Lys Asp Asn Val Asn Ile Leu Thr Gly Tyr Tyr Leu Lys
1520                 1525                1530

Asp Asp Ile Lys Ile Ser Leu Ser Leu Thr Leu Gln Asp Glu Lys
1535                 1540                1545

Thr Ile Lys Leu Asn Ser Val His Leu Asp Glu Ser Gly Val Ala
1550                 1555                1560

Glu Ile Leu Lys Phe Met Asn Arg Lys Gly Asn Thr Asn Thr Ser
1565                 1570                1575

Asp Ser Leu Met Ser Phe Leu Glu Ser Met Asn Ile Lys Ser Ile
1580                 1585                1590
```

```
Phe Val Asn Phe Leu Gln Ser Asn Ile Lys Phe Ile Leu Asp Ala
1595                1600                1605

Asn Phe Ile Ile Ser Gly Thr Thr Ser Ile Gly Gln Phe Glu Phe
1610                1615                1620

Ile Cys Asp Glu Asn Asp Asn Ile Gln Pro Tyr Phe Ile Lys Phe
1625                1630                1635

Asn Thr Leu Glu Thr Asn Tyr Thr Leu Tyr Val Gly Asn Arg Gln
1640                1645                1650

Asn Met Ile Val Glu Pro Asn Tyr Asp Leu Asp Asp Ser Gly Asp
1655                1660                1665

Ile Ser Ser Thr Val Ile Asn Phe Ser Gln Lys Tyr Leu Tyr Gly
1670                1675                1680

Ile Asp Ser Cys Val Asn Lys Val Val Ile Ser Pro Asn Ile Tyr
1685                1690                1695

Thr Asp Glu Ile Asn Ile Thr Pro Val Tyr Glu Thr Asn Asn Thr
1700                1705                1710

Tyr Pro Glu Val Ile Val Leu Asp Ala Asn Tyr Ile Asn Glu Lys
1715                1720                1725

Ile Asn Val Asn Ile Asn Asp Leu Ser Ile Arg Tyr Val Trp Ser
1730                1735                1740

Asn Asp Gly Asn Asp Phe Ile Leu Met Ser Thr Ser Glu Glu Asn
1745                1750                1755

Lys Val Ser Gln Val Lys Ile Arg Phe Val Asn Val Phe Lys Asp
1760                1765                1770

Lys Thr Leu Ala Asn Lys Leu Ser Phe Asn Phe Ser Asp Lys Gln
1775                1780                1785

Asp Val Pro Val Ser Glu Ile Ile Leu Ser Phe Thr Pro Ser Tyr
1790                1795                1800

Tyr Glu Asp Gly Leu Ile Gly Tyr Asp Leu Gly Leu Val Ser Leu
1805                1810                1815

Tyr Asn Glu Lys Phe Tyr Ile Asn Asn Phe Gly Met Met Val Ser
1820                1825                1830

Gly Leu Ile Tyr Ile Asn Asp Ser Leu Tyr Tyr Phe Lys Pro Pro
1835                1840                1845

Val Asn Asn Leu Ile Thr Gly Phe Val Thr Val Gly Asp Asp Lys
1850                1855                1860

Tyr Tyr Phe Asn Pro Ile Asn Gly Gly Ala Ala Ser Ile Gly Glu
1865                1870                1875

Thr Ile Ile Asp Asp Lys Asn Tyr Tyr Phe Asn Gln Ser Gly Val
1880                1885                1890

Leu Gln Thr Gly Val Phe Ser Thr Glu Asp Gly Phe Lys Tyr Phe
1895                1900                1905

Ala Pro Ala Asn Thr Leu Asp Glu Asn Leu Glu Gly Glu Ala Ile
1910                1915                1920

Asp Phe Thr Gly Lys Leu Ile Ile Asp Glu Asn Ile Tyr Tyr Phe
1925                1930                1935

Asp Asp Asn Tyr Arg Gly Ala Val Glu Trp Lys Glu Leu Asp Gly
1940                1945                1950

Glu Met His Tyr Phe Ser Pro Glu Thr Gly Lys Ala Phe Lys Gly
1955                1960                1965

Leu Asn Gln Ile Gly Asp Tyr Lys Tyr Tyr Phe Asn Ser Asp Gly
1970                1975                1980

Val Met Gln Lys Gly Phe Val Ser Ile Asn Asp Asn Lys His Tyr
```

```
             1985                1990                1995
        Phe Asp Asp Ser Gly Val Met Lys Val Gly Tyr Thr Glu Ile Asp
                 2000                2005                2010

Gly Lys His Phe Tyr Phe Ala Glu Asn Gly Glu Met Gln Ile Gly
                 2015                2020                2025

Val Phe Asn Thr Glu Asp Gly Phe Lys Tyr Phe Ala His His Asn
                 2030                2035                2040

Glu Asp Leu Gly Asn Glu Glu Gly Glu Ile Ser Tyr Ser Gly
                 2045                2050                2055

Ile Leu Asn Phe Asn Asn Lys Ile Tyr Tyr Phe Asp Asp Ser Phe
                 2060                2065                2070

Thr Ala Val Val Gly Trp Lys Asp Leu Glu Asp Gly Ser Lys Tyr
                 2075                2080                2085

Tyr Phe Asp Glu Asp Thr Ala Glu Ala Tyr Ile Gly Leu Ser Leu
                 2090                2095                2100

Ile Asn Asp Gly Gln Tyr Tyr Phe Asn Asp Asp Gly Ile Met Gln
                 2105                2110                2115

Val Gly Phe Val Thr Ile Asn Asp Lys Val Phe Tyr Phe Ser Asp
                 2120                2125                2130

Ser Gly Ile Ile Glu Ser Gly Val Gln Asn Ile Asp Asp Asn Tyr
                 2135                2140                2145

Phe Tyr Ile Asp Asp Asn Gly Ile Val Gln Ile Gly Val Phe Asp
                 2150                2155                2160

Thr Ser Asp Gly Tyr Lys Tyr Phe Ala Pro Ala Asn Thr Val Asn
                 2165                2170                2175

Asp Asn Ile Tyr Gly Gln Ala Val Glu Tyr Ser Gly Leu Val Arg
                 2180                2185                2190

Val Gly Glu Asp Val Tyr Tyr Phe Gly Glu Thr Tyr Thr Ile Glu
                 2195                2200                2205

Thr Gly Trp Ile Tyr Asp Met Glu Asn Glu Ser Asp Lys Tyr Tyr
                 2210                2215                2220

Phe Asn Pro Glu Thr Lys Lys Ala Cys Lys Gly Ile Asn Leu Ile
                 2225                2230                2235

Asp Asp Ile Lys Tyr Tyr Phe Asp Glu Lys Gly Ile Met Arg Thr
                 2240                2245                2250

Gly Leu Ile Ser Phe Glu Asn Asn Asn Tyr Tyr Phe Asn Glu Asn
                 2255                2260                2265

Gly Glu Met Gln Phe Gly Tyr Ile Asn Ile Glu Asp Lys Met Phe
                 2270                2275                2280

Tyr Phe Gly Glu Asp Gly Val Met Gln Ile Gly Val Phe Asn Thr
                 2285                2290                2295

Pro Asp Gly Phe Lys Tyr Phe Ala His Gln Asn Thr Leu Asp Glu
                 2300                2305                2310

Asn Phe Glu Gly Glu Ser Ile Asn Tyr Thr Gly Trp Leu Asp Leu
                 2315                2320                2325

Asp Glu Lys Arg Tyr Tyr Phe Thr Asp Glu Tyr Ile Ala Ala Thr
                 2330                2335                2340

Gly Ser Val Ile Ile Asp Gly Glu Glu Tyr Tyr Phe Asp Pro Asp
                 2345                2350                2355

Thr Ala Gln Leu Val Ile Ser Glu
                 2360                2365

<210> SEQ ID NO 2
```

```
<211> LENGTH: 275
<212> TYPE: PRT
<213> ORGANISM: Clostridium difficile

<400> SEQUENCE: 2

Met Gly Leu Ile Tyr Ile Asn Asp Ser Leu Tyr Tyr Phe Lys Pro Pro
1               5                   10                  15

Val Asn Asn Leu Ile Thr Gly Phe Val Thr Val Gly Asp Asp Lys Tyr
            20                  25                  30

Tyr Phe Asn Pro Ile Asn Gly Ala Ala Ser Ile Gly Glu Thr Ile
        35                  40                  45

Ile Asp Asp Lys Asn Tyr Tyr Phe Asn Gln Ser Gly Val Leu Gln Thr
    50                  55                  60

Gly Val Phe Ser Thr Glu Asp Gly Phe Lys Tyr Phe Ala Pro Ala Asn
65                  70                  75                  80

Thr Leu Asp Glu Asn Leu Glu Gly Glu Ala Ile Asp Phe Thr Gly Lys
                85                  90                  95

Leu Ile Ile Asp Glu Asn Ile Tyr Tyr Phe Asp Asp Asn Tyr Arg Gly
            100                 105                 110

Ala Val Glu Trp Lys Glu Leu Asp Gly Glu Met His Tyr Phe Ser Pro
        115                 120                 125

Glu Thr Gly Lys Ala Phe Lys Gly Leu Asn Gln Ile Gly Asp Tyr Lys
130                 135                 140

Tyr Tyr Phe Asn Ser Asp Gly Val Met Gln Lys Gly Phe Val Ser Ile
145                 150                 155                 160

Asn Asp Asn Lys His Tyr Phe Asp Asp Ser Gly Val Met Lys Val Gly
                165                 170                 175

Tyr Thr Glu Ile Asp Gly Lys His Phe Tyr Phe Ala Glu Asn Gly Glu
            180                 185                 190

Met Gln Ile Gly Val Phe Asn Thr Glu Asp Gly Phe Lys Tyr Phe Ala
        195                 200                 205

His His Asn Glu Asp Leu Gly Asn Glu Gly Glu Glu Ile Ser Tyr
210                 215                 220

Ser Gly Ile Leu Asn Phe Asn Asn Lys Ile Tyr Tyr Phe Asp Asp Ser
225                 230                 235                 240

Phe Thr Ala Val Val Gly Trp Lys Asp Leu Glu Asp Gly Ser Lys Tyr
                245                 250                 255

Tyr Phe Asp Glu Asp Thr Ala Glu Ala Tyr Ile Leu Glu His His His
            260                 265                 270

His His His
        275

<210> SEQ ID NO 3
<211> LENGTH: 13
<212> TYPE: PRT
<213> ORGANISM: Clostridium difficile

<400> SEQUENCE: 3

Glu Asp Gly Phe Lys Tyr Phe Ala Pro Ala Asn Thr Leu
1               5                   10

<210> SEQ ID NO 4
<211> LENGTH: 5
<212> TYPE: PRT
<213> ORGANISM: Clostridium difficile

<400> SEQUENCE: 4
```

```
Glu Asn Gly Glu Met
1               5

<210> SEQ ID NO 5
<211> LENGTH: 6
<212> TYPE: PRT
<213> ORGANISM: Clostridium difficile

<400> SEQUENCE: 5

Glu Asp Gly Phe Lys Tyr
1               5

<210> SEQ ID NO 6
<211> LENGTH: 18
<212> TYPE: PRT
<213> ORGANISM: Clostridium difficile

<400> SEQUENCE: 6

Glu Asn Gly Glu Met Gln Ile Gly Val Phe Asn Thr Glu Asp Gly Phe
1               5                   10                  15

Lys Tyr

<210> SEQ ID NO 7
<211> LENGTH: 117
<212> TYPE: PRT
<213> ORGANISM: Clostridium difficile

<400> SEQUENCE: 7

Gly Phe Val Thr Val Gly Asp Asp Lys Tyr Tyr Phe Asn Pro Ile Asn
1               5                   10                  15

Gly Gly Ala Ala Ser Ile Gly Glu Thr Ile Ile Asp Asp Lys Asn Tyr
                20                  25                  30

Tyr Phe Asn Gln Ser Gly Val Leu Gln Thr Gly Val Phe Ser Thr Glu
            35                  40                  45

Asp Gly Phe Lys Tyr Phe Ala Pro Ala Asn Thr Leu Asp Glu Asn Leu
        50                  55                  60

Glu Gly Glu Ala Ile Asp Phe Thr Gly Lys Leu Ile Ile Asp Glu Asn
65                  70                  75                  80

Ile Tyr Tyr Phe Asp Asp Asn Tyr Arg Gly Ala Val Glu Trp Lys Glu
                85                  90                  95

Leu Asp Gly Glu Met His Tyr Phe Ser Pro Glu Thr Gly Lys Ala Phe
            100                 105                 110

Lys Gly Leu Asn Gln
        115

<210> SEQ ID NO 8
<211> LENGTH: 116
<212> TYPE: PRT
<213> ORGANISM: Clostridium difficile

<400> SEQUENCE: 8

Gly Phe Val Ser Ile Asn Asp Asn Lys His Tyr Phe Asp Asp Ser Gly
1               5                   10                  15

Val Met Lys Val Gly Tyr Thr Glu Ile Asp Gly Lys His Phe Tyr Phe
                20                  25                  30

Ala Glu Asn Gly Glu Met Gln Ile Gly Val Phe Asn Thr Glu Asp Gly
            35                  40                  45

Phe Lys Tyr Phe Ala His His Asn Glu Asp Leu Gly Asn Glu Glu Gly
        50                  55                  60
```

```
Glu Glu Ile Ser Tyr Ser Gly Ile Leu Asn Phe Asn Asn Lys Ile Tyr
65                  70                  75                  80

Tyr Phe Asp Asp Ser Phe Thr Ala Val Val Gly Trp Lys Asp Leu Glu
                85                  90                  95

Asp Gly Ser Lys Tyr Tyr Phe Asp Glu Asp Thr Ala Glu Ala Tyr Ile
            100                 105                 110

Gly Leu Ser Leu
            115

<210> SEQ ID NO 9
<211> LENGTH: 118
<212> TYPE: PRT
<213> ORGANISM: Clostridium difficile

<400> SEQUENCE: 9

Gly Phe Val Thr Ile Asn Asp Lys Val Phe Tyr Phe Ser Asp Ser Gly
1               5                   10                  15

Ile Ile Glu Ser Gly Val Gln Asn Ile Asp Asp Asn Tyr Phe Tyr Ile
                20                  25                  30

Asp Asp Asn Gly Ile Val Gln Ile Gly Val Phe Asp Thr Ser Asp Gly
            35                  40                  45

Tyr Lys Tyr Phe Ala Pro Ala Asn Thr Val Asn Asp Asn Ile Tyr Gly
50                  55                  60

Gln Ala Val Glu Tyr Ser Gly Leu Val Arg Val Gly Glu Asp Val Tyr
65                  70                  75                  80

Tyr Phe Gly Glu Thr Tyr Thr Ile Glu Thr Gly Trp Ile Tyr Asp Met
                85                  90                  95

Glu Asn Glu Ser Asp Lys Tyr Tyr Phe Asn Pro Glu Thr Lys Lys Ala
            100                 105                 110

Cys Lys Gly Ile Asn Leu
            115

<210> SEQ ID NO 10
<211> LENGTH: 113
<212> TYPE: PRT
<213> ORGANISM: Clostridium difficile

<400> SEQUENCE: 10

Gly Leu Ile Ser Phe Glu Asn Asn Tyr Tyr Phe Asn Glu Asn Gly
1               5                   10                  15

Glu Met Gln Phe Gly Tyr Ile Asn Ile Glu Asp Lys Met Phe Tyr Phe
                20                  25                  30

Gly Glu Asp Gly Val Met Gln Ile Gly Val Phe Asn Thr Pro Asp Gly
            35                  40                  45

Phe Lys Tyr Phe Ala His Gln Asn Thr Leu Asp Glu Asn Phe Glu Gly
50                  55                  60

Glu Ser Ile Asn Tyr Thr Gly Trp Leu Asp Leu Asp Glu Lys Arg Tyr
65                  70                  75                  80

Tyr Phe Thr Asp Glu Tyr Ile Ala Ala Thr Gly Ser Val Ile Ile Asp
                85                  90                  95

Gly Glu Glu Tyr Tyr Phe Asp Pro Asp Thr Ala Gln Leu Val Ile Ser
            100                 105                 110

Glu

<210> SEQ ID NO 11
<211> LENGTH: 213
<212> TYPE: PRT
```

<213> ORGANISM: Homo sapiens

<400> SEQUENCE: 11

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Thr
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly
    210
```

<210> SEQ ID NO 12
<211> LENGTH: 221
<212> TYPE: PRT
<213> ORGANISM: Homo sapiens

<400> SEQUENCE: 12

```
Glu Val Gln Leu Val Gln Ser Gly Ala Glu Val Lys Lys Ser Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Phe Tyr Pro Gly Asp Ser Ser Thr Arg Tyr Ser Pro Ser Phe
    50                  55                  60

Gln Gly Gln Val Thr Ile Ser Ala Asp Lys Ser Val Asn Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Arg Asn Trp Gly Asn Ala Phe Asp Ile Trp Gly Gln Gly
            100                 105                 110

Thr Met Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
```

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Arg Val Glu Pro Lys Ser
        210                 215                 220

<210> SEQ ID NO 13
<211> LENGTH: 6
<212> TYPE: PRT
<213> ORGANISM: Artificial Sequence
<220> FEATURE:
<223> OTHER INFORMATION: Hex-His tag

<400> SEQUENCE: 13

His His His His His His
1               5

<210> SEQ ID NO 14
<211> LENGTH: 268
<212> TYPE: PRT
<213> ORGANISM: Clostridium difficile

<400> SEQUENCE: 14

Gly Leu Ile Tyr Ile Asn Asp Ser Leu Tyr Tyr Phe Lys Pro Pro Val
1               5                   10                  15

Asn Asn Leu Ile Thr Gly Phe Val Thr Val Gly Asp Asp Lys Tyr Tyr
            20                  25                  30

Phe Asn Pro Ile Asn Gly Gly Ala Ala Ser Ile Gly Glu Thr Ile Ile
        35                  40                  45

Asp Asp Lys Asn Tyr Tyr Phe Asn Gln Ser Gly Val Leu Gln Thr Gly
    50                  55                  60

Val Phe Ser Thr Glu Asp Gly Phe Lys Tyr Phe Ala Pro Ala Asn Thr
65                  70                  75                  80

Leu Asp Glu Asn Leu Glu Gly Glu Ala Ile Asp Phe Thr Gly Lys Leu
                85                  90                  95

Ile Ile Asp Glu Asn Ile Tyr Tyr Phe Asp Asp Asn Tyr Arg Gly Ala
            100                 105                 110

Val Glu Trp Lys Glu Leu Asp Gly Glu Met His Tyr Phe Ser Pro Glu
        115                 120                 125

Thr Gly Lys Ala Phe Lys Gly Leu Asn Gln Ile Gly Asp Tyr Lys Tyr
    130                 135                 140

Tyr Phe Asn Ser Asp Gly Val Met Gln Lys Gly Phe Val Ser Ile Asn
145                 150                 155                 160

Asp Asn Lys His Tyr Phe Asp Asp Ser Gly Val Met Lys Val Gly Tyr
                165                 170                 175

Thr Glu Ile Asp Gly Lys His Phe Tyr Phe Ala Glu Asn Gly Glu Met
            180                 185                 190

Gln Ile Gly Val Phe Asn Thr Glu Asp Gly Phe Lys Tyr Phe Ala His
        195                 200                 205

His Asn Glu Asp Leu Gly Asn Glu Glu Gly Glu Glu Ile Ser Tyr Ser
    210                 215                 220
```

```
Gly Ile Leu Asn Phe Asn Asn Lys Ile Tyr Tyr Phe Asp Asp Ser Phe
225                 230                 235                 240

Thr Ala Val Val Gly Trp Lys Asp Leu Glu Asp Gly Ser Lys Tyr Tyr
                245                 250                 255

Phe Asp Glu Asp Thr Ala Glu Ala Tyr Ile Gly Leu
            260                 265
```

C. DIFFICILE TOXIN B CROP DOMAIN PEPTIDES, ANTIBODIES AND COMPLEXES THEREOF

This Application claims the benefit of U.S. Provisional Patent Application No. 61/875,266; filed Sep. 9, 2013; which is herein incorporated by reference in its entirety.

FIELD OF THE INVENTION

The present invention relates to *C. difficile* polypeptides and complexes thereof with antibodies that bind specifically thereto.

BACKGROUND OF THE INVENTION

*Clostridium difficile* is an anaerobic pathogenic bacterium that causes infection of the colon typified by severe diarrhea, pseudomembranous colitis, and, in extreme cases, colonic rupture, sepsis and death. The symptoms of *C. difficile* infection (CDI) are caused by two exotoxins, toxin A (TcdA) and toxin B (TcdB) that are thought to target colonocytes via similar mechanisms involving glucosylation of small GTPases such as Rac and Rho. Inactivation of these important enzymes leads to morphological changes and eventually cell death, disruption of the colonic trans-epithelial resistance and the initiation and propagation of deleterious inflammatory events. Entry of the toxins into cells occurs through binding of the toxins to receptors on the cell surface, internalization via endocytosis, pH-induced conformational changes including formation of a trans-membrane pore that allows for transport and release (via autoproteolytic cleavage) of the glucosyl-ransferase domain of the toxins into the cytoplasm.

Bezlotoxumab is an anti-*C. difficile* toxin B human monoclonal antibody useful for the treatment and prevention of *C. difficile* infection. Understanding the nature of the bezlotoxumab interaction with the toxin B is important to the design of further therapeutic antibodies and vaccines for treating *C. difficile* infection.

SUMMARY OF THE INVENTION

The present invention provides an isolated polynucleotide (e.g., in a vector) encoding a polypeptide that comprises an amino acid sequence that is at least 80% identical or similar to an amino acid sequence that is selected from the group consisting of: *C. difficile* toxin B amino acids 1834-2367; *C. difficile* toxin B amino acids 1834-2101; *C. difficile* toxin B amino acids 1949-2275; *C. difficile* toxin B amino acids 2102-2367; *C. difficile* toxin B amino acids 1855-1971; *C. difficile* toxin B amino acids 1988-2103; *C. difficile* toxin B amino acids 2120-2237; SEQ ID NO: 14; *C. difficile* toxin B amino acids 2254-2366; EDGFKYFAPANTL (SEQ ID NO: 3); ENGEM (SEQ ID NO: 4); EDGFKY (SEQ ID NO: 5); and ENGEMQIGVFNTEDGFKY (SEQ ID NO: 6). Also provided is an isolated host cell comprising the polynucleotide or vector. The present invention also provides an isolated polypeptide (e.g., in a composition, such as a vaccine, having a carrier, e.g., a pharmaceutically acceptable carrier) comprising an amino acid sequence that is at least 80% identical or similar to an amino acid sequence that is selected from the group consisting of: *C. difficile* toxin B amino acids 1834-2367; *C. difficile* toxin B amino acids 1834-2101; *C. difficile* toxin B amino acids 1949-2275; *C. difficile* toxin B amino acids 2102-2367; *C. difficile* toxin B amino acids 1855-1971; *C. difficile* toxin B amino acids 1988-2103; *C. difficile* toxin B amino acids 2120-2237; *C. difficile* toxin B amino acids 2254-2366; SEQ ID NO: 14; EDGFKYFA-PANTL (SEQ ID NO: 3); ENGEM (SEQ ID NO: 4); EDGFKY (SEQ ID NO: 5); and ENGEMQIGVFNTEDGFKY (SEQ ID NO: 6). The present invention encompasses a polypeptide comprising an amino acid sequence selected from the group consisting of SEQ ID NOs: 2-10. Complexes between any such and an antibody (e.g., bezlotoxumab) or antigen-binding fragment thereof which binds specifically to the polypeptide are part of the present invention. In an embodiment of the invention, the complex (e.g., crystalline or non-crystalline) comprises bezlotoxumab, which comprises a light chain that comprises the amino acid sequence set forth in SEQ ID NO: 11 and a heavy chain that comprises the amino acid sequence set forth in SEQ ID NO: 12; and/or the *C. difficile* toxin B amino acids 1834-2101 comprises the amino acid sequence set forth in SEQ ID NO: 1 which optionally further comprises the C-terminal amino acid sequence LEHHHHHH (SEQ ID NO: 13).

The present invention provides an isolated crystal comprising a bezlotoxumab Fab fragment complexed with *C. difficile* toxin B amino acids 1834-2101 wherein the crystal is characterized by: space group: P21; and unit cell dimensions: a=79.413, b=134.659, c=102.579, α=γ=90°, β=112.559°; optionally, wherein said complex is characterized by structure coordinates comprising a root mean square deviation (RMSD) of conserved residue backbone atoms of less than about 2.0 angstroms when superimposed on backbone atoms described by structural coordinates of Table 1.

The present invention also provides a method for producing a crystalline complex of the present invention (discussed herein) comprising incubating a first solution (e.g., in a drop, hanging or sitting on a surface) comprising 10 mg/ml of the complex, 5 mM phosphate, pH 7.4, 68.5 mM sodium chloride, 1.35 mM potassium chloride and 2.2% polyethylene glycol 4000 in a sealed container in close proximity to a second solution comprising 4.4% polyethylene glycol 4000.

The present invention also provides a method for immunizing an animal or for making an antibody or antigen-binding fragment thereof comprising administering a therapeutically effective amount of any of the polypeptides or vaccines of the present invention, e.g., as discussed herein, to a host animal and, optionally: (i) isolating the antibody or fragment from the host animal; (ii) humanizing the antibody or fragment; (iii) combining the antibody or fragment with a pharmaceutically acceptable carrier; (iv) isolating a splenocyte from the host animal; (v) fusing a splenocyte from the host animal with a myeloma cell; and/or (vi) fusing the light chain immunoglobulin variable region and/or heavy chain immunoglobulin variable region of the antibody or fragment with a human immunoglobulin light chain constant domain and/or human immunoglobulin heavy chain constant domain, respectively.

DETAILED DESCRIPTION OF THE INVENTION

Figure 1:
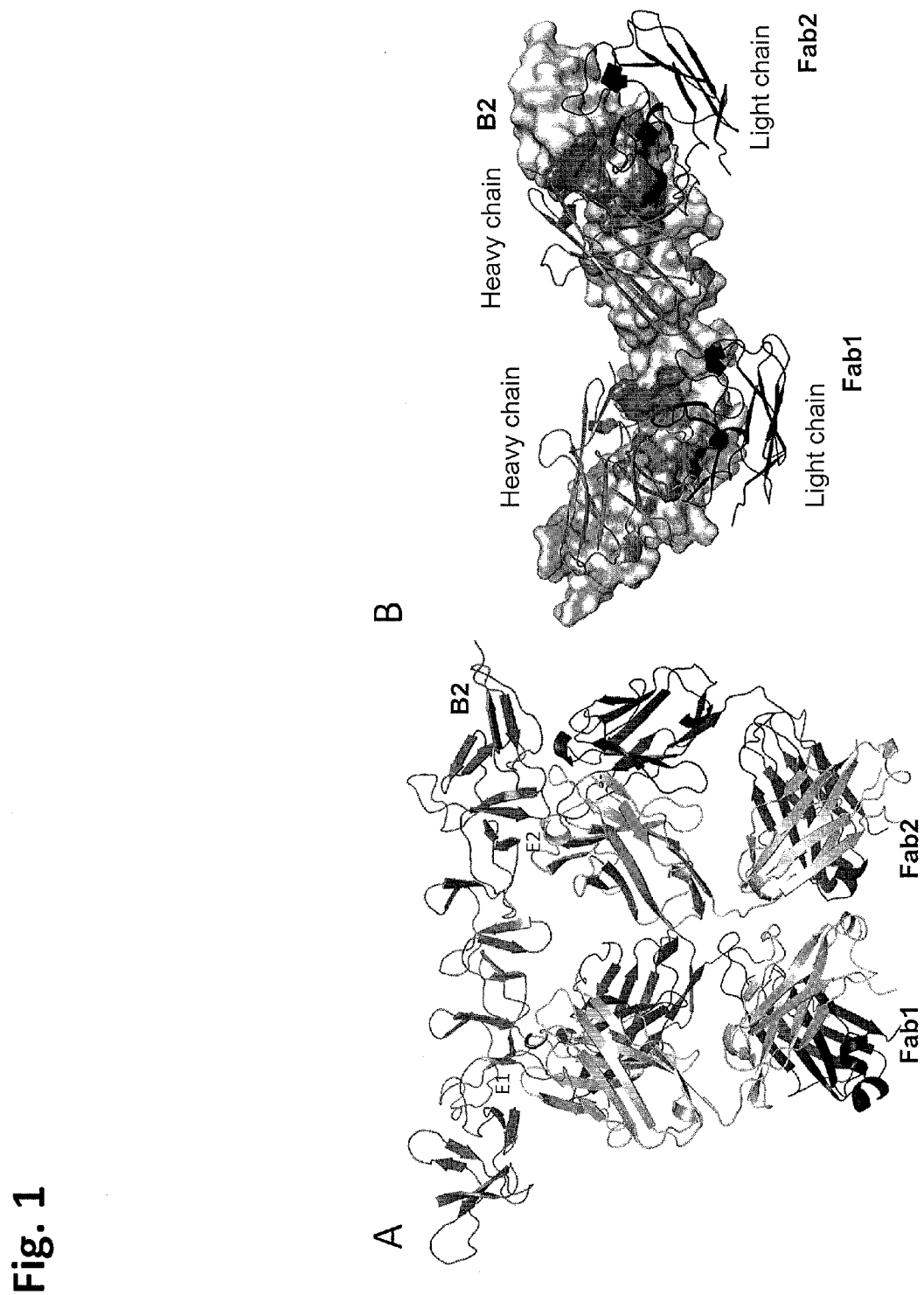
FIG. 1. Crystal structure of the N-terminal half of the TcdB CROP domain (peptide BC2) bound to two bezlotoxumab Fab fragments. A) Side view showing parallel binding of the two Fab fragments (Fab1 and Fab2) to their respective epitopes (referred to herein as E1 and E2). Heavy chains are colored light grey, light chains are colored black. B) bottom-up view showing the Fab fragments bound perpendicularly to the curvature of the CROP domain. Residues of the CROP domain that directly interact with the heavy chains (grey) or light chains (black) of the Fab fragments are also highlighted.

Crystals and crystallization conditions were discovered for an engineered *Clostridium difficile* toxin B (TcdB) construct and a Fab fragment from a monoclonal antibody specific for Toxin TcdB, bezlotoxumab. An *E. coli* expression system was established for the expression and purification of toxin TcdB B construct (*Clostridium difficile* toxin B (TcdB1834-2101)) that was suitable for complexing with the Fab fragment of bezlotoxumab which resulted in the structure determination of toxin *C difficile* toxin B (TcdB$^{(1834-2101)}$) complexed with the Fab fragment. Novel methods are disclosed to engineer a *C. difficile* toxin B TcdB (1834-2101) construct that crystallized and resulted in the three-dimensional structure determination. The present invention also provides a novel crystal form that is a suitable reagent for structure assisted drug design and methods of preparation.

X-ray crystallography and other analyses demonstrated that one molecule of bezlotoxumab bound to two distinct homologous regions within the TcdB CROP domain, partially occluding two of the four putative carbohydrate binding sites. The present method also provides *C. difficile* toxin B immunogenic polypeptide antigens encompassing the binding sites of bezlotoxumab and methods of immunizing an animal with such polypeptide antigens.

Molecular Biology

In accordance with the present invention there may be employed conventional molecular biology, microbiology, and recombinant DNA techniques within the skill of the art. Such techniques are explained fully in the literature. See, e.g., Sambrook, Fritsch & Maniatis, Molecular Cloning: A Laboratory Manual, Second Edition (1989) Cold Spring Harbor Laboratory Press, Cold Spring Harbor, N.Y. (herein "Sambrook, et al., 1989"); DNA Cloning: A Practical Approach, Volumes I and II (DN. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells And Enzymes (IRL Press, (1986)); B. Perbal, A Practical Guide To Molecular Cloning (1984); F. M. Ausubel, et al. (eds.), Current Protocols in Molecular Biology, John Wiley & Sons, Inc. (1994).

A "polynucleotide", "nucleic acid" or "nucleic acid molecule" DNA and RNA (e.g., mRNA), single or double stranded.

An "endogenous" polynucleotide or polypeptide is present normally in a wild-type host cell such as a CHO cell.

A "nucleotide sequence" is a series of nucleotide bases (also called "nucleotides") in a nucleic acid, such as DNA or RNA, and means any chain of two or more nucleotides.

An "amino acid sequence" refers to a series of two or more amino acids in a protein, peptide or polypeptide.

A "protein", "peptide" or "polypeptide" includes a contiguous string of two or more amino acids.

The terms "isolated polynucleotide" or "isolated polypeptide" include a polynucleotide (e.g., RNA or DNA molecule, or a mixed polymer) or a polypeptide, respectively, which are partially (to any degree) or fully separated from other components that are normally found in cells or in recombinant DNA expression systems. These components include, but are not limited to, cell membranes, cell walls, ribosomes, polymerases, serum components and extraneous genomic sequences.

The term "host cell" includes any cell of any organism (e.g., a prokaryotic (such as a bacterial cell such as *E. coli*, e.g., BL21DE3) or eukaryotic cell (such as a fungal, insect or mammalian cells) that is selected, modified, transfected, transformed, grown, or used or manipulated in any way, for the production of a substance by the cell, for example the expression or replication, by the cell, of a gene, a DNA or RNA sequence or a protein. Fungal host cells include *Saccharomyces* cells and *Pichia* cells such as *Pichia pastoris*. Mammalian cells include Chinese hamster ovary cells. Insect cells include *Spodoptera frugiperda* cells, SF-900, SF9, SF21 or *Trichoplusia ni* cells.

The nucleic acids herein may be flanked by natural regulatory (expression control) sequences, or may be associated with heterologous sequences, including promoters, internal ribosome entry sites (IRES) and other ribosome binding site sequences, enhancers, response elements, suppressors, signal sequences, polyadenylation sequences, introns, 5'- and 3'-non-coding regions, and the like.

A coding sequence, such as Bx or $E_x$, is "operably linked to" transcriptional and translational control sequences in a cell when the sequences direct RNA polymerase mediated transcription of the coding sequence into RNA, preferably mRNA, which then may be RNA spliced (if it contains introns) and, optionally, translated into a protein encoded by the coding sequence.

The terms "express" and "expression" mean allowing or causing the information in a gene, RNA or DNA sequence to become manifest; for example, producing a protein by activating the cellular functions involved in transcription and translation of a corresponding gene. A DNA sequence is expressed in or by a cell to form an "expression product" such as an RNA (e.g., mRNA) or a protein. The expression product itself may also be said to be "expressed" by the cell.

The term "vector" includes a vehicle (e.g., a plasmid) by which a DNA or RNA sequence, e.g., encoding a Bx or $E_x$, can be introduced into a host cell, so as to transform the host and, optionally, promote expression and/or replication of the introduced sequence.

Vectors that can be used in this invention include plasmids, viruses, bacteriophage, integratable DNA fragments, and other vehicles that may facilitate introduction of the nucleic acids into the genome of the host. Plasmids are the most commonly used form of vector but all other forms of vectors which serve a similar function and which are, or become, known in the art are suitable for use herein. See, e.g., Pouwels, et al., Cloning Vectors: A Laboratory Manual, 1985 and Supplements, Elsevier, N.Y., and Rodriguez et al., (eds.), Vectors: A Survey of Molecular Cloning Vectors and Their Uses, 1988, Buttersworth, Boston, Mass.

The present invention includes *C. difficile* toxin B Bx or $E_x$ polypeptides having the amino acid sequence of any of SEQ ID NOs: 2-10 as well as such polypeptides having superficial or slight modifications to the amino acid sequences; as well as methods of making and using thereof (as discussed herein). Function-conservative variants of the *C. difficile* toxin B Bx or $E_x$ polypeptides of the invention are also part of the present invention. "Function-conservative variants" are those in which one or more amino acid residues in the protein have been changed without altering the overall conformation and function of the polypeptide, including, but, by no means, limited to, replacement of an amino acid with one having similar properties. Amino acids with similar properties are well known in the art. For example, polar/hydrophilic amino acids which may be interchangeable include asparagine, glutamine, serine, cysteine, threonine, lysine, arginine, histidine, aspartic acid and glutamic acid; nonpolar/hydrophobic amino acids which may be interchangeable include glycine, alanine, valine, leucine, isoleucine, proline, tyrosine, phenylalanine, tryptophan and methionine; acidic amino acids, which may be interchangeable include aspartic acid and glutamic acid and basic amino acids, which may be interchangeable include histidine, lysine and arginine.

Sequence identity refers to exact matches between the amino acids of two sequences which are being compared. Sequence similarity or homology refers to both exact matches between the amino acids of two polypeptides which are being compared in addition to matches between nonidentical, biochemically related amino acids. Biochemically related amino acids which share similar properties and may be interchangeable are discussed herein.

The following references regarding the BLAST algorithm are herein incorporated by reference: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M., et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. 0. Dayhoff (ed.), pp. 353-358, Natl. Biomed. Res. Found., Washington, D.C.; Altschul, S. F., (1991) J. Mol. Biol. 219:555-565; States, D. J., at al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, New York.

A "heterologous" amino acid sequence, as it relates to a polypeptide comprising, consisting of or consisting essentially of a *C. difficile* toxin B polypeptide fused to a heterologous polypeptide, refers to an amino acid sequence which is not contiguous with adjacent amino acid sequences in the *C. difficile* toxin B polypeptide. Such fusions and methods of using and making the same are part of the present invention.

Bezlotoxumab is an antibody known in the art. See e.g. CAS registry no. 1246264-45-8. In an embodiment of the invention, a bezlotoxunnab Fab comprises the light and heavy chain immunoglobulin amino acid sequences:

Light chain:

(SEQ ID NO: 11)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSTWTFGQG

TKVEIKRTVAAPSVFIFPPSDEQLKSGTASVVCLLNNEYPREAKVQWKVDN

ALQSGNSQESVTEQDSKDSTYSLSSTLTLSKADYEKHKVYACEVTHQGLSS

PVTKSFNRG;

Heavy chain:

(SEQ ID NO: 12)
EVQLVQSGAEVKKSGESLKISCKGSGYSFTSYWIGWVRQMPGKGLEWMGIF

YPGDSSTRYSPSFQGQVTISADKSVNTAYLQWSSLKASDTAMYYCARRRNW

GNAFDIWGQGTMVTVSSASTKGPSVFPLAPSSKSTSGGTAALGCLVKDYFP

EPVTVSWNSGALTSGVHTFPAVLQSSGLYSLSSVVTVPSSSLGTQTYICNV

NHKPSNTKVDKRVEPKS.

*C. difficile* Toxin B

Polypeptides (e.g., immunogenic polypeptides) comprising various fragments of the *C. difficile* toxin B are part of the present invention as well as method of use thereof and methods of making such polypeptides. The present invention includes the *C. difficile* toxin B fragment B1 which comprises, consists of or consists essentially of amino acids 1834-2367 of *C. difficile* toxin B; the *C. difficile* toxin B fragment B2 which comprises, consists of or consists essentially of amino acids 1834-2101 or 1834-2099 of *C. difficile* toxin B; the *C. difficile* toxin B fragment B3 which comprises, consists of or consists essentially of amino acids 1949-2275 of *C. difficile* toxin B; and, the *C. difficile* toxin B fragment B4 which comprises, consists of or consists essentially of amino acids 2102-2367 of *C. difficile* toxin B; or any 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299 or 300 contiguous amino acids of a B1, B2, B3 or B4 polypeptide. *C. difficile* toxin B fragments B1, B2, B3 and B4 may be referred to herein, collectively, as "Bx"; thus, Bx refers to B1, B2, B3 and/or B4.

In an embodiment of the invention, *C. difficile* toxin B polypeptide comprises the amino acid sequence:

```
                                                          (SEQ ID NO: 1)
MSLVNRKQLE KMANVRFRTQ EDEYVAILDA LEEYHNMSEN TVVEKYLKLK DINSLTDIYI

DTYKKSGRNK ALKKFKEYLV TEVLELKNNN LTPVEKNLHF VWIGGQINDT AINYINQWKD

VNSDYNVNVF YDSNAFLINT LKKTVVESAI NDTLESFREN LNDPRFDYNK FFRKRMEIIY

DKQKNFINYY KAQREENPEL IDDDIVKTYL SNEYSKEIDE LNTYIEESLN KITQNSGNDV

RNFEEFKNGE SFNLYEQELV ERWNLAAASD ILRISALKEI GGMYLDVDML PGIQPDLFES

IEKPSSVTVD FWEMTKLEAI MKYKEYIPEY TSEHFDMLDE EVQSSFESVL ASKSDKSEIF

SSLGDMEASP LEVKIAFNSK GIINQGLISV KDSYCSNLIV KQIENRYKIL NNSLNPAISE

DNDFNTTTNT FIDSIMAEAN ADNGRFMMEL GKYLRVGFFP DVKTTINLSG PEAYAAAYQD

LLMFKEGSMN IHLIEADLRN FEISKTNISQ STEQEMASLW SFDDARAKAQ FEEYKRNYFE

GSLGEDDNLD FSQNIVVDKE YLLEKISSLA RSSERGYIHY IVQLQGDKIS YEAACNLFAK

TPYDSVLFQK NIEDSEIAYY YNPGDGEIQE IDKYKIPSII SDRPKIKLTF IGHGKDEFNT

DIFAGFDVDS LSTEIEAAID LAKEDISPKS IEINLLGCNM FSYSINVEET YPGKLLLKVK

DKISELMPSI SQDSIIVSAN QYEVRINSEG RRELLDHSGE WINKEESIIK DISSKEYISF

NPKENKITVK SKNLPELSTL LQEIRNNSNS SDIELEEKVM LTECEINVIS NIDTQIVEER

IEEAKNLTSD SINYIKDEFK LIESISDALC DLKQQNELED SHFISFEDIS ETDEGFSIRF

INKETGESIF VETEKTIFSE YANHITEEIS KIKGTIFDTV NGKLVKKVNL DTTHEVNTLN

AAFFIQSLIE YNSSKESLSN LSVAMKVQVY AQLFSTGLNT ITDAAKVVEL VSTALDETID

LLPTLSEGLP IIATIIDGVS LGAAIKELSE TSDPLLRQEI EAKIGIMAVN LTTATTAIIT

SSLGIASGFS ILLVPLAGIS AGIPSLVNNE LVLRDKATKV VDYFKHVSLV ETEGVFTLLD

DKIMMPQDDL VISEIDFNNN SIVLGKCEIW RMEGGSGHTV TDDIDHFFSA PSITYREPHL

SIYDVLEVQK EELDLSKDLM VLPNAPNRVF AWETGWTPGL RSLENDGTKL LDRIRDNYEG

EFYWRYFAFI ADALITTLKP RYEDTNIRIN LDSNTRSFIV PIITTEYIRE KLSYSFYGSG

GTYALSLSQY NMGINIELSE SDVWIIDVDN VVRDVTIESD KIKKGDLIEG ILSTLSIEEN

KIILNSHEIN FSGEVNGSNG FVSLTFSILE GINAIIEVDL LSKSYKLLIS GELKILMLNS

NHIQQKIDYI GFNSELQKNI PYSFVDSEGK ENGFINGSTK EGLFVSELPD VVLISKVYMD

DSKPSFGYYS NNLKDVKVIT KDNVNILTGY YLKDDIKISL SLTLQDEKTI KLNSVHLDES

GVAEILKFMN RKGNTNTSDS LMSFLESMNI KSIFVNFLQS NIKFILDANF IISGTTSIGQ

FEFICDENDN IQPYFIKFNT LETNYTLYVG NRQNMIVEPN YDLDDSGDIS STVINFSQKY

LYGIDSCVNK VVISPNIYTD EINITPVYET NNTYPEVIVL DANYINEKIN VNINDLSIRY

VWSNDGNDFI LMSTSEENKV SQVKIRFVNV FKDKTLANKL SFNFSDKQDV PVSEIILSFT

PSYYEDGLIG YDLGLVSLYN EKFYINNFGM MVSGLIYIND SLYYFKPPVN NLITGFVTVG

DDKYYFNPIN GGAASIGETI IDDKNYYFNQ SGVLQTGVFS TEDGFKYFAP ANTLDENLEG

EAIDFTGKLI IDENIYYFDD NYRGAVEWKE LDGEMHYFSP ETGKAFKGLN QIGDYKYYFN

SDGVMQKGFV SINDNKHYFD DSGVMKVGYT EIDGKHFYFA ENGEMQIGVF NTEDGFKYFA

HHNEDLGNEE GEEISYSGIL NFNNKIYYFD DSFTAVVGWK DLEDGSKYYF DEDTAEAYIG
```

-continued
LSLINDGQYY FNDDGIMQVG FVTINDKVFY FSDSGIIESG VQNIDDNYFY IDDNGIVQIG

VFDTSDGYKY FAPANTVNDN IYGQAVEYSG LVRVGEDVYY FGETYTIETG WIYDMENESD

KYYFNPETKK ACKGINLIDD IKYYFDEKGI MRTGLISFEN NNYYFNENGE MQFGYINIED

KMFYFGEDGV MQIGVFNTPD GFKYFAHQNT LDENFEGESI NYTGWLDLDE KRYYFTDEYI

AATGSVIIDG EEYYFDPDTA QLVISE

In an embodiment of the invention, the *C. difficile* toxin B (TcdB[1834-2101]), also referred to herein as B2, comprises the amino acid sequence:

(SEQ ID NO: 14)
GLIYINDSLY YFKPPVNNLI TGFVTVGDDK YYFNPINGGA ASIGETIIDD KNYYFNQSGV

LQTGVFSTED GFKYFAPANT LDENLEGEAI DFTGKLIIDE NIYYFDDNYR GAVEWKELDG

EMHYFSPETG KAFKGLNQIG DYKYYFNSDG VMQKGFVSIN DNKHYFDDSG VMKVGYTEID

GKHFYFAENG EMQIGVFNTE DGFKYFAHHN EDLGNEEGEE ISYSGILNFN NKIYYFDDSF

TAVVGWKDLE DGSKYYFDED TAEAYIGL;

or (SEQ ID NO: 2)
MGLIYINDSLYYFKPPVNNLITGFVTVGDDKYYFNPINGGAASIGETIIDD

KNYYFNQSGVLQTGVFSTEDGFKYFAPANTLDENLEGEAIDFTGKLIIDEN

IYYFDDNYRGAVEWKELDGEMHYFSPETGKAFKGLNQIGDYKYYFNSDGVM

QKGFVSINDNKHYFDDSGVMKVGYTEIDGKHFYFAENGEMQIGVFNTEDGF

KYFAHHNEDLGNEEGEEISYSGILNFNNKIYYFDDSFTAVVGWKDLEDGSK

YYFDEDTAEAYILEHHHHHH;

or amino acids 2-267 thereof.

The present invention also includes polypeptides comprising, consisting of or consisting essentially of the *C. difficile* toxin B E1, E2, E3 and E4 fragments (which may be collectively referred to, herein, as $E_x$ or *C. difficile* toxin B $E_x$; such that, for example, $E_x$ refers to E1, E2, E3 and/or E4) which comprise, consist of or consist essentially of amino acid sequences as set forth below or any 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117 or 118 contiguous amino acids of an $E_x$ polypeptide.

*C. difficile* toxin B E1 domain: GFVTVGDDKYYFNPING-GAASIGETIIDDKNYYFNQSGVL QTGVESTE[D]GF[K]YFAPANTLDENLEGEAID-FTGKLIIDENIYYFDDNYRGAVEWKELDGEMHYFSPE TGKAFKGLNQ
(SEQ ID NO: 7); wherein, putative carbohydrate binding residues are bracketed and underscored residues are protected by bezlotoxumab in hydrogen-deuterium exchange (HDX-MS) experiments.

*C. difficile* toxin B E2 domain: GETSINDNKHYFDDS-GVMKVGYTEIDGKHFYFAENGEM QIGVFNTE[D]GF[K][Y]FAHHNEDLGNEE-GEEISYSGILNENNKIYYFDDSFTAVVGWKDLEDGSKYYFDED TAEAYIGLSL (SEQ ID NO: 8); wherein, putative carbohydrate binding residues are bracketed and underscored residues are protected by bezlotoxumab in hydrogen-deuterium exchange (HDX-MS) experiments.

*C. difficile* toxin B E3 domain: GFVTINDKVFYFSDSGIIESGVQNID-DNYFYIDDNGIV QIGVFDTSDGYKYFAPANTVND-NIYGQAVEYSGLVRVGEDVYYFGETYTIETGWIYDMENESDKYYFNPE TKKACK-GINL
(SEQ ID NO: 9)

*C. difficile* toxin B E4 domain: GLISFENNNYYFNENGEMQFGY-INIEDKMFYFGEDGVM QIGVENTPDGEKYFAHQNTLDENFEGES-INYTGWLDLDEKRYYFTDEYIAATGSVIIDGEEYYFDPDTAQLVISE
(SEQ ID NO: 10)

$E_x$ polypeptide also refers to fragments of E1 and E2 comprising, consisting of or consisting essentially of:
*C. difficile* toxin B amino acids 1855-2103;
EDGFKYFAPANTL (SEQ ID NO: 3);
ENGEM (SEQ ID NO: 4);
EDGFKY (SEQ ID NO: 5); and/or
ENGEMQIGVFNTEDGFKY (SEQ ID NO: 6);
optionally, wherein any of such $E_x$ polypeptide fragments further include, at the N-terminus, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 contiguous N-terminal amino acids of the *C. difficile* toxin B polypeptide or a heterologous polypeptide and/or, at the C-terminus, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 contiguous C-terminal amino acids of the *C. difficile* toxin B polypeptide or a heterologous polypeptide.

In an embodiment of the invention, a *C. difficile* toxin B Bx or E$_x$ polypeptide comprises an amino acid sequence that is at least about 80-99.9% (e.g., 80, 81, 82, 83, 84, 85, 86, 87, 88, 89, 90, 91, 92, 93, 94, 95, 96, 97, 98, 99, 99.5, 99.9%) identical or similar to an amino acid sequence set forth in any of SEQ ID NOs: 2-10 or a fragment thereof, as discussed herein; when the comparison is performed by a BLAST algorithm wherein the parameters of the algorithm are selected to give the largest match between the respective sequences over the entire length of the respective reference sequences; or any polynucleotide that encodes such a polypeptide. In an embodiment of the invention, the polypeptide binds to bezlotoxumab.

The present invention also includes methods for making a *C. difficile* toxin B Bx or E$_x$ polypeptide comprising introducing a polynucleotide encoding the polypeptide into a host cell and culturing the host cell under conditions favorable to expression of the polypeptide. See e.g., U.S. Pat. No. 4,816,567 (Cabilly et al.).

Polynucleotides encoding *C. difficile* toxin B Bx or E$_x$ polypeptides are, in an embodiment of the invention, introduced or transformed into an appropriate host cell by various techniques well known in the art, e.g., electroporation, protoplast fusion, calcium phosphate precipitation, cell fusion with enveloped DNA, microinjection, and infection with intact virus (see, e.g., Ridgway, 1973, Vectors: Mammalian Expression Vectors, Chapter 24.2, pp. 470-472, Rodriguez and Denhardt eds., Butterworths, Boston, Mass.; Graham et al., 1973, Virology 52:456; Sambrook et al., 1989, Molecular Cloning: A Laboratory Manual, Cold Spring Harbor Laboratories, New York; Davis et al., 1986, Basic Methods in Molecular Biology, Elsevier; and Chu et al., 1981, Gene 13:197).

Cells used in the present invention can be cultured according to standard cell culture techniques, e.g., they can be fixed to a solid surface or grown in suspension in appropriate nutrient media.

The present invention further provides a *C. difficile* toxin B Bx or E$_x$ polypeptide which is immobilized to a solid substrate, e.g., a bead or particle (e.g., glass, silica, plastic, sepharose or agarose).

The present invention further provides fusions of a *C. difficile* toxin B Bx or E$_x$ polypeptide of the present invention, e.g., to a heterologous protein such as a "tag" (e.g., glutathione-S-transferase, (histidine)$_6$, maltose binding protein, chitin binding protein, thioredoxin, green fluorescent protein, hemeagglutinin, myc, FLAG) or an immunoglobulin (IgG, e.g., IgG1, IgG2, IgG3, IgG4).

In an embodiment of the invention, a Bx and/or E$_x$ polypeptide excludes full length wild-type *C. difficile* toxin B, e.g., SEQ ID NO: 1.

Embodiments of the invention include but are not limited to:

1. An isolated polynucleotide encoding a polypeptide that comprises an amino acid sequence that is at least 80% identical or similar to an amino acid sequence that is selected from the group consisting of:
   *C. difficile* toxin B amino acids 1834-2367;
   *C. difficile* toxin B amino acids 1834-2101;
   *C. difficile* toxin B amino acids 1949-2275;
   *C. difficile* toxin B amino acids 2102-2367;
   *C. difficile* toxin B amino acids 1855-1971;
   *C. difficile* toxin B amino acids 1988-2103;
   *C. difficile* toxin B amino acids 2120-2237;
   *C. difficile* toxin B amino acids 2254-2366;
   SEQ ID NO:14;
   EDGFKYFAPANTL (SEQ ID NO: 3);
   ENGEM (SEQ ID NO: 4);
   EDGFKY (SEQ ID NO: 5); and
   ENGEMQIGVFNTEDGFKY (SEQ ID NO: 6).
2. The polynucleotide of embodiment 1 in a vector.
3. An isolated host cell comprising the polynucleotide or vector of any of embodiments 1-2.
4. An isolated polypeptide comprising an amino acid sequence that is at least 80% identical or similar to an amino acid sequence that is selected from the group consisting of:
   *C. difficile* toxin B amino acids 1834-2367;
   *C. difficile* toxin B amino acids 1834-2101;
   *C. difficile* toxin B amino acids 1949-2275;
   *C. difficile* toxin B amino acids 2102-2367;
   *C. difficile* toxin B amino acids 1855-1971;
   *C. difficile* toxin B amino acids 1988-2103;
   *C. difficile* toxin B amino acids 2120-2237;
   *C. difficile* toxin B amino acids 2254-2366;
   SEQ ID NO: 14;
   EDGFKYFAPANTL (SEQ ID NO: 3);
   ENGEM (SEQ ID NO: 4);
   EDGFKY (SEQ ID NO: 5); and
   ENGEMQIGVFNTEDGFKY (SEQ ID NO: 6).
5. The polypeptide of embodiment 4 comprising an amino acid sequence selected from the group consisting of SEQ ID NOs: 2-10 and 14.
6. A vaccine comprising the polypeptide of any of embodiments 4-5 and a pharmaceutically acceptable carrier.
7. A complex between the polypeptide of any of embodiments 4-5 and an antibody or antigen-binding fragment thereof which binds specifically to the polypeptide.
8. The complex of embodiment 7 wherein the antibody or fragment is an antibody which is bezlotoxumab.
9. The complex of any of embodiments 7-8 wherein the bezlotoxumab comprises a light chain that comprises the amino acid sequence set forth in SEQ ID NO: 11 and a heavy chain that comprises the amino acid sequence set forth in SEQ ID NO: 12; and/or the *C. difficile* toxin B amino acids 1834-2101 comprises the amino acid sequence set forth in SEQ ID NO: 2 which optionally further comprises the C-terminal amino acid sequence HHHHHH (SEQ ID NO: 13).
10. A method for immunizing an animal or for making an antibody or antigen-binding fragment thereof comprising administering a therapeutically effective amount of an isolated polypeptide comprising an amino acid sequence that is at least 80% identical or similar to an amino acid sequence that is selected from the group consisting of:

C. difficile toxin B amino acids 1834-2367;
C. difficile toxin B amino acids 1834-2101;
C. difficile toxin B amino acids 1949-2275;
C. difficile toxin B amino acids 2102-2367;
C. difficile toxin B amino acids 1855-1971;
C. difficile toxin B amino acids 1988-2103;
C. difficile toxin B amino acids 2120-2237;
C. difficile toxin B amino acids 2254-2366;
SEQ ID NO: 14;
EDGFKYFAPANTL (SEQ ID NO: 3);
ENGEM (SEQ ID NO: 4);
EDGFKY (SEQ ID NO: 5); and
ENGEMQIGVFNTEDGFKY (SEQ ID NO: 6);
or an amino acid sequence selected from the group consisting of SEQ ID NOs: 2-10 and 14; or a vaccine comprising any of said polypeptides and a pharmaceutically acceptable carrier to a host animal and, optionally:
(i) isolating the antibody or fragment from the host animal;
(ii) humanizing the antibody or fragment;
(iii) combining the antibody or fragment with a pharmaceutically acceptable carrier;
(iv) isolating a splenocyte from the host animal;
(v) fusing a splenocyte from the host animal with a myeloma cell; and/or
(vi) fusing the light chain immunoglobulin variable region and/or heavy chain immunoglobulin variable region of the antibody or fragment with a human immunoglobulin light chain constant domain and/or human immunoglobulin heavy chain constant domain, respectively.

Crystals and Crystallization

The present invention comprises crystalline or soluble, non-crystalline complexes between bezlotoxumab or an antigen-binding fragment thereof and C. difficile toxin B (e.g., Bx or $E_x$) as well as crystallizable compositions or solutions comprising such a complex.

For example, the present invention provides a method for producing crystals of the bezlotoxumab (or an antigen-binding fragment thereof, e.g., a Fab)-C. difficile toxin B (e.g., Bx or $E_x$) complex, comprising crystallizing aqueous buffered solution comprising about 20 mg/ml of the complex, 5 mM phosphate, pH 7.4, 68.5 mM sodium chloride, 1.35 mM potassium chloride buffer and 4.4% polyethylene glycol 4000 (Jena Bioscieneces JBS Single stock (CSS-253)). In an embodiment of the invention, the aqueous solution (e.g., a drop) is crystallized by sealing in a container in close proximity to 4.4% polyethylene glycol 4000 (e.g., 1 microliter aqueous solution and about 0.08 mL of the 4.4% polyethylene glycol 4000 solution). In an embodiment of the invention, the drop is incubated at about 4° C.

Crystallization of a bezlotoxumab (or an antigen-binding fragment thereof, e.g., a Fab)-C. difficile toxin B (e.g., SEQ ID NO: 2) complex may be accomplished by using known methods in the art (Giege, et al. (1994) Acta Crystallogr. D50: 339-350; McPherson, (1990) Eur. J. Biochem. 189: 1-23). Such techniques include hanging drop vapor diffusion, sitting drop vapor diffusion, microbatch and dialysis. In an embodiment of the invention, hanging-drop vapor diffusion (see e.g., McPherson, (1976) J. Biol. Chem. 251: 6300-6303) is used. Both hanging drop and sitting drop vapor diffusion entail a droplet containing purified protein, buffer, and precipitant being allowed to equilibrate with a larger reservoir containing similar buffers and precipitants in higher concentrations. Initially, the droplet of protein solution contains an insufficient concentration of precipitant for crystallization, but as water and other volatile organic components vaporize from the drop and transfers to the reservoir, the precipitant concentration increases to a level optimal for crystallization. This may occur prior to or after reaching equilibrium. Once the system is in equilibrium, these optimum conditions are maintained until the crystallization is complete. The hanging drop method differs from the sitting drop method in the vertical orientation of the protein solution drop within the system. In the microbatch method, protein is mixed with precipitants to achieve supersaturation, the vessel is sealed and set aside until crystals appear. In the dialysis method, protein is retained in a sealed dialysis membrane which is placed into a solution containing precipitant. Equilibration across the membrane increases the precipitant concentration thereby causing the protein to reach supersaturation levels.

The present invention also comprises methods for using the bezlotoxumab (or an antigen-binding fragment thereof, e.g., a Fab)-C. difficile toxin B (e.g., SEQ ID NO: 2) complex crystals of the present invention to make a crystalline complex with a compound comprising soaking, in a liquid medium, a crystalline composition comprising a C. difficile toxin B (e.g., SEQ ID NO: 2) polypeptide complexed with a first compound (e.g., bezlotoxumab or an antigen-binding fragment thereof, e.g., a Fab) with a second compound, e.g., at a molar excess of the second compound (e.g., 2 mM) relative to the bezlotoxumab or antigen-binding fragment thereof, such that a complex forms between C. difficile toxin B (e.g., SEQ ID NO: 2) and the second compound.

The crystals of the present invention have a wide range of uses. For example, high quality crystals are suitable for X-ray or neutron diffraction analysis to determine the three dimensional structure of bezlotoxumab (or an antigen-binding fragment thereof, e.g., a Fab)-C. difficile toxin B (e.g., SEQ ID NO: 2) complexes. Knowledge of these structures and solvent accessible residues allow structure-based design and construction of inhibitors and antagonists for C. difficile toxin B (e.g., SEQ ID NO: 2).

In addition, crystallization itself can be used as a purification method. In some instances, a polypeptide or protein crystallizes from a heterogeneous mixture into crystals. Isolation of such crystals by filtration and/or centrifugation, followed by redissolving the protein affords a purified solution suitable for use in growing high-quality crystals which are preferred for diffraction analysis.

Once a crystal of the present invention is grown, X-ray diffraction data can be collected. One method for determining a structure with X-ray diffraction data includes use of synchrotron radiation, under standard cryogenic condition; however, alternative methods may also be used. For example, crystals can be characterized by using X-rays produced by a conventional source, such as a sealed tube or a rotating anode. Methods of characterization include, but are not limited to, precession photography, oscillation photography and diffractometer data collection.

The crystallizable compositions provided by this invention are amenable to X-ray crystallography for providing the three-dimensional structure of a bezlotoxumab (or an antigen-binding fragment thereof, e.g., a Fab)-C. difficile toxin B (e.g., SEQ ID NO: 2) complex. The present invention includes crystals which effectively diffract X-rays for the determination of the atomic coordinates of bezlotoxumab (or an antigen-binding fragment thereof, e.g., a Fab)-C. difficile toxin B (e.g., SEQ ID NO: 2) complexes to a resolution of greater than about 5.0 Angstroms (e.g., about 4.5 Å, about 4.0 Å, about 3 Å, about 2.5 Å, about 2 Å, about 1 Å, about 0.5 Å), preferably greater than about 4.0 Angströms (e.g., about 3 Å, about 2.5 Å, about 2 Å, about 1 Å, about 0.5 Å), more preferably greater than about 2.8 Angströms (e.g., about 2.5 Å, about 2 Å, about 1 Å, about 0.5 Å) and most preferably greater than about 2.0 Angströms (e.g., about 1.5 Å, about 1.0 Å, about 0.5 Å).

The present invention includes bezlotoxumab (or an antigen-binding fragment thereof, e.g., a Fab)-*C. difficile* toxin B (e.g., SEQ ID NO: 2) soluble (non-crystalline) or crystalline complexes whose three-dimensional structure is described by the structure coordinates set forth in Table 1. The scope of the present invention also includes crystals which possess structural coordinates which are similar, but not identical, to those set forth in Table 1.

The term "structure coordinates" refers to Cartesian coordinates derived from mathematical equations related to the patterns obtained on diffraction of a beam of X-rays by the atoms (scattering centers) of a molecule. The diffraction data are used to calculate electron density maps and to establish the positions of the individual atoms of the molecule.

Those of skill in the art will understand that a set of structure coordinates, for a polypeptide or an polypeptide-complex or a portion thereof, is a relative set of points that define a shape in three dimensions.

The present invention includes crystals exhibiting structural coordinates which are similar to those set forth in Table 1 but for crystallographic permutations of the structure coordinates, fractionalization of the structure coordinates, additions, subtractions, rotations or translations to sets of the structure coordinates or any combinations of the above.

Alternatively, modifications in the crystal structure due to mutations, additions, substitutions, and/or deletions of amino acids, or other changes in any of the components that make up the crystal may also account for variations in structure coordinates. If such variations are within an acceptable standard error as compared to the coordinates of Table 1, the resulting three-dimensional shape is considered to be the same and, accordingly, the modified crystal is considered to be within the scope of the present invention.

Various computational analyses may be necessary to determine whether a crystal is sufficiently similar to the crystals whose structural coordinates are set forth in Table 1 as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. In general, the procedure used in Molecular Similarity to compare structures is, in general, divided into four steps: 1) input the structures to be compared; 2) define the atom equivalences in these structures; 3) perform a fitting operation; and 4) analyze the results.

Generally, each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) or alpha carbon atoms (Cα) only for all conserved residues between the two structures being compared.

When a rigid fitting method is used, the working structure is translated and rotated to obtain an optimum fit with the target structure. The fitting operation uses a least squares fitting algorithm that computes the optimum translation and rotation to be applied to the moving structure, such that the root mean square difference of the fit over the specified pairs of equivalent atom is an absolute minimum. This number, given in Angströms, is reported by QUANTA.

The term "root mean square deviation" (RMSD) is a commonly known term in the art which, in general, means the square root of the arithmetic mean of the squares of the deviations from the mean distance of corresponding atoms. It is a way to express the deviation or variation from a trend or object.

For the purpose of this invention, any set of structure coordinates of a molecule that has a RMSD of conserved residue backbone atoms (N, Cα, C, O) or alpha carbon atoms (Cα) only of less than about 1.5 Å when superimposed—using backbone atoms or alpha carbon atoms—on the relevant structure coordinates of Table 1 are considered identical and the crystals which they characterize are both within the scope of the present invention. In an embodiment of the invention, the root mean square deviation is less than about 1.0 Å, e.g., less than about 0.5 Å, e.g., less than about 0.1 Å.

The term "least squares" refers to a method based on the principle that the best estimate of a value is that in which the sum of the squares of the deviations of observed values is a minimum.

Antibodies and Immunization

Figure 2:
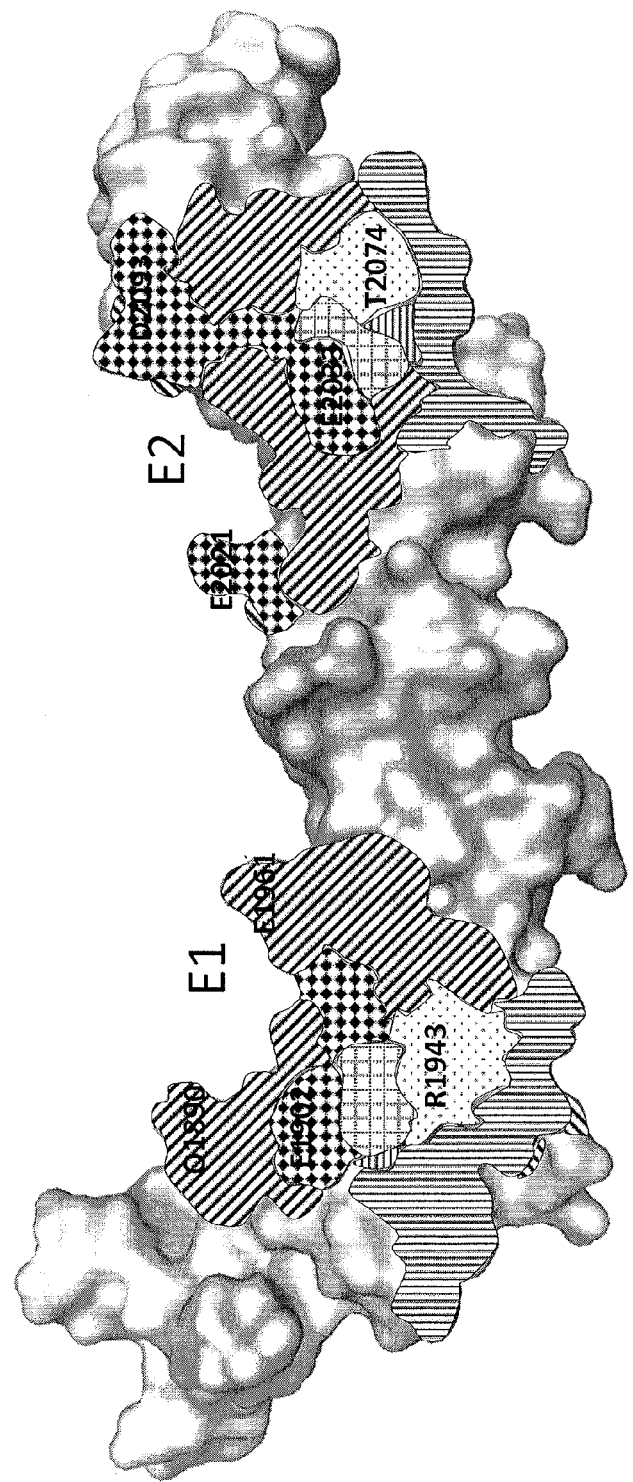
FIG. 2. Map of the regions within the B2 peptide shown to interact with bezlotoxumab by X-ray crystallography (diagonal lines from top left to bottom right) or by HDX-MS (diagonal lines from top right to bottom left), or putatively involved in carbohydrate binding (vertical lines). Overlapping regions are shown as diamonds (X-ray and HDX-MS), dots (X-ray and carbohydrate binding), horizontal lines (HDX-MS and carbohydrate binding) or squares (X-ray, HDX-MS and carbohydrate binding).

The present invention provides a method for making an antibody or antigen-binding fragment thereof that specifically binds to *C. difficile* toxin B (e.g., Bx or $E_x$) comprising immunizing a host animal with a therapeutically effective amount of immunogenic polypeptide which is a fragment of the *C. difficile* toxin B polypeptide (e.g., Bx or $E_x$); e.g., wherein the immunogenic polypeptide includes two carbohydrate binding residues of the toxin B CROP domain that are located in the E1 and E2 domains of said toxin B. For example, wherein the immunogenic polypeptide comprises the structure as depicted in FIG. 2.

*C. difficile* toxin B Bx or $E_x$ polypeptides are, in an embodiment of the invention, used to immunize a host animal (e.g., mammal, rabbit, mouse, rat, dromedary, camel or llama) for the purposes of generating an antibody or antigen-binding fragment thereof (e.g., humanized antibody, a monoclonal antibody, a labeled antibody, a bivalent antibody, a polyclonal antibody, a bispecific antibody, a chimeric antibody, a recombinant antibody, an anti-idiotypic antibody, a humanized antibody, a bispecific antibody, a camelized single domain antibody, a diabody, an scfv, an scfv dimer, a dsfv, a (dsfv)$_2$, a dsFv-dsfv', a bispecific ds diabody, an Fv, an Fab, an Fab', an F(ab')$_2$, or a domain antibody, e.g., which, in an embodiment of the invention, is linked to an immunoglobulin constant region, e.g., a kappa or lambda light chain, gamma-1 heavy chain, gamma-2 heavy chain, gamma-3 heavy chain or gamma-4 heavy chain) that specifically binds to the polypeptide. In an embodiment of the invention, a host animal is not a human.

The present invention also provides a method for immunizing a host animal with a *C. difficile* toxin B Bx or $E_x$ immunogenic polypeptide; or for producing an antibody or antigen-binding fragment thereof that binds specifically to a *C. difficile* toxin B Bx or $E_x$ polypeptide comprising: administering a therapeutically effective amount of a *C. difficile* toxin B Bx or $E_x$ immunogenic polypeptide to the host animal. In an embodiment of the invention, the *C. difficile* toxin B Bx or $E_x$ immunogenic polypeptide is in a vaccine. For example, in an embodiment of the invention, the *C. difficile* toxin B Bx or $E_x$ immunogenic polypeptide is prepared as an injectable composition (e.g., liquid solutions or suspensions) or as a solid form suitable for dissolution or suspension in a liquid vehicle prior to injection. The present invention includes methods wherein the compositions are administered parenterally, e.g., by injection (e.g., subcutaneously or intramuscularly), orally, (e.g., by inhalation), by suppository, or transdermally.

In an embodiment of the invention, a hybridoma is produced from an antibody-producing B-cell of the host animal. In an embodiment of the invention, the method comprises administering a therapeutically effective amount of a C. difficile toxin B Bx or $E_x$ polypeptide to a host animal, isolating an antibody-producing B-cell from the immunized host animal (e.g., by isolating splenocytes from the spleen of the animal) and fusing the B-cell with a myeloma cell (e.g., rat or mouse myeloma), thereby producing the hybridoma; and, optionally, isolating the antibody or antigen-binding fragment thereof from the hybridoma. In an embodiment of the invention, the hybridoma is cultured in a growth medium, such as HAT medium (i.e., medium containing hypoxanthine, aminopterin and thymidine). See e.g., Stites et al. (eds.) Basic and Clinical Immunology (4th ed.), Lange Medical Publications, Los Altos, Calif., and references cited therein; Harlow and Lane (1988) Antibodies: A Laboratory Manual, CSH Press; Goding (1986) Monoclonal Antibodies: Principles and Practice (2d ed.), Academic Press, New York; and Kohler and Milstein (1975) in Nature 256:495-497.

In an embodiment of the invention, a non-human antibody that binds specifically to a C. difficile toxin B polypeptide which is produced by a method as set forth herein (e.g., isolated from a non-human host animal that was immunized with the immunogenic polypeptide) is humanized. Typically, the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to affect binding affinity, such as one or more amino acids which are immediately adjacent to a CDR in the donor immunoglobulin or those within about 3 angstroms as predicted by molecular modeling. The heavy and light chains may each be designed by using any one or all of various position criteria. When combined into an intact antibody, the humanized immunoglobulins of the present invention will be substantially non-immunogenic in humans and retain substantially the same affinity as the donor immunoglobulin to the antigen, such as a protein or other compound containing an epitope.

Various methods for humanizing and modifying antibodies have been described in the art. In an embodiment of the invention, a method for making a humanized anti-C. difficile toxin B Bx or $E_x$ antibody or antigen-binding fragment thereof comprises humanizing the antibody or fragment, e.g., by any of the several methods known in the art. For example, U.S. Pat. No. 5,530,101 (Queen et al.) describes methods to produce humanized antibodies. See also, related methods in U.S. Pat. No. 5,693,761 (Queen et al); U.S. Pat. No. 5,693, 762 (Queen et al); U.S. Pat. No. 5,585,089 (Queen et al).

In one example, U.S. Pat. No. 5,565,332 (Hoogenboom et al.) describes methods for the production of antibodies, and antibody fragments which have similar binding specificity as a parent antibody but which have increased human characteristics. In an embodiment of the invention, anti-C. difficile toxin B polypeptide humanized antibodies are obtained by chain shuffling, using, for example, phage display technology, and a polypeptide comprising a heavy or light chain variable domain of a non-human antibody specific for an antigen of interest is combined with a repertoire of human complementary (light or heavy) chain variable domains. Hybrid pairings that are specific for the antigen of interest are identified and human chains from the selected pairings are combined with a repertoire of human complementary variable domains (heavy or light). In another embodiment of the invention, a component of a CDR from a non-human antibody is combined with a repertoire of component parts of CDRs from human antibodies. From the resulting library of antibody polypeptide dimers, hybrids are selected and used in a second humanizing shuffling step. Alternatively, this second step is eliminated if the hybrid is already of sufficient human character to be of therapeutic value. Methods of modification to increase human character are also described. See also Winter, FEBS Letts 430:92-92 (1998).

As another example, U.S. Pat. No. 6,054,297 (Carter et al.) describes a method for making humanized antibodies by substituting a CDR amino acid sequence for the corresponding human CDR amino acid sequence and/or substituting a FR amino acid sequence for the corresponding human FR amino acid sequences.

As another example, U.S. Pat. No. 5,766,886 (Studnicka et al.) describes methods for identifying the amino acid residues of an antibody variable domain which may be modified without diminishing the native affinity of the antigen binding domain while reducing its immunogenicity with respect to a heterologous species and methods for preparing these modified antibody variable domains which are useful for administration to heterologous species. See also U.S. Pat. No. 5,869,619 (Studnicka).

As discussed, modification of an antibody by any of the methods known in the art is typically designed to achieve increased binding affinity for an antigen and/or reduce immunogenicity of the antibody in the recipient. In one approach, humanized antibodies can be modified to eliminate glycosylation sites in order to increase affinity of the antibody for its cognate antigen (Co et al., Mol Immunol 30:1361-1367 (1993)). Techniques such as "reshaping," "hyperchimerization," and "veneering/resurfacing" have produced humanized antibodies with greater therapeutic potential. (Vaswami et al., Annals of Allergy, Asthma, & Immunol 81:105 (1998); Roguska et al., Prot Engineer 9:895-904 (1996)). See also U.S. Pat. No. 6,072,035 to Hardman et al., which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., J Immunol 62(6): 3663-71 (1999).

In many instances, humanizing antibodies results in a loss of antigen binding capacity. It is therefore preferable to "back mutate" the humanized antibody to include one or more of the amino acid residues found in the original (most often rodent) antibody in an attempt to restore binding affinity of the antibody. See, for example, Saldanha et al., Mol Immunol 36:709-19 (1999).

In an embodiment of the invention, a C. difficile toxin B Bx or $E_x$ polypeptide is used with an antibody phage display library to isolate an antibody or antigen-binding fragment thereof (e.g., ScFv, Fab or nanobody) that binds specifically to polypeptide. In an embodiment of the invention, the method comprises displaying a library of phage molecules (e.g., M13 or Fd) on the surfaces of host cells (e.g., bacterial cells such as E. coli), wherein each phage displays an antibody or antigen-binding fragment thereof on its surface, and selecting the host cells displaying phages having binding specificity for the *C. difficile* toxin B Bx or $E_x$ polypeptide; isolating the host cell and phage from the other host cells and phages and determining the sequence of the antibody or fragment immunoglobulin chains displayed on the phage surface (e.g., by isolating phage genomic DNA and determining the sequence of the portion of the phage genome encoding the antibody or fragment immunoglobulin chains), and, optionally, isolating the antibody or fragment from the phage and/or host cell. See e.g., *Methods in Molecular Biology, Antibody Phage Display Methods and Protocols*, Philippa M. O'Brien & Robert Aitken (eds.), Humana Press, Inc. Totowa, N.J. USA, 2002.

The present invention provides a vaccine or pharmaceutical composition comprising a *C. difficile* toxin B Bx or $E_x$ immunogenic polypeptide and a pharmaceutically acceptable carrier as well as methods of making and using such vaccines and pharmaceutical compositions. For example, the present invention provide a method for making a vaccine or pharmaceutical composition comprising combining a *C. difficile* toxin B Bx or $E_x$ immunogenic polypeptide with a pharmaceutically acceptable carrier and, optionally, other components that are appropriate for use in a vaccine or pharmaceutical composition (e.g., as discussed herein).

Pharmaceutically acceptable carriers which can be included in a pharmaceutical composition or vaccine of the present invention include, for example, large, slowly metabolized, macromolecules, such as proteins, polysaccharides such as latex functionalized sepharose, agarose, cellulose, cellulose beads and the like, polylactic acids, polyglycolic acids, polymeric amino acids such as polyglutamic acid, polylysine, and the like, amino acid copolymers, and inactive virus particles.

Pharmaceutically acceptable salts can be included in a pharmaceutical composition or vaccine of the present invention. For example, such salts can be mineral salts such as hydrochlorides, hydrobromides, phosphates, or sulfates, as well as salts of organic acids such as acetates, proprionates, malonates, or benzoates.

Proteins can be included in a pharmaceutical composition or vaccine of the present invention; e.g., serum albumins (e.g., human serum albumin), keyhole limpet hemocyanin, immunoglobulin molecules, thyroglobulin, ovalbumin, tetanus toxoid, and other proteins well known to those of skill in the art.

Liquids or excipients can be included in a pharmaceutical composition or vaccine of the present invention, e.g., water, saline, glycerol, dextrose, ethanol, as well as substances such as wetting agents, emulsifying agents, or pH buffering agents.

Liposomes which act as a carrier can be included in a pharmaceutical composition or vaccine of the present invention.

Co-stimulatory molecules which improve immunogen presentation to lymphocytes, such as B7-1 or B7-2, or cytokines such as GM-CSF, IL-2, and IL-12, can be included in a pharmaceutical composition or vaccine of the present invention. Optionally, adjuvants can also be included in a composition. Adjuvants which can be used include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides or bacterial cell wall components), such as for example (a) MF59 (U.S. Pat. No. 6,299,884, incorporated herein by reference in its entirety; Chapter 10 in Vaccine design: the subunit and adjuvant approach, eds. Powell & Newman, Plenum Press 1995), containing 5% squalene, 0.5% TWEEN 80, and 0.5% SPAN 85 (optionally containing various amounts of MTP-PE (see below), although not required) formulated into submicron particles using a microfluidizer such as Model 110Y microfluidizer (Microfluidics, Newton, Mass.), (b) SAF, containing 10% squalane, 0.4% TWEEN-80, 5% pluronic-blocked polymer L121, and thr-MDP either microfluidized into a submicron emulsion or vortexed to generate a larger particle size emulsion, and (c) RIBI adjuvant system (RAS), (Ribi Immunochem, Hamilton, Mont.) containing 2% squalene, 0.2% TWEEN-80, and one or more bacterial cell wall components from the group consisting of monophosphorylipid A (MPL), trehalose dimycolate (TDM), and cell wall skeleton (CWS), preferably MPL+CWS (DETOX); (3) saponin adjuvants, such as QS21 or STIMULON (Cambridge Bioscience, Worcester, Mass.) may be used or particles generated therefrom such as ISCOMs (immunostimulating complexes), which ISCOMs may be devoid of additional detergent, see, e.g., WO00/07621; (4) Complete Freund's Adjuvant (CFA) and Incomplete Freund's Adjuvant (IFA); (5) cytolines, such as interleukins (IL-1, IL-2, IL-4, IL-5, IL-6, IL-7, IL-12 (WO99/44636), etc.), interferons (e.g., gamma interferon), macrophage colony stimulating factor (M-CSF), tumor necrosis factor (TNF), etc.; (6) detoxified mutants of a bacterial ADP-ribosylating toxin such as a cholera toxin (CT), a pertussis toxin (PT), or an *E. coli* heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., WO93/13202 and WO92/19265); (7) MPL or 3-O-deacylated MPL (3dMPL) (see, e.g., GB 2220221), EP-A-0689454, optionally in the substantial absence of alum when used with pneumococcal saccharides (see, e.g., WO 00/56358); (8) combinations of 3dMPL with, for example, QS21 and/or oil-in-water emulsions (see, e.g., EP-A-0835318, EP-A-0735898, EP-A-0761231; (9) oligonucleotides comprising CpG motifs (see, e.g., Roman et al. (1997) Nat. Med. 3:849-854; Weiner et al. (1997)Proc. Natl. Acad. Sci. USA 94:10833-10837; Davis et al. (1998) J. Immunol. 160:870-876; Chu et al. (1997) J. Exp. Med. 186:1623-1631; Lipford et al. (1997) Eur. J. Immunol. 27:2340-2344; Moldoveanu et al. (1988) Vaccine 16:1216-1224; Krieg et al. (1995) Nature 374:546-549; Klinman et al. (1996) Proc. Natl. Acad. Sci. USA 93:2879-2883; Belles et al. (1996) J. Immunol. 157:1840-1845; Cowdery et al. (1996) J. Immunol. 156:4570-4575; Halpern et al. (1996) Cell Immunol. 167:72-78; Yamamoto et al. (1988) Jpn. J. Cancer Res. 79:866-873; Stacey et al. (1996) J. Immunol. 157:2116-2122; Messina et al. (1991) J. Immunol. 147:1759-1764; Yi et al. (1996) J. Immunol. 157:4918-4925; Yi et al. (1996) J. Immunol. 157:5394-5402; Yi et al. (1998) J. Immunol. 160:4755-4761; Yi et al. (1998) J. Immunol. 160:5898-5906; WO96/02555, WO98/16247, WO98/18810, WO98/40100, WO98/55495, WO98/37919 and WO 98/52581), such as those containing at least one CG dinucleotide, with cytosine optionally replaced with 5-methylcytosine; (10) a polyoxyethylene ether or a polyoxyethylene ester (see, e.g., WO99/52549); (11) a polyoxyethylene sorbitan ester surfactant in combination with an octoxynol (see, e.g., WO01/21207) or a polyoxyethylene alkyl ether or ester surfactant in combination with at least one additional non-ionic surfactant such as an octoxynol (see e.g., WO01/21152); (12) a saponin and an immunostimulatory oligonucleotide such as a CpG oligonucleotide (see, e.g., WO00/62800); (13) an immunostimulant and a particle of metal salt (see, e.g., WO00/23105); and (14) other substances that act as immunostimulating agents to enhance the effectiveness of the composition.

Muramyl peptides can be included in a pharmaceutical composition or vaccine of the present invention, e.g., N-acetyl-muramyl-L-threonyl-D-isoglutamine (thr-MDP), N-acteyl-normuramyl-L-alanyl-D-isogluatme (nor-MDP), -acetylmuramyl-L-alanyl-D-isogluatminyl-L-alanine-2-(1'-2'-dipahlitoyl-sn- -glycero-3-hydroxyphosphoryloxy)-ethylamine (MTP-PE), etc.

Other adjuvants can be included in a pharmaceutical composition or vaccine of the present invention, e.g., submicron oil-in-water emulsions, e.g., squalene/water emulsions. Submicron oil-in-water emulsions, methods of making the same and immunostimulating agents, such as muramyl peptides, for use in the compositions, are described in detail in WO90/14837 and U.S. Pat. Nos. 6,299,884 and 6,451,325, incorporated herein by reference in their entireties.

Other agents that can, in an embodiment of the invention, be included in a pharmaceutical composition or vaccine of the present invention include immunostimulatory molecules such as immunostimulatory nucleic acid sequences (ISS), including but not limited to, unmethylated CpG motifs, such as CpG oligonucleotides. Oligonucleotides containing unmethylated CpG motifs have been shown to induce activation of B cells, NK cells and antigen-presenting cells (APCs), such as monocytes and macrophages. See, e.g., U.S. Pat. No. 6,207,646. Moreover, the CpG oligonucleotides for use herein may be double- or single-stranded. Double-stranded molecules are more stable in vivo while single-stranded molecules display enhanced immune activity. Additionally, the phosphate backbone may be modified, such as phosphorodithioate-modified, in order to enhance the immunostimulatory activity of the CpG molecule. As described in U.S. Pat. No. 6,207,646, CpG molecules with phosphorothioate backbones preferentially activate B-cells, while those having phosphodiester backbones preferentially activate monocytic (macrophages, dendritic cells and monocytes) and NK cells. CpG molecules can readily be tested for their ability to stimulate an immune response using standard techniques, well known in the art. For example, the ability of the molecule to stimulate a humoral and/or cellular immune response is readily determined using the immunoassays described above. Moreover, the immunogenic compositions can be administered with and without the CpG molecule to determine whether an immune response is enhanced.

A C. difficile toxin B Bx or $E_x$ immunogenic polypeptide is, in an embodiment of the invention, encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; and McGee et al., J. Microencap. (1996). One preferred method for adsorbing macromolecules onto prepared microparticles is described in WO00/050006, incorporated herein by reference in its entirety.

Methods for immunizing a host animal or for making an antibody or antigen-binding fragment thereof that binds specifically to a C. difficile toxin B polypeptide include the step of administering a therapeutically effective amount of C. difficile toxin B Bx or $E_x$ immunogenic polypeptide to the host animal. By "therapeutically effective amount" is meant an amount of a C. difficile toxin B Bx or $E_x$ immunogenic polypeptide or DNA encoding the C. difficile toxin B Bx or $E_x$ polypeptide which will induce an immunological response in the individual to which it is administered, if the composition is to be used as a vaccine or in an immunization. Such a response will generally result in the development in the subject of an antibody-mediated and/or a secretory or cellular immune response to the composition. Such a response may include the production of antibodies from any of the immunological classes, such as immunoglobulins A, D, E, G or M; the proliferation of B and T lymphocytes; the provision of activation, growth and differentiation signals to immunological cells; expansion of helper T cell, suppressor T cell, and/or cytotoxic T cell and/or gamma delta T cell populations. In an embodiment of the invention, the therapeutically effective amount is about 0.1 micrograms to about 200 mg of the polypeptide. An "immunogenic" polypeptide is generally capable of inducing such a response in an individual to whom the polypeptide is administered.

EXAMPLES

The following information is provided for more clearly describing the present invention and should not be construed to limit the present invention. Any and all of the compositions and methods described below fall within the scope of the present invention.

Example 1

The Cloning, Expression and Purification of C. difficile Toxin B (TcdB$^{(1834-2101)}$)

The CROP domain fragments (B1 (1834-2367), B2 (1834-2101), B3 (1949-2275) and B4 (2102-2367)) from C. difficile were cloned into vector pET28a(+) (EMD Biosciences), which encodes a C-terminal His$_6$ tag. The nucleotide sequence was confirmed by DNA sequencing (Genewiz). Bx fragments including B2 (1834-2101) were expressed in E. coli BL21(DE3) (Novagen) in Terrific Broth supplemented with 50 µg ml$^{-1}$ kanamycin for 18 hours at 16° C. with 1 mM IPTG. The cells were harvested by centrifugation for 15 minutes at 6000×g, pellets were resuspended in 50 mM Tris pH 8.0, 0.3 M NaCl, 1 mM DTT, 1 mg ml$^{-1}$ protease inhibitor cocktail III (EMD Biosciences), and then lysed with a microfluidizer. Cell lysate was clarified by centrifugation at 100,000×g for 1 hour at 4° C. The supernatant was filtered and loaded onto a Ni$^{2+}$-IMAC (Qiagen) column equilibrated with 50 mM Tris pH 8.0, 0.3 M NaCl, 10% glycerol and 1 mM DTT. The protein was eluted using an imidazole gradient (0-0.25 M) containing 50 mM Tris pH 8.0, 0.3 M NaCl, 10% glycerol and 1 mM DTT. Fractions containing Bx proteins were pooled, diluted to 50 mM NaCl and further purified by ion exchange chromatography using a Source 15Q column (GE Healthcare). The final storage buffer for Bx proteins was 50 mM Hepes pH 7.5, 0.15 M NaCl. Fractions with >95% pure Bx (as monitored by SDS-PAGE electrophoresis) were collected and concentrated to 5 mg ml$^{-1}$ using a centrifugal concentrator. The molecular weight of Bx was confirmed by ESI-Ion-Trap-MS using a LTQ-XL mass spectrometer and the Xcalibur software platform (Thermo-Fisher Scientific).

The C. difficile toxin B (TcdB$^{(1834-2101)}$) comprises the amino acid sequence:

(SEQ ID NO: 2)
MGLIYINDSLYYFKPPVNNLITGFVTVGDDKYYFNPINGGAASIGETIID

DKNYYFNQSGVLQTGVFSTEDGFKYFAPANTLDENLEGEAIDFTGKLIID

ENIYYFDDNYRGAVEWKELDGEMHYFSPETGKAFKGLNQIGDYKYYFNSD

-continued

GVMQKGFVSINDNKHYFDDSGVMKVGYTEIDGKHFYFAENGEMQIGVFNT

EDGFKYFAHHNEDLGNEEGEEISYSGILNFNNKIYYFDDSFTAVVGWKDL

EDGSKYYFDEDTAEAYILEHHHHHH

Example 2

Preparation of Anti-TcdB Antibody Bezlotoxumab Fab

Fab from bezlotoxumab was generated using the Pierce Fab Preparation Kit (Catalog #44985) following the manufacturer's instructions. Briefly, prepared antibody was incubated with immobilized papain resin at 37° C. for 5 hours. Following the protease digestion, undigested IgG and Fc fragments were removed by running sample through a protein A column. The resulting Fab-containing flow-through was collected and further purified by size exclusion chromatography. N-terminal sequencing was used to confirm the Fab fragment identity.

The anti-TcdB antibody, bezlotoxumab, Fab chains comprise the following amino acid sequences:
Light chain:

(SEQ ID NO: 11)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSTWTFGQG

TKVEIKRTVAAPSVFIEPPSDEQLKSGTASVVCLLNNFYPREAKVQWKVDN

ALQSGNSQESVTEQDSKDSTYSLSSTLTLSKADYEKHKVYACEVTHQGLSS

PVTKSFNRG

Heavy chain:

(SEQ ID NO: 12)
EVQLVQSGAEVKKSGESLKISCKGSGYSFTSYWIGWVRQMPGKGLEWMGIF

YPGDSSTRYSPSFQGQVTISADKSVNTAYLQWSSLKASDTAMYYCARRRNW

GNAFDIWGQGTMVTVSSASTKGPSVFPLAPSSTAALGCLVKDYFPEPVTVS

WNSGALTSGVHTFPAVLQSSGLYSLSSVVTVPSSSLGTQTYICNVNHKPSN

TKVDKRVEPKS

Example 3

Complex Between Anti-TcdB Antibody Bezlotoxumab Fab and *C. difficile* Toxin B (TcdB$^{(1834-2101)}$) and Preparation for Crystallization Purified B2 and Fab fragments were mixed in 1:3 molar ratios and excess Fab was separated by size exclusion chromatography (S200 26/60 column from GE Healthcare). The complex was concentrated to >15 mgs/mL for crystallization trials.

Direct binding with Bx and bezlotoxumab
(a) Temperature-Dependent Fluorescence (TdF)
166 µM Bx in 25 mM HEPES pH 7.5, 0.15 M NaCl was thawed on ice, centrifuged for 5 minutes to remove insoluble material, and diluted 100-fold. Sypro orange (Invitrogen) was prepared with 100% DMSO. To the 1 µM protein solution, Sypro orange was added to a final concentration of 5×. For the TdF experiments with the complex, bezlotoxumab was added at 1:1 stoichiometric amount to 1 µM B2 protein. 10 µl of 'apo' B2 and B2-bezlotoxumab samples were pipetted into a white 384-well PCR plate (Abgene) and sealed with flat ultra clear caps (BioRad).

A TdF assay was conducted with a Roche-PCR instrument (Roche) equipped with a CCD camera for fluorescence detection. The temperature was increased from 20° C. to 80° C. in 0.2° C. increments using a 200 millisecond stabilization delay before reading.

Fluorescence signals were acquired with excitation and emission wavelengths of 490 nm and 560 nm, respectively. A customized analysis program using a non-linear least square method based on the Generalized Reduced Gradient algorithm was used to fit the protein unfolding model (reference). The fluorescence intensity of Sypro Orange dye is generally linearly dependent with temperature. The following parameters were floated during the fitting process: Y intercepts for the intensity of Sypro Orange in both the native and denatured proteins ($Y_n$ and $Y_d$); the associated slopes ($M_n$ and $M_d$); the midpoint of melting ($T_m$); and the enthalpy at the $T_m$ ($\Delta H_m$).

(b) Kinetics of Binding of Toxins Fragments to Bezlotoxumab

The binding of toxin fragments to the antibodies was studied by surface plasmon resonance using BioRad's ProteOn instrument. Surface plasmon resonance is an optical phenomenon that is used in the ProteOn system to monitor binding of two unlabeled molecules in real time. The SPR signal is based on changes in the refractive index at the surface of a gold sensor chip as an analyte flows in a microfluidic channel and binds to a ligand immobilized on the sensor chip. Monitoring the changes in the SPR signal over time produced a sensogram, a plot of the binding response versus time.

For these experiments, the antibody molecules were immobilized to the sensor chip surface as manufacturer recommendations. ProteOn GLC Sensor chip was docked to the system, and after standard cleaning, a mixture of 1×EDC+sNHS was injected over the chip to activate the chip surface. A 5 ug/mL solution of antibody in ProteOn immobilization buffer was injected for 1 min. 1M Ethanolamine HCl was injected for 5 mins to 'cap' any unoccupied reactive sites on the chip surface. Once the immobilization is confirmed, the interaction of the toxins to antibody was measured as a change in the refractive index over time. The ProteOn's 6×6 array allowed for multiple simultaneous injections of different toxin concentrations to obtain a full kinetic profile and equilibrium binding. Toxins fragments were diluted to 100 nM in ProteOn Running Buffer and then serially diluted five times 2-fold for a concentration-range experiment. Following dilution, the toxin molecules were injected in horizontal orientation for 2 minutes (flow rate 25 ul/min) and dissociation was monitored for 1 hour post-injection. Buffer was injected onto channel A6 for use as a reference. The data analyses was carried out using the ProteOn instrument software, with ligand injections corrected using referencing to the Interspot and channel A6. Data was fit using standard equilibrium fitting to determine Kd with steady-state assumptions. For individual toxin fragment-antibody interactions, distinct immobilization experiments were performed.

Results

Selection of Toxin 82 Fragment for Complex Formation Studies

*C. difficile* toxin B CROP domain fragments were overexpressed in *E. coli* as described herein. The toxin B proteins were confirmed to be >95% pure as shown by SDS-PAGE and the identity of the constructs were confirmed by matrix-assisted laser desorption/ionization-time-of-flight mass spectrometry and sequencing. Direct binding experiments using thermal-shift assay and SPR confirmed the bezlotoxumab epitope to be retained within the B2 (1834-2101) region of the toxin B CROP domain. Interestingly, no binding was observed in the region C-terminal to B2, B4 (amino acids 2102-2367). The dissociation constant (Kd=25 nM) for B2 (1834-2101) fragment and bezlotoxumab interaction was representative of the full-length toxin B and bezlotoxumab interaction (Kd=12 nM). B2-bezlotoxumab Fab complex formation was performed at 50% excess of Fab followed by separation of excess Fab from the complex by gel-filtration. The B2-bezlotoxumab Fab complex was concentrated to >15 mgs/mL and confirmed to be monodispersed by dynamic light scattering. Purity was greater than 95% as determined by SDS-PAGE and sequence analysis.

Example 4

Crystallization of Anti-TcdB Antibody Bezlotoxumab Fab-*C. difficile* Toxin B (TcdB$^{(1834-2101)}$) Complex The anti-TcdB antibody bezlotoxumab Fab-*C. difficile* Toxin B (TcdB$^{(1834-2101)}$) complex as described above was crystallized using a sitting-drop vapor diffusion method setup using a Oryx crystallization-robot (Douglas Instruments, LTD) in a MRC-2 (Innovvadyne SD-2) crystallization plate. The anti-TcdB antibody bezlotoxumab Fab-*C. difficile* toxin B (TcdB$^{(1834-2101)}$) complex (0.5 µl; 20 mg/ml) in 10 mM phosphate, pH 7.4, 137 mM sodium chloride, 2.7 mM potassium chloride buffer was mixed with an equal volume of precipitant solution containing 4.4% PEG 4000 (Jena Bioscieneces JBS Single stock (CSS-253)) and sealed in close proximity to 0.08 mL of the precipitant solution. Crystallization plates were incubated at 4° C. and crystals (0.025×0.015 mm) grew over a period of 5-60 days.

Example 5

Figure 4:
FIG. 4. Photomicrograph of anti-TcdB antibody bezlotoxumab Fab-*C. difficile* Toxin B (TcdB$^{(1834-2101)}$) complex. Crystal characteristics: 20 mg/ml; 4.4% PEG 4000; 1 month @ 4° C.; 300× magnification.

Photomicrograph of Anti-TcdB Antibody Bezlotoxumab Fab-*C. difficile* Toxin B (TcdB$^{(1834-2101)}$) Complex An image of the crystal is set forth in FIG. 4.

Example 6

X-Ray Crystallographic Characterization Anti-TcdB Antibody Bezlotoxumab Fab-*C. Difficile* Toxin B (TcdB$^{(1834-2101)}$) Complex Prior to data collection, crystals were harvested at 4° C. and transferred into the reservoir solution with 20% ethyleneglycol added. After a 20 second exposure to this cryoprotectant, the crystals were fished using a cryo-loop and frozen in liquid nitrogen. The frozen crystals were then mounted onto the goniometer at the IMCA-CAT beamline 171D at the Argonne National Laboratory equipped with a nitrogen cooled stream.

X-ray diffraction was collected using a PILATUS 6M detector. Data were integrated and scaled using the XDS as part of the Global Phasing package. The crystal and its analysis are characterized below.

| Space Group | P21 | | | | |
|---|---|---|---|---|---|
| Unit cell | a = 79.413 | b = 134.659 | c = 102.579 | α = γ = 90° | β = 112.559° |
| Low resolution limit | 47.365 | 47.365 | 2.900 | | |
| High resolution limit | 2.890 | 13.316 | 2.890 | | |
| Rmerge | 0.056 | 0.020 | 0.547 | | |
| Ranom | 0.048 | 0.017 | 0.481 | | |
| Rmeas (within (I+/I-) | 0.068 | 0.023 | 0.669 | | |
| Rmeas (all I+ & I-) | 0.066 | 0.024 | 0.645 | | |
| Rpim (within I+/I-) | 0.047 | 0.016 | 0.464 | | |
| Rpim (all I+ & I-) | 0.036 | 0.014 | 0.340 | | |
| Total number of observations | 150967 | 1548 | 1563 | | |
| Total number unique | 44417 | 457 | 455 | | |
| Mean(I)/sd(I) | 17.3 | 47.3 | 2.1 | | |
| Completeness | 99.5 | 97.4 | 100.0 | | |
| Multiplicity | 3.4 | 3.4 | 3.4 | | |

Example 7

Figure 3:
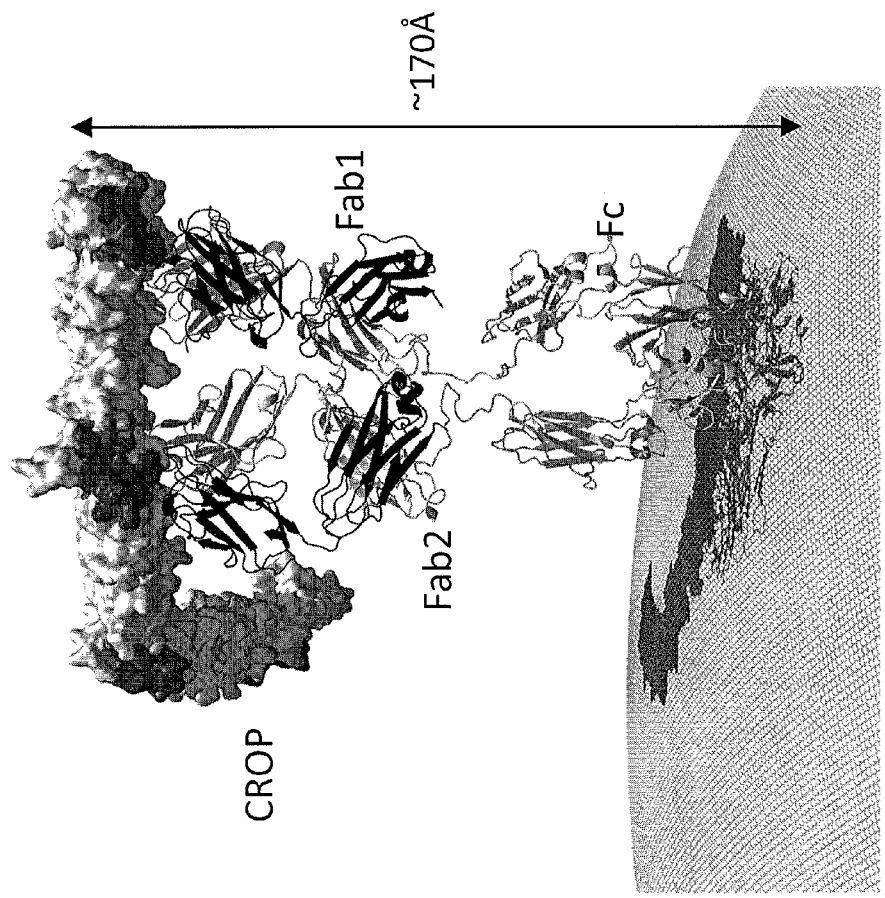
FIG. 3. Model of the TcdB CROP domain bound to a full-length molecule of bezlotoxumab. The C-terminal (left) half of the CROP domain was modeled based on the structure of the B2 peptide and the Fc region of bezlotoxumab is based on published high-resolution structures of human IgG1. The four putative carbohydrate binding regions are shown in dark grey. Heavy chains of bezlotoxumab are colored light grey, light chains are colored black.

Structure Determination of Anti-TcdB Antibody Beziotoxumab Fab-*C. difficile* Toxin B (TcdB$^{(1834-2101)}$) Complex The crystal structure was solved using molecular replacement package MOLREP using the PDB entry 1HZH as the search model for the FAB as well as a manually build toxin B model based on the PDB entry 2G7C. Refinement was done using the program autoBUSTER as part of the Global Phasing package. A pictoral representation of the complex is set forth in FIGS. 1-3.

| Resolution Limits | 42.31-2Å |
|---|---|
| Number of observed reflections | 44385 (99.37%) |
| Number of reflections in test set | 931 (2.1%) |
| Number of protein residues | 1126 |
| Number of solvent atoms | None |
| R-factor | 0.2055 |
| R-free | 0.2404 |
| RMSD bond length | 0.010 Å |
| RMSD bond angles | 1.35° |

TABLE 1

Three-dimensional crystal coordinate for anti-TcdB antibody beziotoxumab Fab –*C. difficile* toxin B (TcdB$^{(1834\text{-}2101)}$) complex.

| | | | | | | | | | | | |
|---|---|---|---|---|---|---|---|---|---|---|---|
| CISPEP | 1 | GLU | A | 2083 | ASP | A | 2084 | 0 | 5.88 | | |
| CISPEP | 2 | SER | A | 75 | VAL | H | 76 | 0 | 10.99 | | |
| CISPEP | 3 | TRP | H | 102 | GLY | H | 103 | 0 | −4.24 | | |
| CISPEP | 4 | PHE | H | 152 | PRO | H | 153 | 0 | −6.82 | | |
| CISPEP | 5 | GLU | H | 154 | PRO | H | 155 | 0 | 8.85 | | |
| CISPEP | 6 | VAL | I | 76 | ASN | I | 77 | 0 | −5.33 | | |
| CISPEP | 7 | TRP | I | 102 | GLY | I | 103 | 0 | −4.56 | | |
| CISPEP | 8 | PHE | I | 152 | PRO | I | 153 | 0 | −5.39 | | |
| CISPEP | 9 | GLU | I | 154 | PRO | I | 155 | 0 | 8.45 | | |
| CISPEP | 10 | ASN | I | 161 | SER | I | 162 | 0 | −10.18 | | |
| CISPEP | 11 | SER | L | 7 | PRO | L | 8 | 0 | −7.19 | | |
| CISPEP | 12 | TYR | L | 92 | GLY | L | 93 | 0 | −5.59 | | |
| CISPEP | 13 | SER | L | 95 | THR | L | 96 | 0 | −28.90 | | |
| CISPEP | 14 | TYR | L | 141 | PRO | L | 142 | 0 | −3.90 | | |
| CISPEP | 15 | SER | M | 7 | PRO | M | 8 | 0 | 9.05 | | |
| CISPEP | 16 | TYR | M | 141 | PRO | M | 142 | 0 | −2.24 | | |
| SSBOND | 1 | CYS | H | 22 | CYS | H | 96 | | | 1555 1555 | 2.03 |
| SSBOND | 2 | CYS | H | 146 | CYS | H | 202 | | | 1555 1555 | 2.03 |
| SSBOND | 3 | CYS | I | 22 | CYS | I | 96 | | | 1555 1555 | 2.03 |
| SSBOND | 4 | CYS | I | 146 | CYS | I | 202 | | | 1555 1555 | 2.03 |
| SSBOND | 5 | CYS | L | 23 | CYS | L | 89 | | | 1555 1555 | 2.09 |
| SSBOND | 6 | CYS | L | 135 | CYS | L | 195 | | | 1555 1555 | 2.05 |
| SSBOND | 7 | CYS | M | 23 | CYS | M | 89 | | | 1555 1555 | 2.06 |
| SSBOND | 8 | CYS | M | 135 | CYS | M | 195 | | | 1555 1555 | 2.04 |
| CRYST1 | 79.413 | 134.659 | 102.579 | 90.00 | 112.56 | 90.00 P 1 21 1 | | | | | |
| ATOM | 1 | N | GLY | A1834 | −8.663 | −68.265 | 21.493 | 1.00 | 71.52 | N | |
| ATOM | 2 | CA | GLY | A1834 | −7.890 | −67.334 | 20.687 | 1.00 | 71.59 | C | |
| ATOM | 3 | C | GLY | A1834 | −7.753 | −65.946 | 21.273 | 1.00 | 75.58 | C | |
| ATOM | 4 | O | GLY | A1834 | −8.122 | −65.723 | 22.430 | 1.00 | 75.39 | O | |
| ATOM | 5 | N | LEU | A1835 | −7.217 | −64.995 | 20.476 | 1.00 | 72.14 | N | |
| ATOM | 6 | CA | LEU | A1835 | −7.009 | −63.628 | 20.962 | 1.00 | 71.92 | C | |
| ATOM | 7 | C | LEU | A1835 | −8.319 | −62.810 | 20.958 | 1.00 | 73.85 | C | |
| ATOM | 8 | O | LEU | A1835 | −9.008 | −62.745 | 19.953 | 1.00 | 72.10 | O | |
| ATOM | 9 | CB | LEU | A1835 | −5.816 | −62.901 | 20.276 | 1.00 | 71.99 | C | |
| ATOM | 10 | CG | LEU | A1835 | −5.878 | −62.422 | 18.839 | 1.00 | 76.89 | C | |
| ATOM | 11 | CD1 | LEU | A1835 | −4.532 | −62.004 | 18.407 | 1.00 | 76.64 | C | |
| ATOM | 12 | CD2 | LEU | A1835 | −6.332 | −63.515 | 17.877 | 1.00 | 81.95 | C | |
| ATOM | 13 | N | ILE | A1836 | −8.680 | −62.273 | 22.144 | 1.00 | 71.06 | N | |
| ATOM | 14 | CA | ILE | A1836 | −9.912 | −61.524 | 22.456 | 1.00 | 71.53 | C | |
| ATOM | 15 | C | ILE | A1836 | −9.593 | −60.140 | 23.032 | 1.00 | 77.30 | C | |
| ATOM | 16 | O | ILE | A1836 | −8.656 | −60.012 | 23.821 | 1.00 | 77.60 | O | |
| ATOM | 17 | CB | ILE | A1836 | −10.781 | −62.315 | 23.497 | 1.00 | 74.59 | C | |
| ATOM | 18 | CG1 | ILE | A1836 | −10.917 | −63.816 | 23.149 | 1.00 | 75.42 | C | |
| ATOM | 19 | CG2 | ILE | A1836 | −12.152 | −61.674 | 23.718 | 1.00 | 74.56 | C | |
| ATOM | 20 | CD1 | ILE | A1836 | −10.742 | −64.761 | 24.329 | 1.00 | 79.98 | C | |
| ATOM | 21 | N | TYR | A1837 | −10.451 | −59.143 | 22.731 | 1.00 | 74.41 | N | |
| ATOM | 22 | CA | TYR | A1837 | −10.353 | −57.777 | 23.233 | 1.00 | 74.39 | C | |
| ATOM | 23 | C | TYR | A1837 | −11.206 | −57.501 | 24.472 | 1.00 | 80.35 | C | |
| ATOM | 24 | O | TYR | A1837 | −12.421 | −57.377 | 24.354 | 1.00 | 79.52 | O | |
| ATOM | 25 | CB | TYR | A1837 | −10.749 | −56.800 | 22.135 | 1.00 | 75.37 | C | |
| ATOM | 26 | CG | TYR | A1837 | −9.577 | −56.306 | 21.328 | 1.00 | 77.69 | C | |
| ATOM | 27 | CD1 | TYR | A1837 | −8.759 | −55.281 | 21.805 | 1.00 | 80.05 | C | |
| ATOM | 28 | CD2 | TYR | A1837 | −9.299 | −56.835 | 20.072 | 1.00 | 78.10 | C | |
| ATOM | 29 | CE1 | TYR | A1837 | −7.681 | −54.811 | 21.059 | 1.00 | 81.52 | C | |
| ATOM | 30 | CE2 | TYR | A1837 | −8.218 | −56.380 | 19.319 | 1.00 | 79.02 | C | |
| ATOM | 31 | CZ | TYR | A1837 | −7.408 | −55.372 | 19.819 | 1.00 | 88.34 | C | |
| ATOM | 32 | OH | TYR | A1837 | −6.342 | −54.919 | 19.081 | 1.00 | 90.72 | O | |
| ATOM | 33 | N | ILE | A1838 | −10.577 | −57.362 | 25.655 | 1.00 | 79.82 | N | |
| ATOM | 34 | CA | ILE | A1838 | −11.298 | −56.987 | 26.890 | 1.00 | 80.48 | C | |
| ATOM | 35 | C | ILE | A1838 | −10.876 | −55.557 | 27.249 | 1.00 | 86.46 | C | |
| ATOM | 36 | O | ILE | A1838 | −9.738 | −55.339 | 27.675 | 1.00 | 86.14 | O | |
| ATOM | 37 | CB | ILE | A1838 | −11.146 | −57.930 | 28.141 | 1.00 | 83.26 | C | |
| ATOM | 38 | CG1 | ILE | A1838 | −10.946 | −59.440 | 27.794 | 1.00 | 83.92 | C | |
| ATOM | 39 | CG2 | ILE | A1838 | −12.296 | −57.741 | 29.132 | 1.00 | 82.79 | C | |
| ATOM | 40 | CD1 | ILE | A1838 | −12.025 | −60.155 | 27.042 | 1.00 | 93.93 | C | |
| ATOM | 41 | N | ASN | A1839 | −11.798 | −54.597 | 27.067 | 1.00 | 84.06 | N | |
| ATOM | 42 | CA | ASN | A1839 | −11.639 | −53.190 | 27.407 | 1.00 | 84.25 | C | |

TABLE1-continued

Three-dimensional crystal coordinate for anti-TcdB antibody beziotoxumab Fab –*C. difficile* toxin B (TcdB$^{(1834-2101)}$) complex.

| ATOM | 43 | C | ASN | A1839 | −10.470 | −52.500 | 26.701 | 1.00 | 88.67 | C |
|------|-----|------|-----|-------|---------|---------|--------|------|--------|---|
| ATOM | 44 | O | ASN | A1839 | −9.507 | −52.077 | 27.365 | 1.00 | 89.38 | O |
| ATOM | 45 | CB | ASN | A1839 | −11.556 | −52.998 | 28.940 | 1.00 | 86.89 | C |
| ATOM | 46 | CG | ASN | A1839 | −12.743 | −52.279 | 29.527 | 1.00 | 122.69 | C |
| ATOM | 47 | ND2 | ASN | A1839 | −12.805 | −50.956 | 29.340 | 1.00 | 115.96 | N |
| ATOM | 48 | OD1 | ASN | A1839 | −13.613 | −52.893 | 30.155 | 1.00 | 119.16 | O |
| ATOM | 49 | N | ASP | A1840 | −10.562 | −52.362 | 25.352 | 1.00 | 83.79 | N |
| ATOM | 50 | CA | ASP | A1840 | −9.580 | −51.647 | 24.503 | 1.00 | 82.70 | C |
| ATOM | 51 | C | ASP | A1840 | −8.159 | −52.258 | 24.499 | 1.00 | 81.64 | C |
| ATOM | 52 | O | ASP | A1840 | −7.329 | −51.871 | 23.670 | 1.00 | 81.83 | O |
| ATOM | 53 | CB | ASP | A1840 | −9.515 | −50.140 | 24.869 | 1.00 | 85.53 | C |
| ATOM | 54 | CG | ASP | A1840 | −10.856 | −49.478 | 25.189 | 1.00 | 103.13 | C |
| ATOM | 55 | OD1 | ASP | A1840 | −11.661 | −49.273 | 24.246 | 1.00 | 105.05 | O |
| ATOM | 56 | OD2 | ASP | A1840 | −11.091 | −49.151 | 26.381 | 1.00 | 108.87 | O |
| ATOM | 57 | N | SER | A1841 | −7.901 | −53.209 | 25.423 | 1.00 | 73.02 | N |
| ATOM | 58 | CA | SER | A1841 | −6.675 | −53.973 | 25.654 | 1.00 | 69.92 | C |
| ATOM | 59 | C | SER | A1841 | −6.860 | −55.435 | 25.110 | 1.00 | 70.40 | C |
| ATOM | 60 | O | SER | A1841 | −7.950 | −56.008 | 25.239 | 1.00 | 71.35 | O |
| ATOM | 61 | CB | SER | A1841 | −6.370 | −53.960 | 27.148 | 1.00 | 70.40 | C |
| ATOM | 62 | OG | SER | A1841 | −5.463 | −54.978 | 27.524 | 1.00 | 76.29 | O |
| ATOM | 63 | N | LEU | A1842 | −5.805 | −56.027 | 24.515 | 1.00 | 61.96 | N |
| ATOM | 64 | CA | LEU | A1842 | −5.867 | −57.356 | 23.891 | 1.00 | 59.80 | C |
| ATOM | 65 | C | LEU | A1842 | −5.308 | −58.523 | 24.756 | 1.00 | 62.98 | C |
| ATOM | 66 | O | LEU | A1842 | −4.245 | −58.411 | 25.372 | 1.00 | 62.17 | O |
| ATOM | 67 | CB | LEU | A1842 | −5.170 | −57.281 | 22.530 | 1.00 | 59.12 | C |
| ATOM | 68 | CG | LEU | A1842 | −5.031 | −58.541 | 21.719 | 1.00 | 62.71 | C |
| ATOM | 69 | CD1 | LEU | A1842 | −6.296 | −58.873 | 21.002 | 1.00 | 62.29 | C |
| ATOM | 70 | CD2 | LEU | A1842 | −3.946 | −58.377 | 20.724 | 1.00 | 65.67 | C |
| ATOM | 71 | N | TYR | A1843 | −6.037 | −59.661 | 24.764 | 1.00 | 58.59 | N |
| ATOM | 72 | CA | TYR | A1843 | −5.719 | −60.839 | 25.573 | 1.00 | 57.40 | C |
| ATOM | 73 | C | TYR | A1843 | −5.747 | −62.129 | 24.754 | 1.00 | 61.57 | C |
| ATOM | 74 | O | TYR | A1843 | −6.229 | −62.110 | 23.635 | 1.00 | 59.90 | O |
| ATOM | 75 | CB | TYR | A1843 | −6.706 | −60.932 | 26.748 | 1.00 | 57.07 | C |
| ATOM | 76 | CG | TYR | A1843 | −6.666 | −59.756 | 27.701 | 1.00 | 58.91 | C |
| ATOM | 77 | CD1 | TYR | A1843 | −7.421 | −58.609 | 27.462 | 1.00 | 60.82 | C |
| ATOM | 78 | CD2 | TYR | A1843 | −5.935 | −59.817 | 28.880 | 1.00 | 60.17 | C |
| ATOM | 79 | CE1 | TYR | A1843 | −7.420 | −57.538 | 28.358 | 1.00 | 61.23 | C |
| ATOM | 80 | CE2 | TYR | A1843 | −5.936 | −58.757 | 29.792 | 1.00 | 61.32 | C |
| ATOM | 81 | CZ | TYR | A1843 | −6.682 | −57.620 | 29.528 | 1.00 | 69.70 | C |
| ATOM | 82 | OH | TYR | A1843 | −6.666 | −56.579 | 30.430 | 1.00 | 72.08 | O |
| ATOM | 83 | N | TYR | A1844 | −5.255 | −63.252 | 25.318 | 1.00 | 59.99 | N |
| ATOM | 84 | CA | TYR | A1844 | −5.271 | −64.558 | 24.648 | 1.00 | 60.51 | C |
| ATOM | 85 | C | TYR | A1844 | −5.772 | −65.643 | 25.594 | 1.00 | 67.14 | C |
| ATOM | 86 | O | TYR | A1844 | −5.310 | −65.713 | 26.736 | 1.00 | 68.13 | O |
| ATOM | 87 | CB | TYR | A1844 | −3.880 | −64.921 | 24.099 | 1.00 | 61.04 | C |
| ATOM | 88 | CG | TYR | A1844 | −3.878 | −66.085 | 23.136 | 1.00 | 62.55 | C |
| ATOM | 89 | CD1 | TYR | A1844 | −4.183 | −65.904 | 21.790 | 1.00 | 64.94 | C |
| ATOM | 90 | CD2 | TYR | A1844 | −3.559 | −67.365 | 23.564 | 1.00 | 63.53 | C |
| ATOM | 91 | CE1 | TYR | A1844 | −4.208 | −66.981 | 20.902 | 1.00 | 66.23 | C |
| ATOM | 92 | CE2 | TYR | A1844 | −3.585 | −68.452 | 22.688 | 1.00 | 64.49 | C |
| ATOM | 93 | CZ | TYR | A1844 | −3.906 | −68.256 | 21.356 | 1.00 | 71.49 | C |
| ATOM | 94 | OH | TYR | A1844 | −3.915 | −69.331 | 20.496 | 1.00 | 71.96 | O |
| ATOM | 95 | N | PHE | A1845 | −6.713 | −66.489 | 25.120 | 1.00 | 64.37 | N |
| ATOM | 96 | CA | PHE | A1845 | −7.290 | −67.587 | 25.912 | 1.00 | 64.42 | C |
| ATOM | 97 | C | PHE | A1845 | −7.306 | −68.893 | 25.156 | 1.00 | 71.28 | C |
| ATOM | 98 | O | PHE | A1845 | −7.541 | −68.895 | 23.949 | 1.00 | 69.30 | O |
| ATOM | 99 | CB | PHE | A1845 | −8.713 | −67.265 | 26.381 | 1.00 | 65.17 | C |
| ATOM | 100 | CG | PHE | A1845 | −8.836 | −66.312 | 27.544 | 1.00 | 65.15 | C |
| ATOM | 101 | CD1 | PHE | A1845 | −8.897 | −64.936 | 27.334 | 1.00 | 66.34 | C |
| ATOM | 102 | CD2 | PHE | A1845 | −8.965 | −66.788 | 28.841 | 1.00 | 65.75 | C |
| ATOM | 103 | CE1 | PHE | A1845 | −9.064 | −64.054 | 28.403 | 1.00 | 66.30 | C |
| ATOM | 104 | CE2 | PHE | A1845 | −9.135 | −65.902 | 29.910 | 1.00 | 68.03 | C |
| ATOM | 105 | CZ | PHE | A1845 | −9.185 | −64.540 | 29.681 | 1.00 | 65.33 | C |
| ATOM | 106 | N | LYS | A1846 | −7.092 | −70.009 | 25.883 | 1.00 | 72.31 | N |
| ATOM | 107 | CA | LYS | A1846 | −7.094 | −71.349 | 25.305 | 1.00 | 74.59 | C |
| ATOM | 108 | C | LYS | A1846 | −8.277 | −72.231 | 25.843 | 1.00 | 82.22 | C |
| ATOM | 109 | O | LYS | A1846 | −8.858 | −71.933 | 26.906 | 1.00 | 79.73 | O |
| ATOM | 110 | CB | LYS | A1846 | −5.716 | −72.033 | 25.439 | 1.00 | 78.13 | C |
| ATOM | 111 | CG | LYS | A1846 | −4.827 | −71.861 | 24.197 | 1.00 | 90.10 | C |
| ATOM | 112 | CD | LYS | A1846 | −3.338 | −72.215 | 24.442 | 1.00 | 94.27 | C |
| ATOM | 113 | CE | LYS | A1846 | −2.981 | −73.680 | 24.316 | 1.00 | 95.69 | C |
| ATOM | 114 | NZ | LYS | A1846 | −2.682 | −74.069 | 22.913 | 1.00 | 98.48 | N |
| ATOM | 115 | O | PRO | A1847 | −11.447 | −74.500 | 26.924 | 1.00 | 91.84 | O |

TABLE 1-continued

Three-dimensional crystal coordinate for anti-TcdB antibody beziotoxumab Fab –*C. difficile* toxin B (TcdB$^{(1834\text{-}2101)}$) complex.

| | | | | | | | | | | |
|---|---|---|---|---|---|---|---|---|---|---|
| ATOM | 116 | N | PRO | A1847 | −8.628 | −73.295 | 25.048 | 1.00 | 82.98 | N |
| ATOM | 117 | CA | PRO | A1847 | −9.787 | −74.156 | 25.344 | 1.00 | 83.46 | C |
| ATOM | 118 | C | PRO | A1847 | −10.221 | −74.448 | 26.782 | 1.00 | 88.45 | C |
| ATOM | 119 | CB | PRO | A1847 | −9.427 | −75.486 | 24.666 | 1.00 | 85.33 | C |
| ATOM | 120 | CG | PRO | A1847 | −8.192 | −75.192 | 23.779 | 1.00 | 90.07 | C |
| ATOM | 121 | CD | PRO | A1847 | −8.050 | −73.699 | 23.749 | 1.00 | 85.36 | C |
| ATOM | 122 | O | PRO | A1848 | −12.126 | −74.959 | 30.041 | 1.00 | 81.38 | O |
| ATOM | 123 | N | PRO | A1848 | −9.383 | −74.707 | 27.820 | 1.00 | 80.46 | N |
| ATOM | 124 | CA | PRO | A1848 | −9.959 | −75.113 | 29.131 | 1.00 | 79.21 | C |
| ATOM | 125 | C | PRO | A1848 | −11.151 | −74.301 | 29.697 | 1.00 | 80.53 | C |
| ATOM | 126 | CB | PRO | A1848 | −8.765 | −75.073 | 30.065 | 1.00 | 81.09 | C |
| ATOM | 127 | CG | PRO | A1848 | −7.618 | −75.446 | 29.157 | 1.00 | 85.72 | C |
| ATOM | 128 | CD | PRO | A1848 | −7.908 | −74.807 | 27.830 | 1.00 | 80.87 | C |
| ATOM | 129 | O | VAL | A1849 | −10.758 | −71.636 | 32.202 | 1.00 | 75.47 | O |
| ATOM | 130 | N | VAL | A1849 | −11.106 | −72.926 | 29.739 | 1.00 | 73.01 | N |
| ATOM | 131 | CA | VAL | A1849 | −12.061 | −71.894 | 30.252 | 1.00 | 71.58 | C |
| ATOM | 132 | C | VAL | A1849 | −11.339 | −71.074 | 31.270 | 1.00 | 74.54 | C |
| ATOM | 133 | CB | VAL | A1849 | −13.531 | −72.232 | 30.727 | 1.00 | 75.25 | C |
| ATOM | 134 | CG1 | VAL | A1849 | −13.562 | −73.024 | 32.039 | 1.00 | 75.61 | C |
| ATOM | 135 | CG2 | VAL | A1849 | −14.378 | −70.959 | 30.889 | 1.00 | 74.26 | C |
| ATOM | 136 | O | ASN | A1850 | −8.478 | −68.740 | 33.031 | 1.00 | 70.85 | O |
| ATOM | 137 | N | ASN | A1850 | −11.383 | −69.739 | 31.106 | 1.00 | 68.40 | N |
| ATOM | 138 | CA | ASN | A1850 | −10.705 | −68.792 | 31.973 | 1.00 | 66.36 | C |
| ATOM | 139 | C | ASN | A1850 | −9.171 | −69.110 | 32.071 | 1.00 | 70.25 | C |
| ATOM | 140 | CB | ASN | A1850 | −11.430 | −68.717 | 33.304 | 1.00 | 61.37 | C |
| ATOM | 141 | CG | ASN | A1850 | −12.517 | −67.674 | 33.314 | 1.00 | 72.74 | C |
| ATOM | 142 | OD1 | ASN | A1850 | −12.399 | −66.611 | 32.681 | 1.00 | 73.75 | O |
| ATOM | 143 | ND2 | ASN | A1850 | −13.554 | −67.903 | 34.113 | 1.00 | 47.82 | N |
| ATOM | 144 | N | ASN | A1851 | −8.664 | −69.801 | 31.032 | 1.00 | 64.86 | N |
| ATOM | 145 | CA | ASN | A1851 | −7.279 | −70.174 | 30.890 | 1.00 | 64.33 | C |
| ATOM | 146 | C | ASN | A1851 | −6.547 | −69.045 | 30.141 | 1.00 | 72.69 | C |
| ATOM | 147 | O | ASN | A1851 | −6.299 | −69.152 | 28.926 | 1.00 | 74.39 | O |
| ATOM | 148 | CB | ASN | A1851 | −7.164 | −71.525 | 30.172 | 1.00 | 57.72 | C |
| ATOM | 149 | CG | ASN | A1851 | −5.754 | −72.004 | 29.913 | 1.00 | 76.78 | C |
| ATOM | 150 | ND2 | ASN | A1851 | −5.584 | −72.760 | 28.845 | 1.00 | 69.89 | N |
| ATOM | 151 | OD1 | ASN | A1851 | −4.799 | −71.692 | 30.641 | 1.00 | 72.87 | O |
| ATOM | 152 | N | LEU | A1852 | −6.221 | −67.941 | 30.870 | 1.00 | 69.27 | N |
| ATOM | 153 | CA | LEU | A1852 | −5.447 | −66.798 | 30.341 | 1.00 | 68.84 | C |
| ATOM | 154 | C | LEU | A1852 | −4.069 | −67.364 | 29.973 | 1.00 | 77.18 | C |
| ATOM | 155 | O | LEU | A1852 | −3.567 | −68.246 | 30.688 | 1.00 | 78.22 | O |
| ATOM | 156 | CB | LEU | A1852 | −5.344 | −65.696 | 31.397 | 1.00 | 67.66 | C |
| ATOM | 157 | CG | LEU | A1852 | −4.730 | −64.390 | 30.982 | 1.00 | 71.13 | C |
| ATOM | 158 | CD1 | LEU | A1852 | −5.687 | −63.554 | 30.164 | 1.00 | 70.52 | C |
| ATOM | 159 | CD2 | LEU | A1852 | −4.314 | −63.606 | 32.198 | 1.00 | 73.66 | C |
| ATOM | 160 | N | ILE | A1853 | −3.502 | −66.963 | 28.826 | 1.00 | 74.70 | N |
| ATOM | 161 | CA | ILE | A1853 | −2.284 | −67.638 | 28.414 | 1.00 | 74.56 | C |
| ATOM | 162 | C | ILE | A1853 | −0.994 | −66.980 | 28.935 | 1.00 | 79.05 | C |
| ATOM | 163 | O | ILE | A1853 | −0.241 | −67.698 | 29.616 | 1.00 | 81.36 | O |
| ATOM | 164 | CB | ILE | A1853 | −2.292 | −67.903 | 26.905 | 1.00 | 77.62 | C |
| ATOM | 165 | CG1 | ILE | A1853 | −3.211 | −69.119 | 26.603 | 1.00 | 78.25 | C |
| ATOM | 166 | CG2 | ILE | A1853 | −0.902 | −68.105 | 26.309 | 1.00 | 78.23 | C |
| ATOM | 167 | CD1 | ILE | A1853 | −2.977 | −70.436 | 27.458 | 1.00 | 87.48 | C |
| ATOM | 168 | N | THR | A1854 | −0.734 | −65.679 | 28.666 | 1.00 | 71.97 | N |
| ATOM | 169 | CA | THR | A1854 | 0.491 | −64.942 | 29.106 | 1.00 | 71.36 | C |
| ATOM | 170 | C | THR | A1854 | 1.848 | −65.465 | 28.474 | 1.00 | 72.73 | C |
| ATOM | 171 | O | THR | A1854 | 2.093 | −66.670 | 28.313 | 1.00 | 71.18 | O |
| ATOM | 172 | CB | THR | A1854 | 0.676 | −64.754 | 30.664 | 1.00 | 77.14 | C |
| ATOM | 173 | CG2 | THR | A1854 | −0.609 | −64.449 | 31.415 | 1.00 | 72.66 | C |
| ATOM | 174 | OG1 | THR | A1854 | 1.357 | −65.865 | 31.249 | 1.00 | 75.95 | O |
| ATOM | 175 | N | GLY | A1855 | 2.715 | −64.514 | 28.145 | 1.00 | 67.78 | N |
| ATOM | 176 | CA | GLY | A1855 | 4.001 | −64.815 | 27.544 | 1.00 | 67.60 | C |
| ATOM | 177 | C | GLY | A1855 | 3.966 | −64.693 | 26.040 | 1.00 | 72.77 | C |
| ATOM | 178 | O | GLY | A1855 | 2.986 | −64.208 | 25.459 | 1.00 | 72.33 | O |
| ATOM | 179 | N | PHE | A1856 | 5.058 | −65.109 | 25.404 | 1.00 | 69.65 | N |
| ATOM | 180 | CA | PHE | A1856 | 5.191 | −65.047 | 23.960 | 1.00 | 69.07 | C |
| ATOM | 181 | C | PHE | A1856 | 4.313 | −66.079 | 23.277 | 1.00 | 73.60 | C |
| ATOM | 182 | O | PHE | A1856 | 4.402 | −67.267 | 23.574 | 1.00 | 74.09 | O |
| ATOM | 183 | CB | PHE | A1856 | 6.661 | −65.213 | 23.536 | 1.00 | 70.48 | C |
| ATOM | 184 | CG | PHE | A1856 | 7.478 | −63.951 | 23.667 | 1.00 | 71.79 | C |
| ATOM | 185 | CD1 | PHE | A1856 | 7.430 | −62.965 | 22.685 | 1.00 | 74.20 | C |
| ATOM | 186 | CD2 | PHE | A1856 | 8.295 | −63.743 | 24.773 | 1.00 | 73.52 | C |
| ATOM | 187 | CE1 | PHE | A1856 | 8.175 | −61.793 | 22.816 | 1.00 | 74.58 | C |

TABLE 1-continued

Three-dimensional crystal coordinate for anti-TcdB antibody beziotoxumab Fab –C. *difficile* toxin B (TcdB$^{(1834-2101)}$) complex.

| ATOM | 188 | CE2 | PHE | A1856 | 9.033 | −62.565 | 24.905 | 1.00 | 76.00 | C |
|------|-----|-----|-----|-------|-------|---------|--------|------|-------|---|
| ATOM | 189 | CZ | PHE | A1856 | 8.961 | −61.596 | 23.928 | 1.00 | 73.75 | C |
| ATOM | 190 | N | VAL | A1857 | 3.425 | −65.614 | 22.402 | 1.00 | 69.56 | N |
| ATOM | 191 | CA | VAL | A1857 | 2.554 | −66.475 | 21.615 | 1.00 | 69.00 | C |
| ATOM | 192 | C | VAL | A1857 | 2.622 | −66.025 | 20.154 | 1.00 | 74.12 | C |
| ATOM | 193 | O | VAL | A1857 | 2.829 | −64.841 | 19.889 | 1.00 | 72.25 | O |
| ATOM | 194 | CB | VAL | A1857 | 1.101 | −66.660 | 22.168 | 1.00 | 71.79 | C |
| ATOM | 195 | CG1 | VAL | A1857 | 0.999 | −66.304 | 23.642 | 1.00 | 71.49 | C |
| ATOM | 196 | CG2 | VAL | A1857 | 0.061 | −65.900 | 21.358 | 1.00 | 71.27 | C |
| ATOM | 197 | N | THR | A1858 | 2.487 | −66.967 | 19.216 | 1.00 | 72.85 | N |
| ATOM | 198 | CA | THR | A1858 | 2.505 | −66.629 | 17.803 | 1.00 | 73.09 | C |
| ATOM | 199 | C | THR | A1858 | 1.136 | −66.930 | 17.245 | 1.00 | 77.82 | C |
| ATOM | 200 | O | THR | A1858 | 0.745 | −68.094 | 17.196 | 1.00 | 78.22 | O |
| ATOM | 201 | CB | THR | A1858 | 3.658 | −67.336 | 17.052 | 1.00 | 82.38 | C |
| ATOM | 202 | CG2 | THR | A1858 | 4.071 | −66.584 | 15.785 | 1.00 | 81.73 | C |
| ATOM | 203 | OG1 | THR | A1858 | 4.793 | −67.483 | 17.916 | 1.00 | 81.55 | O |
| ATOM | 204 | N | VAL | A1859 | 0.377 | −65.879 | 16.905 | 1.00 | 74.20 | N |
| ATOM | 205 | CA | VAL | A1859 | −0.944 | −66.015 | 16.306 | 1.00 | 73.98 | C |
| ATOM | 206 | C | VAL | A1859 | −0.694 | −65.872 | 14.805 | 1.00 | 79.64 | C |
| ATOM | 207 | O | VAL | A1859 | −0.603 | −64.765 | 14.280 | 1.00 | 79.51 | O |
| ATOM | 208 | CB | VAL | A1859 | −1.986 | −65.006 | 16.880 | 1.00 | 77.80 | C |
| ATOM | 209 | CG1 | VAL | A1859 | −3.305 | −65.037 | 16.098 | 1.00 | 77.42 | C |
| ATOM | 210 | CG2 | VAL | A1859 | −2.237 | −65.242 | 18.376 | 1.00 | 77.35 | C |
| ATOM | 211 | N | GLY | A1860 | −0.478 | −67.006 | 14.156 | 1.00 | 77.73 | N |
| ATOM | 212 | CA | GLY | A1860 | −0.186 | −67.065 | 12.732 | 1.00 | 78.39 | C |
| ATOM | 213 | C | GLY | A1860 | 1.223 | −66.623 | 12.390 | 1.00 | 84.94 | C |
| ATOM | 214 | O | GLY | A1860 | 2.210 | −67.268 | 12.767 | 1.00 | 85.02 | O |
| ATOM | 215 | N | ASP | A1861 | 1.329 | −65.520 | 11.662 | 1.00 | 82.76 | N |
| ATOM | 216 | CA | ASP | A1861 | 2.636 | −65.022 | 11.273 | 1.00 | 82.97 | C |
| ATOM | 217 | C | ASP | A1861 | 3.300 | −64.234 | 12.384 | 1.00 | 84.29 | C |
| ATOM | 218 | O | ASP | A1861 | 4.401 | −64.578 | 12.825 | 1.00 | 84.69 | O |
| ATOM | 219 | CB | ASP | A1861 | 2.532 | −64.203 | 9.979 | 1.00 | 85.77 | C |
| ATOM | 220 | CG | ASP | A1861 | 2.592 | −65.083 | 8.748 | 1.00 | 102.92 | C |
| ATOM | 221 | OD2 | ASP | A1861 | 1.670 | −64.987 | 7.906 | 1.00 | 111.73 | O |
| ATOM | 222 | OD1 | ASP | A1861 | 3.561 | −65.890 | 8.635 | 1.00 | 103.30 | O |
| ATOM | 223 | N | ASP | A1862 | 2.591 | −63.210 | 12.867 | 1.00 | 76.83 | N |
| ATOM | 224 | CA | ASP | A1862 | 3.035 | −62.267 | 13.876 | 1.00 | 74.17 | C |
| ATOM | 225 | C | ASP | A1862 | 2.974 | −62.795 | 15.325 | 1.00 | 71.89 | C |
| ATOM | 226 | O | ASP | A1862 | 1.999 | −63.436 | 15.688 | 1.00 | 70.54 | O |
| ATOM | 227 | CB | ASP | A1862 | 2.236 | −60.964 | 13.702 | 1.00 | 75.37 | C |
| ATOM | 228 | CG | ASP | A1862 | 0.772 | −61.165 | 13.370 | 1.00 | 76.57 | C |
| ATOM | 229 | OD2 | ASP | A1862 | 0.275 | −60.493 | 12.444 | 1.00 | 77.05 | O |
| ATOM | 230 | OD1 | ASP | A1862 | 0.112 | −61.939 | 14.075 | 1.00 | 77.16 | O |
| ATOM | 231 | N | LYS | A1863 | 4.046 | −62.524 | 16.136 | 1.00 | 65.81 | N |
| ATOM | 232 | CA | LYS | A1863 | 4.187 | −62.892 | 17.560 | 1.00 | 64.25 | C |
| ATOM | 233 | C | LYS | A1863 | 3.707 | −61.748 | 18.467 | 1.00 | 69.08 | C |
| ATOM | 234 | O | LYS | A1863 | 3.855 | −60.582 | 18.111 | 1.00 | 69.36 | O |
| ATOM | 235 | CB | LYS | A1863 | 5.633 | −63.303 | 17.943 | 1.00 | 63.59 | C |
| ATOM | 236 | N | TYR | A1864 | 3.138 | −62.091 | 19.639 | 1.00 | 64.51 | N |
| ATOM | 237 | CA | TYR | A1864 | 2.639 | −61.160 | 20.654 | 1.00 | 63.59 | C |
| ATOM | 238 | C | TYR | A1864 | 3.286 | −61.500 | 22.009 | 1.00 | 65.98 | C |
| ATOM | 239 | O | TYR | A1864 | 3.877 | −62.577 | 22.156 | 1.00 | 66.29 | O |
| ATOM | 240 | CB | TYR | A1864 | 1.116 | −61.322 | 20.827 | 1.00 | 64.84 | C |
| ATOM | 241 | CG | TYR | A1864 | 0.244 | −60.972 | 19.640 | 1.00 | 66.13 | C |
| ATOM | 242 | CD1 | TYR | A1864 | 0.040 | −61.886 | 18.607 | 1.00 | 67.87 | C |
| ATOM | 243 | CD2 | TYR | A1864 | −0.508 | −59.801 | 19.626 | 1.00 | 66.14 | C |
| ATOM | 244 | CE1 | TYR | A1864 | −0.802 | −61.591 | 17.537 | 1.00 | 68.04 | C |
| ATOM | 245 | CE2 | TYR | A1864 | −1.357 | −59.500 | 18.564 | 1.00 | 66.68 | C |
| ATOM | 246 | CZ | TYR | A1864 | −1.498 | −60.396 | 17.518 | 1.00 | 73.21 | C |
| ATOM | 247 | OH | TYR | A1864 | −2.323 | −60.101 | 16.458 | 1.00 | 74.89 | O |
| ATOM | 248 | N | TYR | A1865 | 3.158 | −60.600 | 23.001 | 1.00 | 59.38 | N |
| ATOM | 249 | CA | TYR | A1865 | 3.615 | −60.908 | 24.343 | 1.00 | 57.99 | C |
| ATOM | 250 | C | TYR | A1865 | 2.545 | −60.444 | 25.293 | 1.00 | 62.72 | C |
| ATOM | 251 | O | TYR | A1865 | 2.267 | −59.250 | 25.371 | 1.00 | 63.59 | O |
| ATOM | 252 | CB | TYR | A1865 | 5.003 | −60.339 | 24.667 | 1.00 | 58.19 | C |
| ATOM | 253 | CG | TYR | A1865 | 5.423 | −60.549 | 26.107 | 1.00 | 58.94 | C |
| ATOM | 254 | CD1 | TYR | A1865 | 5.927 | −61.775 | 26.539 | 1.00 | 60.23 | C |
| ATOM | 255 | CD2 | TYR | A1865 | 5.319 | −59.523 | 27.038 | 1.00 | 60.16 | C |
| ATOM | 256 | CE1 | TYR | A1865 | 6.303 | −61.976 | 27.870 | 1.00 | 61.15 | C |
| ATOM | 257 | CE2 | TYR | A1865 | 5.697 | −59.708 | 28.370 | 1.00 | 61.41 | C |
| ATOM | 258 | CZ | TYR | A1865 | 6.191 | −60.934 | 28.784 | 1.00 | 69.35 | C |
| ATOM | 259 | OH | TYR | A1865 | 6.581 | −61.071 | 30.101 | 1.00 | 70.47 | O |
| ATOM | 260 | N | PHE | A1866 | 1.892 | −61.400 | 25.958 | 1.00 | 59.16 | N |
| ATOM | 261 | CA | PHE | A1866 | 0.809 | −61.127 | 26.887 | 1.00 | 59.65 | C |
| ATOM | 262 | C | PHE | A1866 | 1.418 | −61.002 | 28.268 | 1.00 | 67.40 | C |
| ATOM | 263 | O | PHE | A1866 | 1.775 | −62.003 | 28.904 | 1.00 | 66.45 | O |
| ATOM | 264 | CB | PHE | A1866 | −0.298 | −62.196 | 26.768 | 1.00 | 61.07 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 265 | CG  | PHE | A1866 | −0.898 | −62.232 | 25.384 | 1.00 | 61.63  | C |
| ---- | --- | --- | --- | ----- | ------ | ------- | ------ | ---- | ------ | - |
| ATOM | 266 | CD1 | PHE | A1866 | −1.846 | −61.292 | 24.995 | 1.00 | 65.28  | C |
| ATOM | 267 | CD2 | PHE | A1866 | −0.451 | −63.144 | 24.440 | 1.00 | 62.36  | C |
| ATOM | 268 | CE1 | PHE | A1866 | −2.356 | −61.287 | 23.688 | 1.00 | 66.05  | C |
| ATOM | 269 | CE2 | PHE | A1866 | −0.934 | −63.115 | 23.128 | 1.00 | 64.85  | C |
| ATOM | 270 | CZ  | PHE | A1866 | −1.894 | −62.200 | 22.764 | 1.00 | 63.36  | C |
| ATOM | 271 | N   | ASN | A1867 | 1.627  | −59.734 | 28.677 | 1.00 | 66.33  | N |
| ATOM | 272 | CA  | ASN | A1867 | 2.314  | −59.331 | 29.895 | 1.00 | 67.21  | C |
| ATOM | 273 | C   | ASN | A1867 | 1.739  | −59.948 | 31.179 | 1.00 | 74.67  | C |
| ATOM | 274 | O   | ASN | A1867 | 0.698  | −59.487 | 31.670 | 1.00 | 74.69  | O |
| ATOM | 275 | CB  | ASN | A1867 | 2.390  | −57.807 | 29.984 | 1.00 | 67.84  | C |
| ATOM | 276 | CG  | ASN | A1867 | 3.632  | −57.330 | 30.678 | 1.00 | 94.56  | C |
| ATOM | 277 | ND2 | ASN | A1867 | 3.788  | −56.022 | 30.728 | 1.00 | 89.24  | N |
| ATOM | 278 | OD1 | ASN | A1867 | 4.466  | −58.121 | 31.158 | 1.00 | 88.28  | O |
| ATOM | 279 | N   | PRO | A1868 | 2.426  | −60.971 | 31.754 | 1.00 | 73.85  | N |
| ATOM | 280 | CA  | PRO | A1868 | 1.918  | −61.601 | 32.990 | 1.00 | 74.61  | C |
| ATOM | 281 | C   | PRO | A1868 | 1.896  | −60.683 | 34.203 | 1.00 | 81.70  | C |
| ATOM | 282 | O   | PRO | A1868 | 1.280  | −61.034 | 35.214 | 1.00 | 81.84  | O |
| ATOM | 283 | CB  | PRO | A1868 | 2.818  | −62.824 | 33.187 | 1.00 | 76.13  | C |
| ATOM | 284 | CG  | PRO | A1868 | 4.006  | −62.574 | 32.399 | 1.00 | 80.49  | C |
| ATOM | 285 | CD  | PRO | A1868 | 3.679  | −61.604 | 31.305 | 1.00 | 76.02  | C |
| ATOM | 286 | N   | ILE | A1869 | 2.518  | −59.485 | 34.075 | 1.00 | 80.41  | N |
| ATOM | 287 | CA  | ILE | A1869 | 2.542  | −58.432 | 35.095 | 1.00 | 81.34  | C |
| ATOM | 288 | C   | ILE | A1869 | 1.217  | −57.685 | 35.001 | 1.00 | 87.89  | C |
| ATOM | 289 | O   | ILE | A1869 | 0.644  | −57.322 | 36.033 | 1.00 | 88.86  | O |
| ATOM | 290 | CB  | ILE | A1869 | 3.704  | −57.400 | 34.898 | 1.00 | 84.82  | C |
| ATOM | 291 | CG1 | ILE | A1869 | 5.064  | −58.055 | 34.515 | 1.00 | 85.61  | C |
| ATOM | 292 | CG2 | ILE | A1869 | 3.844  | −56.495 | 36.131 | 1.00 | 85.09  | C |
| ATOM | 293 | CD1 | ILE | A1869 | 6.080  | −57.089 | 33.792 | 1.00 | 90.65  | C |
| ATOM | 294 | N   | ASN | A1870 | 0.763  | −57.406 | 33.755 | 1.00 | 85.01  | N |
| ATOM | 295 | CA  | ASN | A1870 | −0.437 | −56.608 | 33.490 | 1.00 | 84.98  | C |
| ATOM | 296 | C   | ASN | A1870 | −1.664 | −57.423 | 33.072 | 1.00 | 87.40  | C |
| ATOM | 297 | O   | ASN | A1870 | −2.346 | −57.071 | 32.106 | 1.00 | 87.47  | O |
| ATOM | 298 | CB  | ASN | A1870 | −0.126 | −55.506 | 32.480 | 1.00 | 87.00  | C |
| ATOM | 299 | CG  | ASN | A1870 | 0.983  | −54.597 | 32.941 | 1.00 | 113.46 | C |
| ATOM | 300 | ND2 | ASN | A1870 | 1.807  | −54.156 | 31.999 | 1.00 | 106.17 | N |
| ATOM | 301 | OD1 | ASN | A1870 | 1.123  | −54.298 | 34.141 | 1.00 | 106.07 | O |
| ATOM | 302 | N   | GLY | A1871 | −1.963 | −58.451 | 33.867 | 1.00 | 81.65  | N |
| ATOM | 303 | CA  | GLY | A1871 | −3.103 | −59.338 | 33.686 | 1.00 | 80.57  | C |
| ATOM | 304 | C   | GLY | A1871 | −3.179 | −60.078 | 32.365 | 1.00 | 83.08  | C |
| ATOM | 305 | O   | GLY | A1871 | −4.275 | −60.409 | 31.915 | 1.00 | 83.22  | O |
| ATOM | 306 | N   | GLY | A1872 | −2.026 | −60.347 | 31.756 | 1.00 | 77.90  | N |
| ATOM | 307 | CA  | GLY | A1872 | −1.933 | −61.030 | 30.469 | 1.00 | 76.30  | C |
| ATOM | 308 | C   | GLY | A1872 | −2.242 | −60.125 | 29.289 | 1.00 | 75.57  | C |
| ATOM | 309 | O   | GLY | A1872 | −2.570 | −60.623 | 28.204 | 1.00 | 75.56  | O |
| ATOM | 310 | N   | ALA | A1873 | −2.165 | −58.790 | 29.491 | 1.00 | 67.70  | N |
| ATOM | 311 | CA  | ALA | A1873 | −2.443 | −57.844 | 28.415 | 1.00 | 66.62  | C |
| ATOM | 312 | C   | ALA | A1873 | −1.271 | −57.745 | 27.410 | 1.00 | 73.48  | C |
| ATOM | 313 | O   | ALA | A1873 | −0.093 | −57.743 | 27.810 | 1.00 | 72.79  | O |
| ATOM | 314 | CB  | ALA | A1873 | −2.802 | −56.482 | 28.972 | 1.00 | 66.27  | C |
| ATOM | 315 | N   | ALA | A1874 | −1.611 | −57.707 | 26.093 | 1.00 | 70.95  | N |
| ATOM | 316 | CA  | ALA | A1874 | −0.633 | −57.601 | 25.007 | 1.00 | 70.39  | C |
| ATOM | 317 | C   | ALA | A1874 | 0.125  | −56.319 | 25.204 | 1.00 | 75.02  | C |
| ATOM | 318 | O   | ALA | A1874 | −0.477 | −55.281 | 25.529 | 1.00 | 76.22  | O |
| ATOM | 319 | CB  | ALA | A1874 | −1.317 | −57.603 | 23.651 | 1.00 | 70.85  | C |
| ATOM | 320 | N   | SER | A1875 | 1.460  | −56.424 | 25.118 | 1.00 | 69.26  | N |
| ATOM | 321 | CA  | SER | A1875 | 2.382  | −55.316 | 25.310 | 1.00 | 66.55  | C |
| ATOM | 322 | C   | SER | A1875 | 2.413  | −54.486 | 24.054 | 1.00 | 68.80  | C |
| ATOM | 323 | O   | SER | A1875 | 2.480  | −55.034 | 22.955 | 1.00 | 68.22  | O |
| ATOM | 324 | CB  | SER | A1875 | 3.780  | −55.844 | 25.605 | 1.00 | 67.15  | C |
| ATOM | 325 | OG  | SER | A1875 | 3.798  | −56.715 | 26.723 | 1.00 | 68.69  | O |
| ATOM | 326 | N   | ILE | A1876 | 2.297  | −53.168 | 24.211 | 1.00 | 65.36  | N |
| ATOM | 327 | CA  | ILE | A1876 | 2.428  | −52.226 | 23.098 | 1.00 | 64.64  | C |
| ATOM | 328 | C   | ILE | A1876 | 3.671  | −51.377 | 23.382 | 1.00 | 66.43  | C |
| ATOM | 329 | O   | ILE | A1876 | 4.035  | −51.197 | 24.554 | 1.00 | 65.11  | O |
| ATOM | 330 | CB  | ILE | A1876 | 1.146  | −51.424 | 22.677 | 1.00 | 67.37  | C |
| ATOM | 331 | CG1 | ILE | A1876 | 0.735  | −50.374 | 23.707 | 1.00 | 67.29  | C |
| ATOM | 332 | CG2 | ILE | A1876 | −0.027 | −52.364 | 22.339 | 1.00 | 68.45  | C |
| ATOM | 333 | CD1 | ILE | A1876 | 0.230  | −49.078 | 23.070 | 1.00 | 73.82  | C |
| ATOM | 334 | N   | GLY | A1877 | 4.356  | −50.961 | 22.316 | 1.00 | 61.86  | N |
| ATOM | 335 | CA  | GLY | A1877 | 5.582  | −50.181 | 22.414 | 1.00 | 60.49  | C |
| ATOM | 336 | C   | GLY | A1877 | 6.751  | −51.016 | 22.885 | 1.00 | 63.28  | C |
| ATOM | 337 | O   | GLY | A1877 | 6.664  | −52.248 | 22.914 | 1.00 | 63.02  | O |
| ATOM | 338 | N   | GLU | A1878 | 7.844  | −50.340 | 23.288 | 1.00 | 58.99  | N |
| ATOM | 339 | CA  | GLU | A1878 | 9.086  | −50.965 | 23.734 | 1.00 | 57.81  | C |
| ATOM | 340 | C   | GLU | A1878 | 8.942  | −51.536 | 25.127 | 1.00 | 63.28  | C |
| ATOM | 341 | O   | GLU | A1878 | 8.601  | −50.800 | 26.060 | 1.00 | 64.45  | O |

TABLE 1-continued

Three-dimensional crystal coordinate for anti-TcdB antibody beziotoxumab
Fab –*C. difficile* toxin B (TcdB$^{(1834-2101)}$) complex.

| ATOM | 342 | CB | GLU | A1878 | 10.212 | −49.948 | 23.681 | 1.00 | 58.51 | C |
|------|-----|-----|-----|-------|--------|---------|--------|------|-------|---|
| ATOM | 343 | CG | GLU | A1878 | 11.595 | −50.553 | 23.786 | 1.00 | 61.56 | C |
| ATOM | 344 | CD | GLU | A1878 | 12.634 | −49.623 | 24.376 | 1.00 | 75.05 | C |
| ATOM | 345 | OE1 | GLU | A1878 | 12.278 | −48.505 | 24.825 | 1.00 | 67.89 | O |
| ATOM | 346 | OE2 | GLU | A1878 | 13.811 | −50.043 | 24.422 | 1.00 | 65.52 | O |
| ATOM | 347 | N | THR | A1879 | 9.203 | −52.839 | 25.282 | 1.00 | 59.73 | N |
| ATOM | 348 | CA | THR | A1879 | 9.028 | −53.507 | 26.578 | 1.00 | 60.01 | C |
| ATOM | 349 | C | THR | A1879 | 10.169 | −54.495 | 26.906 | 1.00 | 63.22 | C |
| ATOM | 350 | O | THR | A1879 | 10.710 | −55.164 | 26.014 | 1.00 | 63.20 | O |
| ATOM | 351 | CB | THR | A1879 | 7.606 | −54.155 | 26.672 | 1.00 | 67.72 | C |
| ATOM | 352 | CG2 | THR | A1879 | 6.534 | −53.151 | 27.121 | 1.00 | 69.77 | C |
| ATOM | 353 | OG1 | THR | A1879 | 7.209 | −54.610 | 25.382 | 1.00 | 64.67 | O |
| ATOM | 354 | N | ILE | A1880 | 10.522 | −54.577 | 28.207 | 1.00 | 59.04 | N |
| ATOM | 355 | CA | ILE | A1880 | 11.587 | −55.452 | 28.726 | 1.00 | 58.24 | C |
| ATOM | 356 | C | ILE | A1880 | 11.050 | −56.808 | 29.172 | 1.00 | 59.89 | C |
| ATOM | 357 | O | ILE | A1880 | 10.144 | −56.881 | 30.003 | 1.00 | 58.14 | O |
| ATOM | 358 | CB | ILE | A1880 | 12.449 | −54.758 | 29.828 | 1.00 | 60.91 | C |
| ATOM | 359 | CG1 | ILE | A1880 | 13.458 | −53.797 | 29.186 | 1.00 | 61.17 | C |
| ATOM | 360 | CG2 | ILE | A1880 | 13.189 | −55.760 | 30.739 | 1.00 | 60.96 | C |
| ATOM | 361 | CD1 | ILE | A1880 | 12.977 | −52.396 | 29.045 | 1.00 | 72.01 | C |
| ATOM | 362 | N | ILE | A1881 | 11.630 | −57.879 | 28.610 | 1.00 | 56.45 | N |
| ATOM | 363 | CA | ILE | A1881 | 11.281 | −59.259 | 28.917 | 1.00 | 56.22 | C |
| ATOM | 364 | C | ILE | A1881 | 12.591 | −60.015 | 29.101 | 1.00 | 68.16 | C |
| ATOM | 365 | O | ILE | A1881 | 13.359 | −60.139 | 28.141 | 1.00 | 68.80 | O |
| ATOM | 366 | CB | ILE | A1881 | 10.385 | −59.879 | 27.809 | 1.00 | 57.30 | C |
| ATOM | 367 | CG1 | ILE | A1881 | 9.169 | −58.992 | 27.502 | 1.00 | 54.96 | C |
| ATOM | 368 | CG2 | ILE | A1881 | 9.952 | −61.307 | 28.192 | 1.00 | 58.61 | C |
| ATOM | 369 | CD1 | ILE | A1881 | 8.960 | −58.742 | 26.190 | 1.00 | 47.86 | C |
| ATOM | 370 | N | ASP | A1882 | 12.845 | −60.525 | 30.337 | 1.00 | 69.95 | N |
| ATOM | 371 | CA | ASP | A1882 | 14.063 | −61.274 | 30.728 | 1.00 | 70.96 | C |
| ATOM | 372 | C | ASP | A1882 | 15.321 | −60.453 | 30.397 | 1.00 | 74.96 | C |
| ATOM | 373 | O | ASP | A1882 | 16.195 | −60.927 | 29.673 | 1.00 | 74.43 | O |
| ATOM | 374 | CB | ASP | A1882 | 14.122 | −62.684 | 30.067 | 1.00 | 73.24 | C |
| ATOM | 375 | CG | ASP | A1882 | 12.839 | −63.506 | 30.117 | 1.00 | 87.18 | C |
| ATOM | 376 | OD1 | ASP | A1882 | 11.987 | −63.238 | 31.004 | 1.00 | 88.69 | O |
| ATOM | 377 | OD2 | ASP | A1882 | 12.703 | −64.444 | 29.293 | 1.00 | 91.24 | O |
| ATOM | 378 | N | ASP | A1883 | 15.354 | −59.190 | 30.867 | 1.00 | 72.46 | N |
| ATOM | 379 | CA | ASP | A1883 | 16.416 | −58.185 | 30.678 | 1.00 | 72.83 | C |
| ATOM | 380 | C | ASP | A1883 | 16.635 | −57.704 | 29.196 | 1.00 | 72.51 | C |
| ATOM | 381 | O | ASP | A1883 | 17.345 | −56.708 | 28.995 | 1.00 | 72.47 | O |
| ATOM | 382 | CB | ASP | A1883 | 17.748 | −58.632 | 31.309 | 1.00 | 76.07 | C |
| ATOM | 383 | CG | ASP | A1883 | 17.810 | −58.451 | 32.812 | 1.00 | 94.34 | C |
| ATOM | 384 | OD2 | ASP | A1883 | 18.558 | −57.550 | 33.272 | 1.00 | 99.51 | O |
| ATOM | 385 | OD1 | ASP | A1883 | 17.142 | −59.236 | 33.534 | 1.00 | 97.14 | O |
| ATOM | 386 | N | LYS | A1884 | 15.994 | −58.355 | 28.193 | 1.00 | 64.59 | N |
| ATOM | 387 | CA | LYS | A1884 | 16.064 | −57.986 | 26.770 | 1.00 | 62.23 | C |
| ATOM | 388 | C | LYS | A1884 | 15.012 | −56.933 | 26.405 | 1.00 | 68.11 | C |
| ATOM | 389 | O | LYS | A1884 | 13.956 | −56.873 | 27.059 | 1.00 | 69.68 | O |
| ATOM | 390 | CB | LYS | A1884 | 15.865 | −59.215 | 25.897 | 1.00 | 61.76 | C |
| ATOM | 391 | CG | LYS | A1884 | 17.037 | −60.172 | 25.941 | 1.00 | 56.68 | C |
| ATOM | 392 | CD | LYS | A1884 | 16.600 | −61.608 | 25.748 | 1.00 | 53.90 | C |
| ATOM | 393 | CE | LYS | A1884 | 17.743 | −62.522 | 26.041 | 1.00 | 65.18 | C |
| ATOM | 394 | NZ | LYS | A1884 | 18.806 | −62.430 | 24.991 | 1.00 | 84.83 | N |
| ATOM | 395 | N | ASN | A1885 | 15.283 | −56.108 | 25.350 | 1.00 | 62.27 | N |
| ATOM | 396 | CA | ASN | A1885 | 14.340 | −55.076 | 24.889 | 1.00 | 60.87 | C |
| ATOM | 397 | C | ASN | A1885 | 13.714 | −55.477 | 23.561 | 1.00 | 64.18 | C |
| ATOM | 398 | O | ASN | A1885 | 14.438 | −55.852 | 22.637 | 1.00 | 65.05 | O |
| ATOM | 399 | CB | ASN | A1885 | 15.022 | −53.723 | 24.721 | 1.00 | 59.30 | C |
| ATOM | 400 | CG | ASN | A1885 | 15.505 | −53.075 | 25.979 | 1.00 | 83.69 | C |
| ATOM | 401 | ND2 | ASN | A1885 | 16.577 | −53.601 | 26.572 | 1.00 | 76.92 | N |
| ATOM | 402 | OD1 | ASN | A1885 | 14.989 | −52.034 | 26.376 | 1.00 | 76.40 | O |
| ATOM | 403 | N | TYR | A1886 | 12.381 | −55.362 | 23.450 | 1.00 | 59.42 | N |
| ATOM | 404 | CA | TYR | A1886 | 11.613 | −55.677 | 22.231 | 1.00 | 58.99 | C |
| ATOM | 405 | C | TYR | A1886 | 10.644 | −54.535 | 21.937 | 1.00 | 60.38 | C |
| ATOM | 406 | O | TYR | A1886 | 10.346 | −53.742 | 22.822 | 1.00 | 59.47 | O |
| ATOM | 407 | CB | TYR | A1886 | 10.827 | −57.010 | 22.370 | 1.00 | 60.94 | C |
| ATOM | 408 | CG | TYR | A1886 | 11.664 | −58.213 | 22.749 | 1.00 | 63.08 | C |
| ATOM | 409 | CD2 | TYR | A1886 | 12.133 | −59.092 | 21.780 | 1.00 | 64.01 | C |
| ATOM | 410 | CD1 | TYR | A1886 | 11.958 | −58.493 | 24.082 | 1.00 | 65.42 | C |
| ATOM | 411 | CE2 | TYR | A1886 | 12.903 | −60.205 | 22.121 | 1.00 | 65.00 | C |
| ATOM | 412 | CE1 | TYR | A1886 | 12.734 | −59.594 | 24.436 | 1.00 | 66.98 | C |
| ATOM | 413 | CZ | TYR | A1886 | 13.218 | −60.441 | 23.449 | 1.00 | 74.85 | C |
| ATOM | 414 | OH | TYR | A1886 | 13.989 | −61.530 | 23.783 | 1.00 | 78.13 | O |
| ATOM | 415 | N | TYR | A1887 | 10.136 | −54.462 | 20.708 | 1.00 | 56.72 | N |
| ATOM | 416 | CA | TYR | A1887 | 9.196 | −53.424 | 20.303 | 1.00 | 55.95 | C |
| ATOM | 417 | C | TYR | A1887 | 8.019 | −54.059 | 19.648 | 1.00 | 62.34 | C |
| ATOM | 418 | O | TYR | A1887 | 8.181 | −54.892 | 18.755 | 1.00 | 63.22 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 419 | CB  | TYR | A1887 | 9.838  | −52.411 | 19.346 | 1.00 | 56.49 | C |
| ---- | --- | --- | --- | ----- | ------ | ------- | ------ | ---- | ----- | - |
| ATOM | 420 | CG  | TYR | A1887 | 8.982  | −51.182 | 19.111 | 1.00 | 58.05 | C |
| ATOM | 421 | CD1 | TYR | A1887 | 8.040  | −51.149 | 18.083 | 1.00 | 60.72 | C |
| ATOM | 422 | CD2 | TYR | A1887 | 9.104  | −50.054 | 19.922 | 1.00 | 57.29 | C |
| ATOM | 423 | CE1 | TYR | A1887 | 7.225  | −50.039 | 17.881 | 1.00 | 60.64 | C |
| ATOM | 424 | CE2 | TYR | A1887 | 8.317  | −48.926 | 19.710 | 1.00 | 58.22 | C |
| ATOM | 425 | CZ  | TYR | A1887 | 7.376  | −48.925 | 18.685 | 1.00 | 66.58 | C |
| ATOM | 426 | OH  | TYR | A1887 | 6.577  | −47.836 | 18.444 | 1.00 | 64.12 | O |
| ATOM | 427 | N   | PHE | A1888 | 6.827  | −53.636 | 20.080 | 1.00 | 59.77 | N |
| ATOM | 428 | CA  | PHE | A1888 | 5.524  | −54.088 | 19.604 | 1.00 | 59.31 | C |
| ATOM | 429 | C   | PHE | A1888 | 4.746  | −52.906 | 19.005 | 1.00 | 64.78 | C |
| ATOM | 430 | O   | PHE | A1888 | 4.715  | −51.827 | 19.608 | 1.00 | 66.47 | O |
| ATOM | 431 | CB  | PHE | A1888 | 4.751  | −54.678 | 20.790 | 1.00 | 60.58 | C |
| ATOM | 432 | CG  | PHE | A1888 | 5.426  | −55.869 | 21.425 | 1.00 | 61.36 | C |
| ATOM | 433 | CD2 | PHE | A1888 | 6.249  | −55.713 | 22.532 | 1.00 | 63.36 | C |
| ATOM | 434 | CD1 | PHE | A1888 | 5.216  | −57.152 | 20.932 | 1.00 | 63.62 | C |
| ATOM | 435 | CE2 | PHE | A1888 | 6.893  | −56.817 | 23.106 | 1.00 | 66.20 | C |
| ATOM | 436 | CE1 | PHE | A1888 | 5.858  | −58.254 | 21.502 | 1.00 | 64.17 | C |
| ATOM | 437 | CZ  | PHE | A1888 | 6.701  | −58.078 | 22.577 | 1.00 | 64.05 | C |
| ATOM | 438 | N   | ASN | A1889 | 4.090  | −53.095 | 17.855 | 1.00 | 61.08 | N |
| ATOM | 439 | CA  | ASN | A1889 | 3.314  | −51.995 | 17.269 | 1.00 | 61.86 | C |
| ATOM | 440 | C   | ASN | A1889 | 2.036  | −51.668 | 18.069 | 1.00 | 69.87 | C |
| ATOM | 441 | O   | ASN | A1889 | 1.759  | −52.326 | 19.076 | 1.00 | 70.54 | O |
| ATOM | 442 | CB  | ASN | A1889 | 3.021  | −52.217 | 15.787 | 1.00 | 59.59 | C |
| ATOM | 443 | CG  | ASN | A1889 | 2.092  | −53.343 | 15.422 | 1.00 | 71.11 | C |
| ATOM | 444 | OD1 | ASN | A1889 | 1.299  | −53.867 | 16.226 | 1.00 | 65.39 | O |
| ATOM | 445 | ND2 | ASN | A1889 | 2.112  | −53.662 | 14.144 | 1.00 | 56.43 | N |
| ATOM | 446 | N   | GLN | A1890 | 1.260  | −50.652 | 17.626 | 1.00 | 67.79 | N |
| ATOM | 447 | CA  | GLN | A1890 | 0.021  | −50.236 | 18.296 | 1.00 | 67.56 | C |
| ATOM | 448 | C   | GLN | A1890 | −0.958 | −51.402 | 18.518 | 1.00 | 72.76 | C |
| ATOM | 449 | O   | GLN | A1890 | −1.818 | −51.329 | 19.405 | 1.00 | 73.34 | O |
| ATOM | 450 | CB  | GLN | A1890 | −0.649 | −49.116 | 17.493 | 1.00 | 68.82 | C |
| ATOM | 451 | N   | SER | A1891 | −0.787 | −52.497 | 17.741 | 1.00 | 68.98 | N |
| ATOM | 452 | CA  | SER | A1891 | −1.667 | −53.669 | 17.744 | 1.00 | 68.00 | C |
| ATOM | 453 | C   | SER | A1891 | −1.138 | −54.878 | 18.562 | 1.00 | 70.42 | C |
| ATOM | 454 | O   | SER | A1891 | −1.822 | −55.903 | 18.650 | 1.00 | 69.57 | O |
| ATOM | 455 | CB  | SER | A1891 | −2.003 | −54.062 | 16.305 | 1.00 | 69.19 | C |
| ATOM | 456 | OG  | SER | A1891 | −2.623 | −52.982 | 15.615 | 1.00 | 70.47 | O |
| ATOM | 457 | N   | GLY | A1892 | 0.033  | −54.728 | 19.176 | 1.00 | 65.41 | N |
| ATOM | 458 | CA  | GLY | A1892 | 0.640  | −55.760 | 20.011 | 1.00 | 64.37 | C |
| ATOM | 459 | C   | GLY | A1892 | 1.575  | −56.749 | 19.338 | 1.00 | 66.80 | C |
| ATOM | 460 | O   | GLY | A1892 | 2.164  | −57.581 | 20.040 | 1.00 | 66.46 | O |
| ATOM | 461 | N   | VAL | A1893 | 1.731  | −56.674 | 17.985 | 1.00 | 62.32 | N |
| ATOM | 462 | CA  | VAL | A1893 | 2.606  | −57.595 | 17.248 | 1.00 | 62.36 | C |
| ATOM | 463 | C   | VAL | A1893 | 4.053  | −57.120 | 17.292 | 1.00 | 67.97 | C |
| ATOM | 464 | O   | VAL | A1893 | 4.328  | −55.941 | 17.025 | 1.00 | 68.39 | O |
| ATOM | 465 | CB  | VAL | A1893 | 2.168  | −58.004 | 15.797 | 1.00 | 65.99 | C |
| ATOM | 466 | CG1 | VAL | A1893 | 0.691  | −58.336 | 15.714 | 1.00 | 65.48 | C |
| ATOM | 467 | CG2 | VAL | A1893 | 2.503  | −56.953 | 14.773 | 1.00 | 66.53 | C |
| ATOM | 468 | N   | LEU | A1894 | 4.977  | −58.061 | 17.626 | 1.00 | 64.08 | N |
| ATOM | 469 | CA  | LEU | A1894 | 6.436  | −57.873 | 17.703 | 1.00 | 62.79 | C |
| ATOM | 470 | C   | LEU | A1894 | 6.907  | −57.440 | 16.348 | 1.00 | 65.80 | C |
| ATOM | 471 | O   | LEU | A1894 | 6.507  | −58.007 | 15.326 | 1.00 | 66.04 | O |
| ATOM | 472 | CB  | LEU | A1894 | 7.116  | −59.192 | 18.169 | 1.00 | 62.74 | C |
| ATOM | 473 | CG  | LEU | A1894 | 8.652  | −59.374 | 18.362 | 1.00 | 67.28 | C |
| ATOM | 474 | CD1 | LEU | A1894 | 9.280  | −60.058 | 17.180 | 1.00 | 67.06 | C |
| ATOM | 475 | CD2 | LEU | A1894 | 9.403  | −58.092 | 18.824 | 1.00 | 71.88 | C |
| ATOM | 476 | N   | GLN | A1895 | 7.661  | −56.354 | 16.344 | 1.00 | 61.58 | N |
| ATOM | 477 | CA  | GLN | A1895 | 8.201  | −55.736 | 15.141 | 1.00 | 60.00 | C |
| ATOM | 478 | C   | GLN | A1895 | 9.731  | −55.806 | 15.081 | 1.00 | 62.59 | C |
| ATOM | 479 | O   | GLN | A1895 | 10.382 | −55.992 | 16.098 | 1.00 | 61.21 | O |
| ATOM | 480 | CB  | GLN | A1895 | 7.663  | −54.302 | 14.996 | 1.00 | 60.32 | C |
| ATOM | 481 | CG  | GLN | A1895 | 7.241  | −53.991 | 13.575 | 1.00 | 68.33 | C |
| ATOM | 482 | CD  | GLN | A1895 | 5.788  | −54.234 | 13.354 | 1.00 | 96.97 | C |
| ATOM | 483 | NE2 | GLN | A1895 | 5.142  | −53.272 | 12.700 | 1.00 | 97.50 | N |
| ATOM | 484 | OE1 | GLN | A1895 | 5.232  | −55.274 | 13.746 | 1.00 | 91.26 | O |
| ATOM | 485 | N   | THR | A1896 | 10.288 | −55.715 | 13.871 | 1.00 | 61.86 | N |
| ATOM | 486 | CA  | THR | A1896 | 11.730 | −55.733 | 13.581 | 1.00 | 62.37 | C |
| ATOM | 487 | C   | THR | A1896 | 12.125 | −54.414 | 12.866 | 1.00 | 67.69 | C |
| ATOM | 488 | O   | THR | A1896 | 11.273 | −53.746 | 12.247 | 1.00 | 68.05 | O |
| ATOM | 489 | CB  | THR | A1896 | 12.111 | −57.045 | 12.854 | 1.00 | 67.73 | C |
| ATOM | 490 | CG2 | THR | A1896 | 13.481 | −57.000 | 12.204 | 1.00 | 64.65 | C |
| ATOM | 491 | OG1 | THR | A1896 | 12.113 | −58.093 | 13.825 | 1.00 | 71.17 | O |
| ATOM | 492 | N   | GLY | A1897 | 13.393 | −54.040 | 13.017 | 1.00 | 63.08 | N |
| ATOM | 493 | CA  | GLY | A1897 | 13.956 | −52.842 | 12.415 | 1.00 | 62.21 | C |
| ATOM | 494 | C   | GLY | A1897 | 14.335 | −51.752 | 13.397 | 1.00 | 64.94 | C |
| ATOM | 495 | O   | GLY | A1897 | 14.475 | −51.988 | 14.608 | 1.00 | 64.74 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 496 | N | VAL | A1898 | 14.503 | −50.539 | 12.843 | 1.00 | 59.23 | N |
|---|---|---|---|---|---|---|---|---|---|---|
| ATOM | 497 | CA | VAL | A1898 | 14.913 | −49.328 | 13.544 | 1.00 | 57.72 | C |
| ATOM | 498 | C | VAL | A1898 | 13.697 | −48.545 | 13.997 | 1.00 | 61.42 | C |
| ATOM | 499 | O | VAL | A1898 | 12.803 | −48.274 | 13.195 | 1.00 | 60.71 | O |
| ATOM | 500 | CB | VAL | A1898 | 15.934 | −48.492 | 12.725 | 1.00 | 60.37 | C |
| ATOM | 501 | CG1 | VAL | A1898 | 16.603 | −47.435 | 13.600 | 1.00 | 60.26 | C |
| ATOM | 502 | CG2 | VAL | A1898 | 16.998 | −49.396 | 12.106 | 1.00 | 59.60 | C |
| ATOM | 503 | N | PHE | A1899 | 13.635 | −48.243 | 15.313 | 1.00 | 58.94 | N |
| ATOM | 504 | CA | PHE | A1899 | 12.507 | −47.533 | 15.939 | 1.00 | 58.21 | C |
| ATOM | 505 | C | PHE | A1899 | 12.960 | −46.506 | 16.962 | 1.00 | 62.24 | C |
| ATOM | 506 | O | PHE | A1899 | 13.967 | −46.726 | 17.657 | 1.00 | 62.02 | O |
| ATOM | 507 | CB | PHE | A1899 | 11.595 | −48.529 | 16.656 | 1.00 | 59.26 | C |
| ATOM | 508 | CG | PHE | A1899 | 10.878 | −49.505 | 15.764 | 1.00 | 59.74 | C |
| ATOM | 509 | CD2 | PHE | A1899 | 9.600 | −49.238 | 15.307 | 1.00 | 61.76 | C |
| ATOM | 510 | CD1 | PHE | A1899 | 11.455 | −50.719 | 15.433 | 1.00 | 61.31 | C |
| ATOM | 511 | CE2 | PHE | A1899 | 8.927 | −50.150 | 14.510 | 1.00 | 61.93 | C |
| ATOM | 512 | CE1 | PHE | A1899 | 10.783 | −51.628 | 14.631 | 1.00 | 63.49 | C |
| ATOM | 513 | CZ | PHE | A1899 | 9.530 | −51.332 | 14.167 | 1.00 | 61.24 | C |
| ATOM | 514 | N | SER | A1900 | 12.186 | −45.401 | 17.084 | 1.00 | 57.98 | N |
| ATOM | 515 | CA | SER | A1900 | 12.449 | −44.382 | 18.084 | 1.00 | 57.34 | C |
| ATOM | 516 | C | SER | A1900 | 12.085 | −44.935 | 19.461 | 1.00 | 64.83 | C |
| ATOM | 517 | O | SER | A1900 | 11.059 | −45.608 | 19.626 | 1.00 | 63.72 | O |
| ATOM | 518 | CB | SER | A1900 | 11.690 | −43.100 | 17.808 | 1.00 | 57.97 | C |
| ATOM | 519 | OG | SER | A1900 | 12.234 | −42.163 | 18.722 | 1.00 | 66.38 | O |
| ATOM | 520 | N | THR | A1901 | 12.974 | −44.664 | 20.434 | 1.00 | 63.94 | N |
| ATOM | 521 | CA | THR | A1901 | 12.954 | −45.110 | 21.822 | 1.00 | 63.70 | C |
| ATOM | 522 | C | THR | A1901 | 13.285 | −43.932 | 22.728 | 1.00 | 69.76 | C |
| ATOM | 523 | O | THR | A1901 | 13.767 | −42.915 | 22.240 | 1.00 | 70.08 | O |
| ATOM | 524 | CB | THR | A1901 | 14.024 | −46.186 | 21.939 | 1.00 | 70.66 | C |
| ATOM | 525 | CG2 | THR | A1901 | 14.336 | −46.555 | 23.348 | 1.00 | 72.84 | C |
| ATOM | 526 | OG1 | THR | A1901 | 13.599 | −47.333 | 21.207 | 1.00 | 70.45 | O |
| ATOM | 527 | N | GLU | A1902 | 13.047 | −44.071 | 24.054 | 1.00 | 67.81 | N |
| ATOM | 528 | CA | GLU | A1902 | 13.373 | −43.061 | 25.076 | 1.00 | 67.53 | C |
| ATOM | 529 | C | GLU | A1902 | 14.879 | −42.732 | 25.101 | 1.00 | 72.11 | C |
| ATOM | 530 | O | GLU | A1902 | 15.254 | −41.637 | 25.508 | 1.00 | 71.70 | O |
| ATOM | 531 | CB | GLU | A1902 | 12.877 | −43.501 | 26.464 | 1.00 | 68.81 | C |
| ATOM | 532 | CG | GLU | A1902 | 13.235 | −44.933 | 26.838 | 1.00 | 82.07 | C |
| ATOM | 533 | CD | GLU | A1902 | 13.328 | −45.249 | 28.320 | 1.00 | 109.27 | C |
| ATOM | 534 | OE1 | GLU | A1902 | 13.980 | −46.264 | 28.660 | 1.00 | 99.07 | O |
| ATOM | 535 | OE2 | GLU | A1902 | 12.772 | −44.478 | 29.139 | 1.00 | 106.72 | O |
| ATOM | 536 | N | ASP | A1903 | 15.712 | −43.688 | 24.619 | 1.00 | 69.63 | N |
| ATOM | 537 | CA | ASP | A1903 | 17.178 | −43.740 | 24.477 | 1.00 | 68.69 | C |
| ATOM | 538 | C | ASP | A1903 | 17.666 | −43.207 | 23.130 | 1.00 | 71.70 | C |
| ATOM | 539 | O | ASP | A1903 | 18.848 | −42.904 | 22.988 | 1.00 | 72.09 | O |
| ATOM | 540 | CB | ASP | A1903 | 17.596 | −45.215 | 24.504 | 1.00 | 70.00 | C |
| ATOM | 541 | CG | ASP | A1903 | 18.228 | −45.678 | 25.786 | 1.00 | 90.58 | C |
| ATOM | 542 | OD2 | ASP | A1903 | 17.844 | −46.772 | 26.278 | 1.00 | 102.30 | O |
| ATOM | 543 | OD1 | ASP | A1903 | 19.139 | −44.982 | 26.281 | 1.00 | 92.70 | O |
| ATOM | 544 | N | GLY | A1904 | 16.786 | −43.243 | 22.133 | 1.00 | 66.37 | N |
| ATOM | 545 | CA | GLY | A1904 | 17.064 | −42.882 | 20.746 | 1.00 | 64.86 | C |
| ATOM | 546 | C | GLY | A1904 | 16.708 | −44.016 | 19.799 | 1.00 | 65.06 | C |
| ATOM | 547 | O | GLY | A1904 | 15.890 | −44.873 | 20.139 | 1.00 | 64.85 | O |
| ATOM | 548 | N | PHE | A1905 | 17.348 | −44.062 | 18.617 | 1.00 | 57.91 | N |
| ATOM | 549 | CA | PHE | A1905 | 17.062 | −45.104 | 17.640 | 1.00 | 55.37 | C |
| ATOM | 550 | C | PHE | A1905 | 17.712 | −46.429 | 17.974 | 1.00 | 60.44 | C |
| ATOM | 551 | O | PHE | A1905 | 18.927 | −46.573 | 17.885 | 1.00 | 59.00 | O |
| ATOM | 552 | CB | PHE | A1905 | 17.393 | −44.668 | 16.205 | 1.00 | 55.37 | C |
| ATOM | 553 | CG | PHE | A1905 | 16.589 | −43.488 | 15.730 | 1.00 | 54.99 | C |
| ATOM | 554 | CD2 | PHE | A1905 | 17.209 | −42.288 | 15.417 | 1.00 | 56.57 | C |
| ATOM | 555 | CD1 | PHE | A1905 | 15.210 | −43.573 | 15.598 | 1.00 | 56.50 | C |
| ATOM | 556 | CE2 | PHE | A1905 | 16.462 | −41.202 | 14.960 | 1.00 | 59.54 | C |
| ATOM | 557 | CE1 | PHE | A1905 | 14.460 | −42.473 | 15.183 | 1.00 | 56.98 | C |
| ATOM | 558 | CZ | PHE | A1905 | 15.090 | −41.303 | 14.843 | 1.00 | 56.95 | C |
| ATOM | 559 | N | LYS | A1906 | 16.877 | −47.416 | 18.324 | 1.00 | 58.02 | N |
| ATOM | 560 | CA | LYS | A1906 | 17.339 | −48.760 | 18.623 | 1.00 | 57.25 | C |
| ATOM | 561 | C | LYS | A1906 | 17.108 | −49.675 | 17.420 | 1.00 | 59.68 | C |
| ATOM | 562 | O | LYS | A1906 | 16.198 | −49.420 | 16.623 | 1.00 | 58.99 | O |
| ATOM | 563 | CB | LYS | A1906 | 16.591 | −49.286 | 19.843 | 1.00 | 59.40 | C |
| ATOM | 564 | CG | LYS | A1906 | 17.508 | −49.809 | 20.930 | 1.00 | 64.38 | C |
| ATOM | 565 | CD | LYS | A1906 | 16.812 | −49.920 | 22.280 | 1.00 | 63.20 | C |
| ATOM | 566 | CE | LYS | A1906 | 16.690 | −48.589 | 22.962 | 1.00 | 55.76 | C |
| ATOM | 567 | NZ | LYS | A1906 | 16.250 | −48.738 | 24.368 | 1.00 | 64.36 | N |
| ATOM | 568 | N | TYR | A1907 | 17.937 | −50.737 | 17.298 | 1.00 | 54.80 | N |
| ATOM | 569 | CA | TYR | A1907 | 17.815 | −51.762 | 16.265 | 1.00 | 53.34 | C |
| ATOM | 570 | C | TYR | A1907 | 17.262 | −53.059 | 16.919 | 1.00 | 59.25 | C |
| ATOM | 571 | O | TYR | A1907 | 17.987 | −53.765 | 17.643 | 1.00 | 59.25 | O |
| ATOM | 572 | CB | TYR | A1907 | 19.152 | −52.023 | 15.515 | 1.00 | 53.04 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 573 | CG  | TYR | A1907 | 19.053 | −53.034 | 14.381 | 1.00 | 54.65 | C |
| ---- | --- | --- | --- | ----- | ------ | ------- | ------ | ---- | ----- | - |
| ATOM | 574 | CD1 | TYR | A1907 | 17.870 | −53.190 | 13.655 | 1.00 | 57.11 | C |
| ATOM | 575 | CD2 | TYR | A1907 | 20.150 | −53.808 | 14.009 | 1.00 | 54.85 | C |
| ATOM | 576 | CE1 | TYR | A1907 | 17.759 | −54.138 | 12.639 | 1.00 | 56.78 | C |
| ATOM | 577 | CE2 | TYR | A1907 | 20.054 | −54.752 | 12.979 | 1.00 | 55.39 | C |
| ATOM | 578 | CZ  | TYR | A1907 | 18.860 | −54.896 | 12.280 | 1.00 | 62.46 | C |
| ATOM | 579 | OH  | TYR | A1907 | 18.722 | −55.803 | 11.246 | 1.00 | 61.71 | O |
| ATOM | 580 | N   | PHE | A1908 | 15.966 | −53.346 | 16.667 | 1.00 | 55.08 | N |
| ATOM | 581 | CA  | PHE | A1908 | 15.296 | −54.549 | 17.135 | 1.00 | 54.75 | C |
| ATOM | 582 | C   | PHE | A1908 | 15.496 | −55.483 | 15.985 | 1.00 | 61.61 | C |
| ATOM | 583 | O   | PHE | A1908 | 14.709 | −55.518 | 15.038 | 1.00 | 62.33 | O |
| ATOM | 584 | CB  | PHE | A1908 | 13.807 | −54.288 | 17.429 | 1.00 | 56.11 | C |
| ATOM | 585 | CG  | PHE | A1908 | 13.612 | −53.280 | 18.529 | 1.00 | 56.76 | C |
| ATOM | 586 | CD2 | PHE | A1908 | 13.427 | −51.934 | 18.234 | 1.00 | 57.89 | C |
| ATOM | 587 | CD1 | PHE | A1908 | 13.674 | −53.663 | 19.862 | 1.00 | 59.29 | C |
| ATOM | 588 | CE2 | PHE | A1908 | 13.302 | −50.992 | 19.250 | 1.00 | 60.31 | C |
| ATOM | 589 | CE1 | PHE | A1908 | 13.541 | −52.721 | 20.880 | 1.00 | 59.97 | C |
| ATOM | 590 | CZ  | PHE | A1908 | 13.358 | −51.389 | 20.567 | 1.00 | 58.57 | C |
| ATOM | 591 | N   | ALA | A1909 | 16.637 | −56.154 | 16.029 | 1.00 | 60.04 | N |
| ATOM | 592 | CA  | ALA | A1909 | 17.185 | −57.017 | 14.995 | 1.00 | 61.03 | C |
| ATOM | 593 | C   | ALA | A1909 | 16.456 | −58.322 | 14.769 | 1.00 | 69.74 | C |
| ATOM | 594 | O   | ALA | A1909 | 16.041 | −58.939 | 15.751 | 1.00 | 71.44 | O |
| ATOM | 595 | CB  | ALA | A1909 | 18.638 | −57.320 | 15.334 | 1.00 | 61.38 | C |
| ATOM | 596 | N   | PRO | A1910 | 16.435 | −58.871 | 13.525 | 1.00 | 67.56 | N |
| ATOM | 597 | CA  | PRO | A1910 | 15.935 | −60.244 | 13.360 | 1.00 | 67.67 | C |
| ATOM | 598 | C   | PRO | A1910 | 16.856 | −61.237 | 14.119 | 1.00 | 70.95 | C |
| ATOM | 599 | O   | PRO | A1910 | 17.949 | −60.857 | 14.567 | 1.00 | 68.97 | O |
| ATOM | 600 | CB  | PRO | A1910 | 15.978 | −60.463 | 11.835 | 1.00 | 69.05 | C |
| ATOM | 601 | CG  | PRO | A1910 | 16.955 | −59.521 | 11.335 | 1.00 | 72.82 | C |
| ATOM | 602 | CD  | PRO | A1910 | 16.949 | −58.336 | 12.246 | 1.00 | 68.81 | C |
| ATOM | 603 | N   | ALA | A1911 | 16.403 | −62.496 | 14.294 | 1.00 | 67.86 | N |
| ATOM | 604 | CA  | ALA | A1911 | 17.157 | −63.520 | 15.019 | 1.00 | 66.70 | C |
| ATOM | 605 | C   | ALA | A1911 | 18.538 | −63.798 | 14.421 | 1.00 | 73.86 | C |
| ATOM | 606 | O   | ALA | A1911 | 18.711 | −63.776 | 13.192 | 1.00 | 74.19 | O |
| ATOM | 607 | CB  | ALA | A1911 | 16.352 | −64.789 | 15.113 | 1.00 | 66.57 | C |
| ATOM | 608 | N   | ASN | A1912 | 19.527 | −63.987 | 15.323 | 1.00 | 72.19 | N |
| ATOM | 609 | CA  | ASN | A1912 | 20.942 | −64.302 | 15.081 | 1.00 | 72.89 | C |
| ATOM | 610 | C   | ASN | A1912 | 21.699 | −63.223 | 14.232 | 1.00 | 77.20 | C |
| ATOM | 611 | O   | ASN | A1912 | 22.658 | −63.541 | 13.510 | 1.00 | 76.93 | O |
| ATOM | 612 | CB  | ASN | A1912 | 21.095 | −65.727 | 14.496 | 1.00 | 74.76 | C |
| ATOM | 613 | CG  | ASN | A1912 | 20.648 | −66.840 | 15.436 | 1.00 | 98.85 | C |
| ATOM | 614 | ND2 | ASN | A1912 | 19.560 | −67.510 | 15.088 | 1.00 | 91.56 | N |
| ATOM | 615 | OD1 | ASN | A1912 | 21.288 | −67.144 | 16.453 | 1.00 | 90.48 | O |
| ATOM | 616 | N   | THR | A1913 | 21.313 | −61.936 | 14.401 | 1.00 | 72.16 | N |
| ATOM | 617 | CA  | THR | A1913 | 21.941 | −60.802 | 13.717 | 1.00 | 70.19 | C |
| ATOM | 618 | C   | THR | A1913 | 23.300 | −60.465 | 14.375 | 1.00 | 71.11 | C |
| ATOM | 619 | O   | THR | A1913 | 24.255 | −60.157 | 13.669 | 1.00 | 72.27 | O |
| ATOM | 620 | CB  | THR | A1913 | 20.936 | −59.639 | 13.603 | 1.00 | 71.79 | C |
| ATOM | 621 | CG2 | THR | A1913 | 21.586 | −58.295 | 13.389 | 1.00 | 70.02 | C |
| ATOM | 622 | OG1 | THR | A1913 | 20.072 | −59.895 | 12.497 | 1.00 | 69.54 | O |
| ATOM | 623 | N   | LEU | A1914 | 23.396 | −60.561 | 15.693 | 1.00 | 64.56 | N |
| ATOM | 624 | CA  | LEU | A1914 | 24.619 | −60.266 | 16.433 | 1.00 | 64.33 | C |
| ATOM | 625 | C   | LEU | A1914 | 24.519 | −61.083 | 17.719 | 1.00 | 73.12 | C |
| ATOM | 626 | O   | LEU | A1914 | 23.462 | −61.043 | 18.358 | 1.00 | 75.53 | O |
| ATOM | 627 | CB  | LEU | A1914 | 24.589 | −58.773 | 16.783 | 1.00 | 63.91 | C |
| ATOM | 628 | CG  | LEU | A1914 | 25.866 | −57.951 | 17.017 | 1.00 | 68.15 | C |
| ATOM | 629 | CD1 | LEU | A1914 | 25.559 | −56.742 | 17.879 | 1.00 | 66.86 | C |
| ATOM | 630 | CD2 | LEU | A1914 | 26.959 | −58.722 | 17.711 | 1.00 | 73.34 | C |
| ATOM | 631 | N   | ASP | A1915 | 25.594 | −61.808 | 18.115 | 1.00 | 69.69 | N |
| ATOM | 632 | CA  | ASP | A1915 | 25.647 | −62.649 | 19.333 | 1.00 | 69.94 | C |
| ATOM | 633 | C   | ASP | A1915 | 24.364 | −63.499 | 19.582 | 1.00 | 74.02 | C |
| ATOM | 634 | O   | ASP | A1915 | 23.699 | −63.358 | 20.619 | 1.00 | 72.73 | O |
| ATOM | 635 | CB  | ASP | A1915 | 26.008 | −61.834 | 20.591 | 1.00 | 72.32 | C |
| ATOM | 636 | CG  | ASP | A1915 | 27.307 | −61.050 | 20.546 | 1.00 | 90.52 | C |
| ATOM | 637 | OD1 | ASP | A1915 | 28.378 | −61.679 | 20.348 | 1.00 | 93.30 | O |
| ATOM | 638 | OD2 | ASP | A1915 | 27.268 | −59.823 | 20.810 | 1.00 | 96.71 | O |
| ATOM | 639 | N   | GLU | A1916 | 24.016 | −64.354 | 18.591 | 1.00 | 71.26 | N |
| ATOM | 640 | CA  | GLU | A1916 | 22.882 | −65.292 | 18.582 | 1.00 | 70.75 | C |
| ATOM | 641 | C   | GLU | A1916 | 21.619 | −64.737 | 19.254 | 1.00 | 76.02 | C |
| ATOM | 642 | O   | GLU | A1916 | 20.993 | −65.423 | 20.058 | 1.00 | 76.22 | O |
| ATOM | 643 | CB  | GLU | A1916 | 23.291 | −66.650 | 19.170 | 1.00 | 71.68 | C |
| ATOM | 644 | N   | ASN | A1917 | 21.242 | −63.491 | 18.898 | 1.00 | 72.62 | N |
| ATOM | 645 | CA  | ASN | A1917 | 20.077 | −62.792 | 19.444 | 1.00 | 71.63 | C |
| ATOM | 646 | C   | ASN | A1917 | 18.757 | −63.404 | 18.987 | 1.00 | 73.91 | C |
| ATOM | 647 | O   | ASN | A1917 | 18.728 | −64.141 | 18.004 | 1.00 | 73.93 | O |
| ATOM | 648 | CB  | ASN | A1917 | 20.127 | −61.293 | 19.113 | 1.00 | 71.21 | C |
| ATOM | 649 | CG  | ASN | A1917 | 19.918 | −60.946 | 17.657 | 1.00 | 82.37 | C |

TABLE 1-continued

Three-dimensional crystal coordinate for anti-TcdB antibody beziotoxumab Fab –C. difficile toxin B (TcdB$^{(1834-2101)}$) complex.

| | | | | | | | | | |
|---|---|---|---|---|---|---|---|---|---|
| ATOM | 650 | ND2 | ASN | A1917 | 18.668 | −60.741 | 17.260 | 1.00 | 67.55 | N |
| ATOM | 651 | OD1 | ASN | A1917 | 20.875 | −60.770 | 16.901 | 1.00 | 75.65 | O |
| ATOM | 652 | N | LEU | A1918 | 17.671 | −63.071 | 19.694 | 1.00 | 69.14 | N |
| ATOM | 653 | CA | LEU | A1918 | 16.313 | −63.536 | 19.414 | 1.00 | 68.66 | C |
| ATOM | 654 | C | LEU | A1918 | 15.588 | −62.541 | 18.518 | 1.00 | 71.46 | C |
| ATOM | 655 | O | LEU | A1918 | 16.040 | −61.401 | 18.405 | 1.00 | 72.78 | O |
| ATOM | 656 | CB | LEU | A1918 | 15.539 | −63.693 | 20.737 | 1.00 | 68.85 | C |
| ATOM | 657 | CG | LEU | A1918 | 16.213 | −64.507 | 21.860 | 1.00 | 72.82 | C |
| ATOM | 658 | CD1 | LEU | A1918 | 15.495 | −64.305 | 23.193 | 1.00 | 72.20 | C |
| ATOM | 659 | CD2 | LEU | A1918 | 16.326 | −65.980 | 21.501 | 1.00 | 73.24 | C |
| ATOM | 660 | N | GLU | A1919 | 14.463 | −62.947 | 17.899 | 1.00 | 65.68 | N |
| ATOM | 661 | CA | GLU | A1919 | 13.703 | −62.054 | 17.014 | 1.00 | 65.15 | C |
| ATOM | 662 | C | GLU | A1919 | 13.240 | −60.794 | 17.724 | 1.00 | 71.45 | C |
| ATOM | 663 | O | GLU | A1919 | 12.594 | −60.872 | 18.778 | 1.00 | 73.46 | O |
| ATOM | 664 | CB | GLU | A1919 | 12.490 | −62.749 | 16.365 | 1.00 | 65.75 | C |
| ATOM | 665 | CG | GLU | A1919 | 12.766 | −63.353 | 15.008 | 1.00 | 69.76 | C |
| ATOM | 666 | CD | GLU | A1919 | 12.792 | −62.425 | 13.814 | 1.00 | 87.19 | C |
| ATOM | 667 | OE1 | GLU | A1919 | 13.758 | −62.525 | 13.025 | 1.00 | 72.34 | O |
| ATOM | 668 | OE2 | GLU | A1919 | 11.789 | −61.707 | 13.589 | 1.00 | 89.12 | O |
| ATOM | 669 | N | GLY | A1920 | 13.570 | −59.656 | 17.121 | 1.00 | 66.57 | N |
| ATOM | 670 | CA | GLY | A1920 | 13.178 | −58.334 | 17.582 | 1.00 | 65.77 | C |
| ATOM | 671 | C | GLY | A1920 | 13.893 | −57.834 | 18.815 | 1.00 | 67.14 | C |
| ATOM | 672 | O | GLY | A1920 | 13.463 | −56.837 | 19.399 | 1.00 | 68.57 | O |
| ATOM | 673 | N | GLU | A1921 | 14.976 | −58.511 | 19.217 | 1.00 | 59.55 | N |
| ATOM | 674 | CA | GLU | A1921 | 15.777 | −58.120 | 20.365 | 1.00 | 58.93 | C |
| ATOM | 675 | C | GLU | A1921 | 16.627 | −56.922 | 19.971 | 1.00 | 65.32 | C |
| ATOM | 676 | O | GLU | A1921 | 17.268 | −56.933 | 18.908 | 1.00 | 65.67 | O |
| ATOM | 677 | CB | GLU | A1921 | 16.691 | −59.295 | 20.826 | 1.00 | 60.04 | C |
| ATOM | 678 | CG | GLU | A1921 | 17.593 | −58.999 | 22.028 | 1.00 | 67.83 | C |
| ATOM | 679 | CD | GLU | A1921 | 18.591 | −60.056 | 22.487 | 1.00 | 84.67 | C |
| ATOM | 680 | OE1 | GLU | A1921 | 18.486 | −61.229 | 22.054 | 1.00 | 79.22 | O |
| ATOM | 681 | OE2 | GLU | A1921 | 19.449 | −59.718 | 23.336 | 1.00 | 72.68 | O |
| ATOM | 682 | N | ALA | A1922 | 16.653 | −55.894 | 20.833 | 1.00 | 62.76 | N |
| ATOM | 683 | CA | ALA | A1922 | 17.526 | −54.747 | 20.630 | 1.00 | 63.07 | C |
| ATOM | 684 | C | ALA | A1922 | 18.970 | −55.240 | 20.790 | 1.00 | 69.05 | C |
| ATOM | 685 | O | ALA | A1922 | 19.304 | −55.851 | 21.813 | 1.00 | 69.27 | O |
| ATOM | 686 | CB | ALA | A1922 | 17.229 | −53.679 | 21.660 | 1.00 | 63.73 | C |
| ATOM | 687 | N | ILE | A1923 | 19.799 | −55.041 | 19.758 | 1.00 | 66.03 | N |
| ATOM | 688 | CA | ILE | A1923 | 21.204 | −55.474 | 19.782 | 1.00 | 65.12 | C |
| ATOM | 689 | C | ILE | A1923 | 22.204 | −54.305 | 19.951 | 1.00 | 68.94 | C |
| ATOM | 690 | O | ILE | A1923 | 21.921 | −53.150 | 19.580 | 1.00 | 65.95 | O |
| ATOM | 691 | CB | ILE | A1923 | 21.559 | −56.350 | 18.565 | 1.00 | 67.15 | C |
| ATOM | 692 | CG1 | ILE | A1923 | 21.255 | −55.627 | 17.249 | 1.00 | 66.52 | C |
| ATOM | 693 | CG2 | ILE | A1923 | 20.863 | −57.685 | 18.653 | 1.00 | 67.70 | C |
| ATOM | 694 | CD1 | ILE | A1923 | 22.091 | −56.049 | 16.166 | 1.00 | 70.16 | C |
| ATOM | 695 | N | ASP | A1924 | 23.388 | −54.634 | 20.502 | 1.00 | 67.35 | N |
| ATOM | 696 | CA | ASP | A1924 | 24.448 | −53.656 | 20.711 | 1.00 | 68.06 | C |
| ATOM | 697 | C | ASP | A1924 | 25.238 | −53.494 | 19.408 | 1.00 | 74.35 | C |
| ATOM | 698 | O | ASP | A1924 | 26.407 | −53.895 | 19.294 | 1.00 | 75.48 | O |
| ATOM | 699 | CB | ASP | A1924 | 25.316 | −54.012 | 21.938 | 1.00 | 69.39 | C |
| ATOM | 700 | CG | ASP | A1924 | 24.688 | −53.642 | 23.277 | 1.00 | 76.65 | C |
| ATOM | 701 | OD2 | ASP | A1924 | 25.161 | −54.171 | 24.320 | 1.00 | 82.33 | O |
| ATOM | 702 | OD1 | ASP | A1924 | 23.751 | −52.776 | 23.292 | 1.00 | 73.92 | O |
| ATOM | 703 | N | PHE | A1925 | 24.556 | −52.894 | 18.415 | 1.00 | 69.24 | N |
| ATOM | 704 | CA | PHE | A1925 | 25.019 | −52.683 | 17.051 | 1.00 | 67.71 | C |
| ATOM | 705 | C | PHE | A1925 | 25.735 | −51.355 | 16.855 | 1.00 | 71.88 | C |
| ATOM | 706 | O | PHE | A1925 | 25.402 | −50.360 | 17.503 | 1.00 | 71.91 | O |
| ATOM | 707 | CB | PHE | A1925 | 23.814 | −52.786 | 16.102 | 1.00 | 69.17 | C |
| ATOM | 708 | CG | PHE | A1925 | 24.138 | −52.742 | 14.632 | 1.00 | 70.99 | C |
| ATOM | 709 | CD1 | PHE | A1925 | 24.711 | −53.838 | 13.997 | 1.00 | 73.52 | C |
| ATOM | 710 | CD2 | PHE | A1925 | 23.876 | −51.605 | 13.880 | 1.00 | 73.09 | C |
| ATOM | 711 | CE1 | PHE | A1925 | 25.032 | −53.789 | 12.642 | 1.00 | 73.94 | C |
| ATOM | 712 | CE2 | PHE | A1925 | 24.194 | −51.560 | 12.524 | 1.00 | 75.60 | C |
| ATOM | 713 | CZ | PHE | A1925 | 24.772 | −52.651 | 11.917 | 1.00 | 73.26 | C |
| ATOM | 714 | N | THR | A1926 | 26.721 | −51.350 | 15.937 | 1.00 | 67.55 | N |
| ATOM | 715 | CA | THR | A1926 | 27.499 | −50.187 | 15.510 | 1.00 | 66.41 | C |
| ATOM | 716 | C | THR | A1926 | 27.755 | −50.325 | 14.020 | 1.00 | 67.74 | C |
| ATOM | 717 | O | THR | A1926 | 27.757 | −51.443 | 13.483 | 1.00 | 63.87 | O |
| ATOM | 718 | CB | THR | A1926 | 28.800 | −49.969 | 16.325 | 1.00 | 78.79 | C |
| ATOM | 719 | CG2 | THR | A1926 | 28.566 | −49.263 | 17.643 | 1.00 | 77.29 | C |
| ATOM | 720 | OG1 | THR | A1926 | 29.470 | −51.207 | 16.555 | 1.00 | 82.68 | O |
| ATOM | 721 | N | GLY | A1927 | 27.904 | −49.172 | 13.361 | 1.00 | 65.54 | N |
| ATOM | 722 | CA | GLY | A1927 | 28.178 | −49.089 | 11.929 | 1.00 | 64.59 | C |
| ATOM | 723 | C | GLY | A1927 | 26.982 | −48.868 | 11.029 | 1.00 | 64.97 | C |
| ATOM | 724 | O | GLY | A1927 | 25.857 | −48.695 | 11.503 | 1.00 | 63.39 | O |
| ATOM | 725 | N | LYS | A1928 | 27.239 | −48.864 | 9.701 | 1.00 | 60.56 | N |
| ATOM | 726 | CA | LYS | A1928 | 26.218 | −48.721 | 8.658 | 1.00 | 59.23 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 727 | C | LYS | A1928 | 25.210 | −49.864 | 8.763 | 1.00 | 61.78 | C |
|---|---|---|---|---|---|---|---|---|---|---|
| ATOM | 728 | O | LYS | A1928 | 25.538 | −50.940 | 9.270 | 1.00 | 60.25 | O |
| ATOM | 729 | CB | LYS | A1928 | 26.839 | −48.666 | 7.245 | 1.00 | 60.39 | C |
| ATOM | 730 | N | LEU | A1929 | 23.976 | −49.617 | 8.296 | 1.00 | 57.89 | N |
| ATOM | 731 | CA | LEU | A1929 | 22.897 | −50.592 | 8.348 | 1.00 | 56.42 | C |
| ATOM | 732 | C | LEU | A1929 | 21.923 | −50.268 | 7.284 | 1.00 | 59.09 | C |
| ATOM | 733 | O | LEU | A1929 | 21.335 | −49.195 | 7.310 | 1.00 | 58.56 | O |
| ATOM | 734 | CB | LEU | A1929 | 22.198 | −50.530 | 9.728 | 1.00 | 55.83 | C |
| ATOM | 735 | CG | LEU | A1929 | 21.041 | −51.480 | 9.959 | 1.00 | 58.31 | C |
| ATOM | 736 | CD1 | LEU | A1929 | 21.545 | −52.881 | 10.187 | 1.00 | 57.78 | C |
| ATOM | 737 | CD2 | LEU | A1929 | 20.225 | −51.027 | 11.131 | 1.00 | 58.04 | C |
| ATOM | 738 | N | ILE | A1930 | 21.719 | −51.192 | 6.363 | 1.00 | 57.06 | N |
| ATOM | 739 | CA | ILE | A1930 | 20.741 | −50.991 | 5.293 | 1.00 | 57.30 | C |
| ATOM | 740 | C | ILE | A1930 | 19.595 | −51.942 | 5.465 | 1.00 | 65.34 | C |
| ATOM | 741 | O | ILE | A1930 | 19.820 | −53.149 | 5.577 | 1.00 | 65.98 | O |
| ATOM | 742 | CB | ILE | A1930 | 21.339 | −51.081 | 3.860 | 1.00 | 59.05 | C |
| ATOM | 743 | CG1 | ILE | A1930 | 22.521 | −50.122 | 3.683 | 1.00 | 57.50 | C |
| ATOM | 744 | CG2 | ILE | A1930 | 20.259 | −50.831 | 2.791 | 1.00 | 59.96 | C |
| ATOM | 745 | CD1 | ILE | A1930 | 23.672 | −50.776 | 3.340 | 1.00 | 50.54 | C |
| ATOM | 746 | N | ILE | A1931 | 18.371 | −51.403 | 5.465 | 1.00 | 64.55 | N |
| ATOM | 747 | CA | ILE | A1931 | 17.152 | −52.191 | 5.517 | 1.00 | 66.37 | C |
| ATOM | 748 | C | ILE | A1931 | 16.215 | −51.653 | 4.420 | 1.00 | 72.16 | C |
| ATOM | 749 | O | ILE | A1931 | 15.583 | −50.616 | 4.590 | 1.00 | 72.05 | O |
| ATOM | 750 | CB | ILE | A1931 | 16.516 | −52.379 | 6.951 | 1.00 | 70.51 | C |
| ATOM | 751 | CG1 | ILE | A1931 | 15.271 | −53.281 | 6.933 | 1.00 | 72.45 | C |
| ATOM | 752 | CG2 | ILE | A1931 | 16.206 | −51.085 | 7.663 | 1.00 | 72.18 | C |
| ATOM | 753 | CD1 | ILE | A1931 | 15.537 | −54.844 | 7.202 | 1.00 | 90.03 | C |
| ATOM | 754 | N | ASP | A1932 | 16.234 | −52.321 | 3.254 | 1.00 | 71.07 | N |
| ATOM | 755 | CA | ASP | A1932 | 15.409 | −52.040 | 2.068 | 1.00 | 72.94 | C |
| ATOM | 756 | C | ASP | A1932 | 15.519 | −50.582 | 1.582 | 1.00 | 77.63 | C |
| ATOM | 757 | O | ASP | A1932 | 14.544 | −49.814 | 1.658 | 1.00 | 77.05 | O |
| ATOM | 758 | CB | ASP | A1932 | 13.935 | −52.471 | 2.310 | 1.00 | 75.94 | C |
| ATOM | 759 | CG | ASP | A1932 | 13.762 | −53.912 | 2.800 | 1.00 | 96.89 | C |
| ATOM | 760 | OD2 | ASP | A1932 | 12.701 | −54.212 | 3.395 | 1.00 | 109.09 | O |
| ATOM | 761 | OD1 | ASP | A1932 | 14.693 | −54.745 | 2.581 | 1.00 | 97.27 | O |
| ATOM | 762 | N | GLU | A1933 | 16.732 | −50.215 | 1.080 | 1.00 | 74.60 | N |
| ATOM | 763 | CA | GLU | A1933 | 17.115 | −48.867 | 0.616 | 1.00 | 74.59 | C |
| ATOM | 764 | C | GLU | A1933 | 17.523 | −47.908 | 1.761 | 1.00 | 74.85 | C |
| ATOM | 765 | O | GLU | A1933 | 18.496 | −47.166 | 1.613 | 1.00 | 74.64 | O |
| ATOM | 766 | CB | GLU | A1933 | 16.040 | −48.211 | −0.284 | 1.00 | 76.74 | C |
| ATOM | 767 | CG | GLU | A1933 | 16.442 | −48.100 | −1.751 | 1.00 | 94.61 | C |
| ATOM | 768 | CD | GLU | A1933 | 16.270 | −49.365 | −2.574 | 1.00 | 116.46 | C |
| ATOM | 769 | OE1 | GLU | A1933 | 15.106 | −49.727 | −2.864 | 1.00 | 106.09 | O |
| ATOM | 770 | OE2 | GLU | A1933 | 17.296 | −49.984 | −2.945 | 1.00 | 107.14 | O |
| ATOM | 771 | N | ASN | A1934 | 16.773 | −47.915 | 2.882 | 1.00 | 67.82 | N |
| ATOM | 772 | CA | ASN | A1934 | 17.004 | −47.072 | 4.052 | 1.00 | 65.96 | C |
| ATOM | 773 | C | ASN | A1934 | 18.382 | −47.359 | 4.640 | 1.00 | 67.21 | C |
| ATOM | 774 | O | ASN | A1934 | 18.728 | −48.534 | 4.779 | 1.00 | 68.53 | O |
| ATOM | 775 | CB | ASN | A1934 | 15.912 | −47.303 | 5.086 | 1.00 | 65.88 | C |
| ATOM | 776 | CG | ASN | A1934 | 14.507 | −47.134 | 4.537 | 1.00 | 85.69 | C |
| ATOM | 777 | ND2 | ASN | A1934 | 13.757 | −48.232 | 4.509 | 1.00 | 73.05 | N |
| ATOM | 778 | OD1 | ASN | A1934 | 14.084 | −46.035 | 4.123 | 1.00 | 76.06 | O |
| ATOM | 779 | N | ILE | A1935 | 19.199 | −46.295 | 4.903 | 1.00 | 58.46 | N |
| ATOM | 780 | CA | ILE | A1935 | 20.565 | −46.424 | 5.426 | 1.00 | 55.97 | C |
| ATOM | 781 | C | ILE | A1935 | 20.652 | −45.697 | 6.729 | 1.00 | 58.93 | C |
| ATOM | 782 | O | ILE | A1935 | 20.264 | −44.537 | 6.813 | 1.00 | 58.82 | O |
| ATOM | 783 | CB | ILE | A1935 | 21.685 | −45.943 | 4.444 | 1.00 | 58.08 | C |
| ATOM | 784 | CG1 | ILE | A1935 | 21.525 | −46.529 | 3.043 | 1.00 | 58.18 | C |
| ATOM | 785 | CG2 | ILE | A1935 | 23.080 | −46.230 | 4.984 | 1.00 | 56.84 | C |
| ATOM | 786 | CD1 | ILE | A1935 | 21.604 | −45.522 | 1.966 | 1.00 | 63.59 | C |
| ATOM | 787 | N | TYR | A1936 | 21.179 | −46.375 | 7.745 | 1.00 | 55.49 | N |
| ATOM | 788 | CA | TYR | A1936 | 21.345 | −45.838 | 9.088 | 1.00 | 54.87 | C |
| ATOM | 789 | C | TYR | A1936 | 22.789 | −46.027 | 9.496 | 1.00 | 60.31 | C |
| ATOM | 790 | O | TYR | A1936 | 23.436 | −46.975 | 9.050 | 1.00 | 60.14 | O |
| ATOM | 791 | CB | TYR | A1936 | 20.465 | −46.628 | 10.095 | 1.00 | 55.07 | C |
| ATOM | 792 | CG | TYR | A1936 | 18.974 | −46.663 | 9.813 | 1.00 | 55.90 | C |
| ATOM | 793 | CD1 | TYR | A1936 | 18.406 | −47.704 | 9.086 | 1.00 | 57.65 | C |
| ATOM | 794 | CD2 | TYR | A1936 | 18.116 | −45.721 | 10.374 | 1.00 | 56.74 | C |
| ATOM | 795 | CE1 | TYR | A1936 | 17.030 | −47.768 | 8.865 | 1.00 | 58.95 | C |
| ATOM | 796 | CE2 | TYR | A1936 | 16.741 | −45.770 | 10.155 | 1.00 | 57.39 | C |
| ATOM | 797 | CZ | TYR | A1936 | 16.202 | −46.794 | 9.397 | 1.00 | 66.98 | C |
| ATOM | 798 | OH | TYR | A1936 | 14.850 | −46.850 | 9.182 | 1.00 | 71.95 | O |
| ATOM | 799 | N | TYR | A1937 | 23.288 | −45.158 | 10.373 | 1.00 | 57.35 | N |
| ATOM | 800 | CA | TYR | A1937 | 24.595 | −45.359 | 10.979 | 1.00 | 57.23 | C |
| ATOM | 801 | C | TYR | A1937 | 24.379 | −45.388 | 12.482 | 1.00 | 62.50 | C |
| ATOM | 802 | O | TYR | A1937 | 23.817 | −44.438 | 13.049 | 1.00 | 62.48 | O |
| ATOM | 803 | CB | TYR | A1937 | 25.678 | −44.347 | 10.565 | 1.00 | 57.90 | C |

TABLE 1-continued

Three-dimensional crystal coordinate for anti-TcdB antibody beziotoxumab Fab –C. difficile toxin B (TcdB$^{(1834-2101)}$) complex.

| ATOM | 804 | CG  | TYR | A1937 | 26.976 | −44.546 | 11.325 | 1.00 | 60.14  | C |
|------|-----|-----|-----|-------|--------|---------|--------|------|--------|---|
| ATOM | 805 | CD1 | TYR | A1937 | 27.904 | −45.508 | 10.926 | 1.00 | 62.03  | C |
| ATOM | 806 | CD2 | TYR | A1937 | 27.245 | −43.823 | 12.484 | 1.00 | 61.44  | C |
| ATOM | 807 | CE1 | TYR | A1937 | 29.083 | −45.722 | 11.647 | 1.00 | 62.54  | C |
| ATOM | 808 | CE2 | TYR | A1937 | 28.419 | −44.026 | 13.213 | 1.00 | 62.71  | C |
| ATOM | 809 | CZ  | TYR | A1937 | 29.337 | −44.976 | 12.790 | 1.00 | 71.58  | C |
| ATOM | 810 | OH  | TYR | A1937 | 30.494 | −45.170 | 13.519 | 1.00 | 73.68  | O |
| ATOM | 811 | N   | PHE | A1938 | 24.788 | −46.503 | 13.111 | 1.00 | 58.70  | N |
| ATOM | 812 | CA  | PHE | A1938 | 24.672 | −46.708 | 14.527 | 1.00 | 58.43  | C |
| ATOM | 813 | C   | PHE | A1938 | 25.935 | −46.315 | 15.225 | 1.00 | 68.21  | C |
| ATOM | 814 | O   | PHE | A1938 | 26.971 | −46.976 | 15.071 | 1.00 | 69.26  | O |
| ATOM | 815 | CB  | PHE | A1938 | 24.277 | −48.143 | 14.805 | 1.00 | 59.72  | C |
| ATOM | 816 | CG  | PHE | A1938 | 22.783 | −48.288 | 14.923 | 1.00 | 61.80  | C |
| ATOM | 817 | CD1 | PHE | A1938 | 21.948 | −47.978 | 13.850 | 1.00 | 64.96  | C |
| ATOM | 818 | CD2 | PHE | A1938 | 22.202 | −48.707 | 16.113 | 1.00 | 63.85  | C |
| ATOM | 819 | CE1 | PHE | A1938 | 20.565 | −48.086 | 13.967 | 1.00 | 65.45  | C |
| ATOM | 820 | CE2 | PHE | A1938 | 20.814 | −48.823 | 16.225 | 1.00 | 66.68  | C |
| ATOM | 821 | CZ  | PHE | A1938 | 20.006 | −48.516 | 15.152 | 1.00 | 64.50  | C |
| ATOM | 822 | N   | ASP | A1939 | 25.851 | −45.216 | 15.990 | 1.00 | 68.18  | N |
| ATOM | 823 | CA  | ASP | A1939 | 26.935 | −44.651 | 16.795 | 1.00 | 70.26  | C |
| ATOM | 824 | C   | ASP | A1939 | 27.442 | −45.610 | 17.884 | 1.00 | 77.91  | C |
| ATOM | 825 | O   | ASP | A1939 | 26.796 | −46.607 | 18.193 | 1.00 | 76.77  | O |
| ATOM | 826 | CB  | ASP | A1939 | 26.512 | −43.304 | 17.412 | 1.00 | 72.96  | C |
| ATOM | 827 | CG  | ASP | A1939 | 27.519 | −42.187 | 17.177 | 1.00 | 94.34  | C |
| ATOM | 828 | OD1 | ASP | A1939 | 27.451 | −41.536 | 16.092 | 1.00 | 95.53  | O |
| ATOM | 829 | OD2 | ASP | A1939 | 28.383 | −41.961 | 18.073 | 1.00 | 103.76 | O |
| ATOM | 830 | N   | ASP | A1940 | 28.593 | −45.273 | 18.485 | 1.00 | 78.81  | N |
| ATOM | 831 | CA  | ASP | A1940 | 29.284 | −46.041 | 19.533 | 1.00 | 79.65  | C |
| ATOM | 832 | C   | ASP | A1940 | 28.426 | −46.436 | 20.735 | 1.00 | 81.05  | C |
| ATOM | 833 | O   | ASP | A1940 | 28.767 | −47.410 | 21.407 | 1.00 | 80.83  | O |
| ATOM | 834 | CB  | ASP | A1940 | 30.540 | −45.292 | 20.001 | 1.00 | 82.43  | C |
| ATOM | 835 | CG  | ASP | A1940 | 31.658 | −45.343 | 18.972 | 1.00 | 99.10  | C |
| ATOM | 836 | OD2 | ASP | A1940 | 32.188 | −44.264 | 18.619 | 1.00 | 107.14 | O |
| ATOM | 837 | OD1 | ASP | A1940 | 32.001 | −46.467 | 18.515 | 1.00 | 99.97  | O |
| ATOM | 838 | N   | ASN | A1941 | 27.312 | −45.705 | 20.987 | 1.00 | 75.06  | N |
| ATOM | 839 | CA  | ASN | A1941 | 26.387 | −45.966 | 22.090 | 1.00 | 73.29  | C |
| ATOM | 840 | C   | ASN | A1941 | 25.300 | −47.012 | 21.715 | 1.00 | 75.99  | C |
| ATOM | 841 | O   | ASN | A1941 | 24.380 | −47.263 | 22.497 | 1.00 | 75.00  | O |
| ATOM | 842 | CB  | ASN | A1941 | 25.798 | −44.648 | 22.641 | 1.00 | 70.43  | C |
| ATOM | 843 | CG  | ASN | A1941 | 24.805 | −43.906 | 21.770 | 1.00 | 88.96  | C |
| ATOM | 844 | ND2 | ASN | A1941 | 23.974 | −43.089 | 22.412 | 1.00 | 78.77  | N |
| ATOM | 845 | OD1 | ASN | A1941 | 24.795 | −44.000 | 20.537 | 1.00 | 84.32  | O |
| ATOM | 846 | N   | TYR | A1942 | 25.484 | −47.688 | 20.551 | 1.00 | 71.77  | N |
| ATOM | 847 | CA  | TYR | A1942 | 24.599 | −48.703 | 19.964 | 1.00 | 70.37  | C |
| ATOM | 848 | C   | TYR | A1942 | 23.232 | −48.123 | 19.553 | 1.00 | 70.26  | C |
| ATOM | 849 | O   | TYR | A1942 | 22.220 | −48.839 | 19.528 | 1.00 | 70.22  | O |
| ATOM | 850 | CB  | TYR | A1942 | 24.462 | −49.937 | 20.866 | 1.00 | 72.30  | C |
| ATOM | 851 | CG  | TYR | A1942 | 25.752 | −50.370 | 21.524 | 1.00 | 75.37  | C |
| ATOM | 852 | CD1 | TYR | A1942 | 26.825 | −50.833 | 20.766 | 1.00 | 77.65  | C |
| ATOM | 853 | CD2 | TYR | A1942 | 25.890 | −50.354 | 22.908 | 1.00 | 76.42  | C |
| ATOM | 854 | CE1 | TYR | A1942 | 28.007 | −51.264 | 21.368 | 1.00 | 78.28  | C |
| ATOM | 855 | CE2 | TYR | A1942 | 27.063 | −50.792 | 23.524 | 1.00 | 77.58  | C |
| ATOM | 856 | CZ  | TYR | A1942 | 28.127 | −51.235 | 22.748 | 1.00 | 84.39  | C |
| ATOM | 857 | OH  | TYR | A1942 | 29.299 | −51.645 | 23.343 | 1.00 | 82.61  | O |
| ATOM | 858 | N   | ARG | A1943 | 23.224 | −46.817 | 19.213 | 1.00 | 63.25  | N |
| ATOM | 859 | CA  | ARG | A1943 | 22.045 | −46.080 | 18.795 | 1.00 | 61.71  | C |
| ATOM | 860 | C   | ARG | A1943 | 22.272 | −45.255 | 17.523 | 1.00 | 66.12  | C |
| ATOM | 861 | O   | ARG | A1943 | 23.375 | −44.797 | 17.268 | 1.00 | 65.87  | O |
| ATOM | 862 | CB  | ARG | A1943 | 21.502 | −45.241 | 19.944 | 1.00 | 58.57  | C |
| ATOM | 863 | CG  | ARG | A1943 | 20.426 | −45.994 | 20.729 | 1.00 | 60.99  | C |
| ATOM | 864 | CD  | ARG | A1943 | 20.663 | −45.808 | 22.199 | 1.00 | 64.87  | C |
| ATOM | 865 | NE  | ARG | A1943 | 20.002 | −46.794 | 23.064 | 1.00 | 68.43  | N |
| ATOM | 866 | CZ  | ARG | A1943 | 20.379 | −48.055 | 23.251 | 1.00 | 81.62  | C |
| ATOM | 867 | NH1 | ARG | A1943 | 19.755 | −48.812 | 24.139 | 1.00 | 80.20  | N |
| ATOM | 868 | NH2 | ARG | A1943 | 21.360 | −48.582 | 22.523 | 1.00 | 67.07  | N |
| ATOM | 869 | N   | GLY | A1944 | 21.232 | −45.138 | 16.711 | 1.00 | 63.56  | N |
| ATOM | 870 | CA  | GLY | A1944 | 21.253 | −44.435 | 15.439 | 1.00 | 63.83  | C |
| ATOM | 871 | C   | GLY | A1944 | 21.615 | −42.971 | 15.552 | 1.00 | 70.56  | C |
| ATOM | 872 | O   | GLY | A1944 | 21.069 | −42.234 | 16.394 | 1.00 | 70.99  | O |
| ATOM | 873 | N   | ALA | A1945 | 22.558 | −42.559 | 14.688 | 1.00 | 67.20  | N |
| ATOM | 874 | CA  | ALA | A1945 | 23.054 | −41.183 | 14.604 | 1.00 | 66.16  | C |
| ATOM | 875 | C   | ALA | A1945 | 22.162 | −40.359 | 13.696 | 1.00 | 68.46  | C |
| ATOM | 876 | O   | ALA | A1945 | 21.486 | −40.906 | 12.816 | 1.00 | 69.25  | O |
| ATOM | 877 | CB  | ALA | A1945 | 24.486 | −41.163 | 14.084 | 1.00 | 66.46  | C |
| ATOM | 878 | N   | VAL | A1946 | 22.147 | −39.045 | 13.938 | 1.00 | 62.58  | N |
| ATOM | 879 | CA  | VAL | A1946 | 21.400 | −38.055 | 13.157 | 1.00 | 61.13  | C |
| ATOM | 880 | C   | VAL | A1946 | 22.370 | −36.957 | 12.668 | 1.00 | 62.84  | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 881 | O | VAL | A1946 | 23.464 | −36.775 | 13.232 | 1.00 | 62.98 | O |
|---|---|---|---|---|---|---|---|---|---|---|
| ATOM | 882 | CB | VAL | A1946 | 20.125 | −37.483 | 13.864 | 1.00 | 64.42 | C |
| ATOM | 883 | CG1 | VAL | A1946 | 19.070 | −38.563 | 14.084 | 1.00 | 64.21 | C |
| ATOM | 884 | CG2 | VAL | A1946 | 20.458 | −36.788 | 15.177 | 1.00 | 64.08 | C |
| ATOM | 885 | N | GLU | A1947 | 21.978 | −36.270 | 11.599 | 1.00 | 56.36 | N |
| ATOM | 886 | CA | GLU | A1947 | 22.704 | −35.178 | 10.982 | 1.00 | 55.60 | C |
| ATOM | 887 | C | GLU | A1947 | 24.022 | −35.648 | 10.307 | 1.00 | 60.50 | C |
| ATOM | 888 | O | GLU | A1947 | 24.061 | −36.765 | 9.783 | 1.00 | 59.87 | O |
| ATOM | 889 | CB | GLU | A1947 | 22.884 | −34.021 | 11.970 | 1.00 | 56.84 | C |
| ATOM | 890 | CG | GLU | A1947 | 21.532 | −33.481 | 12.425 | 1.00 | 66.55 | C |
| ATOM | 891 | CD | GLU | A1947 | 21.506 | −32.272 | 13.338 | 1.00 | 87.79 | C |
| ATOM | 892 | OE1 | GLU | A1947 | 22.580 | −31.859 | 13.834 | 1.00 | 101.28 | O |
| ATOM | 893 | OE2 | GLU | A1947 | 20.394 | −31.748 | 13.572 | 1.00 | 74.60 | O |
| ATOM | 894 | N | TRP | A1948 | 25.059 | −34.779 | 10.241 | 1.00 | 57.19 | N |
| ATOM | 895 | CA | TRP | A1948 | 26.324 | −35.059 | 9.549 | 1.00 | 56.03 | C |
| ATOM | 896 | C | TRP | A1948 | 27.208 | −36.088 | 10.210 | 1.00 | 60.67 | C |
| ATOM | 897 | O | TRP | A1948 | 27.673 | −35.894 | 11.329 | 1.00 | 61.10 | O |
| ATOM | 898 | CB | TRP | A1948 | 27.136 | −33.789 | 9.299 | 1.00 | 54.14 | C |
| ATOM | 899 | CG | TRP | A1948 | 26.423 | −32.747 | 8.495 | 1.00 | 55.11 | C |
| ATOM | 900 | CD1 | TRP | A1948 | 25.843 | −31.605 | 8.962 | 1.00 | 57.99 | C |
| ATOM | 901 | CD2 | TRP | A1948 | 26.254 | −32.732 | 7.073 | 1.00 | 55.01 | C |
| ATOM | 902 | CE2 | TRP | A1948 | 25.581 | −31.538 | 6.744 | 1.00 | 58.85 | C |
| ATOM | 903 | CE3 | TRP | A1948 | 26.594 | −33.621 | 6.043 | 1.00 | 56.30 | C |
| ATOM | 904 | NE1 | TRP | A1948 | 25.323 | −30.879 | 7.919 | 1.00 | 57.63 | N |
| ATOM | 905 | CZ2 | TRP | A1948 | 25.211 | −31.230 | 5.435 | 1.00 | 58.04 | C |
| ATOM | 906 | CZ3 | TRP | A1948 | 26.284 | −33.277 | 4.740 | 1.00 | 57.66 | C |
| ATOM | 907 | CH2 | TRP | A1948 | 25.596 | −32.098 | 4.447 | 1.00 | 58.07 | C |
| ATOM | 908 | N | LYS | A1949 | 27.484 | −37.162 | 9.485 | 1.00 | 57.22 | N |
| ATOM | 909 | CA | LYS | A1949 | 28.391 | −38.205 | 9.911 | 1.00 | 56.77 | C |
| ATOM | 910 | C | LYS | A1949 | 29.356 | −38.479 | 8.744 | 1.00 | 61.49 | C |
| ATOM | 911 | O | LYS | A1949 | 28.903 | −38.602 | 7.601 | 1.00 | 60.78 | O |
| ATOM | 912 | CB | LYS | A1949 | 27.623 | −39.474 | 10.332 | 1.00 | 58.12 | C |
| ATOM | 913 | CG | LYS | A1949 | 28.504 | −40.512 | 11.039 | 1.00 | 67.04 | C |
| ATOM | 914 | CD | LYS | A1949 | 28.648 | −40.230 | 12.530 | 1.00 | 73.58 | C |
| ATOM | 915 | CE | LYS | A1949 | 30.039 | −40.476 | 13.051 | 1.00 | 76.23 | C |
| ATOM | 916 | NZ | LYS | A1949 | 30.104 | −40.205 | 14.514 | 1.00 | 79.46 | N |
| ATOM | 917 | N | GLU | A1950 | 30.678 | −38.519 | 9.032 | 1.00 | 58.48 | N |
| ATOM | 918 | CA | GLU | A1950 | 31.712 | −38.827 | 8.049 | 1.00 | 58.74 | C |
| ATOM | 919 | C | GLU | A1950 | 32.032 | −40.311 | 8.144 | 1.00 | 65.36 | C |
| ATOM | 920 | O | GLU | A1950 | 32.503 | −40.799 | 9.183 | 1.00 | 64.40 | O |
| ATOM | 921 | CB | GLU | A1950 | 32.967 | −37.958 | 8.202 | 1.00 | 59.95 | C |
| ATOM | 922 | CG | GLU | A1950 | 33.998 | −38.274 | 7.133 | 1.00 | 71.81 | C |
| ATOM | 923 | CD | GLU | A1950 | 35.020 | −37.210 | 6.790 | 1.00 | 96.69 | C |
| ATOM | 924 | OE1 | GLU | A1950 | 35.476 | −37.195 | 5.623 | 1.00 | 97.28 | O |
| ATOM | 925 | OE2 | GLU | A1950 | 35.386 | −36.410 | 7.680 | 1.00 | 90.81 | O |
| ATOM | 926 | N | LEU | A1951 | 31.714 | −41.034 | 7.061 | 1.00 | 64.06 | N |
| ATOM | 927 | CA | LEU | A1951 | 31.875 | −42.482 | 6.976 | 1.00 | 64.41 | C |
| ATOM | 928 | C | LEU | A1951 | 32.839 | −42.836 | 5.889 | 1.00 | 72.03 | C |
| ATOM | 929 | O | LEU | A1951 | 32.583 | −42.607 | 4.708 | 1.00 | 72.77 | O |
| ATOM | 930 | CB | LEU | A1951 | 30.516 | −43.151 | 6.798 | 1.00 | 64.02 | C |
| ATOM | 931 | CG | LEU | A1951 | 29.559 | −42.933 | 7.945 | 1.00 | 68.17 | C |
| ATOM | 932 | CD1 | LEU | A1951 | 28.242 | −43.590 | 7.679 | 1.00 | 68.46 | C |
| ATOM | 933 | CD2 | LEU | A1951 | 30.168 | −43.391 | 9.245 | 1.00 | 70.31 | C |
| ATOM | 934 | N | ASP | A1952 | 33.977 | −43.381 | 6.296 | 1.00 | 71.11 | N |
| ATOM | 935 | CA | ASP | A1952 | 35.114 | −43.616 | 5.409 | 1.00 | 71.53 | C |
| ATOM | 936 | C | ASP | A1952 | 35.607 | −42.201 | 5.062 | 1.00 | 76.90 | C |
| ATOM | 937 | O | ASP | A1952 | 35.871 | −41.423 | 5.997 | 1.00 | 77.33 | O |
| ATOM | 938 | CB | ASP | A1952 | 34.792 | −44.575 | 4.232 | 1.00 | 72.08 | C |
| ATOM | 939 | CG | ASP | A1952 | 34.624 | −46.006 | 4.748 | 1.00 | 72.73 | C |
| ATOM | 940 | OD2 | ASP | A1952 | 33.837 | −46.787 | 4.121 | 1.00 | 71.67 | O |
| ATOM | 941 | OD1 | ASP | A1952 | 35.272 | −46.350 | 5.796 | 1.00 | 70.63 | O |
| ATOM | 942 | N | GLY | A1953 | 35.636 | −41.824 | 3.805 | 1.00 | 73.37 | N |
| ATOM | 943 | CA | GLY | A1953 | 36.056 | −40.456 | 3.512 | 1.00 | 73.97 | C |
| ATOM | 944 | C | GLY | A1953 | 34.922 | −39.589 | 3.009 | 1.00 | 76.92 | C |
| ATOM | 945 | O | GLY | A1953 | 35.159 | −38.497 | 2.473 | 1.00 | 77.71 | O |
| ATOM | 946 | N | GLU | A1954 | 33.686 | −40.087 | 3.188 | 1.00 | 69.62 | N |
| ATOM | 947 | CA | GLU | A1954 | 32.462 | −39.528 | 2.640 | 1.00 | 68.37 | C |
| ATOM | 948 | C | GLU | A1954 | 31.540 | −38.906 | 3.670 | 1.00 | 69.92 | C |
| ATOM | 949 | O | GLU | A1954 | 31.475 | −39.376 | 4.799 | 1.00 | 70.58 | O |
| ATOM | 950 | CB | GLU | A1954 | 31.701 | −40.645 | 1.899 | 1.00 | 69.92 | C |
| ATOM | 951 | CG | GLU | A1954 | 32.551 | −41.568 | 1.022 | 1.00 | 78.86 | C |
| ATOM | 952 | CD | GLU | A1954 | 31.921 | −42.914 | 0.684 | 1.00 | 105.90 | C |
| ATOM | 953 | OE1 | GLU | A1954 | 31.576 | −43.683 | 1.617 | 1.00 | 93.59 | O |
| ATOM | 954 | OE2 | GLU | A1954 | 31.818 | −43.216 | −0.529 | 1.00 | 98.86 | O |
| ATOM | 955 | N | MET | A1955 | 30.786 | −37.887 | 3.267 | 1.00 | 63.73 | N |
| ATOM | 956 | CA | MET | A1955 | 29.840 | −37.248 | 4.154 | 1.00 | 62.76 | C |
| ATOM | 957 | C | MET | A1955 | 28.462 | −37.738 | 3.881 | 1.00 | 64.75 | C |

TABLE1-continued

Three-dimensional crystal coordinate for anti-TcdB antibody beziotoxumab Fab –*C. difficile* toxin B (TcdB$^{(1834-2101)}$) complex.

| ATOM | 958 | O | MET | A1955 | 28.035 | −37.816 | 2.730 | 1.00 | 63.58 | O |
|------|-----|------|-----|-------|--------|---------|--------|------|-------|---|
| ATOM | 959 | CB | MET | A1955 | 29.889 | −35.731 | 4.028 | 1.00 | 65.81 | C |
| ATOM | 960 | CG | MET | A1955 | 30.971 | −35.128 | 4.839 | 1.00 | 70.52 | C |
| ATOM | 961 | SD | MET | A1955 | 30.495 | −35.065 | 6.561 | 1.00 | 75.31 | S |
| ATOM | 962 | CE | MET | A1955 | 31.954 | −34.368 | 7.225 | 1.00 | 71.92 | C |
| ATOM | 963 | N | HIS | A1956 | 27.751 | −38.043 | 4.958 | 1.00 | 61.88 | N |
| ATOM | 964 | CA | HIS | A1956 | 26.376 | −38.524 | 4.965 | 1.00 | 61.82 | C |
| ATOM | 965 | C | HIS | A1956 | 25.523 | −37.616 | 5.866 | 1.00 | 66.45 | C |
| ATOM | 966 | O | HIS | A1956 | 26.061 | −37.039 | 6.818 | 1.00 | 66.19 | O |
| ATOM | 967 | CB | HIS | A1956 | 26.352 | −39.956 | 5.528 | 1.00 | 62.47 | C |
| ATOM | 968 | CG | HIS | A1956 | 27.010 | −40.966 | 4.642 | 1.00 | 65.48 | C |
| ATOM | 969 | CD2 | HIS | A1956 | 26.457 | −41.819 | 3.750 | 1.00 | 66.88 | C |
| ATOM | 970 | ND1 | HIS | A1956 | 28.380 | −41.166 | 4.667 | 1.00 | 66.97 | N |
| ATOM | 971 | CE1 | HIS | A1956 | 28.612 | −42.122 | 3.790 | 1.00 | 66.43 | C |
| ATOM | 972 | NE2 | HIS | A1956 | 27.482 | −42.541 | 3.208 | 1.00 | 66.74 | N |
| ATOM | 973 | N | TYR | A1957 | 24.194 | −37.510 | 5.589 | 1.00 | 62.09 | N |
| ATOM | 974 | CA | TYR | A1957 | 23.285 | −36.736 | 6.441 | 1.00 | 60.53 | C |
| ATOM | 975 | C | TYR | A1957 | 22.072 | −37.566 | 6.793 | 1.00 | 62.47 | C |
| ATOM | 976 | O | TYR | A1957 | 21.194 | −37.773 | 5.961 | 1.00 | 63.68 | O |
| ATOM | 977 | CB | TYR | A1957 | 22.897 | −35.371 | 5.845 | 1.00 | 61.07 | C |
| ATOM | 978 | CG | TYR | A1957 | 22.155 | −34.471 | 6.816 | 1.00 | 62.96 | C |
| ATOM | 979 | CD1 | TYR | A1957 | 22.842 | −33.604 | 7.665 | 1.00 | 63.44 | C |
| ATOM | 980 | CD2 | TYR | A1957 | 20.769 | −34.470 | 6.875 | 1.00 | 65.36 | C |
| ATOM | 981 | CE1 | TYR | A1957 | 22.163 | −32.764 | 8.548 | 1.00 | 63.18 | C |
| ATOM | 982 | CE2 | TYR | A1957 | 20.080 | −33.647 | 7.767 | 1.00 | 65.86 | C |
| ATOM | 983 | CZ | TYR | A1957 | 20.781 | −32.794 | 8.597 | 1.00 | 67.45 | C |
| ATOM | 984 | OH | TYR | A1957 | 20.077 | −31.986 | 9.446 | 1.00 | 66.78 | O |
| ATOM | 985 | N | PHE | A1958 | 22.027 | −38.039 | 8.032 | 1.00 | 55.34 | N |
| ATOM | 986 | CA | PHE | A1958 | 20.937 | −38.837 | 8.571 | 1.00 | 52.89 | C |
| ATOM | 987 | C | PHE | A1958 | 19.818 | −37.931 | 9.071 | 1.00 | 54.94 | C |
| ATOM | 988 | O | PHE | A1958 | 20.089 | −36.950 | 9.739 | 1.00 | 53.78 | O |
| ATOM | 989 | CB | PHE | A1958 | 21.485 | −39.771 | 9.672 | 1.00 | 54.02 | C |
| ATOM | 990 | CG | PHE | A1958 | 22.501 | −40.749 | 9.112 | 1.00 | 54.43 | C |
| ATOM | 991 | CD1 | PHE | A1958 | 22.093 | −41.877 | 8.411 | 1.00 | 56.86 | C |
| ATOM | 992 | CD2 | PHE | A1958 | 23.859 | −40.501 | 9.221 | 1.00 | 56.10 | C |
| ATOM | 993 | CE1 | PHE | A1958 | 23.024 | −42.753 | 7.858 | 1.00 | 58.09 | C |
| ATOM | 994 | CE2 | PHE | A1958 | 24.795 | −41.366 | 8.639 | 1.00 | 59.25 | C |
| ATOM | 995 | CZ | PHE | A1958 | 24.372 | −42.482 | 7.959 | 1.00 | 57.43 | C |
| ATOM | 996 | N | SER | A1959 | 18.565 | −38.232 | 8.709 | 1.00 | 52.58 | N |
| ATOM | 997 | CA | SER | A1959 | 17.379 | −37.464 | 9.082 | 1.00 | 52.44 | C |
| ATOM | 998 | C | SER | A1959 | 17.233 | −37.319 | 10.599 | 1.00 | 57.28 | C |
| ATOM | 999 | O | SER | A1959 | 17.209 | −38.334 | 11.297 | 1.00 | 55.50 | O |
| ATOM | 1000 | CB | SER | A1959 | 16.124 | −38.120 | 8.510 | 1.00 | 56.50 | C |
| ATOM | 1001 | OG | SER | A1959 | 14.919 | −37.533 | 8.981 | 1.00 | 67.89 | O |
| ATOM | 1002 | N | PRO | A1960 | 17.091 | −36.069 | 11.127 | 1.00 | 55.78 | N |
| ATOM | 1003 | CA | PRO | A1960 | 16.858 | −35.897 | 12.567 | 1.00 | 55.22 | C |
| ATOM | 1004 | C | PRO | A1960 | 15.485 | −36.436 | 12.967 | 1.00 | 58.25 | C |
| ATOM | 1005 | O | PRO | A1960 | 15.249 | −36.684 | 14.145 | 1.00 | 58.44 | O |
| ATOM | 1006 | CB | PRO | A1960 | 16.929 | −34.373 | 12.754 | 1.00 | 56.75 | C |
| ATOM | 1007 | CG | PRO | A1960 | 17.540 | −33.839 | 11.503 | 1.00 | 60.76 | C |
| ATOM | 1008 | CD | PRO | A1960 | 17.063 | −34.758 | 10.445 | 1.00 | 57.24 | C |
| ATOM | 1009 | N | GLU | A1961 | 14.603 | −36.653 | 11.977 | 1.00 | 54.12 | N |
| ATOM | 1010 | CA | GLU | A1961 | 13.259 | −37.171 | 12.197 | 1.00 | 54.74 | C |
| ATOM | 1011 | C | GLU | A1961 | 13.237 | −38.716 | 12.289 | 1.00 | 63.20 | C |
| ATOM | 1012 | O | GLU | A1961 | 12.618 | −39.259 | 13.208 | 1.00 | 63.29 | O |
| ATOM | 1013 | CB | GLU | A1961 | 12.249 | −36.646 | 11.141 | 1.00 | 55.66 | C |
| ATOM | 1014 | CG | GLU | A1961 | 12.643 | −35.377 | 10.385 | 1.00 | 67.10 | C |
| ATOM | 1015 | CD | GLU | A1961 | 12.185 | −34.037 | 10.938 | 1.00 | 99.33 | C |
| ATOM | 1016 | OE1 | GLU | A1961 | 13.026 | −33.113 | 11.053 | 1.00 | 97.73 | O |
| ATOM | 1017 | OE2 | GLU | A1961 | 10.970 | −33.885 | 11.194 | 1.00 | 103.38 | O |
| ATOM | 1018 | N | THR | A1962 | 13.931 | −39.424 | 11.354 | 1.00 | 62.21 | N |
| ATOM | 1019 | CA | THR | A1962 | 13.921 | −40.900 | 11.250 | 1.00 | 61.85 | C |
| ATOM | 1020 | C | THR | A1962 | 15.266 | −41.649 | 11.424 | 1.00 | 67.03 | C |
| ATOM | 1021 | O | THR | A1962 | 15.248 | −42.865 | 11.625 | 1.00 | 68.89 | O |
| ATOM | 1022 | CB | THR | A1962 | 13.330 | −41.302 | 9.902 | 1.00 | 67.88 | C |
| ATOM | 1023 | CG2 | THR | A1962 | 11.909 | −40.811 | 9.714 | 1.00 | 65.44 | C |
| ATOM | 1024 | OG1 | THR | A1962 | 14.147 | −40.761 | 8.865 | 1.00 | 74.94 | O |
| ATOM | 1025 | N | GLY | A1963 | 16.394 | −40.953 | 11.310 | 1.00 | 61.48 | N |
| ATOM | 1026 | CA | GLY | A1963 | 17.717 | −41.569 | 11.417 | 1.00 | 60.32 | C |
| ATOM | 1027 | C | GLY | A1963 | 18.251 | −42.138 | 10.106 | 1.00 | 60.23 | C |
| ATOM | 1028 | O | GLY | A1963 | 19.367 | −42.681 | 10.068 | 1.00 | 60.11 | O |
| ATOM | 1029 | N | LYS | A1964 | 17.441 | −41.999 | 9.028 | 1.00 | 50.80 | N |
| ATOM | 1030 | CA | LYS | A1964 | 17.669 | −42.444 | 7.666 | 1.00 | 48.24 | C |
| ATOM | 1031 | C | LYS | A1964 | 18.485 | −41.436 | 6.888 | 1.00 | 52.23 | C |
| ATOM | 1032 | O | LYS | A1964 | 18.111 | −40.256 | 6.819 | 1.00 | 51.68 | O |
| ATOM | 1033 | CB | LYS | A1964 | 16.312 | −42.580 | 6.942 | 1.00 | 49.00 | C |
| ATOM | 1034 | CG | LYS | A1964 | 15.472 | −43.743 | 7.379 | 1.00 | 52.42 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 1035 | CD | LYS | A1964 | 14.155 | −43.689 | 6.697 | 1.00 | 55.61 | C |
|---|---|---|---|---|---|---|---|---|---|---|
| ATOM | 1036 | CE | LYS | A1964 | 13.155 | −44.590 | 7.367 | 1.00 | 55.85 | C |
| ATOM | 1037 | NZ | LYS | A1964 | 11.824 | −44.471 | 6.729 | 1.00 | 63.14 | N |
| ATOM | 1038 | N | ALA | A1965 | 19.528 | −41.925 | 6.192 | 1.00 | 48.75 | N |
| ATOM | 1039 | CA | ALA | A1965 | 20.402 | −41.133 | 5.322 | 1.00 | 47.45 | C |
| ATOM | 1040 | C | ALA | A1965 | 19.583 | −40.494 | 4.233 | 1.00 | 54.84 | C |
| ATOM | 1041 | O | ALA | A1965 | 18.696 | −41.135 | 3.664 | 1.00 | 57.63 | O |
| ATOM | 1042 | CB | ALA | A1965 | 21.470 | −42.016 | 4.699 | 1.00 | 47.30 | C |
| ATOM | 1043 | N | PHE | A1966 | 19.838 | −39.211 | 3.997 | 1.00 | 49.76 | N |
| ATOM | 1044 | CA | PHE | A1966 | 19.226 | −38.399 | 2.971 | 1.00 | 48.42 | C |
| ATOM | 1045 | C | PHE | A1966 | 19.803 | −38.834 | 1.619 | 1.00 | 56.89 | C |
| ATOM | 1046 | O | PHE | A1966 | 21.003 | −39.141 | 1.522 | 1.00 | 56.73 | O |
| ATOM | 1047 | CB | PHE | A1966 | 19.627 | −36.944 | 3.211 | 1.00 | 49.18 | C |
| ATOM | 1048 | CG | PHE | A1966 | 18.771 | −36.081 | 4.102 | 1.00 | 50.07 | C |
| ATOM | 1049 | CD1 | PHE | A1966 | 17.919 | −36.645 | 5.041 | 1.00 | 52.82 | C |
| ATOM | 1050 | CD2 | PHE | A1966 | 18.838 | −34.693 | 4.021 | 1.00 | 51.50 | C |
| ATOM | 1051 | CE1 | PHE | A1966 | 17.127 | −35.834 | 5.864 | 1.00 | 53.51 | C |
| ATOM | 1052 | CE2 | PHE | A1966 | 18.043 | −33.887 | 4.839 | 1.00 | 53.25 | C |
| ATOM | 1053 | CZ | PHE | A1966 | 17.218 | −34.461 | 5.772 | 1.00 | 51.54 | C |
| ATOM | 1054 | N | LYS | A1967 | 18.955 | −38.799 | 0.565 | 1.00 | 55.58 | N |
| ATOM | 1055 | CA | LYS | A1967 | 19.298 | −39.134 | −0.828 | 1.00 | 54.35 | C |
| ATOM | 1056 | C | LYS | A1967 | 18.771 | −38.019 | −1.751 | 1.00 | 57.80 | C |
| ATOM | 1057 | O | LYS | A1967 | 17.715 | −37.440 | −1.471 | 1.00 | 57.71 | O |
| ATOM | 1058 | CB | LYS | A1967 | 18.698 | −40.501 | −1.226 | 1.00 | 54.73 | C |
| ATOM | 1059 | CG | LYS | A1967 | 19.312 | −41.715 | −0.526 | 1.00 | 47.74 | C |
| ATOM | 1060 | CD | LYS | A1967 | 18.557 | −42.976 | −0.903 | 1.00 | 58.24 | C |
| ATOM | 1061 | CE | LYS | A1967 | 18.648 | −44.150 | 0.052 | 1.00 | 69.10 | C |
| ATOM | 1062 | NZ | LYS | A1967 | 17.442 | −45.042 | −0.050 | 1.00 | 77.82 | N |
| ATOM | 1063 | N | GLY | A1968 | 19.512 | −37.724 | −2.819 | 1.00 | 53.39 | N |
| ATOM | 1064 | CA | GLY | A1968 | 19.159 | −36.674 | −3.768 | 1.00 | 53.50 | C |
| ATOM | 1065 | C | GLY | A1968 | 19.364 | −35.289 | −3.186 | 1.00 | 59.43 | C |
| ATOM | 1066 | O | GLY | A1968 | 19.989 | −35.154 | −2.128 | 1.00 | 61.08 | O |
| ATOM | 1067 | N | LEU | A1969 | 18.852 | −34.249 | −3.878 | 1.00 | 54.94 | N |
| ATOM | 1068 | CA | LEU | A1969 | 78.935 | −32.837 | −3.462 | 1.00 | 54.72 | C |
| ATOM | 1069 | C | LEU | A1969 | 18.147 | −32.589 | −2.159 | 1.00 | 60.33 | C |
| ATOM | 1070 | O | LEU | A1969 | 16.982 | −32.975 | −2.057 | 1.00 | 60.48 | O |
| ATOM | 1071 | CB | LEU | A1969 | 18.363 | −31.919 | −4.566 | 1.00 | 54.29 | C |
| ATOM | 1072 | CG | LEU | A1969 | 19.156 | −30.677 | −4.984 | 1.00 | 56.57 | C |
| ATOM | 1073 | CD1 | LEU | A1969 | 18.439 | −29.954 | −6.032 | 1.00 | 55.76 | C |
| ATOM | 1074 | CD2 | LEU | A1969 | 19.327 | −29.724 | −3.861 | 1.00 | 58.24 | C |
| ATOM | 1075 | N | ASN | A1970 | 18.770 | −31.934 | −1.178 | 1.00 | 57.17 | N |
| ATOM | 1076 | CA | ASN | A1970 | 18.112 | −31.685 | 0.099 | 1.00 | 57.22 | C |
| ATOM | 1077 | C | ASN | A1970 | 18.538 | −30.394 | 0.744 | 1.00 | 63.19 | C |
| ATOM | 1078 | O | ASN | A1970 | 19.727 | −30.060 | 0.730 | 1.00 | 63.28 | O |
| ATOM | 1079 | CB | ASN | A1970 | 18.446 | −32.801 | 1.067 | 1.00 | 56.06 | C |
| ATOM | 1080 | CG | ASN | A1970 | 17.595 | −34.017 | 0.942 | 1.00 | 78.85 | C |
| ATOM | 1081 | ND2 | ASN | A1970 | 18.194 | −35.120 | 0.467 | 1.00 | 71.39 | N |
| ATOM | 1082 | OD1 | ASN | A1970 | 16.439 | −34.010 | 1.371 | 1.00 | 68.46 | O |
| ATOM | 1083 | N | GLN | A1971 | 17.590 | −29.708 | 1.400 | 1.00 | 60.17 | N |
| ATOM | 1084 | CA | GLN | A1971 | 17.959 | −28.517 | 2.144 | 1.00 | 59.00 | C |
| ATOM | 1085 | C | GLN | A1971 | 18.320 | −28.902 | 3.566 | 1.00 | 63.99 | C |
| ATOM | 1086 | O | GLN | A1971 | 17.560 | −29.609 | 4.253 | 1.00 | 64.68 | O |
| ATOM | 1087 | CB | GLN | A1971 | 16.874 | −27.464 | 2.142 | 1.00 | 59.28 | C |
| ATOM | 1088 | CG | GLN | A1971 | 17.493 | −26.170 | 2.543 | 1.00 | 65.24 | C |
| ATOM | 1089 | CD | GLN | A1971 | 16.698 | −24.963 | 2.241 | 1.00 | 79.09 | C |
| ATOM | 1090 | NE2 | GLN | A1971 | 16.838 | −23.995 | 3.116 | 1.00 | 68.56 | N |
| ATOM | 1091 | OE1 | GLN | A1971 | 16.026 | −24.857 | 1.211 | 1.00 | 79.57 | O |
| ATOM | 1092 | N | ILE | A1972 | 19.514 | −28.470 | 3.984 | 1.00 | 58.99 | N |
| ATOM | 1093 | CA | ILE | A1972 | 20.054 | −28.679 | 5.328 | 1.00 | 57.39 | C |
| ATOM | 1094 | C | ILE | A1972 | 20.467 | −27.289 | 5.775 | 1.00 | 62.78 | C |
| ATOM | 1095 | O | ILE | A1972 | 21.468 | −26.750 | 5.280 | 1.00 | 63.51 | O |
| ATOM | 1096 | CB | ILE | A1972 | 21.219 | −29.690 | 5.348 | 1.00 | 58.90 | C |
| ATOM | 1097 | CG1 | ILE | A1972 | 20.735 | −31.093 | 4.900 | 1.00 | 59.14 | C |
| ATOM | 1098 | CG2 | ILE | A1972 | 21.877 | −29.712 | 6.728 | 1.00 | 57.48 | C |
| ATOM | 1099 | CD1 | ILE | A1972 | 21.789 | −31.994 | 4.331 | 1.00 | 62.82 | C |
| ATOM | 1100 | N | GLY | A1973 | 19.646 | −26.692 | 6.638 | 1.00 | 58.12 | N |
| ATOM | 1101 | CA | GLY | A1973 | 19.877 | −25.336 | 7.091 | 1.00 | 57.82 | C |
| ATOM | 1102 | C | GLY | A1973 | 19.663 | −24.352 | 5.956 | 1.00 | 62.88 | C |
| ATOM | 1103 | O | GLY | A1973 | 18.745 | −24.521 | 5.143 | 1.00 | 62.80 | O |
| ATOM | 1104 | N | ASP | A1974 | 20.523 | −23.342 | 5.862 | 1.00 | 59.68 | N |
| ATOM | 1105 | CA | ASP | A1974 | 20.354 | −22.348 | 4.811 | 1.00 | 60.93 | C |
| ATOM | 1106 | C | ASP | A1974 | 20.836 | −22.821 | 3.421 | 1.00 | 64.59 | C |
| ATOM | 1107 | O | ASP | A1974 | 20.687 | −22.074 | 2.448 | 1.00 | 65.53 | O |
| ATOM | 1108 | CB | ASP | A1974 | 21.017 | −21.011 | 5.217 | 1.00 | 63.96 | C |
| ATOM | 1109 | CG | ASP | A1974 | 20.853 | −20.625 | 6.680 | 1.00 | 80.43 | C |
| ATOM | 1110 | OD1 | ASP | A1974 | 19.726 | −20.806 | 7.228 | 1.00 | 82.68 | O |
| ATOM | 1111 | OD2 | ASP | A1974 | 21.852 | −20.161 | 7.286 | 1.00 | 84.93 | O |

TABLE 1-continued

Three-dimensional crystal coordinate for anti-TcdB antibody beziotoxumab Fab –*C. difficile* toxin B (TcdB$^{(1834-2101)}$) complex.

| | | | | | | | | | |
|---|---|---|---|---|---|---|---|---|---|
| ATOM | 1112 | N   | TYR | A1975 | 21.395 | −24.042 | 3.315  | 1.00 | 58.47  N |
| ATOM | 1113 | CA  | TYR | A1975 | 21.939 | −24.503 | 2.049  | 1.00 | 57.57  C |
| ATOM | 1114 | C   | TYR | A1975 | 21.387 | −25.814 | 1.566  | 1.00 | 60.11  C |
| ATOM | 1115 | O   | TYR | A1975 | 20.805 | −26.591 | 2.334  | 1.00 | 58.70  O |
| ATOM | 1116 | CB  | TYR | A1975 | 23.476 | −24.569 | 2.077  | 1.00 | 59.21  C |
| ATOM | 1117 | CG  | TYR | A1975 | 24.150 | −23.375 | 2.707  | 1.00 | 61.66  C |
| ATOM | 1118 | CD1 | TYR | A1975 | 24.360 | −22.205 | 1.982  | 1.00 | 64.47  C |
| ATOM | 1119 | CD2 | TYR | A1975 | 24.637 | −23.433 | 4.008  | 1.00 | 62.16  C |
| ATOM | 1120 | CE1 | TYR | A1975 | 24.994 | −21.101 | 2.555  | 1.00 | 66.69  C |
| ATOM | 1121 | CE2 | TYR | A1975 | 25.294 | −22.347 | 4.584  | 1.00 | 63.50  C |
| ATOM | 1122 | CZ  | TYR | A1975 | 25.465 | −21.178 | 3.857  | 1.00 | 75.07  C |
| ATOM | 1123 | OH  | TYR | A1975 | 26.083 | −20.090 | 4.429  | 1.00 | 78.62  O |
| ATOM | 1124 | N   | LYS | A1976 | 21.621 | −26.059 | 0.261  | 1.00 | 56.35  N |
| ATOM | 1125 | CA  | LYS | A1976 | 21.221 | −27.257 | −0.448 | 1.00 | 55.88  C |
| ATOM | 1126 | C   | LYS | A1976 | 22.430 | −28.119 | −0.836 | 1.00 | 59.15  C |
| ATOM | 1127 | O   | LYS | A1976 | 23.495 | −27.605 | −1.195 | 1.00 | 58.02  O |
| ATOM | 1128 | CB  | LYS | A1976 | 20.311 | −26.921 | −1.634 | 1.00 | 57.41  C |
| ATOM | 1129 | CG  | LYS | A1976 | 18.927 | −26.466 | −1.177 | 1.00 | 72.70  C |
| ATOM | 1130 | CD  | LYS | A1976 | 17.898 | −26.531 | −2.305 | 1.00 | 85.66  C |
| ATOM | 1131 | CE  | LYS | A1976 | 17.365 | −25.184 | −2.745 | 1.00 | 95.27  C |
| ATOM | 1132 | NZ  | LYS | A1976 | 16.474 | −25.320 | −3.932 | 1.00 | 101.46 N |
| ATOM | 1133 | N   | TYR | A1977 | 22.273 | −29.435 | −0.670 | 1.00 | 56.15  N |
| ATOM | 1134 | CA  | TYR | A1977 | 23.313 | −30.425 | −0.941 | 1.00 | 56.55  C |
| ATOM | 1135 | C   | TYR | A1977 | 22.739 | −31.568 | −1.748 | 1.00 | 61.20  C |
| ATOM | 1136 | O   | TYR | A1977 | 21.550 | −31.882 | −1.617 | 1.00 | 60.82  O |
| ATOM | 1137 | CB  | TYR | A1977 | 23.855 | −31.017 | 0.377  | 1.00 | 57.55  C |
| ATOM | 1138 | CG  | TYR | A1977 | 24.322 | −29.998 | 1.389  | 1.00 | 59.61  C |
| ATOM | 1139 | CD1 | TYR | A1977 | 23.410 | −29.307 | 2.186  | 1.00 | 62.52  C |
| ATOM | 1140 | CD2 | TYR | A1977 | 25.675 | −29.772 | 1.604  | 1.00 | 59.80  C |
| ATOM | 1141 | CE1 | TYR | A1977 | 23.832 | −28.355 | 3.113  | 1.00 | 63.57  C |
| ATOM | 1142 | CE2 | TYR | A1977 | 26.110 | −28.833 | 2.538  | 1.00 | 61.22  C |
| ATOM | 1143 | CZ  | TYR | A1977 | 25.184 | −28.129 | 3.298  | 1.00 | 70.47  C |
| ATOM | 1144 | OH  | TYR | A1977 | 25.591 | −27.203 | 4.233  | 1.00 | 73.27  O |
| ATOM | 1145 | N   | TYR | A1978 | 23.591 | −32.229 | −2.538 | 1.00 | 57.72  N |
| ATOM | 1146 | CA  | TYR | A1978 | 23.170 | −33.413 | −3.260 | 1.00 | 57.97  C |
| ATOM | 1147 | C   | TYR | A1978 | 23.860 | −34.628 | −2.700 | 1.00 | 64.39  C |
| ATOM | 1148 | O   | TYR | A1978 | 25.093 | −34.639 | −2.530 | 1.00 | 64.75  O |
| ATOM | 1149 | CB  | TYR | A1978 | 23.400 | −33.319 | −4.757 | 1.00 | 58.79  C |
| ATOM | 1150 | CG  | TYR | A1978 | 22.932 | −34.534 | −5.534 | 1.00 | 61.35  C |
| ATOM | 1151 | CD1 | TYR | A1978 | 21.624 | −34.633 | −5.991 | 1.00 | 63.50  C |
| ATOM | 1152 | CD2 | TYR | A1978 | 23.815 | −35.562 | −5.859 | 1.00 | 62.47  C |
| ATOM | 1153 | CE1 | TYR | A1978 | 21.200 | −35.731 | −6.738 | 1.00 | 65.59  C |
| ATOM | 1154 | CE2 | TYR | A1978 | 23.403 | −36.665 | −6.606 | 1.00 | 63.23  C |
| ATOM | 1155 | CZ  | TYR | A1978 | 22.098 | −36.738 | −7.057 | 1.00 | 70.87  C |
| ATOM | 1156 | OH  | TYR | A1978 | 21.693 | −37.812 | −7.810 | 1.00 | 71.32  O |
| ATOM | 1157 | N   | PHE | A1979 | 23.049 | −35.674 | −2.468 | 1.00 | 60.07  N |
| ATOM | 1158 | CA  | PHE | A1979 | 23.514 | −36.951 | −1.988 | 1.00 | 60.15  C |
| ATOM | 1159 | C   | PHE | A1979 | 23.181 | −38.060 | −3.008 | 1.00 | 64.56  C |
| ATOM | 1160 | O   | PHE | A1979 | 22.139 | −38.015 | −3.660 | 1.00 | 64.99  O |
| ATOM | 1161 | CB  | PHE | A1979 | 22.874 | −37.249 | −0.625 | 1.00 | 62.31  C |
| ATOM | 1162 | CG  | PHE | A1979 | 23.205 | −36.268 | 0.479  | 1.00 | 63.21  C |
| ATOM | 1163 | CD2 | PHE | A1979 | 22.394 | −35.163 | 0.717  | 1.00 | 64.74  C |
| ATOM | 1164 | CD1 | PHE | A1979 | 24.305 | −36.466 | 1.302  | 1.00 | 64.84  C |
| ATOM | 1165 | CE2 | PHE | A1979 | 22.687 | −34.269 | 1.747  | 1.00 | 65.94  C |
| ATOM | 1166 | CE1 | PHE | A1979 | 24.600 | −35.564 | 2.328  | 1.00 | 64.68  C |
| ATOM | 1167 | CZ  | PHE | A1979 | 23.781 | −34.482 | 2.547  | 1.00 | 63.26  C |
| ATOM | 1168 | N   | ASN | A1980 | 24.075 | −39.050 | −3.132 | 1.00 | 60.41  N |
| ATOM | 1169 | CA  | ASN | A1980 | 24.001 | −40.271 | −3.951 | 1.00 | 59.45  C |
| ATOM | 1170 | C   | ASN | A1980 | 22.751 | −41.067 | −3.662 | 1.00 | 64.68  C |
| ATOM | 1171 | O   | ASN | A1980 | 22.052 | −40.814 | −2.682 | 1.00 | 65.46  O |
| ATOM | 1172 | CB  | ASN | A1980 | 25.092 | −41.207 | −3.430 | 1.00 | 56.24  C |
| ATOM | 1173 | CG  | ASN | A1980 | 26.274 | −41.404 | −4.274 | 1.00 | 71.50  C |
| ATOM | 1174 | ND2 | ASN | A1980 | 27.107 | −42.326 | −3.838 | 1.00 | 61.50  N |
| ATOM | 1175 | OD1 | ASN | A1980 | 26.473 | −40.736 | −5.288 | 1.00 | 73.16  O |
| ATOM | 1176 | N   | SER | A1981 | 22.609 | −42.180 | −4.375 | 1.00 | 60.78  N |
| ATOM | 1177 | CA  | SER | A1981 | 21.596 | −43.190 | −4.125 | 1.00 | 59.49  C |
| ATOM | 1178 | C   | SER | A1981 | 22.025 | −43.942 | −2.840 | 1.00 | 63.66  C |
| ATOM | 1179 | O   | SER | A1981 | 21.195 | −44.585 | −2.190 | 1.00 | 63.35  O |
| ATOM | 1180 | CB  | SER | A1981 | 21.559 | −44.163 | −5.289 | 1.00 | 62.19  C |
| ATOM | 1181 | OG  | SER | A1981 | 20.384 | −44.943 | −5.192 | 1.00 | 77.10  O |
| ATOM | 1182 | N   | ASP | A1982 | 23.340 | −43.850 | −2.489 | 1.00 | 60.12  N |
| ATOM | 1183 | CA  | ASP | A1982 | 23.975 | −44.436 | −1.309 | 1.00 | 60.12  C |
| ATOM | 1184 | C   | ASP | A1982 | 24.109 | −43.426 | −0.160 | 1.00 | 66.41  C |
| ATOM | 1185 | O   | ASP | A1982 | 24.637 | −43.778 | 0.902  | 1.00 | 67.97  O |
| ATOM | 1186 | CB  | ASP | A1982 | 25.361 | −44.972 | −1.654 | 1.00 | 62.27  C |
| ATOM | 1187 | CG  | ASP | A1982 | 25.401 | −46.157 | −2.607 | 1.00 | 81.10  C |
| ATOM | 1188 | OD2 | ASP | A1982 | 26.427 | −46.307 | −3.323 | 1.00 | 88.48  O |

TABLE 1-continued

Three-dimensional crystal coordinate for anti-TcdB antibody beziotoxumab Fab – *C. difficile* toxin B (TcdB$^{(1834-2101)}$) complex.

| ATOM | 1189 | OD1 | ASP | A1982 | 24.428 | −46.974 | −2.601 | 1.00 | 82.62 | O |
|---|---|---|---|---|---|---|---|---|---|---|
| ATOM | 1190 | N | GLY | A1983 | 23.646 | −42.190 | −0.379 | 1.00 | 60.76 | N |
| ATOM | 1191 | CA | GLY | A1983 | 23.690 | −41.126 | 0.614 | 1.00 | 58.72 | C |
| ATOM | 1192 | C | GLY | A1983 | 25.035 | −40.453 | 0.792 | 1.00 | 59.54 | C |
| ATOM | 1193 | O | GLY | A1983 | 25.289 | −39.857 | 1.836 | 1.00 | 60.99 | O |
| ATOM | 1194 | N | VAL | A1984 | 25.889 | −40.508 | −0.220 | 1.00 | 52.51 | N |
| ATOM | 1195 | CA | VAL | A1984 | 27.206 | −39.891 | −0.176 | 1.00 | 51.03 | C |
| ATOM | 1196 | C | VAL | A1984 | 27.046 | −38.491 | −0.733 | 1.00 | 56.04 | C |
| ATOM | 1197 | O | VAL | A1984 | 26.511 | −38.312 | −1.829 | 1.00 | 56.02 | O |
| ATOM | 1198 | CB | VAL | A1984 | 28.263 | −40.707 | −0.975 | 1.00 | 53.26 | C |
| ATOM | 1199 | CG1 | VAL | A1984 | 29.603 | −39.986 | −1.028 | 1.00 | 52.17 | C |
| ATOM | 1200 | CG2 | VAL | A1984 | 28.432 | −42.114 | −0.408 | 1.00 | 52.88 | C |
| ATOM | 1201 | N | MET | A1985 | 27.524 | −37.498 | 0.008 | 1.00 | 52.34 | N |
| ATOM | 1202 | CA | MET | A1985 | 27.436 | −36.122 | −0.449 | 1.00 | 51.55 | C |
| ATOM | 1203 | C | MET | A1985 | 28.354 | −35.889 | −1.650 | 1.00 | 53.34 | C |
| ATOM | 1204 | O | MET | A1985 | 29.502 | −36.321 | −1.638 | 1.00 | 51.51 | O |
| ATOM | 1205 | CB | MET | A1985 | 27.715 | −35.162 | 0.703 | 1.00 | 53.44 | C |
| ATOM | 1206 | CG | MET | A1985 | 27.456 | −33.711 | 0.377 | 1.00 | 55.57 | C |
| ATOM | 1207 | SD | MET | A1985 | 28.437 | −32.760 | 1.530 | 1.00 | 58.50 | S |
| ATOM | 1208 | CE | MET | A1985 | 30.038 | −33.014 | 0.873 | 1.00 | 54.51 | C |
| ATOM | 1209 | N | GLN | A1986 | 27.819 | −35.209 | −2.683 | 1.00 | 49.94 | N |
| ATOM | 1210 | CA | GLN | A1986 | 28.498 | −34.955 | −3.954 | 1.00 | 49.35 | C |
| ATOM | 1211 | C | GLN | A1986 | 29.116 | −33.563 | −4.080 | 1.00 | 50.60 | C |
| ATOM | 1212 | O | GLN | A1986 | 28.587 | −32.594 | −3.551 | 1.00 | 52.36 | O |
| ATOM | 1213 | CB | GLN | A1986 | 27.539 | −35.250 | −5.131 | 1.00 | 51.02 | C |
| ATOM | 1214 | CG | GLN | A1986 | 27.141 | −36.728 | −5.263 | 1.00 | 56.10 | C |
| ATOM | 1215 | CD | GLN | A1986 | 28.352 | −37.610 | −5.385 | 1.00 | 70.58 | C |
| ATOM | 1216 | NE2 | GLN | A1986 | 28.572 | −38.441 | −4.389 | 1.00 | 64.30 | N |
| ATOM | 1217 | OE1 | GLN | A1986 | 29.140 | −37.493 | −6.323 | 1.00 | 66.71 | O |
| ATOM | 1218 | N | LYS | A1987 | 30.246 | −33.479 | −4.769 | 1.00 | 44.53 | N |
| ATOM | 1219 | CA | LYS | A1987 | 31.031 | −32.258 | −4.985 | 1.00 | 43.02 | C |
| ATOM | 1220 | C | LYS | A1987 | 31.318 | −32.179 | −6.476 | 1.00 | 48.88 | C |
| ATOM | 1221 | O | LYS | A1987 | 31.735 | −33.184 | −7.052 | 1.00 | 48.45 | O |
| ATOM | 1222 | CB | LYS | A1987 | 32.365 | −32.313 | −4.223 | 1.00 | 41.77 | C |
| ATOM | 1223 | CG | LYS | A1987 | 32.227 | −32.293 | −2.710 | 1.00 | 44.36 | C |
| ATOM | 1224 | CD | LYS | A1987 | 33.579 | −32.454 | −2.020 | 1.00 | 45.79 | C |
| ATOM | 1225 | CE | LYS | A1987 | 33.416 | −32.706 | −0.544 | 1.00 | 57.88 | C |
| ATOM | 1226 | NZ | LYS | A1987 | 34.595 | −32.224 | 0.242 | 1.00 | 79.76 | N |
| ATOM | 1227 | N | GLY | A1988 | 31.075 | −30.999 | −7.071 | 1.00 | 44.69 | N |
| ATOM | 1228 | CA | GLY | A1988 | 31.255 | −30.711 | −8.487 | 1.00 | 43.03 | C |
| ATOM | 1229 | C | GLY | A1988 | 29.933 | −30.548 | −9.189 | 1.00 | 47.96 | C |
| ATOM | 1230 | O | GLY | A1988 | 28.918 | −30.256 | −8.556 | 1.00 | 47.75 | O |
| ATOM | 1231 | N | PHE | A1989 | 29.940 | −30.720 | −10.505 | 1.00 | 46.88 | N |
| ATOM | 1232 | CA | PHE | A1989 | 28.749 | −30.607 | −11.354 | 1.00 | 46.99 | C |
| ATOM | 1233 | C | PHE | A1989 | 27.952 | −31.899 | −11.294 | 1.00 | 54.23 | C |
| ATOM | 1234 | O | PHE | A1989 | 28.528 | −32.985 | −11.349 | 1.00 | 55.04 | O |
| ATOM | 1235 | CB | PHE | A1989 | 29.131 | −30.253 | −12.795 | 1.00 | 47.90 | C |
| ATOM | 1236 | CG | PHE | A1989 | 29.634 | −28.846 | −13.014 | 1.00 | 48.70 | C |
| ATOM | 1237 | CD1 | PHE | A1989 | 30.985 | −28.543 | −12.885 | 1.00 | 49.98 | C |
| ATOM | 1238 | CD2 | PHE | A1989 | 28.752 | −27.816 | −13.360 | 1.00 | 51.27 | C |
| ATOM | 1239 | CE1 | PHE | A1989 | 31.452 | −27.232 | −13.126 | 1.00 | 53.01 | C |
| ATOM | 1240 | CE2 | PHE | A1989 | 29.214 | −26.509 | −13.585 | 1.00 | 50.91 | C |
| ATOM | 1241 | CZ | PHE | A1989 | 30.559 | −26.225 | −13.473 | 1.00 | 50.31 | C |
| ATOM | 1242 | N | VAL | A1990 | 26.637 | −31.773 | −11.074 | 1.00 | 52.56 | N |
| ATOM | 1243 | CA | VAL | A1990 | 25.676 | −32.875 | −10.951 | 1.00 | 52.79 | C |
| ATOM | 1244 | C | VAL | A1990 | 24.517 | −32.563 | −11.908 | 1.00 | 59.35 | C |
| ATOM | 1245 | O | VAL | A1990 | 24.055 | −31.418 | −11.974 | 1.00 | 58.03 | O |
| ATOM | 1246 | CB | VAL | A1990 | 25.145 | −33.092 | −9.493 | 1.00 | 56.28 | C |
| ATOM | 1247 | CG1 | VAL | A1990 | 24.225 | −34.307 | −9.407 | 1.00 | 56.36 | C |
| ATOM | 1248 | CG2 | VAL | A1990 | 26.271 | −33.232 | −8.487 | 1.00 | 55.94 | C |
| ATOM | 1249 | N | SER | A1991 | 24.066 | −33.587 | −12.658 | 1.00 | 58.11 | N |
| ATOM | 1250 | CA | SER | A1991 | 22.920 | −33.474 | −13.527 | 1.00 | 58.79 | C |
| ATOM | 1251 | C | SER | A1991 | 21.741 | −33.971 | −12.719 | 1.00 | 65.84 | C |
| ATOM | 1252 | O | SER | A1991 | 21.716 | −35.124 | −12.282 | 1.00 | 65.62 | O |
| ATOM | 1253 | CB | SER | A1991 | 23.109 | −34.275 | −14.809 | 1.00 | 64.13 | C |
| ATOM | 1254 | OG | SER | A1991 | 22.845 | −33.473 | −15.955 | 1.00 | 81.21 | O |
| ATOM | 1255 | N | ILE | A1992 | 20.827 | −33.049 | −12.401 | 1.00 | 65.42 | N |
| ATOM | 1256 | CA | ILE | A1992 | 19.593 | −33.322 | −11.662 | 1.00 | 65.97 | C |
| ATOM | 1257 | C | ILE | A1992 | 18.467 | −32.852 | −12.583 | 1.00 | 74.02 | C |
| ATOM | 1258 | O | ILE | A1992 | 18.419 | −31.657 | −12.942 | 1.00 | 74.46 | O |
| ATOM | 1259 | CB | ILE | A1992 | 19.518 | −32.622 | −10.276 | 1.00 | 68.37 | C |
| ATOM | 1260 | CG1 | ILE | A1992 | 20.753 | −32.892 | −9.400 | 1.00 | 68.18 | C |
| ATOM | 1261 | CG2 | ILE | A1992 | 18.232 | −33.017 | −9.561 | 1.00 | 68.94 | C |
| ATOM | 1262 | CD1 | ILE | A1992 | 20.990 | −31.867 | −8.335 | 1.00 | 71.68 | C |
| ATOM | 1263 | N | ASN | A1993 | 17.586 | −33.811 | −12.983 | 1.00 | 71.62 | N |
| ATOM | 1264 | CA | ASN | A1993 | 16.425 | −33.628 | −13.862 | 1.00 | 71.23 | C |
| ATOM | 1265 | C | ASN | A1993 | 16.765 | −32.879 | −15.150 | 1.00 | 74.25 | C |

TABLE 1-continued

Three-dimensional crystal coordinate for anti-TcdB antibody beziotoxumab Fab –C. difficile toxin B (TcdB$^{(1834\text{-}2101)}$) complex.

| ATOM | 1266 | O | ASN | A1993 | 16.075 | −31.937 | −15.538 | 1.00 | 73.64 | O |
|---|---|---|---|---|---|---|---|---|---|---|
| ATOM | 1267 | CB | ASN | A1993 | 15.267 | −32.978 | −13.099 | 1.00 | 73.82 | C |
| ATOM | 1268 | CG | ASN | A1993 | 14.856 | −33.735 | −11.859 | 1.00 | 103.95 | C |
| ATOM | 1269 | ND2 | ASN | A1993 | 14.037 | −33.098 | −11.031 | 1.00 | 95.36 | N |
| ATOM | 1270 | OD1 | ASN | A1993 | 15.271 | −34.881 | −11.625 | 1.00 | 101.60 | O |
| ATOM | 1271 | N | ASP | A1994 | 17.857 | −33.297 | −15.791 | 1.00 | 71.81 | N |
| ATOM | 1272 | CA | ASP | A1994 | 18.366 | −32.739 | −17.044 | 1.00 | 73.11 | C |
| ATOM | 1273 | C | ASP | A1994 | 18.680 | −31.214 | −16.955 | 1.00 | 75.92 | C |
| ATOM | 1274 | O | ASP | A1994 | 18.411 | −30.448 | −17.884 | 1.00 | 75.92 | O |
| ATOM | 1275 | CB | ASP | A1994 | 17.438 | −33.094 | −18.220 | 1.00 | 76.25 | C |
| ATOM | 1276 | CG | ASP | A1994 | 17.441 | −34.587 | −18.511 | 1.00 | 95.12 | C |
| ATOM | 1277 | OD1 | ASP | A1994 | 18.409 | −35.064 | −19.164 | 1.00 | 97.40 | O |
| ATOM | 1278 | OD2 | ASP | A1994 | 16.495 | −35.294 | −18.048 | 1.00 | 99.30 | O |
| ATOM | 1279 | N | ASN | A1995 | 19.294 | −30.813 | −15.826 | 1.00 | 70.56 | N |
| ATOM | 1280 | CA | ASN | A1995 | 19.778 | −29.470 | −15.509 | 1.00 | 69.14 | C |
| ATOM | 1281 | C | ASN | A1995 | 21.062 | −29.671 | −14.726 | 1.00 | 70.06 | C |
| ATOM | 1282 | O | ASN | A1995 | 21.159 | −30.650 | −13.984 | 1.00 | 70.02 | O |
| ATOM | 1283 | CB | ASN | A1995 | 18.759 | −28.669 | −14.684 | 1.00 | 68.41 | C |
| ATOM | 1284 | CG | ASN | A1995 | 17.487 | −28.339 | −15.440 | 1.00 | 87.19 | C |
| ATOM | 1285 | ND2 | ASN | A1995 | 16.373 | −28.927 | −14.988 | 1.00 | 74.42 | N |
| ATOM | 1286 | OD1 | ASN | A1995 | 17.485 | −27.566 | −16.424 | 1.00 | 74.73 | O |
| ATOM | 1287 | N | LYS | A1996 | 22.064 | −28.786 | −14.925 | 1.00 | 62.84 | N |
| ATOM | 1288 | CA | LYS | A1996 | 23.339 | −28.878 | −14.232 | 1.00 | 60.41 | C |
| ATOM | 1289 | C | LYS | A1996 | 23.355 | −27.958 | −12.992 | 1.00 | 63.76 | C |
| ATOM | 1290 | O | LYS | A1996 | 23.006 | −26.783 | −13.095 | 1.00 | 62.93 | O |
| ATOM | 1291 | CB | LYS | A1996 | 24.524 | −28.622 | −15.183 | 1.00 | 60.20 | C |
| ATOM | 1292 | N | HIS | A1997 | 23.719 | −28.532 | −11.809 | 1.00 | 59.65 | N |
| ATOM | 1293 | CA | HIS | A1997 | 23.864 | −27.860 | −10.504 | 1.00 | 58.31 | C |
| ATOM | 1294 | C | HIS | A1997 | 25.324 | −27.939 | −10.057 | 1.00 | 58.88 | C |
| ATOM | 1295 | O | HIS | A1997 | 26.064 | −28.771 | −10.563 | 1.00 | 57.87 | O |
| ATOM | 1296 | CB | HIS | A1997 | 22.954 | −28.490 | −9.441 | 1.00 | 58.78 | C |
| ATOM | 1297 | CG | HIS | A1997 | 21.486 | −28.368 | −9.714 | 1.00 | 62.26 | C |
| ATOM | 1298 | CD2 | HIS | A1997 | 20.735 | −28.929 | −10.691 | 1.00 | 64.39 | C |
| ATOM | 1299 | ND1 | HIS | A1997 | 20.654 | −27.660 | −8.864 | 1.00 | 64.28 | N |
| ATOM | 1300 | CE1 | HIS | A1997 | 19.433 | −27.790 | −9.362 | 1.00 | 63.82 | C |
| ATOM | 1301 | NE2 | HIS | A1997 | 19.429 | −28.546 | −10.461 | 1.00 | 64.22 | N |
| ATOM | 1302 | N | TYR | A1998 | 25.766 | −27.051 | −9.162 | 1.00 | 54.09 | N |
| ATOM | 1303 | CA | TYR | A1998 | 27.161 | −27.109 | −8.764 | 1.00 | 52.35 | C |
| ATOM | 1304 | C | TYR | A1998 | 27.300 | −27.093 | −7.279 | 1.00 | 56.73 | C |
| ATOM | 1305 | O | TYR | A1998 | 26.832 | −26.174 | −6.627 | 1.00 | 56.28 | O |
| ATOM | 1306 | CB | TYR | A1998 | 27.972 | −25.979 | −9.389 | 1.00 | 52.59 | C |
| ATOM | 1307 | CG | TYR | A1998 | 29.436 | −26.056 | −9.036 | 1.00 | 53.78 | C |
| ATOM | 1308 | CD1 | TYR | A1998 | 30.309 | −26.841 | −9.779 | 1.00 | 57.12 | C |
| ATOM | 1309 | CD2 | TYR | A1998 | 29.944 | −25.379 | −7.937 | 1.00 | 53.27 | C |
| ATOM | 1310 | CE1 | TYR | A1998 | 31.661 | −26.919 | −9.459 | 1.00 | 58.19 | C |
| ATOM | 1311 | CE2 | TYR | A1998 | 31.275 | −25.507 | −7.565 | 1.00 | 54.15 | C |
| ATOM | 1312 | CZ | TYR | A1998 | 32.140 | −26.245 | −8.353 | 1.00 | 64.24 | C |
| ATOM | 1313 | OH | TYR | A1998 | 33.469 | −26.332 | −8.033 | 1.00 | 67.81 | O |
| ATOM | 1314 | N | PHE | A1999 | 28.040 | −28.057 | −6.745 | 1.00 | 52.94 | N |
| ATOM | 1315 | CA | PHE | A1999 | 28.250 | −28.189 | −5.317 | 1.00 | 51.51 | C |
| ATOM | 1316 | C | PHE | A1999 | 29.718 | −27.975 | −5.070 | 1.00 | 56.70 | C |
| ATOM | 1317 | O | PHE | A1999 | 30.545 | −28.648 | −5.681 | 1.00 | 57.56 | O |
| ATOM | 1318 | CB | PHE | A1999 | 27.737 | −29.573 | −4.862 | 1.00 | 52.72 | C |
| ATOM | 1319 | CG | PHE | A1999 | 26.289 | −29.804 | −5.248 | 1.00 | 52.20 | C |
| ATOM | 1320 | CD2 | PHE | A1999 | 25.267 | −29.575 | −4.338 | 1.00 | 53.67 | C |
| ATOM | 1321 | CD1 | PHE | A1999 | 25.950 | −30.196 | −6.540 | 1.00 | 53.52 | C |
| ATOM | 1322 | CE2 | PHE | A1999 | 23.929 | −29.719 | −4.718 | 1.00 | 56.91 | C |
| ATOM | 1323 | CE1 | PHE | A1999 | 24.617 | −30.333 | −6.922 | 1.00 | 54.44 | C |
| ATOM | 1324 | CZ | PHE | A1999 | 23.610 | −30.095 | −6.011 | 1.00 | 54.30 | C |
| ATOM | 1325 | N | ASP | A2000 | 30.049 | −26.976 | −4.247 | 1.00 | 53.98 | N |
| ATOM | 1326 | CA | ASP | A2000 | 31.421 | −26.571 | −3.943 | 1.00 | 54.57 | C |
| ATOM | 1327 | C | ASP | A2000 | 32.178 | −27.614 | −3.113 | 1.00 | 60.61 | C |
| ATOM | 1328 | O | ASP | A2000 | 31.686 | −28.726 | −2.934 | 1.00 | 60.58 | O |
| ATOM | 1329 | CB | ASP | A2000 | 31.446 | −25.159 | −3.291 | 1.00 | 57.24 | C |
| ATOM | 1330 | CG | ASP | A2000 | 30.997 | −25.001 | −1.834 | 1.00 | 68.98 | C |
| ATOM | 1331 | OD1 | ASP | A2000 | 30.540 | −25.995 | −1.236 | 1.00 | 68.76 | O |
| ATOM | 1332 | OD2 | ASP | A2000 | 31.135 | −23.882 | −1.289 | 1.00 | 77.15 | O |
| ATOM | 1333 | N | ASP | A2001 | 33.360 | −27.256 | −2.573 | 1.00 | 57.91 | N |
| ATOM | 1334 | CA | ASP | A2001 | 34.137 | −28.202 | −1.802 | 1.00 | 57.49 | C |
| ATOM | 1335 | C | ASP | A2001 | 33.529 | −28.602 | −0.466 | 1.00 | 65.27 | C |
| ATOM | 1336 | O | ASP | A2001 | 34.077 | −29.475 | 0.218 | 1.00 | 66.85 | O |
| ATOM | 1337 | CB | ASP | A2001 | 35.547 | −27.707 | −1.608 | 1.00 | 58.99 | C |
| ATOM | 1338 | CG | ASP | A2001 | 36.490 | −28.883 | −1.506 | 1.00 | 71.35 | C |
| ATOM | 1339 | OD1 | ASP | A2001 | 36.484 | −29.737 | −2.445 | 1.00 | 74.58 | O |
| ATOM | 1340 | OD2 | ASP | A2001 | 37.203 | −28.985 | −0.475 | 1.00 | 67.55 | O |
| ATOM | 1341 | N | SER | A2002 | 32.393 | −27.997 | −0.102 | 1.00 | 62.53 | N |
| ATOM | 1342 | CA | SER | A2002 | 31.705 | −28.273 | 1.154 | 1.00 | 62.55 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 1343 | C   | SER | A2002 | 30.396 | −28.991 | 0.878  | 1.00 | 67.08 | C |
| ---- | ---- | --- | --- | ----- | ------ | ------- | ------ | ---- | ----- | - |
| ATOM | 1344 | O   | SER | A2002 | 29.693 | −29.374 | 1.826  | 1.00 | 67.66 | O |
| ATOM | 1345 | CB  | SER | A2002 | 31.442 | −26.974 | 1.913  | 1.00 | 67.45 | C |
| ATOM | 1346 | OG  | SER | A2002 | 32.510 | −26.048 | 1.793  | 1.00 | 84.93 | O |
| ATOM | 1347 | N   | GLY | A2003 | 30.089 | −29.161 | −0.414 | 1.00 | 62.84 | N |
| ATOM | 1348 | CA  | GLY | A2003 | 28.876 | −29.796 | −0.916 | 1.00 | 61.75 | C |
| ATOM | 1349 | C   | GLY | A2003 | 27.717 | −28.842 | −1.115 | 1.00 | 65.46 | C |
| ATOM | 1350 | O   | GLY | A2003 | 26.656 | −29.278 | −1.544 | 1.00 | 67.99 | O |
| ATOM | 1351 | N   | VAL | A2004 | 27.897 | −27.541 | −0.832 | 1.00 | 59.94 | N |
| ATOM | 1352 | CA  | VAL | A2004 | 26.822 | −26.553 | −0.914 | 1.00 | 59.38 | C |
| ATOM | 1353 | C   | VAL | A2004 | 26.615 | −26.089 | −2.364 | 1.00 | 63.36 | C |
| ATOM | 1354 | O   | VAL | A2004 | 27.537 | −25.697 | −3.079 | 1.00 | 63.35 | O |
| ATOM | 1355 | CB  | VAL | A2004 | 26.879 | −25.376 | 0.132  | 1.00 | 63.17 | C |
| ATOM | 1356 | CG2 | VAL | A2004 | 26.527 | −24.016 | −0.458 | 1.00 | 62.91 | C |
| ATOM | 1357 | CG1 | VAL | A2004 | 28.170 | −25.332 | 0.938  | 1.00 | 62.63 | C |
| ATOM | 1358 | N   | MET | A2005 | 25.339 | −26.133 | −2.738 | 1.00 | 59.58 | N |
| ATOM | 1359 | CA  | MET | A2005 | 24.693 | −25.899 | −4.017 | 1.00 | 59.03 | C |
| ATOM | 1360 | C   | MET | A2005 | 25.060 | −24.701 | −4.869 | 1.00 | 66.21 | C |
| ATOM | 1361 | O   | MET | A2005 | 24.745 | −24.787 | −6.061 | 1.00 | 71.21 | O |
| ATOM | 1362 | CB  | MET | A2005 | 23.208 | −25.838 | −3.826 | 1.00 | 60.68 | C |
| ATOM | 1363 | CG  | MET | A2005 | 22.484 | −26.799 | −4.698 | 1.00 | 62.38 | C |
| ATOM | 1364 | SD  | MET | A2005 | 21.570 | −25.980 | −5.969 | 1.00 | 64.33 | S |
| ATOM | 1365 | CE  | MET | A2005 | 20.450 | −24.961 | −5.015 | 1.00 | 60.32 | C |
| ATOM | 1366 | N   | LYS | A2006 | 25.639 | −23.601 | −4.350 | 1.00 | 57.55 | N |
| ATOM | 1367 | CA  | LYS | A2006 | 26.096 | −22.465 | −5.202 | 1.00 | 54.47 | C |
| ATOM | 1368 | C   | LYS | A2006 | 25.085 | −21.880 | −6.229 | 1.00 | 57.80 | C |
| ATOM | 1369 | O   | LYS | A2006 | 24.940 | −22.385 | −7.331 | 1.00 | 56.76 | O |
| ATOM | 1370 | CB  | LYS | A2006 | 27.389 | −22.831 | −5.930 | 1.00 | 52.79 | C |
| ATOM | 1371 | CG  | LYS | A2006 | 28.579 | −22.037 | −5.438 | 1.00 | 49.86 | C |
| ATOM | 1372 | CD  | LYS | A2006 | 28.780 | −22.114 | −3.944 | 1.00 | 55.43 | C |
| ATOM | 1373 | CE  | LYS | A2006 | 30.004 | −21.381 | −3.461 | 1.00 | 65.33 | C |
| ATOM | 1374 | NZ  | LYS | A2006 | 29.702 | −19.957 | −3.194 | 1.00 | 62.18 | N |
| ATOM | 1375 | N   | VAL | A2007 | 24.455 | −20.757 | −5.865 | 1.00 | 54.81 | N |
| ATOM | 1376 | CA  | VAL | A2007 | 23.468 | −20.032 | −6.665 | 1.00 | 53.82 | C |
| ATOM | 1377 | C   | VAL | A2007 | 24.056 | −18.665 | −7.101 | 1.00 | 56.65 | C |
| ATOM | 1378 | O   | VAL | A2007 | 24.925 | −18.126 | −6.421 | 1.00 | 59.04 | O |
| ATOM | 1379 | CB  | VAL | A2007 | 22.144 | −19.870 | −5.866 | 1.00 | 57.65 | C |
| ATOM | 1380 | CG2 | VAL | A2007 | 22.391 | −19.285 | −4.485 | 1.00 | 57.37 | C |
| ATOM | 1381 | CG1 | VAL | A2007 | 21.390 | −21.194 | −5.746 | 1.00 | 57.47 | C |
| ATOM | 1382 | N   | GLY | A2008 | 23.590 | −18.137 | −8.223 | 1.00 | 49.14 | N |
| ATOM | 1383 | CA  | GLY | A2008 | 24.062 | −16.874 | −8.763 | 1.00 | 47.83 | C |
| ATOM | 1384 | C   | GLY | A2008 | 25.352 | −17.009 | −9.545 | 1.00 | 54.60 | C |
| ATOM | 1385 | O   | GLY | A2008 | 25.707 | −18.102 | −9.995 | 1.00 | 56.66 | O |
| ATOM | 1386 | N   | TYR | A2009 | 26.068 | −15.879 | −9.717 | 1.00 | 50.17 | N |
| ATOM | 1387 | CA  | TYR | A2009 | 27.341 | −15.738 | −10.430| 1.00 | 48.22 | C |
| ATOM | 1388 | C   | TYR | A2009 | 28.410 | −16.339 | −9.547 | 1.00 | 55.94 | C |
| ATOM | 1389 | O   | TYR | A2009 | 28.648 | −15.841 | −8.439 | 1.00 | 58.16 | O |
| ATOM | 1390 | CB  | TYR | A2009 | 27.586 | −14.248 | −10.655| 1.00 | 46.37 | C |
| ATOM | 1391 | CG  | TYR | A2009 | 28.829 | −13.852 | −11.409| 1.00 | 44.66 | C |
| ATOM | 1392 | CD1 | TYR | A2009 | 29.105 | −14.384 | −12.662| 1.00 | 46.56 | C |
| ATOM | 1393 | CD2 | TYR | A2009 | 29.629 | −12.803 | −10.962| 1.00 | 44.53 | C |
| ATOM | 1394 | CE1 | TYR | A2009 | 30.204 | −13.945 | −13.414| 1.00 | 48.87 | C |
| ATOM | 1395 | CE2 | TYR | A2009 | 30.741 | −12.374 | −11.686| 1.00 | 44.67 | C |
| ATOM | 1396 | CZ  | TYR | A2009 | 31.031 | −12.950 | −12.912| 1.00 | 54.56 | C |
| ATOM | 1397 | OH  | TYR | A2009 | 32.146 | −12.525 | −13.611| 1.00 | 57.23 | O |
| ATOM | 1398 | N   | THR | A2010 | 29.021 | −17.441 | −10.017| 1.00 | 51.77 | N |
| ATOM | 1399 | CA  | THR | A2010 | 30.020 | −18.228 | −9.291 | 1.00 | 50.56 | C |
| ATOM | 1400 | C   | THR | A2010 | 31.345 | −18.335 | −10.052| 1.00 | 53.54 | C |
| ATOM | 1401 | O   | THR | A2010 | 31.318 | −18.590 | −11.262| 1.00 | 53.00 | O |
| ATOM | 1402 | CB  | THR | A2010 | 29.416 | −19.655 | −9.035 | 1.00 | 54.43 | C |
| ATOM | 1403 | CG2 | THR | A2010 | 30.334 | −20.552 | −8.246 | 1.00 | 52.98 | C |
| ATOM | 1404 | OG1 | THR | A2010 | 28.143 | −19.583 | −8.371 | 1.00 | 50.54 | O |
| ATOM | 1405 | N   | GLU | A2011 | 32.500 | −18.205 | −9.336 | 1.00 | 50.33 | N |
| ATOM | 1406 | CA  | GLU | A2011 | 33.842 | −18.430 | −9.903 | 1.00 | 50.92 | C |
| ATOM | 1407 | C   | GLU | A2011 | 34.207 | −19.873 | −9.590 | 1.00 | 58.31 | C |
| ATOM | 1408 | O   | GLU | A2011 | 34.321 | −20.221 | −8.412 | 1.00 | 59.70 | O |
| ATOM | 1409 | CB  | GLU | A2011 | 34.911 | −17.514 | −9.288 | 1.00 | 52.51 | C |
| ATOM | 1410 | CG  | GLU | A2011 | 36.294 | −17.634 | −9.940 | 1.00 | 68.56 | C |
| ATOM | 1411 | CD  | GLU | A2011 | 37.394 | −18.423 | −9.230 | 1.00 | 96.01 | C |
| ATOM | 1412 | OE1 | GLU | A2011 | 37.086 | −19.373 | −8.471 | 1.00 | 74.17 | O |
| ATOM | 1413 | OE2 | GLU | A2011 | 38.582 | −18.110 | −9.477 | 1.00 | 95.09 | O |
| ATOM | 1414 | N   | ILE | A2012 | 34.357 | −20.715 | −10.630| 1.00 | 54.36 | N |
| ATOM | 1415 | CA  | ILE | A2012 | 34.729 | −22.126 | −10.517| 1.00 | 53.40 | C |
| ATOM | 1416 | C   | ILE | A2012 | 36.109 | −22.344 | −11.192| 1.00 | 60.91 | C |
| ATOM | 1417 | O   | ILE | A2012 | 36.208 | −22.620 | −12.408| 1.00 | 59.77 | O |
| ATOM | 1418 | CB  | ILE | A2012 | 33.618 | −23.075 | −11.045| 1.00 | 54.97 | C |
| ATOM | 1419 | CG1 | ILE | A2012 | 32.301 | −22.880 | −10.287| 1.00 | 52.76 | C |

TABLE1-continued

Three-dimensional crystal coordinate for anti-TcdB antibody beziotoxumab
Fab –*C. difficile* toxin B (TcdB$^{(1834-2101)}$) complex.

| ATOM | 1420 | CG2 | ILE | A2012 | 34.065 | −24.552 | −11.005 | 1.00 | 56.87 | C |
|---|---|---|---|---|---|---|---|---|---|---|
| ATOM | 1421 | CD1 | ILE | A2012 | 31.135 | −23.462 | −10.993 | 1.00 | 44.20 | C |
| ATOM | 1422 | N | ASP | A2013 | 37.165 | −22.219 | −10.358 | 1.00 | 59.32 | N |
| ATOM | 1423 | CA | ASP | A2013 | 38.574 | −22.370 | −10.685 | 1.00 | 60.74 | C |
| ATOM | 1424 | C | ASP | A2013 | 39.045 | −21.477 | −11.870 | 1.00 | 65.45 | C |
| ATOM | 1425 | O | ASP | A2013 | 39.682 | −21.951 | −12.825 | 1.00 | 65.72 | O |
| ATOM | 1426 | CB | ASP | A2013 | 38.949 | −23.851 | −10.885 | 1.00 | 64.13 | C |
| ATOM | 1427 | CG | ASP | A2013 | 40.096 | −24.305 | −9.984 | 1.00 | 92.25 | C |
| ATOM | 1428 | OD1 | ASP | A2013 | 41.087 | −23.522 | −9.818 | 1.00 | 91.95 | O |
| ATOM | 1429 | OD2 | ASP | A2013 | 40.011 | −25.437 | −9.435 | 1.00 | 109.31 | O |
| ATOM | 1430 | N | GLY | A2014 | 38.767 | −20.180 | −11.756 | 1.00 | 61.81 | N |
| ATOM | 1431 | CA | GLY | A2014 | 39.149 | −19.185 | −12.759 | 1.00 | 61.01 | C |
| ATOM | 1432 | C | GLY | A2014 | 38.155 | −18.948 | −13.883 | 1.00 | 62.02 | C |
| ATOM | 1433 | O | GLY | A2014 | 38.334 | −18.017 | −14.678 | 1.00 | 61.86 | O |
| ATOM | 1434 | N | LYS | A2015 | 37.114 | −19.794 | −13.966 | 1.00 | 56.00 | N |
| ATOM | 1435 | CA | LYS | A2015 | 36.048 | −19.668 | −14.959 | 1.00 | 55.04 | C |
| ATOM | 1436 | C | LYS | A2015 | 34.822 | −19.201 | −14.200 | 1.00 | 58.63 | C |
| ATOM | 1437 | O | LYS | A2015 | 34.727 | −19.486 | −13.004 | 1.00 | 58.83 | O |
| ATOM | 1438 | CB | LYS | A2015 | 35.769 | −21.012 | −15.681 | 1.00 | 56.51 | C |
| ATOM | 1439 | CG | LYS | A2015 | 36.985 | −21.611 | −16.408 | 1.00 | 59.92 | C |
| ATOM | 1440 | CD | LYS | A2015 | 36.581 | −22.580 | −17.534 | 1.00 | 63.81 | C |
| ATOM | 1441 | CE | LYS | A2015 | 37.687 | −23.513 | −17.997 | 1.00 | 67.98 | C |
| ATOM | 1442 | NZ | LYS | A2015 | 38.984 | −22.812 | −18.259 | 1.00 | 76.06 | N |
| ATOM | 1443 | N | HIS | A2016 | 33.903 | −18.451 | −14.865 | 1.00 | 53.30 | N |
| ATOM | 1444 | CA | HIS | A2016 | 32.662 | −17.982 | −14.241 | 1.00 | 51.20 | C |
| ATOM | 1445 | C | HIS | A2016 | 31.429 | −18.582 | −14.864 | 1.00 | 55.01 | C |
| ATOM | 1446 | O | HIS | A2016 | 31.392 | −18.767 | −16.077 | 1.00 | 54.60 | O |
| ATOM | 1447 | CB | HIS | A2016 | 32.570 | −16.483 | −14.263 | 1.00 | 51.00 | C |
| ATOM | 1448 | CG | HIS | A2016 | 33.468 | −15.830 | −13.284 | 1.00 | 53.82 | C |
| ATOM | 1449 | CD2 | HIS | A2016 | 33.213 | −15.434 | −12.017 | 1.00 | 55.64 | C |
| ATOM | 1450 | ND1 | HIS | A2016 | 34.773 | −15.505 | −13.614 | 1.00 | 55.25 | N |
| ATOM | 1451 | CE1 | HIS | A2016 | 35.269 | −14.910 | −12.545 | 1.00 | 55.26 | C |
| ATOM | 1452 | NE2 | HIS | A2016 | 34.369 | −14.857 | −11.548 | 1.00 | 55.83 | N |
| ATOM | 1453 | N | PHE | A2017 | 30.413 | −18.882 | −14.037 | 1.00 | 51.43 | N |
| ATOM | 1454 | CA | PHE | A2017 | 29.160 | −19.503 | −14.471 | 1.00 | 52.05 | C |
| ATOM | 1455 | C | PHE | A2017 | 27.963 | −18.835 | −13.768 | 1.00 | 56.92 | C |
| ATOM | 1456 | O | PHE | A2017 | 28.147 | −18.140 | −12.771 | 1.00 | 58.36 | O |
| ATOM | 1457 | CB | PHE | A2017 | 29.186 | −21.020 | −14.141 | 1.00 | 54.58 | C |
| ATOM | 1458 | CG | PHE | A2017 | 30.335 | −21.795 | −14.760 | 1.00 | 57.05 | C |
| ATOM | 1459 | CD1 | PHE | A2017 | 31.587 | −21.833 | −14.146 | 1.00 | 60.08 | C |
| ATOM | 1460 | CD2 | PHE | A2017 | 30.170 | −22.482 | −15.959 | 1.00 | 59.03 | C |
| ATOM | 1461 | CE1 | PHE | A2017 | 32.658 | −22.520 | −14.740 | 1.00 | 60.49 | C |
| ATOM | 1462 | CE2 | PHE | A2017 | 31.223 | −23.223 | −16.513 | 1.00 | 61.17 | C |
| ATOM | 1463 | CZ | PHE | A2017 | 32.471 | −23.206 | −15.920 | 1.00 | 58.50 | C |
| ATOM | 1464 | N | TYR | A2018 | 26.741 | −19.059 | −14.251 | 1.00 | 51.09 | N |
| ATOM | 1465 | CA | TYR | A2018 | 25.609 | −18.458 | −13.587 | 1.00 | 49.77 | C |
| ATOM | 1466 | C | TYR | A2018 | 24.544 | −19.490 | −13.273 | 1.00 | 54.72 | C |
| ATOM | 1467 | O | TYR | A2018 | 24.000 | −20.101 | −14.188 | 1.00 | 55.73 | O |
| ATOM | 1468 | CB | TYR | A2018 | 25.042 | −17.269 | −14.390 | 1.00 | 51.12 | C |
| ATOM | 1469 | CG | TYR | A2018 | 23.863 | −16.609 | −13.701 | 1.00 | 54.10 | C |
| ATOM | 1470 | CD2 | TYR | A2018 | 24.052 | −15.567 | −12.799 | 1.00 | 53..76 | C |
| ATOM | 1471 | CD1 | TYR | A2018 | 22.568 | −17.097 | −13.870 | 1.00 | 57.03 | C |
| ATOM | 1472 | CE2 | TYR | A2018 | 22.982 | −15.005 | −12.115 | 1.00 | 54.74 | C |
| ATOM | 1473 | CE1 | TYR | A2018 | 21.491 | −16.547 | −13.182 | 1.00 | 57.35 | C |
| ATOM | 1474 | CZ | TYR | A2018 | 21.700 | −15.490 | −12.317 | 1.00 | 65.48 | C |
| ATOM | 1475 | OH | TYR | A2018 | 20.627 | −14.948 | −11.640 | 1.00 | 71.11 | O |
| ATOM | 1476 | N | PHE | A2019 | 24.195 | −19.633 | −11.981 | 1.00 | 50.87 | N |
| ATOM | 1477 | CA | PHE | A2019 | 23.170 | −20.555 | −11.513 | 1.00 | 50.88 | C |
| ATOM | 1478 | C | PHE | A2019 | 21.922 | −19.796 | −11.083 | 1.00 | 57.13 | C |
| ATOM | 1479 | O | PHE | A2019 | 22.044 | −18.755 | −10.447 | 1.00 | 56.70 | O |
| ATOM | 1480 | CB | PHE | A2019 | 23.719 | −21.390 | −10.347 | 1.00 | 52.60 | C |
| ATOM | 1481 | CG | PHE | A2019 | 24.998 | −22.101 | −10.704 | 1.00 | 53.40 | C |
| ATOM | 1482 | CD2 | PHE | A2019 | 26.230 | −21.552 | −10.376 | 1.00 | 55.07 | C |
| ATOM | 1483 | CD1 | PHE | A2019 | 24.973 | −23.297 | −11.414 | 1.00 | 55.70 | C |
| ATOM | 1484 | CE2 | PHE | A2019 | 27.418 | −22.179 | −10.776 | 1.00 | 58.00 | C |
| ATOM | 1485 | CE1 | PHE | A2019 | 26.158 | −23.925 | −11.801 | 1.00 | 56.06 | C |
| ATOM | 1486 | CZ | PHE | A2019 | 27.370 | −23.358 | −11.488 | 1.00 | 55.56 | C |
| ATOM | 1487 | N | ALA | A2020 | 20.715 | −20.323 | −11.415 | 1.00 | 55.88 | N |
| ATOM | 1488 | CA | ALA | A2020 | 19.416 | −19.725 | −11.045 | 1.00 | 56.10 | C |
| ATOM | 1489 | C | ALA | A2020 | 19.248 | −19.822 | −9.514 | 1.00 | 61.31 | C |
| ATOM | 1490 | O | ALA | A2020 | 20.113 | −20.425 | −8.884 | 1.00 | 59.62 | O |
| ATOM | 1491 | CB | ALA | A2020 | 18.283 | −20.439 | −11.766 | 1.00 | 56.52 | C |
| ATOM | 1492 | N | GLU | A2021 | 18.191 | −19.223 | −8.893 | 1.00 | 60.13 | N |
| ATOM | 1493 | CA | GLU | A2021 | 18.134 | −19.300 | −7.423 | 1.00 | 60.62 | C |
| ATOM | 1494 | C | GLU | A2021 | 17.702 | −20.688 | −6.910 | 1.00 | 63.96 | C |
| ATOM | 1495 | O | GLU | A2021 | 17.698 | −20.924 | −5.702 | 1.00 | 63.66 | O |
| ATOM | 1496 | CB | GLU | A2021 | 17.354 | −18.149 | −6.762 | 1.00 | 62.04 | C |

TABLE 1-continued

Three-dimensional crystal coordinate for anti-TcdB antibody beziotoxumab Fab –C. difficile toxin B (TcdB$^{(1834-2101)}$) complex.

| ATOM | 1497 | CG | GLU | A2021 | 15.842 | −18.168 | −6.807 | 1.00 | 74.70 | C |
|------|------|-----|-----|-------|--------|---------|--------|------|-------|---|
| ATOM | 1498 | CD | GLU | A2021 | 15.238 | −16.983 | −6.077 | 1.00 | 90.33 | C |
| ATOM | 1499 | OE1 | GLU | A2021 | 15.370 | −16.927 | −4.830 | 1.00 | 67.45 | O |
| ATOM | 1500 | OE2 | GLU | A2021 | 14.650 | −16.105 | −6.754 | 1.00 | 82.90 | O |
| ATOM | 1501 | N | ASN | A2022 | 17.443 | −21.613 | −7.829 | 1.00 | 60.89 | N |
| ATOM | 1502 | CA | ASN | A2022 | 17.120 | −22.998 | −7.507 | 1.00 | 60.88 | C |
| ATOM | 1503 | C | ASN | A2022 | 18.357 | −23.882 | −7.768 | 1.00 | 64.92 | C |
| ATOM | 1504 | O | ASN | A2022 | 18.326 | −25.070 | −7.458 | 1.00 | 66.81 | O |
| ATOM | 1505 | CB | ASN | A2022 | 15.899 | −23.470 | −8.295 | 1.00 | 60.88 | C |
| ATOM | 1506 | CG | ASN | A2022 | 16.121 | −23.807 | −9.750 | 1.00 | 86.77 | C |
| ATOM | 1507 | ND2 | ASN | A2022 | 15.368 | −24.796 | −10.203 | 1.00 | 83.79 | N |
| ATOM | 1508 | OD1 | ASN | A2022 | 16.891 | −23.165 | −10.486 | 1.00 | 75.47 | O |
| ATOM | 1509 | N | GLY | A2023 | 19.413 | −23.281 | −8.329 | 1.00 | 57.99 | N |
| ATOM | 1510 | CA | GLY | A2023 | 20.695 | −23.913 | −8.590 | 1.00 | 56.88 | C |
| ATOM | 1511 | C | GLY | A2023 | 21.037 | −24.233 | −10.024 | 1.00 | 61.57 | C |
| ATOM | 1512 | O | GLY | A2023 | 22.215 | −24.451 | −10.331 | 1.00 | 61.44 | O |
| ATOM | 1513 | N | GLU | A2024 | 20.006 | −24.280 | −10.902 | 1.00 | 58.19 | N |
| ATOM | 1514 | CA | GLU | A2024 | 20.085 | −24.645 | −12.327 | 1.00 | 56.90 | C |
| ATOM | 1515 | C | GLU | A2024 | 20.930 | −23.699 | −13.135 | 1.00 | 57.03 | C |
| ATOM | 1516 | O | GLU | A2024 | 20.601 | −22.520 | −13.244 | 1.00 | 56.08 | O |
| ATOM | 1517 | CB | GLU | A2024 | 18.682 | −24.743 | −12.957 | 1.00 | 58.47 | C |
| ATOM | 1518 | CG | GLU | A2024 | 17.756 | −25.789 | −12.355 | 1.00 | 70.33 | C |
| ATOM | 1519 | CD | GLU | A2024 | 16.353 | −25.849 | −12.944 | 1.00 | 101.74 | C |
| ATOM | 1520 | OE1 | GLU | A2024 | 15.974 | −24.927 | −13.707 | 1.00 | 91.90 | O |
| ATOM | 1521 | OE2 | GLU | A2024 | 15.617 | −26.806 | −12.605 | 1.00 | 99.51 | O |
| ATOM | 1522 | N | MET | A2025 | 22.002 | −24.223 | −13.731 | 1.00 | 52.80 | N |
| ATOM | 1523 | CA | MET | A2025 | 22.935 | −23.453 | −14.560 | 1.00 | 52.18 | C |
| ATOM | 1524 | C | MET | A2025 | 22.229 | −22.905 | −15.799 | 1.00 | 58.49 | C |
| ATOM | 1525 | O | MET | A2025 | 21.576 | −23.661 | −16.529 | 1.00 | 59.99 | O |
| ATOM | 1526 | CB | MET | A2025 | 24.141 | −24.306 | −14.952 | 1.00 | 53.72 | C |
| ATOM | 1527 | CG | MET | A2025 | 25.019 | −23.652 | −15.963 | 1.00 | 56.59 | C |
| ATOM | 1528 | SD | MET | A2025 | 26.216 | −24.784 | −16.674 | 1.00 | 59.75 | S |
| ATOM | 1529 | CE | MET | A2025 | 27.612 | −24.133 | −15.961 | 1.00 | 56.08 | C |
| ATOM | 1530 | N | GLN | A2026 | 22.377 | −21.592 | −16.026 | 1.00 | 52.73 | N |
| ATOM | 1531 | CA | GLN | A2026 | 21.732 | −20.869 | −17.105 | 1.00 | 51.12 | C |
| ATOM | 1532 | C | GLN | A2026 | 22.687 | −20.387 | −18.197 | 1.00 | 56.02 | C |
| ATOM | 1533 | O | GLN | A2026 | 23.882 | −20.179 | −17.960 | 1.00 | 55.67 | O |
| ATOM | 1534 | CB | GLN | A2026 | 20.971 | −19.673 | −16.518 | 1.00 | 51.69 | C |
| ATOM | 1535 | CG | GLN | A2026 | 19.884 | −20.039 | −15.513 | 1.00 | 59.35 | C |
| ATOM | 1536 | CD | GLN | A2026 | 18.726 | −20.755 | −16.156 | 1.00 | 77.86 | C |
| ATOM | 1537 | NE2 | GLN | A2026 | 18.340 | −21.893 | −15.589 | 1.00 | 57.18 | N |
| ATOM | 1538 | OE1 | GLN | A2026 | 18.176 | −20.312 | −17.173 | 1.00 | 81.68 | O |
| ATOM | 1539 | N | ILE | A2027 | 22.125 | −20.208 | −19.409 | 1.00 | 53.56 | N |
| ATOM | 1540 | CA | ILE | A2027 | 22.773 | −19.658 | −20.589 | 1.00 | 53.00 | C |
| ATOM | 1541 | C | ILE | A2027 | 21.945 | −18.423 | −20.981 | 1.00 | 58.58 | C |
| ATOM | 1542 | O | ILE | A2027 | 20.712 | −18.467 | −21.033 | 1.00 | 58.66 | O |
| ATOM | 1543 | CB | ILE | A2027 | 22.995 | −20.710 | −21.737 | 1.00 | 55.74 | C |
| ATOM | 1544 | CG1 | ILE | A2027 | 24.256 | −21.568 | −21.470 | 1.00 | 55.57 | C |
| ATOM | 1545 | CG2 | ILE | A2027 | 23.160 | −20.039 | −23.114 | 1.00 | 56.49 | C |
| ATOM | 1546 | CD1 | ILE | A2027 | 24.050 | −22.784 | −20.698 | 1.00 | 57.16 | C |
| ATOM | 1547 | N | GLY | A2028 | 22.635 | −17.314 | −21.153 | 1.00 | 56.57 | N |
| ATOM | 1548 | CA | GLY | A2028 | 22.018 | −16.039 | −21.484 | 1.00 | 57.09 | C |
| ATOM | 1549 | C | GLY | A2028 | 22.673 | −14.902 | −20.742 | 1.00 | 61.11 | C |
| ATOM | 1550 | O | GLY | A2028 | 23.735 | −15.099 | −20.139 | 1.00 | 62.34 | O |
| ATOM | 1551 | N | VAL | A2029 | 22.060 | −13.701 | −20.775 | 1.00 | 55.04 | N |
| ATOM | 1552 | CA | VAL | A2029 | 22.668 | −12.599 | −20.050 | 1.00 | 53.03 | C |
| ATOM | 1553 | C | VAL | A2029 | 21.885 | −12.372 | −18.772 | 1.00 | 55.07 | C |
| ATOM | 1554 | O | VAL | A2029 | 20.651 | −12.395 | −18.776 | 1.00 | 55.33 | O |
| ATOM | 1555 | CB | VAL | A2029 | 22.987 | −11.321 | −20.860 | 1.00 | 55.71 | C |
| ATOM | 1556 | CG1 | VAL | A2029 | 22.980 | −11.571 | −22.365 | 1.00 | 54.71 | C |
| ATOM | 1557 | CG2 | VAL | A2029 | 22.115 | −10.149 | −20.467 | 1.00 | 55.20 | C |
| ATOM | 1558 | N | PHE | A2030 | 22.617 | −12.292 | −17.655 | 1.00 | 49.75 | N |
| ATOM | 1559 | CA | PHE | A2030 | 22.011 | −12.156 | −16.335 | 1.00 | 48.74 | C |
| ATOM | 1560 | C | PHE | A2030 | 22.700 | −11.071 | −15.515 | 1.00 | 53.55 | C |
| ATOM | 1561 | O | PHE | A2030 | 23.837 | −10.675 | −15.836 | 1.00 | 52.44 | O |
| ATOM | 1562 | CB | PHE | A2030 | 22.039 | −13.509 | −15.586 | 1.00 | 49.74 | C |
| ATOM | 1563 | CG | PHE | A2030 | 21.358 | −14.633 | −16.326 | 1.00 | 50.78 | C |
| ATOM | 1564 | CD1 | PHE | A2030 | 19.991 | −14.849 | −16.195 | 1.00 | 52.80 | C |
| ATOM | 1565 | CD2 | PHE | A2030 | 22.081 | −15.478 | −17.162 | 1.00 | 52.35 | C |
| ATOM | 1566 | CE1 | PHE | A2030 | 19.362 | −15.887 | −16.882 | 1.00 | 52.55 | C |
| ATOM | 1567 | CE2 | PHE | A2030 | 21.443 | −16.501 | −17.865 | 1.00 | 53.90 | C |
| ATOM | 1568 | CZ | PHE | A2030 | 20.092 | −16.700 | −17.715 | 1.00 | 51.62 | C |
| ATOM | 1569 | N | ASN | A2031 | 22.006 | −10.621 | −14.439 | 1.00 | 51.25 | N |
| ATOM | 1570 | CA | ASN | A2031 | 22.436 | −9.573 | −13.508 | 1.00 | 52.19 | C |
| ATOM | 1571 | C | ASN | A2031 | 23.408 | −10.080 | −12.432 | 1.00 | 61.49 | C |
| ATOM | 1572 | O | ASN | A2031 | 23.061 | −10.752 | −11.446 | 1.00 | 62.97 | O |
| ATOM | 1573 | CB | ASN | A2031 | 21.246 | −8.872 | −12.903 | 1.00 | 48.83 | C |

TABLE 1-continued

Three-dimensional crystal coordinate for anti-TcdB antibody beziotoxumab Fab –C. difficile toxin B (TcdB$^{(1834-2101)}$) complex.

| ATOM | 1574 | CG | ASN | A2031 | 21.309 | −7.382 | −12.873 | 1.00 | 63.49 | C |
|------|------|------|------|-------|--------|--------|---------|------|-------|---|
| ATOM | 1575 | ND2 | ASN | A2031 | 20.138 | −6.761 | −12.977 | 1.00 | 57.32 | N |
| ATOM | 1576 | OD1 | ASN | A2031 | 22.364 | −6.778 | −12.677 | 1.00 | 58.47 | O |
| ATOM | 1577 | N | THR | A2032 | 24.647 | −9.747 | −12.675 | 1.00 | 59.40 | N |
| ATOM | 1578 | CA | THR | A2032 | 25.826 | −10.109 | −11.934 | 1.00 | 59.17 | C |
| ATOM | 1579 | C | THR | A2032 | 26.256 | −8.871 | −11.134 | 1.00 | 65.21 | C |
| ATOM | 1580 | O | THR | A2032 | 25.952 | −7.743 | −11.542 | 1.00 | 65.60 | O |
| ATOM | 1581 | CB | THR | A2032 | 26.774 | −10.554 | −13.040 | 1.00 | 61.72 | C |
| ATOM | 1582 | CG2 | THR | A2032 | 28.187 | −10.124 | −12.864 | 1.00 | 57.19 | C |
| ATOM | 1583 | OG1 | THR | A2032 | 26.629 | −11.952 | −13.235 | 1.00 | 66.21 | O |
| ATOM | 1584 | N | GLU | A2033 | 26.973 | −9.062 | −10.017 | 1.00 | 60.74 | N |
| ATOM | 1585 | CA | GLU | A2033 | 27.479 | −7.929 | −9.236 | 1.00 | 59.29 | C |
| ATOM | 1586 | C | GLU | A2033 | 28.185 | −6.920 | −10.132 | 1.00 | 60.70 | C |
| ATOM | 1587 | O | GLU | A2033 | 28.059 | −5.727 | −9.884 | 1.00 | 61.77 | O |
| ATOM | 1588 | CB | GLU | A2033 | 28.451 | −8.362 | −8.138 | 1.00 | 60.63 | C |
| ATOM | 1589 | CG | GLU | A2033 | 28.022 | −9.580 | −7.363 | 1.00 | 77.29 | C |
| ATOM | 1590 | CD | GLU | A2033 | 28.534 | −10.868 | −7.963 | 1.00 | 98.43 | C |
| ATOM | 1591 | OE1 | GLU | A2033 | 27.720 | −11.606 | −8.569 | 1.00 | 91.79 | O |
| ATOM | 1592 | OE2 | GLU | A2033 | 29.760 | −11.112 | −7.865 | 1.00 | 89.49 | O |
| ATOM | 1593 | N | ASP | A2034 | 28.906 | −7.386 | −11.167 | 1.00 | 55.03 | N |
| ATOM | 1594 | CA | ASP | A2034 | 29.652 | −6.534 | −12.109 | 1.00 | 54.84 | C |
| ATOM | 1595 | C | ASP | A2034 | 28.755 | −5.823 | −13.153 | 1.00 | 57.65 | C |
| ATOM | 1596 | O | ASP | A2034 | 29.201 | −4.880 | −13.808 | 1.00 | 55.98 | O |
| ATOM | 1597 | CB | ASP | A2034 | 30.715 | −7.364 | −12.853 | 1.00 | 56.76 | C |
| ATOM | 1598 | CG | ASP | A2034 | 31.616 | −8.283 | −12.036 | 1.00 | 68.24 | C |
| ATOM | 1599 | OD2 | ASP | A2034 | 32.416 | −9.022 | −12.648 | 1.00 | 76.50 | O |
| ATOM | 1600 | OD1 | ASP | A2034 | 31.553 | −8.234 | −10.790 | 1.00 | 68.79 | O |
| ATOM | 1601 | N | GLY | A2035 | 27.539 | −6.342 | −13.331 | 1.00 | 54.71 | N |
| ATOM | 1602 | CA | GLY | A2035 | 26.542 | −5.874 | −14.291 | 1.00 | 54.30 | C |
| ATOM | 1603 | C | GLY | A2035 | 25.942 | −7.007 | −15.103 | 1.00 | 56.42 | C |
| ATOM | 1604 | O | GLY | A2035 | 25.994 | −8.162 | −14.681 | 1.00 | 55.59 | O |
| ATOM | 1605 | N | PHE | A2036 | 25.379 | −6.702 | −16.282 | 1.00 | 51.80 | N |
| ATOM | 1606 | CA | PHE | A2036 | 24.822 | −7.763 | −17.125 | 1.00 | 50.49 | C |
| ATOM | 1607 | C | PHE | A2036 | 25.938 | −8.487 | −17.889 | 1.00 | 52.45 | C |
| ATOM | 1608 | O | PHE | A2036 | 26.704 | −7.838 | −18.594 | 1.00 | 50.60 | O |
| ATOM | 1609 | CB | PHE | A2036 | 23.726 | −7.231 | −18.067 | 1.00 | 51.72 | C |
| ATOM | 1610 | CG | PHE | A2036 | 22.364 | −7.099 | −17.433 | 1.00 | 52.34 | C |
| ATOM | 1611 | CD2 | PHE | A2036 | 21.934 | −5.884 | −16.920 | 1.00 | 54.07 | C |
| ATOM | 1612 | CD1 | PHE | A2036 | 21.507 | −8.187 | −17.357 | 1.00 | 54.49 | C |
| ATOM | 1613 | CE2 | PHE | A2036 | 20.669 | −5.760 | −16.342 | 1.00 | 56.53 | C |
| ATOM | 1614 | CE1 | PHE | A2036 | 20.238 | −8.059 | −16.791 | 1.00 | 55.23 | C |
| ATOM | 1615 | CZ | PHE | A2036 | 19.822 | −6.843 | −16.296 | 1.00 | 54.62 | C |
| ATOM | 1616 | N | LYS | A2037 | 26.045 | −9.820 | −17.720 | 1.00 | 49.18 | N |
| ATOM | 1617 | CA | LYS | A2037 | 27.099 | −10.632 | −18.345 | 1.00 | 48.90 | C |
| ATOM | 1618 | C | LYS | A2037 | 26.552 | −11.821 | −19.136 | 1.00 | 53.95 | C |
| ATOM | 1619 | O | LYS | A2037 | 25.505 | −12.397 | −18.782 | 1.00 | 53.62 | O |
| ATOM | 1620 | CB | LYS | A2037 | 28.120 | −11.105 | −17.282 | 1.00 | 50.19 | C |
| ATOM | 1621 | CG | LYS | A2037 | 29.103 | −9.998 | −16.888 | 1.00 | 54.68 | C |
| ATOM | 1622 | CD | LYS | A2037 | 30.203 | −10.460 | −15.960 | 1.00 | 57.32 | C |
| ATOM | 1623 | CE | LYS | A2037 | 31.232 | −9.376 | −15.746 | 1.00 | 56.56 | C |
| ATOM | 1624 | NZ | LYS | A2037 | 32.540 | −9.641 | −16.409 | 1.00 | 58.66 | N |
| ATOM | 1625 | N | TYR | A2038 | 27.305 | −12.220 | −20.173 | 1.00 | 48.94 | N |
| ATOM | 1626 | CA | TYR | A2038 | 26.933 | −13.309 | −21.072 | 1.00 | 47.53 | C |
| ATOM | 1627 | C | TYR | A2038 | 27.591 | −14.631 | −20.699 | 1.00 | 53.99 | C |
| ATOM | 1628 | O | TYR | A2038 | 28.812 | −14.712 | −20.557 | 1.00 | 54.38 | O |
| ATOM | 1629 | CB | TYR | A2038 | 27.237 | −12.900 | −22.516 | 1.00 | 46.82 | C |
| ATOM | 1630 | CG | TYR | A2038 | 26.824 | −13.861 | −23.606 | 1.00 | 45.39 | C |
| ATOM | 1631 | CD1 | TYR | A2038 | 25.682 | −14.647 | −23.479 | 1.00 | 46.81 | C |
| ATOM | 1632 | CD2 | TYR | A2038 | 27.522 | −13.917 | −24.804 | 1.00 | 45.68 | C |
| ATOM | 1633 | CE1 | TYR | A2038 | 25.295 | −15.524 | −24.487 | 1.00 | 47.15 | C |
| ATOM | 1634 | CE2 | TYR | A2038 | 27.149 | −14.789 | −25.818 | 1.00 | 46.48 | C |
| ATOM | 1635 | CZ | TYR | A2038 | 26.036 | −15.592 | −25.656 | 1.00 | 55.01 | C |
| ATOM | 1636 | OH | TYR | A2038 | 25.692 | −16.462 | −26.660 | 1.00 | 58.61 | O |
| ATOM | 1637 | N | PHE | A2039 | 26.749 | −15.662 | −20.534 | 1.00 | 51.20 | N |
| ATOM | 1638 | CA | PHE | A2039 | 27.067 | −17.037 | −20.162 | 1.00 | 51.09 | C |
| ATOM | 1639 | C | PHE | A2039 | 26.639 | −17.843 | −21.367 | 1.00 | 57.37 | C |
| ATOM | 1640 | O | PHE | A2039 | 25.468 | −18.157 | −21.537 | 1.00 | 57.49 | O |
| ATOM | 1641 | CB | PHE | A2039 | 26.299 | −17.408 | −18.856 | 1.00 | 52.58 | C |
| ATOM | 1642 | CG | PHE | A2039 | 26.731 | −16.547 | −17.689 | 1.00 | 53.21 | C |
| ATOM | 1643 | CD2 | PHE | A2039 | 26.020 | −15.407 | −17.349 | 1.00 | 55.74 | C |
| ATOM | 1644 | CD1 | PHE | A2039 | 27.914 | −16.812 | −17.008 | 1.00 | 54.65 | C |
| ATOM | 1645 | CE2 | PHE | A2039 | 26.474 | −14.556 | −16.334 | 1.00 | 58.16 | C |
| ATOM | 1646 | CE1 | PHE | A2039 | 28.359 | −15.967 | −15.993 | 1.00 | 55.14 | C |
| ATOM | 1647 | CZ | PHE | A2039 | 27.642 | −14.840 | −15.674 | 1.00 | 55.21 | C |
| ATOM | 1648 | N | ALA | A2040 | 27.580 | −18.058 | −22.269 | 1.00 | 57.25 | N |
| ATOM | 1649 | CA | ALA | A2040 | 27.351 | −18.628 | −23.585 | 1.00 | 58.93 | C |
| ATOM | 1650 | C | ALA | A2040 | 27.348 | −20.149 | −23.665 | 1.00 | 69.55 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 1651 | O | ALA | A2040 | 27.836 | −20.833 | −22.754 | 1.00 | 69.74 | O |
|------|------|------|------|-------|--------|---------|---------|------|--------|---|
| ATOM | 1652 | CB | ALA | A2040 | 28.376 | −18.054 | −24.551 | 1.00 | 59.26 | C |
| ATOM | 1653 | N | HIS | A2041 | 26.845 | −20.677 | −24.818 | 1.00 | 69.60 | N |
| ATOM | 1654 | CA | HIS | A2041 | 26.827 | −22.108 | −25.135 | 1.00 | 69.71 | C |
| ATOM | 1655 | C | HIS | A2041 | 28.253 | −22.575 | −25.465 | 1.00 | 78.41 | C |
| ATOM | 1656 | O | HIS | A2041 | 29.195 | −21.971 | −24.975 | 1.00 | 78.55 | O |
| ATOM | 1657 | CB | HIS | A2041 | 25.832 | −22.428 | −26.262 | 1.00 | 69.44 | C |
| ATOM | 1658 | CG | HIS | A2041 | 24.449 | −22.735 | −25.780 | 1.00 | 72.46 | C |
| ATOM | 1659 | CD2 | HIS | A2041 | 24.031 | −23.619 | −24.841 | 1.00 | 74.28 | C |
| ATOM | 1660 | ND1 | HIS | A2041 | 23.347 | −22.064 | −26.281 | 1.00 | 74.22 | N |
| ATOM | 1661 | CE1 | HIS | A2041 | 22.297 | −22.566 | −25.645 | 1.00 | 73.72 | C |
| ATOM | 1662 | NE2 | HIS | A2041 | 22.660 | −23.504 | −24.765 | 1.00 | 74.05 | N |
| ATOM | 1663 | N | HIS | A2042 | 28.442 | −23.644 | −26.241 | 1.00 | 78.40 | N |
| ATOM | 1664 | CA | HIS | A2042 | 29.804 | −24.063 | −26.496 | 1.00 | 79.37 | C |
| ATOM | 1665 | C | HIS | A2042 | 30.466 | −23.253 | −27.639 | 1.00 | 86.02 | C |
| ATOM | 1666 | O | HIS | A2042 | 31.318 | −22.428 | −27.334 | 1.00 | 86.23 | O |
| ATOM | 1667 | CB | HIS | A2042 | 29.925 | −25.579 | −26.681 | 1.00 | 80.54 | C |
| ATOM | 1668 | CG | HIS | A2042 | 31.335 | −26.012 | −26.932 | 1.00 | 84.40 | C |
| ATOM | 1669 | CD2 | HIS | A2042 | 32.464 | −25.717 | −26.244 | 1.00 | 86.40 | C |
| ATOM | 1670 | ND1 | HIS | A2042 | 31.676 | −26.740 | −28.061 | 1.00 | 86.52 | N |
| ATOM | 1671 | CE1 | HIS | A2042 | 32.991 | −26.885 | −28.009 | 1.00 | 86.11 | C |
| ATOM | 1672 | NE2 | HIS | A2042 | 33.508 | −26.286 | −26.933 | 1.00 | 86.46 | N |
| ATOM | 1673 | N | ASN | A2043 | 30.101 | −23.473 | −28.919 | 1.00 | 84.63 | N |
| ATOM | 1674 | CA | ASN | A2043 | 30.678 | −22.804 | −30.118 | 1.00 | 86.18 | C |
| ATOM | 1675 | C | ASN | A2043 | 32.185 | −23.079 | −30.374 | 1.00 | 95.12 | C |
| ATOM | 1676 | O | ASN | A2043 | 32.958 | −23.346 | −29.436 | 1.00 | 94.58 | O |
| ATOM | 1677 | CB | ASN | A2043 | 30.426 | −21.280 | −30.147 | 1.00 | 82.89 | C |
| ATOM | 1678 | N | GLU | A2044 | 32.591 | −22.950 | −31.682 | 1.00 | 94.34 | N |
| ATOM | 1679 | CA | GLU | A2044 | 33.960 | −23.058 | −32.240 | 1.00 | 94.43 | C |
| ATOM | 1680 | C | GLU | A2044 | 34.916 | −22.103 | −31.498 | 1.00 | 98.22 | C |
| ATOM | 1681 | O | GLU | A2044 | 36.140 | −22.279 | −31.555 | 1.00 | 96.29 | O |
| ATOM | 1682 | CB | GLU | A2044 | 33.941 | −22.688 | −33.741 | 1.00 | 95.83 | C |
| ATOM | 1683 | N | ASP | A2045 | 34.314 | −21.078 | −30.806 | 1.00 | 95.46 | N |
| ATOM | 1684 | CA | ASP | A2045 | 34.942 | −20.066 | −29.950 | 1.00 | 94.81 | C |
| ATOM | 1685 | C | ASP | A2045 | 35.804 | −20.752 | −28.920 | 1.00 | 96.43 | C |
| ATOM | 1686 | O | ASP | A2045 | 35.414 | −21.810 | −28.392 | 1.00 | 94.58 | O |
| ATOM | 1687 | CB | ASP | A2045 | 33.879 | −19.226 | −29.223 | 1.00 | 96.76 | C |
| ATOM | 1688 | N | LEU | A2046 | 36.974 | −20.133 | −28.652 | 1.00 | 92.60 | N |
| ATOM | 1689 | CA | LEU | A2046 | 38.051 | −20.557 | −27.751 | 1.00 | 92.31 | C |
| ATOM | 1690 | C | LEU | A2046 | 37.578 | −21.417 | −26.559 | 1.00 | 96.73 | C |
| ATOM | 1691 | O | LEU | A2046 | 37.399 | −20.900 | −25.446 | 1.00 | 96.85 | O |
| ATOM | 1692 | CB | LEU | A2046 | 38.886 | −19.355 | −27.276 | 1.00 | 92.15 | C |
| ATOM | 1693 | N | GLY | A2047 | 37.387 | −22.720 | −26.848 | 1.00 | 91.70 | N |
| ATOM | 1694 | CA | GLY | A2047 | 36.957 | −23.799 | −25.962 | 1.00 | 90.32 | C |
| ATOM | 1695 | C | GLY | A2047 | 36.295 | −23.375 | −24.672 | 1.00 | 91.31 | C |
| ATOM | 1696 | O | GLY | A2047 | 36.737 | −23.758 | −23.577 | 1.00 | 92.59 | O |
| ATOM | 1697 | N | ASN | A2048 | 35.252 | −22.540 | −24.802 | 1.00 | 82.26 | N |
| ATOM | 1698 | CA | ASN | A2048 | 34.511 | −22.042 | −23.662 | 1.00 | 78.89 | C |
| ATOM | 1699 | C | ASN | A2048 | 33.560 | −23.124 | −23.248 | 1.00 | 78.66 | C |
| ATOM | 1700 | O | ASN | A2048 | 32.809 | −23.646 | −24.077 | 1.00 | 78.93 | O |
| ATOM | 1701 | CB | ASN | A2048 | 33.782 | −20.747 | −23.989 | 1.00 | 74.45 | C |
| ATOM | 1702 | CG | ASN | A2048 | 32.869 | −20.845 | −25.174 | 1.00 | 73.75 | C |
| ATOM | 1703 | ND2 | ASN | A2048 | 31.602 | −20.802 | −24.917 | 1.00 | 51.21 | N |
| ATOM | 1704 | OD1 | ASN | A2048 | 33.292 | −20.986 | −26.323 | 1.00 | 78.62 | O |
| ATOM | 1705 | N | GLU | A2049 | 33.639 | −23.512 | −21.978 | 1.00 | 71.19 | N |
| ATOM | 1706 | CA | GLU | A2049 | 32.793 | −24.542 | −21.411 | 1.00 | 69.30 | C |
| ATOM | 1707 | C | GLU | A2049 | 31.297 | −24.131 | −21.508 | 1.00 | 67.03 | C |
| ATOM | 1708 | O | GLU | A2049 | 30.999 | −22.948 | −21.713 | 1.00 | 67.99 | O |
| ATOM | 1709 | CB | GLU | A2049 | 33.220 | −24.772 | −19.954 | 1.00 | 71.26 | C |
| ATOM | 1710 | CG | GLU | A2049 | 34.386 | −25.741 | −19.771 | 1.00 | 87.40 | C |
| ATOM | 1711 | CD | GLU | A2049 | 34.532 | −26.247 | −18.342 | 1.00 | 122.54 | C |
| ATOM | 1712 | OE1 | GLU | A2049 | 33.518 | −26.701 | −17.759 | 1.00 | 113.07 | O |
| ATOM | 1713 | OE2 | GLU | A2049 | 35.659 | −26.182 | −17.800 | 1.00 | 125.24 | O |
| ATOM | 1714 | N | GLU | A2050 | 30.361 | −25.098 | −21.404 | 1.00 | 57.39 | N |
| ATOM | 1715 | CA | GLU | A2050 | 28.934 | −24.781 | −21.410 | 1.00 | 54.94 | C |
| ATOM | 1716 | C | GLU | A2050 | 28.683 | −23.799 | −20.282 | 1.00 | 60.40 | C |
| ATOM | 1717 | O | GLU | A2050 | 29.255 | −23.971 | −19.194 | 1.00 | 61.58 | O |
| ATOM | 1718 | CB | GLU | A2050 | 28.097 | −26.011 | −21.096 | 1.00 | 55.07 | C |
| ATOM | 1719 | CG | GLU | A2050 | 27.261 | −26.559 | −22.231 | 1.00 | 59.19 | C |
| ATOM | 1720 | CD | GLU | A2050 | 26.291 | −25.646 | −22.941 | 1.00 | 66.58 | C |
| ATOM | 1721 | OE1 | GLU | A2050 | 25.131 | −25.505 | −22.483 | 1.00 | 51.21 | O |
| ATOM | 1722 | OE2 | GLU | A2050 | 26.670 | −25.162 | −24.031 | 1.00 | 59.83 | O |
| ATOM | 1723 | N | GLY | A2051 | 27.871 | −22.773 | −20.554 | 1.00 | 55.18 | N |
| ATOM | 1724 | CA | GLY | A2051 | 27.479 | −21.767 | −19.570 | 1.00 | 53.81 | C |
| ATOM | 1725 | C | GLY | A2051 | 28.583 | −20.945 | −18.939 | 1.00 | 55.28 | C |
| ATOM | 1726 | O | GLY | A2051 | 28.332 | −20.268 | −17.944 | 1.00 | 57.39 | O |
| ATOM | 1727 | N | GLU | A2052 | 29.795 | −21.003 | −19.491 | 1.00 | 49.04 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 1728 | CA  | GLU | A2052 | 30.956 | −20.231 | −19.039 | 1.00 | 48.53  | C |
|------|------|-----|-----|-------|--------|---------|---------|------|--------|---|
| ATOM | 1729 | C   | GLU | A2052 | 30.761 | −18.768 | −19.496 | 1.00 | 53.55  | C |
| ATOM | 1730 | O   | GLU | A2052 | 30.354 | −18.571 | −20.643 | 1.00 | 53.48  | O |
| ATOM | 1731 | CB  | GLU | A2052 | 32.277 | −20.790 | −19.659 | 1.00 | 48.83  | C |
| ATOM | 1732 | CG  | GLU | A2052 | 33.540 | −20.228 | −19.013 | 1.00 | 53.12  | C |
| ATOM | 1733 | CD  | GLU | A2052 | 34.844 | −20.317 | −19.789 | 1.00 | 80.75  | C |
| ATOM | 1734 | OE1 | GLU | A2052 | 35.006 | −21.255 | −20.601 | 1.00 | 72.05  | O |
| ATOM | 1735 | OE2 | GLU | A2052 | 35.735 | −19.474 | −19.536 | 1.00 | 85.77  | O |
| ATOM | 1736 | N   | GLU | A2053 | 31.085 | −17.767 | −18.613 | 1.00 | 49.25  | N |
| ATOM | 1737 | CA  | GLU | A2053 | 31.023 | −16.322 | −18.867 | 1.00 | 48.79  | C |
| ATOM | 1738 | C   | GLU | A2053 | 31.973 | −15.989 | −19.997 | 1.00 | 54.85  | C |
| ATOM | 1739 | O   | GLU | A2053 | 33.162 | −16.296 | −19.880 | 1.00 | 54.27  | O |
| ATOM | 1740 | CB  | GLU | A2053 | 31.470 | −15.529 | −17.628 | 1.00 | 49.78  | C |
| ATOM | 1741 | CG  | GLU | A2053 | 31.486 | −14.022 | −17.856 | 1.00 | 56.36  | C |
| ATOM | 1742 | CD  | GLU | A2053 | 32.534 | −13.210 | −17.123 | 1.00 | 72.13  | C |
| ATOM | 1743 | OE1 | GLU | A2053 | 32.831 | −13.545 | −15.956 | 1.00 | 50.90  | O |
| ATOM | 1744 | OE2 | GLU | A2053 | 33.029 | −12.212 | −17.698 | 1.00 | 77.64  | O |
| ATOM | 1745 | N   | ILE | A2054 | 31.481 | −15.368 | −21.085 | 1.00 | 53.07  | N |
| ATOM | 1746 | CA  | ILE | A2054 | 32.410 | −15.079 | −22.164 | 1.00 | 53.82  | C |
| ATOM | 1747 | C   | ILE | A2054 | 32.631 | −13.594 | −22.232 | 1.00 | 61.55  | C |
| ATOM | 1748 | O   | ILE | A2054 | 31.673 | −12.840 | −22.169 | 1.00 | 63.50  | O |
| ATOM | 1749 | CB  | ILE | A2054 | 32.120 | −15.759 | −23.553 | 1.00 | 56.84  | C |
| ATOM | 1750 | CG1 | ILE | A2054 | 31.230 | −14.930 | −24.458 | 1.00 | 57.18  | C |
| ATOM | 1751 | CG2 | ILE | A2054 | 31.593 | −17.196 | −23.445 | 1.00 | 57.39  | C |
| ATOM | 1752 | CD1 | ILE | A2054 | 32.075 | −14.260 | −25.543 | 1.00 | 62.65  | C |
| ATOM | 1753 | N   | SER | A2055 | 33.905 | −13.175 | −22.342 | 1.00 | 59.96  | N |
| ATOM | 1754 | CA  | SER | A2055 | 34.335 | −11.779 | −22.448 | 1.00 | 59.70  | C |
| ATOM | 1755 | C   | SER | A2055 | 33.942 | −11.184 | −23.812 | 1.00 | 64.58  | C |
| ATOM | 1756 | O   | SER | A2055 | 34.769 | −10.931 | −24.700 | 1.00 | 64.01  | O |
| ATOM | 1757 | CB  | SER | A2055 | 35.812 | −11.645 | −22.105 | 1.00 | 60.27  | C |
| ATOM | 1758 | OG  | SER | A2055 | 35.922 | −11.878 | −20.709 | 1.00 | 65.22  | O |
| ATOM | 1759 | N   | TYR | A2056 | 32.624 | −10.970 | −23.940 | 1.00 | 61.34  | N |
| ATOM | 1760 | CA  | TYR | A2056 | 31.946 | −10.463 | −25.117 | 1.00 | 61.91  | C |
| ATOM | 1761 | C   | TYR | A2056 | 32.020 | −8.959  | −25.218 | 1.00 | 66.88  | C |
| ATOM | 1762 | O   | TYR | A2056 | 31.973 | −8.245  | −24.205 | 1.00 | 66.36  | O |
| ATOM | 1763 | CB  | TYR | A2056 | 30.472 | −10.870 | −25.075 | 1.00 | 62.94  | C |
| ATOM | 1764 | CG  | TYR | A2056 | 29.842 | −10.952 | −26.445 | 1.00 | 64.16  | C |
| ATOM | 1765 | CD2 | TYR | A2056 | 29.638 | −12.181 | −27.065 | 1.00 | 64.25  | C |
| ATOM | 1766 | CD1 | TYR | A2056 | 29.385 | −9.810  | −27.094 | 1.00 | 66.09  | C |
| ATOM | 1767 | CE2 | TYR | A2056 | 29.029 | −12.268 | −28.314 | 1.00 | 65.00  | C |
| ATOM | 1768 | CE1 | TYR | A2056 | 28.789 | −9.882  | −28.352 | 1.00 | 67.34  | C |
| ATOM | 1769 | CZ  | TYR | A2056 | 28.613 | −11.115 | −28.959 | 1.00 | 73.06  | C |
| ATOM | 1770 | OH  | TYR | A2056 | 27.989 | −11.194 | −30.184 | 1.00 | 74.69  | O |
| ATOM | 1771 | N   | SER | A2057 | 32.097 | −8.478  | −26.459 | 1.00 | 63.01  | N |
| ATOM | 1772 | CA  | SER | A2057 | 32.101 | −7.056  | −26.774 | 1.00 | 62.33  | C |
| ATOM | 1773 | C   | SER | A2057 | 31.394 | −6.850  | −28.119 | 1.00 | 65.29  | C |
| ATOM | 1774 | O   | SER | A2057 | 31.535 | −7.668  | −29.035 | 1.00 | 65.93  | O |
| ATOM | 1775 | CB  | SER | A2057 | 33.514 | −6.501  | −26.780 | 1.00 | 65.10  | C |
| ATOM | 1776 | OG  | SER | A2057 | 34.270 | −7.194  | −27.757 | 1.00 | 80.09  | O |
| ATOM | 1777 | N   | GLY | A2058 | 30.591 | −5.801  | −28.194 | 1.00 | 59.38  | N |
| ATOM | 1778 | CA  | GLY | A2058 | 29.808 | −5.506  | −29.377 | 1.00 | 58.93  | C |
| ATOM | 1779 | C   | GLY | A2058 | 28.388 | −5.981  | −29.210 | 1.00 | 63.73  | C |
| ATOM | 1780 | O   | GLY | A2058 | 28.019 | −6.417  | −28.113 | 1.00 | 64.99  | O |
| ATOM | 1781 | N   | ILE | A2059 | 27.568 | −5.887  | −30.283 | 1.00 | 59.38  | N |
| ATOM | 1782 | CA  | ILE | A2059 | 26.173 | −6.285  | −30.159 | 1.00 | 59.08  | C |
| ATOM | 1783 | C   | ILE | A2059 | 26.064 | −7.803  | −30.090 | 1.00 | 61.17  | C |
| ATOM | 1784 | O   | ILE | A2059 | 26.842 | −8.508  | −30.733 | 1.00 | 62.33  | O |
| ATOM | 1785 | CB  | ILE | A2059 | 25.125 | −5.640  | −31.144 | 1.00 | 62.47  | C |
| ATOM | 1786 | CG1 | ILE | A2059 | 24.787 | −6.532  | −32.329 | 1.00 | 63.33  | C |
| ATOM | 1787 | CG2 | ILE | A2059 | 25.471 | −4.247  | −31.606 | 1.00 | 63.15  | C |
| ATOM | 1788 | CD1 | ILE | A2059 | 23.285 | −6.985  | −32.315 | 1.00 | 77.57  | C |
| ATOM | 1789 | N   | LEU | A2060 | 25.120 | −8.285  | −29.263 | 1.00 | 55.07  | N |
| ATOM | 1790 | CA  | LEU | A2060 | 24.798 | −9.692  | −29.085 | 1.00 | 54.31  | C |
| ATOM | 1791 | C   | LEU | A2060 | 23.331 | −9.907  | −29.445 | 1.00 | 60.14  | C |
| ATOM | 1792 | O   | LEU | A2060 | 22.453 | −9.235  | −28.904 | 1.00 | 61.14  | O |
| ATOM | 1793 | CB  | LEU | A2060 | 25.107 | −10.195 | −27.626 | 1.00 | 53.48  | C |
| ATOM | 1794 | CG  | LEU | A2060 | 24.395 | −11.509 | −27.151 | 1.00 | 56.04  | C |
| ATOM | 1795 | CD1 | LEU | A2060 | 24.847 | −12.725 | −27.948 | 1.00 | 56.01  | C |
| ATOM | 1796 | CD2 | LEU | A2060 | 24.614 | −11.765 | −25.712 | 1.00 | 53.84  | C |
| ATOM | 1797 | N   | ASN | A2061 | 23.061 | −10.845 | −30.336 | 1.00 | 57.14  | N |
| ATOM | 1798 | CA  | ASN | A2061 | 21.679 | −11.156 | −30.643 | 1.00 | 57.87  | C |
| ATOM | 1799 | C   | ASN | A2061 | 21.464 | −12.550 | −30.106 | 1.00 | 62.73  | C |
| ATOM | 1800 | O   | ASN | A2061 | 22.072 | −13.500 | −30.608 | 1.00 | 65.30  | O |
| ATOM | 1801 | CB  | ASN | A2061 | 21.378 | −11.036 | −32.145 | 1.00 | 62.04  | C |
| ATOM | 1802 | CG  | ASN | A2061 | 19.912 | −10.789 | −32.432 | 1.00 | 100.04 | C |
| ATOM | 1803 | ND2 | ASN | A2061 | 19.660 | −9.712  | −33.162 | 1.00 | 94.49  | N |
| ATOM | 1804 | OD1 | ASN | A2061 | 19.001 | −11.542 | −32.005 | 1.00 | 94.34  | O |

TABLE1-continued

Three-dimensional crystal coordinate for anti-TcdB antibody beziotoxumab Fab –*C. difficile* toxin B (TcdB$^{(1834-2101)}$) complex.

| | | | | | | | | | |
|---|---|---|---|---|---|---|---|---|---|
| ATOM | 1805 | N | PHE | A2062 | 20.696 | −12.662 | −29.021 | 1.00 | 56.77 | N |
| ATOM | 1806 | CA | PHE | A2062 | 20.481 | −13.919 | −28.312 | 1.00 | 55.60 | C |
| ATOM | 1807 | C | PHE | A2062 | 19.048 | −14.051 | −27.856 | 1.00 | 60.61 | C |
| ATOM | 1808 | O | PHE | A2062 | 18.583 | −13.161 | −27.174 | 1.00 | 60.36 | O |
| ATOM | 1809 | CB | PHE | A2062 | 21.409 | −13.953 | −27.075 | 1.00 | 56.92 | C |
| ATOM | 1810 | CG | PHE | A2062 | 21.288 | −15.201 | −26.238 | 1.00 | 57.34 | C |
| ATOM | 1811 | CD1 | PHE | A2062 | 20.316 | −15.302 | −25.248 | 1.00 | 58.43 | C |
| ATOM | 1812 | CD2 | PHE | A2062 | 22.129 | −16.290 | −26.459 | 1.00 | 58.63 | C |
| ATOM | 1813 | CE1 | PHE | A2062 | 20.148 | −16.484 | −24.532 | 1.00 | 59.32 | C |
| ATOM | 1814 | CE2 | PHE | A2062 | 21.977 | −17.468 | −25.728 | 1.00 | 61.03 | C |
| ATOM | 1815 | CZ | PHE | A2062 | 20.988 | −17.557 | −24.766 | 1.00 | 59.03 | C |
| ATOM | 1816 | N | ASN | A2063 | 18.389 | −15.196 | −28.138 | 1.00 | 59.47 | N |
| ATOM | 1817 | CA | ASN | A2063 | 17.010 | −15.535 | −27.756 | 1.00 | 60.63 | C |
| ATOM | 1818 | C | ASN | A2063 | 16.006 | −14.424 | −28.140 | 1.00 | 66.22 | C |
| ATOM | 1819 | O | ASN | A2063 | 15.152 | −14.008 | −27.340 | 1.00 | 64.09 | O |
| ATOM | 1820 | CB | ASN | A2063 | 16.905 | −15.950 | −26.264 | 1.00 | 65.36 | C |
| ATOM | 1821 | CG | ASN | A2063 | 15.553 | −16.538 | −25.853 | 1.00 | 97.76 | C |
| ATOM | 1822 | ND2 | ASN | A2063 | 15.025 | −16.086 | −24.719 | 1.00 | 86.96 | N |
| ATOM | 1823 | OD1 | ASN | A2063 | 14.945 | −17.361 | −26.561 | 1.00 | 93.60 | O |
| ATOM | 1824 | N | ASN | A2064 | 16.144 | −13.938 | −29.393 | 1.00 | 65.50 | N |
| ATOM | 1825 | CA | ASN | A2064 | 15.310 | −12.880 | −29.972 | 1.00 | 66.06 | C |
| ATOM | 1826 | C | ASN | A2064 | 15.412 | −11.544 | −29.165 | 1.00 | 67.17 | C |
| ATOM | 1827 | O | ASN | A2064 | 14.497 | −10.713 | −29.206 | 1.00 | 66.48 | O |
| ATOM | 1828 | CB | ASN | A2064 | 13.845 | −13.382 | −30.163 | 1.00 | 71.34 | C |
| ATOM | 1829 | CG | ASN | A2064 | 13.016 | −12.592 | −31.164 | 1.00 | 113.83 | C |
| ATOM | 1830 | ND2 | ASN | A2064 | 11.693 | −12.576 | −30.958 | 1.00 | 106.61 | N |
| ATOM | 1831 | OD1 | ASN | A2064 | 13.536 | −11.991 | −32.126 | 1.00 | 112.24 | O |
| ATOM | 1832 | N | LYS | A2065 | 16.557 | −11.347 | −28.455 | 1.00 | 61.04 | N |
| ATOM | 1833 | CA | LYS | A2065 | 16.868 | −10.163 | −27.643 | 1.00 | 59.46 | C |
| ATOM | 1834 | C | LYS | A2065 | 18.179 | −9.556 | −28.149 | 1.00 | 64.53 | C |
| ATOM | 1835 | O | LYS | A2065 | 19.040 | −10.289 | −28.639 | 1.00 | 65.18 | O |
| ATOM | 1836 | CB | LYS | A2065 | 16.983 | −10.522 | −26.153 | 1.00 | 59.86 | C |
| ATOM | 1837 | CG | LYS | A2065 | 15.662 | −10.876 | −25.461 | 1.00 | 64.04 | C |
| ATOM | 1838 | CD | LYS | A2065 | 15.863 | −11.853 | −24.293 | 1.00 | 68.00 | C |
| ATOM | 1839 | CE | LYS | A2065 | 14.628 | −12.007 | −23.428 | 1.00 | 75.09 | C |
| ATOM | 1840 | NZ | LYS | A2065 | 14.728 | −13.178 | −22.494 | 1.00 | 74.89 | N |
| ATOM | 1841 | N | ILE | A2066 | 18.316 | −8.218 | −28.071 | 1.00 | 59.83 | N |
| ATOM | 1842 | CA | ILE | A2066 | 19.514 | −7.498 | −28.531 | 1.00 | 58.49 | C |
| ATOM | 1843 | C | ILE | A2066 | 20.179 | −6.776 | −27.363 | 1.00 | 61.05 | C |
| ATOM | 1844 | O | ILE | A2066 | 19.520 | −6.070 | −26.599 | 1.00 | 60.81 | O |
| ATOM | 1845 | CB | ILE | A2066 | 19.209 | −6.544 | −29.710 | 1.00 | 60.84 | C |
| ATOM | 1846 | CG1 | ILE | A2066 | 18.666 | −7.315 | −30.897 | 1.00 | 60.69 | C |
| ATOM | 1847 | CG2 | ILE | A2066 | 20.420 | −5.672 | −30.094 | 1.00 | 60.44 | C |
| ATOM | 1848 | CD1 | ILE | A2066 | 17.610 | −6.595 | −31.579 | 1.00 | 68.04 | C |
| ATOM | 1849 | N | TYR | A2067 | 21.494 | −6.951 | −27.253 | 1.00 | 55.38 | N |
| ATOM | 1850 | CA | TYR | A2067 | 22.321 | −6.415 | −26.185 | 1.00 | 53.14 | C |
| ATOM | 1851 | C | TYR | A2067 | 23.532 | −5.796 | −26.804 | 1.00 | 55.62 | C |
| ATOM | 1852 | O | TYR | A2067 | 23.903 | −6.160 | −27.907 | 1.00 | 55.49 | O |
| ATOM | 1853 | CB | TYR | A2067 | 22.790 | −7.576 | −25.283 | 1.00 | 52.53 | C |
| ATOM | 1854 | CG | TYR | A2067 | 21.682 | −8.269 | −24.524 | 1.00 | 53.20 | C |
| ATOM | 1855 | CD2 | TYR | A2067 | 21.152 | −9.478 | −24.970 | 1.00 | 54.25 | C |
| ATOM | 1856 | CD1 | TYR | A2067 | 21.185 | −7.737 | −23.340 | 1.00 | 54.66 | C |
| ATOM | 1857 | CE2 | TYR | A2067 | 20.164 | −10.152 | −24.238 | 1.00 | 55.23 | C |
| ATOM | 1858 | CE1 | TYR | A2067 | 20.172 | −8.375 | −22.626 | 1.00 | 54.79 | C |
| ATOM | 1859 | CZ | TYR | A2067 | 19.680 | −9.595 | −23.062 | 1.00 | 62.01 | C |
| ATOM | 1860 | OH | TYR | A2067 | 18.701 | −10.218 | −22.318 | 1.00 | 63.89 | O |
| ATOM | 1861 | N | TYR | A2068 | 24.180 | −4.896 | −26.095 | 1.00 | 50.45 | N |
| ATOM | 1862 | CA | TYR | A2068 | 25.425 | −4.353 | −26.581 | 1.00 | 49.42 | C |
| ATOM | 1863 | C | TYR | A2068 | 26.318 | −4.429 | −25.395 | 1.00 | 56.65 | C |
| ATOM | 1864 | O | TYR | A2068 | 25.900 | −4.051 | −24.295 | 1.00 | 57.17 | O |
| ATOM | 1865 | CB | TYR | A2068 | 25.302 | −2.905 | −27.088 | 1.00 | 48.92 | C |
| ATOM | 1866 | CG | TYR | A2068 | 26.630 | −2.317 | −27.534 | 1.00 | 48.01 | C |
| ATOM | 1867 | CD1 | TYR | A2068 | 27.130 | −2.554 | −28.819 | 1.00 | 48.44 | C |
| ATOM | 1868 | CD2 | TYR | A2068 | 27.416 | −1.578 | −26.655 | 1.00 | 48.17 | C |
| ATOM | 1869 | CE1 | TYR | A2068 | 28.373 | −2.060 | −29.211 | 1.00 | 46.14 | C |
| ATOM | 1870 | CE2 | TYR | A2068 | 28.661 | −1.080 | −27.038 | 1.00 | 48.20 | C |
| ATOM | 1871 | CZ | TYR | A2068 | 29.134 | −1.321 | −28.312 | 1.00 | 52.91 | C |
| ATOM | 1872 | OH | TYR | A2068 | 30.353 | −0.788 | −28.647 | 1.00 | 56.94 | O |
| ATOM | 1873 | N | PHE | A2069 | 27.546 | −4.917 | −25.611 | 1.00 | 53.68 | N |
| ATOM | 1874 | CA | PHE | A2069 | 28.531 | −5.043 | −24.561 | 1.00 | 53.54 | C |
| ATOM | 1875 | C | PHE | A2069 | 29.737 | −4.152 | −24.848 | 1.00 | 62.22 | C |
| ATOM | 1876 | O | PHE | A2069 | 30.226 | −4.125 | −25.976 | 1.00 | 62.56 | O |
| ATOM | 1877 | CB | PHE | A2069 | 28.948 | −6.514 | −24.435 | 1.00 | 54.36 | C |
| ATOM | 1878 | CG | PHE | A2069 | 27.947 | −7.464 | −23.795 | 1.00 | 54.40 | C |
| ATOM | 1879 | CD1 | PHE | A2069 | 26.835 | −7.910 | −24.501 | 1.00 | 55.73 | C |
| ATOM | 1880 | CD2 | PHE | A2069 | 28.193 | −8.019 | −22.541 | 1.00 | 54.98 | C |
| ATOM | 1881 | CE1 | PHE | A2069 | 25.939 | −8.824 | −23.931 | 1.00 | 55.97 | C |

TABLE 1-continued

Three-dimensional crystal coordinate for anti-TcdB antibody beziotoxumab Fab –C. difficile toxin B (TcdB$^{(1834-2101)}$) complex.

| ATOM | 1882 | CE2 | PHE | A2069 | 27.298 | −8.931 | −21.973 | 1.00 | 57.48 | C |
|---|---|---|---|---|---|---|---|---|---|---|
| ATOM | 1883 | CZ | PHE | A2069 | 26.173 | −9.325 | −22.672 | 1.00 | 55.23 | C |
| ATOM | 1884 | N | ASP | A2070 | 30.212 | −3.412 | −23.842 | 1.00 | 62.07 | N |
| ATOM | 1885 | CA | ASP | A2070 | 31.406 | −2.570 | −23.988 | 1.00 | 63.50 | C |
| ATOM | 1886 | C | ASP | A2070 | 32.645 | −3.370 | −23.551 | 1.00 | 70.43 | C |
| ATOM | 1887 | O | ASP | A2070 | 32.528 | −4.543 | −23.241 | 1.00 | 71.45 | O |
| ATOM | 1888 | CB | ASP | A2070 | 31.258 | −1.269 | −23.168 | 1.00 | 65.93 | C |
| ATOM | 1889 | CG | ASP | A2070 | 31.175 | −1.461 | −21.663 | 1.00 | 76.66 | C |
| ATOM | 1890 | OD2 | ASP | A2070 | 31.665 | −0.579 | −20.924 | 1.00 | 78.26 | O |
| ATOM | 1891 | OD1 | ASP | A2070 | 30.660 | −2.514 | −21.226 | 1.00 | 79.11 | O |
| ATOM | 1892 | N | ASP | A2071 | 33.807 | −2.731 | −23.466 | 1.00 | 68.46 | N |
| ATOM | 1893 | CA | ASP | A2071 | 35.085 | −3.346 | −23.075 | 1.00 | 68.77 | C |
| ATOM | 1894 | C | ASP | A2071 | 35.109 | −3.818 | −21.616 | 1.00 | 69.53 | C |
| ATOM | 1895 | O | ASP | A2071 | 36.113 | −4.350 | −21.147 | 1.00 | 68.95 | O |
| ATOM | 1896 | CB | ASP | A2071 | 36.223 | −2.360 | −23.352 | 1.00 | 72.22 | C |
| ATOM | 1897 | CG | ASP | A2071 | 35.870 | −1.391 | −24.469 | 1.00 | 96.52 | C |
| ATOM | 1898 | OD1 | ASP | A2071 | 35.166 | −0.379 | −24.181 | 1.00 | 106.90 | O |
| ATOM | 1899 | OD2 | ASP | A2071 | 36.170 | −1.710 | −25.652 | 1.00 | 97.80 | O |
| ATOM | 1900 | N | SER | A2072 | 33.997 | −3.623 | −20.913 | 1.00 | 64.73 | N |
| ATOM | 1901 | CA | SER | A2072 | 33.796 | −4.023 | −19.527 | 1.00 | 64.45 | C |
| ATOM | 1902 | C | SER | A2072 | 33.249 | −5.444 | −19.574 | 1.00 | 68.07 | C |
| ATOM | 1903 | O | SER | A2072 | 33.173 | −6.114 | −18.547 | 1.00 | 67.77 | O |
| ATOM | 1904 | CB | SER | A2072 | 32.761 | −3.103 | −18.881 | 1.00 | 68.10 | C |
| ATOM | 1905 | OG | SER | A2072 | 33.175 | −2.524 | −17.655 | 1.00 | 81.11 | O |
| ATOM | 1906 | N | PHE | A2073 | 32.871 | −5.895 | −20.798 | 1.00 | 63.76 | N |
| ATOM | 1907 | CA | PHE | A2073 | 32.233 | −7.167 | −21.142 | 1.00 | 62.58 | C |
| ATOM | 1908 | C | PHE | A2073 | 30.941 | −7.322 | −20.351 | 1.00 | 64.09 | C |
| ATOM | 1909 | O | PHE | A2073 | 30.649 | −8.401 | −19.813 | 1.00 | 64.48 | O |
| ATOM | 1910 | CB | PHE | A2073 | 33.171 | −8.373 | −20.987 | 1.00 | 64.87 | C |
| ATOM | 1911 | CG | PHE | A2073 | 34.588 | −8.163 | −21.452 | 1.00 | 66.60 | C |
| ATOM | 1912 | CD1 | PHE | A2073 | 34.879 | −8.011 | −22.802 | 1.00 | 69.24 | C |
| ATOM | 1913 | CD2 | PHE | A2073 | 35.637 | −8.141 | −20.541 | 1.00 | 68.81 | C |
| ATOM | 1914 | CE1 | PHE | A2073 | 36.190 | −7.818 | −23.229 | 1.00 | 69.89 | C |
| ATOM | 1915 | CE2 | PHE | A2073 | 36.951 | −7.940 | −20.969 | 1.00 | 71.22 | C |
| ATOM | 1916 | CZ | PHE | A2073 | 37.217 | −7.781 | −22.310 | 1.00 | 68.93 | C |
| ATOM | 1917 | N | THR | A2074 | 30.202 | −6.186 | −20.233 | 1.00 | 57.06 | N |
| ATOM | 1918 | CA | THR | A2074 | 28.932 | −6.041 | −19.535 | 1.00 | 54.37 | C |
| ATOM | 1919 | C | THR | A2074 | 28.005 | −5.322 | −20.463 | 1.00 | 56.48 | C |
| ATOM | 1920 | O | THR | A2074 | 28.450 | −4.503 | −21.263 | 1.00 | 55.26 | O |
| ATOM | 1921 | CB | THR | A2074 | 29.079 | −5.237 | −18.246 | 1.00 | 58.68 | C |
| ATOM | 1922 | CG2 | THR | A2074 | 29.879 | −5.951 | −17.174 | 1.00 | 54.46 | C |
| ATOM | 1923 | OG1 | THR | A2074 | 29.692 | −3.995 | −18.554 | 1.00 | 66.60 | O |
| ATOM | 1924 | N | ALA | A2075 | 26.717 | −5.634 | −20.391 | 1.00 | 53.92 | N |
| ATOM | 1925 | CA | ALA | A2075 | 25.736 | −4.946 | −21.221 | 1.00 | 53.69 | C |
| ATOM | 1926 | C | ALA | A2075 | 25.427 | −3.529 | −20.688 | 1.00 | 57.07 | C |
| ATOM | 1927 | O | ALA | A2075 | 25.344 | −3.289 | −19.465 | 1.00 | 56.01 | O |
| ATOM | 1928 | CB | ALA | A2075 | 24.459 | −5.762 | −21.340 | 1.00 | 54.26 | C |
| ATOM | 1929 | N | VAL | A2076 | 25.258 | −2.607 | −21.650 | 1.00 | 52.92 | N |
| ATOM | 1930 | CA | VAL | A2076 | 24.934 | −1.180 | −21.473 | 1.00 | 51.22 | C |
| ATOM | 1931 | C | VAL | A2076 | 23.413 | −0.936 | −21.400 | 1.00 | 56.59 | C |
| ATOM | 1932 | O | VAL | A2076 | 22.619 | −1.682 | −21.978 | 1.00 | 56.50 | O |
| ATOM | 1933 | CB | VAL | A2076 | 25.598 | −0.300 | −22.555 | 1.00 | 51.50 | C |
| ATOM | 1934 | CG1 | VAL | A2076 | 27.108 | −0.345 | −22.443 | 1.00 | 50.30 | C |
| ATOM | 1935 | CG2 | VAL | A2076 | 25.165 | −0.724 | −23.942 | 1.00 | 50.86 | C |
| ATOM | 1936 | N | VAL | A2077 | 23.024 | 0.106 | −20.673 | 1.00 | 53.73 | N |
| ATOM | 1937 | CA | VAL | A2077 | 21.631 | 0.522 | −20.489 | 1.00 | 53.05 | C |
| ATOM | 1938 | C | VAL | A2077 | 21.425 | 1.987 | −20.997 | 1.00 | 58.01 | C |
| ATOM | 1939 | O | VAL | A2077 | 22.398 | 2.735 | −21.108 | 1.00 | 57.41 | O |
| ATOM | 1940 | CB | VAL | A2077 | 21.193 | 0.319 | −19.024 | 1.00 | 56.04 | C |
| ATOM | 1941 | CG1 | VAL | A2077 | 21.149 | −1.163 | −18.654 | 1.00 | 55.46 | C |
| ATOM | 1942 | CG2 | VAL | A2077 | 22.090 | 1.093 | −18.068 | 1.00 | 55.94 | C |
| ATOM | 1943 | N | GLY | A2078 | 20.191 | 2.347 | −21.354 | 1.00 | 55.45 | N |
| ATOM | 1944 | CA | GLY | A2078 | 19.857 | 3.672 | −21.876 | 1.00 | 55.85 | C |
| ATOM | 1945 | C | GLY | A2078 | 20.126 | 3.833 | −23.360 | 1.00 | 61.29 | C |
| ATOM | 1946 | O | GLY | A2078 | 20.129 | 2.841 | −24.098 | 1.00 | 60.92 | O |
| ATOM | 1947 | N | TRP | A2079 | 20.365 | 5.084 | −23.808 | 1.00 | 59.21 | N |
| ATOM | 1948 | CA | TRP | A2079 | 20.641 | 5.395 | −25.230 | 1.00 | 60.01 | C |
| ATOM | 1949 | C | TRP | A2079 | 22.073 | 5.122 | −25.626 | 1.00 | 63.95 | C |
| ATOM | 1950 | O | TRP | A2079 | 22.979 | 5.535 | −24.890 | 1.00 | 63.88 | O |
| ATOM | 1951 | CB | TRP | A2079 | 20.304 | 6.872 | −25.555 | 1.00 | 58.90 | C |
| ATOM | 1952 | CG | TRP | A2079 | 18.842 | 7.151 | −25.507 | 1.00 | 59.68 | C |
| ATOM | 1953 | CD1 | TRP | A2079 | 18.134 | 7.604 | −24.436 | 1.00 | 62.25 | C |
| ATOM | 1954 | CD2 | TRP | A2079 | 17.880 | 6.793 | −26.506 | 1.00 | 60.07 | C |
| ATOM | 1955 | CE2 | TRP | A2079 | 16.607 | 7.110 | −25.992 | 1.00 | 63.24 | C |
| ATOM | 1956 | CE3 | TRP | A2079 | 17.970 | 6.223 | −27.793 | 1.00 | 62.13 | C |
| ATOM | 1957 | NE1 | TRP | A2079 | 16.791 | 7.597 | −24.722 | 1.00 | 61.87 | N |
| ATOM | 1958 | CZ2 | TRP | A2079 | 15.434 | 6.888 | −26.716 | 1.00 | 62.33 | C |

TABLE 1-continued

Three-dimensional crystal coordinate for anti-TcdB antibody beziotoxumab Fab – *C. difficile* toxin B (TcdB$^{(1834-2101)}$) complex.

| ATOM | 1959 | CZ3 | TRP | A2079 | 16.799 | 5.996 | −28.509 | 1.00 | 63.52 | C |
|---|---|---|---|---|---|---|---|---|---|---|
| ATOM | 1960 | CH2 | TRP | A2079 | 15.552 | 6.322 | −27.966 | 1.00 | 63.81 | C |
| ATOM | 1961 | N | LYS | A2080 | 22.289 | 4.516 | −26.818 | 1.00 | 60.52 | N |
| ATOM | 1962 | CA | LYS | A2080 | 23.634 | 4.224 | −27.347 | 1.00 | 61.35 | C |
| ATOM | 1963 | C | LYS | A2080 | 23.671 | 4.391 | −28.859 | 1.00 | 69.22 | C |
| ATOM | 1964 | O | LYS | A2080 | 22.810 | 3.853 | −29.554 | 1.00 | 66.66 | O |
| ATOM | 1965 | CB | LYS | A2080 | 24.097 | 2.794 | −26.926 | 1.00 | 63.99 | C |
| ATOM | 1966 | CG | LYS | A2080 | 25.468 | 2.314 | −27.455 | 1.00 | 66.19 | C |
| ATOM | 1967 | CD | LYS | A2080 | 26.578 | 2.429 | −26.410 | 1.00 | 73.46 | C |
| ATOM | 1968 | CE | LYS | A2080 | 27.714 | 3.350 | −26.814 | 1.00 | 72.44 | C |
| ATOM | 1969 | NZ | LYS | A2080 | 28.158 | 4.179 | −25.656 | 1.00 | 68.42 | N |
| ATOM | 1970 | N | ASP | A2081 | 24.741 | 5.055 | −29.364 | 1.00 | 72.69 | N |
| ATOM | 1971 | CA | ASP | A2081 | 25.006 | 5.356 | −30.779 | 1.00 | 75.11 | C |
| ATOM | 1972 | C | ASP | A2081 | 25.994 | 4.377 | −31.467 | 1.00 | 82.89 | C |
| ATOM | 1973 | O | ASP | A2081 | 25.734 | 3.178 | −31.478 | 1.00 | 82.73 | O |
| ATOM | 1974 | CB | ASP | A2081 | 25.465 | 6.827 | −30.905 | 1.00 | 78.11 | C |
| ATOM | 1975 | CG | ASP | A2081 | 24.332 | 7.843 | −30.776 | 1.00 | 94.06 | C |
| ATOM | 1976 | OD1 | ASP | A2081 | 23.405 | 7.820 | −31.636 | 1.00 | 95.77 | O |
| ATOM | 1977 | OD2 | ASP | A2081 | 24.372 | 8.665 | −29.822 | 1.00 | 98.52 | O |
| ATOM | 1978 | N | LEU | A2082 | 27.077 | 4.897 | −32.095 | 1.00 | 83.84 | N |
| ATOM | 1979 | CA | LEU | A2082 | 28.175 | 4.203 | −32.812 | 1.00 | 85.38 | C |
| ATOM | 1980 | C | LEU | A2082 | 28.173 | 4.476 | −34.327 | 1.00 | 91.49 | C |
| ATOM | 1981 | O | LEU | A2082 | 28.414 | 5.613 | −34.733 | 1.00 | 92.46 | O |
| ATOM | 1982 | CB | LEU | A2082 | 28.272 | 2.685 | −32.523 | 1.00 | 85.58 | C |
| ATOM | 1983 | N | GLU | A2083 | 27.959 | 3.421 | −35.145 | 1.00 | 87.24 | N |
| ATOM | 1984 | CA | GLU | A2083 | 27.933 | 3.396 | −36.607 | 1.00 | 86.27 | C |
| ATOM | 1985 | C | GLU | A2083 | 27.537 | 1.954 | −37.017 | 1.00 | 92.11 | C |
| ATOM | 1986 | O | GLU | A2083 | 27.919 | 1.020 | −36.321 | 1.00 | 92.17 | O |
| ATOM | 1987 | CB | GLU | A2083 | 29.294 | 3.795 | −37.190 | 1.00 | 87.13 | C |
| ATOM | 1988 | O | ASP | A2084 | 23.845 | 3.161 | −38.725 | 1.00 | 93.05 | O |
| ATOM | 1989 | N | ASP | A2084 | 26.728 | 1.735 | −38.061 | 1.00 | 89.74 | N |
| ATOM | 1990 | CA | ASP | A2084 | 26.206 | 2.709 | −39.013 | 1.00 | 89.96 | C |
| ATOM | 1991 | C | ASP | A2084 | 25.011 | 3.515 | −38.481 | 1.00 | 93.76 | C |
| ATOM | 1992 | CB | ASP | A2084 | 25.878 | 2.016 | −40.346 | 1.00 | 91.96 | C |
| ATOM | 1993 | O | GLY | A2085 | 23.283 | 5.800 | −35.057 | 1.00 | 91.47 | O |
| ATOM | 1994 | N | GLY | A2085 | 25.343 | 4.589 | −37.748 | 1.00 | 89.99 | N |
| ATOM | 1995 | CA | GLY | A2085 | 24.420 | 5.551 | −37.145 | 1.00 | 89.20 | C |
| ATOM | 1996 | C | GLY | A2085 | 23.559 | 5.045 | −36.003 | 1.00 | 91.12 | C |
| ATOM | 1997 | N | SER | A2086 | 23.125 | 3.759 | −36.114 | 1.00 | 84.59 | N |
| ATOM | 1998 | CA | SER | A2086 | 22.292 | 2.943 | −35.227 | 1.00 | 82.40 | C |
| ATOM | 1999 | C | SER | A2086 | 22.191 | 3.466 | −33.791 | 1.00 | 83.23 | C |
| ATOM | 2000 | O | SER | A2086 | 23.167 | 3.458 | −33.030 | 1.00 | 83.63 | O |
| ATOM | 2001 | CB | SER | A2086 | 22.749 | 1.487 | −35.254 | 1.00 | 84.96 | C |
| ATOM | 2002 | OG | SER | A2086 | 22.613 | 0.943 | −36.558 | 1.00 | 93.25 | O |
| ATOM | 2003 | N | LYS | A2087 | 21.008 | 4.010 | −33.471 | 1.00 | 75.98 | N |
| ATOM | 2004 | CA | LYS | A2087 | 20.668 | 4.548 | −32.167 | 1.00 | 73.37 | C |
| ATOM | 2005 | C | LYS | A2087 | 19.809 | 3.482 | −31.512 | 1.00 | 71.45 | C |
| ATOM | 2006 | O | LYS | A2087 | 18.855 | 2.996 | −32.107 | 1.00 | 70.41 | O |
| ATOM | 2007 | CB | LYS | A2087 | 19.951 | 5.905 | −32.293 | 1.00 | 76.25 | C |
| ATOM | 2008 | CG | LYS | A2087 | 19.922 | 6.736 | −30.999 | 1.00 | 90.36 | C |
| ATOM | 2009 | CD | LYS | A2087 | 19.641 | 8.229 | −31.270 | 1.00 | 94.79 | C |
| ATOM | 2010 | CE | LYS | A2087 | 19.492 | 9.068 | −30.016 | 1.00 | 99.70 | C |
| ATOM | 2011 | NZ | LYS | A2087 | 20.737 | 9.120 | −29.194 | 1.00 | 107.51 | N |
| ATOM | 2012 | N | TYR | A2088 | 20.246 | 3.019 | −30.345 | 1.00 | 65.07 | N |
| ATOM | 2013 | CA | TYR | A2088 | 19.580 | 1.981 | −29.569 | 1.00 | 62.40 | C |
| ATOM | 2014 | C | TYR | A2088 | 19.152 | 2.535 | −28.228 | 1.00 | 60.35 | C |
| ATOM | 2015 | O | TYR | A2088 | 19.806 | 3.447 | −27.674 | 1.00 | 59.54 | O |
| ATOM | 2016 | CB | TYR | A2088 | 20.559 | 0.829 | −29.276 | 1.00 | 63.26 | C |
| ATOM | 2017 | CG | TYR | A2088 | 20.725 | −0.230 | −30.350 | 1.00 | 64.60 | C |
| ATOM | 2018 | CD2 | TYR | A2088 | 21.809 | −0.195 | −31.227 | 1.00 | 65.33 | C |
| ATOM | 2019 | CD1 | TYR | A2088 | 19.876 | −1.333 | −30.407 | 1.00 | 65.93 | C |
| ATOM | 2020 | CE2 | TYR | A2088 | 22.010 | −1.199 | −32.171 | 1.00 | 66.18 | C |
| ATOM | 2021 | CE1 | TYR | A2088 | 20.056 | −2.335 | −31.361 | 1.00 | 66.44 | C |
| ATOM | 2022 | CZ | TYR | A2088 | 21.125 | −2.260 | −32.244 | 1.00 | 77.85 | C |
| ATOM | 2023 | OH | TYR | A2088 | 21.319 | −3.227 | −33.206 | 1.00 | 85.83 | O |
| ATOM | 2024 | N | TYR | A2089 | 18.067 | 1.959 | −27.689 | 1.00 | 52.18 | N |
| ATOM | 2025 | CA | TYR | A2089 | 17.656 | 2.228 | −26.327 | 1.00 | 50.48 | C |
| ATOM | 2026 | C | TYR | A2089 | 17.566 | 0.884 | −25.654 | 1.00 | 53.59 | C |
| ATOM | 2027 | O | TYR | A2089 | 16.722 | 0.051 | −26.031 | 1.00 | 54.50 | O |
| ATOM | 2028 | CB | TYR | A2089 | 16.379 | 3.059 | −26.158 | 1.00 | 50.76 | C |
| ATOM | 2029 | CG | TYR | A2089 | 16.021 | 3.246 | −24.690 | 1.00 | 51.35 | C |
| ATOM | 2030 | CD2 | TYR | A2089 | 16.493 | 4.339 | −23.970 | 1.00 | 52.15 | C |
| ATOM | 2031 | CD1 | TYR | A2089 | 15.302 | 2.274 | −23.995 | 1.00 | 52.10 | C |
| ATOM | 2032 | CE2 | TYR | A2089 | 16.209 | 4.490 | −22.610 | 1.00 | 51.10 | C |
| ATOM | 2033 | CE1 | TYR | A2089 | 15.046 | 2.398 | −22.626 | 1.00 | 52.69 | C |
| ATOM | 2034 | CZ | TYR | A2089 | 15.466 | 3.528 | −21.948 | 1.00 | 56.77 | C |
| ATOM | 2035 | OH | TYR | A2089 | 15.158 | 3.681 | −20.619 | 1.00 | 57.70 | O |

TABLE 1-continued

Three-dimensional crystal coordinate for anti-TcdB antibody beziotoxumab Fab – *C. difficile* toxin B (TcdB$^{(1834-2101)}$) complex.

| ATOM | 2036 | N   | PHE | A2090 | 18.458 | 0.667  | −24.662 | 1.00 | 47.49  | N |
| ---- | ---- | --- | --- | ----- | ------ | ------ | ------- | ---- | ------ | - |
| ATOM | 2037 | CA  | PHE | A2090 | 18.549 | −0.582 | −23.927 | 1.00 | 46.41  | C |
| ATOM | 2038 | C   | PHE | A2090 | 17.883 | −0.471 | −22.584 | 1.00 | 50.34  | C |
| ATOM | 2039 | O   | PHE | A2090 | 18.292 | 0.339  | −21.765 | 1.00 | 50.39  | O |
| ATOM | 2040 | CB  | PHE | A2090 | 20.010 | −0.967 | −23.796 | 1.00 | 47.76  | C |
| ATOM | 2041 | CG  | PHE | A2090 | 20.690 | −1.290 | −25.106 | 1.00 | 47.12  | C |
| ATOM | 2042 | CD1 | PHE | A2090 | 20.357 | −2.435 | −25.816 | 1.00 | 48.56  | C |
| ATOM | 2043 | CD2 | PHE | A2090 | 21.695 | −0.472 | −25.603 | 1.00 | 46.56  | C |
| ATOM | 2044 | CE1 | PHE | A2090 | 21.005 | −2.743 | −27.006 | 1.00 | 49.39  | C |
| ATOM | 2045 | CE2 | PHE | A2090 | 22.346 | −0.786 | −26.792 | 1.00 | 48.70  | C |
| ATOM | 2046 | CZ  | PHE | A2090 | 21.994 | −1.912 | −27.490 | 1.00 | 46.86  | C |
| ATOM | 2047 | N   | ASP | A2091 | 16.831 | −1.248 | −22.378 | 1.00 | 48.15  | N |
| ATOM | 2048 | CA  | ASP | A2091 | 15.997 | −1.197 | −21.183 | 1.00 | 50.03  | C |
| ATOM | 2049 | C   | ASP | A2091 | 16.815 | −1.132 | −19.907 | 1.00 | 59.30  | C |
| ATOM | 2050 | O   | ASP | A2091 | 17.703 | −1.940 | −19.702 | 1.00 | 58.92  | O |
| ATOM | 2051 | CB  | ASP | A2091 | 14.966 | −2.353 | −21.164 | 1.00 | 51.76  | C |
| ATOM | 2052 | CG  | ASP | A2091 | 13.989 | −2.319 | −20.009 | 1.00 | 66.74  | C |
| ATOM | 2053 | OD1 | ASP | A2091 | 13.698 | −1.211 | −19.509 | 1.00 | 69.97  | O |
| ATOM | 2054 | OD2 | ASP | A2091 | 13.521 | −3.403 | −19.593 | 1.00 | 72.94  | O |
| ATOM | 2055 | N   | GLU | A2092 | 16.538 | −0.147 | −19.064 | 1.00 | 60.29  | N |
| ATOM | 2056 | CA  | GLU | A2092 | 17.279 | 0.024  | −17.805 | 1.00 | 61.71  | C |
| ATOM | 2057 | C   | GLU | A2092 | 17.215 | −1.218 | −16.895 | 1.00 | 65.40  | C |
| ATOM | 2058 | O   | GLU | A2092 | 18.191 | −1.481 | −16.197 | 1.00 | 66.25  | O |
| ATOM | 2059 | CB  | GLU | A2092 | 16.796 | 1.265  | −17.018 | 1.00 | 63.75  | C |
| ATOM | 2060 | CG  | GLU | A2092 | 16.464 | 2.507  | −17.848 | 1.00 | 79.34  | C |
| ATOM | 2061 | CD  | GLU | A2092 | 17.583 | 3.488  | −18.181 | 1.00 | 97.47  | C |
| ATOM | 2062 | OE1 | GLU | A2092 | 17.430 | 4.224  | −19.186 | 1.00 | 102.41 | O |
| ATOM | 2063 | OE2 | GLU | A2092 | 18.571 | 3.577  | −17.412 | 1.00 | 68.33  | O |
| ATOM | 2064 | N   | ASP | A2093 | 16.084 | −1.980 | −16.911 | 1.00 | 59.47  | N |
| ATOM | 2065 | CA  | ASP | A2093 | 15.873 | −3.140 | −16.035 | 1.00 | 57.72  | C |
| ATOM | 2066 | C   | ASP | A2093 | 16.498 | −4.420 | −16.505 | 1.00 | 61.66  | C |
| ATOM | 2067 | O   | ASP | A2093 | 16.951 | −5.220 | −15.676 | 1.00 | 61.40  | O |
| ATOM | 2068 | CB  | ASP | A2093 | 14.381 | −3.415 | −15.828 | 1.00 | 58.57  | C |
| ATOM | 2069 | CG  | ASP | A2093 | 13.492 | −2.216 | −15.598 | 1.00 | 60.96  | C |
| ATOM | 2070 | OD2 | ASP | A2093 | 12.366 | −2.205 | −16.134 | 1.00 | 66.69  | O |
| ATOM | 2071 | OD1 | ASP | A2093 | 13.902 | −1.313 | −14.849 | 1.00 | 58.84  | O |
| ATOM | 2072 | N   | THR | A2094 | 16.451 | −4.656 | −17.831 | 1.00 | 57.93  | N |
| ATOM | 2073 | CA  | THR | A2094 | 16.866 | −5.911 | −18.465 | 1.00 | 56.63  | C |
| ATOM | 2074 | C   | THR | A2094 | 18.075 | −5.821 | −19.350 | 1.00 | 58.47  | C |
| ATOM | 2075 | O   | THR | A2094 | 18.606 | −6.866 | −19.745 | 1.00 | 59.66  | O |
| ATOM | 2076 | CB  | THR | A2094 | 15.710 | −6.450 | −19.316 | 1.00 | 64.58  | C |
| ATOM | 2077 | CG2 | THR | A2094 | 14.436 | −6.707 | −18.497 | 1.00 | 61.31  | C |
| ATOM | 2078 | OG1 | THR | A2094 | 15.455 | −5.535 | −20.391 | 1.00 | 65.58  | O |
| ATOM | 2079 | N   | ALA | A2095 | 18.464 | −4.593 | −19.724 | 1.00 | 51.76  | N |
| ATOM | 2080 | CA  | ALA | A2095 | 19.566 | −4.248 | −20.624 | 1.00 | 50.90  | C |
| ATOM | 2081 | C   | ALA | A2095 | 19.343 | −4.701 | −22.052 | 1.00 | 55.54  | C |
| ATOM | 2082 | O   | ALA | A2095 | 20.277 | −4.600 | −22.843 | 1.00 | 55.71  | O |
| ATOM | 2083 | CB  | ALA | A2095 | 20.904 | −4.728 | −20.098 | 1.00 | 51.76  | C |
| ATOM | 2084 | N   | GLU | A2096 | 18.082 | −5.100 | −22.414 | 1.00 | 52.19  | N |
| ATOM | 2085 | CA  | GLU | A2096 | 17.679 | −5.528 | −23.765 | 1.00 | 52.56  | C |
| ATOM | 2086 | C   | GLU | A2096 | 17.224 | −4.337 | −24.590 | 1.00 | 58.55  | C |
| ATOM | 2087 | O   | GLU | A2096 | 16.564 | −3.447 | −24.045 | 1.00 | 56.53  | O |
| ATOM | 2088 | CB  | GLU | A2096 | 16.482 | −6.479 | −23.727 | 1.00 | 54.29  | C |
| ATOM | 2089 | CG  | GLU | A2096 | 16.570 | −7.699 | −22.842 | 1.00 | 67.16  | C |
| ATOM | 2090 | CD  | GLU | A2096 | 15.224 | −8.358 | −22.621 | 1.00 | 91.71  | C |
| ATOM | 2091 | OE1 | GLU | A2096 | 14.327 | −8.212 | −23.486 | 1.00 | 85.70  | O |
| ATOM | 2092 | OE2 | GLU | A2096 | 15.072 | −9.028 | −21.576 | 1.00 | 90.57  | O |
| ATOM | 2093 | N   | ALA | A2097 | 17.494 | −4.360 | −25.926 | 1.00 | 59.20  | N |
| ATOM | 2094 | CA  | ALA | A2097 | 17.083 | −3.289 | −26.851 | 1.00 | 60.27  | C |
| ATOM | 2095 | C   | ALA | A2097 | 15.582 | −3.292 | −27.020 | 1.00 | 65.84  | C |
| ATOM | 2096 | O   | ALA | A2097 | 14.979 | −4.350 | −27.290 | 1.00 | 65.60  | O |
| ATOM | 2097 | CB  | ALA | A2097 | 17.751 | −3.438 | −28.206 | 1.00 | 60.82  | C |
| ATOM | 2098 | N   | TYR | A2098 | 14.984 | −2.105 | −26.802 | 1.00 | 61.97  | N |
| ATOM | 2099 | CA  | TYR | A2098 | 13.550 | −1.860 | −26.921 | 1.00 | 61.43  | C |
| ATOM | 2100 | C   | TYR | A2098 | 13.248 | −0.998 | −28.142 | 1.00 | 66.78  | C |
| ATOM | 2101 | O   | TYR | A2098 | 12.184 | −1.167 | −28.726 | 1.00 | 66.84  | O |
| ATOM | 2102 | CB  | TYR | A2098 | 13.002 | −1.239 | −25.629 | 1.00 | 62.09  | C |
| ATOM | 2103 | CG  | TYR | A2098 | 12.564 | −2.265 | −24.598 | 1.00 | 65.22  | C |
| ATOM | 2104 | CD2 | TYR | A2098 | 11.453 | −2.040 | −23.790 | 1.00 | 65.91  | C |
| ATOM | 2105 | CD1 | TYR | A2098 | 13.280 | −3.450 | −24.405 | 1.00 | 67.72  | C |
| ATOM | 2106 | CE2 | TYR | A2098 | 11.054 | −2.971 | −22.826 | 1.00 | 66.78  | C |
| ATOM | 2107 | CE1 | TYR | A2098 | 12.886 | −4.392 | −23.451 | 1.00 | 68.73  | C |
| ATOM | 2108 | CZ  | TYR | A2098 | 11.772 | −4.147 | −22.660 | 1.00 | 72.92  | C |
| ATOM | 2109 | OH  | TYR | A2098 | 11.367 | −5.063 | −21.712 | 1.00 | 69.55  | O |
| ATOM | 2110 | O   | ILE | A2099 | 16.568 | 0.599  | −29.909 | 1.00 | 75.12  | O |
| ATOM | 2111 | N   | ILE | A2099 | 14.215 | −0.118 | −28.548 | 1.00 | 63.58  | N |
| ATOM | 2112 | CA  | ILE | A2099 | 14.178 | 0.826  | −29.675 | 1.00 | 63.43  | C |

TABLE 1-continued

Three-dimensional crystal coordinate for anti-TcdB antibody beziotoxumab Fab –C. difficile toxin B (TcdB$^{(1834-2101)}$) complex.

| | | | | | | | | | | |
|---|---|---|---|---|---|---|---|---|---|---|
| ATOM | 2113 | C | ILE | A2099 | | 15.487 | 0.712 | −30.492 | 1.00 | 73.91 C |
| ATOM | 2114 | CB | ILE | A2099 | | 14.000 | 2.285 | −29.123 | 1.00 | 65.17 C |
| ATOM | 2115 | CG1 | ILE | A2099 | | 12.685 | 2.473 | −28.388 | 1.00 | 64.48 C |
| ATOM | 2116 | CG2 | ILE | A2099 | | 14.184 | 3.385 | −30.179 | 1.00 | 65.56 C |
| ATOM | 2117 | CD1 | ILE | A2099 | | 12.772 | 3.517 | −27.319 | 1.00 | 70.37 C |
| ATOM | 2118 | O | LEU | A2100 | | 15.513 | 1.231 | −34.999 | 1.00 | 82.54 O |
| ATOM | 2119 | N | LEU | A2100 | | 15.384 | 0.790 | −31.838 | 1.00 | 73.77 N |
| ATOM | 2120 | CA | LEU | A2100 | | 16.511 | 0.814 | −32.786 | 1.00 | 74.45 C |
| ATOM | 2121 | C | LEU | A2100 | | 16.196 | 1.669 | −34.059 | 1.00 | 83.81 C |
| ATOM | 2122 | CB | LEU | A2100 | | 17.060 | −0.592 | −33.147 | 1.00 | 73.42 C |
| ATOM | 2123 | CG | LEU | A2100 | | 18.096 | −0.687 | −34.305 | 1.00 | 75.70 C |
| ATOM | 2124 | CD1 | LEU | A2100 | | 19.351 | 0.160 | −34.051 | 1.00 | 74.84 C |
| ATOM | 2125 | CD2 | LEU | A2100 | | 18.409 | −2.124 | −34.652 | 1.00 | 74.46 C |
| ATOM | 2126 | O | GLU | A2101 | | 19.045 | 3.781 | −35.419 | 1.00 | 95.82 O |
| ATOM | 2127 | N | GLU | A2101 | | 16.730 | 2.892 | −34.051 | 1.00 | 84.83 N |
| ATOM | 2128 | CA | GLU | A2101 | | 16.661 | 3.859 | −35.137 | 1.00 | 86.55 C |
| ATOM | 2129 | C | GLU | A2101 | | 17.950 | 3.701 | −35.973 | 1.00 | 96.39 C |
| ATOM | 2130 | CB | GLU | A2101 | | 16.573 | 5.292 | −34.567 | 1.00 | 87.63 C |
| ATOM | 2131 | CG | GLU | A2101 | | 15.215 | 5.643 | −33.983 | 1.00 | 96.91 C |
| ATOM | 2132 | CD | GLU | A2101 | | 15.177 | 6.724 | −32.916 | 1.00 | 115.46 C |
| ATOM | 2133 | OE1 | GLU | A2101 | | 16.050 | 7.627 | −32.929 | 1.00 | 88.08 O |
| ATOM | 2134 | OE2 | GLU | A2101 | | 14.242 | 6.681 | −32.080 | 1.00 | 113.17 O |
| ATOM | 2135 | O | HIS | A2102 | | 18.365 | 5.315 | −39.400 | 1.00 | 106.98 O |
| ATOM | 2136 | N | HIS | A2102 | | 17.818 | 3.442 | −37.289 | 1.00 | 97.56 N |
| ATOM | 2137 | CA | HIS | A2102 | | 18.954 | 3.317 | −38.207 | 1.00 | 99.18 C |
| ATOM | 2138 | C | HIS | A2102 | | 19.240 | 4.719 | −38.765 | 1.00 | 106.52 C |
| ATOM | 2139 | CB | HIS | A2102 | | 18.623 | 2.362 | −39.365 | 1.00 | 100.25 C |
| ATOM | 2140 | CG | HIS | A2102 | | 18.061 | 1.038 | −38.952 | 1.00 | 103.99 C |
| ATOM | 2141 | ND1 | HIS | A2102 | | 18.876 | −0.070 | −38.778 | 1.00 | 105.93 N |
| ATOM | 2142 | CD2 | HIS | A2102 | | 16.774 | 0.676 | −38.736 | 1.00 | 105.97 C |
| ATOM | 2143 | CE1 | HIS | A2102 | | 18.063 | −1.063 | −38.448 | 1.00 | 105.42 C |
| ATOM | 2144 | NE2 | HIS | A2102 | | 16.788 | −0.662 | −38.408 | 1.00 | 105.73 N |
| ATOM | 2145 | O | HIS | A2103 | | 22.285 | 5.476 | −40.517 | 1.00 | 108.48 O |
| ATOM | 2146 | N | HIS | A2103 | | 20.432 | 5.265 | −38.499 | 1.00 | 104.51 N |
| ATOM | 2147 | CA | HIS | A2103 | | 20.784 | 6.594 | −39.004 | 1.00 | 105.00 C |
| ATOM | 2148 | C | HIS | A2103 | | 21.654 | 6.511 | −40.267 | 1.00 | 109.03 C |
| ATOM | 2149 | CB | HIS | A2103 | | 21.403 | 7.477 | −37.903 | 1.00 | 106.15 C |
| ATOM | 2150 | CG | HIS | A2103 | | 20.434 | 7.954 | −36.856 | 1.00 | 109.71 C |
| ATOM | 2151 | ND1 | HIS | A2103 | | 19.149 | 7.428 | −36.747 | 1.00 | 111.56 N |
| ATOM | 2152 | CD2 | HIS | A2103 | | 20.602 | 8.892 | −35.892 | 1.00 | 111.46 C |
| ATOM | 2153 | CE1 | HIS | A2103 | | 18.582 | 8.072 | −35.737 | 1.00 | 110.98 C |
| ATOM | 2154 | NE2 | HIS | A2103 | | 19.417 | 8.958 | −35.187 | 1.00 | 111.25 N |
| ATOM | 2155 | O | HIS | A2104 | | 20.666 | 6.345 | −43.445 | 1.00 | 111.19 O |
| ATOM | 2156 | N | HIS | A2104 | | 21.641 | 7.594 | −41.081 | 1.00 | 1105.95 N |
| ATOM | 2157 | CA | HIS | A2104 | | 22.322 | 7.738 | −42.381 | 1.00 | 139.50 C |
| ATOM | 2158 | C | HIS | A2104 | | 21.852 | 6.690 | −43.402 | 1.00 | 157.82 C |
| ATOM | 2159 | CB | HIS | A2104 | | 23.843 | 7.707 | −42.224 | 1.00 | 140.23 C |
| TER | 2160 | | HIS | A2104 | | | | | | |
| ATOM | 2161 | O | GLU | H | 1 | 9.441 | 7.033 | −7.636 | 1.00 | 68.44 O |
| ATOM | 2162 | N | GLU | H | 1 | 7.969 | 8.930 | −9.008 | 1.00 | 68.19 N |
| ATOM | 2163 | CA | GLU | H | 1 | 9.431 | 8.911 | −9.148 | 1.00 | 67.28 C |
| ATOM | 2164 | C | GLU | H | 1 | 10.071 | 7.710 | −8.458 | 1.00 | 69.17 C |
| ATOM | 2165 | CB | GLU | H | 1 | 10.106 | 10.237 | −8.691 | 1.00 | 68.58 C |
| ATOM | 2166 | CG | GLU | H | 1 | 9.363 | 11.054 | −7.643 | 1.00 | 82.60 C |
| ATOM | 2167 | CD | GLU | H | 1 | 10.014 | 11.265 | −6.287 | 1.00 | 113.13 C |
| ATOM | 2168 | OE1 | GLU | H | 1 | 9.309 | 11.074 | −5.270 | 1.00 | 125.63 O |
| ATOM | 2169 | OE2 | GLU | H | 1 | 11.191 | 11.693 | −6.234 | 1.00 | 101.83 O |
| ATOM | 2170 | N | VAL | H | 2 | 11.331 | 7.443 | −8.805 | 1.00 | 63.79 N |
| ATOM | 2171 | CA | VAL | H | 2 | 12.091 | 6.362 | −8.194 | 1.00 | 61.56 C |
| ATOM | 2172 | C | VAL | H | 2 | 12.544 | 6.894 | −6.846 | 1.00 | 65.29 C |
| ATOM | 2173 | O | VAL | H | 2 | 13.154 | 7.972 | −6.778 | 1.00 | 65.35 O |
| ATOM | 2174 | CB | VAL | H | 2 | 13.299 | 5.957 | −9.059 | 1.00 | 63.73 C |
| ATOM | 2175 | CG1 | VAL | H | 2 | 14.048 | 4.784 | −8.445 | 1.00 | 63.00 C |
| ATOM | 2176 | CG2 | VAL | H | 2 | 12.874 | 5.655 | −10.486 | 1.00 | 63.34 C |
| ATOM | 2177 | N | GLN | H | 3 | 12.216 | 6.163 | −5.772 | 1.00 | 60.82 N |
| ATOM | 2178 | CA | GLN | H | 3 | 12.610 | 6.554 | −4.428 | 1.00 | 59.79 C |
| ATOM | 2179 | C | GLN | H | 3 | 12.730 | 5.389 | −3.489 | 1.00 | 61.97 C |
| ATOM | 2180 | O | GLN | H | 3 | 11.982 | 4.425 | −3.631 | 1.00 | 63.13 O |
| ATOM | 2181 | CB | GLN | H | 3 | 11.698 | 7.652 | −3.851 | 1.00 | 61.27 C |
| ATOM | 2182 | CG | GLN | H | 3 | 10.215 | 7.315 | −3.740 | 1.00 | 83.59 C |
| ATOM | 2183 | CD | GLN | H | 3 | 9.364 | 8.550 | −3.520 | 1.00 | 89.95 C |
| ATOM | 2184 | OE1 | GLN | H | 3 | 9.693 | 9.435 | −2.709 | 1.00 | 74.58 O |
| ATOM | 2185 | NE2 | GLN | H | 3 | 8.246 | 8.635 | −4.251 | 1.00 | 80.78 N |
| ATOM | 2186 | N | LEU | H | 4 | 13.693 | 5.468 | −2.541 | 1.00 | 56.35 N |
| ATOM | 2187 | CA | LEU | H | 4 | 13.906 | 4.478 | −1.486 | 1.00 | 55.57 C |
| ATOM | 2188 | C | LEU | H | 4 | 13.626 | 5.214 | −0.175 | 1.00 | 62.48 C |
| ATOM | 2189 | O | LEU | H | 4 | 14.271 | 6.235 | 0.114 | 1.00 | 64.53 O |

TABLE 1-continued

Three-dimensional crystal coordinate for anti-TcdB antibody beziotoxumab
Fab –C. difficile toxin B (TcdB$^{(1834-2101)}$) complex.

| ATOM | 2190 | CB | LEU | H | 4 | 15.329 | 3.873 | −1.489 | 1.00 | 55.12 | C |
|---|---|---|---|---|---|---|---|---|---|---|---|
| ATOM | 2191 | CG | LEU | H | 4 | 15.823 | 3.193 | −2.786 | 1.00 | 59.13 | C |
| ATOM | 2192 | CD1 | LEU | H | 4 | 17.290 | 2.963 | −2.736 | 1.00 | 58.67 | C |
| ATOM | 2193 | CD2 | LEU | H | 4 | 15.148 | 1.884 | −3.032 | 1.00 | 62.20 | C |
| ATOM | 2194 | N | VAL | H | 5 | 12.607 | 4.743 | 0.583 | 1.00 | 57.08 | N |
| ATOM | 2195 | CA | VAL | H | 5 | 12.200 | 5.370 | 1.838 | 1.00 | 55.58 | C |
| ATOM | 2196 | C | VAL | H | 5 | 12.589 | 4.477 | 3.011 | 1.00 | 61.38 | C |
| ATOM | 2197 | O | VAL | H | 5 | 12.166 | 3.332 | 3.085 | 1.00 | 62.44 | O |
| ATOM | 2198 | CB | VAL | H | 5 | 10.703 | 5.759 | 1.831 | 1.00 | 57.54 | C |
| ATOM | 2199 | CG1 | VAL | H | 5 | 10.307 | 6.468 | 3.122 | 1.00 | 56.70 | C |
| ATOM | 2200 | CG2 | VAL | H | 5 | 10.354 | 6.611 | 0.605 | 1.00 | 56.80 | C |
| ATOM | 2201 | N | GLN | H | 6 | 13.400 | 5.001 | 3.919 | 1.00 | 58.16 | N |
| ATOM | 2202 | CA | GLN | H | 6 | 13.873 | 4.204 | 5.030 | 1.00 | 58.68 | C |
| ATOM | 2203 | C | GLN | H | 6 | 13.094 | 4.392 | 6.329 | 1.00 | 65.06 | C |
| ATOM | 2204 | O | GLN | H | 6 | 12.399 | 5.400 | 6.533 | 1.00 | 64.49 | O |
| ATOM | 2205 | CB | GLN | H | 6 | 15.368 | 4.443 | 5.249 | 1.00 | 59.99 | C |
| ATOM | 2206 | CG | GLN | H | 6 | 16.197 | 4.111 | 4.028 | 1.00 | 57.66 | C |
| ATOM | 2207 | CD | GLN | H | 6 | 17.652 | 4.304 | 4.277 | 1.00 | 62.68 | C |
| ATOM | 2208 | OE1 | GLN | H | 6 | 18.307 | 5.104 | 3.612 | 1.00 | 56.53 | O |
| ATOM | 2209 | NE2 | GLN | H | 6 | 18.197 | 3.551 | 5.212 | 1.00 | 60.78 | N |
| ATOM | 2210 | N | SER | H | 7 | 13.222 | 3.389 | 7.219 | 1.00 | 62.67 | N |
| ATOM | 2211 | CA | SER | H | 7 | 12.592 | 3.393 | 8.532 | 1.00 | 62.21 | C |
| ATOM | 2212 | C | SER | H | 7 | 13.193 | 4.522 | 9.391 | 1.00 | 68.54 | C |
| ATOM | 2213 | O | SER | H | 7 | 14.302 | 4.993 | 9.111 | 1.00 | 69.10 | O |
| ATOM | 2214 | CB | SER | H | 7 | 12.706 | 2.025 | 9.205 | 1.00 | 63.38 | C |
| ATOM | 2215 | OG | SER | H | 7 | 14.022 | 1.507 | 9.244 | 1.00 | 67.59 | O |
| ATOM | 2216 | N | GLY | H | 8 | 12.419 | 4.987 | 10.375 | 1.00 | 65.16 | N |
| ATOM | 2217 | CA | GLY | H | 8 | 12.773 | 6.079 | 11.275 | 1.00 | 63.43 | C |
| ATOM | 2218 | C | GLY | H | 8 | 13.988 | 5.811 | 12.128 | 1.00 | 65.31 | C |
| ATOM | 2219 | O | GLY | H | 8 | 14.497 | 4.681 | 12.181 | 1.00 | 62.89 | O |
| ATOM | 2220 | N | ALA | H | 9 | 14.455 | 6.887 | 12.795 | 1.00 | 63.01 | N |
| ATOM | 2221 | CA | ALA | H | 9 | 15.615 | 6.887 | 13.687 | 1.00 | 63.01 | C |
| ATOM | 2222 | C | ALA | H | 9 | 15.439 | 5.887 | 14.837 | 1.00 | 66.54 | C |
| ATOM | 2223 | O | ALA | H | 9 | 14.362 | 5.800 | 15.432 | 1.00 | 66.15 | O |
| ATOM | 2224 | CB | ALA | H | 9 | 15.843 | 8.280 | 14.234 | 1.00 | 63.66 | C |
| ATOM | 2225 | N | GLU | H | 10 | 16.488 | 5.122 | 15.122 | 1.00 | 61.64 | N |
| ATOM | 2226 | CA | GLU | H | 10 | 16.446 | 4.115 | 16.158 | 1.00 | 60.84 | C |
| ATOM | 2227 | C | GLU | H | 10 | 17.409 | 4.408 | 17.300 | 1.00 | 66.76 | C |
| ATOM | 2228 | O | GLU | H | 10 | 18.581 | 4.721 | 17.080 | 1.00 | 67.13 | O |
| ATOM | 2229 | CB | GLU | H | 10 | 16.725 | 2.723 | 15.570 | 1.00 | 61.57 | C |
| ATOM | 2230 | CG | GLU | H | 10 | 15.697 | 2.274 | 14.549 | 1.00 | 71.61 | C |
| ATOM | 2231 | CD | GLU | H | 10 | 14.412 | 1.656 | 15.054 | 1.00 | 98.09 | C |
| ATOM | 2232 | OE1 | GLU | H | 10 | 13.431 | 1.637 | 14.277 | 1.00 | 85.63 | O |
| ATOM | 2233 | OE2 | GLU | H | 10 | 14.385 | 1.164 | 16.205 | 1.00 | 103.61 | O |
| ATOM | 2234 | N | VAL | H | 11 | 16.899 | 4.309 | 18.525 | 1.00 | 63.93 | N |
| ATOM | 2235 | CA | VAL | H | 11 | 17.698 | 4.432 | 19.739 | 1.00 | 64.80 | C |
| ATOM | 2236 | C | VAL | H | 11 | 17.509 | 3.113 | 20.482 | 1.00 | 71.34 | C |
| ATOM | 2237 | O | VAL | H | 11 | 16.382 | 2.778 | 20.876 | 1.00 | 71.33 | O |
| ATOM | 2238 | CB | VAL | H | 11 | 17.399 | 5.664 | 20.626 | 1.00 | 68.88 | C |
| ATOM | 2239 | CG1 | VAL | H | 11 | 18.572 | 5.925 | 21.569 | 1.00 | 68.88 | C |
| ATOM | 2240 | CG2 | VAL | H | 11 | 17.099 | 6.917 | 19.789 | 1.00 | 68.46 | C |
| ATOM | 2241 | N | LYS | H | 12 | 18.602 | 2.329 | 20.580 | 1.00 | 67.93 | N |
| ATOM | 2242 | CA | LYS | H | 12 | 18.602 | 0.994 | 21.157 | 1.00 | 67.74 | C |
| ATOM | 2243 | C | LYS | H | 12 | 19.650 | 0.868 | 22.223 | 1.00 | 74.36 | C |
| ATOM | 2244 | O | LYS | H | 12 | 20.685 | 1.527 | 22.124 | 1.00 | 74.42 | O |
| ATOM | 2245 | CB | LYS | H | 12 | 18.894 | −0.065 | 20.060 | 1.00 | 69.89 | C |
| ATOM | 2246 | CG | LYS | H | 12 | 17.949 | −0.091 | 18.843 | 1.00 | 80.50 | C |
| ATOM | 2247 | CD | LYS | H | 12 | 16.439 | −0.171 | 19.166 | 1.00 | 87.68 | C |
| ATOM | 2248 | CE | LYS | H | 12 | 15.908 | −1.576 | 19.293 | 1.00 | 92.95 | C |
| ATOM | 2249 | NZ | LYS | H | 12 | 14.679 | −1.599 | 20.125 | 1.00 | 99.95 | N |
| ATOM | 2250 | N | LYS | H | 13 | 19.413 | −0.010 | 23.232 | 1.00 | 72.56 | N |
| ATOM | 2251 | CA | LYS | H | 13 | 20.407 | −0.311 | 24.274 | 1.00 | 72.45 | C |
| ATOM | 2252 | C | LYS | H | 13 | 21.344 | −1.360 | 23.668 | 1.00 | 77.07 | C |
| ATOM | 2253 | O | LYS | H | 13 | 20.920 | −2.080 | 22.773 | 1.00 | 76.42 | O |
| ATOM | 2254 | CB | LYS | H | 13 | 19.737 | −0.819 | 25.562 | 1.00 | 74.40 | C |
| ATOM | 2255 | N | SER | H | 14 | 22.620 | −1.417 | 24.090 | 1.00 | 74.98 | N |
| ATOM | 2256 | CA | SER | H | 14 | 23.605 | −2.388 | 23.556 | 1.00 | 74.59 | C |
| ATOM | 2257 | C | SER | H | 14 | 23.115 | −3.845 | 23.748 | 1.00 | 79.27 | C |
| ATOM | 2258 | O | SER | H | 14 | 22.226 | −4.096 | 24.567 | 1.00 | 79.62 | O |
| ATOM | 2259 | CB | SER | H | 14 | 24.971 | −2.213 | 24.216 | 1.00 | 76.29 | C |
| ATOM | 2260 | OG | SER | H | 14 | 25.329 | −0.851 | 24.373 | 1.00 | 84.00 | O |
| ATOM | 2261 | N | GLY | H | 15 | 23.645 | −4.777 | 22.963 | 1.00 | 75.14 | N |
| ATOM | 2262 | CA | GLY | H | 15 | 23.243 | −6.180 | 23.053 | 1.00 | 74.61 | C |
| ATOM | 2263 | C | GLY | H | 15 | 21.885 | −6.552 | 22.467 | 1.00 | 76.37 | C |
| ATOM | 2264 | O | GLY | H | 15 | 21.621 | −7.746 | 22.266 | 1.00 | 75.75 | O |
| ATOM | 2265 | N | GLU | H | 16 | 21.001 | −5.542 | 22.199 | 1.00 | 70.88 | N |
| ATOM | 2266 | CA | GLU | H | 16 | 19.663 | −5.719 | 21.602 | 1.00 | 70.01 | C |

TABLE 1-continued

Three-dimensional crystal coordinate for anti-TcdB antibody beziotoxumab Fab –C. difficile toxin B (TcdB^(1834-2101)) complex.

| | | | | | | | | | | |
|---|---|---|---|---|---|---|---|---|---|---|
| ATOM | 2267 | C | GLU | H | 16 | 19.776 | −6.104 | 20.100 | 1.00 | 75.61 | C |
| ATOM | 2268 | O | GLU | H | 16 | 20.870 | −6.065 | 19.520 | 1.00 | 74.97 | O |
| ATOM | 2269 | CB | GLU | H | 16 | 18.824 | −4.430 | 21.733 | 1.00 | 70.58 | C |
| ATOM | 2270 | CG | GLU | H | 16 | 18.231 | −4.168 | 23.108 | 1.00 | 80.41 | C |
| ATOM | 2271 | CD | GLU | H | 16 | 17.276 | −2.988 | 23.212 | 1.00 | 103.68 | C |
| ATOM | 2272 | OE1 | GLU | H | 16 | 16.532 | −2.730 | 22.242 | 1.00 | 88.29 | O |
| ATOM | 2273 | OE2 | GLU | H | 16 | 17.235 | −2.346 | 24.286 | 1.00 | 111.46 | O |
| ATOM | 2274 | N | SER | H | 17 | 18.646 | −6.456 | 19.469 | 1.00 | 72.15 | N |
| ATOM | 2275 | CA | SER | H | 17 | 18.651 | −6.766 | 18.051 | 1.00 | 71.86 | C |
| ATOM | 2276 | C | SER | H | 17 | 17.794 | −5.781 | 17.278 | 1.00 | 74.46 | C |
| ATOM | 2277 | O | SER | H | 17 | 16.800 | −5.270 | 17.814 | 1.00 | 75.96 | O |
| ATOM | 2278 | CB | SER | H | 17 | 18.285 | −8.218 | 17.805 | 1.00 | 77.34 | C |
| ATOM | 2279 | OG | SER | H | 17 | 19.415 | −8.987 | 18.190 | 1.00 | 94.80 | O |
| ATOM | 2280 | N | LEU | H | 18 | 18.229 | −5.436 | 16.051 | 1.00 | 66.54 | N |
| ATOM | 2281 | CA | LEU | H | 18 | 17.551 | −4.428 | 15.229 | 1.00 | 63.63 | C |
| ATOM | 2282 | C | LEU | H | 18 | 17.471 | −4.889 | 13.776 | 1.00 | 64.48 | C |
| ATOM | 2283 | O | LEU | H | 18 | 18.416 | −5.509 | 13.295 | 1.00 | 63.78 | O |
| ATOM | 2284 | CB | LEU | H | 18 | 18.438 | −3.173 | 15.296 | 1.00 | 62.90 | C |
| ATOM | 2285 | CG | LEU | H | 18 | 17.902 | −1.755 | 15.236 | 1.00 | 65.49 | C |
| ATOM | 2286 | CD1 | LEU | H | 18 | 18.713 | −0.963 | 14.286 | 1.00 | 65.60 | C |
| ATOM | 2287 | CD2 | LEU | H | 18 | 16.439 | −1.656 | 14.927 | 1.00 | 65.00 | C |
| ATOM | 2288 | N | LYS | H | 19 | 16.343 | −4.600 | 13.099 | 1.00 | 60.02 | N |
| ATOM | 2289 | CA | LYS | H | 19 | 16.083 | −4.842 | 11.675 | 1.00 | 60.42 | C |
| ATOM | 2290 | C | LYS | H | 19 | 15.557 | −3.526 | 11.152 | 1.00 | 67.13 | C |
| ATOM | 2291 | O | LYS | H | 19 | 14.552 | −2.988 | 11.667 | 1.00 | 66.65 | O |
| ATOM | 2292 | CB | LYS | H | 19 | 15.067 | −5.971 | 11.391 | 1.00 | 62.90 | C |
| ATOM | 2293 | N | ILE | H | 20 | 16.292 | −2.974 | 10.163 | 1.00 | 64.32 | N |
| ATOM | 2294 | CA | ILE | H | 20 | 16.016 | −1.697 | 9.547 | 1.00 | 63.02 | C |
| ATOM | 2295 | C | ILE | H | 20 | 15.558 | −1.913 | 8.110 | 1.00 | 64.87 | C |
| ATOM | 2296 | O | ILE | H | 20 | 16.033 | −2.819 | 7.432 | 1.00 | 63.63 | O |
| ATOM | 2297 | CB | ILE | H | 20 | 17.232 | −0.772 | 9.778 | 1.00 | 66.79 | C |
| ATOM | 2298 | CG1 | ILE | H | 20 | 16.763 | 0.514 | 10.392 | 1.00 | 68.23 | C |
| ATOM | 2299 | CG2 | ILE | H | 20 | 18.194 | −0.546 | 8.603 | 1.00 | 68.02 | C |
| ATOM | 2300 | CD1 | ILE | H | 20 | 16.786 | 0.491 | 11.823 | 1.00 | 77.59 | C |
| ATOM | 2301 | N | SER | H | 21 | 14.543 | −1.155 | 7.701 | 1.00 | 61.50 | N |
| ATOM | 2302 | CA | SER | H | 21 | 13.936 | −1.315 | 6.393 | 1.00 | 61.51 | C |
| ATOM | 2303 | C | SER | H | 21 | 14.263 | −0.173 | 5.429 | 1.00 | 66.48 | C |
| ATOM | 2304 | O | SER | H | 21 | 14.742 | 0.889 | 5.849 | 1.00 | 67.71 | O |
| ATOM | 2305 | CB | SER | H | 21 | 12.431 | −1.548 | 6.528 | 1.00 | 65.02 | C |
| ATOM | 2306 | OG | SER | H | 21 | 11.619 | −0.393 | 6.388 | 1.00 | 78.17 | O |
| ATOM | 2307 | N | CYS | H | 22 | 14.000 | −0.417 | 4.136 | 1.00 | 60.91 | N |
| ATOM | 2308 | CA | CYS | H | 22 | 14.254 | 0.461 | 3.007 | 1.00 | 60.47 | C |
| ATOM | 2309 | C | CYS | H | 22 | 13.241 | 0.063 | 1.937 | 1.00 | 63.20 | C |
| ATOM | 2310 | O | CYS | H | 22 | 13.403 | −0.979 | 1.291 | 1.00 | 62.84 | O |
| ATOM | 2311 | CB | CYS | H | 22 | 15.692 | 0.247 | 2.532 | 1.00 | 61.32 | C |
| ATOM | 2312 | SG | CYS | H | 22 | 16.074 | 0.895 | 0.878 | 1.00 | 65.44 | S |
| ATOM | 2313 | N | LYS | H | 23 | 12.173 | 0.860 | 1.783 | 1.00 | 58.45 | N |
| ATOM | 2314 | CA | LYS | H | 23 | 11.125 | 0.584 | 0.815 | 1.00 | 57.56 | C |
| ATOM | 2315 | C | LYS | H | 23 | 11.333 | 1.296 | −0.523 | 1.00 | 62.13 | C |
| ATOM | 2316 | O | LYS | H | 23 | 11.323 | 2.540 | −0.603 | 1.00 | 62.72 | O |
| ATOM | 2317 | CB | LYS | H | 23 | 9.730 | 0.883 | 1.379 | 1.00 | 58.80 | C |
| ATOM | 2318 | CG | LYS | H | 23 | 8.681 | −0.127 | 0.880 | 1.00 | 58.77 | C |
| ATOM | 2319 | CD | LYS | H | 23 | 7.306 | 0.469 | 0.601 | 1.00 | 63.19 | C |
| ATOM | 2320 | CE | LYS | H | 23 | 6.226 | −0.587 | 0.460 | 1.00 | 72.87 | C |
| ATOM | 2321 | NZ | LYS | H | 23 | 4.926 | −0.152 | 1.079 | 1.00 | 76.82 | N |
| ATOM | 2322 | N | GLY | H | 24 | 11.515 | 0.487 | −1.554 | 1.00 | 56.07 | N |
| ATOM | 2323 | CA | GLY | H | 24 | 11.652 | 0.965 | −2.915 | 1.00 | 55.44 | C |
| ATOM | 2324 | C | GLY | H | 24 | 10.310 | 1.089 | −3.610 | 1.00 | 57.32 | C |
| ATOM | 2325 | O | GLY | H | 24 | 9.408 | 0.268 | −3.393 | 1.00 | 55.25 | O |
| ATOM | 2326 | N | SER | H | 25 | 10.195 | 2.119 | −4.474 | 1.00 | 53.78 | N |
| ATOM | 2327 | CA | SER | H | 25 | 8.997 | 2.467 | −5.240 | 1.00 | 54.35 | C |
| ATOM | 2328 | C | SER | H | 25 | 9.354 | 3.241 | −6.504 | 1.00 | 60.55 | C |
| ATOM | 2329 | O | SER | H | 25 | 10.353 | 3.961 | −6.514 | 1.00 | 61.37 | O |
| ATOM | 2330 | CB | SER | H | 25 | 8.039 | 3.301 | −4.381 | 1.00 | 58.01 | C |
| ATOM | 2331 | OG | SER | H | 25 | 8.699 | 4.179 | −3.479 | 1.00 | 66.40 | O |
| ATOM | 2332 | N | GLY | H | 26 | 8.505 | 3.140 | −7.531 | 1.00 | 57.46 | N |
| ATOM | 2333 | CA | GLY | H | 26 | 8.700 | 3.858 | −8.795 | 1.00 | 57.24 | C |
| ATOM | 2334 | C | GLY | H | 26 | 9.492 | 3.096 | −9.849 | 1.00 | 60.98 | C |
| ATOM | 2335 | O | GLY | H | 26 | 9.643 | 3.566 | −10.988 | 1.00 | 60.24 | O |
| ATOM | 2336 | N | TYR | H | 27 | 10.000 | 1.902 | −9.470 | 1.00 | 55.67 | N |
| ATOM | 2337 | CA | TYR | H | 27 | 10.812 | 1.069 | −10.337 | 1.00 | 54.96 | C |
| ATOM | 2338 | C | TYR | H | 27 | 10.496 | −0.415 | −10.080 | 1.00 | 60.43 | C |
| ATOM | 2339 | O | TYR | H | 27 | 9.761 | −0.743 | −9.131 | 1.00 | 60.95 | O |
| ATOM | 2340 | CB | TYR | H | 27 | 12.304 | 1.403 | −10.110 | 1.00 | 55.20 | C |
| ATOM | 2341 | CG | TYR | H | 27 | 12.912 | 0.802 | −8.851 | 1.00 | 56.09 | C |
| ATOM | 2342 | CD1 | TYR | H | 27 | 12.695 | 1.376 | −7.604 | 1.00 | 57.54 | C |
| ATOM | 2343 | CD2 | TYR | H | 27 | 13.719 | −0.326 | −8.913 | 1.00 | 57.30 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 2344 | CE1 | TYR | H | 27 | 13.229 | 0.816 | −6.443 | 1.00 | 56.87 | C |
|------|------|-----|-----|---|----|--------|-------|--------|------|-------|---|
| ATOM | 2345 | CE2 | TYR | H | 27 | 14.280 | −0.881 | −7.763 | 1.00 | 58.91 | C |
| ATOM | 2346 | CZ | TYR | H | 27 | 14.020 | −0.314 | −6.525 | 1.00 | 65.82 | C |
| ATOM | 2347 | OH | TYR | H | 27 | 14.570 | −0.851 | −5.384 | 1.00 | 69.33 | O |
| ATOM | 2348 | N | SER | H | 28 | 11.068 | −1.307 | −10.931 | 1.00 | 55.75 | N |
| ATOM | 2349 | CA | SER | H | 28 | 10.945 | −2.760 | −10.822 | 1.00 | 54.83 | C |
| ATOM | 2350 | C | SER | H | 28 | 11.942 | −3.278 | −9.754 | 1.00 | 55.58 | C |
| ATOM | 2351 | O | SER | H | 28 | 13.132 | −3.430 | −10.018 | 1.00 | 54.31 | O |
| ATOM | 2352 | CB | SER | H | 28 | 11.199 | −3.412 | −12.173 | 1.00 | 59.57 | C |
| ATOM | 2353 | OG | SER | H | 28 | 11.370 | −4.813 | −12.006 | 1.00 | 76.32 | O |
| ATOM | 2354 | N | PHE | H | 29 | 11.442 | −3.545 | −8.563 | 1.00 | 50.96 | N |
| ATOM | 2355 | CA | PHE | H | 29 | 12.256 | −3.913 | −7.420 | 1.00 | 50.91 | C |
| ATOM | 2356 | C | PHE | H | 29 | 13.189 | −5.116 | −7.636 | 1.00 | 58.02 | C |
| ATOM | 2357 | O | PHE | H | 29 | 14.333 | −5.080 | −7.164 | 1.00 | 59.90 | O |
| ATOM | 2358 | CB | PHE | H | 29 | 11.361 | −4.117 | −6.195 | 1.00 | 51.98 | C |
| ATOM | 2359 | CG | PHE | H | 29 | 12.085 | −4.430 | −4.909 | 1.00 | 52.70 | C |
| ATOM | 2360 | CD2 | PHE | H | 29 | 12.130 | −5.735 | −4.416 | 1.00 | 54.22 | C |
| ATOM | 2361 | CD1 | PHE | H | 29 | 12.697 | −3.419 | −4.173 | 1.00 | 54.84 | C |
| ATOM | 2362 | CE2 | PHE | H | 29 | 12.775 | −6.024 | −3.213 | 1.00 | 56.91 | C |
| ATOM | 2363 | CE1 | PHE | H | 29 | 13.346 | −3.705 | −2.969 | 1.00 | 55.68 | C |
| ATOM | 2364 | CZ | PHE | H | 29 | 13.386 | −5.009 | −2.498 | 1.00 | 55.40 | C |
| ATOM | 2365 | N | THR | H | 30 | 12.714 | −6.163 | −8.325 | 1.00 | 54.16 | N |
| ATOM | 2366 | CA | THR | H | 30 | 13.475 | −7.407 | −8.591 | 1.00 | 52.91 | C |
| ATOM | 2367 | C | THR | H | 30 | 14.475 | −7.295 | −9.736 | 1.00 | 55.68 | C |
| ATOM | 2368 | O | THR | H | 30 | 15.079 | −8.308 | −10.076 | 1.00 | 58.41 | O |
| ATOM | 2369 | CB | THR | H | 30 | 12.514 | −8.548 | −8.953 | 1.00 | 55.28 | C |
| ATOM | 2370 | OG1 | THR | H | 30 | 11.783 | −8.182 | −10.136 | 1.00 | 56.25 | O |
| ATOM | 2371 | CG2 | THR | H | 30 | 11.562 | −8.897 | −7.826 | 1.00 | 50.65 | C |
| ATOM | 2372 | N | SER | H | 31 | 14.608 | −6.116 | −10.372 | 1.00 | 47.98 | N |
| ATOM | 2373 | CA | SER | H | 31 | 15.487 | −5.898 | −11.521 | 1.00 | 46.50 | C |
| ATOM | 2374 | C | SER | H | 31 | 16.756 | −5.141 | −11.166 | 1.00 | 52.73 | C |
| ATOM | 2375 | O | SER | H | 31 | 17.583 | −4.884 | −12.052 | 1.00 | 52.49 | O |
| ATOM | 2376 | CB | SER | H | 31 | 14.745 | −5.103 | −12.589 | 1.00 | 47.37 | C |
| ATOM | 2377 | OG | SER | H | 31 | 13.676 | −5.822 | −13.173 | 1.00 | 53.09 | O |
| ATOM | 2378 | N | TYR | H | 32 | 16.891 | −4.727 | −9.885 | 1.00 | 50.47 | N |
| ATOM | 2379 | CA | TYR | H | 32 | 18.000 | −3.889 | −9.423 | 1.00 | 50.57 | C |
| ATOM | 2380 | C | TYR | H | 32 | 18.594 | −4.385 | −8.161 | 1.00 | 57.62 | C |
| ATOM | 2381 | O | TYR | H | 32 | 17.856 | −4.837 | −7.291 | 1.00 | 57.77 | O |
| ATOM | 2382 | CB | TYR | H | 32 | 17.498 | −2.452 | −9.180 | 1.00 | 50.48 | C |
| ATOM | 2383 | CG | TYR | H | 32 | 17.120 | −1.753 | −10.464 | 1.00 | 50.56 | C |
| ATOM | 2384 | CD2 | TYR | H | 32 | 18.041 | −0.961 | −11.145 | 1.00 | 50.15 | C |
| ATOM | 2385 | CD1 | TYR | H | 32 | 15.856 | −1.924 | −11.032 | 1.00 | 51.97 | C |
| ATOM | 2386 | CE2 | TYR | H | 32 | 17.707 | −0.335 | −12.344 | 1.00 | 50.84 | C |
| ATOM | 2387 | CE1 | TYR | H | 32 | 15.527 | −1.339 | −12.253 | 1.00 | 52.50 | C |
| ATOM | 2388 | CZ | TYR | H | 32 | 16.454 | −0.537 | −12.902 | 1.00 | 58.94 | C |
| ATOM | 2389 | OH | TYR | H | 32 | 16.153 | 0.048 | −14.107 | 1.00 | 58.77 | O |
| ATOM | 2390 | N | TRP | H | 33 | 19.918 | −4.235 | −8.011 | 1.00 | 55.75 | N |
| ATOM | 2391 | CA | TRP | H | 33 | 20.571 | −4.568 | −6.762 | 1.00 | 56.20 | C |
| ATOM | 2392 | C | TRP | H | 33 | 20.353 | −3.399 | −5.833 | 1.00 | 61.22 | C |
| ATOM | 2393 | O | TRP | H | 33 | 20.250 | −2.256 | −6.289 | 1.00 | 61.04 | O |
| ATOM | 2394 | CB | TRP | H | 33 | 22.063 | −4.760 | −6.948 | 1.00 | 55.63 | C |
| ATOM | 2395 | CG | TRP | H | 33 | 22.424 | −5.974 | −7.738 | 1.00 | 57.32 | C |
| ATOM | 2396 | CD1 | TRP | H | 33 | 22.225 | −6.178 | −9.070 | 1.00 | 60.27 | C |
| ATOM | 2397 | CD2 | TRP | H | 33 | 23.120 | −7.119 | −7.256 | 1.00 | 57.62 | C |
| ATOM | 2398 | NE1 | TRP | H | 33 | 22.745 | −7.388 | −9.444 | 1.00 | 59.87 | N |
| ATOM | 2399 | CE2 | TRP | H | 33 | 23.302 | −7.990 | −8.351 | 1.00 | 61.59 | C |
| ATOM | 2400 | CE3 | TRP | H | 33 | 23.585 | −7.513 | −5.991 | 1.00 | 59.67 | C |
| ATOM | 2401 | CZ2 | TRP | H | 33 | 23.938 | −9.227 | −8.226 | 1.00 | 61.65 | C |
| ATOM | 2402 | CZ3 | TRP | H | 33 | 24.210 | −8.746 | −5.865 | 1.00 | 61.52 | C |
| ATOM | 2403 | CH2 | TRP | H | 33 | 24.382 | −9.587 | −6.972 | 1.00 | 62.17 | C |
| ATOM | 2404 | N | ILE | H | 34 | 20.264 | −3.682 | −4.539 | 1.00 | 59.13 | N |
| ATOM | 2405 | CA | ILE | H | 34 | 20.089 | −2.677 | −3.501 | 1.00 | 59.66 | C |
| ATOM | 2406 | C | ILE | H | 34 | 21.189 | −2.909 | −2.433 | 1.00 | 63.18 | C |
| ATOM | 2407 | O | ILE | H | 34 | 21.386 | −4.033 | −1.981 | 1.00 | 61.66 | O |
| ATOM | 2408 | CB | ILE | H | 34 | 18.614 | −2.549 | −2.978 | 1.00 | 63.07 | C |
| ATOM | 2409 | CG1 | ILE | H | 34 | 18.532 | −2.011 | −1.562 | 1.00 | 64.04 | C |
| ATOM | 2410 | CG2 | ILE | H | 34 | 17.814 | −3.822 | −3.103 | 1.00 | 65.26 | C |
| ATOM | 2411 | CD1 | ILE | H | 34 | 18.374 | −0.604 | −1.517 | 1.00 | 80.43 | C |
| ATOM | 2412 | N | GLY | H | 35 | 21.961 | −1.860 | −2.156 | 1.00 | 60.18 | N |
| ATOM | 2413 | CA | GLY | H | 35 | 23.084 | −1.909 | −1.228 | 1.00 | 59.97 | C |
| ATOM | 2414 | C | GLY | H | 35 | 22.938 | −1.094 | 0.035 | 1.00 | 62.93 | C |
| ATOM | 2415 | O | GLY | H | 35 | 22.070 | −0.226 | 0.112 | 1.00 | 63.93 | O |
| ATOM | 2416 | N | TRP | H | 36 | 23.781 | −1.399 | 1.046 | 1.00 | 56.44 | N |
| ATOM | 2417 | CA | TRP | H | 36 | 23.800 | −0.732 | 2.349 | 1.00 | 54.56 | C |
| ATOM | 2418 | C | TRP | H | 36 | 25.182 | −0.123 | 2.609 | 1.00 | 58.10 | C |
| ATOM | 2419 | O | TRP | H | 36 | 26.206 | −0.800 | 2.472 | 1.00 | 58.81 | O |
| ATOM | 2420 | CB | TRP | H | 36 | 23.342 | −1.657 | 3.498 | 1.00 | 52.55 | C |

TABLE1-continued

Three-dimensional crystal coordinate for anti-TcdB antibody beziotoxumab Fab –C. difficile toxin B (TcdB$^{(1834-2101)}$) complex.

| ATOM | 2421 | CG  | TRP | H | 36 | 21.892 | −2.049 | 3.427  | 1.00 | 53.02 | C |
|------|------|-----|-----|---|----|--------|--------|--------|------|-------|---|
| ATOM | 2422 | CD1 | TRP | H | 36 | 21.364 | −3.121 | 2.768  | 1.00 | 55.61 | C |
| ATOM | 2423 | CD2 | TRP | H | 36 | 20.783 | −1.361 | 4.028  | 1.00 | 52.72 | C |
| ATOM | 2424 | NE1 | TRP | H | 36 | 19.993 | −3.130 | 2.900  | 1.00 | 54.49 | N |
| ATOM | 2425 | CE2 | TRP | H | 36 | 19.611 | −2.056 | 3.661  | 1.00 | 55.76 | C |
| ATOM | 2426 | CE3 | TRP | H | 36 | 20.664 | −0.219 | 4.837  | 1.00 | 54.02 | C |
| ATOM | 2427 | CZ2 | TRP | H | 36 | 18.345 | −1.650 | 4.075  | 1.00 | 55.32 | C |
| ATOM | 2428 | CZ3 | TRP | H | 36 | 19.404 | 0.183  | 5.249  | 1.00 | 55.26 | C |
| ATOM | 2429 | CH2 | TRP | H | 36 | 18.266 | −0.537 | 4.887  | 1.00 | 55.85 | C |
| ATOM | 2430 | N   | VAL | H | 37 | 25.192 | 1.191  | 2.912  | 1.00 | 51.87 | N |
| ATOM | 2431 | CA  | VAL | H | 37 | 26.370 | 2.012  | 3.168  | 1.00 | 49.53 | C |
| ATOM | 2432 | C   | VAL | H | 37 | 26.251 | 2.587  | 4.580  | 1.00 | 55.24 | C |
| ATOM | 2433 | O   | VAL | H | 37 | 25.180 | 3.074  | 4.971  | 1.00 | 56.25 | O |
| ATOM | 2434 | CB  | VAL | H | 37 | 26.501 | 3.134  | 2.098  | 1.00 | 51.25 | C |
| ATOM | 2435 | CG1 | VAL | H | 37 | 27.745 | 3.991  | 2.319  | 1.00 | 49.80 | C |
| ATOM | 2436 | CG2 | VAL | H | 37 | 26.479 | 2.553  | 0.682  | 1.00 | 50.75 | C |
| ATOM | 2437 | N   | ARG | H | 38 | 27.357 | 2.516  | 5.341  | 1.00 | 51.89 | N |
| ATOM | 2438 | CA  | ARG | H | 38 | 27.479 | 3.048  | 6.698  | 1.00 | 51.31 | C |
| ATOM | 2439 | C   | ARG | H | 38 | 28.301 | 4.323  | 6.685  | 1.00 | 55.75 | C |
| ATOM | 2440 | O   | ARG | H | 38 | 29.363 | 4.389  | 6.037  | 1.00 | 55.51 | O |
| ATOM | 2441 | CB  | ARG | H | 38 | 28.137 | 2.020  | 7.656  | 1.00 | 50.27 | C |
| ATOM | 2442 | CG  | ARG | H | 38 | 28.292 | 2.516  | 9.104  | 1.00 | 50.25 | C |
| ATOM | 2443 | CD  | ARG | H | 38 | 28.785 | 1.469  | 10.061 | 1.00 | 53.59 | C |
| ATOM | 2444 | NE  | ARG | H | 38 | 30.222 | 1.203  | 9.938  | 1.00 | 59.32 | N |
| ATOM | 2445 | CZ  | ARG | H | 38 | 30.904 | 0.404  | 10.760 | 1.00 | 72.57 | C |
| ATOM | 2446 | NH1 | ARG | H | 38 | 30.286 | −0.208 | 11.773 | 1.00 | 60.22 | N |
| ATOM | 2447 | NH2 | ARG | H | 38 | 32.205 | 0.208  | 10.576 | 1.00 | 53.44 | N |
| ATOM | 2448 | N   | GLN | H | 39 | 27.829 | 5.307  | 7.470  | 1.00 | 51.93 | N |
| ATOM | 2449 | CA  | GLN | H | 39 | 28.522 | 6.564  | 7.661  | 1.00 | 52.00 | C |
| ATOM | 2450 | C   | GLN | H | 39 | 28.567 | 6.896  | 9.152  | 1.00 | 61.29 | C |
| ATOM | 2451 | O   | GLN | H | 39 | 27.618 | 7.481  | 9.706  | 1.00 | 62.88 | O |
| ATOM | 2452 | CB  | GLN | H | 39 | 27.879 | 7.681  | 6.831  | 1.00 | 52.11 | C |
| ATOM | 2453 | CG  | GLN | H | 39 | 28.608 | 9.006  | 6.962  | 1.00 | 43.61 | C |
| ATOM | 2454 | CD  | GLN | H | 39 | 28.047 | 10.086 | 6.094  | 1.00 | 59.96 | C |
| ATOM | 2455 | OE1 | GLN | H | 39 | 26.848 | 10.383 | 6.113  | 1.00 | 56.09 | O |
| ATOM | 2456 | NE2 | GLN | H | 39 | 28.924 | 10.758 | 5.383  | 1.00 | 50.75 | N |
| ATOM | 2457 | N   | MET | H | 40 | 29.675 | 6.527  | 9.799  | 1.00 | 59.50 | N |
| ATOM | 2458 | CA  | MET | H | 40 | 29.901 | 6.807  | 11.220 | 1.00 | 61.32 | C |
| ATOM | 2459 | C   | MET | H | 40 | 29.869 | 8.318  | 11.482 | 1.00 | 64.80 | C |
| ATOM | 2460 | O   | MET | H | 40 | 30.218 | 9.075  | 10.578 | 1.00 | 64.20 | O |
| ATOM | 2461 | CB  | MET | H | 40 | 31.258 | 6.264  | 11.655 | 1.00 | 65.13 | C |
| ATOM | 2462 | CG  | MET | H | 40 | 31.505 | 4.878  | 11.201 | 1.00 | 71.02 | C |
| ATOM | 2463 | SD  | MET | H | 40 | 31.765 | 3.838  | 12.628 | 1.00 | 77.86 | S |
| ATOM | 2464 | CE  | MET | H | 40 | 33.483 | 3.232  | 12.241 | 1.00 | 74.91 | C |
| ATOM | 2465 | N   | PRO | H | 41 | 29.495 | 8.798  | 12.692 | 1.00 | 60.82 | N |
| ATOM | 2466 | CA  | PRO | H | 41 | 29.471 | 10.249 | 12.925 | 1.00 | 59.95 | C |
| ATOM | 2467 | C   | PRO | H | 41 | 30.777 | 10.967 | 12.605 | 1.00 | 64.00 | C |
| ATOM | 2468 | O   | PRO | H | 41 | 31.866 | 10.566 | 13.056 | 1.00 | 63.16 | O |
| ATOM | 2469 | CB  | PRO | H | 41 | 29.076 | 10.358 | 14.391 | 1.00 | 61.50 | C |
| ATOM | 2470 | CG  | PRO | H | 41 | 28.335 | 9.092  | 14.668 | 1.00 | 65.78 | C |
| ATOM | 2471 | CD  | PRO | H | 41 | 29.092 | 8.069  | 13.908 | 1.00 | 61.71 | C |
| ATOM | 2472 | N   | GLY | H | 42 | 30.643 | 11.967 | 11.733 | 1.00 | 61.01 | N |
| ATOM | 2473 | CA  | GLY | H | 42 | 31.735 | 12.808 | 11.249 | 1.00 | 60.46 | C |
| ATOM | 2474 | C   | GLY | H | 42 | 32.790 | 12.131 | 10.394 | 1.00 | 62.34 | C |
| ATOM | 2475 | O   | GLY | H | 42 | 33.863 | 12.697 | 10.181 | 1.00 | 62.89 | O |
| ATOM | 2476 | N   | LYS | H | 43 | 32.501 | 10.917 | 9.910  | 1.00 | 57.21 | N |
| ATOM | 2477 | CA  | LYS | H | 43 | 33.393 | 10.127 | 9.064  | 1.00 | 55.28 | C |
| ATOM | 2478 | C   | LYS | H | 43 | 32.757 | 10.019 | 7.654  | 1.00 | 57.04 | C |
| ATOM | 2479 | O   | LYS | H | 43 | 31.705 | 10.628 | 7.396  | 1.00 | 53.08 | O |
| ATOM | 2480 | CB  | LYS | H | 43 | 33.698 | 8.751  | 9.726  | 1.00 | 55.93 | C |
| ATOM | 2481 | N   | GLY | H | 44 | 33.417 | 9.274  | 6.760  | 1.00 | 56.02 | N |
| ATOM | 2482 | CA  | GLY | H | 44 | 32.989 | 9.099  | 5.372  | 1.00 | 55.82 | C |
| ATOM | 2483 | C   | GLY | H | 44 | 32.047 | 7.943  | 5.128  | 1.00 | 58.04 | C |
| ATOM | 2484 | O   | GLY | H | 44 | 31.316 | 7.550  | 6.030  | 1.00 | 59.70 | O |
| ATOM | 2485 | N   | LEU | H | 45 | 32.070 | 7.377  | 3.911  | 1.00 | 51.28 | N |
| ATOM | 2486 | CA  | LEU | H | 45 | 31.171 | 6.286  | 3.517  | 1.00 | 48.71 | C |
| ATOM | 2487 | C   | LEU | H | 45 | 31.873 | 4.933  | 3.445  | 1.00 | 54.84 | C |
| ATOM | 2488 | O   | LEU | H | 45 | 32.986 | 4.829  | 2.900  | 1.00 | 54.23 | O |
| ATOM | 2489 | CB  | LEU | H | 45 | 30.469 | 6.608  | 2.176  | 1.00 | 46.95 | C |
| ATOM | 2490 | CG  | LEU | H | 45 | 29.746 | 7.963  | 2.059  | 1.00 | 48.50 | C |
| ATOM | 2491 | CD1 | LEU | H | 45 | 29.328 | 8.237  | 0.624  | 1.00 | 46.80 | C |
| ATOM | 2492 | CD2 | LEU | H | 45 | 28.564 | 8.079  | 3.023  | 1.00 | 47.06 | C |
| ATOM | 2493 | N   | GLU | H | 46 | 31.224 | 3.898  | 4.028  | 1.00 | 52.47 | N |
| ATOM | 2494 | CA  | GLU | H | 46 | 31.732 | 2.525  | 4.047  | 1.00 | 53.12 | C |
| ATOM | 2495 | C   | GLU | H | 46 | 30.701 | 1.608  | 3.429  | 1.00 | 56.86 | C |
| ATOM | 2496 | O   | GLU | H | 46 | 29.576 | 1.527  | 3.936  | 1.00 | 56.42 | O |
| ATOM | 2497 | CB  | GLU | H | 46 | 31.984 | 2.026  | 5.490  | 1.00 | 55.08 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 2498 | CG  | GLU | H | 46 | 33.140 | 2.640   | 6.256   | 1.00 | 67.11 | C |
|------|------|-----|-----|---|----|--------|---------|---------|------|-------|---|
| ATOM | 2499 | CD  | GLU | H | 46 | 32.983 | 2.385   | 7.743   | 1.00 | 89.57 | C |
| ATOM | 2500 | OE1 | GLU | H | 46 | 32.098 | 3.016   | 8.364   | 1.00 | 87.79 | O |
| ATOM | 2501 | OE2 | GLU | H | 46 | 33.691 | 1.498   | 8.271   | 1.00 | 81.48 | O |
| ATOM | 2502 | N   | TRP | H | 47 | 31.083 | 0.865   | 2.375   | 1.00 | 53.24 | N |
| ATOM | 2503 | CA  | TRP | H | 47 | 30.141 | −0.102  | 1.808   | 1.00 | 52.30 | C |
| ATOM | 2504 | C   | TRP | H | 47 | 30.090 | −1.385  | 2.690   | 1.00 | 56.24 | C |
| ATOM | 2505 | O   | TRP | H | 47 | 31.138 | −1.940  | 3.072   | 1.00 | 55.85 | O |
| ATOM | 2506 | CB  | TRP | H | 47 | 30.453 | −0.395  | 0.333   | 1.00 | 50.57 | C |
| ATOM | 2507 | CG  | TRP | H | 47 | 29.639 | −1.515  | −0.245  | 1.00 | 51.38 | C |
| ATOM | 2508 | CD1 | TRP | H | 47 | 28.318 | −1.486  | −0.581  | 1.00 | 54.23 | C |
| ATOM | 2509 | CD2 | TRP | H | 47 | 30.095 | −2.847  | −0.514  | 1.00 | 51.35 | C |
| ATOM | 2510 | NE1 | TRP | H | 47 | 27.918 | −2.723  | −1.037  | 1.00 | 53.85 | N |
| ATOM | 2511 | CE2 | TRP | H | 47 | 28.988 | −3.581  | −0.995  | 1.00 | 55.80 | C |
| ATOM | 2512 | CE3 | TRP | H | 47 | 31.324 | −3.504  | −0.357  | 1.00 | 52.98 | C |
| ATOM | 2513 | CZ2 | TRP | H | 47 | 29.078 | −4.947  | −1.323  | 1.00 | 55.73 | C |
| ATOM | 2514 | CZ3 | TRP | H | 47 | 31.413 | −4.850  | −0.687  | 1.00 | 54.99 | C |
| ATOM | 2515 | CH2 | TRP | H | 47 | 30.309 | −5.551  | −1.192  | 1.00 | 55.79 | C |
| ATOM | 2516 | N   | MET | H | 48 | 28.857 | −1.819  | 3.022   | 1.00 | 51.19 | N |
| ATOM | 2517 | CA  | MET | H | 48 | 28.566 | −2.978  | 3.859   | 1.00 | 49.51 | C |
| ATOM | 2518 | C   | MET | H | 48 | 28.257 | −4.212  | 3.031   | 1.00 | 54.55 | C |
| ATOM | 2519 | O   | MET | H | 48 | 28.913 | −5.239  | 3.225   | 1.00 | 55.50 | O |
| ATOM | 2520 | CB  | MET | H | 48 | 27.394 | −2.675  | 4.814   | 1.00 | 51.28 | C |
| ATOM | 2521 | CG  | MET | H | 48 | 27.659 | −1.535  | 5.759   | 1.00 | 54.07 | C |
| ATOM | 2522 | SD  | MET | H | 48 | 26.240 | −1.136  | 6.789   | 1.00 | 57.69 | S |
| ATOM | 2523 | CE  | MET | H | 48 | 26.269 | −2.410  | 7.920   | 1.00 | 54.01 | C |
| ATOM | 2524 | N   | GLY | H | 49 | 27.261 | −4.104  | 2.143   | 1.00 | 51.30 | N |
| ATOM | 2525 | CA  | GLY | H | 49 | 26.807 | −5.183  | 1.274   | 1.00 | 51.77 | C |
| ATOM | 2526 | C   | GLY | H | 49 | 25.760 | −4.765  | 0.266   | 1.00 | 59.10 | C |
| ATOM | 2527 | O   | GLY | H | 49 | 25.304 | −3.619  | 0.298   | 1.00 | 60.65 | O |
| ATOM | 2528 | N   | ILE | H | 50 | 25.418 | −5.679  | −0.682  | 1.00 | 55.41 | N |
| ATOM | 2529 | CA  | ILE | H | 50 | 24.382 | −5.520  | −1.741  | 1.00 | 54.25 | C |
| ATOM | 2530 | C   | ILE | H | 50 | 23.522 | −6.754  | −1.707  | 1.00 | 55.49 | C |
| ATOM | 2531 | O   | ILE | H | 50 | 23.985 | −7.823  | −1.315  | 1.00 | 54.59 | O |
| ATOM | 2532 | CB  | ILE | H | 50 | 24.898 | −5.405  | −3.216  | 1.00 | 56.97 | C |
| ATOM | 2533 | CG1 | ILE | H | 50 | 26.309 | −5.869  | −3.337  | 1.00 | 59.41 | C |
| ATOM | 2534 | CG2 | ILE | H | 50 | 24.699 | −4.056  | −3.873  | 1.00 | 55.22 | C |
| ATOM | 2535 | CD1 | ILE | H | 50 | 26.430 | −7.316  | −3.666  | 1.00 | 78.35 | C |
| ATOM | 2536 | N   | PHE | H | 51 | 22.346 | −6.643  | −2.305  | 1.00 | 50.94 | N |
| ATOM | 2537 | CA  | PHE | H | 51 | 21.419 | −7.736  | −2.451  | 1.00 | 50.64 | C |
| ATOM | 2538 | C   | PHE | H | 51 | 20.737 | −7.656  | −3.831  | 1.00 | 55.90 | C |
| ATOM | 2539 | O   | PHE | H | 51 | 20.255 | −6.586  | −4.189  | 1.00 | 56.60 | O |
| ATOM | 2540 | CB  | PHE | H | 51 | 20.373 | −7.610  | −1.332  | 1.00 | 52.20 | C |
| ATOM | 2541 | CG  | PHE | H | 51 | 19.392 | −8.749  | −1.239  | 1.00 | 53.05 | C |
| ATOM | 2542 | CD1 | PHE | H | 51 | 18.193 | −8.714  | −1.937  | 1.00 | 54.41 | C |
| ATOM | 2543 | CD2 | PHE | H | 51 | 19.650 | −9.841  | −0.424  | 1.00 | 55.24 | C |
| ATOM | 2544 | CE1 | PHE | H | 51 | 17.299 | −9.765  | −1.854  | 1.00 | 55.14 | C |
| ATOM | 2545 | CE2 | PHE | H | 51 | 18.747 | −10.900 | −0.343  | 1.00 | 57.19 | C |
| ATOM | 2546 | CZ  | PHE | H | 51 | 17.574 | −10.847 | −1.049  | 1.00 | 54.62 | C |
| ATOM | 2547 | N   | TYR | H | 52 | 20.627 | −8.775  | −4.571  | 1.00 | 52.26 | N |
| ATOM | 2548 | CA  | TYR | H | 52 | 19.871 | −8.778  | −5.826  | 1.00 | 52.78 | C |
| ATOM | 2549 | C   | TYR | H | 52 | 18.499 | −9.389  | −5.534  | 1.00 | 61.77 | C |
| ATOM | 2550 | O   | TYR | H | 52 | 18.454 | −10.593 | −5.302  | 1.00 | 64.26 | O |
| ATOM | 2551 | CB  | TYR | H | 52 | 20.577 | −9.578  | −6.952  | 1.00 | 53.66 | C |
| ATOM | 2552 | CG  | TYR | H | 52 | 19.887 | −9.413  | −8.293  | 1.00 | 55.12 | C |
| ATOM | 2553 | CD1 | TYR | H | 52 | 19.063 | −8.319  | −8.545  | 1.00 | 57.69 | C |
| ATOM | 2554 | CD2 | TYR | H | 52 | 20.058 | −10.346 | −9.312  | 1.00 | 55.14 | C |
| ATOM | 2555 | CE1 | TYR | H | 52 | 18.389 | −8.181  | −9.753  | 1.00 | 59.82 | C |
| ATOM | 2556 | CE2 | TYR | H | 52 | 19.372 | −10.226 | −10.524 | 1.00 | 55.70 | C |
| ATOM | 2557 | CZ  | TYR | H | 52 | 18.542 | −9.134  | −10.740 | 1.00 | 65.25 | C |
| ATOM | 2558 | OH  | TYR | H | 52 | 17.888 | −8.921  | −11.928 | 1.00 | 67.27 | O |
| ATOM | 2559 | N   | PRO | H | 53 | 17.366 | −8.648  | −5.525  | 1.00 | 59.45 | N |
| ATOM | 2560 | CA  | PRO | H | 53 | 16.087 | −9.286  | −5.173  | 1.00 | 59.33 | C |
| ATOM | 2561 | C   | PRO | H | 53 | 15.568 | −10.339 | −6.152  | 1.00 | 67.52 | C |
| ATOM | 2562 | O   | PRO | H | 53 | 14.889 | −11.275 | −5.739  | 1.00 | 69.35 | O |
| ATOM | 2563 | CB  | PRO | H | 53 | 15.121 | −8.115  | −5.040  | 1.00 | 60.33 | C |
| ATOM | 2564 | CG  | PRO | H | 53 | 15.950 | −6.920  | −4.943  | 1.00 | 65.07 | C |
| ATOM | 2565 | CD  | PRO | H | 53 | 17.187 | −7.202  | −5.716  | 1.00 | 61.24 | C |
| ATOM | 2566 | O   | GLY | H | 54 | 15.624 | −13.419 | −9.172  | 1.00 | 70.10 | O |
| ATOM | 2567 | N   | GLY | H | 54 | 15.891 | −10.213 | −7.425  | 1.00 | 64.49 | N |
| ATOM | 2568 | CA  | GLY | H | 54 | 15.397 | −11.179 | −8.400  | 1.00 | 64.95 | C |
| ATOM | 2569 | C   | GLY | H | 54 | 16.051 | −12.545 | −8.414  | 1.00 | 69.41 | C |
| ATOM | 2570 | N   | ASP | H | 55 | 17.042 | −12.756 | −7.541  | 1.00 | 65.90 | N |
| ATOM | 2571 | CA  | ASP | H | 55 | 17.928 | −13.918 | −7.457  | 1.00 | 65.98 | C |
| ATOM | 2572 | C   | ASP | H | 55 | 18.178 | −14.317 | −5.987  | 1.00 | 72.33 | C |
| ATOM | 2573 | O   | ASP | H | 55 | 18.671 | −15.417 | −5.707  | 1.00 | 72.95 | O |
| ATOM | 2574 | CB  | ASP | H | 55 | 19.275 | −13.422 | −8.019  | 1.00 | 67.86 | C |

TABLE 1-continued

Three-dimensional crystal coordinate for anti-TcdB antibody beziotoxumab Fab –C. difficile toxin B (TcdB$^{(1834-2101)}$) complex.

| | | | | | | | | | | |
|---|---|---|---|---|---|---|---|---|---|---|
| ATOM | 2575 | CG | ASP | H | 55 | 20.245 | −14.412 | −8.612 | 1.00 | 88.21 | C |
| ATOM | 2576 | OD1 | ASP | H | 55 | 19.926 | −15.623 | −8.634 | 1.00 | 92.27 | O |
| ATOM | 2577 | OD2 | ASP | H | 55 | 21.318 | −13.968 | −9.103 | 1.00 | 94.99 | O |
| ATOM | 2578 | N | SER | H | 56 | 17.941 | −13.358 | −5.065 | 1.00 | 68.85 | N |
| ATOM | 2579 | CA | SER | H | 56 | 18.182 | −13.436 | −3.632 | 1.00 | 68.85 | C |
| ATOM | 2580 | C | SER | H | 56 | 19.688 | −13.578 | −3.305 | 1.00 | 70.75 | C |
| ATOM | 2581 | O | SER | H | 56 | 20.043 | −13.877 | −2.159 | 1.00 | 71.61 | O |
| ATOM | 2582 | CB | SER | H | 56 | 17.314 | −14.502 | −2.955 | 1.00 | 75.57 | C |
| ATOM | 2583 | OG | SER | H | 56 | 17.719 | −15.829 | −3.251 | 1.00 | 91.78 | O |
| ATOM | 2584 | N | SER | H | 57 | 20.578 | −13.292 | −4.288 | 1.00 | 64.86 | N |
| ATOM | 2585 | CA | SER | H | 57 | 22.019 | −13.346 | −4.037 | 1.00 | 63.11 | C |
| ATOM | 2586 | C | SER | H | 57 | 22.478 | −12.123 | −3.285 | 1.00 | 66.50 | C |
| ATOM | 2587 | O | SER | H | 57 | 22.041 | −10.999 | −3.548 | 1.00 | 67.19 | O |
| ATOM | 2588 | CB | SER | H | 57 | 22.855 | −13.580 | −5.295 | 1.00 | 62.90 | C |
| ATOM | 2589 | OG | SER | H | 57 | 22.193 | −13.245 | −6.495 | 1.00 | 66.77 | O |
| ATOM | 2590 | N | THR | H | 58 | 23.305 | −12.360 | −2.287 | 1.00 | 61.53 | N |
| ATOM | 2591 | CA | THR | H | 58 | 23.832 | −11.311 | −1.435 | 1.00 | 60.91 | C |
| ATOM | 2592 | C | THR | H | 58 | 25.350 | −11.429 | −1.430 | 1.00 | 64.49 | C |
| ATOM | 2593 | O | THR | H | 58 | 25.858 | −12.534 | −1.600 | 1.00 | 65.49 | O |
| ATOM | 2594 | CB | THR | H | 58 | 23.173 | −11.329 | −0.029 | 1.00 | 67.27 | C |
| ATOM | 2595 | OG1 | THR | H | 58 | 24.161 | −11.548 | 0.976 | 1.00 | 74.17 | O |
| ATOM | 2596 | CG2 | THR | H | 58 | 22.068 | −12.374 | 0.130 | 1.00 | 61.48 | C |
| ATOM | 2597 | N | ARG | H | 59 | 26.070 | −10.299 | −1.295 | 1.00 | 59.51 | N |
| ATOM | 2598 | CA | ARG | H | 59 | 27.538 | −10.247 | −1.217 | 1.00 | 59.08 | C |
| ATOM | 2599 | C | ARG | H | 59 | 27.913 | −9.134 | −0.241 | 1.00 | 63.75 | C |
| ATOM | 2600 | O | ARG | H | 59 | 27.375 | −8.030 | −0.342 | 1.00 | 65.31 | O |
| ATOM | 2601 | CB | ARG | H | 59 | 28.254 | −10.070 | −2.588 | 1.00 | 56.56 | C |
| ATOM | 2602 | CG | ARG | H | 59 | 27.836 | −10.964 | −3.771 | 1.00 | 61.15 | C |
| ATOM | 2603 | CD | ARG | H | 59 | 28.314 | −12.422 | −3.818 | 1.00 | 64.78 | C |
| ATOM | 2604 | NE | ARG | H | 59 | 27.883 | −13.056 | −5.066 | 1.00 | 72.85 | N |
| ATOM | 2605 | CZ | ARG | H | 59 | 27.029 | −14.075 | −5.168 | 1.00 | 97.07 | C |
| ATOM | 2606 | NH1 | ARG | H | 59 | 26.421 | −14.554 | −4.089 | 1.00 | 86.62 | N |
| ATOM | 2607 | NH2 | ARG | H | 59 | 26.683 | −14.539 | −6.361 | 1.00 | 93.15 | N |
| ATOM | 2608 | N | TYR | H | 60 | 28.794 | −9.434 | 0.721 | 1.00 | 58.80 | N |
| ATOM | 2609 | CA | TYR | H | 60 | 29.175 | −8.503 | 1.778 | 1.00 | 58.15 | C |
| ATOM | 2610 | C | TYR | H | 60 | 30.574 | −8.003 | 1.644 | 1.00 | 64.40 | C |
| ATOM | 2611 | O | TYR | H | 60 | 31.367 | −8.561 | 0.884 | 1.00 | 64.95 | O |
| ATOM | 2612 | CB | TYR | H | 60 | 29.052 | −9.185 | 3.144 | 1.00 | 58.41 | C |
| ATOM | 2613 | CG | TYR | H | 60 | 27.660 | −9.657 | 3.478 | 1.00 | 59.47 | C |
| ATOM | 2614 | CD1 | TYR | H | 60 | 26.706 | −8.775 | 3.985 | 1.00 | 61.16 | C |
| ATOM | 2615 | CD2 | TYR | H | 60 | 27.302 | −10.995 | 3.331 | 1.00 | 59.67 | C |
| ATOM | 2616 | CE1 | TYR | H | 60 | 25.424 | −9.212 | 4.328 | 1.00 | 61.11 | C |
| ATOM | 2617 | CE2 | TYR | H | 60 | 26.014 | −11.440 | 3.650 | 1.00 | 60.32 | C |
| ATOM | 2618 | CZ | TYR | H | 60 | 25.079 | −10.543 | 4.150 | 1.00 | 66.87 | C |
| ATOM | 2619 | OH | TYR | H | 60 | 23.811 | −10.962 | 4.457 | 1.00 | 64.63 | O |
| ATOM | 2620 | N | SER | H | 61 | 30.890 | −6.950 | 2.410 | 1.00 | 61.78 | N |
| ATOM | 2621 | CA | SER | H | 61 | 32.240 | −6.432 | 2.513 | 1.00 | 62.68 | C |
| ATOM | 2622 | C | SER | H | 61 | 32.901 | −7.370 | 3.512 | 1.00 | 70.07 | C |
| ATOM | 2623 | O | SER | H | 61 | 32.273 | −7.661 | 4.535 | 1.00 | 71.48 | O |
| ATOM | 2624 | CB | SER | H | 61 | 32.228 | −5.021 | 3.085 | 1.00 | 66.24 | C |
| ATOM | 2625 | OG | SER | H | 61 | 33.534 | −4.481 | 3.193 | 1.00 | 71.95 | O |
| ATOM | 2626 | N | PRO | H | 62 | 34.126 | −7.885 | 3.267 | 1.00 | 66.67 | N |
| ATOM | 2627 | CA | PRO | H | 62 | 34.754 | −8.777 | 4.262 | 1.00 | 66.83 | C |
| ATOM | 2628 | C | PRO | H | 62 | 34.744 | −8.223 | 5.698 | 1.00 | 72.86 | C |
| ATOM | 2629 | O | PRO | H | 62 | 34.664 | −8.999 | 6.657 | 1.00 | 75.15 | O |
| ATOM | 2630 | CB | PRO | H | 62 | 36.165 | −9.009 | 3.716 | 1.00 | 68.15 | C |
| ATOM | 2631 | CG | PRO | H | 62 | 36.342 | −8.040 | 2.626 | 1.00 | 72.46 | C |
| ATOM | 2632 | CD | PRO | H | 62 | 35.005 | −7.672 | 2.106 | 1.00 | 67.89 | C |
| ATOM | 2633 | N | SER | H | 63 | 34.718 | −6.887 | 5.837 | 1.00 | 67.24 | N |
| ATOM | 2634 | CA | SER | H | 63 | 34.651 | −6.192 | 7.121 | 1.00 | 66.52 | C |
| ATOM | 2635 | C | SER | H | 63 | 33.244 | −6.223 | 7.801 | 1.00 | 68.13 | C |
| ATOM | 2636 | O | SER | H | 63 | 33.131 | −5.919 | 8.989 | 1.00 | 67.98 | O |
| ATOM | 2637 | CB | SER | H | 63 | 35.153 | −4.764 | 6.960 | 1.00 | 71.41 | C |
| ATOM | 2638 | OG | SER | H | 63 | 34.513 | −4.143 | 5.856 | 1.00 | 85.45 | O |
| ATOM | 2639 | N | PHE | H | 64 | 32.191 | −6.590 | 7.058 | 1.00 | 62.90 | N |
| ATOM | 2640 | CA | PHE | H | 64 | 30.810 | −6.691 | 7.565 | 1.00 | 61.82 | C |
| ATOM | 2641 | C | PHE | H | 64 | 30.241 | −8.132 | 7.520 | 1.00 | 65.04 | C |
| ATOM | 2642 | O | PHE | H | 64 | 29.173 | −8.408 | 8.076 | 1.00 | 62.75 | O |
| ATOM | 2643 | CB | PHE | H | 64 | 29.889 | −5.694 | 6.845 | 1.00 | 62.66 | C |
| ATOM | 2644 | CG | PHE | H | 64 | 30.190 | −4.258 | 7.206 | 1.00 | 62.68 | C |
| ATOM | 2645 | CD2 | PHE | H | 64 | 29.542 | −3.642 | 8.270 | 1.00 | 62.88 | C |
| ATOM | 2646 | CD1 | PHE | H | 64 | 31.126 | −3.524 | 6.487 | 1.00 | 63.96 | C |
| ATOM | 2647 | CE2 | PHE | H | 64 | 29.830 | −2.323 | 8.611 | 1.00 | 64.49 | C |
| ATOM | 2648 | CE1 | PHE | H | 64 | 31.413 | −2.205 | 6.835 | 1.00 | 63.26 | C |
| ATOM | 2649 | CZ | PHE | H | 64 | 30.768 | −1.618 | 7.897 | 1.00 | 61.65 | C |
| ATOM | 2650 | N | GLN | H | 65 | 31.003 | −9.042 | 6.895 | 1.00 | 63.04 | N |
| ATOM | 2651 | CA | GLN | H | 65 | 30.706 | −10.460 | 6.768 | 1.00 | 63.66 | C |

TABLE 1-continued

Three-dimensional crystal coordinate for anti-TcdB antibody beziotoxumab Fab –C. difficile toxin B (TcdB$^{(1834-2101)}$) complex.

| ATOM | 2652 | C | GLN | H | 65 | 30.537 | −11.073 | 8.164 | 1.00 | 69.94 | C |
|---|---|---|---|---|---|---|---|---|---|---|---|
| ATOM | 2653 | O | GLN | H | 65 | 31.476 | −11.049 | 8.971 | 1.00 | 70.49 | O |
| ATOM | 2654 | CB | GLN | H | 65 | 31.851 | −11.151 | 5.993 | 1.00 | 64.58 | C |
| ATOM | 2655 | CG | GLN | H | 65 | 31.544 | −12.568 | 5.523 | 1.00 | 77.14 | C |
| ATOM | 2656 | CD | GLN | H | 65 | 30.409 | −12.643 | 4.533 | 1.00 | 94.32 | C |
| ATOM | 2657 | OE1 | GLN | H | 65 | 29.301 | −13.061 | 4.879 | 1.00 | 84.32 | O |
| ATOM | 2658 | NE2 | GLN | H | 65 | 30.670 | −12.252 | 3.281 | 1.00 | 93.29 | N |
| ATOM | 2659 | N | GLY | H | 66 | 29.328 | −11.552 | 8.448 | 1.00 | 66.97 | N |
| ATOM | 2660 | CA | GLY | H | 66 | 29.002 | −12.164 | 9.736 | 1.00 | 66.59 | C |
| ATOM | 2661 | C | GLY | H | 66 | 28.348 | −11.241 | 10.749 | 1.00 | 69.82 | C |
| ATOM | 2662 | O | GLY | H | 66 | 27.380 | −11.632 | 11.405 | 1.00 | 68.83 | O |
| ATOM | 2663 | N | GLN | H | 67 | 28.862 | −9.998 | 10.866 | 1.00 | 67.45 | N |
| ATOM | 2664 | CA | GLN | H | 67 | 28.392 | −8.948 | 11.789 | 1.00 | 66.63 | C |
| ATOM | 2665 | C | GLN | H | 67 | 26.958 | −8.442 | 11.528 | 1.00 | 67.93 | C |
| ATOM | 2666 | O | GLN | H | 67 | 26.299 | −7.923 | 12.444 | 1.00 | 67.73 | O |
| ATOM | 2667 | CB | GLN | H | 67 | 29.381 | −7.761 | 11.812 | 1.00 | 67.84 | C |
| ATOM | 2668 | CG | GLN | H | 67 | 30.613 | −7.991 | 12.692 | 1.00 | 77.72 | C |
| ATOM | 2669 | CD | GLN | H | 67 | 31.752 | −8.628 | 11.945 | 1.00 | 96.95 | C |
| ATOM | 2670 | OE1 | GLN | H | 67 | 32.648 | −7.945 | 11.429 | 1.00 | 99.03 | O |
| ATOM | 2671 | NE2 | GLN | H | 67 | 31.760 | −9.951 | 11.893 | 1.00 | 81.49 | N |
| ATOM | 2672 | N | VAL | H | 68 | 26.483 | −8.594 | 10.285 | 1.00 | 63.50 | N |
| ATOM | 2673 | CA | VAL | H | 68 | 25.163 | −8.116 | 9.840 | 1.00 | 63.11 | C |
| ATOM | 2674 | C | VAL | H | 68 | 24.595 | −9.072 | 8.764 | 1.00 | 66.35 | C |
| ATOM | 2675 | O | VAL | H | 68 | 25.365 | −9.856 | 8.199 | 1.00 | 66.54 | O |
| ATOM | 2676 | CB | VAL | H | 68 | 25.356 | −6.634 | 9.334 | 1.00 | 66.51 | C |
| ATOM | 2677 | CG1 | VAL | H | 68 | 25.635 | −6.533 | 7.835 | 1.00 | 65.51 | C |
| ATOM | 2678 | CG2 | VAL | H | 68 | 24.207 | −5.745 | 9.742 | 1.00 | 66.39 | C |
| ATOM | 2679 | N | THR | H | 69 | 23.264 | −9.041 | 8.494 | 1.00 | 62.86 | N |
| ATOM | 2680 | CA | THR | H | 69 | 22.678 | −9.843 | 7.385 | 1.00 | 62.62 | C |
| ATOM | 2681 | C | THR | H | 69 | 21.687 | −8.984 | 6.578 | 1.00 | 65.21 | C |
| ATOM | 2682 | O | THR | H | 69 | 20.882 | −8.246 | 7.158 | 1.00 | 63.66 | O |
| ATOM | 2683 | CB | THR | H | 69 | 22.091 | −11.270 | 7.745 | 1.00 | 70.51 | C |
| ATOM | 2684 | OG1 | THR | H | 69 | 20.793 | −11.173 | 8.338 | 1.00 | 65.42 | O |
| ATOM | 2685 | CG2 | THR | H | 69 | 23.020 | −12.145 | 8.609 | 1.00 | 71.08 | C |
| ATOM | 2686 | N | ILE | H | 70 | 21.769 | −9.084 | 5.238 | 1.00 | 62.31 | N |
| ATOM | 2687 | CA | ILE | H | 70 | 20.895 | −8.365 | 4.305 | 1.00 | 62.69 | C |
| ATOM | 2688 | C | ILE | H | 70 | 19.870 | −9.335 | 3.687 | 1.00 | 66.14 | C |
| ATOM | 2689 | O | ILE | H | 70 | 20.199 | −10.458 | 3.298 | 1.00 | 66.81 | O |
| ATOM | 2690 | CB | ILE | H | 70 | 21.683 | −7.522 | 3.260 | 1.00 | 66.60 | C |
| ATOM | 2691 | CG1 | ILE | H | 70 | 22.740 | −6.639 | 3.950 | 1.00 | 67.56 | C |
| ATOM | 2692 | CG2 | ILE | H | 70 | 20.732 | −6.659 | 2.408 | 1.00 | 68.33 | C |
| ATOM | 2693 | CD1 | ILE | H | 70 | 23.706 | −5.934 | 3.032 | 1.00 | 77.48 | C |
| ATOM | 2694 | N | SER | H | 71 | 18.623 | −8.910 | 3.659 | 1.00 | 60.74 | N |
| ATOM | 2695 | CA | SER | H | 71 | 17.513 | −9.707 | 3.182 | 1.00 | 59.41 | C |
| ATOM | 2696 | C | SER | H | 71 | 16.553 | −8.761 | 2.533 | 1.00 | 63.91 | C |
| ATOM | 2697 | O | SER | H | 71 | 16.791 | −7.548 | 2.541 | 1.00 | 62.24 | O |
| ATOM | 2698 | CB | SER | H | 71 | 16.828 | −10.377 | 4.368 | 1.00 | 61.45 | C |
| ATOM | 2699 | OG | SER | H | 71 | 16.503 | −9.432 | 5.378 | 1.00 | 67.52 | O |
| ATOM | 2700 | N | ALA | H | 72 | 15.472 | −9.303 | 1.954 | 1.00 | 63.07 | N |
| ATOM | 2701 | CA | ALA | H | 72 | 14.458 | −8.470 | 1.347 | 1.00 | 63.99 | C |
| ATOM | 2702 | C | ALA | H | 72 | 13.091 | −9.101 | 1.225 | 1.00 | 71.62 | C |
| ATOM | 2703 | O | ALA | H | 72 | 12.908 | −10.304 | 1.288 | 1.00 | 70.41 | O |
| ATOM | 2704 | CB | ALA | H | 72 | 14.911 | −7.955 | −0.013 | 1.00 | 64.43 | C |
| ATOM | 2705 | N | ASP | H | 73 | 12.145 | −8.189 | 1.204 | 1.00 | 72.32 | N |
| ATOM | 2706 | CA | ASP | H | 73 | 10.754 | −8.079 | 0.844 | 1.00 | 73.15 | C |
| ATOM | 2707 | C | ASP | H | 73 | 9.951 | −9.262 | 0.662 | 1.00 | 81.23 | C |
| ATOM | 2708 | O | ASP | H | 73 | 10.169 | −9.994 | −0.321 | 1.00 | 81.83 | O |
| ATOM | 2709 | CB | ASP | H | 73 | 10.686 | −7.353 | −0.495 | 1.00 | 74.68 | C |
| ATOM | 2710 | N | LYS | H | 74 | 8.841 | −9.307 | 1.450 | 1.00 | 79.46 | N |
| ATOM | 2711 | CA | LYS | H | 74 | 7.728 | −10.244 | 1.274 | 1.00 | 80.12 | C |
| ATOM | 2712 | C | LYS | H | 74 | 6.974 | −9.688 | −0.014 | 1.00 | 83.68 | C |
| ATOM | 2713 | O | LYS | H | 74 | 5.834 | −10.048 | −0.331 | 1.00 | 81.83 | O |
| ATOM | 2714 | CB | LYS | H | 74 | 6.826 | −10.197 | 2.525 | 1.00 | 83.06 | C |
| ATOM | 2715 | N | SER | H | 75 | 7.705 | −8.774 | −0.717 | 1.00 | 79.54 | N |
| ATOM | 2716 | CA | SER | H | 75 | 7.452 | −7.959 | −1.889 | 1.00 | 77.17 | C |
| ATOM | 2717 | C | SER | H | 75 | 5.988 | −7.502 | −1.875 | 1.00 | 78.35 | C |
| ATOM | 2718 | O | SER | H | 75 | 5.155 | −8.270 | −2.317 | 1.00 | 77.47 | O |
| ATOM | 2719 | CB | SER | H | 75 | 7.951 | −8.650 | −3.155 | 1.00 | 77.15 | C |
| ATOM | 2720 | OG | SER | H | 75 | 9.320 | −9.026 | −3.009 | 1.00 | 71.86 | O |
| ATOM | 2721 | N | VAL | H | 76 | 5.611 | −6.361 | −1.187 | 1.00 | 73.84 | N |
| ATOM | 2722 | CA | VAL | H | 76 | 6.339 | −5.221 | −0.526 | 1.00 | 72.60 | C |
| ATOM | 2723 | C | VAL | H | 76 | 7.784 | −5.052 | −0.977 | 1.00 | 76.45 | C |
| ATOM | 2724 | O | VAL | H | 76 | 8.632 | −5.845 | −0.599 | 1.00 | 78.46 | O |
| ATOM | 2725 | CB | VAL | H | 76 | 6.266 | −5.162 | 1.023 | 1.00 | 74.84 | C |
| ATOM | 2726 | CG1 | VAL | H | 76 | 4.931 | −4.596 | 1.478 | 1.00 | 74.69 | C |
| ATOM | 2727 | CG2 | VAL | H | 76 | 6.558 | −6.507 | 1.681 | 1.00 | 73.90 | C |
| ATOM | 2728 | N | ASN | H | 77 | 8.067 | −4.032 | −1.781 | 1.00 | 69.34 | N |

TABLE 1-continued

Three-dimensional crystal coordinate for anti-TcdB antibody beziotoxumab Fab –C. difficile toxin B (TcdB$^{(1834-2101)}$) complex.

| ATOM | 2729 | CA | ASN | H | 77 | 9.408 | −3.797 | −2.311 | 1.00 | 66.86 | C |
|---|---|---|---|---|---|---|---|---|---|---|---|
| ATOM | 2730 | C | ASN | H | 77 | 10.298 | −3.243 | −1.188 | 1.00 | 66.33 | C |
| ATOM | 2731 | O | ASN | H | 77 | 10.584 | −2.050 | −1.183 | 1.00 | 66.18 | O |
| ATOM | 2732 | CB | ASN | H | 77 | 9.312 | −2.784 | −3.437 | 1.00 | 65.77 | C |
| ATOM | 2733 | CG | ASN | H | 77 | 8.323 | −3.041 | −4.539 | 1.00 | 80.85 | C |
| ATOM | 2734 | OD1 | ASN | H | 77 | 7.832 | −2.089 | −5.159 | 1.00 | 85.12 | O |
| ATOM | 2735 | ND2 | ASN | H | 77 | 8.133 | −4.293 | −4.921 | 1.00 | 63.18 | N |
| ATOM | 2736 | N | THR | H | 78 | 10.739 | −4.098 | −0.252 | 1.00 | 59.82 | N |
| ATOM | 2737 | CA | THR | H | 78 | 11.460 | −3.677 | 0.943 | 1.00 | 59.85 | C |
| ATOM | 2738 | C | THR | H | 78 | 12.766 | −4.412 | 1.212 | 1.00 | 64.29 | C |
| ATOM | 2739 | O | THR | H | 78 | 12.760 | −5.623 | 1.347 | 1.00 | 62.62 | O |
| ATOM | 2740 | CB | THR | H | 78 | 10.520 | −3.786 | 2.169 | 1.00 | 67.62 | C |
| ATOM | 2741 | OG1 | THR | H | 78 | 9.257 | −3.209 | 1.846 | 1.00 | 72.02 | O |
| ATOM | 2742 | CG2 | THR | H | 78 | 11.074 | −3.109 | 3.401 | 1.00 | 62.57 | C |
| ATOM | 2743 | N | ALA | H | 79 | 13.882 | −3.665 | 1.377 | 1.00 | 60.90 | N |
| ATOM | 2744 | CA | ALA | H | 79 | 15.157 | −4.292 | 1.721 | 1.00 | 60.00 | C |
| ATOM | 2745 | C | ALA | H | 79 | 15.382 | −4.167 | 3.228 | 1.00 | 61.88 | C |
| ATOM | 2746 | O | ALA | H | 79 | 14.929 | −3.197 | 3.847 | 1.00 | 60.57 | O |
| ATOM | 2747 | CB | ALA | H | 79 | 16.296 | −3.653 | 0.951 | 1.00 | 60.60 | C |
| ATOM | 2748 | N | TYR | H | 80 | 16.092 | −5.147 | 3.813 | 1.00 | 57.35 | N |
| ATOM | 2749 | CA | TYR | H | 80 | 16.364 | −5.172 | 5.245 | 1.00 | 56.14 | C |
| ATOM | 2750 | C | TYR | H | 80 | 17.854 | −5.303 | 5.616 | 1.00 | 57.58 | C |
| ATOM | 2751 | O | TYR | H | 80 | 18.601 | −6.028 | 4.966 | 1.00 | 55.12 | O |
| ATOM | 2752 | CB | TYR | H | 80 | 15.534 | −6.285 | 5.936 | 1.00 | 57.24 | C |
| ATOM | 2753 | CG | TYR | H | 80 | 14.025 | −6.150 | 5.780 | 1.00 | 59.46 | C |
| ATOM | 2754 | CD1 | TYR | H | 80 | 13.304 | −5.239 | 6.545 | 1.00 | 61.18 | C |
| ATOM | 2755 | CD2 | TYR | H | 80 | 13.315 | −6.966 | 4.902 | 1.00 | 60.81 | C |
| ATOM | 2756 | CE1 | TYR | H | 80 | 11.920 | −5.110 | 6.414 | 1.00 | 60.32 | C |
| ATOM | 2757 | CE2 | TYR | H | 80 | 11.926 | −6.854 | 4.768 | 1.00 | 61.96 | C |
| ATOM | 2758 | CZ | TYR | H | 80 | 11.232 | −5.922 | 5.530 | 1.00 | 69.32 | C |
| ATOM | 2759 | OH | TYR | H | 80 | 9.867 | −5.768 | 5.410 | 1.00 | 69.55 | O |
| ATOM | 2760 | N | LEU | H | 81 | 18.264 | −4.601 | 6.690 | 1.00 | 54.99 | N |
| ATOM | 2761 | CA | LEU | H | 81 | 19.584 | −4.696 | 7.312 | 1.00 | 54.90 | C |
| ATOM | 2762 | C | LEU | H | 81 | 19.346 | −5.062 | 8.766 | 1.00 | 60.74 | C |
| ATOM | 2763 | O | LEU | H | 81 | 18.605 | −4.359 | 9.452 | 1.00 | 59.61 | O |
| ATOM | 2764 | CB | LEU | H | 81 | 20.375 | −3.386 | 7.222 | 1.00 | 54.90 | C |
| ATOM | 2765 | CG | LEU | H | 81 | 21.837 | −3.443 | 7.690 | 1.00 | 57.77 | C |
| ATOM | 2766 | CD1 | LEU | H | 81 | 22.673 | −4.302 | 6.772 | 1.00 | 58.61 | C |
| ATOM | 2767 | CD2 | LEU | H | 81 | 22.425 | −2.093 | 7.706 | 1.00 | 55.35 | C |
| ATOM | 2768 | N | GLN | H | 82 | 19.937 | −6.165 | 9.235 | 1.00 | 61.13 | N |
| ATOM | 2769 | CA | GLN | H | 82 | 19.699 | −6.582 | 10.610 | 1.00 | 63.15 | C |
| ATOM | 2770 | C | GLN | H | 82 | 20.955 | −7.069 | 11.351 | 1.00 | 71.51 | C |
| ATOM | 2771 | O | GLN | H | 82 | 21.883 | −7.637 | 10.752 | 1.00 | 71.27 | O |
| ATOM | 2772 | CB | GLN | H | 82 | 18.547 | −7.612 | 10.724 | 1.00 | 64.76 | C |
| ATOM | 2773 | CG | GLN | H | 82 | 18.800 | −8.973 | 10.070 | 1.00 | 89.64 | C |
| ATOM | 2774 | CD | GLN | H | 82 | 18.028 | −10.067 | 10.760 | 1.00 | 108.55 | C |
| ATOM | 2775 | OE1 | GLN | H | 82 | 18.530 | −10.721 | 11.689 | 1.00 | 109.00 | O |
| ATOM | 2776 | NE2 | GLN | H | 82 | 16.797 | −10.294 | 10.310 | 1.00 | 90.25 | N |
| ATOM | 2777 | N | TRP | H | 83 | 20.958 | −6.810 | 12.673 | 1.00 | 70.63 | N |
| ATOM | 2778 | CA | TRP | H | 83 | 22.002 | −7.182 | 13.621 | 1.00 | 71.87 | C |
| ATOM | 2779 | C | TRP | H | 83 | 21.386 | −8.066 | 14.708 | 1.00 | 80.04 | C |
| ATOM | 2780 | O | TRP | H | 83 | 20.257 | −7.824 | 15.162 | 1.00 | 79.90 | O |
| ATOM | 2781 | CB | TRP | H | 83 | 22.587 | −5.932 | 14.336 | 1.00 | 69.80 | C |
| ATOM | 2782 | CG | TRP | H | 83 | 23.252 | −4.909 | 13.463 | 1.00 | 70.04 | C |
| ATOM | 2783 | CD1 | TRP | H | 83 | 24.591 | −4.765 | 13.233 | 1.00 | 72.80 | C |
| ATOM | 2784 | CD2 | TRP | H | 83 | 22.611 | −3.822 | 12.788 | 1.00 | 69.67 | C |
| ATOM | 2785 | NE1 | TRP | H | 83 | 24.817 | −3.674 | 12.419 | 1.00 | 71.75 | N |
| ATOM | 2786 | CE2 | TRP | H | 83 | 23.617 | −3.084 | 12.126 | 1.00 | 72.76 | C |
| ATOM | 2787 | CE3 | TRP | H | 83 | 21.269 | −3.415 | 12.652 | 1.00 | 71.01 | C |
| ATOM | 2788 | CZ2 | TRP | H | 83 | 23.322 | −1.983 | 11.323 | 1.00 | 72.02 | C |
| ATOM | 2789 | CZ3 | TRP | H | 83 | 20.980 | −2.307 | 11.879 | 1.00 | 72.22 | C |
| ATOM | 2790 | CH2 | TRP | H | 83 | 21.998 | −1.601 | 11.229 | 1.00 | 72.92 | C |
| ATOM | 2791 | N | SER | H | 84 | 22.154 | −9.058 | 15.145 | 1.00 | 78.78 | N |
| ATOM | 2792 | CA | SER | H | 84 | 21.818 | −9.923 | 16.266 | 1.00 | 79.55 | C |
| ATOM | 2793 | C | SER | H | 84 | 22.892 | −9.502 | 17.273 | 1.00 | 85.26 | C |
| ATOM | 2794 | O | SER | H | 84 | 24.087 | −9.822 | 17.073 | 1.00 | 86.47 | O |
| ATOM | 2795 | CB | SER | H | 84 | 21.964 | −11.396 | 15.883 | 1.00 | 84.03 | C |
| ATOM | 2796 | OG | SER | H | 84 | 20.924 | −11.822 | 15.015 | 1.00 | 95.49 | O |
| ATOM | 2797 | N | SER | H | 85 | 22.488 | −8.660 | 18.268 | 1.00 | 79.09 | N |
| ATOM | 2798 | CA | SER | H | 85 | 23.340 | −8.040 | 19.311 | 1.00 | 77.27 | C |
| ATOM | 2799 | C | SER | H | 85 | 24.213 | −6.859 | 18.778 | 1.00 | 77.19 | C |
| ATOM | 2800 | O | SER | H | 85 | 25.351 | −7.047 | 18.316 | 1.00 | 75.18 | O |
| ATOM | 2801 | CB | SER | H | 85 | 24.181 | −9.058 | 20.086 | 1.00 | 78.84 | C |
| ATOM | 2802 | OG | SER | H | 85 | 24.768 | −8.480 | 21.243 | 1.00 | 82.84 | O |
| ATOM | 2803 | N | LEU | H | 86 | 23.637 | −5.636 | 18.892 | 1.00 | 72.21 | N |
| ATOM | 2804 | CA | LEU | H | 86 | 24.193 | −4.333 | 18.509 | 1.00 | 71.76 | C |
| ATOM | 2805 | C | LEU | H | 86 | 25.289 | −3.852 | 19.477 | 1.00 | 76.64 | C |

TABLE1-continued

Three-dimensional crystal coordinate for anti-TcdB antibody beziotoxumab Fab –C. difficile toxin B (TcdB$^{(1834-2101)}$) complex.

| ATOM | 2806 | O | LEU | H | 86 | 25.010 | −3.685 | 20.666 | 1.00 | 76.71 | O |
|---|---|---|---|---|---|---|---|---|---|---|---|
| ATOM | 2807 | CB | LEU | H | 86 | 23.075 | −3.272 | 18.531 | 1.00 | 71.26 | C |
| ATOM | 2808 | CG | LEU | H | 86 | 22.085 | −3.222 | 17.395 | 1.00 | 75.90 | C |
| ATOM | 2809 | CD1 | LEU | H | 86 | 20.850 | −2.455 | 17.824 | 1.00 | 76.18 | C |
| ATOM | 2810 | CD2 | LEU | H | 86 | 22.690 | −2.557 | 16.180 | 1.00 | 78.29 | C |
| ATOM | 2811 | N | LYS | H | 87 | 26.517 | −3.583 | 18.969 | 1.00 | 72.41 | N |
| ATOM | 2812 | CA | LYS | H | 87 | 27.610 | −3.005 | 19.768 | 1.00 | 70.71 | C |
| ATOM | 2813 | C | LYS | H | 87 | 27.382 | −1.441 | 19.768 | 1.00 | 74.48 | C |
| ATOM | 2814 | O | LYS | H | 87 | 26.676 | −0.937 | 18.889 | 1.00 | 74.24 | O |
| ATOM | 2815 | CB | LYS | H | 87 | 28.984 | −3.417 | 19.178 | 1.00 | 70.76 | C |
| ATOM | 2816 | N | ALA | H | 88 | 27.918 | −0.685 | 20.755 | 1.00 | 70.72 | N |
| ATOM | 2817 | CA | ALA | H | 88 | 27.765 | 0.792 | 20.739 | 1.00 | 70.52 | C |
| ATOM | 2818 | C | ALA | H | 88 | 28.508 | 1.360 | 19.502 | 1.00 | 73.06 | C |
| ATOM | 2819 | O | ALA | H | 88 | 28.102 | 2.368 | 18.915 | 1.00 | 71.60 | O |
| ATOM | 2820 | CB | ALA | H | 88 | 28.333 | 1.404 | 22.009 | 1.00 | 71.21 | C |
| ATOM | 2821 | N | SER | H | 89 | 29.563 | 0.626 | 19.090 | 1.00 | 67.91 | N |
| ATOM | 2822 | CA | SER | H | 89 | 30.421 | 0.784 | 17.935 | 1.00 | 67.22 | C |
| ATOM | 2823 | C | SER | H | 89 | 29.619 | 0.891 | 16.613 | 1.00 | 71.98 | C |
| ATOM | 2824 | O | SER | H | 89 | 30.172 | 1.295 | 15.593 | 1.00 | 73.38 | O |
| ATOM | 2825 | CB | SER | H | 89 | 31.319 | −0.443 | 17.860 | 1.00 | 72.28 | C |
| ATOM | 2826 | OG | SER | H | 89 | 32.534 | −0.146 | 17.198 | 1.00 | 90.02 | O |
| ATOM | 2827 | N | ASP | H | 90 | 28.339 | 0.475 | 16.625 | 1.00 | 67.85 | N |
| ATOM | 2828 | CA | ASP | H | 90 | 27.408 | 0.478 | 15.492 | 1.00 | 66.48 | C |
| ATOM | 2829 | C | ASP | H | 90 | 26.618 | 1.782 | 15.391 | 1.00 | 68.65 | C |
| ATOM | 2830 | O | ASP | H | 90 | 25.804 | 1.906 | 14.465 | 1.00 | 68.47 | O |
| ATOM | 2831 | CB | ASP | H | 90 | 26.429 | −0.717 | 15.575 | 1.00 | 67.84 | C |
| ATOM | 2832 | CG | ASP | H | 90 | 27.041 | −2.110 | 15.569 | 1.00 | 77.99 | C |
| ATOM | 2833 | OD1 | ASP | H | 90 | 28.230 | −2.253 | 15.142 | 1.00 | 77.78 | O |
| ATOM | 2834 | OD2 | ASP | H | 90 | 26.335 | −3.066 | 15.970 | 1.00 | 85.82 | O |
| ATOM | 2835 | N | THR | H | 91 | 26.829 | 2.745 | 16.344 | 1.00 | 63.50 | N |
| ATOM | 2836 | CA | THR | H | 91 | 26.184 | 4.070 | 16.308 | 1.00 | 62.14 | C |
| ATOM | 2837 | C | THR | H | 91 | 26.731 | 4.787 | 15.050 | 1.00 | 63.73 | C |
| ATOM | 2838 | O | THR | H | 91 | 27.914 | 5.153 | 15.024 | 1.00 | 62.31 | O |
| ATOM | 2839 | CB | THR | H | 91 | 26.448 | 4.867 | 17.592 | 1.00 | 65.24 | C |
| ATOM | 2840 | OG1 | THR | H | 91 | 26.072 | 4.078 | 18.709 | 1.00 | 64.85 | O |
| ATOM | 2841 | CG2 | THR | H | 91 | 25.705 | 6.206 | 17.624 | 1.00 | 60.37 | C |
| ATOM | 2842 | N | ALA | H | 92 | 25.891 | 4.846 | 13.971 | 1.00 | 58.43 | N |
| ATOM | 2843 | CA | ALA | H | 92 | 26.186 | 5.406 | 12.644 | 1.00 | 56.37 | C |
| ATOM | 2844 | C | ALA | H | 92 | 24.908 | 5.644 | 11.832 | 1.00 | 58.35 | C |
| ATOM | 2845 | O | ALA | H | 92 | 23.818 | 5.247 | 12.259 | 1.00 | 56.99 | O |
| ATOM | 2846 | CB | ALA | H | 92 | 27.094 | 4.457 | 11.887 | 1.00 | 56.89 | C |
| ATOM | 2847 | N | MET | H | 93 | 25.048 | 6.322 | 10.678 | 1.00 | 55.58 | N |
| ATOM | 2848 | CA | MET | H | 93 | 23.964 | 6.584 | 9.726 | 1.00 | 55.97 | C |
| ATOM | 2849 | C | MET | H | 93 | 23.995 | 5.485 | 8.716 | 1.00 | 59.98 | C |
| ATOM | 2850 | O | MET | H | 93 | 25.077 | 5.120 | 8.228 | 1.00 | 60.68 | O |
| ATOM | 2851 | CB | MET | H | 93 | 24.150 | 7.910 | 9.010 | 1.00 | 58.86 | C |
| ATOM | 2852 | CG | MET | H | 93 | 23.171 | 8.941 | 9.442 | 1.00 | 63.86 | C |
| ATOM | 2853 | SD | MET | H | 93 | 21.581 | 8.687 | 8.679 | 1.00 | 68.93 | S |
| ATOM | 2854 | CE | MET | H | 93 | 20.775 | 10.130 | 9.179 | 1.00 | 65.34 | C |
| ATOM | 2855 | N | TYR | H | 94 | 22.829 | 4.917 | 8.425 | 1.00 | 54.82 | N |
| ATOM | 2856 | CA | TYR | H | 94 | 22.748 | 3.817 | 7.482 | 1.00 | 52.98 | C |
| ATOM | 2857 | C | TYR | H | 94 | 21.902 | 4.193 | 6.315 | 1.00 | 55.89 | C |
| ATOM | 2858 | O | TYR | H | 94 | 20.760 | 4.634 | 6.468 | 1.00 | 53.38 | O |
| ATOM | 2859 | CB | TYR | H | 94 | 22.277 | 2.521 | 8.162 | 1.00 | 53.06 | C |
| ATOM | 2860 | CG | TYR | H | 94 | 23.258 | 2.005 | 9.202 | 1.00 | 51.98 | C |
| ATOM | 2861 | CD1 | TYR | H | 94 | 24.342 | 1.217 | 8.833 | 1.00 | 52.51 | C |
| ATOM | 2862 | CD2 | TYR | H | 94 | 23.115 | 2.330 | 10.551 | 1.00 | 51.91 | C |
| ATOM | 2863 | CE1 | TYR | H | 94 | 25.257 | 0.763 | 9.777 | 1.00 | 52.51 | C |
| ATOM | 2864 | CE2 | TYR | H | 94 | 24.021 | 1.865 | 11.508 | 1.00 | 52.16 | C |
| ATOM | 2865 | CZ | TYR | H | 94 | 25.106 | 1.105 | 11.113 | 1.00 | 56.25 | C |
| ATOM | 2866 | OH | TYR | H | 94 | 26.025 | 0.670 | 12.045 | 1.00 | 56.69 | O |
| ATOM | 2867 | N | TYR | H | 95 | 22.516 | 4.092 | 5.133 | 1.00 | 53.56 | N |
| ATOM | 2868 | CA | TYR | H | 95 | 21.888 | 4.411 | 3.862 | 1.00 | 52.33 | C |
| ATOM | 2869 | C | TYR | H | 95 | 21.728 | 3.163 | 3.020 | 1.00 | 56.95 | C |
| ATOM | 2870 | O | TYR | H | 95 | 22.621 | 2.320 | 2.997 | 1.00 | 55.53 | O |
| ATOM | 2871 | CB | TYR | H | 95 | 22.763 | 5.406 | 3.086 | 1.00 | 52.04 | C |
| ATOM | 2872 | CG | TYR | H | 95 | 22.903 | 6.775 | 3.710 | 1.00 | 52.21 | C |
| ATOM | 2873 | CD1 | TYR | H | 95 | 21.867 | 7.706 | 3.636 | 1.00 | 53.99 | C |
| ATOM | 2874 | CD2 | TYR | H | 95 | 24.108 | 7.180 | 4.292 | 1.00 | 51.79 | C |
| ATOM | 2875 | CE1 | TYR | H | 95 | 22.002 | 8.978 | 4.183 | 1.00 | 55.27 | C |
| ATOM | 2876 | CE2 | TYR | H | 95 | 24.260 | 8.459 | 4.823 | 1.00 | 52.19 | C |
| ATOM | 2877 | CZ | TYR | H | 95 | 23.206 | 9.361 | 4.756 | 1.00 | 63.06 | C |
| ATOM | 2878 | OH | TYR | H | 95 | 23.338 | 10.631 | 5.276 | 1.00 | 68.00 | O |
| ATOM | 2879 | N | CYS | H | 96 | 20.606 | 3.056 | 2.311 | 1.00 | 55.60 | N |
| ATOM | 2880 | CA | CYS | H | 96 | 20.410 | 2.015 | 1.324 | 1.00 | 56.73 | C |
| ATOM | 2881 | C | CYS | H | 96 | 20.346 | 2.796 | 0.021 | 1.00 | 56.54 | C |
| ATOM | 2882 | O | CYS | H | 96 | 19.775 | 3.886 | −0.042 | 1.00 | 54.02 | O |

TABLE 1-continued

Three-dimensional crystal coordinate for anti-TcdB antibody beziotoxumab
Fab –C. difficile toxin B (TcdB$^{(1834-2101)}$) complex.

| ATOM | 2883 | CB | CYS | H | 96 | 19.137 | 1.205 | 1.552 | 1.00 | 59.38 | C |
|------|------|------|-----|---|-----|--------|--------|---------|------|-------|---|
| ATOM | 2884 | SG | CYS | H | 96 | 17.625 | 2.153 | 1.265 | 1.00 | 65.20 | S |
| ATOM | 2885 | N | ALA | H | 97 | 20.937 | 2.247 | −1.012 | 1.00 | 52.41 | N |
| ATOM | 2886 | CA | ALA | H | 97 | 20.941 | 2.839 | −2.324 | 1.00 | 51.53 | C |
| ATOM | 2887 | C | ALA | H | 97 | 20.675 | 1.735 | −3.347 | 1.00 | 56.69 | C |
| ATOM | 2888 | O | ALA | H | 97 | 21.040 | 0.583 | −3.104 | 1.00 | 57.59 | O |
| ATOM | 2889 | CB | ALA | H | 97 | 22.297 | 3.456 | −2.578 | 1.00 | 51.98 | C |
| ATOM | 2890 | N | ARG | H | 98 | 20.065 | 2.051 | −4.489 | 1.00 | 52.08 | N |
| ATOM | 2891 | CA | ARG | H | 98 | 19.927 | 0.999 | −5.477 | 1.00 | 51.87 | C |
| ATOM | 2892 | C | ARG | H | 98 | 20.966 | 1.213 | −6.513 | 1.00 | 54.86 | C |
| ATOM | 2893 | O | ARG | H | 98 | 21.307 | 2.361 | −6.785 | 1.00 | 55.30 | O |
| ATOM | 2894 | CB | ARG | H | 98 | 18.522 | 0.825 | −6.053 | 1.00 | 53.96 | C |
| ATOM | 2895 | CG | ARG | H | 98 | 18.113 | 1.890 | −7.012 | 1.00 | 60.94 | C |
| ATOM | 2896 | CD | ARG | H | 98 | 17.599 | 1.280 | −8.258 | 1.00 | 47.40 | C |
| ATOM | 2897 | NE | ARG | H | 98 | 17.756 | 2.262 | −9.316 | 1.00 | 48.43 | N |
| ATOM | 2898 | CZ | ARG | H | 98 | 16.781 | 2.625 | −10.127 | 1.00 | 65.16 | C |
| ATOM | 2899 | NH1 | ARG | H | 98 | 15.583 | 2.068 | −10.023 | 1.00 | 54.02 | N |
| ATOM | 2900 | NH2 | ARG | H | 98 | 16.997 | 3.537 | −11.064 | 1.00 | 51.25 | N |
| ATOM | 2901 | O | ARG | H | 99 | 21.089 | −0.334 | −9.744 | 1.00 | 55.00 | O |
| ATOM | 2902 | N | ARG | H | 99 | 21.539 | 0.106 | −7.020 | 1.00 | 49.38 | N |
| ATOM | 2903 | CA | ARG | H | 99 | 22.639 | 0.089 | −7.972 | 1.00 | 48.12 | C |
| ATOM | 2904 | C | ARG | H | 99 | 22.132 | 0.218 | −9.402 | 1.00 | 53.68 | C |
| ATOM | 2905 | CB | ARG | H | 99 | 23.414 | −1.227 | −7.803 | 1.00 | 45.76 | C |
| ATOM | 2906 | CG | ARG | H | 99 | 24.800 | −1.254 | −8.449 | 1.00 | 51.48 | C |
| ATOM | 2907 | CD | ARG | H | 99 | 25.209 | −2.638 | −8.910 | 1.00 | 45.06 | C |
| ATOM | 2908 | NE | ARG | H | 99 | 24.451 | −3.067 | −10.085 | 1.00 | 53.92 | N |
| ATOM | 2909 | CZ | ARG | H | 99 | 24.508 | −4.291 | −10.594 | 1.00 | 62.73 | C |
| ATOM | 2910 | NH1 | ARG | H | 99 | 25.285 | −5.210 | −10.040 | 1.00 | 39.49 | N |
| ATOM | 2911 | NH2 | ARG | H | 99 | 23.768 | −4.614 | −11.649 | 1.00 | 45.86 | N |
| ATOM | 2912 | O | ARG | H | 100 | 23.880 | −0.930 | −11.839 | 1.00 | 58.84 | O |
| ATOM | 2913 | N | ARG | H | 100 | 22.892 | 0.922 | −10.238 | 1.00 | 50.31 | N |
| ATOM | 2914 | CA | ARG | H | 100 | 22.633 | 1.089 | −11.667 | 1.00 | 50.34 | C |
| ATOM | 2915 | C | ARG | H | 100 | 22.986 | −0.223 | −12.338 | 1.00 | 56.80 | C |
| ATOM | 2916 | CB | ARG | H | 100 | 23.556 | 2.162 | −12.229 | 1.00 | 48.23 | C |
| ATOM | 2917 | CG | ARG | H | 100 | 22.880 | 3.509 | −12.375 | 1.00 | 51.28 | C |
| ATOM | 2918 | CD | ARG | H | 100 | 23.698 | 4.479 | −13.189 | 1.00 | 43.85 | C |
| ATOM | 2919 | NE | ARG | H | 100 | 23.878 | 4.031 | −14.571 | 1.00 | 45.57 | N |
| ATOM | 2920 | CZ | ARG | H | 100 | 23.111 | 4.393 | −15.597 | 1.00 | 66.06 | C |
| ATOM | 2921 | NH1 | ARG | H | 100 | 22.075 | 5.209 | −15.410 | 1.00 | 69.25 | N |
| ATOM | 2922 | NH2 | ARG | H | 100 | 23.367 | 3.937 | −16.815 | 1.00 | 47.88 | N |
| ATOM | 2923 | O | ASN | H | 101 | 23.929 | −2.575 | −16.093 | 1.00 | 56.71 | O |
| ATOM | 2924 | N | ASN | H | 101 | 22.328 | −0.564 | −13.467 | 1.00 | 51.88 | N |
| ATOM | 2925 | CA | ASN | H | 101 | 22.645 | −1.840 | −14.135 | 1.00 | 51.03 | C |
| ATOM | 2926 | C | ASN | H | 101 | 23.793 | −1.717 | −15.213 | 1.00 | 55.10 | C |
| ATOM | 2927 | CB | ASN | H | 101 | 21.388 | −2.523 | −14.675 | 1.00 | 47.82 | C |
| ATOM | 2928 | CG | ASN | H | 101 | 20.420 | −3.054 | −13.628 | 1.00 | 59.25 | C |
| ATOM | 2929 | OD1 | ASN | H | 101 | 20.798 | −3.548 | −12.530 | 1.00 | 65.96 | O |
| ATOM | 2930 | ND2 | ASN | H | 101 | 19.130 | −2.997 | −13.981 | 1.00 | 30.49 | N |
| ATOM | 2931 | O | TRP | H | 102 | 25.609 | 2.000 | −15.151 | 1.00 | 61.85 | O |
| ATOM | 2932 | N | TRP | H | 102 | 24.674 | −0.699 | −15.027 | 1.00 | 49.34 | N |
| ATOM | 2933 | CA | TRP | H | 102 | 25.924 | −0.317 | −15.707 | 1.00 | 47.30 | C |
| ATOM | 2934 | C | TRP | H | 102 | 26.353 | 1.028 | −15.049 | 1.00 | 58.96 | C |
| ATOM | 2935 | CB | TRP | H | 102 | 25.700 | −0.121 | −17.213 | 1.00 | 44.02 | C |
| ATOM | 2936 | CG | TRP | H | 102 | 26.982 | −0.021 | −17.993 | 1.00 | 44.14 | C |
| ATOM | 2937 | CD1 | TRP | H | 102 | 27.575 | −1.015 | −18.731 | 1.00 | 46.64 | C |
| ATOM | 2938 | CD2 | TRP | H | 102 | 27.900 | 1.095 | −18.007 | 1.00 | 43.27 | C |
| ATOM | 2939 | NE1 | TRP | H | 102 | 28.800 | −0.590 | −19.194 | 1.00 | 45.46 | N |
| ATOM | 2940 | CE2 | TRP | H | 102 | 29.007 | 0.714 | −18.796 | 1.00 | 46.60 | C |
| ATOM | 2941 | CE3 | TRP | H | 102 | 27.887 | 2.389 | −17.437 | 1.00 | 43.78 | C |
| ATOM | 2942 | CZ2 | TRP | H | 102 | 30.069 | 1.589 | −19.058 | 1.00 | 45.50 | C |
| ATOM | 2943 | CZ3 | TRP | H | 102 | 28.954 | 3.239 | −17.667 | 1.00 | 44.46 | C |
| ATOM | 2944 | CH2 | TRP | H | 102 | 30.023 | 2.844 | −18.481 | 1.00 | 45.06 | C |
| ATOM | 2945 | O | GLY | H | 103 | 29.744 | 1.033 | −12.185 | 1.00 | 61.74 | O |
| ATOM | 2946 | N | GLY | H | 103 | 27.516 | 1.167 | −14.422 | 1.00 | 57.33 | N |
| ATOM | 2947 | CA | GLY | H | 103 | 28.560 | 0.210 | −14.122 | 1.00 | 57.19 | C |
| ATOM | 2948 | C | GLY | H | 103 | 28.816 | 0.355 | −12.631 | 1.00 | 60.45 | C |
| ATOM | 2949 | O | ASN | H | 104 | 27.676 | 0.693 | −8.355 | 1.00 | 52.85 | O |
| ATOM | 2950 | N | ASN | H | 104 | 27.838 | −0.115 | −11.887 | 1.00 | 55.30 | N |
| ATOM | 2951 | CA | ASN | H | 104 | 27.773 | −0.328 | −10.469 | 1.00 | 51.39 | C |
| ATOM | 2952 | C | ASN | H | 104 | 27.691 | 0.886 | −9.569 | 1.00 | 52.60 | C |
| ATOM | 2953 | CB | ASN | H | 104 | 28.901 | −1.223 | −10.046 | 1.00 | 52.22 | C |
| ATOM | 2954 | CG | ASN | H | 104 | 28.707 | −2.654 | −10.494 | 1.00 | 63.75 | C |
| ATOM | 2955 | OD1 | ASN | H | 104 | 27.653 | −3.072 | −11.013 | 1.00 | 52.23 | O |
| ATOM | 2956 | ND2 | ASN | H | 104 | 29.719 | −3.442 | −10.274 | 1.00 | 57.94 | N |
| ATOM | 2957 | N | ALA | H | 105 | 27.454 | 2.090 | −10.101 | 1.00 | 47.63 | N |
| ATOM | 2958 | CA | ALA | H | 105 | 27.250 | 3.267 | −9.237 | 1.00 | 45.74 | C |
| ATOM | 2959 | C | ALA | H | 105 | 25.881 | 3.187 | −8.565 | 1.00 | 50.08 | C |

TABLE 1-continued

Three-dimensional crystal coordinate for anti-TcdB antibody beziotoxumab Fab –C. difficile toxin B (TcdB$^{(1834-2101)}$) complex.

| ATOM | 2960 | O | ALA | H | 105 | 25.002 | 2.520 | −9.104 | 1.00 | 50.66 | O |
|---|---|---|---|---|---|---|---|---|---|---|---|
| ATOM | 2961 | CB | ALA | H | 105 | 27.371 | 4.539 | −10.044 | 1.00 | 45.67 | C |
| ATOM | 2962 | N | PHE | H | 106 | 25.692 | 3.812 | −7.380 | 1.00 | 46.97 | N |
| ATOM | 2963 | CA | PHE | H | 106 | 24.393 | 3.791 | −6.688 | 1.00 | 46.47 | C |
| ATOM | 2964 | C | PHE | H | 106 | 23.676 | 5.029 | −7.079 | 1.00 | 51.03 | C |
| ATOM | 2965 | O | PHE | H | 106 | 24.028 | 6.103 | −6.586 | 1.00 | 52.54 | O |
| ATOM | 2966 | CB | PHE | H | 106 | 24.573 | 3.732 | −5.168 | 1.00 | 48.38 | C |
| ATOM | 2967 | CG | PHE | H | 106 | 25.256 | 2.471 | −4.689 | 1.00 | 49.81 | C |
| ATOM | 2968 | CD1 | PHE | H | 106 | 24.666 | 1.224 | −4.883 | 1.00 | 50.41 | C |
| ATOM | 2969 | CD2 | PHE | H | 106 | 26.519 | 2.523 | −4.107 | 1.00 | 50.74 | C |
| ATOM | 2970 | CE1 | PHE | H | 106 | 25.310 | 0.059 | −4.464 | 1.00 | 49.97 | C |
| ATOM | 2971 | CE2 | PHE | H | 106 | 27.166 | 1.353 | −3.705 | 1.00 | 52.62 | C |
| ATOM | 2972 | CZ | PHE | H | 106 | 26.556 | 0.130 | −3.891 | 1.00 | 49.76 | C |
| ATOM | 2973 | N | ASP | H | 107 | 22.703 | 4.908 | −8.000 | 1.00 | 47.06 | N |
| ATOM | 2974 | CA | ASP | H | 107 | 22.003 | 6.065 | −8.555 | 1.00 | 47.41 | C |
| ATOM | 2975 | C | ASP | H | 107 | 20.910 | 6.680 | −7.648 | 1.00 | 55.81 | C |
| ATOM | 2976 | O | ASP | H | 107 | 20.735 | 7.909 | −7.701 | 1.00 | 57.59 | O |
| ATOM | 2977 | CB | ASP | H | 107 | 21.445 | 5.764 | −9.954 | 1.00 | 48.51 | C |
| ATOM | 2978 | CG | ASP | H | 107 | 20.383 | 4.689 | −10.054 | 1.00 | 58.36 | C |
| ATOM | 2979 | OD1 | ASP | H | 107 | 20.173 | 3.966 | −9.061 | 1.00 | 61.37 | O |
| ATOM | 2980 | OD2 | ASP | H | 107 | 19.763 | 4.564 | −11.137 | 1.00 | 61.48 | O |
| ATOM | 2981 | N | ILE | H | 108 | 20.169 | 5.863 | −6.845 | 1.00 | 51.61 | N |
| ATOM | 2982 | CA | ILE | H | 108 | 19.117 | 6.391 | −5.962 | 1.00 | 50.68 | C |
| ATOM | 2983 | C | ILE | H | 108 | 19.441 | 6.044 | −4.534 | 1.00 | 52.42 | C |
| ATOM | 2984 | O | ILE | H | 108 | 19.818 | 4.913 | −4.286 | 1.00 | 51.92 | O |
| ATOM | 2985 | CB | ILE | H | 108 | 17.676 | 6.014 | −6.406 | 1.00 | 53.67 | C |
| ATOM | 2986 | CG1 | ILE | H | 108 | 17.118 | 7.092 | −7.359 | 1.00 | 52.54 | C |
| ATOM | 2987 | CG2 | ILE | H | 108 | 16.713 | 5.847 | −5.233 | 1.00 | 55.16 | C |
| ATOM | 2988 | CD1 | ILE | H | 108 | 17.330 | 6.843 | −8.722 | 1.00 | 56.19 | C |
| ATOM | 2989 | N | TRP | H | 109 | 19.379 | 7.048 | −3.617 | 1.00 | 48.02 | N |
| ATOM | 2990 | CA | TRP | H | 109 | 19.720 | 6.892 | −2.196 | 1.00 | 47.47 | C |
| ATOM | 2991 | C | TRP | H | 109 | 18.511 | 7.099 | −1.266 | 1.00 | 53.80 | C |
| ATOM | 2992 | O | TRP | H | 109 | 17.601 | 7.856 | −1.586 | 1.00 | 55.48 | O |
| ATOM | 2993 | CB | TRP | H | 109 | 20.903 | 7.829 | −1.793 | 1.00 | 44.39 | C |
| ATOM | 2994 | CG | TRP | H | 109 | 22.235 | 7.481 | −2.403 | 1.00 | 44.39 | C |
| ATOM | 2995 | CD1 | TRP | H | 109 | 22.600 | 7.612 | −3.715 | 1.00 | 47.24 | C |
| ATOM | 2996 | CD2 | TRP | H | 109 | 23.396 | 6.980 | −1.715 | 1.00 | 43.92 | C |
| ATOM | 2997 | NE1 | TRP | H | 109 | 23.915 | 7.238 | −3.890 | 1.00 | 46.25 | N |
| ATOM | 2998 | CE2 | TRP | H | 109 | 24.416 | 6.806 | −2.682 | 1.00 | 47.79 | C |
| ATOM | 2999 | CE3 | TRP | H | 109 | 23.677 | 6.644 | −0.373 | 1.00 | 44.28 | C |
| ATOM | 3000 | CZ2 | TRP | H | 109 | 25.699 | 6.318 | −2.344 | 1.00 | 46.31 | C |
| ATOM | 3001 | CZ3 | TRP | H | 109 | 24.940 | 6.152 | −0.052 | 1.00 | 44.72 | C |
| ATOM | 3002 | CH2 | TRP | H | 109 | 25.934 | 6.001 | −1.029 | 1.00 | 45.00 | C |
| ATOM | 3003 | N | GLY | H | 110 | 18.520 | 6.425 | −0.129 | 1.00 | 50.34 | N |
| ATOM | 3004 | CA | GLY | H | 110 | 17.496 | 6.594 | 0.890 | 1.00 | 50.70 | C |
| ATOM | 3005 | C | GLY | H | 110 | 17.844 | 7.788 | 1.754 | 1.00 | 56.66 | C |
| ATOM | 3006 | O | GLY | H | 110 | 18.992 | 8.232 | 1.747 | 1.00 | 58.25 | O |
| ATOM | 3007 | N | GLN | H | 111 | 16.873 | 8.344 | 2.485 | 1.00 | 53.44 | N |
| ATOM | 3008 | CA | GLN | H | 111 | 17.126 | 9.507 | 3.357 | 1.00 | 53.30 | C |
| ATOM | 3009 | C | GLN | H | 111 | 18.123 | 9.216 | 4.493 | 1.00 | 59.37 | C |
| ATOM | 3010 | O | GLN | H | 111 | 18.797 | 10.126 | 4.968 | 1.00 | 61.40 | O |
| ATOM | 3011 | CB | GLN | H | 111 | 15.811 | 10.095 | 3.905 | 1.00 | 54.40 | C |
| ATOM | 3012 | CG | GLN | H | 111 | 15.213 | 9.393 | 5.136 | 1.00 | 47.13 | C |
| ATOM | 3013 | CD | GLN | H | 111 | 14.240 | 8.264 | 4.865 | 1.00 | 64.42 | C |
| ATOM | 3014 | OE1 | GLN | H | 111 | 14.043 | 7.796 | 3.738 | 1.00 | 62.66 | O |
| ATOM | 3015 | NE2 | GLN | H | 111 | 13.624 | 7.784 | 5.922 | 1.00 | 62.40 | N |
| ATOM | 3016 | N | GLY | H | 112 | 18.221 | 7.952 | 4.873 | 1.00 | 56.18 | N |
| ATOM | 3017 | CA | GLY | H | 112 | 19.090 | 7.480 | 5.932 | 1.00 | 56.09 | C |
| ATOM | 3018 | C | GLY | H | 112 | 18.306 | 7.101 | 7.164 | 1.00 | 61.49 | C |
| ATOM | 3019 | O | GLY | H | 112 | 17.174 | 7.558 | 7.355 | 1.00 | 61.44 | O |
| ATOM | 3020 | N | THR | H | 113 | 18.898 | 6.224 | 7.984 | 1.00 | 58.70 | N |
| ATOM | 3021 | CA | THR | H | 113 | 18.331 | 5.787 | 9.252 | 1.00 | 58.80 | C |
| ATOM | 3022 | C | THR | H | 113 | 19.420 | 5.985 | 10.308 | 1.00 | 63.64 | C |
| ATOM | 3023 | O | THR | H | 113 | 20.469 | 5.330 | 10.219 | 1.00 | 63.23 | O |
| ATOM | 3024 | CB | THR | H | 113 | 17.823 | 4.324 | 9.211 | 1.00 | 65.82 | C |
| ATOM | 3025 | OG1 | THR | H | 113 | 16.766 | 4.171 | 8.257 | 1.00 | 69.38 | O |
| ATOM | 3026 | CG2 | THR | H | 113 | 17.347 | 3.849 | 10.572 | 1.00 | 61.52 | C |
| ATOM | 3027 | N | MET | H | 114 | 19.179 | 6.882 | 11.303 | 1.00 | 60.14 | N |
| ATOM | 3028 | CA | MET | H | 114 | 20.161 | 7.106 | 12.353 | 1.00 | 59.89 | C |
| ATOM | 3029 | C | MET | H | 114 | 20.014 | 6.022 | 13.374 | 1.00 | 65.10 | C |
| ATOM | 3030 | O | MET | H | 114 | 18.925 | 5.819 | 13.908 | 1.00 | 66.14 | O |
| ATOM | 3031 | CB | MET | H | 114 | 20.051 | 8.515 | 12.979 | 1.00 | 62.50 | C |
| ATOM | 3032 | CG | MET | H | 114 | 21.186 | 8.852 | 13.943 | 1.00 | 66.89 | C |
| ATOM | 3033 | SD | MET | H | 114 | 22.837 | 8.929 | 13.167 | 1.00 | 72.90 | S |
| ATOM | 3034 | CE | MET | H | 114 | 23.888 | 8.121 | 14.438 | 1.00 | 68.92 | C |
| ATOM | 3035 | N | VAL | H | 115 | 21.093 | 5.282 | 13.610 | 1.00 | 61.55 | N |
| ATOM | 3036 | CA | VAL | H | 115 | 21.094 | 4.198 | 14.589 | 1.00 | 61.01 | C |

TABLE 1-continued

Three-dimensional crystal coordinate for anti-TcdB antibody beziotoxumab Fab –C. difficile toxin B (TcdB$^{(1834-2101)}$) complex.

| ATOM | 3037 | C | VAL | H | 115 | 22.055 | 4.570 | 15.724 | 1.00 | 68.25 | C |
|---|---|---|---|---|---|---|---|---|---|---|---|
| ATOM | 3038 | O | VAL | H | 115 | 23.281 | 4.527 | 15.552 | 1.00 | 68.88 | O |
| ATOM | 3039 | CB | VAL | H | 115 | 21.376 | 2.811 | 13.951 | 1.00 | 63.65 | C |
| ATOM | 3040 | CG1 | VAL | H | 115 | 21.498 | 1.720 | 15.012 | 1.00 | 62.84 | C |
| ATOM | 3041 | CG2 | VAL | H | 115 | 20.295 | 2.449 | 12.938 | 1.00 | 63.40 | C |
| ATOM | 3042 | N | THR | H | 116 | 21.467 | 5.004 | 16.862 | 1.00 | 65.55 | N |
| ATOM | 3043 | CA | THR | H | 116 | 22.152 | 5.401 | 18.105 | 1.00 | 65.09 | C |
| ATOM | 3044 | C | THR | H | 116 | 22.114 | 4.179 | 19.047 | 1.00 | 66.36 | C |
| ATOM | 3045 | O | THR | H | 116 | 21.013 | 3.706 | 19.333 | 1.00 | 65.25 | O |
| ATOM | 3046 | CB | THR | H | 116 | 21.468 | 6.656 | 18.723 | 1.00 | 70.15 | C |
| ATOM | 3047 | OG1 | THR | H | 116 | 20.847 | 7.462 | 17.704 | 1.00 | 67.81 | O |
| ATOM | 3048 | CG2 | THR | H | 116 | 22.423 | 7.498 | 19.545 | 1.00 | 66.81 | C |
| ATOM | 3049 | N | VAL | H | 117 | 23.302 | 3.634 | 19.458 | 1.00 | 61.95 | N |
| ATOM | 3050 | CA | VAL | H | 117 | 23.472 | 2.448 | 20.340 | 1.00 | 62.42 | C |
| ATOM | 3051 | C | VAL | H | 117 | 24.314 | 2.742 | 21.624 | 1.00 | 68.67 | C |
| ATOM | 3052 | O | VAL | H | 117 | 25.547 | 2.810 | 21.543 | 1.00 | 68.02 | O |
| ATOM | 3053 | CB | VAL | H | 117 | 24.058 | 1.192 | 19.623 | 1.00 | 66.34 | C |
| ATOM | 3054 | CG1 | VAL | H | 117 | 23.986 | −0.036 | 20.533 | 1.00 | 66.42 | C |
| ATOM | 3055 | CG2 | VAL | H | 117 | 23.376 | 0.913 | 18.290 | 1.00 | 66.07 | C |
| ATOM | 3056 | N | SER | H | 118 | 23.657 | 2.782 | 22.810 | 1.00 | 66.45 | N |
| ATOM | 3057 | CA | SER | H | 118 | 24.306 | 3.052 | 24.108 | 1.00 | 65.78 | C |
| ATOM | 3058 | C | SER | H | 118 | 23.777 | 2.191 | 25.263 | 1.00 | 70.89 | C |
| ATOM | 3059 | O | SER | H | 118 | 22.569 | 1.911 | 25.316 | 1.00 | 71.47 | O |
| ATOM | 3060 | CB | SER | H | 118 | 24.085 | 4.519 | 24.485 | 1.00 | 65.29 | C |
| ATOM | 3061 | OG | SER | H | 118 | 24.907 | 4.959 | 25.555 | 1.00 | 68.49 | O |
| ATOM | 3062 | N | SER | H | 119 | 24.650 | 1.904 | 26.266 | 1.00 | 66.28 | N |
| ATOM | 3063 | CA | SER | H | 119 | 24.219 | 1.259 | 27.532 | 1.00 | 64.79 | C |
| ATOM | 3064 | C | SER | H | 119 | 23.426 | 2.272 | 28.411 | 1.00 | 63.69 | C |
| ATOM | 3065 | O | SER | H | 119 | 22.745 | 1.874 | 29.351 | 1.00 | 63.41 | O |
| ATOM | 3066 | CB | SER | H | 119 | 25.419 | 0.692 | 28.297 | 1.00 | 68.73 | C |
| ATOM | 3067 | OG | SER | H | 119 | 26.358 | 1.693 | 28.659 | 1.00 | 79.39 | O |
| ATOM | 3068 | N | ALA | H | 120 | 23.510 | 3.572 | 28.066 | 1.00 | 57.76 | N |
| ATOM | 3069 | CA | ALA | H | 120 | 22.864 | 4.686 | 28.742 | 1.00 | 56.97 | C |
| ATOM | 3070 | C | ALA | H | 120 | 21.349 | 4.650 | 28.627 | 1.00 | 63.07 | C |
| ATOM | 3071 | O | ALA | H | 120 | 20.804 | 4.003 | 27.725 | 1.00 | 63.69 | O |
| ATOM | 3072 | CB | ALA | H | 120 | 23.391 | 6.005 | 28.204 | 1.00 | 57.12 | C |
| ATOM | 3073 | N | SER | H | 121 | 20.683 | 5.391 | 29.527 | 1.00 | 59.50 | N |
| ATOM | 3074 | CA | SER | H | 121 | 19.240 | 5.499 | 29.604 | 1.00 | 60.12 | C |
| ATOM | 3075 | C | SER | H | 121 | 18.842 | 6.961 | 29.473 | 1.00 | 63.89 | C |
| ATOM | 3076 | O | SER | H | 121 | 19.634 | 7.829 | 29.842 | 1.00 | 65.66 | O |
| ATOM | 3077 | CB | SER | H | 121 | 18.762 | 4.950 | 30.946 | 1.00 | 66.07 | C |
| ATOM | 3078 | OG | SER | H | 121 | 19.551 | 3.838 | 31.340 | 1.00 | 81.48 | O |
| ATOM | 3079 | N | THR | H | 122 | 17.621 | 7.233 | 28.989 | 1.00 | 58.12 | N |
| ATOM | 3080 | CA | THR | H | 122 | 17.087 | 8.574 | 28.817 | 1.00 | 58.48 | C |
| ATOM | 3081 | C | THR | H | 122 | 17.198 | 9.442 | 30.084 | 1.00 | 68.58 | C |
| ATOM | 3082 | O | THR | H | 122 | 16.421 | 9.279 | 31.044 | 1.00 | 71.19 | O |
| ATOM | 3083 | CB | THR | H | 122 | 15.643 | 8.543 | 28.293 | 1.00 | 60.77 | C |
| ATOM | 3084 | OG1 | THR | H | 122 | 15.516 | 7.588 | 27.248 | 1.00 | 61.19 | O |
| ATOM | 3085 | CG2 | THR | H | 122 | 15.172 | 9.903 | 27.821 | 1.00 | 55.16 | C |
| ATOM | 3086 | N | LYS | H | 123 | 18.194 | 10.348 | 30.078 | 1.00 | 66.00 | N |
| ATOM | 3087 | CA | LYS | H | 123 | 18.456 | 11.334 | 31.125 | 1.00 | 65.83 | C |
| ATOM | 3088 | C | LYS | H | 123 | 18.253 | 12.707 | 30.500 | 1.00 | 72.08 | C |
| ATOM | 3089 | O | LYS | H | 123 | 18.637 | 12.929 | 29.352 | 1.00 | 72.25 | O |
| ATOM | 3090 | CB | LYS | H | 123 | 19.873 | 11.185 | 31.738 | 1.00 | 66.63 | C |
| ATOM | 3091 | N | GLY | H | 124 | 17.584 | 13.587 | 31.223 | 1.00 | 70.52 | N |
| ATOM | 3092 | CA | GLY | H | 124 | 17.344 | 14.958 | 30.782 | 1.00 | 70.71 | C |
| ATOM | 3093 | C | GLY | H | 124 | 18.552 | 15.852 | 31.021 | 1.00 | 75.03 | C |
| ATOM | 3094 | O | GLY | H | 124 | 19.391 | 15.555 | 31.891 | 1.00 | 74.65 | O |
| ATOM | 3095 | N | PRO | H | 125 | 18.660 | 16.966 | 30.257 | 1.00 | 71.42 | N |
| ATOM | 3096 | CA | PRO | H | 125 | 19.816 | 17.870 | 30.421 | 1.00 | 71.26 | C |
| ATOM | 3097 | C | PRO | H | 125 | 19.812 | 18.710 | 31.697 | 1.00 | 78.29 | C |
| ATOM | 3098 | O | PRO | H | 125 | 18.749 | 18.989 | 32.268 | 1.00 | 79.33 | O |
| ATOM | 3099 | CB | PRO | H | 125 | 19.693 | 18.800 | 29.213 | 1.00 | 72.37 | C |
| ATOM | 3100 | CG | PRO | H | 125 | 18.226 | 18.842 | 28.909 | 1.00 | 76.30 | C |
| ATOM | 3101 | CD | PRO | H | 125 | 17.743 | 17.447 | 29.198 | 1.00 | 72.35 | C |
| ATOM | 3102 | N | SER | H | 126 | 21.009 | 19.153 | 32.111 | 1.00 | 74.62 | N |
| ATOM | 3103 | CA | SER | H | 126 | 21.216 | 20.084 | 33.221 | 1.00 | 73.97 | C |
| ATOM | 3104 | C | SER | H | 126 | 21.532 | 21.396 | 32.512 | 1.00 | 79.67 | C |
| ATOM | 3105 | O | SER | H | 126 | 22.214 | 21.370 | 31.487 | 1.00 | 81.18 | O |
| ATOM | 3106 | CB | SER | H | 126 | 22.423 | 19.669 | 34.059 | 1.00 | 75.14 | C |
| ATOM | 3107 | OG | SER | H | 126 | 22.330 | 18.357 | 34.583 | 1.00 | 77.89 | O |
| ATOM | 3108 | N | VAL | H | 127 | 21.021 | 22.524 | 32.992 | 1.00 | 75.65 | N |
| ATOM | 3109 | CA | VAL | H | 127 | 21.315 | 23.807 | 32.336 | 1.00 | 75.07 | C |
| ATOM | 3110 | C | VAL | H | 127 | 22.026 | 24.731 | 33.319 | 1.00 | 82.70 | C |
| ATOM | 3111 | O | VAL | H | 127 | 21.512 | 25.023 | 34.408 | 1.00 | 83.14 | O |
| ATOM | 3112 | CB | VAL | H | 127 | 20.107 | 24.478 | 31.616 | 1.00 | 76.83 | C |
| ATOM | 3113 | CG1 | VAL | H | 127 | 20.518 | 25.791 | 30.956 | 1.00 | 76.16 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 3114 | CG2 | VAL | H | 127 | 19.480 | 23.537 | 30.587 | 1.00 | 76.11 | C |
|------|------|-----|-----|---|-----|--------|--------|--------|------|-------|---|
| ATOM | 3115 | N | PHE | H | 128 | 23.240 | 25.135 | 32.945 | 1.00 | 80.69 | N |
| ATOM | 3116 | CA | PHE | H | 128 | 24.086 | 26.029 | 33.728 | 1.00 | 81.26 | C |
| ATOM | 3117 | C | PHE | H | 128 | 24.387 | 27.283 | 32.921 | 1.00 | 88.81 | C |
| ATOM | 3118 | O | PHE | H | 128 | 24.598 | 27.175 | 31.711 | 1.00 | 89.76 | O |
| ATOM | 3119 | CB | PHE | H | 128 | 25.389 | 25.327 | 34.120 | 1.00 | 82.93 | C |
| ATOM | 3120 | CG | PHE | H | 128 | 25.164 | 24.003 | 34.812 | 1.00 | 84.36 | C |
| ATOM | 3121 | CD1 | PHE | H | 128 | 24.499 | 23.941 | 36.031 | 1.00 | 87.04 | C |
| ATOM | 3122 | CD2 | PHE | H | 128 | 25.612 | 22.816 | 34.243 | 1.00 | 86.57 | C |
| ATOM | 3123 | CE1 | PHE | H | 128 | 24.277 | 22.713 | 36.663 | 1.00 | 87.59 | C |
| ATOM | 3124 | CE2 | PHE | H | 128 | 25.397 | 21.587 | 34.882 | 1.00 | 89.02 | C |
| ATOM | 3125 | CZ | PHE | H | 128 | 24.743 | 21.547 | 36.094 | 1.00 | 86.48 | C |
| ATOM | 3126 | N | PRO | H | 129 | 24.426 | 28.489 | 33.529 | 1.00 | 86.52 | N |
| ATOM | 3127 | CA | PRO | H | 129 | 24.707 | 29.679 | 32.717 | 1.00 | 86.26 | C |
| ATOM | 3128 | C | PRO | H | 129 | 26.193 | 29.893 | 32.433 | 1.00 | 89.67 | C |
| ATOM | 3129 | O | PRO | H | 129 | 27.058 | 29.434 | 33.182 | 1.00 | 89.25 | O |
| ATOM | 3130 | CB | PRO | H | 129 | 24.091 | 30.821 | 33.534 | 1.00 | 88.01 | C |
| ATOM | 3131 | CG | PRO | H | 129 | 24.188 | 30.352 | 34.954 | 1.00 | 92.58 | C |
| ATOM | 3132 | CD | PRO | H | 129 | 24.220 | 28.840 | 34.953 | 1.00 | 88.16 | C |
| ATOM | 3133 | N | LEU | H | 130 | 26.470 | 30.577 | 31.315 | 1.00 | 85.74 | N |
| ATOM | 3134 | CA | LEU | H | 130 | 27.801 | 30.989 | 30.898 | 1.00 | 85.11 | C |
| ATOM | 3135 | C | LEU | H | 130 | 27.711 | 32.523 | 30.964 | 1.00 | 91.81 | C |
| ATOM | 3136 | O | LEU | H | 130 | 27.365 | 33.184 | 29.984 | 1.00 | 91.69 | O |
| ATOM | 3137 | CB | LEU | H | 130 | 28.149 | 30.449 | 29.484 | 1.00 | 84.16 | C |
| ATOM | 3138 | CG | LEU | H | 130 | 28.257 | 28.919 | 29.307 | 1.00 | 86.33 | C |
| ATOM | 3139 | CD1 | LEU | H | 130 | 28.333 | 28.554 | 27.861 | 1.00 | 85.71 | C |
| ATOM | 3140 | CD2 | LEU | H | 130 | 29.463 | 28.352 | 30.014 | 1.00 | 85.49 | C |
| ATOM | 3141 | N | ALA | H | 131 | 27.897 | 33.059 | 32.188 | 1.00 | 89.95 | N |
| ATOM | 3142 | CA | ALA | H | 131 | 27.756 | 34.478 | 32.532 | 1.00 | 90.15 | C |
| ATOM | 3143 | C | ALA | H | 131 | 28.803 | 35.397 | 31.906 | 1.00 | 93.97 | C |
| ATOM | 3144 | O | ALA | H | 131 | 29.988 | 35.015 | 31.848 | 1.00 | 93.16 | O |
| ATOM | 3145 | CB | ALA | H | 131 | 27.773 | 34.646 | 34.039 | 1.00 | 91.09 | C |
| ATOM | 3146 | N | PRO | H | 132 | 28.399 | 36.646 | 31.520 | 1.00 | 90.34 | N |
| ATOM | 3147 | CA | PRO | H | 132 | 29.376 | 37.615 | 30.980 | 1.00 | 91.03 | C |
| ATOM | 3148 | C | PRO | H | 132 | 30.303 | 38.209 | 32.064 | 1.00 | 99.48 | C |
| ATOM | 3149 | O | PRO | H | 132 | 30.061 | 37.985 | 33.257 | 1.00 | 99.35 | O |
| ATOM | 3150 | CB | PRO | H | 132 | 28.491 | 38.688 | 30.324 | 1.00 | 92.23 | C |
| ATOM | 3151 | CG | PRO | H | 132 | 27.077 | 38.207 | 30.439 | 1.00 | 95.50 | C |
| ATOM | 3152 | CD | PRO | H | 132 | 27.047 | 37.235 | 31.557 | 1.00 | 91.00 | C |
| ATOM | 3153 | O | SER | H | 133 | 32.071 | 41.764 | 33.467 | 1.00 | 107.94 | O |
| ATOM | 3154 | N | SER | H | 133 | 31.361 | 38.971 | 31.664 | 1.00 | 99.36 | N |
| ATOM | 3155 | CA | SER | H | 133 | 32.331 | 39.534 | 32.621 | 1.00 | 100.73 | C |
| ATOM | 3156 | C | SER | H | 133 | 32.524 | 41.073 | 32.548 | 1.00 | 107.55 | C |
| ATOM | 3157 | CB | SER | H | 133 | 33.680 | 38.814 | 32.531 | 1.00 | 104.49 | C |
| ATOM | 3158 | OG | SER | H | 133 | 34.106 | 38.576 | 31.200 | 1.00 | 112.57 | O |
| ATOM | 3159 | O | SER | H | 134 | 33.829 | 44.431 | 29.316 | 1.00 | 96.01 | O |
| ATOM | 3160 | N | SER | H | 134 | 33.238 | 41.595 | 31.505 | 1.00 | 105.12 | N |
| ATOM | 3161 | CA | SER | H | 134 | 33.543 | 43.031 | 31.291 | 1.00 | 126.89 | C |
| ATOM | 3162 | C | SER | H | 134 | 33.995 | 43.320 | 29.837 | 1.00 | 146.61 | C |
| ATOM | 3163 | CB | SER | H | 134 | 34.609 | 43.516 | 32.274 | 1.00 | 129.10 | C |
| ATOM | 3164 | OG | SER | H | 134 | 35.794 | 42.740 | 32.190 | 1.00 | 134.50 | O |
| ATOM | 3165 | N | THR | H | 141 | 31.455 | 44.601 | 22.588 | 1.00 | 89.53 | N |
| ATOM | 3166 | CA | THR | H | 141 | 30.603 | 43.413 | 22.715 | 1.00 | 89.60 | C |
| ATOM | 3167 | C | THR | H | 141 | 31.096 | 42.413 | 23.779 | 1.00 | 92.55 | C |
| ATOM | 3168 | O | THR | H | 141 | 32.304 | 42.268 | 24.025 | 1.00 | 91.21 | O |
| ATOM | 3169 | CB | THR | H | 141 | 30.363 | 42.682 | 21.363 | 1.00 | 99.87 | C |
| ATOM | 3170 | OG1 | THR | H | 141 | 31.518 | 41.931 | 21.007 | 1.00 | 102.71 | O |
| ATOM | 3171 | CG2 | THR | H | 141 | 29.944 | 43.614 | 20.221 | 1.00 | 98.70 | C |
| ATOM | 3172 | N | ALA | H | 142 | 30.124 | 41.695 | 24.367 | 1.00 | 87.95 | N |
| ATOM | 3173 | CA | ALA | H | 142 | 30.302 | 40.658 | 25.378 | 1.00 | 86.26 | C |
| ATOM | 3174 | C | ALA | H | 142 | 29.690 | 39.325 | 24.876 | 1.00 | 87.16 | C |
| ATOM | 3175 | O | ALA | H | 142 | 28.817 | 39.326 | 23.991 | 1.00 | 85.84 | O |
| ATOM | 3176 | CB | ALA | H | 142 | 29.614 | 41.091 | 26.663 | 1.00 | 86.79 | C |
| ATOM | 3177 | N | ALA | H | 143 | 30.138 | 38.198 | 25.458 | 1.00 | 81.75 | N |
| ATOM | 3178 | CA | ALA | H | 143 | 29.597 | 36.882 | 25.135 | 1.00 | 81.00 | C |
| ATOM | 3179 | C | ALA | H | 143 | 29.012 | 36.208 | 26.361 | 1.00 | 83.96 | C |
| ATOM | 3180 | O | ALA | H | 143 | 29.586 | 36.295 | 27.450 | 1.00 | 83.50 | O |
| ATOM | 3181 | CB | ALA | H | 143 | 30.662 | 35.994 | 24.526 | 1.00 | 81.71 | C |
| ATOM | 3182 | N | LEU | H | 144 | 27.873 | 35.522 | 26.167 | 1.00 | 79.59 | N |
| ATOM | 3183 | CA | LEU | H | 144 | 27.148 | 34.731 | 27.169 | 1.00 | 78.46 | C |
| ATOM | 3184 | C | LEU | H | 144 | 26.520 | 33.490 | 26.511 | 1.00 | 82.83 | C |
| ATOM | 3185 | O | LEU | H | 144 | 26.336 | 33.469 | 25.292 | 1.00 | 83.73 | O |
| ATOM | 3186 | CB | LEU | H | 144 | 26.078 | 35.573 | 27.889 | 1.00 | 78.01 | C |
| ATOM | 3187 | CG | LEU | H | 144 | 24.996 | 36.224 | 27.033 | 1.00 | 81.78 | C |
| ATOM | 3188 | CD1 | LEU | H | 144 | 23.726 | 35.431 | 27.089 | 1.00 | 81.89 | C |
| ATOM | 3189 | CD2 | LEU | H | 144 | 24.715 | 37.611 | 27.507 | 1.00 | 83.50 | C |
| ATOM | 3190 | N | GLY | H | 145 | 26.172 | 32.489 | 27.312 | 1.00 | 78.11 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 3191 | CA | GLY | H | 145 | 25.542 | 31.281 | 26.798 | 1.00 | 77.45 | C |
|---|---|---|---|---|---|---|---|---|---|---|---|
| ATOM | 3192 | C | GLY | H | 145 | 24.984 | 30.346 | 27.842 | 1.00 | 81.68 | C |
| ATOM | 3193 | O | GLY | H | 145 | 24.836 | 30.718 | 29.003 | 1.00 | 81.48 | O |
| ATOM | 3194 | N | CYS | H | 146 | 24.654 | 29.127 | 27.423 | 1.00 | 78.83 | N |
| ATOM | 3195 | CA | CYS | H | 146 | 24.119 | 28.079 | 28.285 | 1.00 | 78.72 | C |
| ATOM | 3196 | C | CYS | H | 146 | 24.900 | 26.821 | 28.114 | 1.00 | 77.01 | C |
| ATOM | 3197 | O | CYS | H | 146 | 25.276 | 26.481 | 27.003 | 1.00 | 77.28 | O |
| ATOM | 3198 | CB | CYS | H | 146 | 22.645 | 27.838 | 27.994 | 1.00 | 80.70 | C |
| ATOM | 3199 | SG | CYS | H | 146 | 21.536 | 28.956 | 28.873 | 1.00 | 85.97 | S |
| ATOM | 3200 | N | LEU | H | 147 | 25.102 | 26.105 | 29.194 | 1.00 | 69.65 | N |
| ATOM | 3201 | CA | LEU | H | 147 | 25.778 | 24.840 | 29.156 | 1.00 | 68.83 | C |
| ATOM | 3202 | C | LEU | H | 147 | 24.713 | 23.723 | 29.319 | 1.00 | 74.59 | C |
| ATOM | 3203 | O | LEU | H | 147 | 24.180 | 23.536 | 30.410 | 1.00 | 75.30 | O |
| ATOM | 3204 | CB | LEU | H | 147 | 26.867 | 24.808 | 30.240 | 1.00 | 68.22 | C |
| ATOM | 3205 | CG | LEU | H | 147 | 27.623 | 23.500 | 30.450 | 1.00 | 72.37 | C |
| ATOM | 3206 | CD1 | LEU | H | 147 | 28.478 | 23.146 | 29.264 | 1.00 | 72.45 | C |
| ATOM | 3207 | CD2 | LEU | H | 147 | 28.477 | 23.568 | 31.684 | 1.00 | 74.09 | C |
| ATOM | 3208 | N | VAL | H | 148 | 24.355 | 23.041 | 28.209 | 1.00 | 70.28 | N |
| ATOM | 3209 | CA | VAL | H | 148 | 23.395 | 21.918 | 28.162 | 1.00 | 68.93 | C |
| ATOM | 3210 | C | VAL | H | 148 | 24.225 | 20.633 | 28.457 | 1.00 | 72.54 | C |
| ATOM | 3211 | O | VAL | H | 148 | 24.805 | 20.045 | 27.545 | 1.00 | 72.00 | O |
| ATOM | 3212 | CB | VAL | H | 148 | 22.674 | 21.866 | 26.782 | 1.00 | 71.15 | C |
| ATOM | 3213 | CG1 | VAL | H | 148 | 21.662 | 20.735 | 26.725 | 1.00 | 70.59 | C |
| ATOM | 3214 | CG2 | VAL | H | 148 | 22.017 | 23.199 | 26.445 | 1.00 | 70.27 | C |
| ATOM | 3215 | N | LYS | H | 149 | 24.340 | 20.254 | 29.738 | 1.00 | 68.84 | N |
| ATOM | 3216 | CA | LYS | H | 149 | 25.184 | 19.134 | 30.151 | 1.00 | 68.19 | C |
| ATOM | 3217 | C | LYS | H | 149 | 24.443 | 17.871 | 30.568 | 1.00 | 76.07 | C |
| ATOM | 3218 | O | LYS | H | 149 | 23.331 | 17.936 | 31.087 | 1.00 | 76.54 | O |
| ATOM | 3219 | CB | LYS | H | 149 | 26.129 | 19.574 | 31.280 | 1.00 | 68.22 | C |
| ATOM | 3220 | CG | LYS | H | 149 | 27.496 | 18.927 | 31.191 | 1.00 | 55.28 | C |
| ATOM | 3221 | CD | LYS | H | 149 | 28.135 | 18.700 | 32.539 | 1.00 | 51.22 | C |
| ATOM | 3222 | CE | LYS | H | 149 | 29.423 | 17.918 | 32.429 | 1.00 | 51.45 | C |
| ATOM | 3223 | NZ | LYS | H | 149 | 29.618 | 16.939 | 33.545 | 1.00 | 59.13 | N |
| ATOM | 3224 | N | ASP | H | 150 | 25.103 | 16.715 | 30.338 | 1.00 | 74.79 | N |
| ATOM | 3225 | CA | ASP | H | 150 | 24.751 | 15.339 | 30.697 | 1.00 | 74.86 | C |
| ATOM | 3226 | C | ASP | H | 150 | 23.357 | 14.832 | 30.253 | 1.00 | 78.06 | C |
| ATOM | 3227 | O | ASP | H | 150 | 22.677 | 14.153 | 31.024 | 1.00 | 76.98 | O |
| ATOM | 3228 | CB | ASP | H | 150 | 24.941 | 15.128 | 32.201 | 1.00 | 76.59 | C |
| ATOM | 3229 | CG | ASP | H | 150 | 26.391 | 15.010 | 32.603 | 1.00 | 89.20 | C |
| ATOM | 3230 | OD1 | ASP | H | 150 | 27.109 | 14.158 | 32.011 | 1.00 | 88.80 | O |
| ATOM | 3231 | OD2 | ASP | H | 150 | 26.804 | 15.731 | 33.543 | 1.00 | 98.73 | O |
| ATOM | 3232 | N | TYR | H | 151 | 22.985 | 15.063 | 28.987 | 1.00 | 74.57 | N |
| ATOM | 3233 | CA | TYR | H | 151 | 21.716 | 14.534 | 28.480 | 1.00 | 74.16 | C |
| ATOM | 3234 | C | TYR | H | 151 | 21.904 | 13.240 | 27.662 | 1.00 | 75.20 | C |
| ATOM | 3235 | O | TYR | H | 151 | 23.030 | 12.824 | 27.396 | 1.00 | 73.73 | O |
| ATOM | 3236 | CB | TYR | H | 151 | 20.929 | 15.599 | 27.699 | 1.00 | 76.05 | C |
| ATOM | 3237 | CG | TYR | H | 151 | 21.560 | 16.032 | 26.396 | 1.00 | 79.09 | C |
| ATOM | 3238 | CD2 | TYR | H | 151 | 21.238 | 15.399 | 25.199 | 1.00 | 80.28 | C |
| ATOM | 3239 | CD1 | TYR | H | 151 | 22.450 | 17.105 | 26.351 | 1.00 | 81.22 | C |
| ATOM | 3240 | CE2 | TYR | H | 151 | 21.812 | 15.801 | 23.992 | 1.00 | 81.62 | C |
| ATOM | 3241 | CE1 | TYR | H | 151 | 23.040 | 17.509 | 25.153 | 1.00 | 81.21 | C |
| ATOM | 3242 | CZ | TYR | H | 151 | 22.707 | 16.861 | 23.974 | 1.00 | 87.75 | C |
| ATOM | 3243 | OH | TYR | H | 151 | 23.237 | 17.277 | 22.782 | 1.00 | 86.37 | O |
| ATOM | 3244 | N | PHE | H | 152 | 20.786 | 12.604 | 27.287 | 1.00 | 70.84 | N |
| ATOM | 3245 | CA | PHE | H | 152 | 20.708 | 11.382 | 26.481 | 1.00 | 69.36 | C |
| ATOM | 3246 | C | PHE | H | 152 | 19.234 | 11.050 | 26.169 | 1.00 | 71.84 | C |
| ATOM | 3247 | O | PHE | H | 152 | 18.400 | 11.082 | 27.066 | 1.00 | 70.50 | O |
| ATOM | 3248 | CB | PHE | H | 152 | 21.380 | 10.176 | 27.183 | 1.00 | 70.73 | C |
| ATOM | 3249 | CG | PHE | H | 152 | 21.396 | 8.934 | 26.323 | 1.00 | 72.19 | C |
| ATOM | 3250 | CD1 | PHE | H | 152 | 22.417 | 8.719 | 25.404 | 1.00 | 75.60 | C |
| ATOM | 3251 | CD2 | PHE | H | 152 | 20.361 | 8.007 | 26.390 | 1.00 | 73.06 | C |
| ATOM | 3252 | CE1 | PHE | H | 152 | 22.395 | 7.607 | 24.567 | 1.00 | 75.83 | C |
| ATOM | 3253 | CE2 | PHE | H | 152 | 20.342 | 6.901 | 25.553 | 1.00 | 75.59 | C |
| ATOM | 3254 | CZ | PHE | H | 152 | 21.355 | 6.712 | 24.642 | 1.00 | 73.98 | C |
| ATOM | 3255 | N | PRO | H | 153 | 18.893 | 10.652 | 24.936 | 1.00 | 69.10 | N |
| ATOM | 3256 | CA | PRO | H | 153 | 19.730 | 10.603 | 23.736 | 1.00 | 68.69 | C |
| ATOM | 3257 | C | PRO | H | 153 | 19.643 | 11.932 | 22.973 | 1.00 | 71.75 | C |
| ATOM | 3258 | O | PRO | H | 153 | 18.919 | 12.853 | 23.369 | 1.00 | 69.85 | O |
| ATOM | 3259 | CB | PRO | H | 153 | 19.108 | 9.436 | 22.961 | 1.00 | 70.19 | C |
| ATOM | 3260 | CG | PRO | H | 153 | 17.617 | 9.555 | 23.273 | 1.00 | 75.00 | C |
| ATOM | 3261 | CD | PRO | H | 153 | 17.505 | 10.256 | 24.621 | 1.00 | 70.77 | C |
| ATOM | 3262 | N | GLU | H | 154 | 20.370 | 12.015 | 21.859 | 1.00 | 69.05 | N |
| ATOM | 3263 | CA | GLU | H | 154 | 20.359 | 13.190 | 21.001 | 1.00 | 68.46 | C |
| ATOM | 3264 | C | GLU | H | 154 | 18.979 | 13.255 | 20.327 | 1.00 | 73.33 | C |
| ATOM | 3265 | O | GLU | H | 154 | 18.406 | 12.188 | 20.054 | 1.00 | 72.74 | O |
| ATOM | 3266 | CB | GLU | H | 154 | 21.462 | 13.074 | 19.942 | 1.00 | 69.41 | C |
| ATOM | 3267 | CG | GLU | H | 154 | 22.778 | 13.698 | 20.364 | 1.00 | 79.20 | C |

TABLE1-continued

Three-dimensional crystal coordinate for anti-TcdB antibody beziotoxumab
Fab –*C. difficile* toxin B (TcdB$^{(1834-2101)}$) complex.

| ATOM | 3268 | CD  | GLU | H | 154 | 22.945 | 15.158 | 19.992 | 1.00 | 105.78 | C |
|------|------|-----|-----|---|-----|--------|--------|--------|------|--------|---|
| ATOM | 3269 | OE1 | GLU | H | 154 | 23.837 | 15.439 | 19.160 | 1.00 | 97.73  | O |
| ATOM | 3270 | OE2 | GLU | H | 154 | 22.213 | 16.020 | 20.537 | 1.00 | 100.70 | O |
| ATOM | 3271 | N   | PRO | H | 155 | 18.360 | 14.448 | 20.138 | 1.00 | 69.72  | N |
| ATOM | 3272 | CA  | PRO | H | 155 | 18.873 | 15.810 | 20.330 | 1.00 | 69.14  | C |
| ATOM | 3273 | C   | PRO | H | 155 | 18.205 | 16.685 | 21.408 | 1.00 | 73.87  | C |
| ATOM | 3274 | O   | PRO | H | 155 | 17.149 | 16.360 | 21.950 | 1.00 | 74.02  | O |
| ATOM | 3275 | CB  | PRO | H | 155 | 18.560 | 16.426 | 18.963 | 1.00 | 70.32  | C |
| ATOM | 3276 | CG  | PRO | H | 155 | 17.237 | 15.755 | 18.539 | 1.00 | 74.28  | C |
| ATOM | 3277 | CD  | PRO | H | 155 | 17.085 | 14.506 | 19.400 | 1.00 | 70.56  | C |
| ATOM | 3278 | N   | VAL | H | 156 | 18.821 | 17.850 | 21.651 | 1.00 | 70.69  | N |
| ATOM | 3279 | CA  | VAL | H | 156 | 18.317 | 18.965 | 22.452 | 1.00 | 70.00  | C |
| ATOM | 3280 | C   | VAL | H | 156 | 18.158 | 20.126 | 21.451 | 1.00 | 75.36  | C |
| ATOM | 3281 | O   | VAL | H | 156 | 18.849 | 20.145 | 20.419 | 1.00 | 74.45  | O |
| ATOM | 3282 | CB  | VAL | H | 156 | 19.198 | 19.385 | 23.666 | 1.00 | 73.08  | C |
| ATOM | 3283 | CG1 | VAL | H | 156 | 19.208 | 18.327 | 24.748 | 1.00 | 73.12  | C |
| ATOM | 3284 | CG2 | VAL | H | 156 | 20.614 | 19.753 | 23.259 | 1.00 | 72.48  | C |
| ATOM | 3285 | N   | THR | H | 157 | 17.240 | 21.069 | 21.732 | 1.00 | 72.99  | N |
| ATOM | 3286 | CA  | THR | H | 157 | 17.048 | 22.253 | 20.889 | 1.00 | 72.39  | C |
| ATOM | 3287 | C   | THR | H | 157 | 17.204 | 23.493 | 21.748 | 1.00 | 74.74  | C |
| ATOM | 3288 | O   | THR | H | 157 | 16.537 | 23.610 | 22.774 | 1.00 | 75.08  | O |
| ATOM | 3289 | CB  | THR | H | 157 | 15.699 | 22.244 | 20.156 | 1.00 | 81.78  | C |
| ATOM | 3290 | OG1 | THR | H | 157 | 14.644 | 22.471 | 21.092 | 1.00 | 79.43  | O |
| ATOM | 3291 | CG2 | THR | H | 157 | 15.463 | 20.969 | 19.356 | 1.00 | 83.70  | C |
| ATOM | 3292 | N   | VAL | H | 158 | 18.077 | 24.417 | 21.336 | 1.00 | 69.87  | N |
| ATOM | 3293 | CA  | VAL | H | 158 | 18.273 | 25.671 | 22.057 | 1.00 | 69.47  | C |
| ATOM | 3294 | C   | VAL | H | 158 | 17.803 | 26.853 | 21.210 | 1.00 | 75.77  | C |
| ATOM | 3295 | O   | VAL | H | 158 | 17.971 | 26.854 | 19.988 | 1.00 | 75.40  | O |
| ATOM | 3296 | CB  | VAL | H | 158 | 19.708 | 25.877 | 22.631 | 1.00 | 72.60  | C |
| ATOM | 3297 | CG1 | VAL | H | 158 | 19.704 | 26.959 | 23.709 | 1.00 | 72.36  | C |
| ATOM | 3298 | CG2 | VAL | H | 158 | 20.291 | 24.576 | 23.197 | 1.00 | 72.01  | C |
| ATOM | 3299 | N   | SER | H | 159 | 17.158 | 27.828 | 21.869 | 1.00 | 74.83  | N |
| ATOM | 3300 | CA  | SER | H | 159 | 16.663 | 29.097 | 21.313 | 1.00 | 75.25  | C |
| ATOM | 3301 | C   | SER | H | 159 | 16.941 | 30.177 | 22.369 | 1.00 | 81.84  | C |
| ATOM | 3302 | O   | SER | H | 159 | 17.260 | 29.834 | 23.528 | 1.00 | 80.85  | O |
| ATOM | 3303 | CB  | SER | H | 159 | 15.172 | 29.018 | 21.011 | 1.00 | 77.68  | C |
| ATOM | 3304 | OG  | SER | H | 159 | 14.429 | 28.732 | 22.183 | 1.00 | 86.05  | O |
| ATOM | 3305 | N   | TRP | H | 160 | 16.907 | 31.469 | 21.972 | 1.00 | 79.51  | N |
| ATOM | 3306 | CA  | TRP | H | 160 | 17.243 | 32.417 | 23.010 | 1.00 | 79.36  | C |
| ATOM | 3307 | C   | TRP | H | 160 | 16.004 | 33.134 | 23.534 | 1.00 | 88.25  | C |
| ATOM | 3308 | O   | TRP | H | 160 | 15.286 | 32.485 | 24.287 | 1.00 | 89.93  | O |
| ATOM | 3309 | CB  | TRP | H | 160 | 18.415 | 33.311 | 22.635 | 1.00 | 76.85  | C |
| ATOM | 3310 | CG  | TRP | H | 160 | 19.680 | 32.554 | 22.920 | 1.00 | 76.82  | C |
| ATOM | 3311 | CD1 | TRP | H | 160 | 20.275 | 31.635 | 22.104 | 1.00 | 79.34  | C |
| ATOM | 3312 | CD2 | TRP | H | 160 | 20.328 | 32.427 | 24.201 | 1.00 | 76.15  | C |
| ATOM | 3313 | NE1 | TRP | H | 160 | 21.292 | 30.989 | 22.776 | 1.00 | 77.99  | N |
| ATOM | 3314 | CE2 | TRP | H | 160 | 21.367 | 31.480 | 24.054 | 1.00 | 79.11  | C |
| ATOM | 3315 | CE3 | TRP | H | 160 | 20.151 | 33.045 | 25.449 | 1.00 | 76.92  | C |
| ATOM | 3316 | CZ2 | TRP | H | 160 | 22.249 | 31.169 | 25.092 | 1.00 | 78.05  | C |
| ATOM | 3317 | CZ3 | TRP | H | 160 | 21.033 | 32.743 | 26.473 | 1.00 | 78.16  | C |
| ATOM | 3318 | CH2 | TRP | H | 160 | 22.065 | 31.811 | 26.291 | 1.00 | 78.67  | C |
| ATOM | 3319 | N   | ASN | H | 161 | 15.749 | 34.411 | 23.248 | 1.00 | 85.68  | N |
| ATOM | 3320 | CA  | ASN | H | 161 | 14.580 | 35.045 | 23.865 | 1.00 | 85.17  | C |
| ATOM | 3321 | C   | ASN | H | 161 | 13.296 | 34.618 | 23.120 | 1.00 | 90.52  | C |
| ATOM | 3322 | O   | ASN | H | 161 | 12.770 | 35.343 | 22.273 | 1.00 | 90.27  | O |
| ATOM | 3323 | CB  | ASN | H | 161 | 14.790 | 36.564 | 24.008 | 1.00 | 82.54  | C |
| ATOM | 3324 | CG  | ASN | H | 161 | 15.999 | 36.973 | 24.861 | 1.00 | 89.87  | C |
| ATOM | 3325 | OD1 | ASN | H | 161 | 16.390 | 36.325 | 25.857 | 1.00 | 65.77  | O |
| ATOM | 3326 | ND2 | ASN | H | 161 | 16.608 | 38.091 | 24.494 | 1.00 | 86.31  | N |
| ATOM | 3327 | N   | SER | H | 162 | 12.836 | 33.381 | 23.444 | 1.00 | 88.08  | N |
| ATOM | 3328 | CA  | SER | H | 162 | 11.733 | 32.590 | 22.880 | 1.00 | 88.26  | C |
| ATOM | 3329 | C   | SER | H | 162 | 12.031 | 32.234 | 21.433 | 1.00 | 93.81  | C |
| ATOM | 3330 | O   | SER | H | 162 | 12.178 | 31.059 | 21.102 | 1.00 | 94.35  | O |
| ATOM | 3331 | CB  | SER | H | 162 | 10.380 | 33.237 | 23.110 | 1.00 | 91.08  | C |
| ATOM | 3332 | OG  | SER | H | 162 | 10.114 | 33.057 | 24.492 | 1.00 | 98.80  | O |
| ATOM | 3333 | O   | GLY | H | 163 | 14.831 | 34.107 | 19.763 | 1.00 | 96.22  | O |
| ATOM | 3334 | N   | GLY | H | 163 | 12.199 | 33.256 | 20.621 | 1.00 | 91.08  | N |
| ATOM | 3335 | CA  | GLY | H | 163 | 12.683 | 33.215 | 19.253 | 1.00 | 91.28  | C |
| ATOM | 3336 | C   | GLY | H | 163 | 13.708 | 34.321 | 19.295 | 1.00 | 95.65  | C |
| ATOM | 3337 | N   | ALA | H | 164 | 13.218 | 35.538 | 18.990 | 1.00 | 90.91  | N |
| ATOM | 3338 | CA  | ALA | H | 164 | 13.774 | 36.894 | 19.026 | 1.00 | 90.33  | C |
| ATOM | 3339 | C   | ALA | H | 164 | 15.279 | 37.038 | 18.737 | 1.00 | 91.85  | C |
| ATOM | 3340 | O   | ALA | H | 164 | 15.641 | 37.711 | 17.761 | 1.00 | 92.21  | O |
| ATOM | 3341 | CB  | ALA | H | 164 | 13.431 | 37.555 | 20.352 | 1.00 | 91.23  | C |
| ATOM | 3342 | N   | LEU | H | 165 | 16.140 | 36.463 | 19.595 | 1.00 | 85.44  | N |
| ATOM | 3343 | CA  | LEU | H | 165 | 17.588 | 36.482 | 19.437 | 1.00 | 83.74  | C |
| ATOM | 3344 | C   | LEU | H | 165 | 18.066 | 35.277 | 18.593 | 1.00 | 84.83  | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 3345 | O | LEU | H | 165 | 17.984 | 34.123 | 19.027 | 1.00 | 83.89 | O |
|------|------|-----|-----|---|-----|--------|--------|--------|------|-------|---|
| ATOM | 3346 | CB | LEU | H | 165 | 18.253 | 36.527 | 20.818 | 1.00 | 83.32 | C |
| ATOM | 3347 | CG | LEU | H | 165 | 19.754 | 36.722 | 20.872 | 1.00 | 87.57 | C |
| ATOM | 3348 | CD1 | LEU | H | 165 | 20.174 | 38.058 | 20.271 | 1.00 | 87.39 | C |
| ATOM | 3349 | CD2 | LEU | H | 165 | 20.230 | 36.626 | 22.290 | 1.00 | 89.82 | C |
| ATOM | 3350 | N | THR | H | 166 | 18.501 | 35.571 | 17.359 | 1.00 | 80.20 | N |
| ATOM | 3351 | CA | THR | H | 166 | 19.012 | 34.612 | 16.364 | 1.00 | 79.60 | C |
| ATOM | 3352 | C | THR | H | 166 | 20.417 | 35.030 | 15.885 | 1.00 | 81.42 | C |
| ATOM | 3353 | O | THR | H | 166 | 21.260 | 34.168 | 15.624 | 1.00 | 80.32 | O |
| ATOM | 3354 | CB | THR | H | 166 | 18.048 | 34.478 | 15.164 | 1.00 | 87.84 | C |
| ATOM | 3355 | OG1 | THR | H | 166 | 17.753 | 35.768 | 14.632 | 1.00 | 93.24 | O |
| ATOM | 3356 | CG2 | THR | H | 166 | 16.767 | 33.781 | 15.519 | 1.00 | 85.45 | C |
| ATOM | 3357 | N | SER | H | 167 | 20.641 | 36.360 | 15.761 | 1.00 | 76.92 | N |
| ATOM | 3358 | CA | SER | H | 167 | 21.887 | 36.986 | 15.331 | 1.00 | 76.18 | C |
| ATOM | 3359 | C | SER | H | 167 | 23.020 | 36.727 | 16.331 | 1.00 | 79.38 | C |
| ATOM | 3360 | O | SER | H | 167 | 22.868 | 36.963 | 17.536 | 1.00 | 79.58 | O |
| ATOM | 3361 | CB | SER | H | 167 | 21.693 | 38.487 | 15.122 | 1.00 | 78.74 | C |
| ATOM | 3362 | OG | SER | H | 167 | 21.902 | 38.882 | 13.771 | 1.00 | 88.18 | O |
| ATOM | 3363 | N | GLY | H | 168 | 24.133 | 36.216 | 15.809 | 1.00 | 73.96 | N |
| ATOM | 3364 | CA | GLY | H | 168 | 25.330 | 35.937 | 16.592 | 1.00 | 72.77 | C |
| ATOM | 3365 | C | GLY | H | 168 | 25.236 | 34.769 | 17.548 | 1.00 | 74.46 | C |
| ATOM | 3366 | O | GLY | H | 168 | 26.099 | 34.632 | 18.427 | 1.00 | 72.98 | O |
| ATOM | 3367 | N | VAL | H | 169 | 24.195 | 33.912 | 17.370 | 1.00 | 69.82 | N |
| ATOM | 3368 | CA | VAL | H | 169 | 23.971 | 32.718 | 18.187 | 1.00 | 68.77 | C |
| ATOM | 3369 | C | VAL | H | 169 | 24.753 | 31.581 | 17.557 | 1.00 | 71.88 | C |
| ATOM | 3370 | O | VAL | H | 169 | 24.715 | 31.402 | 16.329 | 1.00 | 71.03 | O |
| ATOM | 3371 | CB | VAL | H | 169 | 22.468 | 32.344 | 18.358 | 1.00 | 72.62 | C |
| ATOM | 3372 | CG1 | VAL | H | 169 | 22.298 | 31.075 | 19.194 | 1.00 | 72.13 | C |
| ATOM | 3373 | CG2 | VAL | H | 169 | 21.663 | 33.489 | 18.959 | 1.00 | 72.61 | C |
| ATOM | 3374 | N | HIS | H | 170 | 25.467 | 30.825 | 18.407 | 1.00 | 68.09 | N |
| ATOM | 3375 | CA | HIS | H | 170 | 26.250 | 29.664 | 18.025 | 1.00 | 67.18 | C |
| ATOM | 3376 | C | HIS | H | 170 | 25.915 | 28.479 | 18.913 | 1.00 | 69.53 | C |
| ATOM | 3377 | O | HIS | H | 170 | 26.428 | 28.387 | 20.034 | 1.00 | 69.70 | O |
| ATOM | 3378 | CB | HIS | H | 170 | 27.760 | 29.954 | 18.057 | 1.00 | 68.04 | C |
| ATOM | 3379 | CG | HIS | H | 170 | 28.263 | 30.834 | 16.953 | 1.00 | 71.41 | C |
| ATOM | 3380 | ND1 | HIS | H | 170 | 28.010 | 30.547 | 15.630 | 1.00 | 73.27 | N |
| ATOM | 3381 | CD2 | HIS | H | 170 | 29.044 | 31.939 | 17.022 | 1.00 | 72.88 | C |
| ATOM | 3382 | CE1 | HIS | H | 170 | 28.614 | 31.502 | 14.939 | 1.00 | 72.75 | C |
| ATOM | 3383 | NE2 | HIS | H | 170 | 29.251 | 32.358 | 15.736 | 1.00 | 72.78 | N |
| ATOM | 3384 | N | THR | H | 171 | 25.030 | 27.580 | 18.425 | 1.00 | 64.33 | N |
| ATOM | 3385 | CA | THR | H | 171 | 24.702 | 26.359 | 19.161 | 1.00 | 63.69 | C |
| ATOM | 3386 | C | THR | H | 171 | 25.667 | 25.318 | 18.619 | 1.00 | 65.99 | C |
| ATOM | 3387 | O | THR | H | 171 | 25.764 | 25.131 | 17.410 | 1.00 | 65.78 | O |
| ATOM | 3388 | CB | THR | H | 171 | 23.208 | 25.998 | 19.100 | 1.00 | 69.19 | C |
| ATOM | 3389 | OG1 | THR | H | 171 | 22.428 | 27.122 | 19.532 | 1.00 | 67.31 | O |
| ATOM | 3390 | CG2 | THR | H | 171 | 22.873 | 24.809 | 19.979 | 1.00 | 66.43 | C |
| ATOM | 3391 | N | PHE | H | 172 | 26.466 | 24.742 | 19.495 | 1.00 | 61.93 | N |
| ATOM | 3392 | CA | PHE | H | 172 | 27.509 | 23.831 | 19.079 | 1.00 | 61.74 | C |
| ATOM | 3393 | C | PHE | H | 172 | 27.040 | 22.408 | 18.940 | 1.00 | 68.65 | C |
| ATOM | 3394 | O | PHE | H | 172 | 26.147 | 21.976 | 19.676 | 1.00 | 69.26 | O |
| ATOM | 3395 | CB | PHE | H | 172 | 28.685 | 23.895 | 20.060 | 1.00 | 63.30 | C |
| ATOM | 3396 | CG | PHE | H | 172 | 29.523 | 25.136 | 19.929 | 1.00 | 64.97 | C |
| ATOM | 3397 | CD1 | PHE | H | 172 | 30.565 | 25.197 | 19.014 | 1.00 | 68.24 | C |
| ATOM | 3398 | CD2 | PHE | H | 172 | 29.285 | 26.245 | 20.736 | 1.00 | 67.16 | C |
| ATOM | 3399 | CE1 | PHE | H | 172 | 31.354 | 26.345 | 18.906 | 1.00 | 68.83 | C |
| ATOM | 3400 | CE2 | PHE | H | 172 | 30.074 | 27.395 | 20.624 | 1.00 | 70.07 | C |
| ATOM | 3401 | CZ | PHE | H | 172 | 31.103 | 27.436 | 19.708 | 1.00 | 68.09 | C |
| ATOM | 3402 | N | PRO | H | 173 | 27.692 | 21.626 | 18.047 | 1.00 | 65.16 | N |
| ATOM | 3403 | CA | PRO | H | 173 | 27.370 | 20.196 | 17.947 | 1.00 | 63.80 | C |
| ATOM | 3404 | C | PRO | H | 173 | 27.667 | 19.498 | 19.267 | 1.00 | 65.74 | C |
| ATOM | 3405 | O | PRO | H | 173 | 28.674 | 19.837 | 19.915 | 1.00 | 65.25 | O |
| ATOM | 3406 | CB | PRO | H | 173 | 28.343 | 19.702 | 16.875 | 1.00 | 65.28 | C |
| ATOM | 3407 | CG | PRO | H | 173 | 28.699 | 20.897 | 16.101 | 1.00 | 70.29 | C |
| ATOM | 3408 | CD | PRO | H | 173 | 28.775 | 21.983 | 17.109 | 1.00 | 66.61 | C |
| ATOM | 3409 | N | ALA | H | 174 | 26.792 | 18.548 | 19.677 | 1.00 | 60.29 | N |
| ATOM | 3410 | CA | ALA | H | 174 | 26.978 | 17.828 | 20.935 | 1.00 | 59.85 | C |
| ATOM | 3411 | C | ALA | H | 174 | 28.227 | 16.968 | 20.924 | 1.00 | 67.21 | C |
| ATOM | 3412 | O | ALA | H | 174 | 28.643 | 16.492 | 19.872 | 1.00 | 67.94 | O |
| ATOM | 3413 | CB | ALA | H | 174 | 25.778 | 16.981 | 21.234 | 1.00 | 60.18 | C |
| ATOM | 3414 | N | VAL | H | 175 | 28.846 | 16.803 | 22.090 | 1.00 | 65.32 | N |
| ATOM | 3415 | CA | VAL | H | 175 | 30.056 | 15.995 | 22.242 | 1.00 | 65.82 | C |
| ATOM | 3416 | C | VAL | H | 175 | 29.686 | 14.890 | 23.210 | 1.00 | 69.04 | C |
| ATOM | 3417 | O | VAL | H | 175 | 29.086 | 15.171 | 24.252 | 1.00 | 72.23 | O |
| ATOM | 3418 | CB | VAL | H | 175 | 31.285 | 16.809 | 22.751 | 1.00 | 70.88 | C |
| ATOM | 3419 | CG1 | VAL | H | 175 | 32.566 | 16.005 | 22.594 | 1.00 | 71.09 | C |
| ATOM | 3420 | CG2 | VAL | H | 175 | 31.426 | 18.146 | 22.028 | 1.00 | 70.98 | C |
| ATOM | 3421 | N | LEU | H | 176 | 29.999 | 13.646 | 22.865 | 1.00 | 60.13 | N |

TABLE1-continued

Three-dimensional crystal coordinate for anti-TcdB antibody beziotoxumab Fab –*C. difficile* toxin B (TcdB$^{(1834-2101)}$) complex.

| ATOM | 3422 | CA | LEU | H | 176 | 29.682 | 12.528 | 23.717 | 1.00 | 57.94 | C |
|---|---|---|---|---|---|---|---|---|---|---|---|
| ATOM | 3423 | C | LEU | H | 176 | 30.787 | 12.359 | 24.720 | 1.00 | 63.95 | C |
| ATOM | 3424 | O | LEU | H | 176 | 31.928 | 12.094 | 24.345 | 1.00 | 64.11 | O |
| ATOM | 3425 | CB | LEU | H | 176 | 29.472 | 11.245 | 22.904 | 1.00 | 56.99 | C |
| ATOM | 3426 | CG | LEU | H | 176 | 29.234 | 9.971 | 23.719 | 1.00 | 58.82 | C |
| ATOM | 3427 | CD1 | LEU | H | 176 | 27.830 | 9.933 | 24.300 | 1.00 | 58.05 | C |
| ATOM | 3428 | CD2 | LEU | H | 176 | 29.536 | 8.780 | 22.912 | 1.00 | 55.10 | C |
| ATOM | 3429 | N | GLN | H | 177 | 30.432 | 12.491 | 26.002 | 1.00 | 62.62 | N |
| ATOM | 3430 | CA | GLN | H | 177 | 31.341 | 12.389 | 27.148 | 1.00 | 63.25 | C |
| ATOM | 3431 | C | GLN | H | 177 | 31.619 | 10.916 | 27.444 | 1.00 | 69.03 | C |
| ATOM | 3432 | O | GLN | H | 177 | 30.870 | 10.064 | 26.984 | 1.00 | 69.16 | O |
| ATOM | 3433 | CB | GLN | H | 177 | 30.718 | 13.082 | 28.374 | 1.00 | 64.11 | C |
| ATOM | 3434 | CG | GLN | H | 177 | 30.239 | 14.501 | 28.105 | 1.00 | 58.48 | C |
| ATOM | 3435 | CD | GLN | H | 177 | 29.434 | 15.027 | 29.265 | 1.00 | 81.68 | C |
| ATOM | 3436 | OE1 | GLN | H | 177 | 29.980 | 15.561 | 30.232 | 1.00 | 85.33 | O |
| ATOM | 3437 | NE2 | GLN | H | 177 | 28.121 | 14.887 | 29.209 | 1.00 | 63.59 | N |
| ATOM | 3438 | N | SER | H | 178 | 32.678 | 10.619 | 28.218 | 1.00 | 66.60 | N |
| ATOM | 3439 | CA | SER | H | 178 | 33.075 | 9.261 | 28.613 | 1.00 | 66.89 | C |
| ATOM | 3440 | C | SER | H | 178 | 31.994 | 8.599 | 29.474 | 1.00 | 72.73 | C |
| ATOM | 3441 | O | SER | H | 178 | 31.926 | 7.369 | 29.537 | 1.00 | 73.01 | O |
| ATOM | 3442 | CB | SER | H | 178 | 34.385 | 9.312 | 29.389 | 1.00 | 71.67 | C |
| ATOM | 3443 | OG | SER | H | 178 | 34.293 | 10.201 | 30.493 | 1.00 | 85.01 | O |
| ATOM | 3444 | N | SER | H | 179 | 31.148 | 9.433 | 30.138 | 1.00 | 69.53 | N |
| ATOM | 3445 | CA | SER | H | 179 | 30.018 | 9.043 | 30.989 | 1.00 | 68.56 | C |
| ATOM | 3446 | C | SER | H | 179 | 28.893 | 8.325 | 30.215 | 1.00 | 72.76 | C |
| ATOM | 3447 | O | SER | H | 179 | 28.038 | 7.686 | 30.833 | 1.00 | 73.86 | O |
| ATOM | 3448 | CB | SER | H | 179 | 29.439 | 10.279 | 31.673 | 1.00 | 70.45 | C |
| ATOM | 3449 | OG | SER | H | 179 | 28.756 | 11.135 | 30.774 | 1.00 | 75.20 | O |
| ATOM | 3450 | N | GLY | H | 180 | 28.883 | 8.476 | 28.888 | 1.00 | 67.26 | N |
| ATOM | 3451 | CA | GLY | H | 180 | 27.863 | 7.932 | 27.996 | 1.00 | 65.57 | C |
| ATOM | 3452 | C | GLY | H | 180 | 26.788 | 8.953 | 27.663 | 1.00 | 66.65 | C |
| ATOM | 3453 | O | GLY | H | 180 | 25.941 | 8.717 | 26.792 | 1.00 | 67.40 | O |
| ATOM | 3454 | N | LEU | H | 181 | 26.811 | 10.089 | 28.368 | 1.00 | 60.09 | N |
| ATOM | 3455 | CA | LEU | H | 181 | 25.891 | 11.201 | 28.189 | 1.00 | 59.38 | C |
| ATOM | 3456 | C | LEU | H | 181 | 26.507 | 12.278 | 27.299 | 1.00 | 64.34 | C |
| ATOM | 3457 | O | LEU | H | 181 | 27.737 | 12.393 | 27.233 | 1.00 | 65.19 | O |
| ATOM | 3458 | CB | LEU | H | 181 | 25.555 | 11.805 | 29.552 | 1.00 | 59.07 | C |
| ATOM | 3459 | CG | LEU | H | 181 | 24.991 | 10.847 | 30.569 | 1.00 | 62.24 | C |
| ATOM | 3460 | CD1 | LEU | H | 181 | 25.261 | 11.323 | 31.946 | 1.00 | 61.54 | C |
| ATOM | 3461 | CD2 | LEU | H | 181 | 23.531 | 10.612 | 30.327 | 1.00 | 63.54 | C |
| ATOM | 3462 | N | TYR | H | 182 | 25.658 | 13.055 | 26.617 | 1.00 | 60.27 | N |
| ATOM | 3463 | CA | TYR | H | 182 | 26.072 | 14.142 | 25.737 | 1.00 | 61.36 | C |
| ATOM | 3464 | C | TYR | H | 182 | 26.000 | 15.487 | 26.462 | 1.00 | 68.94 | C |
| ATOM | 3465 | O | TYR | H | 182 | 25.169 | 15.703 | 27.368 | 1.00 | 69.01 | O |
| ATOM | 3466 | CB | TYR | H | 182 | 25.160 | 14.234 | 24.498 | 1.00 | 63.71 | C |
| ATOM | 3467 | CG | TYR | H | 182 | 25.165 | 13.029 | 23.581 | 1.00 | 68.44 | C |
| ATOM | 3468 | CD1 | TYR | H | 182 | 26.160 | 12.863 | 22.620 | 1.00 | 70.58 | C |
| ATOM | 3469 | CD2 | TYR | H | 182 | 24.127 | 12.105 | 23.608 | 1.00 | 70.09 | C |
| ATOM | 3470 | CE1 | TYR | H | 182 | 26.136 | 11.792 | 21.729 | 1.00 | 71.24 | C |
| ATOM | 3471 | CE2 | TYR | H | 182 | 24.096 | 11.024 | 22.729 | 1.00 | 71.99 | C |
| ATOM | 3472 | CZ | TYR | H | 182 | 25.103 | 10.872 | 21.786 | 1.00 | 82.39 | C |
| ATOM | 3473 | OH | TYR | H | 182 | 25.072 | 9.812 | 20.899 | 1.00 | 85.40 | O |
| ATOM | 3474 | N | SER | H | 183 | 26.838 | 16.416 | 25.995 | 1.00 | 65.76 | N |
| ATOM | 3475 | CA | SER | H | 183 | 26.928 | 17.789 | 26.456 | 1.00 | 64.58 | C |
| ATOM | 3476 | C | SER | H | 183 | 27.215 | 18.699 | 25.246 | 1.00 | 66.50 | C |
| ATOM | 3477 | O | SER | H | 183 | 27.839 | 18.266 | 24.269 | 1.00 | 65.55 | O |
| ATOM | 3478 | CB | SER | H | 183 | 28.011 | 17.904 | 27.525 | 1.00 | 68.41 | C |
| ATOM | 3479 | OG | SER | H | 183 | 28.627 | 19.178 | 27.587 | 1.00 | 81.74 | O |
| ATOM | 3480 | N | LEU | H | 184 | 26.718 | 19.944 | 25.313 | 1.00 | 61.74 | N |
| ATOM | 3481 | CA | LEU | H | 184 | 26.912 | 21.015 | 24.339 | 1.00 | 60.15 | C |
| ATOM | 3482 | C | LEU | H | 184 | 26.682 | 22.385 | 24.968 | 1.00 | 63.45 | C |
| ATOM | 3483 | O | LEU | H | 184 | 25.995 | 22.483 | 25.989 | 1.00 | 62.38 | O |
| ATOM | 3484 | CB | LEU | H | 184 | 26.026 | 20.843 | 23.074 | 1.00 | 59.77 | C |
| ATOM | 3485 | CG | LEU | H | 184 | 24.479 | 21.010 | 23.120 | 1.00 | 63.36 | C |
| ATOM | 3486 | CD1 | LEU | H | 184 | 24.055 | 22.451 | 23.213 | 1.00 | 62.92 | C |
| ATOM | 3487 | CD2 | LEU | H | 184 | 23.880 | 20.540 | 21.828 | 1.00 | 64.40 | C |
| ATOM | 3488 | N | SER | H | 185 | 27.187 | 23.454 | 24.305 | 1.00 | 59.82 | N |
| ATOM | 3489 | CA | SER | H | 185 | 26.926 | 24.839 | 24.700 | 1.00 | 58.06 | C |
| ATOM | 3490 | C | SER | H | 185 | 26.310 | 25.601 | 23.560 | 1.00 | 63.53 | C |
| ATOM | 3491 | O | SER | H | 185 | 26.613 | 25.358 | 22.390 | 1.00 | 62.49 | O |
| ATOM | 3492 | CB | SER | H | 185 | 28.188 | 25.561 | 25.156 | 1.00 | 56.76 | C |
| ATOM | 3493 | OG | SER | H | 185 | 28.759 | 24.990 | 26.319 | 1.00 | 61.77 | O |
| ATOM | 3494 | N | SER | H | 186 | 25.419 | 26.513 | 23.914 | 1.00 | 62.53 | N |
| ATOM | 3495 | CA | SER | H | 186 | 24.832 | 27.485 | 23.004 | 1.00 | 63.12 | C |
| ATOM | 3496 | C | SER | H | 186 | 25.291 | 28.842 | 23.546 | 1.00 | 66.60 | C |
| ATOM | 3497 | O | SER | H | 186 | 25.088 | 29.140 | 24.724 | 1.00 | 62.93 | O |
| ATOM | 3498 | CB | SER | H | 186 | 23.315 | 27.408 | 22.985 | 1.00 | 66.48 | C |

TABLE 1-continued

Three-dimensional crystal coordinate for anti-TcdB antibody beziotoxumab
Fab –C. difficile toxin B (TcdB$^{(1834-2101)}$) complex.

| ATOM | 3499 | OG  | SER | H | 186 | 22.789 | 28.512 | 22.266 | 1.00 | 72.86  | O |
| ---- | ---- | --- | --- | - | --- | ------ | ------ | ------ | ---- | ------ | - |
| ATOM | 3500 | N   | VAL | H | 187 | 25.969 | 29.621 | 22.692 | 1.00 | 65.49  | N |
| ATOM | 3501 | CA  | VAL | H | 187 | 26.527 | 30.931 | 23.032 | 1.00 | 65.67  | C |
| ATOM | 3502 | C   | VAL | H | 187 | 25.975 | 32.019 | 22.111 | 1.00 | 72.63  | C |
| ATOM | 3503 | O   | VAL | H | 187 | 25.458 | 31.700 | 21.039 | 1.00 | 72.76  | O |
| ATOM | 3504 | CB  | VAL | H | 187 | 28.082 | 30.908 | 23.053 | 1.00 | 68.21  | C |
| ATOM | 3505 | CG1 | VAL | H | 187 | 28.610 | 29.903 | 24.069 | 1.00 | 67.25  | C |
| ATOM | 3506 | CG2 | VAL | H | 187 | 28.659 | 30.630 | 21.670 | 1.00 | 68.02  | C |
| ATOM | 3507 | N   | VAL | H | 188 | 26.073 | 33.300 | 22.537 | 1.00 | 70.67  | N |
| ATOM | 3508 | CA  | VAL | H | 188 | 25.628 | 34.476 | 21.776 | 1.00 | 71.01  | C |
| ATOM | 3509 | C   | VAL | H | 188 | 26.442 | 35.705 | 22.173 | 1.00 | 78.69  | C |
| ATOM | 3510 | O   | VAL | H | 188 | 26.671 | 35.942 | 23.362 | 1.00 | 78.75  | O |
| ATOM | 3511 | CB  | VAL | H | 188 | 24.081 | 34.716 | 21.825 | 1.00 | 74.53  | C |
| ATOM | 3512 | CG1 | VAL | H | 188 | 23.588 | 35.065 | 23.234 | 1.00 | 74.55  | C |
| ATOM | 3513 | CG2 | VAL | H | 188 | 23.627 | 35.756 | 20.800 | 1.00 | 73.89  | C |
| ATOM | 3514 | N   | THR | H | 189 | 26.916 | 36.456 | 21.164 | 1.00 | 78.31  | N |
| ATOM | 3515 | CA  | THR | H | 189 | 27.648 | 37.710 | 21.357 | 1.00 | 78.94  | C |
| ATOM | 3516 | C   | THR | H | 189 | 26.647 | 38.836 | 21.253 | 1.00 | 85.28  | C |
| ATOM | 3517 | O   | THR | H | 189 | 25.874 | 38.908 | 20.283 | 1.00 | 83.52  | O |
| ATOM | 3518 | CB  | THR | H | 189 | 28.855 | 37.862 | 20.410 | 1.00 | 84.05  | C |
| ATOM | 3519 | OG1 | THR | H | 189 | 28.505 | 37.464 | 19.078 | 1.00 | 84.59  | O |
| ATOM | 3520 | CG2 | THR | H | 189 | 30.076 | 37.099 | 20.902 | 1.00 | 78.76  | C |
| ATOM | 3521 | N   | VAL | H | 190 | 26.614 | 39.674 | 22.296 | 1.00 | 85.83  | N |
| ATOM | 3522 | CA  | VAL | H | 190 | 25.699 | 40.820 | 22.407 | 1.00 | 87.45  | C |
| ATOM | 3523 | C   | VAL | H | 190 | 26.463 | 42.114 | 22.750 | 1.00 | 94.58  | C |
| ATOM | 3524 | O   | VAL | H | 190 | 27.584 | 42.005 | 23.269 | 1.00 | 93.70  | O |
| ATOM | 3525 | CB  | VAL | H | 190 | 24.571 | 40.552 | 23.440 | 1.00 | 91.39  | C |
| ATOM | 3526 | CG1 | VAL | H | 190 | 23.501 | 39.637 | 22.867 | 1.00 | 91.33  | C |
| ATOM | 3527 | CG2 | VAL | H | 190 | 25.122 | 40.012 | 24.759 | 1.00 | 91.21  | C |
| ATOM | 3528 | N   | PRO | H | 191 | 25.882 | 43.336 | 22.525 | 1.00 | 93.59  | N |
| ATOM | 3529 | CA  | PRO | H | 191 | 26.590 | 44.569 | 22.945 | 1.00 | 93.87  | C |
| ATOM | 3530 | C   | PRO | H | 191 | 26.706 | 44.656 | 24.478 | 1.00 | 98.30  | C |
| ATOM | 3531 | O   | PRO | H | 191 | 25.755 | 44.290 | 25.172 | 1.00 | 96.93  | O |
| ATOM | 3532 | CB  | PRO | H | 191 | 25.705 | 45.700 | 22.389 | 1.00 | 95.48  | C |
| ATOM | 3533 | CG  | PRO | H | 191 | 24.738 | 45.043 | 21.443 | 1.00 | 99.50  | C |
| ATOM | 3534 | CD  | PRO | H | 191 | 24.563 | 43.653 | 21.930 | 1.00 | 94.99  | C |
| ATOM | 3535 | N   | SER | H | 192 | 27.871 | 45.113 | 25.005 | 1.00 | 96.49  | N |
| ATOM | 3536 | CA  | SER | H | 192 | 28.133 | 45.255 | 26.451 | 1.00 | 97.24  | C |
| ATOM | 3537 | C   | SER | H | 192 | 27.137 | 46.192 | 27.165 | 1.00 | 103.72 | C |
| ATOM | 3538 | O   | SER | H | 192 | 26.878 | 46.021 | 28.361 | 1.00 | 103.11 | O |
| ATOM | 3539 | CB  | SER | H | 192 | 29.561 | 45.727 | 26.697 | 1.00 | 100.57 | C |
| ATOM | 3540 | OG  | SER | H | 192 | 30.490 | 44.681 | 26.477 | 1.00 | 108.92 | O |
| ATOM | 3541 | N   | SER | H | 193 | 26.573 | 47.165 | 26.412 | 1.00 | 101.84 | N |
| ATOM | 3542 | CA  | SER | H | 193 | 25.578 | 48.139 | 26.862 | 1.00 | 101.96 | C |
| ATOM | 3543 | C   | SER | H | 193 | 24.220 | 47.489 | 27.214 | 1.00 | 109.48 | C |
| ATOM | 3544 | O   | SER | H | 193 | 23.465 | 48.050 | 28.015 | 1.00 | 110.43 | O |
| ATOM | 3545 | CB  | SER | H | 193 | 25.386 | 49.224 | 25.804 | 1.00 | 103.28 | C |
| ATOM | 3546 | OG  | SER | H | 193 | 24.898 | 48.714 | 24.574 | 1.00 | 106.17 | O |
| ATOM | 3547 | N   | SER | H | 194 | 23.914 | 46.320 | 26.607 | 1.00 | 106.99 | N |
| ATOM | 3548 | CA  | SER | H | 194 | 22.672 | 45.555 | 26.793 | 1.00 | 107.18 | C |
| ATOM | 3549 | C   | SER | H | 194 | 22.581 | 44.876 | 28.162 | 1.00 | 111.78 | C |
| ATOM | 3550 | O   | SER | H | 194 | 21.481 | 44.692 | 28.672 | 1.00 | 110.97 | O |
| ATOM | 3551 | CB  | SER | H | 194 | 22.518 | 44.515 | 25.689 | 1.00 | 110.81 | C |
| ATOM | 3552 | OG  | SER | H | 194 | 22.818 | 45.053 | 24.410 | 1.00 | 118.86 | O |
| ATOM | 3553 | N   | LEU | H | 195 | 23.731 | 44.495 | 28.743 | 1.00 | 109.85 | N |
| ATOM | 3554 | CA  | LEU | H | 195 | 23.857 | 43.836 | 30.052 | 1.00 | 110.40 | C |
| ATOM | 3555 | C   | LEU | H | 195 | 23.241 | 44.725 | 31.155 | 1.00 | 116.52 | C |
| ATOM | 3556 | O   | LEU | H | 195 | 23.771 | 45.797 | 31.474 | 1.00 | 117.26 | O |
| ATOM | 3557 | CB  | LEU | H | 195 | 25.350 | 43.558 | 30.332 | 1.00 | 110.26 | C |
| ATOM | 3558 | CG  | LEU | H | 195 | 26.015 | 42.313 | 29.704 | 1.00 | 114.47 | C |
| ATOM | 3559 | CD1 | LEU | H | 195 | 25.876 | 42.264 | 28.195 | 1.00 | 114.70 | C |
| ATOM | 3560 | CD2 | LEU | H | 195 | 27.483 | 42.295 | 30.014 | 1.00 | 116.29 | C |
| ATOM | 3561 | N   | GLY | H | 196 | 22.100 | 44.292 | 31.680 | 1.00 | 112.85 | N |
| ATOM | 3562 | CA  | GLY | H | 196 | 21.354 | 45.053 | 32.675 | 1.00 | 112.46 | C |
| ATOM | 3563 | C   | GLY | H | 196 | 20.040 | 45.544 | 32.100 | 1.00 | 115.92 | C |
| ATOM | 3564 | O   | GLY | H | 196 | 18.991 | 45.374 | 32.728 | 1.00 | 116.50 | O |
| ATOM | 3565 | N   | THR | H | 197 | 20.087 | 46.128 | 30.879 | 1.00 | 110.80 | N |
| ATOM | 3566 | CA  | THR | H | 197 | 18.918 | 46.611 | 30.124 | 1.00 | 109.86 | C |
| ATOM | 3567 | C   | THR | H | 197 | 18.097 | 45.402 | 29.616 | 1.00 | 111.00 | C |
| ATOM | 3568 | O   | THR | H | 197 | 16.924 | 45.260 | 29.978 | 1.00 | 110.52 | O |
| ATOM | 3569 | CB  | THR | H | 197 | 19.373 | 47.511 | 28.946 | 1.00 | 119.84 | C |
| ATOM | 3570 | OG1 | THR | H | 197 | 20.330 | 48.471 | 29.405 | 1.00 | 120.80 | O |
| ATOM | 3571 | CG2 | THR | H | 197 | 18.207 | 48.206 | 28.236 | 1.00 | 117.23 | C |
| ATOM | 3572 | N   | GLN | H | 198 | 18.735 | 44.538 | 28.785 | 1.00 | 105.39 | N |
| ATOM | 3573 | CA  | GLN | H | 198 | 18.157 | 43.336 | 28.181 | 1.00 | 103.86 | C |
| ATOM | 3574 | C   | GLN | H | 198 | 18.371 | 42.056 | 28.975 | 1.00 | 104.53 | C |
| ATOM | 3575 | O   | GLN | H | 198 | 19.450 | 41.819 | 29.532 | 1.00 | 102.56 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 3576 | CB | GLN | H | 198 | 18.635 | 43.138 | 26.733 | 1.00 | 104.95 | C |
|---|---|---|---|---|---|---|---|---|---|---|---|
| ATOM | 3577 | CG | GLN | H | 198 | 17.526 | 43.291 | 25.689 | 1.00 | 116.31 | C |
| ATOM | 3578 | CD | GLN | H | 198 | 16.363 | 42.345 | 25.903 | 1.00 | 133.91 | C |
| ATOM | 3579 | OE1 | GLN | H | 198 | 16.426 | 41.159 | 25.568 | 1.00 | 128.86 | O |
| ATOM | 3580 | NE2 | GLN | H | 198 | 15.279 | 42.849 | 26.485 | 1.00 | 126.96 | N |
| ATOM | 3581 | N | THR | H | 199 | 17.323 | 41.217 | 28.985 | 1.00 | 100.21 | N |
| ATOM | 3582 | CA | THR | H | 199 | 17.286 | 39.926 | 29.670 | 1.00 | 98.85 | C |
| ATOM | 3583 | C | THR | H | 199 | 17.563 | 38.817 | 28.670 | 1.00 | 98.22 | C |
| ATOM | 3584 | O | THR | H | 199 | 16.967 | 38.791 | 27.583 | 1.00 | 97.55 | O |
| ATOM | 3585 | CB | THR | H | 199 | 15.949 | 39.722 | 30.405 | 1.00 | 108.82 | C |
| ATOM | 3586 | OG1 | THR | H | 199 | 15.412 | 40.988 | 30.809 | 1.00 | 111.77 | O |
| ATOM | 3587 | CG2 | THR | H | 199 | 16.086 | 38.794 | 31.610 | 1.00 | 106.28 | C |
| ATOM | 3588 | N | TYR | H | 200 | 18.478 | 37.905 | 29.044 | 1.00 | 91.51 | N |
| ATOM | 3589 | CA | TYR | H | 200 | 18.890 | 36.777 | 28.213 | 1.00 | 89.21 | C |
| ATOM | 3590 | C | TYR | H | 200 | 18.540 | 35.434 | 28.852 | 1.00 | 89.00 | C |
| ATOM | 3591 | O | TYR | H | 200 | 19.100 | 35.062 | 29.883 | 1.00 | 87.67 | O |
| ATOM | 3592 | CB | TYR | H | 200 | 20.383 | 36.892 | 27.845 | 1.00 | 89.85 | C |
| ATOM | 3593 | CG | TYR | H | 200 | 20.690 | 38.141 | 27.038 | 1.00 | 91.63 | C |
| ATOM | 3594 | CD1 | TYR | H | 200 | 20.245 | 38.276 | 25.724 | 1.00 | 93.42 | C |
| ATOM | 3595 | CD2 | TYR | H | 200 | 21.371 | 39.214 | 27.607 | 1.00 | 92.54 | C |
| ATOM | 3596 | CE1 | TYR | H | 200 | 20.486 | 39.439 | 24.991 | 1.00 | 93.61 | C |
| ATOM | 3597 | CE2 | TYR | H | 200 | 21.617 | 40.386 | 26.881 | 1.00 | 93.46 | C |
| ATOM | 3598 | CZ | TYR | H | 200 | 21.176 | 40.490 | 25.569 | 1.00 | 101.76 | C |
| ATOM | 3599 | OH | TYR | H | 200 | 21.414 | 41.622 | 24.817 | 1.00 | 104.21 | O |
| ATOM | 3600 | N | ILE | H | 201 | 17.567 | 34.736 | 28.255 | 1.00 | 84.11 | N |
| ATOM | 3601 | CA | ILE | H | 201 | 17.109 | 33.420 | 28.708 | 1.00 | 83.70 | C |
| ATOM | 3602 | C | ILE | H | 201 | 17.265 | 32.437 | 27.555 | 1.00 | 86.26 | C |
| ATOM | 3603 | O | ILE | H | 201 | 16.851 | 32.749 | 26.437 | 1.00 | 85.36 | O |
| ATOM | 3604 | CB | ILE | H | 201 | 15.630 | 33.423 | 29.214 | 1.00 | 86.75 | C |
| ATOM | 3605 | CG1 | ILE | H | 201 | 15.337 | 34.583 | 30.177 | 1.00 | 87.36 | C |
| ATOM | 3606 | CG2 | ILE | H | 201 | 15.263 | 32.076 | 29.851 | 1.00 | 86.33 | C |
| ATOM | 3607 | CD1 | ILE | H | 201 | 13.954 | 35.106 | 30.054 | 1.00 | 93.78 | C |
| ATOM | 3608 | N | CYS | H | 202 | 17.848 | 31.254 | 27.822 | 1.00 | 81.72 | N |
| ATOM | 3609 | CA | CYS | H | 202 | 17.963 | 30.222 | 26.798 | 1.00 | 81.35 | C |
| ATOM | 3610 | C | CYS | H | 202 | 16.877 | 29.175 | 27.005 | 1.00 | 84.05 | C |
| ATOM | 3611 | O | CYS | H | 202 | 16.646 | 28.744 | 28.140 | 1.00 | 83.61 | O |
| ATOM | 3612 | CB | CYS | H | 202 | 19.355 | 29.601 | 26.772 | 1.00 | 81.81 | C |
| ATOM | 3613 | SG | CYS | H | 202 | 19.696 | 28.481 | 28.149 | 1.00 | 85.97 | S |
| ATOM | 3614 | N | ASN | H | 203 | 16.194 | 28.780 | 25.921 | 1.00 | 79.41 | N |
| ATOM | 3615 | CA | ASN | H | 203 | 15.147 | 27.764 | 26.016 | 1.00 | 78.12 | C |
| ATOM | 3616 | C | ASN | H | 203 | 15.636 | 26.429 | 25.460 | 1.00 | 77.93 | C |
| ATOM | 3617 | O | ASN | H | 203 | 15.749 | 26.242 | 24.240 | 1.00 | 76.12 | O |
| ATOM | 3618 | CB | ASN | H | 203 | 13.849 | 28.217 | 25.356 | 1.00 | 81.94 | C |
| ATOM | 3619 | CG | ASN | H | 203 | 13.629 | 29.709 | 25.309 | 1.00 | 101.25 | C |
| ATOM | 3620 | OD1 | ASN | H | 203 | 13.490 | 30.278 | 24.232 | 1.00 | 89.90 | O |
| ATOM | 3621 | ND2 | ASN | H | 203 | 13.564 | 30.367 | 26.465 | 1.00 | 94.35 | N |
| ATOM | 3622 | N | VAL | H | 204 | 15.968 | 25.528 | 26.390 | 1.00 | 73.17 | N |
| ATOM | 3623 | CA | VAL | H | 204 | 16.489 | 24.188 | 26.148 | 1.00 | 73.22 | C |
| ATOM | 3624 | C | VAL | H | 204 | 15.335 | 23.184 | 26.234 | 1.00 | 77.20 | C |
| ATOM | 3625 | O | VAL | H | 204 | 14.699 | 23.064 | 27.282 | 1.00 | 76.50 | O |
| ATOM | 3626 | CB | VAL | H | 204 | 17.643 | 23.826 | 27.135 | 1.00 | 77.03 | C |
| ATOM | 3627 | CG1 | VAL | H | 204 | 18.255 | 22.460 | 26.799 | 1.00 | 76.89 | C |
| ATOM | 3628 | CG2 | VAL | H | 204 | 18.717 | 24.916 | 27.165 | 1.00 | 76.33 | C |
| ATOM | 3629 | N | ASN | H | 205 | 15.079 | 22.463 | 25.125 | 1.00 | 73.54 | N |
| ATOM | 3630 | CA | ASN | H | 205 | 14.018 | 21.458 | 25.006 | 1.00 | 72.14 | C |
| ATOM | 3631 | C | ASN | H | 205 | 14.626 | 20.106 | 24.648 | 1.00 | 72.33 | C |
| ATOM | 3632 | O | ASN | H | 205 | 15.451 | 20.040 | 23.744 | 1.00 | 72.16 | O |
| ATOM | 3633 | CB | ASN | H | 205 | 12.988 | 21.894 | 23.955 | 1.00 | 74.82 | C |
| ATOM | 3634 | CG | ASN | H | 205 | 11.641 | 21.249 | 24.137 | 1.00 | 108.35 | C |
| ATOM | 3635 | OD1 | ASN | H | 205 | 10.876 | 21.605 | 25.043 | 1.00 | 106.08 | O |
| ATOM | 3636 | ND2 | ASN | H | 205 | 11.326 | 20.277 | 23.286 | 1.00 | 100.19 | N |
| ATOM | 3637 | N | HIS | H | 206 | 14.254 | 19.047 | 25.384 | 1.00 | 67.46 | N |
| ATOM | 3638 | CA | HIS | H | 206 | 14.729 | 17.671 | 25.191 | 1.00 | 67.14 | C |
| ATOM | 3639 | C | HIS | H | 206 | 13.544 | 16.726 | 25.287 | 1.00 | 71.23 | C |
| ATOM | 3640 | O | HIS | H | 206 | 13.201 | 16.214 | 26.367 | 1.00 | 69.57 | O |
| ATOM | 3641 | CB | HIS | H | 206 | 15.833 | 17.296 | 26.188 | 1.00 | 67.72 | C |
| ATOM | 3642 | CG | HIS | H | 206 | 16.373 | 15.901 | 26.017 | 1.00 | 71.21 | C |
| ATOM | 3643 | ND1 | HIS | H | 206 | 16.412 | 15.008 | 27.075 | 1.00 | 73.23 | N |
| ATOM | 3644 | CD2 | HIS | H | 206 | 16.917 | 15.305 | 24.932 | 1.00 | 72.61 | C |
| ATOM | 3645 | CE1 | HIS | H | 206 | 16.950 | 13.898 | 26.594 | 1.00 | 72.31 | C |
| ATOM | 3646 | NE2 | HIS | H | 206 | 17.276 | 14.031 | 25.313 | 1.00 | 72.43 | N |
| ATOM | 3647 | N | LYS | H | 207 | 12.900 | 16.546 | 24.121 | 1.00 | 67.38 | N |
| ATOM | 3648 | CA | LYS | H | 207 | 11.699 | 15.736 | 23.910 | 1.00 | 65.82 | C |
| ATOM | 3649 | C | LYS | H | 207 | 11.820 | 14.300 | 24.459 | 1.00 | 69.89 | C |
| ATOM | 3650 | O | LYS | H | 207 | 10.898 | 13.884 | 25.181 | 1.00 | 68.86 | O |
| ATOM | 3651 | CB | LYS | H | 207 | 11.272 | 15.745 | 22.434 | 1.00 | 65.83 | C |
| ATOM | 3652 | CG | LYS | H | 207 | 10.854 | 17.101 | 21.909 | 1.00 | 69.85 | C |

TABLE 1-continued

Three-dimensional crystal coordinate for anti-TcdB antibody beziotoxumab Fab –C. *difficile* toxin B (TcdB$^{(1834-2101)}$) complex.

| ATOM | 3653 | CD | LYS | H | 207 | 10.315 | 16.932 | 20.505 | 1.00 | 82.99 | C |
|---|---|---|---|---|---|---|---|---|---|---|---|
| ATOM | 3654 | CE | LYS | H | 207 | 9.934 | 18.235 | 19.852 | 1.00 | 97.08 | C |
| ATOM | 3655 | NZ | LYS | H | 207 | 9.336 | 17.995 | 18.511 | 1.00 | 106.00 | N |
| ATOM | 3656 | N | PRO | H | 208 | 12.936 | 13.547 | 24.207 | 1.00 | 66.82 | N |
| ATOM | 3657 | CA | PRO | H | 208 | 13.037 | 12.179 | 24.751 | 1.00 | 67.05 | C |
| ATOM | 3658 | C | PRO | H | 208 | 12.805 | 12.021 | 26.262 | 1.00 | 73.14 | C |
| ATOM | 3659 | O | PRO | H | 208 | 12.263 | 11.008 | 26.666 | 1.00 | 72.32 | O |
| ATOM | 3660 | CB | PRO | H | 208 | 14.445 | 11.749 | 24.351 | 1.00 | 68.42 | C |
| ATOM | 3661 | CG | PRO | H | 208 | 14.754 | 12.528 | 23.146 | 1.00 | 72.65 | C |
| ATOM | 3662 | CD | PRO | H | 208 | 14.124 | 13.862 | 23.383 | 1.00 | 68.20 | C |
| ATOM | 3663 | N | SER | H | 209 | 13.200 | 13.002 | 27.083 | 1.00 | 73.44 | N |
| ATOM | 3664 | CA | SER | H | 209 | 12.984 | 12.982 | 28.537 | 1.00 | 74.50 | C |
| ATOM | 3665 | C | SER | H | 209 | 11.890 | 13.992 | 28.930 | 1.00 | 81.53 | C |
| ATOM | 3666 | O | SER | H | 209 | 11.545 | 14.101 | 30.108 | 1.00 | 80.71 | O |
| ATOM | 3667 | CB | SER | H | 209 | 14.286 | 13.284 | 29.276 | 1.00 | 77.35 | C |
| ATOM | 3668 | OG | SER | H | 209 | 14.671 | 14.645 | 29.166 | 1.00 | 83.97 | O |
| ATOM | 3669 | N | ASN | H | 210 | 11.339 | 14.709 | 27.924 | 1.00 | 81.27 | N |
| ATOM | 3670 | CA | ASN | H | 210 | 10.331 | 15.768 | 28.051 | 1.00 | 82.68 | C |
| ATOM | 3671 | C | ASN | H | 210 | 10.757 | 16.843 | 29.082 | 1.00 | 86.20 | C |
| ATOM | 3672 | O | ASN | H | 210 | 10.043 | 17.125 | 30.051 | 1.00 | 86.37 | O |
| ATOM | 3673 | CB | ASN | H | 210 | 8.923 | 15.215 | 28.306 | 1.00 | 88.32 | C |
| ATOM | 3674 | CG | ASN | H | 210 | 7.836 | 16.233 | 28.050 | 1.00 | 117.12 | C |
| ATOM | 3675 | OD1 | ASN | H | 210 | 7.195 | 16.731 | 28.987 | 1.00 | 111.93 | O |
| ATOM | 3676 | ND2 | ASN | H | 210 | 7.645 | 16.605 | 26.783 | 1.00 | 108.25 | N |
| ATOM | 3677 | N | THR | H | 211 | 11.962 | 17.409 | 28.861 | 1.00 | 81.24 | N |
| ATOM | 3678 | CA | THR | H | 211 | 12.576 | 18.449 | 29.688 | 1.00 | 79.78 | C |
| ATOM | 3679 | C | THR | H | 211 | 12.536 | 19.769 | 28.921 | 1.00 | 82.66 | C |
| ATOM | 3680 | O | THR | H | 211 | 13.063 | 19.849 | 27.815 | 1.00 | 81.53 | O |
| ATOM | 3681 | CB | THR | H | 211 | 14.022 | 18.042 | 30.072 | 1.00 | 81.62 | C |
| ATOM | 3682 | OG1 | THR | H | 211 | 14.014 | 16.786 | 30.735 | 1.00 | 80.25 | O |
| ATOM | 3683 | CG2 | THR | H | 211 | 14.704 | 19.048 | 30.963 | 1.00 | 77.41 | C |
| ATOM | 3684 | N | LYS | H | 212 | 11.872 | 20.782 | 29.495 | 1.00 | 79.85 | N |
| ATOM | 3685 | CA | LYS | H | 212 | 11.787 | 22.141 | 28.961 | 1.00 | 79.58 | C |
| ATOM | 3686 | C | LYS | H | 212 | 12.298 | 23.057 | 30.080 | 1.00 | 84.68 | C |
| ATOM | 3687 | O | LYS | H | 212 | 11.655 | 23.194 | 31.126 | 1.00 | 84.13 | O |
| ATOM | 3688 | CB | LYS | H | 212 | 10.365 | 22.502 | 28.491 | 1.00 | 80.88 | C |
| ATOM | 3689 | N | VAL | H | 213 | 13.519 | 23.587 | 29.892 | 1.00 | 81.98 | N |
| ATOM | 3690 | CA | VAL | H | 213 | 14.231 | 24.468 | 30.827 | 1.00 | 81.76 | C |
| ATOM | 3691 | C | VAL | H | 213 | 14.367 | 25.865 | 30.203 | 1.00 | 87.76 | C |
| ATOM | 3692 | O | VAL | H | 213 | 14.467 | 25.995 | 28.983 | 1.00 | 88.45 | O |
| ATOM | 3693 | CB | VAL | H | 213 | 15.633 | 23.898 | 31.194 | 1.00 | 84.86 | C |
| ATOM | 3694 | CG1 | VAL | H | 213 | 16.292 | 24.694 | 32.318 | 1.00 | 84.42 | C |
| ATOM | 3695 | CG2 | VAL | H | 213 | 15.559 | 22.426 | 31.566 | 1.00 | 84.38 | C |
| ATOM | 3696 | N | ASP | H | 214 | 14.363 | 26.900 | 31.045 | 1.00 | 85.23 | N |
| ATOM | 3697 | CA | ASP | H | 214 | 14.567 | 28.292 | 30.646 | 1.00 | 85.23 | C |
| ATOM | 3698 | C | ASP | H | 214 | 15.474 | 28.918 | 31.733 | 1.00 | 90.42 | C |
| ATOM | 3699 | O | ASP | H | 214 | 14.973 | 29.335 | 32.788 | 1.00 | 91.23 | O |
| ATOM | 3700 | CB | ASP | H | 214 | 13.228 | 29.051 | 30.487 | 1.00 | 86.86 | C |
| ATOM | 3701 | CG | ASP | H | 214 | 12.209 | 28.383 | 29.585 | 1.00 | 100.37 | C |
| ATOM | 3702 | OD1 | ASP | H | 214 | 12.330 | 28.520 | 28.355 | 1.00 | 101.22 | O |
| ATOM | 3703 | OD2 | ASP | H | 214 | 11.280 | 27.735 | 30.115 | 1.00 | 109.12 | O |
| ATOM | 3704 | N | LYS | H | 215 | 16.815 | 28.880 | 31.529 | 1.00 | 85.82 | N |
| ATOM | 3705 | CA | LYS | H | 215 | 17.777 | 29.456 | 32.482 | 1.00 | 85.11 | C |
| ATOM | 3706 | C | LYS | H | 215 | 18.098 | 30.897 | 32.099 | 1.00 | 91.42 | C |
| ATOM | 3707 | O | LYS | H | 215 | 18.388 | 31.182 | 30.934 | 1.00 | 91.39 | O |
| ATOM | 3708 | CB | LYS | H | 215 | 19.064 | 28.628 | 32.605 | 1.00 | 86.08 | C |
| ATOM | 3709 | N | ARG | H | 216 | 17.993 | 31.815 | 33.074 | 1.00 | 89.40 | N |
| ATOM | 3710 | CA | ARG | H | 216 | 18.306 | 33.224 | 32.866 | 1.00 | 89.14 | C |
| ATOM | 3711 | C | ARG | H | 216 | 19.809 | 33.379 | 33.079 | 1.00 | 91.83 | C |
| ATOM | 3712 | O | ARG | H | 216 | 20.343 | 32.990 | 34.136 | 1.00 | 90.26 | O |
| ATOM | 3713 | CB | ARG | H | 216 | 17.501 | 34.152 | 33.804 | 1.00 | 90.12 | C |
| ATOM | 3714 | CG | ARG | H | 216 | 17.921 | 35.622 | 33.696 | 1.00 | 105.64 | C |
| ATOM | 3715 | CD | ARG | H | 216 | 17.318 | 36.491 | 34.770 | 1.00 | 122.84 | C |
| ATOM | 3716 | NE | ARG | H | 216 | 15.952 | 36.871 | 34.419 | 1.00 | 138.90 | N |
| ATOM | 3717 | CZ | ARG | H | 216 | 15.175 | 37.649 | 35.162 | 1.00 | 157.20 | C |
| ATOM | 3718 | NH1 | ARG | H | 216 | 15.619 | 38.137 | 36.315 | 1.00 | 148.31 | N |
| ATOM | 3719 | NH2 | ARG | H | 216 | 13.945 | 37.945 | 34.760 | 1.00 | 142.54 | N |
| ATOM | 3720 | N | VAL | H | 217 | 20.485 | 33.892 | 32.029 | 1.00 | 87.94 | N |
| ATOM | 3721 | CA | VAL | H | 217 | 21.917 | 34.161 | 32.021 | 1.00 | 87.62 | C |
| ATOM | 3722 | C | VAL | H | 217 | 22.040 | 35.636 | 32.386 | 1.00 | 92.65 | C |
| ATOM | 3723 | O | VAL | H | 217 | 21.584 | 36.529 | 31.645 | 1.00 | 92.05 | O |
| ATOM | 3724 | CB | VAL | H | 217 | 22.614 | 33.791 | 30.682 | 1.00 | 91.18 | C |
| ATOM | 3725 | CG1 | VAL | H | 217 | 24.131 | 33.955 | 30.782 | 1.00 | 90.91 | C |
| ATOM | 3726 | CG2 | VAL | H | 217 | 22.261 | 32.369 | 30.254 | 1.00 | 90.75 | C |
| ATOM | 3727 | N | GLU | H | 218 | 22.571 | 35.858 | 33.593 | 1.00 | 90.11 | N |
| ATOM | 3728 | CA | GLU | H | 218 | 22.759 | 37.161 | 34.209 | 1.00 | 90.36 | C |
| ATOM | 3729 | C | GLU | H | 218 | 24.234 | 37.321 | 34.562 | 1.00 | 94.71 | C |

TABLE 1-continued

Three-dimensional crystal coordinate for anti-TcdB antibody beziotoxumab Fab –*C. difficile* toxin B (TcdB$^{(1834-2101)}$) complex.

| | | | | | | | | | | |
|---|---|---|---|---|---|---|---|---|---|---|
| ATOM | 3730 | O | GLU | H | 218 | 24.889 | 36.308 | 34.841 | 1.00 | 92.91 | O |
| ATOM | 3731 | CB | GLU | H | 218 | 21.899 | 37.255 | 35.484 | 1.00 | 91.87 | C |
| ATOM | 3732 | N | PRO | H | 219 | 24.778 | 38.569 | 34.574 | 1.00 | 93.14 | N |
| ATOM | 3733 | CA | PRO | H | 219 | 26.189 | 38.737 | 34.949 | 1.00 | 94.14 | C |
| ATOM | 3734 | C | PRO | H | 219 | 26.394 | 38.372 | 36.419 | 1.00 | 103.62 | C |
| ATOM | 3735 | O | PRO | H | 219 | 25.557 | 38.730 | 37.261 | 1.00 | 103.35 | O |
| ATOM | 3736 | CB | PRO | H | 219 | 26.447 | 40.233 | 34.710 | 1.00 | 95.26 | C |
| ATOM | 3737 | CG | PRO | H | 219 | 25.277 | 40.739 | 33.922 | 1.00 | 98.79 | C |
| ATOM | 3738 | CD | PRO | H | 219 | 24.139 | 39.876 | 34.295 | 1.00 | 94.25 | C |
| ATOM | 3739 | N | LYS | H | 220 | 27.486 | 37.629 | 36.725 | 1.00 | 104.16 | N |
| ATOM | 3740 | CA | LYS | H | 220 | 27.826 | 37.213 | 38.099 | 1.00 | 105.54 | C |
| ATOM | 3741 | C | LYS | H | 220 | 28.246 | 38.436 | 38.943 | 1.00 | 113.00 | C |
| ATOM | 3742 | O | LYS | H | 220 | 29.038 | 39.264 | 38.463 | 1.00 | 114.08 | O |
| ATOM | 3743 | CB | LYS | H | 220 | 28.952 | 36.162 | 38.092 | 1.00 | 107.74 | C |
| ATOM | 3744 | N | SER | H | 221 | 27.705 | 38.567 | 40.177 | 1.00 | 109.26 | N |
| ATOM | 3745 | CA | SER | H | 221 | 28.023 | 39.699 | 41.062 | 1.00 | 129.46 | C |
| ATOM | 3746 | C | SER | H | 221 | 29.202 | 39.401 | 42.014 | 1.00 | 147.96 | C |
| ATOM | 3747 | O | SER | H | 221 | 30.343 | 39.807 | 41.761 | 1.00 | 98.37 | O |
| ATOM | 3748 | CB | SER | H | 221 | 26.786 | 40.130 | 41.845 | 1.00 | 131.99 | C |
| ATOM | 3749 | OG | SER | H | 221 | 25.775 | 40.642 | 40.993 | 1.00 | 137.81 | O |
| TER | 3750 | | SER | H | 221 | | | | | | |
| ATOM | 3751 | O | GLU | I | 1 | 9.402 | −22.914 | 13.399 | 1.00 | 74.01 | O |
| ATOM | 3752 | N | GLU | I | 1 | 10.278 | −21.223 | 11.441 | 1.00 | 72.08 | N |
| ATOM | 3753 | CA | GLU | I | 1 | 11.266 | −21.823 | 12.342 | 1.00 | 71.16 | C |
| ATOM | 3754 | C | GLU | I | 1 | 10.631 | −22.865 | 13.249 | 1.00 | 74.24 | C |
| ATOM | 3755 | CB | GLU | I | 1 | 12.000 | −20.745 | 13.184 | 1.00 | 72.20 | C |
| ATOM | 3756 | N | VAL | I | 2 | 11.484 | −23.701 | 13.857 | 1.00 | 69.17 | N |
| ATOM | 3757 | CA | VAL | I | 2 | 11.051 | −24.715 | 14.806 | 1.00 | 67.41 | C |
| ATOM | 3758 | C | VAL | I | 2 | 10.766 | −23.993 | 16.117 | 1.00 | 74.49 | C |
| ATOM | 3759 | O | VAL | I | 2 | 11.646 | −23.293 | 16.639 | 1.00 | 75.46 | O |
| ATOM | 3760 | CB | VAL | I | 2 | 12.108 | −25.810 | 14.997 | 1.00 | 67.91 | C |
| ATOM | 3761 | CG1 | VAL | I | 2 | 11.591 | −26.891 | 15.934 | 1.00 | 67.12 | C |
| ATOM | 3762 | CG2 | VAL | I | 2 | 12.510 | −26.402 | 13.659 | 1.00 | 67.48 | C |
| ATOM | 3763 | N | GLN | I | 3 | 9.533 | −24.136 | 16.626 | 1.00 | 70.89 | N |
| ATOM | 3764 | CA | GLN | I | 3 | 9.146 | −23.514 | 17.882 | 1.00 | 70.90 | C |
| ATOM | 3765 | C | GLN | I | 3 | 8.023 | −24.252 | 18.592 | 1.00 | 74.03 | C |
| ATOM | 3766 | O | GLN | I | 3 | 7.176 | −24.860 | 17.947 | 1.00 | 73.56 | O |
| ATOM | 3767 | CB | GLN | I | 3 | 8.824 | −22.005 | 17.713 | 1.00 | 71.84 | C |
| ATOM | 3768 | CG | GLN | I | 3 | 7.703 | −21.651 | 16.755 | 1.00 | 82.85 | C |
| ATOM | 3769 | CD | GLN | I | 3 | 7.731 | −20.181 | 16.430 | 1.00 | 105.96 | C |
| ATOM | 3770 | OE1 | GLN | I | 3 | 7.912 | −19.324 | 17.306 | 1.00 | 102.80 | O |
| ATOM | 3771 | NE2 | GLN | I | 3 | 7.561 | −19.856 | 15.153 | 1.00 | 100.00 | N |
| ATOM | 3772 | N | LEU | I | 4 | 8.051 | −24.202 | 19.929 | 1.00 | 69.87 | N |
| ATOM | 3773 | CA | LEU | I | 4 | 7.028 | −24.744 | 20.823 | 1.00 | 69.29 | C |
| ATOM | 3774 | C | LEU | I | 4 | 6.432 | −23.534 | 21.557 | 1.00 | 72.45 | C |
| ATOM | 3775 | O | LEU | I | 4 | 7.163 | −22.794 | 22.219 | 1.00 | 71.84 | O |
| ATOM | 3776 | CB | LEU | I | 4 | 7.597 | −25.778 | 21.828 | 1.00 | 68.78 | C |
| ATOM | 3777 | CG | LEU | I | 4 | 8.328 | −27.001 | 21.257 | 1.00 | 72.35 | C |
| ATOM | 3778 | CD1 | LEU | I | 4 | 9.067 | −27.723 | 22.331 | 1.00 | 72.35 | C |
| ATOM | 3779 | CD2 | LEU | I | 4 | 7.378 | −27.977 | 20.611 | 1.00 | 74.53 | C |
| ATOM | 3780 | N | VAL | I | 5 | 5.126 | −23.288 | 21.370 | 1.00 | 67.81 | N |
| ATOM | 3781 | CA | VAL | I | 5 | 4.427 | −22.147 | 21.967 | 1.00 | 66.19 | C |
| ATOM | 3782 | C | VAL | I | 5 | 3.497 | −22.633 | 23.072 | 1.00 | 69.92 | C |
| ATOM | 3783 | O | VAL | I | 5 | 2.596 | −23.432 | 22.835 | 1.00 | 70.92 | O |
| ATOM | 3784 | CB | VAL | I | 5 | 3.708 | −21.282 | 20.901 | 1.00 | 68.60 | C |
| ATOM | 3785 | CG1 | VAL | I | 5 | 3.070 | −20.053 | 21.529 | 1.00 | 67.69 | C |
| ATOM | 3786 | CG2 | VAL | I | 5 | 4.660 | −20.886 | 19.775 | 1.00 | 68.31 | C |
| ATOM | 3787 | N | GLN | I | 6 | 3.714 | −22.154 | 24.274 | 1.00 | 65.56 | N |
| ATOM | 3788 | CA | GLN | I | 6 | 2.917 | −22.605 | 25.396 | 1.00 | 65.61 | C |
| ATOM | 3789 | C | GLN | I | 6 | 1.739 | −21.688 | 25.760 | 1.00 | 72.18 | C |
| ATOM | 3790 | O | GLN | I | 6 | 1.696 | −20.499 | 25.403 | 1.00 | 71.66 | O |
| ATOM | 3791 | CB | GLN | I | 6 | 3.812 | −22.852 | 26.602 | 1.00 | 66.09 | C |
| ATOM | 3792 | CG | GLN | I | 6 | 4.881 | −23.871 | 26.318 | 1.00 | 67.08 | C |
| ATOM | 3793 | CD | GLN | I | 6 | 5.727 | −24.133 | 27.510 | 1.00 | 72.81 | C |
| ATOM | 3794 | OE1 | GLN | I | 6 | 6.938 | −23.936 | 27.478 | 1.00 | 70.43 | O |
| ATOM | 3795 | NE2 | GLN | I | 6 | 5.108 | −24.620 | 28.574 | 1.00 | 56.37 | N |
| ATOM | 3796 | N | SER | I | 7 | 0.766 | −22.278 | 26.479 | 1.00 | 69.41 | N |
| ATOM | 3797 | CA | SER | I | 7 | −0.410 | −21.578 | 26.945 | 1.00 | 69.10 | C |
| ATOM | 3798 | C | SER | I | 7 | 0.007 | −20.487 | 27.963 | 1.00 | 76.06 | C |
| ATOM | 3799 | O | SER | I | 7 | 1.099 | −20.576 | 28.558 | 1.00 | 76.85 | O |
| ATOM | 3800 | CB | SER | I | 7 | −1.437 | −22.558 | 27.518 | 1.00 | 68.90 | C |
| ATOM | 3801 | OG | SER | I | 7 | −0.911 | −23.449 | 28.487 | 1.00 | 69.05 | O |
| ATOM | 3802 | N | GLY | I | 8 | −0.843 | −19.455 | 28.094 | 1.00 | 71.65 | N |
| ATOM | 3803 | CA | GLY | I | 8 | −0.654 | −18.320 | 28.986 | 1.00 | 70.58 | C |
| ATOM | 3804 | C | GLY | I | 8 | −0.525 | −18.675 | 30.456 | 1.00 | 73.44 | C |
| ATOM | 3805 | O | GLY | I | 8 | −0.791 | −19.812 | 30.873 | 1.00 | 70.91 | O |
| ATOM | 3806 | N | ALA | I | 9 | −0.098 | −17.675 | 31.243 | 1.00 | 72.22 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 3807 | CA | ALA | I | 9 | 0.088 | −17.766 | 32.688 | 1.00 | 72.69 | C |
|---|---|---|---|---|---|---|---|---|---|---|---|
| ATOM | 3808 | C | ALA | I | 9 | −1.219 | −18.156 | 33.386 | 1.00 | 78.61 | C |
| ATOM | 3809 | O | ALA | I | 9 | −2.294 | −17.644 | 33.048 | 1.00 | 78.66 | O |
| ATOM | 3810 | CB | ALA | I | 9 | 0.594 | −16.437 | 33.222 | 1.00 | 73.25 | C |
| ATOM | 3811 | N | GLU | I | 10 | −1.120 | −19.077 | 34.341 | 1.00 | 75.84 | N |
| ATOM | 3812 | CA | GLU | I | 10 | −2.277 | −19.558 | 35.063 | 1.00 | 76.46 | C |
| ATOM | 3813 | C | GLU | I | 10 | −2.225 | −19.221 | 36.539 | 1.00 | 82.81 | C |
| ATOM | 3814 | O | GLU | I | 10 | −1.209 | −19.429 | 37.205 | 1.00 | 82.16 | O |
| ATOM | 3815 | CB | GLU | I | 10 | −2.450 | −21.072 | 34.865 | 1.00 | 78.04 | C |
| ATOM | 3816 | CG | GLU | I | 10 | −2.709 | −21.476 | 33.424 | 1.00 | 90.94 | C |
| ATOM | 3817 | CD | GLU | I | 10 | −4.126 | −21.368 | 32.896 | 1.00 | 116.83 | C |
| ATOM | 3818 | OE1 | GLU | I | 10 | −4.283 | −21.290 | 31.655 | 1.00 | 111.63 | O |
| ATOM | 3819 | OE2 | GLU | I | 10 | −5.078 | −21.393 | 33.712 | 1.00 | 115.99 | O |
| ATOM | 3820 | N | VAL | I | 11 | −3.338 | −18.690 | 37.047 | 1.00 | 81.59 | N |
| ATOM | 3821 | CA | VAL | I | 11 | −3.521 | −18.408 | 38.470 | 1.00 | 81.14 | C |
| ATOM | 3822 | C | VAL | I | 11 | −4.732 | −19.235 | 38.892 | 1.00 | 83.64 | C |
| ATOM | 3823 | O | VAL | I | 11 | −5.846 | −19.016 | 38.390 | 1.00 | 82.52 | O |
| ATOM | 3824 | CB | VAL | I | 11 | −3.662 | −16.914 | 38.858 | 1.00 | 84.07 | C |
| ATOM | 3825 | CG1 | VAL | I | 11 | −3.321 | −16.734 | 40.333 | 1.00 | 83.20 | C |
| ATOM | 3826 | CG2 | VAL | I | 11 | −2.801 | −16.005 | 37.973 | 1.00 | 83.77 | C |
| ATOM | 3827 | N | LYS | I | 12 | −4.484 | −20.237 | 39.745 | 1.00 | 79.43 | N |
| ATOM | 3828 | CA | LYS | I | 12 | −5.497 | −21.172 | 40.203 | 1.00 | 79.84 | C |
| ATOM | 3829 | C | LYS | I | 12 | −5.524 | −21.237 | 41.706 | 1.00 | 86.22 | C |
| ATOM | 3830 | O | LYS | I | 12 | −4.474 | −21.081 | 42.333 | 1.00 | 87.01 | O |
| ATOM | 3831 | CB | LYS | I | 12 | −5.198 | −22.597 | 39.661 | 1.00 | 82.18 | C |
| ATOM | 3832 | CG | LYS | I | 12 | −5.085 | −22.749 | 38.125 | 1.00 | 91.72 | C |
| ATOM | 3833 | CD | LYS | I | 12 | −6.256 | −22.187 | 37.303 | 1.00 | 97.26 | C |
| ATOM | 3834 | CE | LYS | I | 12 | −7.395 | −23.155 | 37.094 | 1.00 | 102.17 | C |
| ATOM | 3835 | NZ | LYS | I | 12 | −8.669 | −22.427 | 36.838 | 1.00 | 111.39 | N |
| ATOM | 3836 | N | LYS | I | 13 | −6.712 | −21.512 | 42.290 | 1.00 | 82.90 | N |
| ATOM | 3837 | CA | LYS | I | 13 | −6.845 | −21.715 | 43.735 | 1.00 | 82.79 | C |
| ATOM | 3838 | C | LYS | I | 13 | −6.412 | −23.169 | 44.011 | 1.00 | 85.28 | C |
| ATOM | 3839 | O | LYS | I | 13 | −6.502 | −23.995 | 43.109 | 1.00 | 84.54 | O |
| ATOM | 3840 | CB | LYS | I | 13 | −8.285 | −21.435 | 44.225 | 1.00 | 85.23 | C |
| ATOM | 3841 | N | SER | I | 14 | −5.895 | −23.467 | 45.211 | 1.00 | 81.97 | N |
| ATOM | 3842 | CA | SER | I | 14 | −5.435 | −24.814 | 45.579 | 1.00 | 82.20 | C |
| ATOM | 3843 | C | SER | I | 14 | −6.560 | −25.878 | 45.400 | 1.00 | 86.66 | C |
| ATOM | 3844 | O | SER | I | 14 | −7.744 | −25.513 | 45.383 | 1.00 | 87.74 | O |
| ATOM | 3845 | CB | SER | I | 14 | −4.881 | −24.814 | 47.008 | 1.00 | 85.78 | C |
| ATOM | 3846 | OG | SER | I | 14 | −4.119 | −23.651 | 47.316 | 1.00 | 93.93 | O |
| ATOM | 3847 | N | GLY | I | 15 | −6.173 | −27.145 | 45.187 | 1.00 | 81.09 | N |
| ATOM | 3848 | CA | GLY | I | 15 | −7.084 | −28.276 | 44.989 | 1.00 | 79.61 | C |
| ATOM | 3849 | C | GLY | I | 15 | −7.796 | −28.382 | 43.643 | 1.00 | 79.62 | C |
| ATOM | 3850 | O | GLY | I | 15 | −8.335 | −29.452 | 43.322 | 1.00 | 77.38 | O |
| ATOM | 3851 | N | GLU | I | 16 | −7.858 | −27.252 | 42.867 | 1.00 | 74.66 | N |
| ATOM | 3852 | CA | GLU | I | 16 | −8.456 | −27.159 | 41.525 | 1.00 | 74.04 | C |
| ATOM | 3853 | C | GLU | I | 16 | −7.691 | −28.067 | 40.525 | 1.00 | 81.04 | C |
| ATOM | 3854 | O | GLU | I | 16 | −6.645 | −28.630 | 40.867 | 1.00 | 81.55 | O |
| ATOM | 3855 | CB | GLU | I | 16 | −8.413 | −25.705 | 41.000 | 1.00 | 74.78 | C |
| ATOM | 3856 | CG | GLU | I | 16 | −9.461 | −24.761 | 41.568 | 1.00 | 81.12 | C |
| ATOM | 3857 | CD | GLU | I | 16 | −9.541 | −23.385 | 40.920 | 1.00 | 108.65 | C |
| ATOM | 3858 | OE1 | GLU | I | 16 | −9.329 | −23.281 | 39.691 | 1.00 | 113.72 | O |
| ATOM | 3859 | OE2 | GLU | I | 16 | −9.875 | −22.414 | 41.635 | 1.00 | 106.73 | O |
| ATOM | 3860 | N | SER | I | 17 | −8.199 | −28.193 | 39.281 | 1.00 | 77.41 | N |
| ATOM | 3861 | CA | SER | I | 17 | −7.521 | −28.991 | 38.265 | 1.00 | 76.16 | C |
| ATOM | 3862 | C | SER | I | 17 | −7.120 | −28.151 | 37.079 | 1.00 | 78.93 | C |
| ATOM | 3863 | O | SER | I | 17 | −7.802 | −27.169 | 36.761 | 1.00 | 80.06 | O |
| ATOM | 3864 | CB | SER | I | 17 | −8.342 | −30.208 | 37.884 | 1.00 | 79.27 | C |
| ATOM | 3865 | OG | SER | I | 17 | −8.252 | −31.116 | 38.972 | 1.00 | 86.97 | O |
| ATOM | 3866 | N | LEU | I | 18 | −5.972 | −28.489 | 36.457 | 1.00 | 72.35 | N |
| ATOM | 3867 | CA | LEU | I | 18 | −5.428 | −27.702 | 35.338 | 1.00 | 69.83 | C |
| ATOM | 3868 | C | LEU | I | 18 | −4.777 | −28.559 | 34.237 | 1.00 | 67.70 | C |
| ATOM | 3869 | O | LEU | I | 18 | −4.134 | −29.561 | 34.540 | 1.00 | 64.52 | O |
| ATOM | 3870 | CB | LEU | I | 18 | −4.416 | −26.680 | 35.920 | 1.00 | 69.44 | C |
| ATOM | 3871 | CG | LEU | I | 18 | −3.584 | −25.779 | 35.008 | 1.00 | 73.20 | C |
| ATOM | 3872 | CD2 | LEU | I | 18 | −2.568 | −25.059 | 35.815 | 1.00 | 76.20 | C |
| ATOM | 3873 | CD1 | LEU | I | 18 | −4.442 | −24.750 | 34.275 | 1.00 | 72.76 | C |
| ATOM | 3874 | N | LYS | I | 19 | −4.966 | −28.142 | 32.964 | 1.00 | 62.41 | N |
| ATOM | 3875 | CA | LYS | I | 19 | −4.369 | −28.749 | 31.776 | 1.00 | 62.11 | C |
| ATOM | 3876 | C | LYS | I | 19 | −3.697 | −27.616 | 31.026 | 1.00 | 66.97 | C |
| ATOM | 3877 | O | LYS | I | 19 | −4.342 | −26.609 | 30.694 | 1.00 | 66.47 | O |
| ATOM | 3878 | CB | LYS | I | 19 | −5.390 | −29.481 | 30.872 | 1.00 | 64.31 | C |
| ATOM | 3879 | N | ILE | I | 20 | −2.381 | −27.773 | 30.804 | 1.00 | 63.63 | N |
| ATOM | 3880 | CA | ILE | I | 20 | −1.539 | −26.799 | 30.149 | 1.00 | 63.55 | C |
| ATOM | 3881 | C | ILE | I | 20 | −1.067 | −27.353 | 28.808 | 1.00 | 65.55 | C |
| ATOM | 3882 | O | ILE | I | 20 | −0.819 | −28.551 | 28.678 | 1.00 | 64.15 | O |
| ATOM | 3883 | CB | ILE | I | 20 | −0.442 | −26.336 | 31.156 | 1.00 | 68.03 | C |

TABLE1-continued

Three-dimensional crystal coordinate for anti-TcdB antibody beziotoxumab Fab – C. difficile toxin B (TcdB$^{(1834-2101)}$) complex.

| ATOM | 3884 | CG1 | ILE | I | 20 | −0.426 | −24.851 | 31.233 | 1.00 | 69.53 | C |
|---|---|---|---|---|---|---|---|---|---|---|---|
| ATOM | 3885 | CG2 | ILE | I | 20 | 0.972 | −26.910 | 30.992 | 1.00 | 70.47 | C |
| ATOM | 3886 | CD1 | ILE | I | 20 | −1.289 | −24.363 | 32.284 | 1.00 | 86.23 | C |
| ATOM | 3887 | N | SER | I | 21 | −1.042 | −26.495 | 27.793 | 1.00 | 61.79 | N |
| ATOM | 3888 | CA | SER | I | 21 | −0.704 | −26.892 | 26.436 | 1.00 | 60.81 | C |
| ATOM | 3889 | C | SER | I | 21 | 0.663 | −26.366 | 25.981 | 1.00 | 68.04 | C |
| ATOM | 3890 | O | SER | I | 21 | 1.248 | −25.476 | 26.610 | 1.00 | 68.19 | O |
| ATOM | 3891 | CB | SER | I | 21 | −1.832 | −26.509 | 25.473 | 1.00 | 61.52 | C |
| ATOM | 3892 | OG | SER | I | 21 | −1.657 | −25.282 | 24.780 | 1.00 | 65.99 | O |
| ATOM | 3893 | N | CYS | I | 22 | 1.160 | −26.950 | 24.881 | 1.00 | 66.76 | N |
| ATOM | 3894 | CA | CYS | I | 22 | 2.448 | −26.693 | 24.249 | 1.00 | 66.80 | C |
| ATOM | 3895 | C | CYS | I | 22 | 2.267 | −27.046 | 22.773 | 1.00 | 69.52 | C |
| ATOM | 3896 | O | CYS | I | 22 | 2.194 | −28.225 | 22.438 | 1.00 | 70.87 | O |
| ATOM | 3897 | CB | CYS | I | 22 | 3.500 | −27.573 | 24.925 | 1.00 | 67.34 | C |
| ATOM | 3898 | SG | CYS | I | 22 | 5.059 | −27.755 | 24.020 | 1.00 | 71.25 | S |
| ATOM | 3899 | N | LYS | I | 23 | 2.137 | −26.035 | 21.909 | 1.00 | 63.65 | N |
| ATOM | 3900 | CA | LYS | I | 23 | 1.926 | −26.220 | 20.479 | 1.00 | 63.15 | C |
| ATOM | 3901 | C | LYS | I | 23 | 3.233 | −26.174 | 19.670 | 1.00 | 69.44 | C |
| ATOM | 3902 | O | LYS | I | 23 | 3.928 | −25.161 | 19.651 | 1.00 | 70.73 | O |
| ATOM | 3903 | CB | LYS | I | 23 | 0.901 | −25.199 | 19.938 | 1.00 | 64.21 | C |
| ATOM | 3904 | CG | LYS | I | 23 | 0.077 | −25.702 | 18.764 | 1.00 | 70.59 | C |
| ATOM | 3905 | CD | LYS | I | 23 | −0.371 | −24.564 | 17.894 | 1.00 | 70.74 | C |
| ATOM | 3906 | CE | LYS | I | 23 | −1.320 | −24.994 | 16.807 | 1.00 | 75.88 | C |
| ATOM | 3907 | NZ | LYS | I | 23 | −1.823 | −23.816 | 16.052 | 1.00 | 77.40 | N |
| ATOM | 3908 | N | GLY | I | 24 | 3.505 | −27.251 | 18.952 | 1.00 | 66.16 | N |
| ATOM | 3909 | CA | GLY | I | 24 | 4.680 | −27.368 | 18.098 | 1.00 | 66.34 | C |
| ATOM | 3910 | C | GLY | I | 24 | 4.390 | −27.033 | 16.647 | 1.00 | 72.26 | C |
| ATOM | 3911 | O | GLY | I | 24 | 3.400 | −27.505 | 16.079 | 1.00 | 72.25 | O |
| ATOM | 3912 | N | SER | I | 25 | 5.277 | −26.228 | 16.037 | 1.00 | 69.59 | N |
| ATOM | 3913 | CA | SER | I | 25 | 5.206 | −25.773 | 14.649 | 1.00 | 69.70 | C |
| ATOM | 3914 | C | SER | I | 25 | 6.621 | −25.687 | 14.053 | 1.00 | 76.45 | C |
| ATOM | 3915 | O | SER | I | 25 | 7.578 | −25.457 | 14.789 | 1.00 | 78.61 | O |
| ATOM | 3916 | CB | SER | I | 25 | 4.525 | −24.408 | 14.582 | 1.00 | 71.86 | C |
| ATOM | 3917 | OG | SER | I | 25 | 5.121 | −23.460 | 15.456 | 1.00 | 77.84 | O |
| ATOM | 3918 | N | GLY | I | 26 | 6.743 | −25.868 | 12.739 | 1.00 | 71.71 | N |
| ATOM | 3919 | CA | GLY | I | 26 | 8.012 | −25.783 | 12.019 | 1.00 | 70.14 | C |
| ATOM | 3920 | C | GLY | I | 26 | 8.717 | −27.103 | 11.808 | 1.00 | 71.91 | C |
| ATOM | 3921 | O | GLY | I | 26 | 9.726 | −27.162 | 11.095 | 1.00 | 71.26 | O |
| ATOM | 3922 | N | TYR | I | 27 | 8.183 | −28.173 | 12.424 | 1.00 | 67.15 | N |
| ATOM | 3923 | CA | TYR | I | 27 | 8.761 | −29.511 | 12.367 | 1.00 | 66.02 | C |
| ATOM | 3924 | C | TYR | I | 27 | 7.659 | −30.580 | 12.355 | 1.00 | 70.09 | C |
| ATOM | 3925 | O | TYR | I | 27 | 6.483 | −30.263 | 12.554 | 1.00 | 70.73 | O |
| ATOM | 3926 | CB | TYR | I | 27 | 9.745 | −29.693 | 13.560 | 1.00 | 66.29 | C |
| ATOM | 3927 | CG | TYR | I | 27 | 9.088 | −30.010 | 14.892 | 1.00 | 65.63 | C |
| ATOM | 3928 | CD1 | TYR | I | 27 | 8.610 | −28.998 | 15.719 | 1.00 | 64.96 | C |
| ATOM | 3929 | CD2 | TYR | I | 27 | 8.952 | −31.325 | 15.326 | 1.00 | 67.23 | C |
| ATOM | 3930 | CE1 | TYR | I | 27 | 8.001 | −29.293 | 16.939 | 1.00 | 64.99 | C |
| ATOM | 3931 | CE2 | TYR | I | 27 | 8.348 | −31.630 | 16.542 | 1.00 | 65.45 | C |
| ATOM | 3932 | CZ | TYR | I | 27 | 7.869 | −30.614 | 17.341 | 1.00 | 66.35 | C |
| ATOM | 3933 | OH | TYR | I | 27 | 7.249 | −30.949 | 18.512 | 1.00 | 61.90 | O |
| ATOM | 3934 | N | SER | I | 28 | 8.054 | −31.848 | 12.125 | 1.00 | 65.69 | N |
| ATOM | 3935 | CA | SER | I | 28 | 7.151 | −32.997 | 12.117 | 1.00 | 64.88 | C |
| ATOM | 3936 | C | SER | I | 28 | 6.896 | −33.464 | 13.571 | 1.00 | 67.07 | C |
| ATOM | 3937 | O | SER | I | 28 | 7.731 | −34.153 | 14.163 | 1.00 | 67.27 | O |
| ATOM | 3938 | CB | SER | I | 28 | 7.740 | −34.114 | 11.257 | 1.00 | 67.26 | C |
| ATOM | 3939 | OG | SER | I | 28 | 7.169 | −35.378 | 11.552 | 1.00 | 73.93 | O |
| ATOM | 3940 | N | PHE | I | 29 | 5.749 | −33.073 | 14.134 | 1.00 | 60.79 | N |
| ATOM | 3941 | CA | PHE | I | 29 | 5.377 | −33.349 | 15.519 | 1.00 | 59.73 | C |
| ATOM | 3942 | C | PHE | I | 29 | 5.447 | −34.816 | 15.943 | 1.00 | 64.28 | C |
| ATOM | 3943 | O | PHE | I | 29 | 5.705 | −35.084 | 17.116 | 1.00 | 64.67 | O |
| ATOM | 3944 | CB | PHE | I | 29 | 3.990 | −32.768 | 15.821 | 1.00 | 61.26 | C |
| ATOM | 3945 | CG | PHE | I | 29 | 3.525 | −32.852 | 17.266 | 1.00 | 62.75 | C |
| ATOM | 3946 | CD2 | PHE | I | 29 | 2.613 | −33.828 | 17.668 | 1.00 | 63.89 | C |
| ATOM | 3947 | CD1 | PHE | I | 29 | 3.952 | −31.920 | 18.209 | 1.00 | 64.88 | C |
| ATOM | 3948 | CE2 | PHE | I | 29 | 2.152 | −33.875 | 18.985 | 1.00 | 65.99 | C |
| ATOM | 3949 | CE1 | PHE | I | 29 | 3.508 | −31.986 | 19.532 | 1.00 | 64.91 | C |
| ATOM | 3950 | CZ | PHE | I | 29 | 2.621 | −32.971 | 19.910 | 1.00 | 64.13 | C |
| ATOM | 3951 | N | THR | I | 30 | 5.211 | −35.756 | 15.019 | 1.00 | 61.41 | N |
| ATOM | 3952 | CA | THR | I | 30 | 5.167 | −37.199 | 15.327 | 1.00 | 60.69 | C |
| ATOM | 3953 | C | THR | I | 30 | 6.518 | −37.852 | 15.354 | 1.00 | 64.98 | C |
| ATOM | 3954 | O | THR | I | 30 | 6.626 | −38.999 | 15.792 | 1.00 | 65.33 | O |
| ATOM | 3955 | CB | THR | I | 30 | 4.231 | −37.949 | 14.363 | 1.00 | 60.87 | C |
| ATOM | 3956 | OG1 | THR | I | 30 | 4.363 | −37.412 | 13.044 | 1.00 | 60.09 | O |
| ATOM | 3957 | CG2 | THR | I | 30 | 2.780 | −37.893 | 14.802 | 1.00 | 56.61 | C |
| ATOM | 3958 | N | SER | I | 31 | 7.542 | −37.141 | 14.858 | 1.00 | 61.01 | N |
| ATOM | 3959 | CA | SER | I | 31 | 8.915 | −37.628 | 14.748 | 1.00 | 60.89 | C |
| ATOM | 3960 | C | SER | I | 31 | 9.814 | −37.329 | 15.968 | 1.00 | 65.50 | C |

TABLE 1-continued

Three-dimensional crystal coordinate for anti-TcdB antibody beziotoxumab
Fab –*C. difficile* toxin B (TcdB$^{(1834-2101)}$) complex.

| ATOM | 3961 | O   | SER | I | 31 | 10.944 | −37.854 | 16.043 | 1.00 | 66.52  | O |
|------|------|-----|-----|---|----|--------|---------|--------|------|--------|---|
| ATOM | 3962 | CB  | SER | I | 31 | 9.555  | −37.060 | 13.493 | 1.00 | 64.19  | C |
| ATOM | 3963 | OG  | SER | I | 31 | 8.801  | −37.401 | 12.345 | 1.00 | 74.65  | O |
| ATOM | 3964 | N   | TYR | I | 32 | 9.316  | −36.502 | 16.920 | 1.00 | 58.86  | N |
| ATOM | 3965 | CA  | TYR | I | 32 | 10.090 | −36.116 | 18.091 | 1.00 | 57.29  | C |
| ATOM | 3966 | C   | TYR | I | 32 | 9.369  | −36.328 | 19.391 | 1.00 | 61.91  | C |
| ATOM | 3967 | O   | TYR | I | 32 | 8.208  | −35.940 | 19.497 | 1.00 | 62.97  | O |
| ATOM | 3968 | CB  | TYR | I | 32 | 10.501 | −34.643 | 18.000 | 1.00 | 56.76  | C |
| ATOM | 3969 | CG  | TYR | I | 32 | 11.403 | −34.317 | 16.840 | 1.00 | 57.85  | C |
| ATOM | 3970 | CD2 | TYR | I | 32 | 12.788 | −34.266 | 16.998 | 1.00 | 57.52  | C |
| ATOM | 3971 | CD1 | TYR | I | 32 | 10.877 | −34.015 | 15.586 | 1.00 | 60.39  | C |
| ATOM | 3972 | CE2 | TYR | I | 32 | 13.626 | −33.949 | 15.930 | 1.00 | 57.30  | C |
| ATOM | 3973 | CE1 | TYR | I | 32 | 11.704 | −33.673 | 14.517 | 1.00 | 61.02  | C |
| ATOM | 3974 | CZ  | TYR | I | 32 | 13.078 | −33.659 | 14.690 | 1.00 | 65.11  | C |
| ATOM | 3975 | OH  | TYR | I | 32 | 13.873 | −33.299 | 13.636 | 1.00 | 69.43  | O |
| ATOM | 3976 | N   | TRP | I | 33 | 10.086 | −36.846 | 20.413 | 1.00 | 57.69  | N |
| ATOM | 3977 | CA  | TRP | I | 33 | 9.588  | −36.962 | 21.783 | 1.00 | 57.15  | C |
| ATOM | 3978 | C   | TRP | I | 33 | 9.554  | −35.550 | 22.368 | 1.00 | 62.63  | C |
| ATOM | 3979 | O   | TRP | I | 33 | 10.367 | −34.703 | 21.987 | 1.00 | 61.83  | O |
| ATOM | 3980 | CB  | TRP | I | 33 | 10.513 | −37.817 | 22.645 | 1.00 | 55.19  | C |
| ATOM | 3981 | CG  | TRP | I | 33 | 10.500 | −39.265 | 22.287 | 1.00 | 55.50  | C |
| ATOM | 3982 | CD1 | TRP | I | 33 | 10.896 | −39.822 | 21.106 | 1.00 | 58.27  | C |
| ATOM | 3983 | CD2 | TRP | I | 33 | 10.176 | −40.351 | 23.156 | 1.00 | 55.17  | C |
| ATOM | 3984 | NE1 | TRP | I | 33 | 10.823 | −41.189 | 21.182 | 1.00 | 57.64  | N |
| ATOM | 3985 | CE2 | TRP | I | 33 | 10.373 | −41.543 | 22.429 | 1.00 | 59.21  | C |
| ATOM | 3986 | CE3 | TRP | I | 33 | 9.683  | −40.435 | 24.469 | 1.00 | 56.43  | C |
| ATOM | 3987 | CZ2 | TRP | I | 33 | 10.064 | −42.803 | 22.963 | 1.00 | 58.66  | C |
| ATOM | 3988 | CZ3 | TRP | I | 33 | 9.405  | −41.686 | 25.007 | 1.00 | 57.70  | C |
| ATOM | 3989 | CH2 | TRP | I | 33 | 9.596  | −42.850 | 24.259 | 1.00 | 58.37  | C |
| ATOM | 3990 | N   | ILE | I | 34 | 8.615  | −35.293 | 23.281 | 1.00 | 60.52  | N |
| ATOM | 3991 | CA  | ILE | I | 34 | 8.423  | −33.968 | 23.861 | 1.00 | 60.27  | C |
| ATOM | 3992 | C   | ILE | I | 34 | 8.280  | −34.103 | 25.379 | 1.00 | 64.45  | C |
| ATOM | 3993 | O   | ILE | I | 34 | 7.510  | −34.935 | 25.851 | 1.00 | 64.21  | O |
| ATOM | 3994 | CB  | ILE | I | 34 | 7.283  | −33.214 | 23.114 | 1.00 | 63.07  | C |
| ATOM | 3995 | CG1 | ILE | I | 34 | 6.979  | −31.864 | 23.725 | 1.00 | 64.36  | C |
| ATOM | 3996 | CG2 | ILE | I | 34 | 6.025  | −34.033 | 22.956 | 1.00 | 64.11  | C |
| ATOM | 3997 | CD1 | ILE | I | 34 | 6.790  | −30.832 | 22.682 | 1.00 | 76.51  | C |
| ATOM | 3998 | N   | GLY | I | 35 | 9.114  | −33.362 | 26.113 | 1.00 | 60.99  | N |
| ATOM | 3999 | CA  | GLY | I | 35 | 9.191  | −33.446 | 27.570 | 1.00 | 60.47  | C |
| ATOM | 4000 | C   | GLY | I | 35 | 8.761  | −32.221 | 28.343 | 1.00 | 61.90  | C |
| ATOM | 4001 | O   | GLY | I | 35 | 8.635  | −31.135 | 27.775 | 1.00 | 60.92  | O |
| ATOM | 4002 | N   | TRP | I | 36 | 8.515  | −32.407 | 29.650 | 1.00 | 57.98  | N |
| ATOM | 4003 | CA  | TRP | I | 36 | 8.080  | −31.354 | 30.577 | 1.00 | 58.04  | C |
| ATOM | 4004 | C   | TRP | I | 36 | 9.080  | −31.215 | 31.731 | 1.00 | 64.17  | C |
| ATOM | 4005 | O   | TRP | I | 36 | 9.437  | −32.203 | 32.392 | 1.00 | 63.35  | O |
| ATOM | 4006 | CB  | TRP | I | 36 | 6.636  | −31.574 | 31.076 | 1.00 | 56.24  | C |
| ATOM | 4007 | CG  | TRP | I | 36 | 5.591  | −31.424 | 30.002 | 1.00 | 57.43  | C |
| ATOM | 4008 | CD1 | TRP | I | 36 | 5.118  | −32.405 | 29.179 | 1.00 | 60.28  | C |
| ATOM | 4009 | CD2 | TRP | I | 36 | 4.902  | −30.211 | 29.619 | 1.00 | 57.34  | C |
| ATOM | 4010 | NE1 | TRP | I | 36 | 4.195  | −31.877 | 28.290 | 1.00 | 59.51  | N |
| ATOM | 4011 | CE2 | TRP | I | 36 | 4.057  | −30.533 | 28.529 | 1.00 | 60.44  | C |
| ATOM | 4012 | CE3 | TRP | I | 36 | 4.920  | −28.882 | 30.092 | 1.00 | 58.90  | C |
| ATOM | 4013 | CZ2 | TRP | I | 36 | 3.244  | −29.579 | 27.901 | 1.00 | 59.80  | C |
| ATOM | 4014 | CZ3 | TRP | I | 36 | 4.101  | −27.937 | 29.477 | 1.00 | 60.39  | C |
| ATOM | 4015 | CH2 | TRP | I | 36 | 3.264  | −28.290 | 28.405 | 1.00 | 60.79  | C |
| ATOM | 4016 | N   | VAL | I | 37 | 9.572  | −29.976 | 31.916 | 1.00 | 62.07  | N |
| ATOM | 4017 | CA  | VAL | I | 37 | 10.571 | −29.593 | 32.912 | 1.00 | 62.56  | C |
| ATOM | 4018 | C   | VAL | I | 37 | 9.962  | −28.517 | 33.810 | 1.00 | 67.37  | C |
| ATOM | 4019 | O   | VAL | I | 37 | 9.327  | −27.573 | 33.307 | 1.00 | 64.75  | O |
| ATOM | 4020 | CB  | VAL | I | 37 | 11.883 | −29.092 | 32.223 | 1.00 | 66.31  | C |
| ATOM | 4021 | CG1 | VAL | I | 37 | 12.956 | −28.723 | 33.234 | 1.00 | 65.80  | C |
| ATOM | 4022 | CG2 | VAL | I | 37 | 12.429 | −30.116 | 31.234 | 1.00 | 66.10  | C |
| ATOM | 4023 | N   | ARG | I | 38 | 10.157 | −28.676 | 35.138 | 1.00 | 66.86  | N |
| ATOM | 4024 | CA  | ARG | I | 38 | 9.701  | −27.747 | 36.169 | 1.00 | 68.05  | C |
| ATOM | 4025 | C   | ARG | I | 38 | 10.889 | −26.940 | 36.707 | 1.00 | 74.93  | C |
| ATOM | 4026 | O   | ARG | I | 38 | 11.946 | −27.507 | 36.999 | 1.00 | 74.31  | O |
| ATOM | 4027 | CB  | ARG | I | 38 | 9.006  | −28.504 | 37.331 | 1.00 | 67.75  | C |
| ATOM | 4028 | CG  | ARG | I | 38 | 8.500  | −27.591 | 38.452 | 1.00 | 71.79  | C |
| ATOM | 4029 | CD  | ARG | I | 38 | 7.694  | −28.311 | 39.504 | 1.00 | 87.98  | C |
| ATOM | 4030 | NE  | ARG | I | 38 | 8.525  | −29.075 | 40.437 | 1.00 | 100.56 | N |
| ATOM | 4031 | CZ  | ARG | I | 38 | 8.054  | −29.690 | 41.517 | 1.00 | 112.67 | C |
| ATOM | 4032 | NH1 | ARG | I | 38 | 6.762  | −29.636 | 41.809 | 1.00 | 101.01 | N |
| ATOM | 4033 | NH2 | ARG | I | 38 | 8.869  | −30.374 | 42.308 | 1.00 | 97.53  | N |
| ATOM | 4034 | N   | GLN | I | 39 | 10.703 | −25.624 | 36.855 | 1.00 | 73.42  | N |
| ATOM | 4035 | CA  | GLN | I | 39 | 11.682 | −24.716 | 37.435 | 1.00 | 74.06  | C |
| ATOM | 4036 | C   | GLN | I | 39 | 11.002 | −23.972 | 38.608 | 1.00 | 83.18  | C |
| ATOM | 4037 | O   | GLN | I | 39 | 10.327 | −22.944 | 38.388 | 1.00 | 83.31  | O |

TABLE 1-continued

Three-dimensional crystal coordinate for anti-TcdB antibody beziotoxumab Fab –*C. difficile* toxin B (TcdB$^{(1834-2101)}$) complex.

| | | | | | | | | | | |
|---|---|---|---|---|---|---|---|---|---|---|
| ATOM | 4038 | CB | GLN | I | 39 | 12.246 | −23.750 | 36.367 | 1.00 | 74.63 C |
| ATOM | 4039 | CG | GLN | I | 39 | 13.290 | −22.773 | 36.912 | 1.00 | 81.64 C |
| ATOM | 4040 | CD | GLN | I | 39 | 13.967 | −21.958 | 35.847 | 1.00 | 95.43 C |
| ATOM | 4041 | OE1 | GLN | I | 39 | 13.371 | −21.058 | 35.237 | 1.00 | 91.60 O |
| ATOM | 4042 | NE2 | GLN | I | 39 | 15.249 | −22.221 | 35.649 | 1.00 | 82.03 N |
| ATOM | 4043 | N | MET | I | 40 | 11.159 | −24.510 | 39.852 | 1.00 | 82.05 N |
| ATOM | 4044 | CA | MET | I | 40 | 10.600 | −23.892 | 41.073 | 1.00 | 83.44 C |
| ATOM | 4045 | C | MET | I | 40 | 11.135 | −22.454 | 41.172 | 1.00 | 89.91 C |
| ATOM | 4046 | O | MET | I | 40 | 12.262 | −22.245 | 40.727 | 1.00 | 90.05 O |
| ATOM | 4047 | CB | MET | I | 40 | 11.000 | −24.685 | 42.324 | 1.00 | 86.17 C |
| ATOM | 4048 | CG | MET | I | 40 | 10.386 | −26.071 | 42.395 | 1.00 | 90.46 C |
| ATOM | 4049 | SD | MET | I | 40 | 9.331 | −26.351 | 43.842 | 1.00 | 95.11 S |
| ATOM | 4050 | CE | MET | I | 40 | 7.983 | −25.267 | 43.468 | 1.00 | 91.89 C |
| ATOM | 4051 | N | PRO | I | 41 | 10.384 | −21.431 | 41.659 | 1.00 | 88.42 N |
| ATOM | 4052 | CA | PRO | I | 41 | 10.936 | −20.055 | 41.652 | 1.00 | 88.60 C |
| ATOM | 4053 | C | PRO | I | 41 | 12.289 | −19.910 | 42.350 | 1.00 | 89.80 C |
| ATOM | 4054 | O | PRO | I | 41 | 12.505 | −20.447 | 43.450 | 1.00 | 87.55 O |
| ATOM | 4055 | CB | PRO | I | 41 | 9.831 | −19.203 | 42.292 | 1.00 | 90.37 C |
| ATOM | 4056 | CG | PRO | I | 41 | 8.598 | −19.985 | 42.082 | 1.00 | 94.63 C |
| ATOM | 4057 | CD | PRO | I | 41 | 9.015 | −21.437 | 42.206 | 1.00 | 90.21 C |
| ATOM | 4058 | N | GLY | I | 42 | 13.212 | −19.290 | 41.614 | 1.00 | 85.86 N |
| ATOM | 4059 | CA | GLY | I | 42 | 14.593 | −19.060 | 42.029 | 1.00 | 85.71 C |
| ATOM | 4060 | C | GLY | I | 42 | 15.470 | −20.295 | 42.163 | 1.00 | 88.60 C |
| ATOM | 4061 | O | GLY | I | 42 | 16.568 | −20.208 | 42.715 | 1.00 | 88.65 O |
| ATOM | 4062 | N | LYS | I | 43 | 14.988 | −21.456 | 41.693 | 1.00 | 83.66 N |
| ATOM | 4063 | CA | LYS | I | 43 | 15.708 | −22.733 | 41.730 | 1.00 | 81.93 C |
| ATOM | 4064 | C | LYS | I | 43 | 16.029 | −23.146 | 40.266 | 1.00 | 83.54 C |
| ATOM | 4065 | O | LYS | I | 43 | 15.772 | −22.366 | 39.329 | 1.00 | 83.06 O |
| ATOM | 4066 | CB | LYS | I | 43 | 14.909 | −23.799 | 42.518 | 1.00 | 83.00 C |
| ATOM | 4067 | N | GLY | I | 44 | 16.620 | −24.326 | 40.096 | 1.00 | 77.42 N |
| ATOM | 4068 | CA | GLY | I | 44 | 17.028 | −24.838 | 38.793 | 1.00 | 75.70 C |
| ATOM | 4069 | C | GLY | I | 44 | 15.974 | −25.633 | 38.052 | 1.00 | 75.88 C |
| ATOM | 4070 | O | GLY | I | 44 | 14.783 | −25.391 | 38.224 | 1.00 | 76.37 O |
| ATOM | 4071 | N | LEU | I | 45 | 16.410 | −26.622 | 37.244 | 1.00 | 68.72 N |
| ATOM | 4072 | CA | LEU | I | 45 | 15.530 | −27.436 | 36.393 | 1.00 | 65.41 C |
| ATOM | 4073 | C | LEU | I | 45 | 15.316 | −28.859 | 36.907 | 1.00 | 71.62 C |
| ATOM | 4074 | O | LEU | I | 45 | 16.273 | −29.523 | 37.316 | 1.00 | 71.65 O |
| ATOM | 4075 | CB | LEU | I | 45 | 16.043 | −27.435 | 34.940 | 1.00 | 63.32 C |
| ATOM | 4076 | CG | LEU | I | 45 | 16.360 | −26.055 | 34.318 | 1.00 | 65.48 C |
| ATOM | 4077 | CD1 | LEU | I | 45 | 17.107 | −26.170 | 33.009 | 1.00 | 64.91 C |
| ATOM | 4078 | CD2 | LEU | I | 45 | 15.141 | −25.202 | 34.150 | 1.00 | 65.18 C |
| ATOM | 4079 | N | GLU | I | 46 | 14.043 | −29.309 | 36.917 | 1.00 | 69.73 N |
| ATOM | 4080 | CA | GLU | I | 46 | 13.634 | −30.671 | 37.326 | 1.00 | 69.90 C |
| ATOM | 4081 | C | GLU | I | 46 | 12.877 | −31.347 | 36.191 | 1.00 | 71.66 C |
| ATOM | 4082 | O | GLU | I | 46 | 11.846 | −30.824 | 35.746 | 1.00 | 69.77 O |
| ATOM | 4083 | CB | GLU | I | 46 | 12.688 | −30.654 | 38.528 | 1.00 | 71.45 C |
| ATOM | 4084 | CG | GLU | I | 46 | 13.263 | −30.217 | 39.854 | 1.00 | 82.95 C |
| ATOM | 4085 | CD | GLU | I | 46 | 12.143 | −29.855 | 40.810 | 1.00 | 108.09 C |
| ATOM | 4086 | OE1 | GLU | I | 46 | 11.545 | −28.765 | 40.631 | 1.00 | 91.03 O |
| ATOM | 4087 | OE2 | GLU | I | 46 | 11.807 | −30.700 | 41.677 | 1.00 | 104.43 O |
| ATOM | 4088 | N | TRP | I | 47 | 13.349 | −32.522 | 35.755 | 1.00 | 67.36 N |
| ATOM | 4089 | CA | TRP | I | 47 | 12.620 | −33.231 | 34.705 | 1.00 | 66.61 C |
| ATOM | 4090 | C | TRP | I | 47 | 11.404 | −33.988 | 35.303 | 1.00 | 70.00 C |
| ATOM | 4091 | O | TRP | I | 47 | 11.537 | −34.680 | 36.325 | 1.00 | 67.96 O |
| ATOM | 4092 | CB | TRP | I | 47 | 13.546 | −34.135 | 33.888 | 1.00 | 64.48 C |
| ATOM | 4093 | CG | TRP | I | 47 | 12.815 | −35.022 | 32.933 | 1.00 | 64.76 C |
| ATOM | 4094 | CD1 | TRP | I | 47 | 12.229 | −34.663 | 31.751 | 1.00 | 67.48 C |
| ATOM | 4095 | CD2 | TRP | I | 47 | 12.584 | −36.427 | 33.091 | 1.00 | 64.21 C |
| ATOM | 4096 | NE1 | TRP | I | 47 | 11.644 | −35.764 | 31.163 | 1.00 | 66.79 N |
| ATOM | 4097 | CE2 | TRP | I | 47 | 11.837 | −36.858 | 31.972 | 1.00 | 68.07 C |
| ATOM | 4098 | CE3 | TRP | I | 47 | 12.916 | −37.362 | 34.087 | 1.00 | 64.98 C |
| ATOM | 4099 | CZ2 | TRP | I | 47 | 11.417 | −38.181 | 31.827 | 1.00 | 67.32 C |
| ATOM | 4100 | CZ3 | TRP | I | 47 | 12.500 | −38.674 | 33.939 | 1.00 | 66.41 C |
| ATOM | 4101 | CH2 | TRP | I | 47 | 11.784 | −39.080 | 32.813 | 1.00 | 67.15 C |
| ATOM | 4102 | N | MET | I | 48 | 10.221 | −33.807 | 34.663 | 1.00 | 66.56 N |
| ATOM | 4103 | CA | MET | I | 48 | 8.934 | −34.386 | 35.070 | 1.00 | 65.76 C |
| ATOM | 4104 | C | MET | I | 48 | 8.604 | −35.648 | 34.291 | 1.00 | 67.95 C |
| ATOM | 4105 | O | MET | I | 48 | 8.364 | −36.680 | 34.904 | 1.00 | 65.85 O |
| ATOM | 4106 | CB | MET | I | 48 | 7.806 | −33.361 | 34.903 | 1.00 | 68.05 C |
| ATOM | 4107 | CG | MET | I | 48 | 7.995 | −32.120 | 35.739 | 1.00 | 71.63 C |
| ATOM | 4108 | SD | MET | I | 48 | 6.733 | −30.878 | 35.446 | 1.00 | 75.98 S |
| ATOM | 4109 | CE | MET | I | 48 | 5.403 | −31.584 | 36.272 | 1.00 | 72.85 C |
| ATOM | 4110 | N | GLY | I | 49 | 8.593 | −35.541 | 32.955 | 1.00 | 65.12 N |
| ATOM | 4111 | CA | GLY | I | 49 | 8.310 | −36.636 | 32.028 | 1.00 | 64.44 C |
| ATOM | 4112 | C | GLY | I | 49 | 8.508 | −36.285 | 30.563 | 1.00 | 66.69 C |
| ATOM | 4113 | O | GLY | I | 49 | 8.785 | −35.129 | 30.237 | 1.00 | 64.21 O |
| ATOM | 4114 | N | ILE | I | 50 | 8.412 | −37.304 | 29.672 | 1.00 | 64.86 N |

TABLE1-continued

Three-dimensional crystal coordinate for anti-TcdB antibody beziotoxumab Fab –*C. difficile* toxin B (TcdB$^{(1834-2101)}$) complex.

| ATOM | 4115 | CA | ILE | I | 50 | 8.520 | −37.213 | 28.193 | 1.00 | 64.38 | C |
|---|---|---|---|---|---|---|---|---|---|---|---|
| ATOM | 4116 | C | ILE | I | 50 | 7.363 | −37.980 | 27.644 | 1.00 | 67.11 | C |
| ATOM | 4117 | O | ILE | I | 50 | 6.898 | −38.938 | 28.260 | 1.00 | 65.22 | O |
| ATOM | 4118 | CB | ILE | I | 50 | 9.803 | −37.841 | 27.526 | 1.00 | 67.39 | C |
| ATOM | 4119 | CG1 | ILE | I | 50 | 10.525 | −38.798 | 28.470 | 1.00 | 69.16 | C |
| ATOM | 4120 | CG2 | ILE | I | 50 | 10.759 | −36.834 | 26.901 | 1.00 | 65.25 | C |
| ATOM | 4121 | CD1 | ILE | I | 50 | 10.063 | −40.199 | 28.364 | 1.00 | 83.75 | C |
| ATOM | 4122 | N | PHE | I | 51 | 6.991 | −37.640 | 26.420 | 1.00 | 64.44 | N |
| ATOM | 4123 | CA | PHE | I | 51 | 5.925 | −38.274 | 25.683 | 1.00 | 63.50 | C |
| ATOM | 4124 | C | PHE | I | 51 | 6.355 | −38.474 | 24.231 | 1.00 | 63.70 | C |
| ATOM | 4125 | O | PHE | I | 51 | 6.980 | −37.576 | 23.663 | 1.00 | 62.37 | O |
| ATOM | 4126 | CB | PHE | I | 51 | 4.695 | −37.348 | 25.732 | 1.00 | 65.37 | C |
| ATOM | 4127 | CG | PHE | I | 51 | 3.470 | −37.981 | 25.126 | 1.00 | 67.10 | C |
| ATOM | 4128 | CD2 | PHE | I | 51 | 3.068 | −37.659 | 23.836 | 1.00 | 69.71 | C |
| ATOM | 4129 | CD1 | PHE | I | 51 | 2.749 | −38.941 | 25.824 | 1.00 | 68.50 | C |
| ATOM | 4130 | CE2 | PHE | I | 51 | 1.966 | −38.274 | 23.266 | 1.00 | 70.24 | C |
| ATOM | 4131 | CE1 | PHE | I | 51 | 1.638 | −39.543 | 25.256 | 1.00 | 71.23 | C |
| ATOM | 4132 | CZ | PHE | I | 51 | 1.248 | −39.197 | 23.984 | 1.00 | 69.49 | C |
| ATOM | 4133 | N | TYR | I | 52 | 5.971 | −39.603 | 23.611 | 1.00 | 58.21 | N |
| ATOM | 4134 | CA | TYR | I | 52 | 6.235 | −39.783 | 22.195 | 1.00 | 58.01 | C |
| ATOM | 4135 | C | TYR | I | 52 | 4.950 | −39.632 | 21.401 | 1.00 | 66.37 | C |
| ATOM | 4136 | O | TYR | I | 52 | 4.136 | −40.548 | 21.395 | 1.00 | 66.71 | O |
| ATOM | 4137 | CB | TYR | I | 52 | 6.951 | −41.098 | 21.842 | 1.00 | 58.63 | C |
| ATOM | 4138 | CG | TYR | I | 52 | 7.366 | −41.193 | 20.377 | 1.00 | 59.77 | C |
| ATOM | 4139 | CD1 | TYR | I | 52 | 7.748 | −40.060 | 19.662 | 1.00 | 62.49 | C |
| ATOM | 4140 | CD2 | TYR | I | 52 | 7.463 | −42.423 | 19.738 | 1.00 | 59.51 | C |
| ATOM | 4141 | CE1 | TYR | I | 52 | 8.151 | −40.144 | 18.332 | 1.00 | 64.97 | C |
| ATOM | 4142 | CE2 | TYR | I | 52 | 7.826 | −42.517 | 18.398 | 1.00 | 60.69 | C |
| ATOM | 4143 | CZ | TYR | I | 52 | 8.184 | −41.375 | 17.699 | 1.00 | 71.54 | C |
| ATOM | 4144 | OH | TYR | I | 52 | 8.568 | −41.453 | 16.379 | 1.00 | 71.88 | O |
| ATOM | 4145 | N | PRO | I | 53 | 4.764 | −38.501 | 20.685 | 1.00 | 65.38 | N |
| ATOM | 4146 | CA | PRO | I | 53 | 3.547 | −38.323 | 19.869 | 1.00 | 65.71 | C |
| ATOM | 4147 | C | PRO | I | 53 | 3.180 | −39.459 | 18.887 | 1.00 | 71.34 | C |
| ATOM | 4148 | O | PRO | I | 53 | 2.002 | −39.755 | 18.747 | 1.00 | 72.34 | O |
| ATOM | 4149 | CB | PRO | I | 53 | 3.843 | −37.019 | 19.118 | 1.00 | 67.04 | C |
| ATOM | 4150 | CG | PRO | I | 53 | 4.716 | −36.270 | 20.047 | 1.00 | 70.50 | C |
| ATOM | 4151 | CD | PRO | I | 53 | 5.620 | −37.298 | 20.614 | 1.00 | 66.14 | C |
| ATOM | 4152 | O | GLY | I | 54 | 3.940 | −43.426 | 16.809 | 1.00 | 74.29 | O |
| ATOM | 4153 | N | GLY | I | 54 | 4.161 | −40.071 | 18.226 | 1.00 | 68.35 | N |
| ATOM | 4154 | CA | GLY | I | 54 | 3.907 | −41.088 | 17.212 | 1.00 | 68.65 | C |
| ATOM | 4155 | C | GLY | I | 54 | 3.895 | −42.534 | 17.661 | 1.00 | 73.95 | C |
| ATOM | 4156 | N | ASP | I | 55 | 3.794 | −42.775 | 18.986 | 1.00 | 69.60 | N |
| ATOM | 4157 | CA | ASP | I | 55 | 3.792 | −44.083 | 19.659 | 1.00 | 69.20 | C |
| ATOM | 4158 | C | ASP | I | 55 | 2.867 | −44.029 | 20.885 | 1.00 | 75.40 | C |
| ATOM | 4159 | O | ASP | I | 55 | 2.448 | −45.070 | 21.412 | 1.00 | 75.17 | O |
| ATOM | 4160 | CB | ASP | I | 55 | 5.213 | −44.324 | 20.180 | 1.00 | 71.13 | C |
| ATOM | 4161 | CG | ASP | I | 55 | 5.700 | −45.734 | 20.429 | 1.00 | 88.45 | C |
| ATOM | 4162 | OD1 | ASP | I | 55 | 4.920 | −46.678 | 20.218 | 1.00 | 93.48 | O |
| ATOM | 4163 | OD2 | ASP | I | 55 | 6.888 | −45.896 | 20.805 | 1.00 | 94.33 | O |
| ATOM | 4164 | N | SER | I | 56 | 2.623 | −42.801 | 21.387 | 1.00 | 72.73 | N |
| ATOM | 4165 | CA | SER | I | 56 | 1.876 | −42.466 | 22.594 | 1.00 | 72.43 | C |
| ATOM | 4166 | C | SER | I | 56 | 2.561 | −43.002 | 23.863 | 1.00 | 75.15 | C |
| ATOM | 4167 | O | SER | I | 56 | 1.942 | −42.996 | 24.925 | 1.00 | 75.21 | O |
| ATOM | 4168 | CB | SER | I | 56 | 0.404 | −42.866 | 22.490 | 1.00 | 77.56 | C |
| ATOM | 4169 | OG | SER | I | 56 | −0.340 | −41.817 | 21.886 | 1.00 | 89.97 | O |
| ATOM | 4170 | N | SER | I | 57 | 3.860 | −43.398 | 23.778 | 1.00 | 71.33 | N |
| ATOM | 4171 | CA | SER | I | 57 | 4.591 | −43.900 | 24.957 | 1.00 | 71.28 | C |
| ATOM | 4172 | C | SER | I | 57 | 5.001 | −42.765 | 25.835 | 1.00 | 75.85 | C |
| ATOM | 4173 | O | SER | I | 57 | 5.425 | −41.715 | 25.349 | 1.00 | 75.79 | O |
| ATOM | 4174 | CB | SER | I | 57 | 5.780 | −44.804 | 24.612 | 1.00 | 74.12 | C |
| ATOM | 4175 | OG | SER | I | 57 | 6.242 | −44.661 | 23.281 | 1.00 | 80.60 | O |
| ATOM | 4176 | N | THR | I | 58 | 4.794 | −42.943 | 27.127 | 1.00 | 73.23 | N |
| ATOM | 4177 | CA | THR | I | 58 | 5.115 | −41.931 | 28.115 | 1.00 | 73.74 | C |
| ATOM | 4178 | C | THR | I | 58 | 5.986 | −42.571 | 29.178 | 1.00 | 79.05 | C |
| ATOM | 4179 | O | THR | I | 58 | 5.844 | −43.767 | 29.415 | 1.00 | 79.82 | O |
| ATOM | 4180 | CB | THR | I | 58 | 3.820 | −41.188 | 28.645 | 1.00 | 81.60 | C |
| ATOM | 4181 | OG1 | THR | I | 58 | 3.703 | −41.330 | 30.054 | 1.00 | 80.87 | O |
| ATOM | 4182 | CG2 | THR | I | 58 | 2.514 | −41.666 | 28.004 | 1.00 | 78.87 | C |
| ATOM | 4183 | N | ARG | I | 59 | 6.899 | −41.788 | 29.793 | 1.00 | 75.67 | N |
| ATOM | 4184 | CA | ARG | I | 59 | 7.758 | −42.183 | 30.921 | 1.00 | 75.09 | C |
| ATOM | 4185 | C | ARG | I | 59 | 7.927 | −40.978 | 31.834 | 1.00 | 77.95 | C |
| ATOM | 4186 | O | ARG | I | 59 | 8.230 | −39.889 | 31.347 | 1.00 | 76.23 | O |
| ATOM | 4187 | CB | ARG | I | 59 | 9.091 | −42.807 | 30.482 | 1.00 | 75.50 | C |
| ATOM | 4188 | CG | ARG | I | 59 | 8.906 | −44.279 | 30.145 | 1.00 | 90.00 | C |
| ATOM | 4189 | CD | ARG | I | 59 | 9.430 | −44.684 | 28.783 | 1.00 | 99.22 | C |
| ATOM | 4190 | NE | ARG | I | 59 | 8.887 | −45.985 | 28.360 | 1.00 | 100.63 | N |
| ATOM | 4191 | CZ | ARG | I | 59 | 8.870 | −46.443 | 27.113 | 1.00 | 118.22 | C |

TABLE 1-continued

Three-dimensional crystal coordinate for anti-TcdB antibody beziotoxumab Fab –C. difficile toxin B (TcdB$^{(1834-2101)}$) complex.

| | | | | | | | | | | |
|---|---|---|---|---|---|---|---|---|---|---|
| ATOM | 4192 | NH | ARG | I | 59 | 8.317 | −47.617 | 26.839 | 1.00 | 104.68 | N |
| ATOM | 4193 | NH2 | ARG | I | 59 | 9.531 | −45.805 | 26.153 | 1.00 | 113.99 | N |
| ATOM | 4194 | N | TYR | I | 60 | 7.595 | −41.149 | 33.138 | 1.00 | 75.39 | N |
| ATOM | 4195 | CA | TYR | I | 60 | 7.634 | −40.086 | 34.166 | 1.00 | 74.89 | C |
| ATOM | 4196 | C | TYR | I | 60 | 8.795 | −40.270 | 35.157 | 1.00 | 82.20 | C |
| ATOM | 4197 | O | TYR | I | 60 | 9.238 | −41.409 | 35.400 | 1.00 | 82.64 | O |
| ATOM | 4198 | CB | TYR | I | 60 | 6.320 | −40.053 | 34.993 | 1.00 | 73.75 | C |
| ATOM | 4199 | CG | TYR | I | 60 | 5.048 | −39.877 | 34.196 | 1.00 | 72.22 | C |
| ATOM | 4200 | CD1 | TYR | I | 60 | 4.626 | −38.616 | 33.791 | 1.00 | 73.60 | C |
| ATOM | 4201 | CD2 | TYR | I | 60 | 4.225 | −40.958 | 33.916 | 1.00 | 72.14 | C |
| ATOM | 4202 | CE1 | TYR | I | 60 | 3.440 | −38.442 | 33.083 | 1.00 | 73.63 | C |
| ATOM | 4203 | CE2 | TYR | I | 60 | 3.025 | −40.794 | 33.226 | 1.00 | 72.67 | C |
| ATOM | 4204 | CZ | TYR | I | 60 | 2.642 | −39.535 | 32.800 | 1.00 | 78.09 | C |
| ATOM | 4205 | OH | TYR | I | 60 | 1.502 | −39.376 | 32.055 | 1.00 | 76.21 | O |
| ATOM | 4206 | N | SER | I | 61 | 9.234 | −39.143 | 35.776 | 1.00 | 79.09 | N |
| ATOM | 4207 | CA | SER | I | 61 | 10.258 | −39.125 | 36.813 | 1.00 | 79.20 | C |
| ATOM | 4208 | C | SER | I | 61 | 9.595 | −39.776 | 38.008 | 1.00 | 84.62 | C |
| ATOM | 4209 | O | SER | I | 61 | 8.444 | −39.430 | 38.279 | 1.00 | 84.52 | O |
| ATOM | 4210 | CB | SER | I | 61 | 10.619 | −37.691 | 37.176 | 1.00 | 83.03 | C |
| ATOM | 4211 | OG | SER | I | 61 | 11.631 | −37.628 | 38.168 | 1.00 | 91.50 | O |
| ATOM | 4212 | N | PRO | I | 62 | 10.238 | −40.734 | 38.723 | 1.00 | 81.17 | N |
| ATOM | 4213 | CA | PRO | I | 62 | 9.557 | −41.356 | 39.881 | 1.00 | 80.59 | C |
| ATOM | 4214 | C | PRO | I | 62 | 8.957 | −40.341 | 40.864 | 1.00 | 85.77 | C |
| ATOM | 4215 | O | PRO | I | 62 | 7.941 | −40.629 | 41.501 | 1.00 | 86.46 | O |
| ATOM | 4216 | CB | PRO | I | 62 | 10.632 | −42.244 | 40.515 | 1.00 | 82.02 | C |
| ATOM | 4217 | CG | PRO | I | 62 | 11.914 | −41.877 | 39.849 | 1.00 | 86.48 | C |
| ATOM | 4218 | CD | PRO | I | 62 | 11.591 | −41.288 | 38.522 | 1.00 | 82.17 | C |
| ATOM | 4219 | N | SER | I | 63 | 9.525 | −39.129 | 40.913 | 1.00 | 82.61 | N |
| ATOM | 4220 | CA | SER | I | 63 | 9.057 | −38.024 | 41.757 | 1.00 | 83.30 | C |
| ATOM | 4221 | C | SER | I | 63 | 7.771 | −37.317 | 41.236 | 1.00 | 87.98 | C |
| ATOM | 4222 | O | SER | I | 63 | 7.136 | −36.574 | 41.989 | 1.00 | 87.96 | O |
| ATOM | 4223 | CB | SER | I | 63 | 10.182 | −37.015 | 41.971 | 1.00 | 88.09 | C |
| ATOM | 4224 | OG | SER | I | 63 | 10.792 | −36.675 | 40.734 | 1.00 | 100.11 | O |
| ATOM | 4225 | N | PHE | I | 64 | 7.393 | −37.542 | 39.962 | 1.00 | 84.31 | N |
| ATOM | 4226 | CA | PHE | I | 64 | 6.191 | −36.958 | 39.339 | 1.00 | 83.68 | C |
| ATOM | 4227 | C | PHE | I | 64 | 5.159 | −38.024 | 38.921 | 1.00 | 90.07 | C |
| ATOM | 4228 | O | PHE | I | 64 | 4.036 | −37.684 | 38.538 | 1.00 | 89.38 | O |
| ATOM | 4229 | CB | PHE | I | 64 | 6.567 | −36.043 | 38.171 | 1.00 | 84.83 | C |
| ATOM | 4230 | CG | PHE | I | 64 | 7.272 | −34.783 | 38.607 | 1.00 | 86.15 | C |
| ATOM | 4231 | CD2 | PHE | I | 64 | 6.554 | −33.629 | 38.898 | 1.00 | 87.83 | C |
| ATOM | 4232 | CD1 | PHE | I | 64 | 8.656 | −34.753 | 38.750 | 1.00 | 88.94 | C |
| ATOM | 4233 | CE2 | PHE | I | 64 | 7.209 | −32.466 | 39.319 | 1.00 | 90.51 | C |
| ATOM | 4234 | CE1 | PHE | I | 64 | 9.309 | −33.590 | 39.171 | 1.00 | 89.74 | C |
| ATOM | 4235 | CZ | PHE | I | 64 | 8.582 | −32.454 | 39.450 | 1.00 | 88.45 | C |
| ATOM | 4236 | N | GLN | I | 65 | 5.542 | −39.315 | 39.040 | 1.00 | 88.24 | N |
| ATOM | 4237 | CA | GLN | I | 65 | 4.721 | −40.486 | 38.750 | 1.00 | 88.48 | C |
| ATOM | 4238 | C | GLN | I | 65 | 3.462 | −40.450 | 39.614 | 1.00 | 93.18 | C |
| ATOM | 4239 | O | GLN | I | 65 | 3.552 | −40.454 | 40.845 | 1.00 | 92.74 | O |
| ATOM | 4240 | CB | GLN | I | 65 | 5.539 | −41.764 | 39.018 | 1.00 | 89.93 | C |
| ATOM | 4241 | CG | GLN | I | 65 | 4.926 | −43.055 | 38.476 | 1.00 | 100.99 | C |
| ATOM | 4242 | CD | GLN | I | 65 | 4.786 | −43.075 | 36.972 | 1.00 | 113.06 | C |
| ATOM | 4243 | OE1 | GLN | I | 65 | 3.690 | −42.909 | 36.432 | 1.00 | 105.20 | O |
| ATOM | 4244 | NE2 | GLN | I | 65 | 5.892 | −43.280 | 36.267 | 1.00 | 106.70 | N |
| ATOM | 4245 | N | GLY | I | 66 | 2.314 | −40.341 | 38.954 | 1.00 | 90.49 | N |
| ATOM | 4246 | CA | GLY | I | 66 | 1.017 | −40.281 | 39.620 | 1.00 | 90.22 | C |
| ATOM | 4247 | C | GLY | I | 66 | 0.477 | −38.881 | 39.834 | 1.00 | 92.06 | C |
| ATOM | 4248 | O | GLY | I | 66 | −0.707 | −38.634 | 39.583 | 1.00 | 92.64 | O |
| ATOM | 4249 | N | GLN | I | 67 | 1.344 | −37.951 | 40.290 | 1.00 | 85.34 | N |
| ATOM | 4250 | CA | GLN | I | 67 | 1.006 | −36.550 | 40.590 | 1.00 | 83.34 | C |
| ATOM | 4251 | C | GLN | I | 67 | 0.558 | −35.719 | 39.375 | 1.00 | 81.57 | C |
| ATOM | 4252 | O | GLN | I | 67 | −0.133 | −34.720 | 39.546 | 1.00 | 80.11 | O |
| ATOM | 4253 | CB | GLN | I | 67 | 2.182 | −35.851 | 41.314 | 1.00 | 84.85 | C |
| ATOM | 4254 | CG | GLN | I | 67 | 2.280 | −36.163 | 42.810 | 1.00 | 101.47 | C |
| ATOM | 4255 | CD | GLN | I | 67 | 3.123 | −37.382 | 43.103 | 1.00 | 119.87 | C |
| ATOM | 4256 | OE1 | GLN | I | 67 | 4.325 | −37.291 | 43.374 | 1.00 | 116.31 | O |
| ATOM | 4257 | NE2 | GLN | I | 67 | 2.510 | −38.548 | 43.083 | 1.00 | 108.56 | N |
| ATOM | 4258 | N | VAL | I | 68 | 0.957 | −36.127 | 38.162 | 1.00 | 75.55 | N |
| ATOM | 4259 | CA | VAL | I | 68 | 0.676 | −35.423 | 36.904 | 1.00 | 73.75 | C |
| ATOM | 4260 | C | VAL | I | 68 | 0.494 | −36.451 | 35.750 | 1.00 | 75.01 | C |
| ATOM | 4261 | O | VAL | I | 68 | 0.921 | −37.607 | 35.907 | 1.00 | 73.95 | O |
| ATOM | 4262 | CB | VAL | I | 68 | 1.847 | −34.403 | 36.665 | 1.00 | 76.57 | C |
| ATOM | 4263 | CG1 | VAL | I | 68 | 2.977 | −34.965 | 35.793 | 1.00 | 76.18 | C |
| ATOM | 4264 | CG2 | VAL | I | 68 | 1.349 | −33.083 | 36.128 | 1.00 | 75.91 | C |
| ATOM | 4265 | N | THR | I | 69 | −0.159 | −36.058 | 34.623 | 1.00 | 70.31 | N |
| ATOM | 4266 | CA | THR | I | 69 | −0.267 | −36.938 | 33.438 | 1.00 | 70.03 | C |
| ATOM | 4267 | C | THR | I | 69 | 0.048 | −36.150 | 32.150 | 1.00 | 73.35 | C |
| ATOM | 4268 | O | THR | I | 69 | −0.423 | −35.019 | 31.978 | 1.00 | 72.58 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 4269 | CB  | THR | I | 69 | -1.579 | -37.814 | 33.303 | 1.00 | 77.09  | C |
|------|------|-----|-----|---|----|--------|---------|--------|------|--------|---|
| ATOM | 4270 | OG1 | THR | I | 69 | -2.674 | -37.051 | 32.812 | 1.00 | 76.75  | O |
| ATOM | 4271 | CG2 | THR | I | 69 | -1.982 | -38.571 | 34.576 | 1.00 | 73.34  | C |
| ATOM | 4272 | N   | ILE | I | 70 | 0.862  | -36.765 | 31.256 | 1.00 | 69.72  | N |
| ATOM | 4273 | CA  | ILE | I | 70 | 1.244  | -36.189 | 29.959 | 1.00 | 69.38  | C |
| ATOM | 4274 | C   | ILE | I | 70 | 0.493  | -36.912 | 28.809 | 1.00 | 72.07  | C |
| ATOM | 4275 | O   | ILE | I | 70 | 0.353  | -38.147 | 28.813 | 1.00 | 71.77  | O |
| ATOM | 4276 | CB  | ILE | I | 70 | 2.785  | -36.136 | 29.760 | 1.00 | 72.93  | C |
| ATOM | 4277 | CG1 | ILE | I | 70 | 3.463  | -35.480 | 30.977 | 1.00 | 74.42  | C |
| ATOM | 4278 | CG2 | ILE | I | 70 | 3.156  | -35.368 | 28.487 | 1.00 | 73.42  | C |
| ATOM | 4279 | CD1 | ILE | I | 70 | 4.972  | -35.562 | 31.032 | 1.00 | 84.01  | C |
| ATOM | 4280 | N   | SER | I | 71 | -0.003 | -36.114 | 27.842 | 1.00 | 66.82  | N |
| ATOM | 4281 | CA  | SER | I | 71 | -0.783 | -36.538 | 26.684 | 1.00 | 66.46  | C |
| ATOM | 4282 | C   | SER | I | 71 | -0.490 | -35.610 | 25.493 | 1.00 | 70.99  | C |
| ATOM | 4283 | O   | SER | I | 71 | 0.271  | -34.658 | 25.683 | 1.00 | 69.16  | O |
| ATOM | 4284 | CB  | SER | I | 71 | -2.266 | -36.489 | 27.037 | 1.00 | 71.58  | C |
| ATOM | 4285 | OG  | SER | I | 71 | -2.689 | -35.191 | 27.436 | 1.00 | 85.36  | O |
| ATOM | 4286 | N   | ALA | I | 72 | -1.088 | -35.861 | 24.272 | 1.00 | 70.17  | N |
| ATOM | 4287 | CA  | ALA | I | 72 | -0.850 | -35.010 | 23.087 | 1.00 | 70.80  | C |
| ATOM | 4288 | C   | ALA | I | 72 | -2.048 | -34.852 | 22.081 | 1.00 | 78.31  | C |
| ATOM | 4289 | O   | ALA | I | 72 | -3.069 | -35.519 | 22.203 | 1.00 | 76.70  | O |
| ATOM | 4290 | CB  | ALA | I | 72 | 0.400  | -35.458 | 22.346 | 1.00 | 71.18  | C |
| ATOM | 4291 | N   | ASP | I | 73 | -1.739 | -34.108 | 20.979 | 1.00 | 79.39  | N |
| ATOM | 4292 | CA  | ASP | I | 73 | -2.323 | -33.306 | 19.883 | 1.00 | 80.77  | C |
| ATOM | 4293 | C   | ASP | I | 73 | -3.846 | -33.260 | 19.769 | 1.00 | 91.41  | C |
| ATOM | 4294 | O   | ASP | I | 73 | -4.319 | -32.249 | 19.229 | 1.00 | 93.01  | O |
| ATOM | 4295 | CB  | ASP | I | 73 | -1.703 | -33.543 | 18.474 | 1.00 | 81.30  | C |
| ATOM | 4296 | CG  | ASP | I | 73 | -2.083 | -34.740 | 17.623 | 1.00 | 78.85  | C |
| ATOM | 4297 | OD1 | ASP | I | 73 | -2.609 | -35.729 | 18.186 | 1.00 | 80.14  | O |
| ATOM | 4298 | OD2 | ASP | I | 73 | -1.750 | -34.732 | 16.406 | 1.00 | 69.70  | O |
| ATOM | 4299 | N   | LYS | I | 74 | -4.618 | -34.244 | 20.270 | 1.00 | 1.00   | N |
| ATOM | 4300 | CA  | LYS | I | 74 | -6.093 | -34.212 | 20.158 | 1.00 | 92.24  | C |
| ATOM | 4301 | C   | LYS | I | 74 | -6.571 | -33.798 | 18.710 | 1.00 | 100.40 | C |
| ATOM | 4302 | O   | LYS | I | 74 | -7.631 | -33.167 | 18.555 | 1.00 | 100.59 | O |
| ATOM | 4303 | CB  | LYS | I | 74 | -6.710 | -33.324 | 21.268 | 1.00 | 93.89  | C |
| ATOM | 4304 | N   | SER | I | 75 | -5.723 | -34.163 | 17.671 | 1.00 | 98.60  | N |
| ATOM | 4305 | CA  | SER | I | 75 | -5.732 | -33.966 | 16.191 | 1.00 | 98.59  | C |
| ATOM | 4306 | C   | SER | I | 75 | -4.436 | -33.287 | 15.661 | 1.00 | 99.64  | C |
| ATOM | 4307 | O   | SER | I | 75 | -3.675 | -33.911 | 14.929 | 1.00 | 98.81  | O |
| ATOM | 4308 | CB  | SER | I | 75 | -6.987 | -33.253 | 15.667 | 1.00 | 104.16 | C |
| ATOM | 4309 | OG  | SER | I | 75 | -6.968 | -31.839 | 15.800 | 1.00 | 115.75 | O |
| ATOM | 4310 | N   | VAL | I | 76 | -4.197 | -32.025 | 16.049 | 1.00 | 94.32  | N |
| ATOM | 4311 | CA  | VAL | I | 76 | -3.057 | -31.189 | 15.658 | 1.00 | 93.00  | C |
| ATOM | 4312 | C   | VAL | I | 76 | -2.877 | -30.118 | 16.769 | 1.00 | 93.20  | C |
| ATOM | 4313 | O   | VAL | I | 76 | -3.884 | -29.501 | 17.148 | 1.00 | 93.06  | O |
| ATOM | 4314 | CB  | VAL | I | 76 | -3.270 | -30.523 | 14.251 | 1.00 | 96.92  | C |
| ATOM | 4315 | CG1 | VAL | I | 76 | -2.864 | -31.451 | 13.103 | 1.00 | 96.68  | C |
| ATOM | 4316 | CG2 | VAL | I | 76 | -4.698 | -30.009 | 14.059 | 1.00 | 96.64  | C |
| ATOM | 4317 | N   | ASN | I | 77 | -1.651 | -29.845 | 17.300 | 1.00 | 85.28  | N |
| ATOM | 4318 | CA  | ASN | I | 77 | -0.302 | -30.427 | 17.141 | 1.00 | 82.19  | C |
| ATOM | 4319 | C   | ASN | I | 77 | 0.331  | -30.008 | 18.471 | 1.00 | 79.73  | C |
| ATOM | 4320 | O   | ASN | I | 77 | 1.399  | -29.388 | 18.542 | 1.00 | 76.85  | O |
| ATOM | 4321 | CB  | ASN | I | 77 | 0.421  | -29.767 | 15.965 | 1.00 | 79.82  | C |
| ATOM | 4322 | CG  | ASN | I | 77 | 0.965  | -30.725 | 14.945 | 1.00 | 99.33  | C |
| ATOM | 4323 | OD1 | ASN | I | 77 | 1.725  | -30.334 | 14.059 | 1.00 | 91.34  | O |
| ATOM | 4324 | ND2 | ASN | I | 77 | 0.582  | -31.998 | 15.025 | 1.00 | 95.27  | N |
| ATOM | 4325 | N   | THR | I | 78 | -0.402 | -30.342 | 19.536 | 1.00 | 73.21  | N |
| ATOM | 4326 | CA  | THR | I | 78 | -0.230 | -29.856 | 20.877 | 1.00 | 71.31  | C |
| ATOM | 4327 | C   | THR | I | 78 | -0.026 | -30.918 | 21.932 | 1.00 | 72.10  | C |
| ATOM | 4328 | O   | THR | I | 78 | -0.820 | -31.828 | 22.030 | 1.00 | 71.60  | O |
| ATOM | 4329 | CB  | THR | I | 78 | -1.493 | -29.010 | 21.163 | 1.00 | 81.35  | C |
| ATOM | 4330 | OG1 | THR | I | 78 | -1.652 | -28.005 | 20.150 | 1.00 | 80.64  | O |
| ATOM | 4331 | CG2 | THR | I | 78 | -1.498 | -28.387 | 22.530 | 1.00 | 80.17  | C |
| ATOM | 4332 | N   | ALA | I | 79 | 0.968  | -30.738 | 22.812 | 1.00 | 67.11  | N |
| ATOM | 4333 | CA  | ALA | I | 79 | 1.181  | -31.660 | 23.935 | 1.00 | 64.60  | C |
| ATOM | 4334 | C   | ALA | I | 79 | 0.499  | -31.072 | 25.194 | 1.00 | 63.25  | C |
| ATOM | 4335 | O   | ALA | I | 79 | 0.217  | -29.881 | 25.231 | 1.00 | 61.77  | O |
| ATOM | 4336 | CB  | ALA | I | 79 | 2.668  | -31.888 | 24.158 | 1.00 | 64.79  | C |
| ATOM | 4337 | N   | TYR | I | 80 | 0.218  | -31.901 | 26.194 | 1.00 | 57.65  | N |
| ATOM | 4338 | CA  | TYR | I | 80 | -0.475 | -31.475 | 27.395 | 1.00 | 57.66  | C |
| ATOM | 4339 | C   | TYR | I | 80 | 0.147  | -31.978 | 28.709 | 1.00 | 62.18  | C |
| ATOM | 4340 | O   | TYR | I | 80 | 0.619  | -33.116 | 28.791 | 1.00 | 62.72  | O |
| ATOM | 4341 | CB  | TYR | I | 80 | -1.976 | -31.907 | 27.331 | 1.00 | 59.76  | C |
| ATOM | 4342 | CG  | TYR | I | 80 | -2.766 | -31.336 | 26.167 | 1.00 | 62.34  | C |
| ATOM | 4343 | CD1 | TYR | I | 80 | -3.185 | -30.006 | 26.167 | 1.00 | 64.68  | C |
| ATOM | 4344 | CD2 | TYR | I | 80 | -3.133 | -32.135 | 25.086 | 1.00 | 62.66  | C |
| ATOM | 4345 | CE1 | TYR | I | 80 | -3.895 | -29.468 | 25.089 | 1.00 | 65.28  | C |

TABLE1-continued

Three-dimensional crystal coordinate for anti-TcdB antibody beziotoxumab
Fab –*C. difficile* toxin B (TcdB$^{(1834-2101)}$) complex.

| | | | | | | | | | | |
|---|---|---|---|---|---|---|---|---|---|---|
| ATOM | 4346 | CE2 | TYR | I | 80 | −3.840 | −31.607 | 24.001 | 1.00 | 63.23 | C |
| ATOM | 4347 | CZ | TYR | I | 80 | −4.216 | −30.270 | 24.007 | 1.00 | 70.75 | C |
| ATOM | 4348 | OH | TYR | I | 80 | −4.901 | −29.720 | 22.948 | 1.00 | 71.51 | O |
| ATOM | 4349 | N | LEU | I | 81 | 0.096 | −31.125 | 29.747 | 1.00 | 58.86 | N |
| ATOM | 4350 | CA | LEU | I | 81 | 0.487 | −31.450 | 31.116 | 1.00 | 59.81 | C |
| ATOM | 4351 | C | LEU | I | 81 | −0.731 | −31.157 | 31.992 | 1.00 | 67.58 | C |
| ATOM | 4352 | O | LEU | I | 81 | −1.258 | −30.042 | 31.938 | 1.00 | 67.30 | O |
| ATOM | 4353 | CB | LEU | I | 81 | 1.702 | −30.631 | 31.599 | 1.00 | 59.07 | C |
| ATOM | 4354 | CG | LEU | I | 81 | 2.285 | −31.027 | 32.970 | 1.00 | 61.30 | C |
| ATOM | 4355 | CD1 | LEU | I | 81 | 2.914 | −32.399 | 32.927 | 1.00 | 60.54 | C |
| ATOM | 4356 | CD2 | LEU | I | 81 | 3.321 | −30.054 | 33.384 | 1.00 | 63.67 | C |
| ATOM | 4357 | N | GLN | I | 82 | −1.197 | −32.147 | 32.772 | 1.00 | 66.44 | N |
| ATOM | 4358 | CA | GLN | I | 82 | −2.378 | −31.910 | 33.597 | 1.00 | 67.86 | C |
| ATOM | 4359 | C | GLN | I | 82 | −2.291 | −32.493 | 35.014 | 1.00 | 73.19 | C |
| ATOM | 4360 | O | GLN | I | 82 | −1.650 | −33.524 | 35.240 | 1.00 | 73.14 | O |
| ATOM | 4361 | CB | GLN | I | 82 | −3.682 | −32.352 | 32.889 | 1.00 | 69.72 | C |
| ATOM | 4362 | CG | GLN | I | 82 | −3.837 | −33.848 | 32.632 | 1.00 | 90.54 | C |
| ATOM | 4363 | CD | GLN | I | 82 | −5.290 | −34.258 | 32.627 | 1.00 | 111.89 | C |
| ATOM | 4364 | OE1 | GLN | I | 82 | −5.859 | −34.640 | 33.661 | 1.00 | 108.87 | O |
| ATOM | 4365 | NE2 | GLN | I | 82 | −5.920 | −34.195 | 31.461 | 1.00 | 100.24 | N |
| ATOM | 4366 | N | TRP | I | 83 | −2.947 | −31.791 | 35.960 | 1.00 | 70.46 | N |
| ATOM | 4367 | CA | TRP | I | 83 | −3.041 | −32.135 | 37.381 | 1.00 | 70.66 | C |
| ATOM | 4368 | C | TRP | I | 83 | −4.510 | −32.291 | 37.760 | 1.00 | 83.37 | C |
| ATOM | 4369 | O | TRP | I | 83 | −5.361 | −31.516 | 37.300 | 1.00 | 84.96 | O |
| ATOM | 4370 | CB | TRP | I | 83 | −2.461 | −31.011 | 38.286 | 1.00 | 67.04 | C |
| ATOM | 4371 | CG | TRP | I | 83 | −1.010 | −30.675 | 38.104 | 1.00 | 65.59 | C |
| ATOM | 4372 | CD1 | TRP | I | 83 | 0.032 | −31.091 | 38.880 | 1.00 | 67.89 | C |
| ATOM | 4373 | CD2 | TRP | I | 83 | −0.461 | −29.758 | 37.148 | 1.00 | 64.38 | C |
| ATOM | 4374 | NE1 | TRP | I | 83 | 1.203 | −30.534 | 38.434 | 1.00 | 66.56 | N |
| ATOM | 4375 | CE2 | TRP | I | 83 | 0.930 | −29.705 | 37.374 | 1.00 | 67.50 | C |
| ATOM | 4376 | CE3 | TRP | I | 83 | −1.011 | −28.988 | 36.101 | 1.00 | 64.98 | C |
| ATOM | 4377 | CZ2 | TRP | I | 83, | 1.785 | −28.932 | 36.579 | 1.00 | 66.36 | C |
| ATOM | 4378 | CZ3 | TRP | I | 83 | −0.168 | −28.213 | 35.323 | 1.00 | 65.88 | C |
| ATOM | 4379 | CH2 | TRP | I | 83 | 1.212 | −28.187 | 35.565 | 1.00 | 66.44 | C |
| ATOM | 4380 | N | SER | I | 84 | −4.792 | −33.263 | 38.630 | 1.00 | 83.28 | N |
| ATOM | 4381 | CA | SER | I | 84 | −6.094 | −33.482 | 39.235 | 1.00 | 84.74 | C |
| ATOM | 4382 | C | SER | I | 84 | −5.807 | −33.129 | 40.692 | 1.00 | 93.19 | C |
| ATOM | 4383 | O | SER | I | 84 | −5.148 | −33.916 | 41.385 | 1.00 | 95.27 | O |
| ATOM | 4384 | CB | SER | I | 84 | −6.526 | −34.937 | 39.079 | 1.00 | 88.92 | C |
| ATOM | 4385 | OG | SER | I | 84 | −6.876 | −35.232 | 37.735 | 1.00 | 101.14 | O |
| ATOM | 4386 | N | SER | I | 85 | −6.174 | −31.891 | 41.111 | 1.00 | 89.53 | N |
| ATOM | 4387 | CA | SER | I | 85 | −5.928 | −31.286 | 42.444 | 1.00 | 89.26 | C |
| ATOM | 4388 | C | SER | I | 85 | −4.475 | −30.773 | 42.632 | 1.00 | 89.34 | C |
| ATOM | 4389 | O | SER | I | 85 | −3.577 | −31.497 | 43.083 | 1.00 | 86.85 | O |
| ATOM | 4390 | CB | SER | I | 85 | −6.364 | −32.178 | 43.613 | 1.00 | 94.50 | C |
| ATOM | 4391 | OG | SER | I | 85 | −6.388 | −31.460 | 44.840 | 1.00 | 105.28 | O |
| ATOM | 4392 | N | LEU | I | 86 | −4.300 | −29.472 | 42.306 | 1.00 | 85.26 | N |
| ATOM | 4393 | CA | LEU | I | 86 | −3.078 | −28.661 | 42.400 | 1.00 | 84.31 | C |
| ATOM | 4394 | C | LEU | I | 86 | −2.733 | −28.260 | 43.859 | 1.00 | 89.59 | C |
| ATOM | 4395 | O | LEU | I | 86 | −3.532 | −27.576 | 44.517 | 1.00 | 90.45 | O |
| ATOM | 4396 | CB | LEU | I | 86 | −3.269 | −27.343 | 41.606 | 1.00 | 83.44 | C |
| ATOM | 4397 | CG | LEU | I | 86 | −3.192 | −27.372 | 40.098 | 1.00 | 87.09 | C |
| ATOM | 4398 | CD1 | LEU | I | 86 | −3.835 | −26.140 | 39.529 | 1.00 | 86.96 | C |
| ATOM | 4399 | CD2 | LEU | I | 86 | −1.753 | −27.452 | 39.629 | 1.00 | 88.11 | C |
| ATOM | 4400 | N | LYS | I | 87 | −1.528 | −28.633 | 44.340 | 1.00 | 84.50 | N |
| ATOM | 4401 | CA | LYS | I | 87 | −1.033 | −28.200 | 45.652 | 1.00 | 83.18 | C |
| ATOM | 4402 | C | LYS | I | 87 | −0.394 | −26.771 | 45.458 | 1.00 | 86.42 | C |
| ATOM | 4403 | O | LYS | I | 87 | −0.062 | −26.419 | 44.320 | 1.00 | 85.59 | O |
| ATOM | 4404 | CB | LYS | I | 87 | −0.021 | −29.225 | 46.206 | 1.00 | 84.21 | C |
| ATOM | 4405 | N | ALA | I | 88 | −0.263 | −25.932 | 46.525 | 1.00 | 82.35 | N |
| ATOM | 4406 | CA | ALA | I | 88 | 0.391 | −24.608 | 46.369 | 1.00 | 81.39 | C |
| ATOM | 4407 | C | ALA | I | 88 | 1.879 | −24.834 | 45.989 | 1.00 | 83.21 | C |
| ATOM | 4408 | O | ALA | I | 88 | 2.490 | −24.034 | 45.267 | 1.00 | 81.39 | O |
| ATOM | 4409 | CB | ALA | I | 88 | 0.297 | −23.805 | 47.653 | 1.00 | 81.83 | C |
| ATOM | 4410 | N | SER | I | 89 | 2.405 | −25.995 | 46.449 | 1.00 | 77.71 | N |
| ATOM | 4411 | CA | SER | I | 89 | 3.713 | −26.583 | 46.219 | 1.00 | 76.69 | C |
| ATOM | 4412 | C | SER | I | 89 | 4.057 | −26.688 | 44.707 | 1.00 | 79.47 | C |
| ATOM | 4413 | O | SER | I | 89 | 5.223 | −26.881 | 44.368 | 1.00 | 78.46 | O |
| ATOM | 4414 | CB | SER | I | 89 | 3.708 | −27.980 | 46.822 | 1.00 | 79.81 | C |
| ATOM | 4415 | OG | SER | I | 89 | 5.014 | −28.405 | 47.163 | 1.00 | 88.15 | O |
| ATOM | 4416 | N | ASP | I | 90 | 3.034 | −26.605 | 43.826 | 1.00 | 74.80 | N |
| ATOM | 4417 | CA | ASP | I | 90 | 3.127 | −26.696 | 42.370 | 1.00 | 74.14 | C |
| ATOM | 4418 | C | ASP | I | 90 | 3.345 | −25.336 | 41.713 | 1.00 | 79.15 | C |
| ATOM | 4419 | O | ASP | I | 90 | 3.435 | −25.278 | 40.484 | 1.00 | 78.89 | O |
| ATOM | 4420 | CB | ASP | I | 90 | 1.871 | −27.369 | 41.770 | 1.00 | 76.00 | C |
| ATOM | 4421 | CG | ASP | I | 90 | 1.555 | −28.787 | 42.228 | 1.00 | 87.45 | C |
| ATOM | 4422 | OD1 | ASP | I | 90 | 2.475 | −29.472 | 42.755 | 1.00 | 87.05 | O |

TABLE 1-continued

Three-dimensional crystal coordinate for anti-TcdB antibody beziotoxumab Fab – *C. difficile* toxin B (TcdB$^{(1834-2101)}$) complex.

| ATOM | 4423 | OD2 | ASP | I | 90 | 0.394 | −29.229 | 42.029 | 1.00 | 93.28 | O |
|---|---|---|---|---|---|---|---|---|---|---|---|
| ATOM | 4424 | N | THR | I | 91 | 3.414 | −24.236 | 42.512 | 1.00 | 76.58 | N |
| ATOM | 4425 | CA | THR | I | 91 | 3.692 | −22.884 | 41.995 | 1.00 | 75.82 | C |
| ATOM | 4426 | C | THR | I | 91 | 5.131 | −22.896 | 41.470 | 1.00 | 77.90 | C |
| ATOM | 4427 | O | THR | I | 91 | 6.079 | −23.005 | 42.267 | 1.00 | 78.03 | O |
| ATOM | 4428 | CB | THR | I | 91 | 3.503 | −21.808 | 43.081 | 1.00 | 84.76 | C |
| ATOM | 4429 | OG1 | THR | I | 91 | 2.202 | −21.940 | 43.653 | 1.00 | 85.48 | O |
| ATOM | 4430 | CG2 | THR | I | 91 | 3.727 | −20.383 | 42.555 | 1.00 | 80.94 | C |
| ATOM | 4431 | N | ALA | I | 92 | 5.271 | −22.858 | 40.119 | 1.00 | 70.28 | N |
| ATOM | 4432 | CA | ALA | I | 92 | 6.538 | −22.900 | 39.395 | 1.00 | 67.23 | C |
| ATOM | 4433 | C | ALA | I | 92 | 6.360 | −22.529 | 37.932 | 1.00 | 69.35 | C |
| ATOM | 4434 | O | ALA | I | 92 | 5.259 | −22.188 | 37.490 | 1.00 | 68.20 | O |
| ATOM | 4435 | CB | ALA | I | 92 | 7.145 | −24.291 | 39.500 | 1.00 | 67.44 | C |
| ATOM | 4436 | N | MET | I | 93 | 7.467 | −22.595 | 37.174 | 1.00 | 65.74 | N |
| ATOM | 4437 | CA | MET | I | 93 | 7.501 | −22.346 | 35.742 | 1.00 | 64.17 | C |
| ATOM | 4438 | C | MET | I | 93 | 7.582 | −23.684 | 35.076 | 1.00 | 68.18 | C |
| ATOM | 4439 | O | MET | I | 93 | 8.363 | −24.555 | 35.498 | 1.00 | 68.24 | O |
| ATOM | 4440 | CB | MET | I | 93 | 8.719 | −21.536 | 35.363 | 1.00 | 66.08 | C |
| ATOM | 4441 | CG | MET | I | 93 | 8.382 | −20.150 | 34.974 | 1.00 | 69.26 | C |
| ATOM | 4442 | SD | MET | I | 93 | 7.741 | −20.104 | 33.317 | 1.00 | 72.55 | S |
| ATOM | 4443 | CE | MET | I | 93 | 7.650 | −18.368 | 33.068 | 1.00 | 68.53 | C |
| ATOM | 4444 | N | TYR | I | 94 | 6.735 | −23.880 | 34.067 | 1.00 | 63.25 | N |
| ATOM | 4445 | CA | TYR | I | 94 | 6.693 | −25.149 | 33.363 | 1.00 | 60.98 | C |
| ATOM | 4446 | C | TYR | I | 94 | 7.073 | −24.959 | 31.937 | 1.00 | 64.06 | C |
| ATOM | 4447 | O | TYR | I | 94 | 6.514 | −24.109 | 31.230 | 1.00 | 62.49 | O |
| ATOM | 4448 | CB | TYR | I | 94 | 5.338 | −25.849 | 33.534 | 1.00 | 60.50 | C |
| ATOM | 4449 | CG | TYR | I | 94 | 5.063 | −26.255 | 34.967 | 1.00 | 59.82 | C |
| ATOM | 4450 | CD1 | TYR | I | 94 | 5.554 | −27.448 | 35.479 | 1.00 | 61.25 | C |
| ATOM | 4451 | CD2 | TYR | I | 94 | 4.327 | −25.437 | 35.815 | 1.00 | 59.54 | C |
| ATOM | 4452 | CE1 | TYR | I | 94 | 5.317 | −27.818 | 36.797 | 1.00 | 62.07 | C |
| ATOM | 4453 | CE2 | TYR | I | 94 | 4.081 | −25.800 | 37.136 | 1.00 | 59.80 | C |
| ATOM | 4454 | CZ | TYR | I | 94 | 4.595 | −26.983 | 37.630 | 1.00 | 66.38 | C |
| ATOM | 4455 | OH | TYR | I | 94 | 4.372 | −27.357 | 38.935 | 1.00 | 68.06 | O |
| ATOM | 4456 | N | TYR | I | 95 | 8.100 | −25.710 | 31.543 | 1.00 | 60.91 | N |
| ATOM | 4457 | CA | TYR | I | 95 | 8.634 | −25.689 | 30.195 | 1.00 | 60.38 | C |
| ATOM | 4458 | C | TYR | I | 95 | 8.391 | −27.024 | 29.518 | 1.00 | 65.05 | C |
| ATOM | 4459 | O | TYR | I | 95 | 8.510 | −28.073 | 30.161 | 1.00 | 63.60 | O |
| ATOM | 4460 | CB | TYR | I | 95 | 10.160 | −25.433 | 30.236 | 1.00 | 60.07 | C |
| ATOM | 4461 | CG | TYR | I | 95 | 10.580 | −24.071 | 30.756 | 1.00 | 59.37 | C |
| ATOM | 4462 | CD1 | TYR | I | 95 | 10.440 | −22.927 | 29.970 | 1.00 | 59.89 | C |
| ATOM | 4463 | CD2 | TYR | I | 95 | 11.193 | −23.935 | 32.003 | 1.00 | 59.43 | C |
| ATOM | 4464 | CE1 | TYR | I | 95 | 10.852 | −21.676 | 30.431 | 1.00 | 59.09 | C |
| ATOM | 4465 | CE2 | TYR | I | 95 | 11.617 | −22.687 | 32.472 | 1.00 | 59.72 | C |
| ATOM | 4466 | CZ | TYR | I | 95 | 11.452 | −21.561 | 31.676 | 1.00 | 67.71 | C |
| ATOM | 4467 | OH | TYR | I | 95 | 11.857 | −20.323 | 32.114 | 1.00 | 73.56 | O |
| ATOM | 4468 | N | CYS | I | 96 | 8.071 | −26.983 | 28.221 | 1.00 | 62.75 | N |
| ATOM | 4469 | CA | CYS | I | 96 | 8.017 | −28.179 | 27.398 | 1.00 | 63.23 | C |
| ATOM | 4470 | C | CYS | I | 96 | 9.169 | −27.978 | 26.438 | 1.00 | 62.49 | C |
| ATOM | 4471 | O | CYS | I | 96 | 9.415 | −26.862 | 25.945 | 1.00 | 60.11 | O |
| ATOM | 4472 | CB | CYS | I | 96 | 6.695 | −28.348 | 26.658 | 1.00 | 65.65 | C |
| ATOM | 4473 | SG | CYS | I | 96 | 6.422 | −27.098 | 25.373 | 1.00 | 71.03 | S |
| ATOM | 4474 | N | ALA | I | 97 | 9.923 | −29.045 | 26.251 | 1.00 | 57.68 | N |
| ATOM | 4475 | CA | ALA | I | 97 | 11.071 | −29.060 | 25.372 | 1.00 | 56.23 | C |
| ATOM | 4476 | C | ALA | I | 97 | 11.038 | −30.278 | 24.459 | 1.00 | 59.50 | C |
| ATOM | 4477 | O | ALA | I | 97 | 10.720 | −31.393 | 24.906 | 1.00 | 58.81 | O |
| ATOM | 4478 | CB | ALA | I | 97 | 12.349 | −29.049 | 26.192 | 1.00 | 56.36 | C |
| ATOM | 4479 | N | ARG | I | 98 | 11.357 | −30.054 | 23.176 | 1.00 | 55.47 | N |
| ATOM | 4480 | CA | ARG | I | 98 | 11.461 | −31.098 | 22.168 | 1.00 | 55.28 | C |
| ATOM | 4481 | C | ARG | I | 98 | 12.777 | −31.812 | 22.431 | 1.00 | 61.66 | C |
| ATOM | 4482 | O | ARG | I | 98 | 13.764 | −31.151 | 22.727 | 1.00 | 63.73 | O |
| ATOM | 4483 | CB | ARG | I | 98 | 11.483 | −30.495 | 20.747 | 1.00 | 52.20 | C |
| ATOM | 4484 | CG | ARG | I | 98 | 11.349 | −31.539 | 19.639 | 1.00 | 52.52 | C |
| ATOM | 4485 | CD | ARG | I | 98 | 11.504 | −30.982 | 18.241 | 1.00 | 54.41 | C |
| ATOM | 4486 | NE | ARG | I | 98 | 12.901 | −30.807 | 17.814 | 1.00 | 48.01 | N |
| ATOM | 4487 | CZ | ARG | I | 98 | 13.266 | −30.458 | 16.581 | 1.00 | 59.84 | C |
| ATOM | 4488 | NH1 | ARG | I | 98 | 12.350 | −30.264 | 15.637 | 1.00 | 51.11 | N |
| ATOM | 4489 | NH2 | ARG | I | 98 | 14.543 | −30.305 | 16.281 | 1.00 | 45.05 | N |
| ATOM | 4490 | O | ARG | I | 99 | 13.856 | −34.443 | 20.116 | 1.00 | 64.14 | O |
| ATOM | 4491 | N | ARG | I | 99 | 12.798 | −33.139 | 22.308 | 1.00 | 57.21 | N |
| ATOM | 4492 | CA | ARG | I | 99 | 13.994 | −33.960 | 22.466 | 1.00 | 56.50 | C |
| ATOM | 4493 | C | ARG | I | 99 | 14.598 | −34.244 | 21.092 | 1.00 | 63.16 | C |
| ATOM | 4494 | CB | ARG | I | 99 | 13.627 | −35.288 | 23.147 | 1.00 | 51.74 | C |
| ATOM | 4495 | CG | ARG | I | 99 | 14.816 | −36.095 | 23.603 | 1.00 | 45.77 | C |
| ATOM | 4496 | CD | ARG | I | 99 | 14.501 | −37.572 | 23.688 | 1.00 | 42.04 | C |
| ATOM | 4497 | NE | ARG | I | 99 | 14.370 | −38.130 | 22.346 | 1.00 | 58.63 | N |
| ATOM | 4498 | CZ | ARG | I | 99 | 14.239 | −39.420 | 22.085 | 1.00 | 61.42 | C |
| ATOM | 4499 | NH1 | ARG | I | 99 | 14.217 | −40.302 | 23.072 | 1.00 | 50.73 | N |

TABLE 1-continued

Three-dimensional crystal coordinate for anti-TcdB antibody beziotoxumab
Fab –*C. difficile* toxin B (TcdB$^{(1834-2101)}$) complex.

| ATOM | 4500 | NH2 | ARG | I | 99 | 14.132 | −39.842 | 20.835 | 1.00 | 35.29 | N |
|---|---|---|---|---|---|---|---|---|---|---|---|
| ATOM | 4501 | O | ARG | I | 100 | 16.551 | −36.807 | 20.705 | 1.00 | 64.10 | O |
| ATOM | 4502 | N | ARG | I | 100 | 15.949 | −34.294 | 21.034 | 1.00 | 60.27 | N |
| ATOM | 4503 | CA | ARG | I | 100 | 16.763 | −34.632 | 19.853 | 1.00 | 59.52 | C |
| ATOM | 4504 | C | ARG | I | 100 | 16.686 | −36.120 | 19.691 | 1.00 | 63.15 | C |
| ATOM | 4505 | CB | ARG | I | 100 | 18.224 | −34.262 | 20.103 | 1.00 | 58.50 | C |
| ATOM | 4506 | CG | ARG | I | 100 | 18.631 | −32.957 | 19.451 | 1.00 | 64.68 | C |
| ATOM | 4507 | CD | ARG | I | 100 | 20.119 | −32.753 | 19.529 | 1.00 | 58.81 | C |
| ATOM | 4508 | NE | ARG | I | 100 | 20.829 | −33.756 | 18.744 | 1.00 | 47.62 | N |
| ATOM | 4509 | CZ | ARG | I | 100 | 21.323 | −33.540 | 17.541 | 1.00 | 71.53 | C |
| ATOM | 4510 | NH1 | ARG | I | 100 | 21.231 | −32.333 | 16.987 | 1.00 | 78.73 | N |
| ATOM | 4511 | NH2 | ARG | I | 100 | 21.969 | −34.502 | 16.901 | 1.00 | 51.18 | N |
| ATOM | 4512 | O | ASN | I | 101 | 18.281 | −39.914 | 17.759 | 1.00 | 64.71 | O |
| ATOM | 4513 | N | ASN | I | 101 | 16.786 | −36.642 | 18.455 | 1.00 | 59.46 | N |
| ATOM | 4514 | CA | ASN | I | 101 | 16.695 | −38.106 | 18.275 | 1.00 | 59.62 | C |
| ATOM | 4515 | C | ASN | I | 101 | 18.101 | −38.828 | 18.321 | 1.00 | 65.32 | C |
| ATOM | 4516 | CB | ASN | I | 101 | 15.855 | −38.474 | 17.039 | 1.00 | 56.27 | C |
| ATOM | 4517 | CG | ASN | I | 101 | 14.353 | −38.221 | 17.174 | 1.00 | 72.37 | C |
| ATOM | 4518 | OD1 | ASN | I | 101 | 13.709 | −38.370 | 18.238 | 1.00 | 71.10 | O |
| ATOM | 4519 | ND2 | ASN | I | 101 | 13.745 | −37.856 | 16.070 | 1.00 | 57.18 | N |
| ATOM | 4520 | O | TRP | I | 102 | 21.126 | −36.321 | 19.592 | 1.00 | 74.00 | O |
| ATOM | 4521 | N | TRP | I | 102 | 19.043 | −38.219 | 19.094 | 1.00 | 63.87 | N |
| ATOM | 4522 | CA | TRP | I | 102 | 20.408 | −38.604 | 19.514 | 1.00 | 64.27 | C |
| ATOM | 4523 | C | TRP | I | 102 | 20.981 | −37.351 | 20.243 | 1.00 | 70.98 | C |
| ATOM | 4524 | CB | TRP | I | 102 | 21.310 | −38.967 | 18.306 | 1.00 | 62.63 | C |
| ATOM | 4525 | CG | TRP | I | 102 | 22.592 | −39.644 | 18.711 | 1.00 | 63.21 | C |
| ATOM | 4526 | CD1 | TRP | I | 102 | 22.858 | −40.981 | 18.664 | 1.00 | 65.96 | C |
| ATOM | 4527 | CD2 | TRP | I | 102 | 23.739 | −39.028 | 19.342 | 1.00 | 62.93 | C |
| ATOM | 4528 | NE1 | TRP | I | 102 | 24.082 | −41.244 | 19.247 | 1.00 | 64.91 | N |
| ATOM | 4529 | CE2 | TRP | I | 102 | 24.654 | −40.058 | 19.645 | 1.00 | 66.07 | C |
| ATOM | 4530 | CE3 | TRP | I | 102 | 24.077 | −37.698 | 19.694 | 1.00 | 63.76 | C |
| ATOM | 4531 | CZ2 | TRP | I | 102 | 25.889 | −39.801 | 20.249 | 1.00 | 64.77 | C |
| ATOM | 4532 | CZ3 | TRP | I | 102 | 25.285 | −37.451 | 20.319 | 1.00 | 64.30 | C |
| ATOM | 4533 | CH2 | TRP | I | 102 | 26.181 | −38.493 | 20.574 | 1.00 | 64.84 | C |
| ATOM | 4534 | O | GLY | I | 103 | 21.296 | −37.339 | 24.652 | 1.00 | 71.15 | O |
| ATOM | 4535 | N | GLY | I | 103 | 21.359 | −37.382 | 21.516 | 1.00 | 65.69 | N |
| ATOM | 4536 | CA | GLY | I | 103 | 21.271 | −38.432 | 22.505 | 1.00 | 65.61 | C |
| ATOM | 4537 | C | GLY | I | 103 | 20.625 | −37.785 | 23.714 | 1.00 | 70.41 | C |
| ATOM | 4538 | O | ASN | I | 104 | 17.741 | −35.244 | 25.942 | 1.00 | 66.47 | O |
| ATOM | 4539 | N | ASN | I | 104 | 19.313 | −37.585 | 23.585 | 1.00 | 65.24 | N |
| ATOM | 4540 | CA | ASN | I | 104 | 18.354 | −37.117 | 24.569 | 1.00 | 63.92 | C |
| ATOM | 4541 | C | ASN | I | 104 | 18.482 | −35.642 | 25.043 | 1.00 | 66.08 | C |
| ATOM | 4542 | CB | ASN | I | 104 | 18.337 | −38.085 | 25.749 | 1.00 | 61.56 | C |
| ATOM | 4543 | CG | ASN | I | 104 | 17.759 | −39.424 | 25.340 | 1.00 | 66.74 | C |
| ATOM | 4544 | OD1 | ASN | I | 104 | 17.575 | −39.730 | 24.154 | 1.00 | 66.49 | O |
| ATOM | 4545 | ND2 | ASN | I | 104 | 17.453 | −40.248 | 26.300 | 1.00 | 49.13 | N |
| ATOM | 4546 | N | ALA | 1 | 105 | 19.293 | −34.808 | 24.401 | 1.00 | 60.63 | N |
| ATOM | 4547 | CA | ALA | I | 105 | 19.333 | −33.405 | 24.827 | 1.00 | 59.30 | C |
| ATOM | 4548 | C | ALA | I | 105 | 18.075 | −32.730 | 24.293 | 1.00 | 62.73 | C |
| ATOM | 4549 | O | ALA | I | 105 | 17.596 | −33.137 | 23.237 | 1.00 | 63.08 | O |
| ATOM | 4550 | CB | ALA | I | 105 | 20.575 | −32.714 | 24.283 | 1.00 | 59.60 | C |
| ATOM | 4551 | N | PHE | I | 106 | 17.527 | −31.734 | 25.030 | 1.00 | 57.33 | N |
| ATOM | 4552 | CA | PHE | I | 106 | 16.332 | −30.978 | 24.680 | 1.00 | 55.96 | C |
| ATOM | 4553 | C | PHE | I | 106 | 16.730 | −29.821 | 23.824 | 1.00 | 60.51 | C |
| ATOM | 4554 | O | PHE | I | 106 | 17.249 | −28.852 | 24.343 | 1.00 | 62.91 | O |
| ATOM | 4555 | CB | PHE | I | 106 | 15.638 | −30.502 | 25.945 | 1.00 | 58.12 | C |
| ATOM | 4556 | CG | PHE | I | 106 | 15.087 | −31.647 | 26.758 | 1.00 | 60.72 | C |
| ATOM | 4557 | CD1 | PHE | I | 106 | 14.035 | −32.422 | 26.276 | 1.00 | 64.19 | C |
| ATOM | 4558 | CD2 | PHE | I | 106 | 15.617 | −31.950 | 28.006 | 1.00 | 64.01 | C |
| ATOM | 4559 | CE1 | PHE | I | 106 | 13.521 | −33.473 | 27.030 | 1.00 | 65.41 | C |
| ATOM | 4560 | CE2 | PHE | I | 106 | 15.113 | −33.010 | 28.755 | 1.00 | 67.43 | C |
| ATOM | 4561 | CZ | PHE | I | 106 | 14.065 | −33.761 | 28.263 | 1.00 | 65.76 | C |
| ATOM | 4562 | N | ASP | I | 107 | 16.499 | −29.909 | 22.514 | 1.00 | 56.13 | N |
| ATOM | 4563 | CA | ASP | I | 107 | 16.970 | −28.945 | 21.531 | 1.00 | 55.91 | C |
| ATOM | 4564 | C | ASP | I | 107 | 16.065 | −27.739 | 21.278 | 1.00 | 62.29 | C |
| ATOM | 4565 | O | ASP | I | 107 | 16.569 | −26.706 | 20.828 | 1.00 | 62.36 | O |
| ATOM | 4566 | CB | ASP | I | 107 | 17.295 | −29.655 | 20.209 | 1.00 | 57.96 | C |
| ATOM | 4567 | CG | ASP | I | 107 | 16.159 | −30.377 | 19.472 | 1.00 | 70.40 | C |
| ATOM | 4568 | OD1 | ASP | I | 107 | 15.045 | −30.505 | 20.050 | 1.00 | 72.67 | O |
| ATOM | 4569 | OD2 | ASP | I | 107 | 16.388 | −30.821 | 18.325 | 1.00 | 71.67 | O |
| ATOM | 4570 | N | ILE | I | 108 | 14.756 | −27.853 | 21.498 | 1.00 | 60.10 | N |
| ATOM | 4571 | CA | ILE | I | 108 | 13.869 | −26.692 | 21.326 | 1.00 | 60.37 | C |
| ATOM | 4572 | C | ILE | I | 108 | 13.048 | −26.544 | 22.568 | 1.00 | 63.34 | C |
| ATOM | 4573 | O | ILE | I | 108 | 12.552 | −27.553 | 23.042 | 1.00 | 64.00 | O |
| ATOM | 4574 | CB | ILE | I | 108 | 13.056 | −26.690 | 19.996 | 1.00 | 64.09 | C |
| ATOM | 4575 | CG1 | ILE | I | 108 | 13.851 | −25.966 | 18.904 | 1.00 | 64.91 | C |
| ATOM | 4576 | CG2 | ILE | I | 108 | 11.715 | −25.991 | 20.145 | 1.00 | 65.36 | C |

TABLE 1-continued

Three-dimensional crystal coordinate for anti-TcdB antibody beziotoxumab
Fab –*C. difficile* toxin B (TcdB$^{(1834-2101)}$) complex.

| ATOM | 4577 | CD1 | ILE | I | 108 | 14.669 | −26.811 | 18.079 | 1.00 | 71.15 | C |
|---|---|---|---|---|---|---|---|---|---|---|---|
| ATOM | 4578 | N | TRP | I | 109 | 12.968 | −25.319 | 23.149 | 1.00 | 58.89 | N |
| ATOM | 4579 | CA | TRP | I | 109 | 12.229 | −25.045 | 24.401 | 1.00 | 57.56 | C |
| ATOM | 4580 | C | TRP | I | 109 | 11.059 | −24.066 | 24.196 | 1.00 | 63.90 | C |
| ATOM | 4581 | O | TRP | I | 109 | 11.104 | −23.193 | 23.316 | 1.00 | 61.82 | O |
| ATOM | 4582 | CB | TRP | I | 109 | 13.177 | −24.510 | 25.506 | 1.00 | 54.89 | C |
| ATOM | 4583 | CG | TRP | I | 109 | 14.206 | −25.487 | 26.010 | 1.00 | 54.39 | C |
| ATOM | 4584 | CD1 | TRP | I | 109 | 15.312 | −25.931 | 25.346 | 1.00 | 57.11 | C |
| ATOM | 4585 | CD2 | TRP | I | 109 | 14.250 | −26.091 | 27.310 | 1.00 | 53.33 | C |
| ATOM | 4586 | NE1 | TRP | I | 109 | 16.011 | −26.824 | 26.132 | 1.00 | 56.23 | N |
| ATOM | 4587 | CE2 | TRP | I | 109 | 15.375 | −26.948 | 27.339 | 1.00 | 57.12 | C |
| ATOM | 4588 | CE3 | TRP | I | 109 | 13.424 | −26.025 | 28.436 | 1.00 | 53.93 | C |
| ATOM | 4589 | CZ2 | TRP | I | 109 | 15.694 | −27.732 | 28.451 | 1.00 | 55.94 | C |
| ATOM | 4590 | CZ3 | TRP | I | 109 | 13.745 | −26.794 | 29.539 | 1.00 | 55.13 | C |
| ATOM | 4591 | CH2 | TRP | I | 109 | 14.884 | −27.615 | 29.551 | 1.00 | 55.66 | C |
| ATOM | 4592 | N | GLY | I | 110 | 10.018 | −24.240 | 25.008 | 1.00 | 64.25 | N |
| ATOM | 4593 | CA | GLY | I | 110 | 8.859 | −23.355 | 25.007 | 1.00 | 65.21 | C |
| ATOM | 4594 | C | GLY | I | 110 | 9.153 | −22.128 | 25.845 | 1.00 | 71.13 | C |
| ATOM | 4595 | O | GLY | I | 110 | 10.077 | −22.164 | 26.664 | 1.00 | 70.25 | O |
| ATOM | 4596 | N | GLN | I | 111 | 8.394 | −21.025 | 25.655 | 1.00 | 69.24 | N |
| ATOM | 4597 | CA | GLN | I | 111 | 8.612 | −19.787 | 26.426 | 1.00 | 69.09 | C |
| ATOM | 4598 | C | GLN | I | 111 | 8.388 | −19.976 | 27.938 | 1.00 | 74.19 | C |
| ATOM | 4599 | O | GLN | I | 111 | 8.975 | −19.246 | 28.748 | 1.00 | 75.00 | O |
| ATOM | 4600 | CB | GLN | I | 111 | 7.775 | −18.617 | 25.873 | 1.00 | 69.81 | C |
| ATOM | 4601 | CG | GLN | I | 111 | 6.313 | −18.553 | 26.344 | 1.00 | 68.69 | C |
| ATOM | 4602 | CD | GLN | I | 111 | 5.304 | −19.277 | 25.496 | 1.00 | 79.87 | C |
| ATOM | 4603 | OE1 | GLN | I | 111 | 5.623 | −20.009 | 24.562 | 1.00 | 77.58 | O |
| ATOM | 4604 | NE2 | GLN | I | 111 | 4.046 | −19.087 | 25.824 | 1.00 | 74.33 | N |
| ATOM | 4605 | N | GLY | I | 112 | 7.568 | −20.965 | 28.282 | 1.00 | 69.18 | N |
| ATOM | 4606 | CA | GLY | I | 112 | 7.231 | −21.292 | 29.654 | 1.00 | 68.76 | C |
| ATOM | 4607 | C | GLY | I | 112 | 5.817 | −20.879 | 29.982 | 1.00 | 72.83 | C |
| ATOM | 4608 | O | GLY | I | 112 | 5.235 | −20.009 | 29.317 | 1.00 | 72.62 | O |
| ATOM | 4609 | N | THR | I | 113 | 5.240 | −21.543 | 30.984 | 1.00 | 69.37 | N |
| ATOM | 4610 | CA | THR | I | 113 | 3.898 | −21.244 | 31.480 | 1.00 | 69.37 | C |
| ATOM | 4611 | C | THR | I | 113 | 4.031 | −21.073 | 32.990 | 1.00 | 73.62 | C |
| ATOM | 4612 | O | THR | I | 113 | 4.402 | −22.037 | 33.680 | 1.00 | 74.10 | O |
| ATOM | 4613 | CB | THR | I | 113 | 2.866 | −22.347 | 31.117 | 1.00 | 75.92 | C |
| ATOM | 4614 | OG1 | THR | I | 113 | 2.709 | −22.448 | 29.703 | 1.00 | 77.02 | O |
| ATOM | 4615 | CG2 | THR | I | 113 | 1.511 | −22.097 | 31.741 | 1.00 | 71.97 | C |
| ATOM | 4616 | N | MET | I | 114 | 3.738 | −19.853 | 33.499 | 1.00 | 68.94 | N |
| ATOM | 4617 | CA | MET | I | 114 | 3.825 | −19.612 | 34.930 | 1.00 | 69.17 | C |
| ATOM | 4618 | C | MET | I | 114 | 2.570 | −20.125 | 35.586 | 1.00 | 75.49 | C |
| ATOM | 4619 | O | MET | I | 114 | 1.468 | −19.731 | 35.209 | 1.00 | 75.78 | O |
| ATOM | 4620 | CB | MET | I | 114 | 4.110 | −18.125 | 35.267 | 1.00 | 71.15 | C |
| ATOM | 4621 | CG | MET | I | 114 | 4.394 | −17.881 | 36.754 | 1.00 | 74.06 | C |
| ATOM | 4622 | SD | MET | I | 114 | 5.920 | −18.639 | 37.375 | 1.00 | 77.83 | S |
| ATOM | 4623 | CE | MET | I | 114 | 5.398 | −19.238 | 39.001 | 1.00 | 73.87 | C |
| ATOM | 4624 | N | VAL | I | 115 | 2.735 | −21.053 | 36.518 | 1.00 | 74.20 | N |
| ATOM | 4625 | CA | VAL | I | 115 | 1.610 | −21.640 | 37.227 | 1.00 | 75.92 | C |
| ATOM | 4626 | C | VAL | I | 115 | 1.717 | −21.248 | 38.690 | 1.00 | 82.15 | C |
| ATOM | 4627 | O | VAL | I | 115 | 2.560 | −21.770 | 39.430 | 1.00 | 80.62 | O |
| ATOM | 4628 | CB | VAL | I | 115 | 1.456 | −23.177 | 36.988 | 1.00 | 80.77 | C |
| ATOM | 4629 | CG1 | VAL | I | 115 | 0.340 | −23.778 | 37.850 | 1.00 | 80.34 | C |
| ATOM | 4630 | CG2 | VAL | I | 115 | 1.206 | −23.481 | 35.507 | 1.00 | 80.85 | C |
| ATOM | 4631 | N | THR | I | 116 | 0.865 | −20.299 | 39.082 | 1.00 | 81.34 | N |
| ATOM | 4632 | CA | THR | I | 116 | 0.771 | −19.743 | 40.422 | 1.00 | 81.86 | C |
| ATOM | 4633 | C | THR | I | 116 | −0.438 | −20.396 | 41.101 | 1.00 | 87.53 | C |
| ATOM | 4634 | O | THR | I | 116 | −1.546 | −20.317 | 40.561 | 1.00 | 86.65 | O |
| ATOM | 4635 | CB | THR | I | 116 | 0.724 | −18.204 | 40.327 | 1.00 | 89.20 | C |
| ATOM | 4636 | OG1 | THR | I | 116 | 1.448 | −17.765 | 39.159 | 1.00 | 84.58 | O |
| ATOM | 4637 | CG2 | THR | I | 116 | 1.262 | −17.527 | 41.582 | 1.00 | 87.40 | C |
| ATOM | 4638 | N | VAL | I | 117 | −0.199 | −21.108 | 42.239 | 1.00 | 86.38 | N |
| ATOM | 4639 | CA | VAL | I | 117 | −1.211 | −21.852 | 43.018 | 1.00 | 87.45 | C |
| ATOM | 4640 | C | VAL | I | 117 | −1.279 | −21.397 | 44.494 | 1.00 | 95.37 | C |
| ATOM | 4641 | O | VAL | I | 117 | −0.450 | −21.818 | 45.305 | 1.00 | 95.88 | O |
| ATOM | 4642 | CB | VAL | I | 117 | −1.048 | −23.410 | 42.956 | 1.00 | 91.11 | C |
| ATOM | 4643 | CG1 | VAL | I | 117 | −2.248 | −24.109 | 43.587 | 1.00 | 91.00 | C |
| ATOM | 4644 | CG2 | VAL | I | 117 | −0.826 | −23.917 | 41.537 | 1.00 | 90.87 | C |
| ATOM | 4645 | N | SER | I | 118 | −2.286 | −20.588 | 44.858 | 1.00 | 93.36 | N |
| ATOM | 4646 | CA | SER | I | 118 | −2.483 | −20.203 | 46.263 | 1.00 | 93.40 | C |
| ATOM | 4647 | C | SER | I | 118 | −3.958 | −20.006 | 46.607 | 1.00 | 95.19 | C |
| ATOM | 4648 | O | SER | I | 118 | −4.772 | −19.679 | 45.731 | 1.00 | 94.74 | O |
| ATOM | 4649 | CB | SER | I | 118 | −1.624 | −18.999 | 46.672 | 1.00 | 98.35 | C |
| ATOM | 4650 | OG | SER | I | 118 | −2.147 | −17.720 | 46.348 | 1.00 | 107.14 | O |
| ATOM | 4651 | N | SER | I | 119 | −4.286 | −20.210 | 47.895 | 1.00 | 89.69 | N |
| ATOM | 4652 | CA | SER | I | 119 | −5.623 | −20.049 | 48.473 | 1.00 | 88.21 | C |
| ATOM | 4653 | C | SER | I | 119 | −6.121 | −18.561 | 48.449 | 1.00 | 89.81 | C |

TABLE 1-continued

Three-dimensional crystal coordinate for anti-TcdB antibody beziotoxumab Fab –C. difficile toxin B (TcdB$^{(1834-2101)}$) complex.

| ATOM | 4654 | O | SER | I | 119 | −7.306 | −18.295 | 48.673 | 1.00 | 89.99 | O |
|---|---|---|---|---|---|---|---|---|---|---|---|
| ATOM | 4655 | CB | SER | I | 119 | −5.637 | −20.595 | 49.897 | 1.00 | 90.18 | C |
| ATOM | 4656 | OG | SER | I | 119 | −4.758 | −19.868 | 50.737 | 1.00 | 92.44 | O |
| ATOM | 4657 | N | ALA | I | 120 | −5.207 | −17.609 | 48.157 | 1.00 | 83.84 | N |
| ATOM | 4658 | CA | ALA | I | 120 | −5.442 | −16.164 | 48.067 | 1.00 | 81.80 | C |
| ATOM | 4659 | C | ALA | I | 120 | −6.378 | −15.788 | 46.926 | 1.00 | 83.10 | C |
| ATOM | 4660 | O | ALA | I | 120 | −6.582 | −16.575 | 46.005 | 1.00 | 82.12 | O |
| ATOM | 4661 | CB | ALA | I | 120 | −4.114 | −15.432 | 47.916 | 1.00 | 82.06 | C |
| ATOM | 4662 | N | SER | I | 121 | −6.927 | −14.571 | 46.985 | 1.00 | 79.17 | N |
| ATOM | 4663 | CA | SER | I | 121 | −7.861 | −14.034 | 45.999 | 1.00 | 79.25 | C |
| ATOM | 4664 | C | SER | I | 121 | −7.354 | −12.700 | 45.489 | 1.00 | 82.86 | C |
| ATOM | 4665 | O | SER | I | 121 | −6.668 | −11.993 | 46.231 | 1.00 | 82.44 | O |
| ATOM | 4666 | CB | SER | I | 121 | −9.238 | −13.841 | 46.630 | 1.00 | 83.90 | C |
| ATOM | 4667 | OG | SER | I | 121 | −9.490 | −14.807 | 47.641 | 1.00 | 94.48 | O |
| ATOM | 4668 | N | THR | I | 122 | −7.731 | −12.334 | 44.243 | 1.00 | 79.20 | N |
| ATOM | 4669 | CA | THR | I | 122 | −7.310 | −11.096 | 43.585 | 1.00 | 79.37 | C |
| ATOM | 4670 | C | THR | I | 122 | −7.609 | −9.848 | 44.424 | 1.00 | 87.44 | C |
| ATOM | 4671 | O | THR | I | 122 | −8.758 | −9.401 | 44.504 | 1.00 | 88.29 | O |
| ATOM | 4672 | CB | THR | I | 122 | −7.864 | −10.992 | 42.154 | 1.00 | 83.93 | C |
| ATOM | 4673 | OG1 | THR | I | 122 | −7.631 | −12.213 | 41.466 | 1.00 | 83.39 | O |
| ATOM | 4674 | CG2 | THR | I | 122 | −7.242 | −9.856 | 41.357 | 1.00 | 83.42 | C |
| ATOM | 4675 | N | LYS | I | 123 | −6.549 | −9.310 | 45.063 | 1.00 | 85.28 | N |
| ATOM | 4676 | CA | LYS | I | 123 | −6.545 | −8.080 | 45.853 | 1.00 | 84.99 | C |
| ATOM | 4677 | C | LYS | I | 123 | −5.632 | −7.086 | 45.147 | 1.00 | 91.44 | C |
| ATOM | 4678 | O | LYS | I | 123 | −4.590 | −7.462 | 44.602 | 1.00 | 91.05 | O |
| ATOM | 4679 | CB | LYS | I | 123 | −6.051 | −8.327 | 47.289 | 1.00 | 86.21 | C |
| ATOM | 4680 | N | GLY | I | 124 | −6.039 | −5.830 | 45.145 | 1.00 | 90.07 | N |
| ATOM | 4681 | CA | GLY | I | 124 | −5.259 | −4.754 | 44.544 | 1.00 | 90.55 | C |
| ATOM | 4682 | C | GLY | I | 124 | −4.180 | −4.246 | 45.485 | 1.00 | 95.76 | C |
| ATOM | 4683 | O | GLY | I | 124 | −4.203 | −4.562 | 46.683 | 1.00 | 95.81 | O |
| ATOM | 4684 | N | PRO | I | 125 | −3.228 | −3.425 | 44.988 | 1.00 | 92.42 | N |
| ATOM | 4685 | CA | PRO | I | 125 | −2.150 | −2.935 | 45.871 | 1.00 | 91.97 | C |
| ATOM | 4686 | C | PRO | I | 125 | −2.395 | −1.602 | 46.601 | 1.00 | 95.20 | C |
| ATOM | 4687 | O | PRO | I | 125 | −3.072 | −0.705 | 46.083 | 1.00 | 94.78 | O |
| ATOM | 4688 | CB | PRO | I | 125 | −0.970 | −2.806 | 44.910 | 1.00 | 93.56 | C |
| ATOM | 4689 | CG | PRO | I | 125 | −1.591 | −2.502 | 43.571 | 1.00 | 97.61 | C |
| ATOM | 4690 | CD | PRO | I | 125 | −3.022 | −2.983 | 43.592 | 1.00 | 93.48 | C |
| ATOM | 4691 | N | SER | I | 126 | −1.787 | −1.454 | 47.789 | 1.00 | 91.14 | N |
| ATOM | 4692 | CA | SER | I | 126 | −1.820 | −0.215 | 48.565 | 1.00 | 90.71 | C |
| ATOM | 4693 | C | SER | I | 126 | −0.483 | 0.475 | 48.253 | 1.00 | 96.04 | C |
| ATOM | 4694 | O | SER | I | 126 | 0.571 | −0.082 | 48.571 | 1.00 | 95.98 | O |
| ATOM | 4695 | CB | SER | I | 126 | −1.928 | −0.516 | 50.055 | 1.00 | 93.12 | C |
| ATOM | 4696 | OG | SER | I | 126 | −2.948 | −1.451 | 50.362 | 1.00 | 100.72 | O |
| ATOM | 4697 | N | VAL | I | 127 | −0.526 | 1.640 | 47.564 | 1.00 | 93.21 | N |
| ATOM | 4698 | CA | VAL | I | 127 | 0.656 | 2.409 | 47.123 | 1.00 | 93.25 | C |
| ATOM | 4699 | C | VAL | I | 127 | 0.979 | 3.585 | 48.090 | 1.00 | 96.42 | C |
| ATOM | 4700 | O | VAL | I | 127 | 0.316 | 4.627 | 48.042 | 1.00 | 96.23 | O |
| ATOM | 4701 | CB | VAL | I | 127 | 0.538 | 2.872 | 45.625 | 1.00 | 97.69 | C |
| ATOM | 4702 | CG1 | VAL | I | 127 | 1.805 | 3.590 | 45.143 | 1.00 | 97.64 | C |
| ATOM | 4703 | CG2 | VAL | I | 127 | 0.204 | 1.705 | 44.697 | 1.00 | 97.45 | C |
| ATOM | 4704 | N | PHE | I | 128 | 2.028 | 3.403 | 48.935 | 1.00 | 92.71 | N |
| ATOM | 4705 | CA | PHE | I | 128 | 2.544 | 4.343 | 49.946 | 1.00 | 92.43 | C |
| ATOM | 4706 | C | PHE | I | 128 | 3.824 | 5.035 | 49.464 | 1.00 | 99.28 | C |
| ATOM | 4707 | O | PHE | I | 128 | 4.641 | 4.378 | 48.807 | 1.00 | 98.69 | O |
| ATOM | 4708 | CB | PHE | I | 128 | 2.844 | 3.602 | 51.260 | 1.00 | 93.31 | C |
| ATOM | 4709 | CG | PHE | I | 128 | 1.689 | 2.798 | 51.773 | 1.00 | 93.93 | C |
| ATOM | 4710 | CD1 | PHE | I | 128 | 0.482 | 3.411 | 52.094 | 1.00 | 96.22 | C |
| ATOM | 4711 | CD2 | PHE | I | 128 | 1.795 | 1.426 | 51.919 | 1.00 | 95.72 | C |
| ATOM | 4712 | CE1 | PHE | I | 128 | −0.600 | 2.662 | 52.548 | 1.00 | 96.99 | C |
| ATOM | 4713 | CE2 | PHE | I | 128 | 0.714 | 0.677 | 52.387 | 1.00 | 98.52 | C |
| ATOM | 4714 | CZ | PHE | I | 128 | −0.469 | 1.304 | 52.718 | 1.00 | 96.33 | C |
| ATOM | 4715 | N | PRO | I | 129 | 4.048 | 6.344 | 49.766 | 1.00 | 97.35 | N |
| ATOM | 4716 | CA | PRO | I | 129 | 5.285 | 6.978 | 49.285 | 1.00 | 96.99 | C |
| ATOM | 4717 | C | PRO | I | 129 | 6.500 | 6.668 | 50.161 | 1.00 | 100.02 | C |
| ATOM | 4718 | O | PRO | I | 129 | 6.367 | 6.350 | 51.352 | 1.00 | 100.09 | O |
| ATOM | 4719 | CB | PRO | I | 129 | 4.938 | 8.469 | 49.266 | 1.00 | 98.62 | C |
| ATOM | 4720 | CG | PRO | I | 129 | 3.908 | 8.634 | 50.346 | 1.00 | 103.21 | C |
| ATOM | 4721 | CD | PRO | I | 129 | 3.209 | 7.302 | 50.526 | 1.00 | 98.88 | C |
| ATOM | 4722 | N | LEU | I | 130 | 7.688 | 6.726 | 49.540 | 1.00 | 94.69 | N |
| ATOM | 4723 | CA | LEU | I | 130 | 8.980 | 6.571 | 50.197 | 1.00 | 93.24 | C |
| ATOM | 4724 | C | LEU | I | 130 | 9.610 | 7.963 | 50.007 | 1.00 | 96.86 | C |
| ATOM | 4725 | O | LEU | I | 130 | 10.310 | 8.220 | 49.025 | 1.00 | 96.71 | O |
| ATOM | 4726 | CB | LEU | I | 130 | 9.812 | 5.425 | 49.567 | 1.00 | 92.58 | C |
| ATOM | 4727 | CG | LEU | I | 130 | 9.251 | 3.989 | 49.674 | 1.00 | 95.46 | C |
| ATOM | 4728 | CD1 | LEU | I | 130 | 10.007 | 3.044 | 48.774 | 1.00 | 95.36 | C |
| ATOM | 4729 | CD2 | LEU | I | 130 | 9.276 | 3.470 | 51.096 | 1.00 | 95.72 | C |
| ATOM | 4730 | N | ALA | I | 131 | 9.215 | 8.893 | 50.902 | 1.00 | 92.62 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 4731 | CA | ALA | I | 131 | 9.565 | 10.309 | 50.906 | 1.00 | 92.20 | C |
|------|------|----|-----|---|-----|-------|--------|--------|------|-------|---|
| ATOM | 4732 | C | ALA | I | 131 | 11.039 | 10.605 | 51.108 | 1.00 | 98.03 | C |
| ATOM | 4733 | O | ALA | I | 131 | 11.683 | 9.974 | 51.959 | 1.00 | 96.98 | O |
| ATOM | 4734 | CB | ALA | I | 131 | 8.737 | 11.053 | 51.942 | 1.00 | 92.74 | C |
| ATOM | 4735 | N | PRO | I | 132 | 11.577 | 11.597 | 50.344 | 1.00 | 96.54 | N |
| ATOM | 4736 | CA | PRO | I | 132 | 12.998 | 11.954 | 50.506 | 1.00 | 96.97 | C |
| ATOM | 4737 | C | PRO | I | 132 | 13.297 | 12.506 | 51.899 | 1.00 | 103.35 | C |
| ATOM | 4738 | O | PRO | I | 132 | 12.482 | 13.257 | 52.470 | 1.00 | 102.40 | O |
| ATOM | 4739 | CB | PRO | I | 132 | 13.242 | 13.003 | 49.409 | 1.00 | 98.18 | C |
| ATOM | 4740 | CG | PRO | I | 132 | 12.069 | 12.942 | 48.510 | 1.00 | 102.01 | C |
| ATOM | 4741 | CD | PRO | I | 132 | 10.924 | 12.448 | 49.325 | 1.00 | 97.63 | C |
| ATOM | 4742 | O | SER | I | 133 | 15.807 | 14.507 | 52.813 | 1.00 | 109.86 | O |
| ATOM | 4743 | N | SER | I | 133 | 14.451 | 12.087 | 52.463 | 1.00 | 101.65 | N |
| ATOM | 4744 | CA | SER | I | 133 | 14.895 | 12.517 | 53.790 | 1.00 | 101.99 | C |
| ATOM | 4745 | C | SER | I | 133 | 15.217 | 14.008 | 53.782 | 1.00 | 109.26 | C |
| ATOM | 4746 | CB | SER | I | 133 | 16.122 | 11.726 | 54.233 | 1.00 | 103.60 | C |
| ATOM | 4747 | OG | SER | I | 133 | 16.386 | 11.918 | 55.614 | 1.00 | 108.96 | O |
| ATOM | 4748 | O | SER | I | 134 | 17.179 | 17.419 | 54.952 | 1.00 | 111.11 | O |
| ATOM | 4749 | N | SER | I | 134 | 14.823 | 14.722 | 54.857 | 1.00 | 106.59 | N |
| ATOM | 4750 | CA | SER | I | 134 | 15.131 | 16.145 | 55.024 | 1.00 | 106.65 | C |
| ATOM | 4751 | C | SER | I | 134 | 16.659 | 16.329 | 55.193 | 1.00 | 111.62 | C |
| ATOM | 4752 | CB | SER | I | 134 | 14.358 | 16.739 | 56.198 | 1.00 | 109.65 | C |
| ATOM | 4753 | OG | SER | I | 134 | 14.300 | 15.863 | 57.313 | 1.00 | 117.05 | O |
| ATOM | 4754 | O | LYS | I | 135 | 20.125 | 16.292 | 54.067 | 1.00 | 119.04 | O |
| ATOM | 4755 | N | LYS | I | 135 | 17.367 | 15.231 | 55.543 | 1.00 | 109.47 | N |
| ATOM | 4756 | CA | LYS | I | 135 | 18.812 | 15.148 | 55.693 | 1.00 | 110.34 | C |
| ATOM | 4757 | C | LYS | I | 135 | 19.486 | 15.267 | 54.316 | 1.00 | 118.67 | C |
| ATOM | 4758 | CB | LYS | I | 135 | 19.208 | 13.841 | 56.402 | 1.00 | 112.25 | C |
| ATOM | 4759 | O | SER | I | 136 | 20.432 | 16.303 | 51.319 | 1.00 | 123.06 | O |
| ATOM | 4760 | N | SER | I | 136 | 19.294 | 14.246 | 53.421 | 1.00 | 117.45 | N |
| ATOM | 4761 | CA | SER | I | 136 | 19.815 | 14.078 | 52.038 | 1.00 | 118.01 | C |
| ATOM | 4762 | C | SER | I | 136 | 20.830 | 15.157 | 51.580 | 1.00 | 123.25 | C |
| ATOM | 4763 | CB | SER | I | 136 | 18.670 | 13.954 | 51.031 | 1.00 | 121.12 | C |
| ATOM | 4764 | OG | SER | I | 136 | 17.952 | 15.165 | 50.859 | 1.00 | 128.40 | O |
| ATOM | 4765 | O | THR | I | 137 | 22.882 | 16.248 | 48.894 | 1.00 | 123.47 | O |
| ATOM | 4766 | N | THR | I | 137 | 22.143 | 14.765 | 51.502 | 1.00 | 120.14 | N |
| ATOM | 4767 | CA | THR | I | 137 | 23.329 | 15.590 | 51.162 | 1.00 | 119.74 | C |
| ATOM | 4768 | C | THR | I | 137 | 23.006 | 16.621 | 50.065 | 1.00 | 123.40 | C |
| ATOM | 4769 | CB | THR | I | 137 | 24.577 | 14.708 | 50.834 | 1.00 | 127.04 | C |
| ATOM | 4770 | OG1 | THR | I | 137 | 24.439 | 14.087 | 49.554 | 1.00 | 128.39 | O |
| ATOM | 4771 | CG2 | THR | I | 137 | 24.866 | 13.645 | 51.900 | 1.00 | 123.70 | C |
| ATOM | 4772 | O | SER | I | 138 | 24.670 | 19.226 | 48.769 | 1.00 | 120.71 | O |
| ATOM | 4773 | N | SER | I | 138 | 22.780 | 17.901 | 50.469 | 1.00 | 119.16 | N |
| ATOM | 4774 | CA | SER | I | 138 | 22.405 | 18.996 | 49.558 | 1.00 | 118.61 | C |
| ATOM | 4775 | C | SER | I | 138 | 23.466 | 19.274 | 48.486 | 1.00 | 121.40 | C |
| ATOM | 4776 | CB | SER | I | 138 | 22.034 | 20.263 | 50.322 | 1.00 | 121.85 | C |
| ATOM | 4777 | OG | SER | I | 138 | 21.179 | 21.080 | 49.537 | 1.00 | 129.21 | O |
| ATOM | 4778 | O | GLY | I | 139 | 23.874 | 18.272 | 44.136 | 1.00 | 117.83 | O |
| ATOM | 4779 | N | GLY | I | 139 | 22.992 | 19.500 | 47.257 | 1.00 | 116.67 | N |
| ATOM | 4780 | CA | GLY | I | 139 | 23.828 | 19.685 | 46.076 | 1.00 | 115.68 | C |
| ATOM | 4781 | C | GLY | I | 139 | 23.991 | 18.353 | 45.367 | 1.00 | 117.62 | C |
| ATOM | 4782 | O | GLY | I | 140 | 22.137 | 15.918 | 44.869 | 1.00 | 106.65 | O |
| ATOM | 4783 | N | GLY | I | 140 | 24.221 | 17.308 | 46.175 | 1.00 | 110.84 | N |
| ATOM | 4784 | CA | GLY | I | 140 | 24.357 | 15.917 | 45.760 | 1.00 | 108.70 | C |
| ATOM | 4785 | C | GLY | I | 140 | 23.032 | 15.261 | 45.416 | 1.00 | 107.45 | C |
| ATOM | 4786 | N | THR | I | 141 | 22.896 | 13.947 | 45.720 | 1.00 | 100.21 | N |
| ATOM | 4787 | CA | THR | I | 141 | 21.696 | 13.184 | 45.353 | 1.00 | 97.96 | C |
| ATOM | 4788 | C | THR | I | 141 | 20.905 | 12.616 | 46.538 | 1.00 | 99.17 | C |
| ATOM | 4789 | O | THR | I | 141 | 21.464 | 12.258 | 47.580 | 1.00 | 98.05 | O |
| ATOM | 4790 | CB | THR | I | 141 | 22.007 | 12.056 | 44.327 | 1.00 | 96.77 | C |
| ATOM | 4791 | OG1 | THR | I | 141 | 22.607 | 10.942 | 44.984 | 1.00 | 91.02 | O |
| ATOM | 4792 | CG2 | THR | I | 141 | 22.864 | 12.515 | 43.133 | 1.00 | 92.83 | C |
| ATOM | 4793 | N | ALA | I | 142 | 19.590 | 12.496 | 46.321 | 1.00 | 94.79 | N |
| ATOM | 4794 | CA | ALA | I | 142 | 18.594 | 11.963 | 47.248 | 1.00 | 94.09 | C |
| ATOM | 4795 | C | ALA | I | 142 | 17.849 | 10.784 | 46.605 | 1.00 | 95.35 | C |
| ATOM | 4796 | O | ALA | I | 142 | 17.808 | 10.669 | 45.373 | 1.00 | 93.87 | O |
| ATOM | 4797 | CB | ALA | I | 142 | 17.596 | 13.060 | 47.606 | 1.00 | 94.93 | C |
| ATOM | 4798 | N | ALA | I | 143 | 17.246 | 9.918 | 47.442 | 1.00 | 90.67 | N |
| ATOM | 4799 | CA | ALA | I | 143 | 16.456 | 8.789 | 46.961 | 1.00 | 89.84 | C |
| ATOM | 4800 | C | ALA | I | 143 | 15.020 | 8.871 | 47.445 | 1.00 | 93.12 | C |
| ATOM | 4801 | O | ALA | I | 143 | 14.766 | 9.241 | 48.594 | 1.00 | 94.15 | O |
| ATOM | 4802 | CB | ALA | I | 143 | 17.072 | 7.473 | 47.395 | 1.00 | 90.50 | C |
| ATOM | 4803 | N | LEU | I | 144 | 14.082 | 8.517 | 46.553 | 1.00 | 87.96 | N |
| ATOM | 4804 | CA | LEU | I | 144 | 12.638 | 8.443 | 46.791 | 1.00 | 86.62 | C |
| ATOM | 4805 | C | LEU | I | 144 | 12.049 | 7.255 | 46.019 | 1.00 | 91.15 | C |
| ATOM | 4806 | O | LEU | I | 144 | 12.664 | 6.781 | 45.064 | 1.00 | 89.73 | O |
| ATOM | 4807 | CB | LEU | I | 144 | 11.928 | 9.756 | 46.413 | 1.00 | 85.89 | C |

TABLE 1-continued

Three-dimensional crystal coordinate for anti-TcdB antibody beziotoxumab Fab – *C. difficile* toxin B (TcdB$^{(1834-2101)}$) complex.

| ATOM | 4808 | CG  | LEU | I | 144 | 12.065 | 10.252  | 44.984 | 1.00 | 88.65  | C |
| ---- | ---- | --- | --- | - | --- | ------ | ------- | ------ | ---- | ------ | - |
| ATOM | 4809 | CD1 | LEU | I | 144 | 10.843 | 9.923   | 44.184 | 1.00 | 88.53  | C |
| ATOM | 4810 | CD2 | LEU | I | 144 | 12.255 | 11.719  | 44.964 | 1.00 | 89.24  | C |
| ATOM | 4811 | N   | GLY | I | 145 | 10.871 | 6.801   | 46.425 | 1.00 | 89.47  | N |
| ATOM | 4812 | CA  | GLY | I | 145 | 10.212 | 5.690   | 45.758 | 1.00 | 89.42  | C |
| ATOM | 4813 | C   | GLY | I | 145 | 8.773  | 5.448   | 46.155 | 1.00 | 93.08  | C |
| ATOM | 4814 | O   | GLY | I | 145 | 8.130  | 6.313   | 46.760 | 1.00 | 92.16  | O |
| ATOM | 4815 | N   | CYS | I | 146 | 8.283  | 4.228   | 45.846 | 1.00 | 89.47  | N |
| ATOM | 4816 | CA  | CYS | I | 146 | 6.928  | 3.753   | 46.136 | 1.00 | 88.68  | C |
| ATOM | 4817 | C   | CYS | I | 146 | 6.917  | 2.396   | 46.837 | 1.00 | 87.38  | C |
| ATOM | 4818 | O   | CYS | I | 146 | 7.780  | 1.562   | 46.583 | 1.00 | 86.24  | O |
| ATOM | 4819 | CB  | CYS | I | 146 | 6.061  | 3.755   | 44.876 | 1.00 | 89.65  | C |
| ATOM | 4820 | SG  | CYS | I | 146 | 5.636  | 5.415   | 44.309 | 1.00 | 94.46  | S |
| ATOM | 4821 | N   | LEU | I | 147 | 5.960  | 2.199   | 47.747 | 1.00 | 81.04  | N |
| ATOM | 4822 | CA  | LEU | I | 147 | 5.785  | 0.940   | 48.443 | 1.00 | 79.87  | C |
| ATOM | 4823 | C   | LEU | I | 147 | 4.465  | 0.319   | 47.973 | 1.00 | 86.78  | C |
| ATOM | 4824 | O   | LEU | I | 147 | 3.394  | 0.687   | 48.462 | 1.00 | 87.19  | O |
| ATOM | 4825 | CB  | LEU | I | 147 | 5.843  | 1.104   | 49.970 | 1.00 | 78.70  | C |
| ATOM | 4826 | CG  | LEU | I | 147 | 5.531  | -0.144  | 50.779 | 1.00 | 81.69  | C |
| ATOM | 4827 | CD1 | LEU | I | 147 | 6.532  | -1.225  | 50.530 | 1.00 | 80.60  | C |
| ATOM | 4828 | CD2 | LEU | I | 147 | 5.423  | 0.173   | 52.242 | 1.00 | 84.29  | C |
| ATOM | 4829 | N   | VAL | I | 148 | 4.556  | -0.596  | 46.984 | 1.00 | 83.92  | N |
| ATOM | 4830 | CA  | VAL | I | 148 | 3.427  | -1.328  | 46.402 | 1.00 | 83.30  | C |
| ATOM | 4831 | C   | VAL | I | 148 | 3.204  | -2.527  | 47.338 | 1.00 | 87.17  | C |
| ATOM | 4832 | O   | VAL | I | 148 | 3.831  | -3.569  | 47.162 | 1.00 | 86.56  | O |
| ATOM | 4833 | CB  | VAL | I | 148 | 3.728  | -1.740  | 44.928 | 1.00 | 86.52  | C |
| ATOM | 4834 | CG1 | VAL | I | 148 | 2.542  | -2.463  | 44.303 | 1.00 | 86.44  | C |
| ATOM | 4835 | CG2 | VAL | I | 148 | 4.134  | -0.535  | 44.073 | 1.00 | 85.65  | C |
| ATOM | 4836 | N   | LYS | I | 149 | 2.392  | -2.329  | 48.398 | 1.00 | 84.85  | N |
| ATOM | 4837 | CA  | LYS | I | 149 | 2.137  | -3.336  | 49.430 | 1.00 | 84.88  | C |
| ATOM | 4838 | C   | LYS | I | 149 | 0.813  | -4.067  | 49.266 | 1.00 | 91.28  | C |
| ATOM | 4839 | O   | LYS | I | 149 | -0.152 | -3.507  | 48.742 | 1.00 | 90.02  | O |
| ATOM | 4840 | CB  | LYS | I | 149 | 2.265  | -2.745  | 50.850 | 1.00 | 86.36  | C |
| ATOM | 4841 | N   | ASP | I | 150 | 0.803  | -5.345  | 49.723 | 1.00 | 90.59  | N |
| ATOM | 4842 | CA  | ASP | I | 150 | -0.288 | -6.329  | 49.752 | 1.00 | 90.77  | C |
| ATOM | 4843 | C   | ASP | I | 150 | -1.144 | -6.368  | 48.449 | 1.00 | 94.40  | C |
| ATOM | 4844 | O   | ASP | I | 150 | -2.120 | -5.623  | 48.303 | 1.00 | 93.76  | O |
| ATOM | 4845 | CB  | ASP | I | 150 | -1.149 | -6.140  | 51.012 | 1.00 | 92.68  | C |
| ATOM | 4846 | CG  | ASP | I | 150 | -0.374 | -6.310  | 52.307 | 1.00 | 106.15 | C |
| ATOM | 4847 | OD1 | ASP | I | 150 | 0.064  | -7.457  | 52.601 | 1.00 | 109.72 | O |
| ATOM | 4848 | OD2 | ASP | I | 150 | -0.196 | -5.304  | 53.024 | 1.00 | 108.69 | O |
| ATOM | 4849 | N   | TYR | I | 151 | -0.739 | -7.238  | 47.502 | 1.00 | 90.14  | N |
| ATOM | 4850 | CA  | TYR | I | 151 | -1.427 | -7.431  | 46.224 | 1.00 | 89.25  | C |
| ATOM | 4851 | C   | TYR | I | 151 | -1.380 | -8.886  | 45.748 | 1.00 | 89.59  | C |
| ATOM | 4852 | O   | TYR | I | 151 | -0.535 | -9.670  | 46.183 | 1.00 | 87.99  | O |
| ATOM | 4853 | CB  | TYR | I | 151 | -0.928 | -6.451  | 45.137 | 1.00 | 91.18  | C |
| ATOM | 4854 | CG  | TYR | I | 151 | 0.427  | -6.768  | 44.528 | 1.00 | 95.03  | C |
| ATOM | 4855 | CD1 | TYR | I | 151 | 0.552  | -7.695  | 43.491 | 1.00 | 97.94  | C |
| ATOM | 4856 | CD2 | TYR | I | 151 | 1.567  | -6.068  | 44.911 | 1.00 | 95.50  | C |
| ATOM | 4857 | CE1 | TYR | I | 151 | 1.790  | -7.973  | 42.911 | 1.00 | 98.31  | C |
| ATOM | 4858 | CE2 | TYR | I | 151 | 2.809  | -6.332  | 44.329 | 1.00 | 95.99  | C |
| ATOM | 4859 | CZ  | TYR | I | 151 | 2.912  | -7.279  | 43.325 | 1.00 | 101.86 | C |
| ATOM | 4860 | OH  | TYR | I | 151 | 4.121  | -7.530  | 42.730 | 1.00 | 101.50 | O |
| ATOM | 4861 | N   | PHE | I | 152 | -2.303 | -9.232  | 44.845 | 1.00 | 85.38  | N |
| ATOM | 4862 | CA  | PHE | I | 152 | -2.427 | -10.560 | 44.254 | 1.00 | 84.53  | C |
| ATOM | 4863 | C   | PHE | I | 152 | -3.239 | -10.536 | 42.957 | 1.00 | 89.25  | C |
| ATOM | 4864 | O   | PHE | I | 152 | -4.292 | -9.899  | 42.910 | 1.00 | 88.28  | O |
| ATOM | 4865 | CB  | PHE | I | 152 | -3.060 | -11.562 | 45.237 | 1.00 | 85.62  | C |
| ATOM | 4866 | CG  | PHE | I | 152 | -2.835 | -12.994 | 44.837 | 1.00 | 86.53  | C |
| ATOM | 4867 | CD1 | PHE | I | 152 | -1.678 | -13.663 | 45.213 | 1.00 | 88.88  | C |
| ATOM | 4868 | CD2 | PHE | I | 152 | -3.762 | -13.668 | 44.054 | 1.00 | 88.88  | C |
| ATOM | 4869 | CE1 | PHE | I | 152 | -1.455 | -14.983 | 44.815 | 1.00 | 91.47  | C |
| ATOM | 4870 | CE2 | PHE | I | 152 | -3.534 | -14.981 | 43.650 | 1.00 | 89.70  | C |
| ATOM | 4871 | CZ  | PHE | I | 152 | -2.381 | -15.629 | 44.031 | 1.00 | 89.17  | C |
| ATOM | 4872 | N   | PRO | I | 153 | -2.803 | -11.274 | 41.910 | 1.00 | 86.54  | N |
| ATOM | 4873 | CA  | PRO | I | 153 | -1.554 | -12.051 | 41.792 | 1.00 | 86.21  | C |
| ATOM | 4874 | C   | PRO | I | 153 | -0.435 | -11.203 | 41.165 | 1.00 | 90.56  | C |
| ATOM | 4875 | O   | PRO | I | 153 | -0.620 | -9.991  | 40.972 | 1.00 | 90.08  | O |
| ATOM | 4876 | CB  | PRO | I | 153 | -1.989 | -13.214 | 40.894 | 1.00 | 87.65  | C |
| ATOM | 4877 | CG  | PRO | I | 153 | -3.146 | -12.648 | 40.034 | 1.00 | 91.68  | C |
| ATOM | 4878 | CD  | PRO | I | 153 | -3.578 | -11.341 | 40.657 | 1.00 | 87.36  | C |
| ATOM | 4879 | N   | GLU | I | 154 | 0.720  | -11.829 | 40.838 | 1.00 | 87.04  | N |
| ATOM | 4880 | CA  | GLU | I | 154 | 1.807  | -11.150 | 40.133 | 1.00 | 86.47  | C |
| ATOM | 4881 | C   | GLU | I | 154 | 1.349  | -11.006 | 38.663 | 1.00 | 92.03  | C |
| ATOM | 4882 | O   | GLU | I | 154 | 0.627  | -11.887 | 38.187 | 1.00 | 92.57  | O |
| ATOM | 4883 | CB  | GLU | I | 154 | 3.087  | -12.001 | 40.205 | 1.00 | 87.28  | C |
| ATOM | 4884 | CG  | GLU | I | 154 | 4.027  | -11.624 | 41.337 | 1.00 | 93.92  | C |

TABLE 1-continued

Three-dimensional crystal coordinate for anti-TcdB antibody beziotoxumab Fab –C. *difficile* toxin B (TcdB$^{(1834-2101)}$) complex.

| ATOM | 4885 | CD | GLU | I | 154 | 5.041 | −10.535 | 41.024 | 1.00 | 108.42 | C |
|---|---|---|---|---|---|---|---|---|---|---|---|
| ATOM | 4886 | OE1 | GLU | I | 154 | 6.254 | −10.849 | 41.050 | 1.00 | 114.38 | O |
| ATOM | 4887 | OE2 | GLU | I | 154 | 4.639 | −9.370 | 40.778 | 1.00 | 83.15 | O |
| ATOM | 4888 | N | PRO | I | 155 | 1.642 | −9.908 | 37.935 | 1.00 | 89.32 | N |
| ATOM | 4889 | CA | PRO | I | 155 | 2.525 | −8.784 | 38.258 | 1.00 | 89.38 | C |
| ATOM | 4890 | C | PRO | I | 155 | 1.876 | −7.392 | 38.384 | 1.00 | 92.57 | C |
| ATOM | 4891 | O | PRO | I | 155 | 0.715 | −7.173 | 38.011 | 1.00 | 91.20 | O |
| ATOM | 4892 | CB | PRO | I | 155 | 3.443 | −8.766 | 37.024 | 1.00 | 90.92 | C |
| ATOM | 4893 | CG | PRO | I | 155 | 2.509 | −9.189 | 35.863 | 1.00 | 95.18 | C |
| ATOM | 4894 | CD | PRO | I | 155 | 1.284 | −9.849 | 36.504 | 1.00 | 90.95 | C |
| ATOM | 4895 | N | VAL | I | 156 | 2.697 | −6.434 | 38.854 | 1.00 | 89.14 | N |
| ATOM | 4896 | CA | VAL | I | 156 | 2.415 | −5.004 | 38.897 | 1.00 | 89.18 | C |
| ATOM | 4897 | C | VAL | I | 156 | 3.462 | −4.368 | 37.979 | 1.00 | 93.38 | C |
| ATOM | 4898 | O | VAL | I | 156 | 4.532 | −4.966 | 37.781 | 1.00 | 92.47 | O |
| ATOM | 4899 | CB | VAL | I | 156 | 2.429 | −4.359 | 40.316 | 1.00 | 93.34 | C |
| ATOM | 4900 | CG1 | VAL | I | 156 | 1.265 | −4.847 | 41.173 | 1.00 | 93.11 | C |
| ATOM | 4901 | CG2 | VAL | I | 156 | 3.762 | −4.559 | 41.031 | 1.00 | 93.24 | C |
| ATOM | 4902 | N | THR | I | 157 | 3.160 | −3.186 | 37.404 | 1.00 | 90.16 | N |
| ATOM | 4903 | CA | THR | I | 157 | 4.106 | −2.453 | 36.554 | 1.00 | 90.00 | C |
| ATOM | 4904 | C | THR | I | 157 | 4.266 | −1.044 | 37.094 | 1.00 | 93.54 | C |
| ATOM | 4905 | O | THR | I | 157 | 3.268 | −0.349 | 37.283 | 1.00 | 93.08 | O |
| ATOM | 4906 | CB | THR | I | 157 | 3.686 | −2.432 | 35.078 | 1.00 | 100.22 | C |
| ATOM | 4907 | OG1 | THR | I | 157 | 2.551 | −1.573 | 34.915 | 1.00 | 105.88 | O |
| ATOM | 4908 | CG2 | THR | I | 157 | 3.422 | −3.822 | 34.507 | 1.00 | 96.38 | C |
| ATOM | 4909 | N | VAL | I | 158 | 5.510 | −0.622 | 37.350 | 1.00 | 90.13 | N |
| ATOM | 4910 | CA | VAL | I | 158 | 5.793 | 0.730 | 37.839 | 1.00 | 89.42 | C |
| ATOM | 4911 | C | VAL | I | 158 | 6.566 | 1.542 | 36.790 | 1.00 | 94.55 | C |
| ATOM | 4912 | O | VAL | I | 158 | 7.432 | 1.001 | 36.091 | 1.00 | 93.59 | O |
| ATOM | 4913 | CB | VAL | I | 158 | 6.458 | 0.782 | 39.235 | 1.00 | 92.29 | C |
| ATOM | 4914 | CG1 | VAL | I | 158 | 6.300 | 2.171 | 39.848 | 1.00 | 92.21 | C |
| ATOM | 4915 | CG2 | VAL | I | 158 | 5.887 | −0.280 | 40.176 | 1.00 | 91.59 | C |
| ATOM | 4916 | N | SER | I | 159 | 6.202 | 2.833 | 36.664 | 1.00 | 92.98 | N |
| ATOM | 4917 | CA | SER | I | 159 | 6.797 | 3.847 | 35.774 | 1.00 | 93.53 | C |
| ATOM | 4918 | C | SER | I | 159 | 6.814 | 5.180 | 36.542 | 1.00 | 98.16 | C |
| ATOM | 4919 | O | SER | I | 159 | 6.191 | 5.234 | 37.613 | 1.00 | 96.98 | O |
| ATOM | 4920 | CB | SER | I | 159 | 5.974 | 3.990 | 34.495 | 1.00 | 97.29 | C |
| ATOM | 4921 | OG | SER | I | 159 | 4.648 | 4.397 | 34.781 | 1.00 | 107.32 | O |
| ATOM | 4922 | N | TRP | I | 160 | 7.452 | 6.275 | 36.005 | 1.00 | 95.47 | N |
| ATOM | 4923 | CA | TRP | I | 160 | 7.460 | 7.535 | 36.767 | 1.00 | 95.61 | C |
| ATOM | 4924 | C | TRP | I | 160 | 6.866 | 8.771 | 35.990 | 1.00 | 103.64 | C |
| ATOM | 4925 | O | TRP | I | 160 | 7.088 | 9.931 | 36.367 | 1.00 | 101.80 | O |
| ATOM | 4926 | CB | TRP | I | 160 | 8.847 | 7.798 | 37.370 | 1.00 | 93.26 | C |
| ATOM | 4927 | CG | TRP | I | 160 | 9.170 | 6.844 | 38.503 | 1.00 | 93.33 | C |
| ATOM | 4928 | CD1 | TRP | I | 160 | 9.706 | 5.592 | 38.392 | 1.00 | 95.87 | C |
| ATOM | 4929 | CD2 | TRP | I | 160 | 8.909 | 7.043 | 39.905 | 1.00 | 92.79 | C |
| ATOM | 4930 | NE1 | TRP | I | 160 | 9.824 | 5.011 | 39.635 | 1.00 | 94.61 | N |
| ATOM | 4931 | CE2 | TRP | I | 160 | 9.341 | 5.878 | 40.582 | 1.00 | 95.97 | C |
| ATOM | 4932 | CE3 | TRP | I | 160 | 8.375 | 8.104 | 40.660 | 1.00 | 93.72 | C |
| ATOM | 4933 | CZ2 | TRP | I | 160 | 9.255 | 5.744 | 41.975 | 1.00 | 94.88 | C |
| ATOM | 4934 | CZ3 | TRP | I | 160 | 8.300 | 7.972 | 42.041 | 1.00 | 94.71 | C |
| ATOM | 4935 | CH2 | TRP | I | 160 | 8.737 | 6.804 | 42.683 | 1.00 | 95.08 | C |
| ATOM | 4936 | N | ASN | I | 161 | 5.983 | 8.461 | 35.008 | 1.00 | 105.27 | N |
| ATOM | 4937 | CA | ASN | I | 161 | 5.127 | 9.302 | 34.143 | 1.00 | 107.48 | C |
| ATOM | 4938 | C | ASN | I | 161 | 5.781 | 10.452 | 33.359 | 1.00 | 115.17 | C |
| ATOM | 4939 | O | ASN | I | 161 | 6.446 | 11.309 | 33.954 | 1.00 | 114.89 | O |
| ATOM | 4940 | CB | ASN | I | 161 | 3.910 | 9.885 | 34.883 | 1.00 | 110.08 | C |
| ATOM | 4941 | CG | ASN | I | 161 | 2.679 | 9.939 | 33.991 | 1.00 | 131.37 | C |
| ATOM | 4942 | OD1 | ASN | I | 161 | 2.298 | 10.998 | 33.481 | 1.00 | 125.82 | O |
| ATOM | 4943 | ND2 | ASN | I | 161 | 2.094 | 8.780 | 33.682 | 1.00 | 120.55 | N |
| ATOM | 4944 | N | SER | I | 162 | 5.446 | 10.568 | 32.032 | 1.00 | 114.07 | N |
| ATOM | 4945 | CA | SER | I | 162 | 4.683 | 9.594 | 31.193 | 1.00 | 114.46 | C |
| ATOM | 4946 | C | SER | I | 162 | 5.747 | 8.600 | 30.683 | 1.00 | 118.36 | C |
| ATOM | 4947 | O | SER | I | 162 | 6.044 | 8.492 | 29.481 | 1.00 | 118.03 | O |
| ATOM | 4948 | CB | SER | I | 162 | 3.952 | 10.309 | 30.045 | 1.00 | 118.09 | C |
| ATOM | 4949 | OG | SER | I | 162 | 4.806 | 10.967 | 29.119 | 1.00 | 124.68 | O |
| ATOM | 4950 | O | GLY | I | 163 | 8.672 | 8.275 | 33.302 | 1.00 | 117.39 | O |
| ATOM | 4951 | N | GLY | I | 163 | 6.324 | 7.910 | 31.660 | 1.00 | 113.88 | N |
| ATOM | 4952 | CA | GLY | I | 163 | 7.543 | 7.146 | 31.547 | 1.00 | 113.35 | C |
| ATOM | 4953 | C | GLY | I | 163 | 8.516 | 8.181 | 32.079 | 1.00 | 116.16 | C |
| ATOM | 4954 | N | ALA | I | 164 | 8.975 | 9.112 | 31.175 | 1.00 | 109.50 | N |
| ATOM | 4955 | CA | ALA | I | 164 | 9.881 | 10.276 | 31.385 | 1.00 | 107.85 | C |
| ATOM | 4956 | C | ALA | I | 164 | 11.158 | 9.989 | 32.230 | 1.00 | 109.07 | C |
| ATOM | 4957 | O | ALA | I | 164 | 12.285 | 10.146 | 31.729 | 1.00 | 109.05 | O |
| ATOM | 4958 | CB | ALA | I | 164 | 9.119 | 11.459 | 31.959 | 1.00 | 108.30 | C |
| ATOM | 4959 | N | LEU | I | 165 | 10.971 | 9.599 | 33.504 | 1.00 | 102.24 | N |
| ATOM | 4960 | CA | LEU | I | 165 | 12.030 | 9.231 | 34.424 | 1.00 | 100.47 | C |
| ATOM | 4961 | C | LEU | I | 165 | 12.305 | 7.715 | 34.321 | 1.00 | 103.07 | C |

TABLE1-continued

Three-dimensional crystal coordinate for anti-TcdB antibody beziotoxumab
Fab –*C. difficile* toxin B (TcdB$^{(1834-2101)}$) complex.

| ATOM | 4962 | O | LEU | I | 165 | 11.457 | 6.888 | 34.677 | 1.00 | 101.94 | O |
|---|---|---|---|---|---|---|---|---|---|---|---|
| ATOM | 4963 | CB | LEU | I | 165 | 11.658 | 9.671 | 35.845 | 1.00 | 99.97 | C |
| ATOM | 4964 | CG | LEU | I | 165 | 12.689 | 9.497 | 36.941 | 1.00 | 103.60 | C |
| ATOM | 4965 | CD1 | LEU | I | 165 | 13.919 | 10.329 | 36.679 | 1.00 | 103.01 | C |
| ATOM | 4966 | CD2 | LEU | I | 165 | 12.100 | 9.883 | 38.262 | 1.00 | 106.28 | C |
| ATOM | 4967 | N | THR | I | 166 | 13.484 | 7.377 | 33.761 | 1.00 | 99.45 | N |
| ATOM | 4968 | CA | THR | I | 166 | 13.985 | 6.011 | 33.544 | 1.00 | 98.72 | C |
| ATOM | 4969 | C | THR | I | 166 | 15.361 | 5.827 | 34.204 | 1.00 | 100.98 | C |
| ATOM | 4970 | O | THR | I | 166 | 15.660 | 4.742 | 34.711 | 1.00 | 99.89 | O |
| ATOM | 4971 | CB | THR | I | 166 | 14.059 | 5.680 | 32.035 | 1.00 | 105.94 | C |
| ATOM | 4972 | OG1 | THR | I | 166 | 14.779 | 6.703 | 31.346 | 1.00 | 106.52 | O |
| ATOM | 4973 | CG2 | THR | I | 166 | 12.699 | 5.503 | 31.404 | 1.00 | 103.49 | C |
| ATOM | 4974 | N | SER | I | 167 | 16.195 | 6.897 | 34.169 | 1.00 | 97.09 | N |
| ATOM | 4975 | CA | SER | I | 167 | 17.552 | 6.963 | 34.719 | 1.00 | 96.17 | C |
| ATOM | 4976 | C | SER | I | 167 | 17.537 | 6.820 | 36.236 | 1.00 | 98.21 | C |
| ATOM | 4977 | O | SER | I | 167 | 16.808 | 7.543 | 36.930 | 1.00 | 97.76 | O |
| ATOM | 4978 | CB | SER | I | 167 | 18.224 | 8.281 | 34.327 | 1.00 | 99.05 | C |
| ATOM | 4979 | OG | SER | I | 167 | 19.375 | 8.112 | 33.518 | 1.00 | 106.96 | O |
| ATOM | 4980 | N | GLY | I | 168 | 18.327 | 5.867 | 36.725 | 1.00 | 93.26 | N |
| ATOM | 4981 | CA | GLY | I | 168 | 18.487 | 5.598 | 38.150 | 1.00 | 92.27 | C |
| ATOM | 4982 | C | GLY | I | 168 | 17.290 | 4.994 | 38.850 | 1.00 | 93.84 | C |
| ATOM | 4983 | O | GLY | I | 168 | 17.239 | 5.010 | 40.085 | 1.00 | 93.83 | O |
| ATOM | 4984 | N | VAL | I | 169 | 16.328 | 4.449 | 38.068 | 1.00 | 87.52 | N |
| ATOM | 4985 | CA | VAL | I | 169 | 15.117 | 3.796 | 38.577 | 1.00 | 85.23 | C |
| ATOM | 4986 | C | VAL | I | 169 | 15.452 | 2.344 | 38.847 | 1.00 | 86.23 | C |
| ATOM | 4987 | O | VAL | I | 169 | 16.071 | 1.689 | 37.998 | 1.00 | 86.89 | O |
| ATOM | 4988 | CB | VAL | I | 169 | 13.886 | 3.921 | 37.636 | 1.00 | 87.95 | C |
| ATOM | 4989 | CG1 | VAL | I | 169 | 12.668 | 3.205 | 38.223 | 1.00 | 87.55 | C |
| ATOM | 4990 | CG2 | VAL | I | 169 | 13.550 | 5.382 | 37.343 | 1.00 | 87.52 | C |
| ATOM | 4991 | N | HIS | I | 170 | 15.044 | 1.854 | 40.031 | 1.00 | 79.52 | N |
| ATOM | 4992 | CA | HIS | I | 170 | 15.216 | 0.483 | 40.473 | 1.00 | 78.66 | C |
| ATOM | 4993 | C | HIS | I | 170 | 13.893 | −0.091 | 40.970 | 1.00 | 81.41 | C |
| ATOM | 4994 | O | HIS | I | 170 | 13.495 | 0.170 | 42.106 | 1.00 | 80.23 | O |
| ATOM | 4995 | CB | HIS | I | 170 | 16.304 | 0.361 | 41.553 | 1.00 | 79.63 | C |
| ATOM | 4996 | CG | HIS | I | 170 | 17.706 | 0.531 | 41.045 | 1.00 | 83.75 | C |
| ATOM | 4997 | ND1 | HIS | I | 170 | 18.194 | −0.222 | 39.977 | 1.00 | 85.96 | N |
| ATOM | 4998 | CD2 | HIS | I | 170 | 18.703 | 1.321 | 41.510 | 1.00 | 85.58 | C |
| ATOM | 4999 | CE1 | HIS | I | 170 | 19.453 | 0.160 | 39.816 | 1.00 | 85.19 | C |
| ATOM | 5000 | NE2 | HIS | I | 170 | 19.805 | 1.082 | 40.716 | 1.00 | 85.39 | N |
| ATOM | 5001 | N | THR | I | 171 | 13.190 | −0.853 | 40.105 | 1.00 | 77.41 | N |
| ATOM | 5002 | CA | THR | I | 171 | 11.955 | −1.526 | 40.508 | 1.00 | 76.29 | C |
| ATOM | 5003 | C | THR | I | 171 | 12.399 | −2.902 | 40.982 | 1.00 | 78.77 | C |
| ATOM | 5004 | O | THR | I | 171 | 13.127 | −3.595 | 40.268 | 1.00 | 79.69 | O |
| ATOM | 5005 | CB | THR | I | 171 | 10.883 | −1.496 | 39.414 | 1.00 | 82.12 | C |
| ATOM | 5006 | OG1 | THR | I | 171 | 10.661 | −0.144 | 38.993 | 1.00 | 78.45 | O |
| ATOM | 5007 | CG2 | THR | I | 171 | 9.563 | −2.075 | 39.892 | 1.00 | 83.56 | C |
| ATOM | 5008 | N | PHE | I | 172 | 12.080 | −3.235 | 42.224 | 1.00 | 73.25 | N |
| ATOM | 5009 | CA | PHE | I | 172 | 12.551 | −4.468 | 42.815 | 1.00 | 73.28 | C |
| ATOM | 5010 | C | PHE | I | 172 | 11.671 | −5.642 | 42.561 | 1.00 | 80.56 | C |
| ATOM | 5011 | O | PHE | I | 172 | 10.454 | −5.474 | 42.490 | 1.00 | 81.22 | O |
| ATOM | 5012 | CB | PHE | I | 172 | 12.757 | −4.302 | 44.322 | 1.00 | 74.96 | C |
| ATOM | 5013 | CG | PHE | I | 172 | 13.980 | −3.499 | 44.686 | 1.00 | 76.33 | C |
| ATOM | 5014 | CD1 | PHE | I | 172 | 15.217 | −4.110 | 44.808 | 1.00 | 79.01 | C |
| ATOM | 5015 | CD2 | PHE | I | 172 | 13.890 | −2.134 | 44.924 | 1.00 | 78.58 | C |
| ATOM | 5016 | CE1 | PHE | I | 172 | 16.349 | −3.363 | 45.116 | 1.00 | 80.34 | C |
| ATOM | 5017 | CE2 | PHE | I | 172 | 15.020 | −1.391 | 45.261 | 1.00 | 81.64 | C |
| ATOM | 5018 | CZ | PHE | I | 172 | 16.242 | −2.010 | 45.359 | 1.00 | 79.92 | C |
| ATOM | 5019 | N | PRO | I | 173 | 12.257 | −6.863 | 42.489 | 1.00 | 79.18 | N |
| ATOM | 5020 | CA | PRO | I | 173 | 11.428 | −8.068 | 42.341 | 1.00 | 79.05 | C |
| ATOM | 5021 | C | PRO | I | 173 | 10.516 | −8.227 | 43.553 | 1.00 | 82.42 | C |
| ATOM | 5022 | O | PRO | I | 173 | 10.926 | −7.925 | 44.678 | 1.00 | 81.70 | O |
| ATOM | 5023 | CB | PRO | I | 173 | 12.457 | −9.203 | 42.303 | 1.00 | 80.80 | C |
| ATOM | 5024 | CG | PRO | I | 173 | 13.727 | −8.558 | 41.897 | 1.00 | 85.65 | C |
| ATOM | 5025 | CD | PRO | I | 173 | 13.692 | −7.217 | 42.540 | 1.00 | 81.35 | C |
| ATOM | 5026 | N | ALA | I | 174 | 9.270 | −8.675 | 43.312 | 1.00 | 78.53 | N |
| ATOM | 5027 | CA | ALA | I | 174 | 8.291 | −8.874 | 44.366 | 1.00 | 77.80 | C |
| ATOM | 5028 | C | ALA | I | 174 | 8.696 | −9.995 | 45.302 | 1.00 | 81.36 | C |
| ATOM | 5029 | O | ALA | I | 174 | 9.369 | −10.938 | 44.896 | 1.00 | 80.31 | O |
| ATOM | 5030 | CB | ALA | I | 174 | 6.929 | −9.157 | 43.769 | 1.00 | 78.45 | C |
| ATOM | 5031 | N | VAL | I | 175 | 8.318 | −9.859 | 46.569 | 1.00 | 79.11 | N |
| ATOM | 5032 | CA | VAL | I | 175 | 8.562 | −10.851 | 47.606 | 1.00 | 78.98 | C |
| ATOM | 5033 | C | VAL | I | 175 | 7.202 | −11.259 | 48.130 | 1.00 | 84.62 | C |
| ATOM | 5034 | O | VAL | I | 175 | 6.365 | −10.397 | 48.406 | 1.00 | 85.14 | O |
| ATOM | 5035 | CB | VAL | I | 175 | 9.518 | −10.376 | 48.733 | 1.00 | 81.98 | C |
| ATOM | 5036 | CG1 | VAL | I | 175 | 10.942 | −10.245 | 48.210 | 1.00 | 81.35 | C |
| ATOM | 5037 | CG2 | VAL | I | 175 | 9.049 | −9.064 | 49.363 | 1.00 | 81.82 | C |
| ATOM | 5038 | N | LEU | I | 176 | 6.943 | −12.562 | 48.181 | 1.00 | 81.22 | N |

TABLE 1-continued

Three-dimensional crystal coordinate for anti-TcdB antibody beziotoxumab
Fab –*C. difficile* toxin B (TcdB$^{(1834-2101)}$) complex.

| ATOM | 5039 | CA | LEU | I | 176 | 5.679 | −13.063 | 48.677 | 1.00 | 80.56 | C |
|---|---|---|---|---|---|---|---|---|---|---|---|
| ATOM | 5040 | C | LEU | I | 176 | 5.790 | −13.055 | 50.176 | 1.00 | 84.36 | C |
| ATOM | 5041 | O | LEU | I | 176 | 6.702 | −13.658 | 50.742 | 1.00 | 82.52 | O |
| ATOM | 5042 | CB | LEU | I | 176 | 5.375 | −14.486 | 48.141 | 1.00 | 80.78 | C |
| ATOM | 5043 | CG | LEU | I | 176 | 4.112 | −15.178 | 48.720 | 1.00 | 85.45 | C |
| ATOM | 5044 | CD1 | LEU | I | 176 | 2.863 | −14.836 | 47.919 | 1.00 | 85.54 | C |
| ATOM | 5045 | CD2 | LEU | I | 176 | 4.309 | −16.673 | 48.858 | 1.00 | 85.48 | C |
| ATOM | 5046 | N | GLN | I | 177 | 4.862 | −12.350 | 50.816 | 1.00 | 83.92 | N |
| ATOM | 5047 | CA | GLN | I | 177 | 4.763 | −12.236 | 52.279 | 1.00 | 84.30 | C |
| ATOM | 5048 | C | GLN | I | 177 | 4.141 | −13.527 | 52.868 | 1.00 | 90.28 | C |
| ATOM | 5049 | O | GLN | I | 177 | 3.617 | −14.366 | 52.124 | 1.00 | 90.10 | O |
| ATOM | 5050 | CB | GLN | I | 177 | 3.922 | −10.992 | 52.664 | 1.00 | 84.92 | C |
| ATOM | 5051 | CG | GLN | I | 177 | 4.341 | −9.706 | 51.937 | 1.00 | 88.13 | C |
| ATOM | 5052 | CD | GLN | I | 177 | 3.544 | −8.508 | 52.367 | 1.00 | 100.73 | C |
| ATOM | 5053 | OE1 | GLN | I | 177 | 3.772 | −7.949 | 53.442 | 1.00 | 101.57 | O |
| ATOM | 5054 | NE2 | GLN | I | 177 | 2.604 | −8.078 | 51.535 | 1.00 | 82.04 | N |
| ATOM | 5055 | N | SER | I | 178 | 4.208 | −13.679 | 54.201 | 1.00 | 88.20 | N |
| ATOM | 5056 | CA | SER | I | 178 | 3.597 | −14.794 | 54.948 | 1.00 | 88.55 | C |
| ATOM | 5057 | C | SER | I | 178 | 2.066 | −14.720 | 54.852 | 1.00 | 91.50 | C |
| ATOM | 5058 | O | SER | I | 178 | 1.387 | −15.742 | 55.000 | 1.00 | 90.72 | O |
| ATOM | 5059 | CB | SER | I | 178 | 4.018 | −14.737 | 56.415 | 1.00 | 93.39 | C |
| ATOM | 5060 | OG | SER | I | 178 | 3.822 | −13.437 | 56.950 | 1.00 | 104.56 | O |
| ATOM | 5061 | N | SER | I | 179 | 1.544 | −13.493 | 54.593 | 1.00 | 87.52 | N |
| ATOM | 5062 | CA | SER | I | 179 | 0.130 | −13.144 | 54.425 | 1.00 | 87.08 | C |
| ATOM | 5063 | C | SER | I | 179 | −0.521 | −13.793 | 53.200 | 1.00 | 90.02 | C |
| ATOM | 5064 | O | SER | I | 179 | −1.748 | −13.856 | 53.123 | 1.00 | 88.99 | O |
| ATOM | 5065 | CB | SER | I | 179 | −0.031 | −11.625 | 54.347 | 1.00 | 90.71 | C |
| ATOM | 5066 | OG | SER | I | 179 | 0.453 | −11.091 | 53.126 | 1.00 | 100.84 | O |
| ATOM | 5067 | N | GLY | I | 180 | 0.306 | −14.222 | 52.247 | 1.00 | 86.83 | N |
| ATOM | 5068 | CA | GLY | I | 180 | −0.127 | −14.821 | 50.990 | 1.00 | 86.26 | C |
| ATOM | 5069 | C | GLY | I | 180 | −0.163 | −13.819 | 49.858 | 1.00 | 89.12 | C |
| ATOM | 5070 | O | GLY | I | 180 | −0.425 | −14.198 | 48.714 | 1.00 | 88.61 | O |
| ATOM | 5071 | N | LEU | I | 181 | 0.138 | −12.529 | 50.172 | 1.00 | 85.62 | N |
| ATOM | 5072 | CA | LEU | I | 181 | 0.127 | −11.388 | 49.232 | 1.00 | 85.21 | C |
| ATOM | 5073 | C | LEU | I | 181 | 1.527 | −10.921 | 48.872 | 1.00 | 87.98 | C |
| ATOM | 5074 | O | LEU | I | 181 | 2.435 | −10.997 | 49.693 | 1.00 | 87.94 | O |
| ATOM | 5075 | CB | LEU | I | 181 | −0.686 | −10.205 | 49.794 | 1.00 | 85.31 | C |
| ATOM | 5076 | CG | LEU | I | 181 | −2.181 | −10.438 | 50.030 | 1.00 | 89.61 | C |
| ATOM | 5077 | CD1 | LEU | I | 181 | −2.453 | −10.925 | 51.456 | 1.00 | 89.27 | C |
| ATOM | 5078 | CD2 | LEU | I | 181 | −2.960 | −9.178 | 49.767 | 1.00 | 92.33 | C |
| ATOM | 5079 | N | TYR | I | 182 | 1.706 | −10.453 | 47.645 | 1.00 | 84.03 | N |
| ATOM | 5080 | CA | TYR | I | 182 | 3.004 | −10.004 | 47.142 | 1.00 | 84.04 | C |
| ATOM | 5081 | C | TYR | I | 182 | 3.263 | −8.538 | 47.466 | 1.00 | 87.97 | C |
| ATOM | 5082 | O | TYR | I | 182 | 2.319 | −7.751 | 47.582 | 1.00 | 86.84 | O |
| ATOM | 5083 | CB | TYR | I | 182 | 3.094 | −10.211 | 45.613 | 1.00 | 85.21 | C |
| ATOM | 5084 | CG | TYR | I | 182 | 3.075 | −11.655 | 45.149 | 1.00 | 86.64 | C |
| ATOM | 5085 | CD1 | TYR | I | 182 | 4.205 | −12.454 | 45.256 | 1.00 | 88.62 | C |
| ATOM | 5086 | CD2 | TYR | I | 182 | 1.961 | −12.187 | 44.506 | 1.00 | 87.24 | C |
| ATOM | 5087 | CE1 | TYR | I | 182 | 4.217 | −13.763 | 44.775 | 1.00 | 89.74 | C |
| ATOM | 5088 | CE2 | TYR | I | 182 | 1.962 | −13.494 | 44.015 | 1.00 | 87.97 | C |
| ATOM | 5089 | CZ | TYR | I | 182 | 3.092 | −14.283 | 44.159 | 1.00 | 92.80 | C |
| ATOM | 5090 | OH | TYR | I | 182 | 3.122 | −15.579 | 43.693 | 1.00 | 86.97 | O |
| ATOM | 5091 | N | SER | I | 183 | 4.555 | −8.164 | 47.571 | 1.00 | 85.19 | N |
| ATOM | 5092 | CA | SER | I | 183 | 4.973 | −6.785 | 47.823 | 1.00 | 84.83 | C |
| ATOM | 5093 | C | SER | I | 183 | 6.319 | −6.421 | 47.207 | 1.00 | 87.34 | C |
| ATOM | 5094 | O | SER | I | 183 | 7.255 | −7.219 | 47.249 | 1.00 | 87.11 | O |
| ATOM | 5095 | CB | SER | I | 183 | 4.977 | −6.484 | 49.316 | 1.00 | 89.01 | C |
| ATOM | 5096 | OG | SER | I | 183 | 3.656 | −6.241 | 49.764 | 1.00 | 99.89 | O |
| ATOM | 5097 | N | LEU | I | 184 | 6.413 | −5.205 | 46.648 | 1.00 | 82.67 | N |
| ATOM | 5098 | CA | LEU | I | 184 | 7.656 | −4.685 | 46.086 | 1.00 | 82.67 | C |
| ATOM | 5099 | C | LEU | I | 184 | 7.821 | −3.174 | 46.271 | 1.00 | 86.31 | C |
| ATOM | 5100 | O | LEU | I | 184 | 6.862 | −2.484 | 46.639 | 1.00 | 86.20 | O |
| ATOM | 5101 | CB | LEU | I | 184 | 7.865 | −5.084 | 44.614 | 1.00 | 82.76 | C |
| ATOM | 5102 | CG | LEU | I | 184 | 6.866 | −4.630 | 43.548 | 1.00 | 87.40 | C |
| ATOM | 5103 | CD1 | LEU | I | 184 | 7.155 | −3.225 | 43.049 | 1.00 | 86.84 | C |
| ATOM | 5104 | CD2 | LEU | I | 184 | 6.964 | −5.540 | 42.365 | 1.00 | 91.94 | C |
| ATOM | 5105 | N | SER | I | 185 | 9.044 | −2.665 | 45.987 | 1.00 | 81.21 | N |
| ATOM | 5106 | CA | SER | I | 185 | 9.365 | −1.245 | 46.063 | 1.00 | 79.97 | C |
| ATOM | 5107 | C | SER | I | 185 | 10.032 | −0.782 | 44.749 | 1.00 | 84.08 | C |
| ATOM | 5108 | O | SER | I | 185 | 10.873 | −1.502 | 44.208 | 1.00 | 83.89 | O |
| ATOM | 5109 | CB | SER | I | 185 | 10.276 | −0.953 | 47.259 | 1.00 | 80.99 | C |
| ATOM | 5110 | OG | SER | I | 185 | 9.792 | −1.437 | 48.504 | 1.00 | 81.72 | O |
| ATOM | 5111 | N | SER | I | 186 | 9.612 | 0.390 | 44.214 | 1.00 | 80.23 | N |
| ATOM | 5112 | CA | SER | I | 186 | 10.243 | 1.037 | 43.056 | 1.00 | 79.94 | C |
| ATOM | 5113 | C | SER | I | 186 | 10.863 | 2.325 | 43.589 | 1.00 | 83.41 | C |
| ATOM | 5114 | O | SER | I | 186 | 10.166 | 3.164 | 44.157 | 1.00 | 81.52 | O |
| ATOM | 5115 | CB | SER | I | 186 | 9.251 | 1.361 | 41.942 | 1.00 | 82.34 | C |

TABLE1-continued

Three-dimensional crystal coordinate for anti-TcdB antibody beziotoxumab Fab –*C. difficile* toxin B (TcdB$^{(1834-2101)}$) complex.

| ATOM | 5116 | OG  | SER | I | 186 | 9.876  | 2.160  | 40.945 | 1.00 | 85.14  | O |
|------|------|-----|-----|---|-----|--------|--------|--------|------|--------|---|
| ATOM | 5117 | N   | VAL | I | 187 | 12.183 | 2.447  | 43.441 | 1.00 | 80.65  | N |
| ATOM | 5118 | CA  | VAL | I | 187 | 12.960 | 3.587  | 43.933 | 1.00 | 80.16  | C |
| ATOM | 5119 | C   | VAL | I | 187 | 13.687 | 4.299  | 42.784 | 1.00 | 85.19  | C |
| ATOM | 5120 | O   | VAL | I | 187 | 13.859 | 3.718  | 41.713 | 1.00 | 84.52  | O |
| ATOM | 5121 | CB  | VAL | I | 187 | 13.925 | 3.175  | 45.088 | 1.00 | 82.67  | C |
| ATOM | 5122 | CG1 | VAL | I | 187 | 13.162 | 2.572  | 46.271 | 1.00 | 82.08  | C |
| ATOM | 5123 | CG2 | VAL | I | 187 | 15.013 | 2.226  | 44.592 | 1.00 | 82.02  | C |
| ATOM | 5124 | N   | VAL | I | 188 | 14.089 | 5.559  | 43.008 | 1.00 | 83.84  | N |
| ATOM | 5125 | CA  | VAL | I | 188 | 14.817 | 6.386  | 42.040 | 1.00 | 84.15  | C |
| ATOM | 5126 | C   | VAL | I | 188 | 15.692 | 7.406  | 42.782 | 1.00 | 88.55  | C |
| ATOM | 5127 | O   | VAL | I | 188 | 15.230 | 8.045  | 43.733 | 1.00 | 87.29  | O |
| ATOM | 5128 | CB  | VAL | I | 188 | 13.910 | 7.024  | 40.924 | 1.00 | 87.46  | C |
| ATOM | 5129 | CG1 | VAL | I | 188 | 12.920 | 8.044  | 41.493 | 1.00 | 86.52  | C |
| ATOM | 5130 | CG2 | VAL | I | 188 | 14.740 | 7.631  | 39.788 | 1.00 | 87.23  | C |
| ATOM | 5131 | N   | THR | I | 189 | 16.968 | 7.508  | 42.365 | 1.00 | 86.26  | N |
| ATOM | 5132 | CA  | THR | I | 189 | 17.916 | 8.484  | 42.891 | 1.00 | 86.21  | C |
| ATOM | 5133 | C   | THR | I | 189 | 17.875 | 9.696  | 41.978 | 1.00 | 91.22  | C |
| ATOM | 5134 | O   | THR | I | 189 | 18.007 | 9.568  | 40.762 | 1.00 | 89.89  | O |
| ATOM | 5135 | CB  | THR | I | 189 | 19.322 | 7.904  | 43.115 | 1.00 | 90.42  | C |
| ATOM | 5136 | OG1 | THR | I | 189 | 19.705 | 7.089  | 42.008 | 1.00 | 93.39  | O |
| ATOM | 5137 | CG2 | THR | I | 189 | 19.428 | 7.114  | 44.413 | 1.00 | 85.93  | C |
| ATOM | 5138 | N   | VAL | I | 190 | 17.611 | 10.863 | 42.570 | 1.00 | 90.14  | N |
| ATOM | 5139 | CA  | VAL | I | 190 | 17.502 | 12.152 | 41.877 | 1.00 | 90.60  | C |
| ATOM | 5140 | C   | VAL | I | 190 | 18.400 | 13.214 | 42.540 | 1.00 | 97.62  | C |
| ATOM | 5141 | O   | VAL | I | 190 | 18.760 | 13.026 | 43.708 | 1.00 | 97.62  | O |
| ATOM | 5142 | CB  | VAL | I | 190 | 16.023 | 12.637 | 41.807 | 1.00 | 94.09  | C |
| ATOM | 5143 | CG1 | VAL | I | 190 | 15.246 | 11.891 | 40.728 | 1.00 | 93.88  | C |
| ATOM | 5144 | CG2 | VAL | I | 190 | 15.324 | 12.558 | 43.168 | 1.00 | 93.53  | C |
| ATOM | 5145 | N   | PRO | I | 191 | 18.740 | 14.349 | 41.860 | 1.00 | 96.00  | N |
| ATOM | 5146 | CA  | PRO | I | 191 | 19.527 | 15.401 | 42.544 | 1.00 | 95.98  | C |
| ATOM | 5147 | C   | PRO | I | 191 | 18.718 | 16.060 | 43.680 | 1.00 | 98.22  | C |
| ATOM | 5148 | O   | PRO | I | 191 | 17.513 | 16.275 | 43.516 | 1.00 | 96.71  | O |
| ATOM | 5149 | CB  | PRO | I | 191 | 19.835 | 16.414 | 41.420 | 1.00 | 97.89  | C |
| ATOM | 5150 | CG  | PRO | I | 191 | 19.458 | 15.738 | 40.137 | 1.00 | 102.10 | C |
| ATOM | 5151 | CD  | PRO | I | 191 | 18.395 | 14.753 | 40.479 | 1.00 | 97.54  | C |
| ATOM | 5152 | N   | SER | I | 192 | 19.371 | 16.360 | 44.832 | 1.00 | 94.89  | N |
| ATOM | 5153 | CA  | SER | I | 192 | 18.747 | 16.988 | 46.010 | 1.00 | 94.73  | C |
| ATOM | 5154 | C   | SER | I | 192 | 18.123 | 18.352 | 45.705 | 1.00 | 99.92  | C |
| ATOM | 5155 | O   | SER | I | 192 | 17.158 | 18.751 | 46.368 | 1.00 | 100.04 | O |
| ATOM | 5156 | CB  | SER | I | 192 | 19.749 | 17.112 | 47.152 | 1.00 | 97.74  | C |
| ATOM | 5157 | OG  | SER | I | 192 | 19.975 | 15.853 | 47.764 | 1.00 | 105.99 | O |
| ATOM | 5158 | N   | SER | I | 193 | 18.669 | 19.050 | 44.687 | 1.00 | 97.04  | N |
| ATOM | 5159 | CA  | SER | I | 193 | 18.215 | 20.360 | 44.203 | 1.00 | 97.18  | C |
| ATOM | 5160 | C   | SER | I | 193 | 16.815 | 20.307 | 43.542 | 1.00 | 100.08 | C |
| ATOM | 5161 | O   | SER | I | 193 | 16.111 | 21.319 | 43.519 | 1.00 | 99.79  | O |
| ATOM | 5162 | CB  | SER | I | 193 | 19.239 | 20.949 | 43.232 | 1.00 | 101.65 | C |
| ATOM | 5163 | OG  | SER | I | 193 | 19.431 | 20.148 | 42.075 | 1.00 | 111.92 | O |
| ATOM | 5164 | N   | SER | I | 194 | 16.426 | 19.130 | 43.012 | 1.00 | 95.40  | N |
| ATOM | 5165 | CA  | SER | I | 194 | 15.153 | 18.879 | 42.328 | 1.00 | 94.30  | C |
| ATOM | 5166 | C   | SER | I | 194 | 13.944 | 18.852 | 43.278 | 1.00 | 97.25  | C |
| ATOM | 5167 | O   | SER | I | 194 | 12.842 | 19.201 | 42.864 | 1.00 | 96.45  | O |
| ATOM | 5168 | CB  | SER | I | 194 | 15.227 | 17.568 | 41.553 | 1.00 | 97.30  | C |
| ATOM | 5169 | OG  | SER | I | 194 | 16.446 | 17.437 | 40.839 | 1.00 | 106.38 | O |
| ATOM | 5170 | N   | LEU | I | 195 | 14.152 | 18.424 | 44.538 | 1.00 | 93.34  | N |
| ATOM | 5171 | CA  | LEU | I | 195 | 13.137 | 18.338 | 45.591 | 1.00 | 93.10  | C |
| ATOM | 5172 | C   | LEU | I | 195 | 12.506 | 19.727 | 45.832 | 1.00 | 97.84  | C |
| ATOM | 5173 | O   | LEU | I | 195 | 13.165 | 20.642 | 46.346 | 1.00 | 97.78  | O |
| ATOM | 5174 | CB  | LEU | I | 195 | 13.812 | 17.823 | 46.882 | 1.00 | 93.18  | C |
| ATOM | 5175 | CG  | LEU | I | 195 | 14.048 | 16.320 | 47.074 | 1.00 | 97.71  | C |
| ATOM | 5176 | CD1 | LEU | I | 195 | 14.826 | 15.686 | 45.905 | 1.00 | 97.43  | C |
| ATOM | 5177 | CD2 | LEU | I | 195 | 14.804 | 16.080 | 48.373 | 1.00 | 100.80 | C |
| ATOM | 5178 | N   | GLY | I | 196 | 11.257 | 19.880 | 45.413 | 1.00 | 94.64  | N |
| ATOM | 5179 | CA  | GLY | I | 196 | 10.540 | 21.147 | 45.509 | 1.00 | 94.76  | C |
| ATOM | 5180 | C   | GLY | I | 196 | 10.274 | 21.716 | 44.130 | 1.00 | 100.03 | C |
| ATOM | 5181 | O   | GLY | I | 196 | 9.144  | 22.114 | 43.831 | 1.00 | 99.76  | O |
| ATOM | 5182 | N   | THR | I | 197 | 11.314 | 21.722 | 43.266 | 1.00 | 97.57  | N |
| ATOM | 5183 | CA  | THR | I | 197 | 11.245 | 22.177 | 41.867 | 1.00 | 98.16  | C |
| ATOM | 5184 | C   | THR | I | 197 | 10.445 | 21.149 | 41.026 | 1.00 | 102.84 | C |
| ATOM | 5185 | O   | THR | I | 197 | 9.413  | 21.499 | 40.441 | 1.00 | 102.18 | O |
| ATOM | 5186 | CB  | THR | I | 197 | 12.678 | 22.367 | 41.297 | 1.00 | 109.28 | C |
| ATOM | 5187 | OG1 | THR | I | 197 | 13.473 | 23.115 | 42.215 | 1.00 | 111.17 | O |
| ATOM | 5188 | CG2 | THR | I | 197 | 12.695 | 23.025 | 39.914 | 1.00 | 107.72 | C |
| ATOM | 5189 | N   | GLN | I | 198 | 10.944 | 19.884 | 40.979 | 1.00 | 99.80  | N |
| ATOM | 5190 | CA  | GLN | I | 198 | 10.373 | 18.762 | 40.235 | 1.00 | 99.75  | C |
| ATOM | 5191 | C   | GLN | I | 198 | 9.413  | 17.892 | 41.028 | 1.00 | 103.58 | C |
| ATOM | 5192 | O   | GLN | I | 198 | 9.638  | 17.601 | 42.211 | 1.00 | 102.87 | O |

TABLE1-continued

Three-dimensional crystal coordinate for anti-TcdB antibody beziotoxumab Fab –C. difficile toxin B (TcdB$^{(1834-2101)}$) complex.

| ATOM | 5193 | CB | GLN | I | 198 | 11.465 | 17.882 | 39.599 | 1.00 | 101.22 | C |
| ATOM | 5194 | CG | GLN | I | 198 | 11.490 | 17.919 | 38.068 | 1.00 | 118.24 | C |
| ATOM | 5195 | CD | GLN | I | 198 | 10.187 | 17.495 | 37.441 | 1.00 | 137.84 | C |
| ATOM | 5196 | OE1 | GLN | I | 198 | 9.875 | 16.307 | 37.344 | 1.00 | 133.10 | O |
| ATOM | 5197 | NE2 | GLN | I | 198 | 9.391 | 18.463 | 37.013 | 1.00 | 131.29 | N |
| ATOM | 5198 | N | THR | I | 199 | 8.352 | 17.449 | 40.331 | 1.00 | 100.25 | N |
| ATOM | 5199 | CA | THR | I | 199 | 7.290 | 16.596 | 40.858 | 1.00 | 100.08 | C |
| ATOM | 5200 | C | THR | I | 199 | 7.553 | 15.157 | 40.464 | 1.00 | 103.20 | C |
| ATOM | 5201 | O | THR | I | 199 | 7.827 | 14.873 | 39.293 | 1.00 | 102.49 | O |
| ATOM | 5202 | CB | THR | I | 199 | 5.903 | 17.074 | 40.393 | 1.00 | 109.09 | C |
| ATOM | 5203 | OG1 | THR | I | 199 | 5.922 | 18.490 | 40.190 | 1.00 | 109.74 | O |
| ATOM | 5204 | CG2 | THR | I | 199 | 4.807 | 16.712 | 41.385 | 1.00 | 108.29 | C |
| ATOM | 5205 | N | TYR | I | 200 | 7.474 | 14.254 | 41.455 | 1.00 | 99.52 | N |
| ATOM | 5206 | CA | TYR | I | 200 | 7.714 | 12.825 | 41.271 | 1.00 | 99.29 | C |
| ATOM | 5207 | C | TYR | I | 200 | 6.472 | 12.000 | 41.575 | 1.00 | 104.26 | C |
| ATOM | 5208 | O | TYR | I | 200 | 6.025 | 11.951 | 42.727 | 1.00 | 104.99 | O |
| ATOM | 5209 | CB | TYR | I | 200 | 8.939 | 12.368 | 42.092 | 1.00 | 100.04 | C |
| ATOM | 5210 | CG | TYR | I | 200 | 10.216 | 13.054 | 41.664 | 1.00 | 101.65 | C |
| ATOM | 5211 | CD1 | TYR | I | 200 | 10.807 | 12.766 | 40.436 | 1.00 | 103.79 | C |
| ATOM | 5212 | CD2 | TYR | I | 200 | 10.806 | 14.036 | 42.459 | 1.00 | 102.17 | C |
| ATOM | 5213 | CE1 | TYR | I | 200 | 11.959 | 13.425 | 40.014 | 1.00 | 104.59 | C |
| ATOM | 5214 | CE2 | TYR | I | 200 | 11.963 | 14.700 | 42.050 | 1.00 | 102.87 | C |
| ATOM | 5215 | CZ | TYR | I | 200 | 12.536 | 14.388 | 40.825 | 1.00 | 109.36 | C |
| ATOM | 5216 | OH | TYR | I | 200 | 13.680 | 15.015 | 40.404 | 1.00 | 107.27 | O |
| ATOM | 5217 | N | ILE | I | 201 | 5.879 | 11.397 | 40.520 | 1.00 | 99.44 | N |
| ATOM | 5218 | CA | ILE | I | 201 | 4.689 | 10.544 | 40.635 | 1.00 | 98.10 | C |
| ATOM | 5219 | C | ILE | I | 201 | 5.017 | 9.175 | 40.064 | 1.00 | 99.19 | C |
| ATOM | 5220 | O | ILE | I | 201 | 5.558 | 9.094 | 38.955 | 1.00 | 98.53 | O |
| ATOM | 5221 | CB | ILE | I | 201 | 3.431 | 11.143 | 39.924 | 1.00 | 101.06 | C |
| ATOM | 5222 | CG1 | ILE | I | 201 | 3.221 | 12.639 | 40.253 | 1.00 | 101.01 | C |
| ATOM | 5223 | CG2 | ILE | I | 201 | 2.161 | 10.315 | 40.231 | 1.00 | 101.90 | C |
| ATOM | 5224 | CD1 | ILE | I | 201 | 2.652 | 13.423 | 39.137 | 1.00 | 106.55 | C |
| ATOM | 5225 | N | CYS | I | 202 | 4.677 | 8.105 | 40.803 | 1.00 | 93.61 | N |
| ATOM | 5226 | CA | CYS | I | 202 | 4.863 | 6.745 | 40.304 | 1.00 | 92.43 | C |
| ATOM | 5227 | C | CYS | I | 202 | 3.544 | 6.189 | 39.789 | 1.00 | 95.34 | C |
| ATOM | 5228 | O | CYS | I | 202 | 2.517 | 6.343 | 40.447 | 1.00 | 94.15 | O |
| ATOM | 5229 | CB | CYS | I | 202 | 5.503 | 5.823 | 41.342 | 1.00 | 91.95 | C |
| ATOM | 5230 | SG | CYS | I | 202 | 4.408 | 5.310 | 42.690 | 1.00 | 94.91 | S |
| ATOM | 5231 | N | ASN | I | 203 | 3.567 | 5.560 | 38.607 | 1.00 | 91.63 | N |
| ATOM | 5232 | CA | ASN | I | 203 | 2.357 | 4.973 | 38.035 | 1.00 | 90.93 | C |
| ATOM | 5233 | C | ASN | I | 203 | 2.388 | 3.456 | 38.167 | 1.00 | 93.62 | C |
| ATOM | 5234 | O | ASN | I | 203 | 3.119 | 2.765 | 37.443 | 1.00 | 92.60 | O |
| ATOM | 5235 | CB | ASN | I | 203 | 2.115 | 5.423 | 36.595 | 1.00 | 91.76 | C |
| ATOM | 5236 | CG | ASN | I | 203 | 2.697 | 6.764 | 36.230 | 1.00 | 101.68 | C |
| ATOM | 5237 | OD1 | ASN | I | 203 | 3.525 | 6.854 | 35.320 | 1.00 | 90.18 | O |
| ATOM | 5238 | ND2 | ASN | I | 203 | 2.267 | 7.829 | 36.912 | 1.00 | 89.26 | N |
| ATOM | 5239 | N | VAL | I | 204 | 1.617 | 2.962 | 39.150 | 1.00 | 90.03 | N |
| ATOM | 5240 | CA | VAL | I | 204 | 1.477 | 1.553 | 39.514 | 1.00 | 89.87 | C |
| ATOM | 5241 | C | VAL | I | 204 | 0.212 | 1.000 | 38.850 | 1.00 | 95.64 | C |
| ATOM | 5242 | O | VAL | I | 204 | −0.892 | 1.490 | 39.109 | 1.00 | 96.06 | O |
| ATOM | 5243 | CB | VAL | I | 204 | 1.460 | 1.356 | 41.052 | 1.00 | 92.93 | C |
| ATOM | 5244 | CG1 | VAL | I | 204 | 1.432 | −0.124 | 41.417 | 1.00 | 92.58 | C |
| ATOM | 5245 | CG2 | VAL | I | 204 | 2.644 | 2.048 | 41.712 | 1.00 | 92.56 | C |
| ATOM | 5246 | N | ASN | I | 205 | 0.384 | −0.016 | 37.986 | 1.00 | 91.97 | N |
| ATOM | 5247 | CA | ASN | I | 205 | −0.698 | −0.664 | 37.249 | 1.00 | 90.90 | C |
| ATOM | 5248 | C | ASN | I | 205 | −0.737 | −2.149 | 37.606 | 1.00 | 91.48 | C |
| ATOM | 5249 | O | ASN | I | 205 | 0.305 | −2.800 | 37.584 | 1.00 | 91.03 | O |
| ATOM | 5250 | CB | ASN | I | 205 | −0.507 | −0.456 | 35.739 | 1.00 | 92.29 | C |
| ATOM | 5251 | CG | ASN | I | 205 | −1.778 | −0.568 | 34.949 | 1.00 | 122.49 | C |
| ATOM | 5252 | OD1 | ASN | I | 205 | −2.617 | 0.342 | 34.950 | 1.00 | 118.21 | O |
| ATOM | 5253 | ND2 | ASN | I | 205 | −1.946 | −1.692 | 34.255 | 1.00 | 115.15 | N |
| ATOM | 5254 | N | HIS | I | 206 | −1.920 | −2.659 | 38.001 | 1.00 | 85.66 | N |
| ATOM | 5255 | CA | HIS | I | 206 | −2.144 | −4.060 | 38.363 | 1.00 | 84.39 | C |
| ATOM | 5256 | C | HIS | I | 206 | −3.400 | −4.536 | 37.628 | 1.00 | 91.22 | C |
| ATOM | 5257 | O | HIS | I | 206 | −4.499 | −4.460 | 38.190 | 1.00 | 92.66 | O |
| ATOM | 5258 | CB | HIS | I | 206 | −2.276 | −4.219 | 39.898 | 1.00 | 83.58 | C |
| ATOM | 5259 | CG | HIS | I | 206 | −2.454 | −5.634 | 40.381 | 1.00 | 85.52 | C |
| ATOM | 5260 | ND1 | HIS | I | 206 | −3.532 | −5.995 | 41.159 | 1.00 | 86.50 | N |
| ATOM | 5261 | CD2 | HIS | I | 206 | −1.665 | −6.721 | 40.208 | 1.00 | 85.91 | C |
| ATOM | 5262 | CE1 | HIS | I | 206 | −3.373 | −7.279 | 41.427 | 1.00 | 85.16 | C |
| ATOM | 5263 | NE2 | HIS | I | 206 | −2.261 | −7.756 | 40.883 | 1.00 | 85.28 | N |
| ATOM | 5264 | N | LYS | I | 207 | −3.238 | −5.004 | 36.360 | 1.00 | 87.41 | N |
| ATOM | 5265 | CA | LYS | I | 207 | −4.311 | −5.487 | 35.480 | 1.00 | 86.80 | C |
| ATOM | 5266 | C | LYS | I | 207 | −5.221 | −6.568 | 36.119 | 1.00 | 89.94 | C |
| ATOM | 5267 | O | LYS | I | 207 | −6.446 | −6.422 | 36.007 | 1.00 | 89.76 | O |
| ATOM | 5268 | CB | LYS | I | 207 | −3.764 | −5.951 | 34.128 | 1.00 | 89.18 | C |
| ATOM | 5269 | CG | LYS | I | 207 | −3.243 | −4.803 | 33.269 | 1.00 | 107.36 | C |

TABLE 1-continued

Three-dimensional crystal coordinate for anti-TcdB antibody beziotoxumab Fab – C. difficile toxin B (TcdB$^{(1834-2101)}$) complex.

| ATOM | 5270 | CD  | LYS | I | 207 | −3.384 | −5.089 | 31.763 | 1.00 | 118.88 | C |
| ---- | ---- | --- | --- | - | --- | ------ | ------ | ------ | ---- | ------ | - |
| ATOM | 5271 | CE  | LYS | I | 207 | −3.345 | −3.841 | 30.909 | 1.00 | 122.49 | C |
| ATOM | 5272 | NZ  | LYS | I | 207 | −3.882 | −4.093 | 29.547 | 1.00 | 128.34 | N |
| ATOM | 5273 | N   | PRO | I | 208 | −4.692 | −7.588 | 36.857 | 1.00 | 85.34  | N |
| ATOM | 5274 | CA  | PRO | I | 208 | −5.588 | −8.593 | 37.468 | 1.00 | 85.22  | C |
| ATOM | 5275 | C   | PRO | I | 208 | −6.734 | −8.056 | 38.333 | 1.00 | 91.56  | C |
| ATOM | 5276 | O   | PRO | I | 208 | −7.811 | −8.654 | 38.323 | 1.00 | 92.55  | O |
| ATOM | 5277 | CB  | PRO | I | 208 | −4.637 | −9.464 | 38.273 | 1.00 | 86.25  | C |
| ATOM | 5278 | CG  | PRO | I | 208 | −3.367 | −9.371 | 37.546 | 1.00 | 90.08  | C |
| ATOM | 5279 | CD  | PRO | I | 208 | −3.279 | −7.946 | 37.100 | 1.00 | 85.81  | C |
| ATOM | 5280 | N   | SER | I | 209 | −6.524 | −6.945 | 39.058 | 1.00 | 88.43  | N |
| ATOM | 5281 | CA  | SER | I | 209 | −7.569 | −6.321 | 39.880 | 1.00 | 88.53  | C |
| ATOM | 5282 | C   | SER | I | 209 | −8.039 | −5.005 | 39.232 | 1.00 | 94.68  | C |
| ATOM | 5283 | O   | SER | I | 209 | −8.931 | −4.335 | 39.765 | 1.00 | 94.42  | O |
| ATOM | 5284 | CB  | SER | I | 209 | −7.073 | −6.081 | 41.307 | 1.00 | 90.18  | C |
| ATOM | 5285 | OG  | SER | I | 209 | −6.133 | −5.021 | 41.368 | 1.00 | 92.10  | O |
| ATOM | 5286 | N   | ASN | I | 210 | −7.444 | −4.661 | 38.065 | 1.00 | 92.80  | N |
| ATOM | 5287 | CA  | ASN | I | 210 | −7.674 | −3.434 | 37.289 | 1.00 | 93.56  | C |
| ATOM | 5288 | C   | ASN | I | 210 | −7.505 | −2.164 | 38.162 | 1.00 | 100.86 | C |
| ATOM | 5289 | O   | ASN | I | 210 | −8.404 | −1.323 | 38.256 | 1.00 | 100.99 | O |
| ATOM | 5290 | CB  | ASN | I | 210 | −9.002 | −3.465 | 36.523 | 1.00 | 92.98  | C |
| ATOM | 5291 | CG  | ASN | I | 210 | −9.068 | −2.426 | 35.432 | 1.00 | 126.19 | C |
| ATOM | 5292 | OD1 | ASN | I | 210 | −9.774 | −1.413 | 35.542 | 1.00 | 124.57 | O |
| ATOM | 5293 | ND2 | ASN | I | 210 | −8.289 | −2.626 | 34.377 | 1.00 | 119.03 | N |
| ATOM | 5294 | N   | THR | I | 211 | −6.333 | −2.069 | 38.821 | 1.00 | 98.98  | N |
| ATOM | 5295 | CA  | THR | I | 211 | −5.926 | −0.976 | 39.697 | 1.00 | 98.88  | C |
| ATOM | 5296 | C   | THR | I | 211 | −4.841 | −0.148 | 38.998 | 1.00 | 103.26 | C |
| ATOM | 5297 | O   | THR | I | 211 | −3.792 | −0.677 | 38.629 | 1.00 | 102.52 | O |
| ATOM | 5298 | CB  | THR | I | 211 | −5.439 | −1.534 | 41.048 | 1.00 | 107.14 | C |
| ATOM | 5299 | OG1 | THR | I | 211 | −6.460 | −2.342 | 41.623 | 1.00 | 108.44 | O |
| ATOM | 5300 | CG2 | THR | I | 211 | −5.079 | −0.449 | 42.036 | 1.00 | 105.02 | C |
| ATOM | 5301 | N   | LYS | I | 212 | −5.124 | 1.144  | 38.797 | 1.00 | 100.60 | N |
| ATOM | 5302 | CA  | LYS | I | 212 | −4.204 | 2.127  | 38.234 | 1.00 | 100.59 | C |
| ATOM | 5303 | C   | LYS | I | 212 | −4.117 | 3.254  | 39.266 | 1.00 | 105.67 | C |
| ATOM | 5304 | O   | LYS | I | 212 | −5.098 | 3.975  | 39.487 | 1.00 | 105.80 | O |
| ATOM | 5305 | CB  | LYS | I | 212 | −4.668 | 2.627  | 36.853 | 1.00 | 102.53 | C |
| ATOM | 5306 | N   | VAL | I | 213 | −2.974 | 3.316  | 39.978 | 1.00 | 102.19 | N |
| ATOM | 5307 | CA  | VAL | I | 213 | −2.668 | 4.294  | 41.033 | 1.00 | 101.69 | C |
| ATOM | 5308 | C   | VAL | I | 213 | −1.552 | 5.227  | 40.551 | 1.00 | 106.53 | C |
| ATOM | 5309 | O   | VAL | I | 213 | −0.685 | 4.809  | 39.784 | 1.00 | 105.74 | O |
| ATOM | 5310 | CB  | VAL | I | 213 | −2.257 | 3.591  | 42.357 | 1.00 | 104.67 | C |
| ATOM | 5311 | CG1 | VAL | I | 213 | −2.139 | 4.585  | 43.509 | 1.00 | 104.20 | C |
| ATOM | 5312 | CG2 | VAL | I | 213 | −3.225 | 2.478  | 42.717 | 1.00 | 104.32 | C |
| ATOM | 5313 | N   | ASP | I | 214 | −1.585 | 6.489  | 40.997 | 1.00 | 104.44 | N |
| ATOM | 5314 | CA  | ASP | I | 214 | −0.563 | 7.492  | 40.710 | 1.00 | 104.54 | C |
| ATOM | 5315 | C   | ASP | I | 214 | −0.325 | 8.260  | 42.024 | 1.00 | 108.75 | C |
| ATOM | 5316 | O   | ASP | I | 214 | −1.078 | 9.195  | 42.327 | 1.00 | 109.23 | O |
| ATOM | 5317 | CB  | ASP | I | 214 | −0.982 | 8.428  | 39.551 | 1.00 | 106.26 | C |
| ATOM | 5318 | CG  | ASP | I | 214 | −1.412 | 7.724  | 38.274 | 1.00 | 115.43 | C |
| ATOM | 5319 | OD1 | ASP | I | 214 | −0.525 | 7.297  | 37.503 | 1.00 | 115.86 | O |
| ATOM | 5320 | OD2 | ASP | I | 214 | −2.637 | 7.614  | 38.041 | 1.00 | 120.00 | O |
| ATOM | 5321 | N   | LYS | I | 215 | 0.654  | 7.797  | 42.852 | 1.00 | 103.72 | N |
| ATOM | 5322 | CA  | LYS | I | 215 | 0.977  | 8.436  | 44.133 | 1.00 | 102.46 | C |
| ATOM | 5323 | C   | LYS | I | 215 | 2.082  | 9.467  | 43.943 | 1.00 | 104.99 | C |
| ATOM | 5324 | O   | LYS | I | 215 | 3.107  | 9.164  | 43.328 | 1.00 | 104.18 | O |
| ATOM | 5325 | CB  | LYS | I | 215 | 1.352  | 7.413  | 45.221 | 1.00 | 103.82 | C |
| ATOM | 5326 | N   | ARG | I | 216 | 1.849  | 10.701 | 44.427 | 1.00 | 100.87 | N |
| ATOM | 5327 | CA  | ARG | I | 216 | 2.841  | 11.770 | 44.371 | 1.00 | 100.02 | C |
| ATOM | 5328 | C   | ARG | I | 216 | 3.745  | 11.610 | 45.584 | 1.00 | 103.73 | C |
| ATOM | 5329 | O   | ARG | I | 216 | 3.265  | 11.555 | 46.728 | 1.00 | 102.77 | O |
| ATOM | 5330 | CB  | ARG | I | 216 | 2.198  | 13.169 | 44.337 | 1.00 | 98.05  | C |
| ATOM | 5331 | N   | VAL | I | 217 | 5.048  | 11.446 | 45.312 | 1.00 | 100.47 | N |
| ATOM | 5332 | CA  | VAL | I | 217 | 6.097  | 11.308 | 46.315 | 1.00 | 100.20 | C |
| ATOM | 5333 | C   | VAL | I | 217 | 6.667  | 12.711 | 46.508 | 1.00 | 103.67 | C |
| ATOM | 5334 | O   | VAL | I | 217 | 7.272  | 13.284 | 45.600 | 1.00 | 103.43 | O |
| ATOM | 5335 | CB  | VAL | I | 217 | 7.180  | 10.251 | 45.955 | 1.00 | 104.02 | C |
| ATOM | 5336 | CG1 | VAL | I | 217 | 8.155  | 10.044 | 47.114 | 1.00 | 103.66 | C |
| ATOM | 5337 | CG2 | VAL | I | 217 | 6.543  | 8.923  | 45.555 | 1.00 | 103.86 | C |
| ATOM | 5338 | N   | GLU | I | 218 | 6.367  | 13.287 | 47.668 | 1.00 | 99.65  | N |
| ATOM | 5339 | CA  | GLU | I | 218 | 6.759  | 14.622 | 48.078 | 1.00 | 99.26  | C |
| ATOM | 5340 | C   | GLU | I | 218 | 7.491  | 14.505 | 49.411 | 1.00 | 104.37 | C |
| ATOM | 5341 | O   | GLU | I | 218 | 7.182  | 13.572 | 50.163 | 1.00 | 104.79 | O |
| ATOM | 5342 | CB  | GLU | I | 218 | 5.496  | 15.492 | 48.253 | 1.00 | 100.40 | C |
| ATOM | 5343 | N   | PRO | I | 219 | 8.438  | 15.422 | 49.753 | 1.00 | 100.90 | N |
| ATOM | 5344 | CA  | PRO | I | 219 | 9.084  | 15.349 | 51.085 | 1.00 | 100.44 | C |
| ATOM | 5345 | C   | PRO | I | 219 | 8.065  | 15.621 | 52.187 | 1.00 | 104.04 | C |
| ATOM | 5346 | O   | PRO | I | 219 | 7.237  | 16.515 | 52.016 | 1.00 | 102.72 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 5347 | CB | PRO | I | 219 | 10.161 | 16.432 | 51.026 | 1.00 | 102.16 | C |
|---|---|---|---|---|---|---|---|---|---|---|---|
| ATOM | 5348 | CG | PRO | I | 219 | 10.250 | 16.841 | 49.573 | 1.00 | 106.47 | C |
| ATOM | 5349 | CD | PRO | I | 219 | 8.908 | 16.596 | 48.996 | 1.00 | 102.05 | C |
| ATOM | 5350 | N | LYS | I | 220 | 8.066 | 14.808 | 53.265 | 1.00 | 102.64 | N |
| ATOM | 5351 | CA | LYS | I | 220 | 7.091 | 14.939 | 54.366 | 1.00 | 103.70 | C |
| ATOM | 5352 | C | LYS | I | 220 | 7.249 | 16.261 | 55.136 | 1.00 | 110.40 | C |
| ATOM | 5353 | O | LYS | I | 220 | 8.376 | 16.610 | 55.498 | 1.00 | 111.16 | O |
| ATOM | 5354 | CB | LYS | I | 220 | 7.171 | 13.732 | 55.323 | 1.00 | 105.91 | C |
| ATOM | 5355 | N | SER | I | 221 | 6.132 | 16.995 | 55.375 | 1.00 | 106.89 | N |
| ATOM | 5356 | CA | SER | I | 221 | 6.155 | 18.268 | 56.115 | 1.00 | 132.69 | C |
| ATOM | 5357 | C | SER | I | 221 | 5.808 | 18.070 | 57.595 | 1.00 | 138.71 | C |
| ATOM | 5358 | O | SER | I | 221 | 6.693 | 18.077 | 58.450 | 1.00 | 94.08 | O |
| ATOM | 5359 | CB | SER | I | 221 | 5.214 | 19.290 | 55.479 | 1.00 | 136.40 | C |
| ATOM | 5360 | OG | SER | I | 221 | 5.649 | 19.682 | 54.187 | 1.00 | 145.00 | O |
| TER | 5361 |  | SER | I | 221 |  |  |  |  |  |  |
| ATOM | 5362 | N | GLU | L | 1 | 43.840 | −4.581 | −1.942 | 1.00 | 76.65 | N |
| ATOM | 5363 | CA | GLU | L | 1 | 42.800 | −4.307 | −2.937 | 1.00 | 75.39 | C |
| ATOM | 5364 | C | GLU | L | 1 | 42.920 | −2.883 | −3.543 | 1.00 | 74.34 | C |
| ATOM | 5365 | O | GLU | L | 1 | 44.010 | −2.286 | −3.496 | 1.00 | 74.64 | O |
| ATOM | 5366 | CB | GLU | L | 1 | 41.389 | −4.595 | −2.373 | 1.00 | 76.74 | C |
| ATOM | 5367 | CG | GLU | L | 1 | 41.096 | −3.960 | −1.024 | 1.00 | 90.05 | C |
| ATOM | 5368 | CD | GLU | L | 1 | 39.969 | −2.946 | −0.986 | 1.00 | 127.88 | C |
| ATOM | 5369 | OE1 | GLU | L | 1 | 38.918 | −3.181 | −1.627 | 1.00 | 131.29 | O |
| ATOM | 5370 | OE2 | GLU | L | 1 | 40.121 | −1.933 | −0.266 | 1.00 | 128.74 | O |
| ATOM | 5371 | N | ILE | L | 2 | 41.809 | −2.374 | −4.139 | 1.00 | 64.37 | N |
| ATOM | 5372 | CA | ILE | L | 2 | 41.697 | −1.070 | −4.805 | 1.00 | 61.76 | C |
| ATOM | 5373 | C | ILE | L | 2 | 41.564 | 0.026 | −3.741 | 1.00 | 63.68 | C |
| ATOM | 5374 | O | ILE | L | 2 | 40.692 | −0.065 | −2.882 | 1.00 | 62.95 | O |
| ATOM | 5375 | CB | ILE | L | 2 | 40.507 | −1.020 | −5.829 | 1.00 | 63.86 | C |
| ATOM | 5376 | CG1 | ILE | L | 2 | 40.096 | −2.423 | −6.384 | 1.00 | 64.69 | C |
| ATOM | 5377 | CG2 | ILE | L | 2 | 40.789 | −0.051 | −6.956 | 1.00 | 61.48 | C |
| ATOM | 5378 | CD1 | ILE | L | 2 | 39.087 | −3.313 | −5.447 | 1.00 | 74.86 | C |
| ATOM | 5379 | N | VAL | L | 3 | 42.440 | 1.040 | −3.764 | 1.00 | 59.17 | N |
| ATOM | 5380 | CA | VAL | L | 3 | 42.382 | 2.102 | −2.754 | 1.00 | 58.55 | C |
| ATOM | 5381 | C | VAL | L | 3 | 42.274 | 3.458 | −3.430 | 1.00 | 63.92 | C |
| ATOM | 5382 | O | VAL | L | 3 | 43.122 | 3.818 | −4.246 | 1.00 | 65.38 | O |
| ATOM | 5383 | CB | VAL | L | 3 | 43.521 | 2.057 | −1.693 | 1.00 | 61.39 | C |
| ATOM | 5384 | CG1 | VAL | L | 3 | 43.314 | 3.123 | −0.627 | 1.00 | 60.22 | C |
| ATOM | 5385 | CG2 | VAL | L | 3 | 43.647 | 0.676 | −1.051 | 1.00 | 61.24 | C |
| ATOM | 5386 | N | LEU | L | 4 | 41.221 | 4.205 | −3.088 | 1.00 | 59.30 | N |
| ATOM | 5387 | CA | LEU | L | 4 | 40.953 | 5.517 | −3.651 | 1.00 | 57.48 | C |
| ATOM | 5388 | C | LEU | L | 4 | 41.399 | 6.607 | −2.699 | 1.00 | 64.10 | C |
| ATOM | 5389 | O | LEU | L | 4 | 40.854 | 6.780 | −1.601 | 1.00 | 63.55 | O |
| ATOM | 5390 | CB | LEU | L | 4 | 39.470 | 5.672 | −4.059 | 1.00 | 56.04 | C |
| ATOM | 5391 | CG | LEU | L | 4 | 38.928 | 4.676 | −5.083 | 1.00 | 57.88 | C |
| ATOM | 5392 | CD1 | LEU | L | 4 | 37.463 | 4.717 | −5.106 | 1.00 | 57.94 | C |
| ATOM | 5393 | CD2 | LEU | L | 4 | 39.444 | 4.957 | −6.473 | 1.00 | 58.42 | C |
| ATOM | 5394 | N | THR | L | 5 | 42.423 | 7.337 | −3.137 | 1.00 | 63.66 | N |
| ATOM | 5395 | CA | THR | L | 5 | 43.040 | 8.436 | −2.392 | 1.00 | 64.20 | C |
| ATOM | 5396 | C | THR | L | 5 | 42.701 | 9.742 | −3.093 | 1.00 | 65.99 | C |
| ATOM | 5397 | O | THR | L | 5 | 43.087 | 9.932 | −4.242 | 1.00 | 65.87 | O |
| ATOM | 5398 | CB | THR | L | 5 | 44.542 | 8.162 | −2.139 | 1.00 | 77.59 | C |
| ATOM | 5399 | OG1 | THR | L | 5 | 44.999 | 7.070 | −2.971 | 1.00 | 86.18 | O |
| ATOM | 5400 | CG2 | THR | L | 5 | 44.812 | 7.788 | −0.688 | 1.00 | 75.97 | C |
| ATOM | 5401 | N | GLN | L | 6 | 41.883 | 10.581 | −2.435 | 1.00 | 60.60 | N |
| ATOM | 5402 | CA | GLN | L | 6 | 41.429 | 11.873 | −2.944 | 1.00 | 60.22 | C |
| ATOM | 5403 | C | GLN | L | 6 | 42.286 | 13.024 | −2.431 | 1.00 | 65.56 | C |
| ATOM | 5404 | O | GLN | L | 6 | 42.730 | 13.006 | −1.285 | 1.00 | 66.05 | O |
| ATOM | 5405 | CB | GLN | L | 6 | 39.979 | 12.141 | −2.516 | 1.00 | 61.42 | C |
| ATOM | 5406 | CG | GLN | L | 6 | 38.939 | 11.315 | −3.246 | 1.00 | 62.54 | C |
| ATOM | 5407 | CD | GLN | L | 6 | 37.564 | 11.830 | −2.964 | 1.00 | 68.46 | C |
| ATOM | 5408 | OE1 | GLN | L | 6 | 36.795 | 11.201 | −2.238 | 1.00 | 55.25 | O |
| ATOM | 5409 | NE2 | GLN | L | 6 | 37.230 | 12.999 | −3.528 | 1.00 | 65.75 | N |
| ATOM | 5410 | N | SER | L | 7 | 42.475 | 14.052 | −3.259 | 1.00 | 61.31 | N |
| ATOM | 5411 | CA | SER | L | 7 | 43.252 | 15.224 | −2.884 | 1.00 | 60.17 | C |
| ATOM | 5412 | C | SER | L | 7 | 42.599 | 16.478 | −3.445 | 1.00 | 64.92 | C |
| ATOM | 5413 | O | SER | L | 7 | 42.052 | 16.429 | −4.560 | 1.00 | 67.65 | O |
| ATOM | 5414 | CB | SER | L | 7 | 44.686 | 15.114 | −3.374 | 1.00 | 63.23 | C |
| ATOM | 5415 | OG | SER | L | 7 | 44.735 | 15.009 | −4.787 | 1.00 | 79.06 | O |
| ATOM | 5416 | N | PRO | L | 8 | 42.654 | 17.611 | −2.692 | 1.00 | 56.71 | N |
| ATOM | 5417 | CA | PRO | L | 8 | 43.151 | 17.733 | −1.315 | 1.00 | 55.97 | C |
| ATOM | 5418 | C | PRO | L | 8 | 42.048 | 17.250 | −0.334 | 1.00 | 62.32 | C |
| ATOM | 5419 | O | PRO | L | 8 | 40.961 | 16.828 | −0.759 | 1.00 | 61.56 | O |
| ATOM | 5420 | CB | PRO | L | 8 | 43.400 | 19.230 | −1.199 | 1.00 | 56.81 | C |
| ATOM | 5421 | CG | PRO | L | 8 | 42.309 | 19.846 | −2.023 | 1.00 | 60.28 | C |
| ATOM | 5422 | CD | PRO | L | 8 | 42.030 | 18.869 | −3.147 | 1.00 | 56.08 | C |
| ATOM | 5423 | N | GLY | L | 9 | 42.315 | 17.326 | 0.959 | 1.00 | 59.31 | N |

TABLE 1-continued

Three-dimensional crystal coordinate for anti-TcdB antibody beziotoxumab Fab –C. difficile toxin B (TcdB$^{(1834-2101)}$) complex.

| ATOM | 5424 | CA | GLY | L | 9 | 41.305 | 16.985 | 1.947 | 1.00 | 59.40 | C |
|---|---|---|---|---|---|---|---|---|---|---|---|
| ATOM | 5425 | C | GLY | L | 9 | 40.289 | 18.102 | 2.040 | 1.00 | 64.25 | C |
| ATOM | 5426 | O | GLY | L | 9 | 39.093 | 17.862 | 2.240 | 1.00 | 64.26 | O |
| ATOM | 5427 | N | THR | L | 10 | 40.775 | 19.342 | 1.907 | 1.00 | 61.63 | N |
| ATOM | 5428 | CA | THR | L | 10 | 39.930 | 20.532 | 1.899 | 1.00 | 61.59 | C |
| ATOM | 5429 | C | THR | L | 10 | 40.382 | 21.483 | 0.814 | 1.00 | 65.77 | C |
| ATOM | 5430 | O | THR | L | 10 | 41.576 | 21.761 | 0.664 | 1.00 | 66.69 | O |
| ATOM | 5431 | CB | THR | L | 10 | 39.781 | 21.190 | 3.267 | 1.00 | 63.98 | C |
| ATOM | 5432 | OG1 | THR | L | 10 | 39.617 | 20.174 | 4.254 | 1.00 | 63.13 | O |
| ATOM | 5433 | CG2 | THR | L | 10 | 38.580 | 22.122 | 3.322 | 1.00 | 60.61 | C |
| ATOM | 5434 | N | LEU | L | 11 | 39.422 | 21.905 | 0.014 | 1.00 | 60.13 | N |
| ATOM | 5435 | CA | LEU | L | 11 | 39.635 | 22.811 | −1.077 | 1.00 | 59.18 | C |
| ATOM | 5436 | C | LEU | L | 11 | 38.891 | 24.041 | −0.718 | 1.00 | 60.46 | C |
| ATOM | 5437 | O | LEU | L | 11 | 37.663 | 24.015 | −0.619 | 1.00 | 59.29 | O |
| ATOM | 5438 | CB | LEU | L | 11 | 39.083 | 22.186 | −2.364 | 1.00 | 60.38 | C |
| ATOM | 5439 | CG | LEU | L | 11 | 39.413 | 22.861 | −3.699 | 1.00 | 66.20 | C |
| ATOM | 5440 | CD1 | LEU | L | 11 | 40.901 | 22.936 | −3.927 | 1.00 | 67.21 | C |
| ATOM | 5441 | CD2 | LEU | L | 11 | 38.775 | 22.111 | −4.847 | 1.00 | 68.71 | C |
| ATOM | 5442 | N | SER | L | 12 | 39.645 | 25.113 | −0.434 | 1.00 | 57.16 | N |
| ATOM | 5443 | CA | SER | L | 12 | 39.115 | 26.427 | −0.070 | 1.00 | 55.56 | C |
| ATOM | 5444 | C | SER | L | 12 | 39.179 | 27.327 | −1.302 | 1.00 | 56.24 | C |
| ATOM | 5445 | O | SER | L | 12 | 40.267 | 27.602 | −1.805 | 1.00 | 55.47 | O |
| ATOM | 5446 | CB | SER | L | 12 | 39.910 | 27.018 | 1.088 | 1.00 | 58.46 | C |
| ATOM | 5447 | OG | SER | L | 12 | 39.908 | 26.104 | 2.171 | 1.00 | 68.18 | O |
| ATOM | 5448 | N | LEU | L | 13 | 38.008 | 27.673 | −1.844 | 1.00 | 50.92 | N |
| ATOM | 5449 | CA | LEU | L | 13 | 37.847 | 28.522 | −3.015 | 1.00 | 51.13 | C |
| ATOM | 5450 | C | LEU | L | 13 | 36.652 | 29.445 | −2.765 | 1.00 | 56.65 | C |
| ATOM | 5451 | O | LOU | L | 13 | 35.786 | 29.135 | −1.944 | 1.00 | 56.69 | O |
| ATOM | 5452 | CB | LEU | L | 13 | 37.575 | 27.680 | −4.275 | 1.00 | 52.02 | C |
| ATOM | 5453 | CG | LOU | L | 13 | 38.497 | 26.496 | −4.621 | 1.00 | 57.97 | C |
| ATOM | 5454 | CD1 | LEU | L | 13 | 37.857 | 25.620 | −5.658 | 1.00 | 59.35 | C |
| ATOM | 5455 | CD2 | LEU | L | 13 | 39.854 | 26.953 | −5.139 | 1.00 | 57.90 | C |
| ATOM | 5456 | N | SER | L | 14 | 36.598 | 30.565 | −3.463 | 1.00 | 54.88 | N |
| ATOM | 5457 | CA | SER | L | 14 | 35.506 | 31.515 | −3.311 | 1.00 | 56.51 | C |
| ATOM | 5458 | C | SER | L | 14 | 34.353 | 31.246 | −4.311 | 1.00 | 63.77 | C |
| ATOM | 5459 | O | SER | L | 14 | 34.608 | 30.671 | −5.370 | 1.00 | 64.16 | O |
| ATOM | 5460 | CB | SER | L | 14 | 36.028 | 32.942 | −3.428 | 1.00 | 60.01 | C |
| ATOM | 5461 | OG | SER | L | 14 | 37.318 | 32.964 | −4.019 | 1.00 | 66.90 | O |
| ATOM | 5462 | N | PRO | L | 15 | 33.086 | 31.637 | −4.028 | 1.00 | 62.16 | N |
| ATOM | 5463 | CA | PRO | L | 15 | 32.007 | 31.355 | −5.006 | 1.00 | 62.97 | C |
| ATOM | 5464 | C | PRO | L | 15 | 32.283 | 31.943 | −6.388 | 1.00 | 69.17 | C |
| ATOM | 5465 | O | PRO | L | 15 | 32.821 | 33.048 | −6.483 | 1.00 | 70.89 | O |
| ATOM | 5466 | CB | PRO | L | 15 | 30.742 | 31.942 | −4.348 | 1.00 | 64.59 | C |
| ATOM | 5467 | CG | PRO | L | 15 | 31.083 | 32.029 | −2.889 | 1.00 | 68.60 | C |
| ATOM | 5468 | CD | PRO | L | 15 | 32.561 | 32.305 | −2.816 | 1.00 | 63.66 | C |
| ATOM | 5469 | N | GLY | L | 16 | 31.952 | 31.177 | −7.429 | 1.00 | 65.22 | N |
| ATOM | 5470 | CA | GLY | L | 16 | 32.160 | 31.561 | −8.819 | 1.00 | 65.61 | C |
| ATOM | 5471 | C | GLY | L | 16 | 33.429 | 30.983 | −9.414 | 1.00 | 70.80 | C |
| ATOM | 5472 | O | GLY | L | 16 | 33.583 | 30.932 | −10.640 | 1.00 | 71.00 | O |
| ATOM | 5473 | N | GLU | L | 17 | 34.345 | 30.533 | −8.545 | 1.00 | 67.70 | N |
| ATOM | 5474 | CA | GLU | L | 17 | 35.628 | 29.948 | −8.933 | 1.00 | 67.64 | C |
| ATOM | 5475 | C | GLU | L | 17 | 35.501 | 28.521 | −9.500 | 1.00 | 71.32 | C |
| ATOM | 5476 | O | GLU | L | 17 | 34.507 | 27.817 | −9.249 | 1.00 | 71.00 | O |
| ATOM | 5477 | CB | GLU | L | 17 | 36.580 | 29.970 | −7.722 | 1.00 | 69.03 | C |
| ATOM | 5478 | CG | GLU | L | 17 | 37.876 | 30.713 | −7.948 | 1.00 | 81.01 | C |
| ATOM | 5479 | CD | GLU | L | 17 | 37.761 | 32.213 | −8.132 | 1.00 | 101.69 | C |
| ATOM | 5480 | OE1 | GLU | L | 17 | 37.774 | 32.927 | −7.105 | 1.00 | 115.11 | O |
| ATOM | 5481 | OE2 | GLU | L | 17 | 37.671 | 32.677 | −9.294 | 1.00 | 80.18 | O |
| ATOM | 5482 | N | ARG | L | 18 | 36.528 | 28.102 | −10.252 | 1.00 | 66.65 | N |
| ATOM | 5483 | CA | ARG | L | 18 | 36.577 | 26.750 | −10.806 | 1.00 | 65.66 | C |
| ATOM | 5484 | C | ARG | L | 18 | 37.182 | 25.772 | −9.788 | 1.00 | 69.31 | C |
| ATOM | 5485 | O | ARG | L | 18 | 38.275 | 26.016 | −9.254 | 1.00 | 69.79 | O |
| ATOM | 5486 | CB | ARG | L | 18 | 37.368 | 26.710 | −12.116 | 1.00 | 63.17 | C |
| ATOM | 5487 | CG | ARG | L | 18 | 36.944 | 25.552 | −12.998 | 1.00 | 71.89 | C |
| ATOM | 5488 | CD | ARG | L | 18 | 37.568 | 25.643 | −14.368 | 1.00 | 78.44 | C |
| ATOM | 5489 | NE | ARG | L | 18 | 38.813 | 24.880 | −14.439 | 1.00 | 78.79 | N |
| ATOM | 5490 | CZ | ARG | L | 18 | 39.016 | 23.862 | −15.269 | 1.00 | 92.94 | C |
| ATOM | 5491 | NH | ARG | L | 18 | 38.061 | 23.486 | −16.117 | 1.00 | 81.79 | N |
| ATOM | 5492 | NH2 | ARG | L | 18 | 40.182 | 23.220 | −15.270 | 1.00 | 69.25 | N |
| ATOM | 5493 | N | ALA | L | 19 | 36.470 | 24.655 | −9.540 | 1.00 | 63.87 | N |
| ATOM | 5494 | CA | ALA | L | 19 | 36.919 | 23.607 | −8.631 | 1.00 | 62.35 | C |
| ATOM | 5495 | C | ALA | L | 19 | 37.340 | 22.395 | −9.410 | 1.00 | 64.04 | C |
| ATOM | 5496 | O | ALA | L | 19 | 36.640 | 21.974 | −10.325 | 1.00 | 63.04 | O |
| ATOM | 5497 | CB | ALA | L | 19 | 35.824 | 23.242 | −7.644 | 1.00 | 62.93 | C |
| ATOM | 5498 | N | THR | L | 20 | 38.497 | 21.837 | −9.040 | 1.00 | 60.53 | N |
| ATOM | 5499 | CA | THR | L | 20 | 39.100 | 20.639 | −9.615 | 1.00 | 59.52 | C |
| ATOM | 5500 | C | THR | L | 20 | 39.464 | 19.741 | −8.441 | 1.00 | 62.35 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 5501 | O | THR | L | 20 | 40.343 | 20.092 | −7.648 | 1.00 | 64.48 | O |
|---|---|---|---|---|---|---|---|---|---|---|---|
| ATOM | 5502 | CB | THR | L | 20 | 40.294 | 21.035 | −10.504 | 1.00 | 69.04 | C |
| ATOM | 5503 | OG1 | THR | L | 20 | 39.789 | 21.538 | −11.739 | 1.00 | 65.66 | O |
| ATOM | 5504 | CG2 | THR | L | 20 | 41.243 | 19.882 | −10.774 | 1.00 | 70.57 | C |
| ATOM | 5505 | N | LEU | L | 21 | 38.759 | 18.602 | −8.322 | 1.00 | 55.37 | N |
| ATOM | 5506 | CA | LEU | L | 21 | 38.911 | 17.588 | −7.279 | 1.00 | 53.33 | C |
| ATOM | 5507 | C | LEU | L | 21 | 39.521 | 16.371 | −7.901 | 1.00 | 56.28 | C |
| ATOM | 5508 | O | LEU | L | 21 | 39.085 | 15.965 | −8.978 | 1.00 | 54.74 | O |
| ATOM | 5509 | CB | LEU | L | 21 | 37.534 | 17.203 | −6.720 | 1.00 | 53.05 | C |
| ATOM | 5510 | CG | LEU | L | 21 | 36.842 | 18.161 | −5.764 | 1.00 | 56.61 | C |
| ATOM | 5511 | CD1 | LEU | L | 21 | 36.021 | 19.182 | −6.513 | 1.00 | 57.81 | C |
| ATOM | 5512 | CD2 | LEU | L | 21 | 35.891 | 17.432 | −4.928 | 1.00 | 57.63 | C |
| ATOM | 5513 | N | SER | L | 22 | 40.507 | 15.770 | −7.220 | 1.00 | 54.45 | N |
| ATOM | 5514 | CA | SER | L | 22 | 41.245 | 14.598 | −7.691 | 1.00 | 54.75 | C |
| ATOM | 5515 | C | SER | L | 22 | 40.877 | 13.317 | −6.941 | 1.00 | 60.88 | C |
| ATOM | 5516 | O | SER | L | 22 | 40.475 | 13.357 | −5.775 | 1.00 | 62.48 | O |
| ATOM | 5517 | CB | SER | L | 22 | 42.745 | 14.854 | −7.588 | 1.00 | 59.96 | C |
| ATOM | 5518 | OG | SER | L | 22 | 43.519 | 13.671 | −7.726 | 1.00 | 77.31 | O |
| ATOM | 5519 | N | CYS | L | 23 | 41.044 | 12.187 | −7.632 | 1.00 | 56.85 | N |
| ATOM | 5520 | CA | CYS | L | 23 | 40.812 | 10.829 | −7.186 | 1.00 | 56.90 | C |
| ATOM | 5521 | C | CYS | L | 23 | 41.881 | 9.996 | −7.859 | 1.00 | 64.35 | C |
| ATOM | 5522 | O | CYS | L | 23 | 41.936 | 9.928 | −9.088 | 1.00 | 63.96 | O |
| ATOM | 5523 | CB | CYS | L | 23 | 39.418 | 10.364 | −7.585 | 1.00 | 57.47 | C |
| ATOM | 5524 | SG | CYS | L | 23 | 38.960 | 8.708 | −6.986 | 1.00 | 61.77 | S |
| ATOM | 5525 | N | ARG | L | 24 | 42.795 | 9.444 | −7.056 | 1.00 | 63.39 | N |
| ATOM | 5526 | CA | ARG | L | 24 | 43.869 | 8.600 | −7.541 | 1.00 | 63.01 | C |
| ATOM | 5527 | C | ARG | L | 24 | 43.661 | 7.201 | −6.993 | 1.00 | 67.02 | C |
| ATOM | 5528 | O | ARG | L | 24 | 43.376 | 7.029 | −5.806 | 1.00 | 67.83 | O |
| ATOM | 5529 | CB | ARG | L | 24 | 45.253 | 9.175 | −7.190 | 1.00 | 63.63 | C |
| ATOM | 5530 | CG | ARG | L | 24 | 46.389 | 8.567 | −8.024 | 1.00 | 76.92 | C |
| ATOM | 5531 | CD | ARG | L | 24 | 47.725 | 9.244 | −7.799 | 1.00 | 91.95 | C |
| ATOM | 5532 | NE | ARG | L | 24 | 48.063 | 10.170 | −8.885 | 1.00 | 111.61 | N |
| ATOM | 5533 | CZ | ARG | L | 24 | 49.103 | 11.004 | −8.878 | 1.00 | 131.05 | C |
| ATOM | 5534 | NH1 | ARG | L | 24 | 49.913 | 11.060 | −7.828 | 1.00 | 118.00 | N |
| ATOM | 5535 | NH2 | ARG | L | 24 | 49.334 | 11.796 | −9.917 | 1.00 | 120.58 | N |
| ATOM | 5536 | N | ALA | L | 25 | 43.732 | 6.211 | −7.881 | 1.00 | 63.07 | N |
| ATOM | 5537 | CA | ALA | L | 25 | 43.548 | 4.799 | −7.555 | 1.00 | 62.13 | C |
| ATOM | 5538 | C | ALA | L | 25 | 44.897 | 4.116 | −7.349 | 1.00 | 65.91 | C |
| ATOM | 5539 | O | ALA | L | 25 | 45.891 | 4.463 | −8.011 | 1.00 | 65.87 | O |
| ATOM | 5540 | CB | ALA | L | 25 | 42.776 | 4.104 | −8.659 | 1.00 | 62.30 | C |
| ATOM | 5541 | N | SER | L | 26 | 44.922 | 3.143 | −6.421 | 1.00 | 61.59 | N |
| ATOM | 5542 | CA | SER | L | 26 | 46.098 | 2.351 | −6.037 | 1.00 | 60.66 | C |
| ATOM | 5543 | C | SER | L | 26 | 46.623 | 1.470 | −7.191 | 1.00 | 65.58 | C |
| ATOM | 5544 | O | SER | L | 26 | 47.784 | 1.042 | −7.182 | 1.00 | 64.91 | O |
| ATOM | 5545 | CB | SER | L | 26 | 45.755 | 1.485 | −4.833 | 1.00 | 61.45 | C |
| ATOM | 5546 | OG | SER | L | 26 | 44.809 | 0.488 | −5.180 | 1.00 | 62.91 | O |
| ATOM | 5547 | N | GLN | L | 27 | 45.737 | 1.185 | −8.161 | 1.00 | 62.63 | N |
| ATOM | 5548 | CA | GLN | L | 27 | 45.980 | 0.385 | −9.356 | 1.00 | 61.67 | C |
| ATOM | 5549 | C | GLN | L | 27 | 45.072 | 0.860 | −10.467 | 1.00 | 66.39 | C |
| ATOM | 5550 | O | GLN | L | 27 | 44.036 | 1.459 | −10.185 | 1.00 | 66.06 | O |
| ATOM | 5551 | CB | GLN | L | 27 | 45.755 | −1.122 | −9.069 | 1.00 | 62.52 | C |
| ATOM | 5552 | CG | GLN | L | 27 | 44.336 | −1.515 | −8.661 | 1.00 | 68.66 | C |
| ATOM | 5553 | CD | GLN | L | 27 | 44.334 | −2.805 | −7.883 | 1.00 | 85.50 | C |
| ATOM | 5554 | OE1 | GLN | L | 27 | 44.101 | −3.885 | −8.430 | 1.00 | 71.84 | O |
| ATOM | 5555 | NE2 | GLN | L | 27 | 44.592 | −2.718 | −6.577 | 1.00 | 87.24 | N |
| ATOM | 5556 | N | SER | L | 28 | 45.457 | 0.592 | −11.722 | 1.00 | 65.99 | N |
| ATOM | 5557 | CA | SER | L | 28 | 44.683 | 0.937 | −12.916 | 1.00 | 67.33 | C |
| ATOM | 5558 | C | SER | L | 28 | 43.285 | 0.318 | −12.830 | 1.00 | 71.73 | C |
| ATOM | 5559 | O | SER | L | 28 | 43.124 | −0.836 | −12.387 | 1.00 | 70.64 | O |
| ATOM | 5560 | CB | SER | L | 28 | 45.397 | 0.498 | −14.193 | 1.00 | 71.59 | C |
| ATOM | 5561 | OG | SER | L | 28 | 44.675 | 0.917 | −15.341 | 1.00 | 82.75 | O |
| ATOM | 5562 | N | VAL | L | 29 | 42.276 | 1.134 | −13.181 | 1.00 | 68.32 | N |
| ATOM | 5563 | CA | VAL | L | 29 | 40.914 | 0.678 | −13.048 | 1.00 | 68.37 | C |
| ATOM | 5564 | C | VAL | L | 29 | 39.982 | 1.186 | −14.196 | 1.00 | 70.91 | C |
| ATOM | 5565 | O | VAL | L | 29 | 40.327 | 2.140 | −14.920 | 1.00 | 72.04 | O |
| ATOM | 5566 | CB | VAL | L | 29 | 40.424 | 0.994 | −11.614 | 1.00 | 72.10 | C |
| ATOM | 5567 | CG1 | VAL | L | 29 | 40.206 | 2.488 | −11.376 | 1.00 | 71.14 | C |
| ATOM | 5568 | CG2 | VAL | L | 29 | 39.229 | 0.121 | −11.242 | 1.00 | 72.13 | C |
| ATOM | 5569 | N | SER | L | 30 | 38.851 | 0.457 | −14.406 | 1.00 | 63.77 | N |
| ATOM | 5570 | CA | SER | L | 30 | 37.902 | 0.737 | −15.473 | 1.00 | 62.68 | C |
| ATOM | 5571 | C | SER | L | 30 | 37.160 | 2.046 | −15.246 | 1.00 | 67.91 | C |
| ATOM | 5572 | O | SER | L | 30 | 36.764 | 2.371 | −14.117 | 1.00 | 68.65 | O |
| ATOM | 5573 | CB | SER | L | 30 | 36.909 | −0.406 | −15.615 | 1.00 | 64.54 | C |
| ATOM | 5574 | OG | SER | L | 30 | 36.113 | −0.217 | −16.770 | 1.00 | 70.01 | O |
| ATOM | 5575 | N | SER | L | 31 | 36.984 | 2.806 | −16.324 | 1.00 | 63.51 | N |
| ATOM | 5576 | CA | SER | L | 31 | 36.280 | 4.088 | −16.287 | 1.00 | 61.49 | C |
| ATOM | 5577 | C | SER | L | 31 | 34.807 | 3.869 | −16.060 | 1.00 | 62.45 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 5578 | O   | SER | L | 31 | 34.143 | 4.761  | −15.552 | 1.00 | 64.72 | O |
|------|------|-----|-----|---|----|--------|--------|---------|------|-------|---|
| ATOM | 5579 | CB  | SER | L | 31 | 36.513 | 4.880  | −17.566 | 1.00 | 62.63 | C |
| ATOM | 5580 | OG  | SER | L | 31 | 37.832 | 5.396  | −17.564 | 1.00 | 69.48 | O |
| ATOM | 5581 | N   | SER | L | 32 | 34.319 | 2.659  | −16.365 | 1.00 | 53.62 | N |
| ATOM | 5582 | CA  | SER | L | 32 | 32.926 | 2.235  | −16.227 | 1.00 | 51.91 | C |
| ATOM | 5583 | C   | SER | L | 32 | 32.499 | 2.242  | −14.777 | 1.00 | 56.02 | C |
| ATOM | 5584 | O   | SER | L | 32 | 31.367 | 2.615  | −14.453 | 1.00 | 55.69 | O |
| ATOM | 5585 | CB  | SER | L | 32 | 32.761 | 0.820  | −16.790 | 1.00 | 53.89 | C |
| ATOM | 5586 | OG  | SER | L | 32 | 33.310 | 0.715  | −18.100 | 1.00 | 62.45 | O |
| ATOM | 5587 | N   | TYR | L | 33 | 33.429 | 1.841  | −13.899 | 1.00 | 52.80 | N |
| ATOM | 5588 | CA  | TYR | L | 33 | 33.193 | 1.671  | −12.484 | 1.00 | 52.05 | C |
| ATOM | 5589 | C   | TYR | L | 33 | 33.486 | 2.897  | −11.640 | 1.00 | 54.87 | C |
| ATOM | 5590 | O   | TYR | L | 33 | 33.274 | 2.844  | −10.420 | 1.00 | 54.42 | O |
| ATOM | 5591 | CB  | TYR | L | 33 | 33.959 | 0.445  | −11.997 | 1.00 | 53.54 | C |
| ATOM | 5592 | CG  | TYR | L | 33 | 33.426 | −0.835 | −12.592 | 1.00 | 55.98 | C |
| ATOM | 5593 | CD1 | TYR | L | 33 | 32.096 | −1.205 | −12.422 | 1.00 | 58.45 | C |
| ATOM | 5594 | CD2 | TYR | L | 33 | 34.234 | −1.653 | −13.362 | 1.00 | 57.43 | C |
| ATOM | 5595 | CE1 | TYR | L | 33 | 31.590 | −2.368 | −12.991 | 1.00 | 60.29 | C |
| ATOM | 5596 | CE2 | TYR | L | 33 | 33.752 | −2.839 | −13.905 | 1.00 | 59.26 | C |
| ATOM | 5597 | CZ  | TYR | L | 33 | 32.427 | −3.199 | −13.717 | 1.00 | 69.64 | C |
| ATOM | 5598 | OH  | TYR | L | 33 | 31.942 | −4.381 | −14.255 | 1.00 | 72.42 | O |
| ATOM | 5599 | N   | LEU | L | 34 | 33.879 | 4.025  | −12.282 | 1.00 | 50.54 | N |
| ATOM | 5600 | CA  | LEU | L | 34 | 34.154 | 5.251  | −11.546 | 1.00 | 49.35 | C |
| ATOM | 5601 | C   | LEU | L | 34 | 32.950 | 6.173  | −11.427 | 1.00 | 54.13 | C |
| ATOM | 5602 | O   | LEU | L | 34 | 32.388 | 6.617  | −12.436 | 1.00 | 56.03 | O |
| ATOM | 5603 | CB  | LEU | L | 34 | 35.375 | 6.028  | −12.053 | 1.00 | 48.74 | C |
| ATOM | 5604 | CG  | LEU | L | 34 | 35.906 | 6.924  | −10.937 | 1.00 | 52.85 | C |
| ATOM | 5605 | CD1 | LEU | L | 34 | 37.155 | 6.412  | −10.318 | 1.00 | 52.09 | C |
| ATOM | 5606 | CD2 | LEU | L | 34 | 35.898 | 8.349  | −11.302 | 1.00 | 56.62 | C |
| ATOM | 5607 | N   | ALA | L | 35 | 32.595 | 6.500  | −10.178 | 1.00 | 47.55 | N |
| ATOM | 5608 | CA  | ALA | L | 35 | 31.494 | 7.398  | −9.869  | 1.00 | 46.13 | C |
| ATOM | 5609 | C   | ALA | L | 35 | 31.885 | 8.479  | −8.850  | 1.00 | 50.63 | C |
| ATOM | 5610 | O   | ALA | L | 35 | 32.807 | 8.283  | −8.042  | 1.00 | 50.38 | O |
| ATOM | 5611 | CB  | ALA | L | 35 | 30.301 | 6.607  | −9.365  | 1.00 | 46.62 | C |
| ATOM | 5612 | N   | TRP | L | 36 | 31.161 | 9.626  | −8.886  | 1.00 | 46.06 | N |
| ATOM | 5613 | CA  | TRP | L | 36 | 31.352 | 10.738 | −7.955  | 1.00 | 44.33 | C |
| ATOM | 5614 | C   | TRP | L | 36 | 30.037 | 11.037 | −7.292  | 1.00 | 46.41 | C |
| ATOM | 5615 | O   | TRP | L | 36 | 29.018 | 11.108 | −7.972  | 1.00 | 46.88 | O |
| ATOM | 5616 | CB  | TRP | L | 36 | 31.869 | 11.988 | −8.669  | 1.00 | 42.07 | C |
| ATOM | 5617 | CG  | TRP | L | 36 | 33.291 | 11.901 | −9.126  | 1.00 | 42.39 | C |
| ATOM | 5618 | CD1 | TRP | L | 36 | 33.738 | 11.438 | −10.329 | 1.00 | 45.04 | C |
| ATOM | 5619 | CD2 | TRP | L | 36 | 34.448 | 12.360 | −8.415  | 1.00 | 42.32 | C |
| ATOM | 5620 | NE1 | TRP | L | 36 | 35.105 | 11.567 | −10.410 | 1.00 | 44.27 | N |
| ATOM | 5621 | CE2 | TRP | L | 36 | 35.569 | 12.123 | −9.243  | 1.00 | 45.94 | C |
| ATOM | 5622 | CE3 | TRP | L | 36 | 34.647 | 12.975 | −7.168  | 1.00 | 43.58 | C |
| ATOM | 5623 | CZ2 | TRP | L | 36 | 36.868 | 12.449 | −8.849  | 1.00 | 45.08 | C |
| ATOM | 5624 | CZ3 | TRP | L | 36 | 35.935 | 13.314 | −6.786  | 1.00 | 44.83 | C |
| ATOM | 5625 | CH2 | TRP | L | 36 | 37.026 | 13.041 | −7.615  | 1.00 | 45.40 | C |
| ATOM | 5626 | N   | TYR | L | 37 | 30.070 | 11.228 | −5.972  | 1.00 | 42.14 | N |
| ATOM | 5627 | CA  | TYR | L | 37 | 28.914 | 11.547 | −5.132  | 1.00 | 41.65 | C |
| ATOM | 5628 | C   | TYR | L | 37 | 29.149 | 12.854 | −4.441  | 1.00 | 45.17 | C |
| ATOM | 5629 | O   | TYR | L | 37 | 30.284 | 13.158 | −4.088  | 1.00 | 45.97 | O |
| ATOM | 5630 | CB  | TYR | L | 37 | 28.646 | 10.449 | −4.053  | 1.00 | 41.70 | C |
| ATOM | 5631 | CG  | TYR | L | 37 | 28.451 | 9.076  | −4.646  | 1.00 | 43.68 | C |
| ATOM | 5632 | CD2 | TYR | L | 37 | 27.181 | 8.600  | −4.949  | 1.00 | 44.78 | C |
| ATOM | 5633 | CD1 | TYR | L | 37 | 29.538 | 8.272  | −4.959  | 1.00 | 45.68 | C |
| ATOM | 5634 | CE2 | TYR | L | 37 | 26.999 | 7.356  | −5.548  | 1.00 | 45.08 | C |
| ATOM | 5635 | CE1 | TYR | L | 37 | 29.372 | 7.044  | −5.584  | 1.00 | 47.36 | C |
| ATOM | 5636 | CZ  | TYR | L | 37 | 28.103 | 6.590  | −5.879  | 1.00 | 51.21 | C |
| ATOM | 5637 | OH  | TYR | L | 37 | 27.978 | 5.359  | −6.462  | 1.00 | 50.20 | O |
| ATOM | 5638 | N   | GLN | L | 38 | 28.066 | 13.588 | −4.183  | 1.00 | 41.87 | N |
| ATOM | 5639 | CA  | GLN | L | 38 | 28.036 | 14.829 | −3.427  | 1.00 | 41.89 | C |
| ATOM | 5640 | C   | GLN | L | 38 | 27.257 | 14.592 | −2.153  | 1.00 | 48.12 | C |
| ATOM | 5641 | O   | GLN | L | 38 | 26.209 | 13.962 | −2.196  | 1.00 | 48.45 | O |
| ATOM | 5642 | CB  | GLN | L | 38 | 27.359 | 15.956 | −4.245  | 1.00 | 43.38 | C |
| ATOM | 5643 | CG  | GLN | L | 38 | 27.344 | 17.326 | −3.533  | 1.00 | 54.50 | C |
| ATOM | 5644 | CD  | GLN | L | 38 | 26.492 | 18.354 | −4.208  | 1.00 | 76.26 | C |
| ATOM | 5645 | OE1 | GLN | L | 38 | 25.294 | 18.144 | −4.457  | 1.00 | 70.37 | O |
| ATOM | 5646 | NE2 | GLN | L | 38 | 27.094 | 19.500 | −4.485  | 1.00 | 71.83 | N |
| ATOM | 5647 | N   | GLN | L | 39 | 27.715 | 15.149 | −1.029  | 1.00 | 46.94 | N |
| ATOM | 5648 | CA  | GLN | L | 39 | 26.962 | 15.073 | 0.217   | 1.00 | 46.32 | C |
| ATOM | 5649 | C   | GLN | L | 39 | 26.909 | 16.429 | 0.884   | 1.00 | 54.04 | C |
| ATOM | 5650 | O   | GLN | L | 39 | 27.897 | 16.885 | 1.465   | 1.00 | 54.99 | O |
| ATOM | 5651 | CB  | GLN | L | 39 | 27.549 | 14.033 | 1.151   | 1.00 | 46.93 | C |
| ATOM | 5652 | CG  | GLN | L | 39 | 26.668 | 13.784 | 2.364   | 1.00 | 40.23 | C |
| ATOM | 5653 | CD  | GLN | L | 39 | 27.269 | 12.743 | 3.254   | 1.00 | 54.48 | C |
| ATOM | 5654 | OE1 | GLN | L | 39 | 28.505 | 12.635 | 3.425   | 1.00 | 50.09 | O |

TABLE 1-continued

Three-dimensional crystal coordinate for anti-TcdB antibody beziotoxumab
Fab –C. difficile toxin B (TcdB$^{(1834-2101)}$) complex.

| ATOM | 5655 | NE2 | GLN | L | 39 | 26.391 | 12.004 | 3.882 | 1.00 | 42.51 | N |
|---|---|---|---|---|---|---|---|---|---|---|---|
| ATOM | 5656 | N | LYS | L | 40 | 25.737 | 17.079 | 0.790 | 1.00 | 52.83 | N |
| ATOM | 5657 | CA | LYS | L | 40 | 25.466 | 18.387 | 1.387 | 1.00 | 52.18 | C |
| ATOM | 5658 | C | LYS | L | 40 | 25.361 | 18.184 | 2.896 | 1.00 | 59.58 | C |
| ATOM | 5659 | O | LYS | L | 40 | 25.092 | 17.055 | 3.326 | 1.00 | 59.65 | O |
| ATOM | 5660 | CB | LYS | L | 40 | 24.176 | 18.972 | 0.800 | 1.00 | 52.66 | C |
| ATOM | 5661 | CG | LYS | L | 40 | 24.402 | 19.761 | −0.475 | 1.00 | 55.38 | C |
| ATOM | 5662 | CD | LYS | L | 40 | 23.248 | 19.594 | −1.483 | 1.00 | 57.60 | C |
| ATOM | 5663 | CE | LYS | L | 40 | 23.528 | 20.411 | −2.735 | 1.00 | 62.62 | C |
| ATOM | 5664 | NZ | LYS | L | 40 | 22.316 | 20.737 | −3.542 | 1.00 | 54.05 | N |
| ATOM | 5665 | N | PRO | L | 41 | 25.588 | 19.216 | 3.744 | 1.00 | 59.16 | N |
| ATOM | 5666 | CA | PRO | L | 41 | 25.509 | 18.983 | 5.202 | 1.00 | 59.42 | C |
| ATOM | 5667 | C | PRO | L | 41 | 24.128 | 18.524 | 5.676 | 1.00 | 63.78 | C |
| ATOM | 5668 | O | PRO | L | 41 | 23.107 | 19.084 | 5.246 | 1.00 | 63.64 | O |
| ATOM | 5669 | CB | PRO | L | 41 | 25.906 | 20.331 | 5.802 | 1.00 | 60.80 | C |
| ATOM | 5670 | CG | PRO | L | 41 | 26.547 | 21.086 | 4.688 | 1.00 | 64.84 | C |
| ATOM | 5671 | CD | PRO | L | 41 | 25.904 | 20.625 | 3.446 | 1.00 | 60.22 | C |
| ATOM | 5672 | N | GLY | L | 42 | 24.119 | 17.469 | 6.489 | 1.00 | 60.54 | N |
| ATOM | 5673 | CA | GLY | L | 42 | 22.896 | 16.888 | 7.044 | 1.00 | 61.23 | C |
| ATOM | 5674 | C | GLY | L | 42 | 21.948 | 16.258 | 6.036 | 1.00 | 65.97 | C |
| ATOM | 5675 | O | GLY | L | 42 | 20.743 | 16.139 | 6.293 | 1.00 | 65.95 | O |
| ATOM | 5676 | N | GLN | L | 43 | 22.501 | 15.833 | 4.882 | 1.00 | 61.39 | N |
| ATOM | 5677 | CA | GLN | L | 43 | 21.766 | 15.223 | 3.778 | 1.00 | 59.34 | C |
| ATOM | 5678 | C | GLN | L | 43 | 22.441 | 13.933 | 3.344 | 1.00 | 58.69 | C |
| ATOM | 5679 | O | GLN | L | 43 | 23.592 | 13.656 | 3.719 | 1.00 | 58.73 | O |
| ATOM | 5680 | CB | GLN | L | 43 | 21.656 | 16.205 | 2.593 | 1.00 | 60.64 | C |
| ATOM | 5681 | CG | GLN | L | 43 | 20.802 | 17.437 | 2.883 | 1.00 | 61.94 | C |
| ATOM | 5682 | CD | GLN | L | 43 | 20.337 | 18.089 | 1.615 | 1.00 | 84.44 | C |
| ATOM | 5683 | OE1 | GLN | L | 43 | 19.518 | 17.539 | 0.874 | 1.00 | 81.09 | O |
| ATOM | 5684 | NE2 | GLN | L | 43 | 20.812 | 19.298 | 1.353 | 1.00 | 81.58 | N |
| ATOM | 5685 | N | ALA | L | 44 | 21.700 | 13.127 | 2.567 | 1.00 | 51.53 | N |
| ATOM | 5686 | CA | ALA | L | 44 | 22.193 | 11.846 | 2.058 | 1.00 | 49.32 | C |
| ATOM | 5687 | C | ALA | L | 44 | 23.117 | 12.079 | 0.870 | 1.00 | 48.57 | C |
| ATOM | 5688 | O | ALA | L | 44 | 22.938 | 13.078 | 0.170 | 1.00 | 45.05 | O |
| ATOM | 5689 | CB | ALA | L | 44 | 21.021 | 10.961 | 1.635 | 1.00 | 49.71 | C |
| ATOM | 5690 | N | PRO | L | 45 | 24.098 | 11.180 | 0.593 | 1.00 | 45.87 | N |
| ATOM | 5691 | CA | PRO | L | 45 | 24.909 | 11.348 | −0.619 | 1.00 | 45.35 | C |
| ATOM | 5692 | C | PRO | L | 45 | 24.017 | 11.237 | −1.864 | 1.00 | 51.05 | C |
| ATOM | 5693 | O | PRO | L | 45 | 22.953 | 10.601 | −1.817 | 1.00 | 51.85 | O |
| ATOM | 5694 | CB | PRO | L | 45 | 25.882 | 10.155 | −0.570 | 1.00 | 46.92 | C |
| ATOM | 5695 | CG | PRO | L | 45 | 25.840 | 9.661 | 0.833 | 1.00 | 51.74 | C |
| ATOM | 5696 | CD | PRO | L | 45 | 24.462 | 9.936 | 1.304 | 1.00 | 47.72 | C |
| ATOM | 5697 | N | ARG | L | 46 | 24.421 | 11.875 | −2.965 | 1.00 | 47.06 | N |
| ATOM | 5698 | CA | ARG | L | 46 | 23.697 | 11.775 | −4.228 | 1.00 | 47.38 | C |
| ATOM | 5699 | C | ARG | L | 46 | 24.689 | 11.592 | −5.351 | 1.00 | 52.81 | C |
| ATOM | 5700 | O | ARG | L | 46 | 25.791 | 12.138 | −5.283 | 1.00 | 54.12 | O |
| ATOM | 5701 | CB | ARG | L | 46 | 22.743 | 12.957 | −4.488 | 1.00 | 49.52 | C |
| ATOM | 5702 | CG | ARG | L | 46 | 23.391 | 14.313 | −4.715 | 1.00 | 54.55 | C |
| ATOM | 5703 | CD | ARG | L | 46 | 22.369 | 15.329 | −5.161 | 1.00 | 58.70 | C |
| ATOM | 5704 | NE | ARG | L | 46 | 23.027 | 16.567 | −5.584 | 1.00 | 71.05 | N |
| ATOM | 5705 | CZ | ARG | L | 46 | 22.537 | 17.411 | −6.485 | 1.00 | 81.32 | C |
| ATOM | 5706 | NH1 | ARG | L | 46 | 21.361 | 17.172 | −7.061 | 1.00 | 71.34 | N |
| ATOM | 5707 | NH2 | ARG | L | 46 | 23.217 | 18.501 | −6.817 | 1.00 | 60.17 | N |
| ATOM | 5708 | N | LEU | L | 47 | 24.318 | 10.782 | −6.373 | 1.00 | 46.09 | N |
| ATOM | 5709 | CA | LEU | L | 47 | 25.178 | 10.532 | −7.523 | 1.00 | 42.81 | C |
| ATOM | 5710 | C | LEU | L | 47 | 25.216 | 11.791 | −8.390 | 1.00 | 52.55 | C |
| ATOM | 5711 | O | LEU | L | 47 | 24.172 | 12.429 | −8.621 | 1.00 | 54.44 | O |
| ATOM | 5712 | CB | LEU | L | 47 | 24.674 | 9.324 | −8.334 | 1.00 | 40.60 | C |
| ATOM | 5713 | CG | LEU | L | 47 | 25.544 | 8.833 | −9.483 | 1.00 | 42.90 | C |
| ATOM | 5714 | CD1 | LEU | L | 47 | 26.797 | 8.194 | −8.993 | 1.00 | 42.54 | C |
| ATOM | 5715 | CD2 | LEU | L | 47 | 24.812 | 7.856 | −10.319 | 1.00 | 42.71 | C |
| ATOM | 5716 | N | LEU | L | 48 | 26.436 | 12.161 | −8.822 | 1.00 | 48.70 | N |
| ATOM | 5717 | CA | LEU | L | 48 | 26.700 | 13.251 | −9.729 | 1.00 | 48.38 | C |
| ATOM | 5718 | C | LEU | L | 48 | 27.143 | 12.674 | −11.070 | 1.00 | 52.68 | C |
| ATOM | 5719 | O | LEU | L | 48 | 26.590 | 13.049 | −12.101 | 1.00 | 54.63 | O |
| ATOM | 5720 | CB | LEU | L | 48 | 27.834 | 14.167 | −9.215 | 1.00 | 48.81 | C |
| ATOM | 5721 | CG | LEU | L | 48 | 27.633 | 15.004 | −7.973 | 1.00 | 53.56 | C |
| ATOM | 5722 | CD1 | LEU | L | 48 | 28.867 | 15.827 | −7.710 | 1.00 | 53.53 | C |
| ATOM | 5723 | CD2 | LEU | L | 48 | 26.402 | 15.895 | −8.072 | 1.00 | 54.71 | C |
| ATOM | 5724 | N | ILE | L | 49 | 28.185 | 11.820 | −11.067 | 1.00 | 47.45 | N |
| ATOM | 5725 | CA | ILE | L | 49 | 28.823 | 11.292 | −12.283 | 1.00 | 46.28 | C |
| ATOM | 5726 | C | ILE | L | 49 | 28.986 | 9.807 | −12.205 | 1.00 | 50.07 | C |
| ATOM | 5727 | O | ILE | L | 49 | 29.499 | 9.328 | −11.203 | 1.00 | 51.65 | O |
| ATOM | 5728 | CB | ILE | L | 49 | 30.217 | 11.969 | −12.441 | 1.00 | 48.99 | C |
| ATOM | 5729 | CG1 | ILE | L | 49 | 30.131 | 13.515 | −12.588 | 1.00 | 49.35 | C |
| ATOM | 5730 | CG2 | ILE | L | 49 | 31.042 | 11.350 | −13.540 | 1.00 | 49.62 | C |
| ATOM | 5731 | CD1 | ILE | L | 49 | 29.374 | 14.075 | −13.820 | 1.00 | 66.24 | C |

TABLE1-continued

Three-dimensional crystal coordinate for anti-TcdB antibody beziotoxumab Fab –C. difficile toxin B (TcdB$^{(1834-2101)}$) complex.

| ATOM | 5732 | N | TYR | L | 50 | 28.570 | 9.075 | −13.237 | 1.00 | 46.08 | N |
|------|------|-----|-----|---|----|--------|--------|---------|------|-------|---|
| ATOM | 5733 | CA | TYR | L | 50 | 28.755 | 7.616 | −13.329 | 1.00 | 47.00 | C |
| ATOM | 5734 | C | TYR | L | 50 | 29.584 | 7.303 | −14.574 | 1.00 | 55.42 | C |
| ATOM | 5735 | O | TYR | L | 50 | 29.579 | 8.107 | −15.504 | 1.00 | 58.41 | O |
| ATOM | 5736 | CB | TYR | L | 50 | 27.423 | 6.865 | −13.368 | 1.00 | 47.76 | C |
| ATOM | 5737 | CG | TYR | L | 50 | 26.556 | 7.168 | −14.571 | 1.00 | 50.55 | C |
| ATOM | 5738 | CD2 | TYR | L | 50 | 26.553 | 6.330 | −15.684 | 1.00 | 50.95 | C |
| ATOM | 5739 | CD1 | TYR | L | 50 | 25.654 | 8.230 | −14.554 | 1.00 | 53.41 | C |
| ATOM | 5740 | CE2 | TYR | L | 50 | 25.716 | 6.577 | −16.774 | 1.00 | 51.53 | C |
| ATOM | 5741 | CE1 | TYR | L | 50 | 24.830 | 8.499 | −15.644 | 1.00 | 56.04 | C |
| ATOM | 5742 | CZ | TYR | L | 50 | 24.865 | 7.672 | −16.751 | 1.00 | 63.78 | C |
| ATOM | 5743 | OH | TYR | L | 50 | 24.050 | 7.986 | −17.808 | 1.00 | 70.91 | O |
| ATOM | 5744 | N | GLY | L | 51 | 30.305 | 6.180 | −14.585 | 1.00 | 50.73 | N |
| ATOM | 5745 | CA | GLY | L | 51 | 31.108 | 5.790 | −15.741 | 1.00 | 49.89 | C |
| ATOM | 5746 | C | GLY | L | 51 | 32.177 | 6.793 | −16.123 | 1.00 | 52.97 | C |
| ATOM | 5747 | O | GLY | L | 51 | 32.515 | 6.927 | −17.307 | 1.00 | 51.22 | O |
| ATOM | 5748 | N | ALA | L | 52 | 32.732 | 7.480 | −15.080 | 1.00 | 50.41 | N |
| ATOM | 5749 | CA | ALA | L | 52 | 33.811 | 8.483 | −15.058 | 1.00 | 49.57 | C |
| ATOM | 5750 | C | ALA | L | 52 | 33.456 | 9.829 | −15.630 | 1.00 | 54.00 | C |
| ATOM | 5751 | O | ALA | L | 52 | 33.902 | 10.817 | −15.068 | 1.00 | 55.55 | O |
| ATOM | 5752 | CB | ALA | L | 52 | 35.075 | 7.961 | −15.725 | 1.00 | 49.96 | C |
| ATOM | 5753 | N | SER | L | 53 | 32.668 | 9.896 | −16.718 | 1.00 | 50.16 | N |
| ATOM | 5754 | CA | SER | L | 53 | 32.327 | 11.139 | −17.428 | 1.00 | 49.72 | C |
| ATOM | 5755 | C | SER | L | 53 | 30.836 | 11.429 | −17.598 | 1.00 | 54.51 | C |
| ATOM | 5756 | O | SER | L | 53 | 30.489 | 12.578 | −17.913 | 1.00 | 55.03 | O |
| ATOM | 5757 | CB | SER | L | 53 | 32.969 | 11.137 | −18.811 | 1.00 | 51.07 | C |
| ATOM | 5758 | OG | SER | L | 53 | 32.341 | 10.160 | −19.628 | 1.00 | 59.00 | O |
| ATOM | 5759 | N | SER | L | 54 | 29.969 | 10.402 | −17.453 | 1.00 | 49.58 | N |
| ATOM | 5760 | CA | SER | L | 54 | 28.526 | 10.550 | −17.656 | 1.00 | 50.28 | C |
| ATOM | 5761 | C | SER | L | 54 | 27.895 | 11.196 | −16.465 | 1.00 | 57.85 | C |
| ATOM | 5762 | O | SER | L | 54 | 28.249 | 10.893 | −15.335 | 1.00 | 60.46 | O |
| ATOM | 5763 | CB | SER | L | 54 | 27.853 | 9.218 | −17.978 | 1.00 | 54.13 | C |
| ATOM | 5764 | OG | SER | L | 54 | 28.531 | 8.480 | −18.986 | 1.00 | 66.01 | O |
| ATOM | 5765 | N | ARG | L | 55 | 26.993 | 12.117 | −16.717 | 1.00 | 54.32 | N |
| ATOM | 5766 | CA | ARG | L | 55 | 26.343 | 12.922 | −15.700 | 1.00 | 54.47 | C |
| ATOM | 5767 | C | ARG | L | 55 | 25.013 | 12.270 | −15.298 | 1.00 | 60.79 | C |
| ATOM | 5768 | O | ARG | L | 55 | 24.189 | 11.972 | −16.170 | 1.00 | 61.13 | O |
| ATOM | 5769 | CB | ARG | L | 55 | 26.139 | 14.326 | −16.299 | 1.00 | 52.96 | C |
| ATOM | 5770 | CG | ARG | L | 55 | 26.083 | 15.486 | −15.327 | 1.00 | 56.57 | C |
| ATOM | 5771 | CD | ARG | L | 55 | 26.736 | 16.759 | −15.861 | 1.00 | 57.92 | C |
| ATOM | 5772 | NE | ARG | L | 55 | 26.307 | 17.113 | −17.213 | 1.00 | 69.09 | N |
| ATOM | 5773 | CZ | ARG | L | 55 | 27.102 | 17.615 | −18.155 | 1.00 | 92.62 | C |
| ATOM | 5774 | NH1 | ARG | L | 55 | 28.388 | 17.847 | −17.899 | 1.00 | 77.09 | N |
| ATOM | 5775 | NH2 | ARG | L | 55 | 26.622 | 17.884 | −19.359 | 1.00 | 89.25 | N |
| ATOM | 5776 | N | ALA | L | 56 | 24.806 | 12.039 | −13.979 | 1.00 | 56.98 | N |
| ATOM | 5777 | CA | ALA | L | 56 | 23.572 | 11.452 | −13.431 | 1.00 | 56.48 | C |
| ATOM | 5778 | C | ALA | L | 56 | 22.366 | 12.357 | −13.728 | 1.00 | 64.03 | C |
| ATOM | 5779 | O | ALA | L | 56 | 22.563 | 13.535 | −14.037 | 1.00 | 63.71 | O |
| ATOM | 5780 | CB | ALA | L | 56 | 23.713 | 11.214 | −11.938 | 1.00 | 56.46 | C |
| ATOM | 5781 | N | THR | L | 57 | 21.127 | 11.808 | −13.676 | 1.00 | 62.70 | N |
| ATOM | 5782 | CA | THR | L | 57 | 19.903 | 12.557 | −13.994 | 1.00 | 62.87 | C |
| ATOM | 5783 | C | THR | L | 57 | 19.742 | 13.832 | −13.156 | 1.00 | 68.09 | C |
| ATOM | 5784 | O | THR | L | 57 | 19.866 | 13.779 | −11.932 | 1.00 | 67.23 | O |
| ATOM | 5785 | CB | THR | L | 57 | 18.651 | 11.668 | −13.921 | 1.00 | 69.04 | C |
| ATOM | 5786 | OG1 | THR | L | 57 | 18.968 | 10.338 | −14.311 | 1.00 | 67.95 | O |
| ATOM | 5787 | CG2 | THR | L | 57 | 17.535 | 12.172 | −14.815 | 1.00 | 69.51 | C |
| ATOM | 5788 | N | GLY | L | 58 | 19.483 | 14.955 | −13.847 | 1.00 | 65.41 | N |
| ATOM | 5789 | CA | GLY | L | 58 | 19.256 | 16.269 | −13.244 | 1.00 | 64.91 | C |
| ATOM | 5790 | C | GLY | L | 58 | 20.476 | 16.915 | −12.621 | 1.00 | 69.06 | C |
| ATOM | 5791 | O | GLY | L | 58 | 20.359 | 17.761 | −11.716 | 1.00 | 69.23 | O |
| ATOM | 5792 | N | ILE | L | 59 | 21.663 | 16.521 | −13.100 | 1.00 | 63.55 | N |
| ATOM | 5793 | CA | ILE | L | 59 | 22.885 | 17.094 | −12.566 | 1.00 | 61.71 | C |
| ATOM | 5794 | C | ILE | L | 59 | 23.345 | 18.247 | −13.469 | 1.00 | 67.28 | C |
| ATOM | 5795 | O | ILE | L | 59 | 23.663 | 18.001 | −14.642 | 1.00 | 67.39 | O |
| ATOM | 5796 | CB | ILE | L | 59 | 23.990 | 16.028 | −12.245 | 1.00 | 62.50 | C |
| ATOM | 5797 | CG1 | ILE | L | 59 | 23.525 | 15.014 | −11.156 | 1.00 | 60.69 | C |
| ATOM | 5798 | CG2 | ILE | L | 59 | 25.342 | 16.658 | −11.874 | 1.00 | 62.20 | C |
| ATOM | 5799 | CD1 | ILE | L | 59 | 22.962 | 15.573 | −9.830 | 1.00 | 48.93 | C |
| ATOM | 5800 | N | PRO | L | 60 | 23.394 | 19.494 | −12.895 | 1.00 | 63.13 | N |
| ATOM | 5801 | CA | PRO | L | 60 | 23.872 | 20.672 | −13.648 | 1.00 | 62.71 | C |
| ATOM | 5802 | C | PRO | L | 60 | 25.130 | 20.487 | −14.498 | 1.00 | 67.42 | C |
| ATOM | 5803 | O | PRO | L | 60 | 26.055 | 19.774 | −14.091 | 1.00 | 67.74 | O |
| ATOM | 5804 | CB | PRO | L | 60 | 24.161 | 21.679 | −12.538 | 1.00 | 64.53 | C |
| ATOM | 5805 | CG | PRO | L | 60 | 23.224 | 21.328 | −11.456 | 1.00 | 68.23 | C |
| ATOM | 5806 | CD | PRO | L | 60 | 23.037 | 19.861 | −11.504 | 1.00 | 63.68 | C |
| ATOM | 5807 | N | ASP | L | 61 | 25.187 | 21.188 | −15.653 | 1.00 | 63.73 | N |
| ATOM | 5808 | CA | ASP | L | 61 | 26.301 | 21.146 | −16.612 | 1.00 | 63.33 | C |

TABLE 1-continued

Three-dimensional crystal coordinate for anti-TcdB antibody beziotoxumab Fab –C. difficile toxin B (TcdB$^{(1834-2101)}$) complex.

| ATOM | 5809 | C   | ASP | L | 61 | 27.636 | 21.612 | −16.034 | 1.00 | 62.99  | C |
|------|------|-----|-----|---|----|--------|--------|---------|------|--------|---|
| ATOM | 5810 | O   | ASP | L | 61 | 28.684 | 21.305 | −16.620 | 1.00 | 60.28  | O |
| ATOM | 5811 | CB  | ASP | L | 61 | 25.980 | 21.959 | −17.882 | 1.00 | 66.94  | C |
| ATOM | 5812 | CG  | ASP | L | 61 | 24.605 | 21.701 | −18.477 | 1.00 | 90.60  | C |
| ATOM | 5813 | OD1 | ASP | L | 61 | 23.595 | 22.126 | −17.852 | 1.00 | 94.51  | O |
| ATOM | 5814 | OD2 | ASP | L | 61 | 24.537 | 21.107 | −19.582 | 1.00 | 95.59  | O |
| ATOM | 5815 | N   | ARG | L | 62 | 27.614 | 22.363 | −14.901 | 1.00 | 59.82  | N |
| ATOM | 5816 | CA  | ARG | L | 62 | 28.859 | 22.838 | −14.263 | 1.00 | 59.65  | C |
| ATOM | 5817 | C   | ARG | L | 62 | 29.693 | 21.656 | −13.733 | 1.00 | 63.14  | C |
| ATOM | 5818 | O   | ARG | L | 62 | 30.932 | 21.724 | −13.693 | 1.00 | 62.83  | O |
| ATOM | 5819 | CB  | ARG | L | 62 | 28.613 | 23.926 | −13.200 | 1.00 | 56.72  | C |
| ATOM | 5820 | CG  | ARG | L | 62 | 27.738 | 23.515 | −12.033 | 1.00 | 59.13  | C |
| ATOM | 5821 | CD  | ARG | L | 62 | 27.408 | 24.749 | −11.233 | 1.00 | 59.60  | C |
| ATOM | 5822 | NE  | ARG | L | 62 | 26.724 | 24.442 | −9.982  | 1.00 | 65.52  | N |
| ATOM | 5823 | CZ  | ARG | L | 62 | 25.407 | 24.375 | −9.838  | 1.00 | 84.67  | C |
| ATOM | 5824 | NH1 | ARG | L | 62 | 24.607 | 24.575 | −10.879 | 1.00 | 76.96  | N |
| ATOM | 5825 | NH2 | ARG | L | 62 | 24.877 | 24.105 | −8.653  | 1.00 | 73.58  | N |
| ATOM | 5826 | N   | PHE | L | 63 | 28.991 | 20.554 | −13.397 | 1.00 | 57.17  | N |
| ATOM | 5827 | CA  | PHE | L | 63 | 29.606 | 19.309 | −12.972 | 1.00 | 56.22  | C |
| ATOM | 5828 | C   | PHE | L | 63 | 30.072 | 18.514 | −14.217 | 1.00 | 63.19  | C |
| ATOM | 5829 | O   | PHE | L | 63 | 29.263 | 18.193 | −15.100 | 1.00 | 64.84  | O |
| ATOM | 5830 | CB  | PHE | L | 63 | 28.641 | 18.496 | −12.099 | 1.00 | 56.29  | C |
| ATOM | 5831 | CG  | PHE | L | 63 | 28.344 | 19.127 | −10.749 | 1.00 | 56.11  | C |
| ATOM | 5832 | CD1 | PHE | L | 63 | 29.298 | 19.118 | −9.728  | 1.00 | 56.41  | C |
| ATOM | 5833 | CD2 | PHE | L | 63 | 27.102 | 19.685 | −10.482 | 1.00 | 56.25  | C |
| ATOM | 5834 | CE1 | PHE | L | 63 | 29.026 | 19.686 | −8.486  | 1.00 | 55.15  | C |
| ATOM | 5835 | CE2 | PHE | L | 63 | 26.835 | 20.256 | −9.238  | 1.00 | 57.30  | C |
| ATOM | 5836 | CZ  | PHE | L | 63 | 27.800 | 20.242 | −8.249  | 1.00 | 54.72  | C |
| ATOM | 5837 | N   | SER | L | 64 | 31.389 | 18.258 | −14.303 | 1.00 | 56.81  | N |
| ATOM | 5838 | CA  | SER | L | 64 | 32.011 | 17.522 | −15.396 | 1.00 | 54.91  | C |
| ATOM | 5839 | C   | SER | L | 64 | 32.984 | 16.487 | −14.789 | 1.00 | 58.65  | C |
| ATOM | 5840 | O   | SER | L | 64 | 33.655 | 16.781 | −13.788 | 1.00 | 57.31  | O |
| ATOM | 5841 | CB  | SER | L | 64 | 32.707 | 18.499 | −16.337 | 1.00 | 55.44  | C |
| ATOM | 5842 | OG  | SER | L | 64 | 33.870 | 17.989 | −16.966 | 1.00 | 59.84  | O |
| ATOM | 5843 | N   | GLY | L | 65 | 33.005 | 15.279 | −15.368 | 1.00 | 54.81  | N |
| ATOM | 5844 | CA  | GLY | L | 65 | 33.865 | 14.185 | −14.927 | 1.00 | 53.66  | C |
| ATOM | 5845 | C   | GLY | L | 65 | 34.801 | 13.727 | −16.011 | 1.00 | 58.15  | C |
| ATOM | 5846 | O   | GLY | L | 65 | 34.396 | 13.640 | −17.166 | 1.00 | 60.10  | O |
| ATOM | 5847 | N   | SER | L | 66 | 36.057 | 13.430 | −15.663 | 1.00 | 54.74  | N |
| ATOM | 5848 | CA  | SER | L | 66 | 37.095 | 13.005 | −16.631 | 1.00 | 54.86  | C |
| ATOM | 5849 | C   | SER | L | 66 | 38.179 | 12.173 | −15.970 | 1.00 | 58.41  | C |
| ATOM | 5850 | O   | SER | L | 66 | 38.235 | 12.103 | −14.735 | 1.00 | 59.23  | O |
| ATOM | 5851 | CB  | SER | L | 66 | 37.755 | 14.225 | −17.276 | 1.00 | 60.23  | C |
| ATOM | 5852 | OG  | SER | L | 66 | 38.174 | 15.157 | −16.286 | 1.00 | 78.66  | O |
| ATOM | 5853 | N   | GLY | L | 67 | 39.038 | 11.583 | −16.800 | 1.00 | 53.96  | N |
| ATOM | 5854 | CA  | GLY | L | 67 | 40.164 | 10.755 | −16.372 | 1.00 | 54.54  | C |
| ATOM | 5855 | C   | GLY | L | 67 | 40.129 | 9.341  | −16.915 | 1.00 | 60.66  | C |
| ATOM | 5856 | O   | GLY | L | 67 | 39.127 | 8.936  | −17.516 | 1.00 | 63.09  | O |
| ATOM | 5857 | N   | SER | L | 68 | 41.224 | 8.586  | −16.708 | 1.00 | 56.17  | N |
| ATOM | 5858 | CA  | SER | L | 68 | 41.388 | 7.170  | −17.069 | 1.00 | 57.09  | C |
| ATOM | 5859 | C   | SER | L | 68 | 42.566 | 6.554  | −16.281 | 1.00 | 63.38  | C |
| ATOM | 5860 | O   | SER | L | 68 | 43.379 | 7.287  | −15.708 | 1.00 | 62.58  | O |
| ATOM | 5861 | CB  | SER | L | 68 | 41.616 | 6.988  | −18.567 | 1.00 | 61.84  | C |
| ATOM | 5862 | OG  | SER | L | 68 | 42.996 | 7.052  | −18.902 | 1.00 | 74.23  | O |
| ATOM | 5863 | N   | GLY | L | 69 | 42.651 | 5.224  | −16.283 | 1.00 | 61.34  | N |
| ATOM | 5864 | CA  | GLY | L | 69 | 43.727 | 4.508  | −15.610 | 1.00 | 61.65  | C |
| ATOM | 5865 | C   | GLY | L | 69 | 43.673 | 4.590  | −14.101 | 1.00 | 65.89  | C |
| ATOM | 5866 | O   | GLY | L | 69 | 42.922 | 3.841  | −13.468 | 1.00 | 66.36  | O |
| ATOM | 5867 | N   | THR | L | 70 | 44.465 | 5.506  | −13.520 | 1.00 | 61.20  | N |
| ATOM | 5868 | CA  | THR | L | 70 | 44.548 | 5.704  | −12.064 | 1.00 | 60.43  | C |
| ATOM | 5869 | C   | THR | L | 70 | 44.127 | 7.104  | −11.640 | 1.00 | 63.32  | C |
| ATOM | 5870 | O   | THR | L | 70 | 43.723 | 7.262  | −10.497 | 1.00 | 63.15  | O |
| ATOM | 5871 | CB  | THR | L | 70 | 45.973 | 5.403  | −11.519 | 1.00 | 68.78  | C |
| ATOM | 5872 | OG1 | THR | L | 70 | 46.935 | 6.230  | −12.178 | 1.00 | 66.44  | O |
| ATOM | 5873 | CG2 | THR | L | 70 | 46.371 | 3.957  | −11.668 | 1.00 | 67.13  | C |
| ATOM | 5874 | N   | ASP | L | 71 | 44.238 | 8.117  | −12.527 | 1.00 | 59.61  | N |
| ATOM | 5875 | CA  | ASP | L | 71 | 43.905 | 9.496  | −12.186 | 1.00 | 59.92  | C |
| ATOM | 5876 | C   | ASP | L | 71 | 42.598 | 9.978  | −12.763 | 1.00 | 61.40  | C |
| ATOM | 5877 | O   | ASP | L | 71 | 42.436 | 10.027 | −13.979 | 1.00 | 61.27  | O |
| ATOM | 5878 | CB  | ASP | L | 71 | 45.046 | 10.441 | −12.555 | 1.00 | 63.66  | C |
| ATOM | 5879 | CG  | ASP | L | 71 | 46.282 | 10.294 | −11.669 | 1.00 | 92.94  | C |
| ATOM | 5880 | OD1 | ASP | L | 71 | 46.738 | 9.139  | −11.459 | 1.00 | 95.34  | O |
| ATOM | 5881 | OD2 | ASP | L | 71 | 46.814 | 11.336 | −11.214 | 1.00 | 106.83 | O |
| ATOM | 5882 | N   | PHE | L | 72 | 41.668 | 10.358 | −11.864 | 1.00 | 56.44  | N |
| ATOM | 5883 | CA  | PHE | L | 72 | 40.316 | 10.845 | −12.182 | 1.00 | 54.76  | C |
| ATOM | 5884 | C   | PHE | L | 72 | 40.081 | 12.228 | −11.589 | 1.00 | 58.38  | C |
| ATOM | 5885 | O   | PHE | L | 72 | 40.806 | 12.621 | −10.667 | 1.00 | 59.77  | O |

TABLE 1-continued

Three-dimensional crystal coordinate for anti-TcdB antibody beziotoxumab Fab –C. *difficile* toxin B (TcdB$^{(1834-2101)}$) complex.

| ATOM | 5886 | CB | PHE | L | 72 | 39.241 | 9.832 | −11.761 | 1.00 | 55.16 | C |
|---|---|---|---|---|---|---|---|---|---|---|---|
| ATOM | 5887 | CG | PHE | L | 72 | 39.353 | 8.500 | −12.478 | 1.00 | 55.60 | C |
| ATOM | 5888 | CD1 | PHE | L | 72 | 38.709 | 8.290 | −13.697 | 1.00 | 57.70 | C |
| ATOM | 5889 | CD2 | PHE | L | 72 | 40.134 | 7.469 | −11.956 | 1.00 | 55.85 | C |
| ATOM | 5890 | CE1 | PHE | L | 72 | 38.834 | 7.073 | −14.376 | 1.00 | 56.96 | C |
| ATOM | 5891 | CE2 | PHE | L | 72 | 40.257 | 6.248 | −12.634 | 1.00 | 57.87 | C |
| ATOM | 5892 | CZ | PHE | L | 72 | 39.615 | 6.066 | −13.843 | 1.00 | 55.66 | C |
| ATOM | 5893 | N | THR | L | 73 | 39.144 | 13.005 | −12.179 | 1.00 | 52.38 | N |
| ATOM | 5894 | CA | THR | L | 73 | 38.911 | 14.387 | −11.794 | 1.00 | 51.35 | C |
| ATOM | 5895 | C | THR | L | 73 | 37.463 | 14.799 | −11.914 | 1.00 | 55.32 | C |
| ATOM | 5896 | O | THR | L | 73 | 36.836 | 14.620 | −12.968 | 1.00 | 57.20 | O |
| ATOM | 5897 | CB | THR | L | 73 | 39.775 | 15.337 | −12.713 | 1.00 | 60.15 | C |
| ATOM | 5898 | OG1 | THR | L | 73 | 41.135 | 14.918 | −12.768 | 1.00 | 57.14 | O |
| ATOM | 5899 | CG2 | THR | L | 73 | 39.728 | 16.808 | −12.295 | 1.00 | 59.35 | C |
| ATOM | 5900 | N | LEU | L | 74 | 36.966 | 15.454 | −10.870 | 1.00 | 49.47 | N |
| ATOM | 5901 | CA | LEU | L | 74 | 35.641 | 16.066 | −10.897 | 1.00 | 47.79 | C |
| ATOM | 5902 | C | LEU | L | 74 | 35.895 | 17.574 | −11.000 | 1.00 | 52.87 | C |
| ATOM | 5903 | O | LEU | L | 74 | 36.695 | 18.138 | −10.235 | 1.00 | 51.22 | O |
| ATOM | 5904 | CB | LEU | L | 74 | 34.829 | 15.746 | −9.631 | 1.00 | 46.50 | C |
| ATOM | 5905 | CG | LEU | L | 74 | 33.443 | 16.376 | −9.546 | 1.00 | 48.05 | C |
| ATOM | 5906 | CD1 | LEU | L | 74 | 32.435 | 15.584 | −10.343 | 1.00 | 47.27 | C |
| ATOM | 5907 | CD2 | LEU | L | 74 | 32.989 | 16.501 | −8.122 | 1.00 | 47.46 | C |
| ATOM | 5908 | N | THR | L | 75 | 35.199 | 18.220 | −11.940 | 1.00 | 50.79 | N |
| ATOM | 5909 | CA | THR | L | 75 | 35.316 | 19.651 | −12.183 | 1.00 | 49.97 | C |
| ATOM | 5910 | C | THR | L | 75 | 33.990 | 20.353 | −11.955 | 1.00 | 53.61 | C |
| ATOM | 5911 | O | THR | L | 75 | 32.943 | 19.837 | −12.346 | 1.00 | 53.92 | O |
| ATOM | 5912 | CB | THR | L | 75 | 35.863 | 19.889 | −13.607 | 1.00 | 56.93 | C |
| ATOM | 5913 | OG1 | THR | L | 75 | 36.945 | 18.990 | −13.857 | 1.00 | 60.43 | O |
| ATOM | 5914 | CG2 | THR | L | 75 | 36.340 | 21.311 | −13.821 | 1.00 | 54.29 | C |
| ATOM | 5915 | N | ILE | L | 76 | 34.031 | 21.522 | −11.309 | 1.00 | 50.54 | N |
| ATOM | 5916 | CA | ILE | L | 76 | 32.871 | 22.399 | −11.103 | 1.00 | 50.78 | C |
| ATOM | 5917 | C | ILE | L | 76 | 33.331 | 23.707 | −11.737 | 1.00 | 60.08 | C |
| ATOM | 5918 | O | ILE | L | 76 | 34.189 | 24.385 | −11.169 | 1.00 | 61.97 | O |
| ATOM | 5919 | CB | ILE | L | 76 | 32.427 | 22.546 | −9.606 | 1.00 | 53.05 | C |
| ATOM | 5920 | CG1 | ILE | L | 76 | 32.232 | 21.178 | −8.925 | 1.00 | 53.30 | C |
| ATOM | 5921 | CG2 | ILE | L | 76 | 31.145 | 23.342 | −9.500 | 1.00 | 52.76 | C |
| ATOM | 5922 | CD1 | ILE | L | 76 | 32.540 | 21.126 | −7.447 | 1.00 | 52.48 | C |
| ATOM | 5923 | N | SER | L | 77 | 32.841 | 24.010 | −12.959 | 1.00 | 58.65 | N |
| ATOM | 5924 | CA | SER | L | 77 | 33.228 | 25.199 | −13.757 | 1.00 | 58.47 | C |
| ATOM | 5925 | C | SER | L | 77 | 33.037 | 26.554 | −13.041 | 1.00 | 64.07 | C |
| ATOM | 5926 | O | SER | L | 77 | 33.833 | 27.482 | −13.229 | 1.00 | 66.93 | O |
| ATOM | 5927 | CB | SER | L | 77 | 32.486 | 25.204 | −15.084 | 1.00 | 60.87 | C |
| ATOM | 5928 | OG | SER | L | 77 | 31.089 | 25.350 | −14.888 | 1.00 | 69.89 | O |
| ATOM | 5929 | N | ARG | L | 78 | 32.008 | 26.646 | −12.211 | 1.00 | 57.66 | N |
| ATOM | 5930 | CA | ARG | L | 78 | 31.686 | 27.831 | −11.440 | 1.00 | 58.28 | C |
| ATOM | 5931 | C | ARG | L | 78 | 30.956 | 27.366 | −10.167 | 1.00 | 62.17 | C |
| ATOM | 5932 | O | ARG | L | 78 | 29.841 | 26.826 | −10.263 | 1.00 | 61.13 | O |
| ATOM | 5933 | CB | ARG | L | 78 | 30.813 | 28.786 | −12.290 | 1.00 | 61.58 | C |
| ATOM | 5934 | CG | ARG | L | 78 | 30.027 | 29.872 | −11.530 | 1.00 | 73.53 | C |
| ATOM | 5935 | CD | ARG | L | 78 | 29.401 | 30.894 | −12.458 | 1.00 | 89.57 | C |
| ATOM | 5936 | NE | ARG | L | 78 | 30.443 | 31.640 | −13.163 | 1.00 | 106.00 | N |
| ATOM | 5937 | CZ | ARG | L | 78 | 30.828 | 32.871 | −12.856 | 1.00 | 125.30 | C |
| ATOM | 5938 | NH1 | ARG | L | 78 | 31.809 | 33.452 | −13.533 | 1.00 | 108.46 | N |
| ATOM | 5939 | NH2 | ARG | L | 78 | 30.200 | 33.553 | −11.902 | 1.00 | 116.44 | N |
| ATOM | 5940 | N | LEU | L | 79 | 31.600 | 27.537 | −8.986 | 1.00 | 56.93 | N |
| ATOM | 5941 | CA | LEU | L | 79 | 31.026 | 27.123 | −7.707 | 1.00 | 55.62 | C |
| ATOM | 5942 | C | LEU | L | 79 | 29.865 | 28.015 | −7.263 | 1.00 | 58.48 | C |
| ATOM | 5943 | O | LEU | L | 79 | 30.039 | 29.202 | −7.010 | 1.00 | 57.44 | O |
| ATOM | 5944 | CB | LEU | L | 79 | 32.090 | 27.080 | −6.595 | 1.00 | 55.43 | C |
| ATOM | 5945 | CG | LEU | L | 79 | 33.165 | 26.011 | −6.643 | 1.00 | 59.69 | C |
| ATOM | 5946 | CD1 | LEU | L | 79 | 34.273 | 26.353 | −5.684 | 1.00 | 59.92 | C |
| ATOM | 5947 | CD2 | LEU | L | 79 | 32.613 | 24.661 | −6.268 | 1.00 | 61.04 | C |
| ATOM | 5948 | N | GLU | L | 80 | 28.692 | 27.425 | −7.133 | 1.00 | 55.72 | N |
| ATOM | 5949 | CA | GLU | L | 80 | 27.503 | 28.098 | −6.659 | 1.00 | 56.06 | C |
| ATOM | 5950 | C | GLU | L | 80 | 27.493 | 27.943 | −5.117 | 1.00 | 63.06 | C |
| ATOM | 5951 | O | GLU | L | 80 | 28.318 | 27.187 | −4.586 | 1.00 | 61.48 | O |
| ATOM | 5952 | CB | GLU | L | 80 | 26.240 | 27.500 | −7.328 | 1.00 | 57.16 | C |
| ATOM | 5953 | CG | GLU | L | 80 | 26.093 | 27.786 | −8.818 | 1.00 | 69.05 | C |
| ATOM | 5954 | CD | GLU | L | 80 | 26.127 | 29.238 | −9.263 | 1.00 | 103.17 | C |
| ATOM | 5955 | OE1 | GLU | L | 80 | 25.392 | 30.066 | −8.677 | 1.00 | 117.15 | O |
| ATOM | 5956 | OE2 | GLU | L | 80 | 26.874 | 29.542 | −10.222 | 1.00 | 97.16 | O |
| ATOM | 5957 | N | PRO | L | 81 | 26.614 | 28.656 | −4.358 | 1.00 | 62.24 | N |
| ATOM | 5958 | CA | PRO | L | 81 | 26.621 | 28.493 | −2.889 | 1.00 | 62.76 | C |
| ATOM | 5959 | C | PRO | L | 81 | 26.330 | 27.055 | −2.442 | 1.00 | 68.81 | C |
| ATOM | 5960 | O | PRO | L | 81 | 26.957 | 26.542 | −1.508 | 1.00 | 69.54 | O |
| ATOM | 5961 | CB | PRO | L | 81 | 25.516 | 29.455 | −2.431 | 1.00 | 63.90 | C |
| ATOM | 5962 | CG | PRO | L | 81 | 25.371 | 30.418 | −3.524 | 1.00 | 67.14 | C |

TABLE 1-continued

Three-dimensional crystal coordinate for anti-TcdB antibody beziotoxumab Fab – C. difficile toxin B (TcdB$^{(1834-2101)}$) complex.

| ATOM | 5963 | CD | PRO | L | 81 | 25.582 | 29.631 | −4.767 | 1.00 | 62.53 | C |
|------|------|-----|-----|---|----|--------|--------|--------|------|-------|---|
| ATOM | 5964 | N | GLU | L | 82 | 25.399 | 26.396 | −3.154 | 1.00 | 65.21 | N |
| ATOM | 5965 | CA | GLU | L | 82 | 24.954 | 25.018 | −2.909 | 1.00 | 64.35 | C |
| ATOM | 5966 | C | GLU | L | 82 | 26.076 | 23.979 | −3.063 | 1.00 | 63.66 | C |
| ATOM | 5967 | O | GLU | L | 82 | 26.049 | 22.969 | −2.366 | 1.00 | 63.43 | O |
| ATOM | 5968 | CB | GLU | L | 82 | 23.717 | 24.663 | −3.780 | 1.00 | 65.92 | C |
| ATOM | 5969 | CG | GLU | L | 82 | 23.779 | 25.077 | −5.250 | 1.00 | 80.48 | C |
| ATOM | 5970 | CD | GLU | L | 82 | 23.206 | 26.429 | −5.669 | 1.00 | 109.48 | C |
| ATOM | 5971 | OE1 | GLU | L | 82 | 23.019 | 27.319 | −4.803 | 1.00 | 94.67 | O |
| ATOM | 5972 | OE2 | GLU | L | 82 | 22.974 | 26.608 | −6.889 | 1.00 | 105.83 | O |
| ATOM | 5973 | N | ASP | L | 83 | 27.091 | 24.281 | −3.898 | 1.00 | 56.53 | N |
| ATOM | 5974 | CA | ASP | L | 83 | 28.233 | 23.422 | −4.252 | 1.00 | 54.91 | C |
| ATOM | 5975 | C | ASP | L | 83 | 29.275 | 23.214 | −3.152 | 1.00 | 56.94 | C |
| ATOM | 5976 | O | ASP | L | 83 | 30.140 | 22.350 | −3.303 | 1.00 | 57.35 | O |
| ATOM | 5977 | CB | ASP | L | 83 | 28.911 | 23.930 | −5.537 | 1.00 | 55.47 | C |
| ATOM | 5978 | CG | ASP | L | 83 | 28.005 | 23.903 | −6.775 | 1.00 | 63.26 | C |
| ATOM | 5979 | OD1 | ASP | L | 83 | 26.887 | 23.305 | −6.706 | 1.00 | 62.97 | O |
| ATOM | 5980 | OD2 | ASP | L | 83 | 28.401 | 24.464 | −7.799 | 1.00 | 70.85 | O |
| ATOM | 5981 | N | PHE | L | 84 | 29.174 | 23.936 | −2.037 | 1.00 | 50.62 | N |
| ATOM | 5982 | CA | PHE | L | 84 | 30.096 | 23.724 | −0.923 | 1.00 | 48.57 | C |
| ATOM | 5983 | C | PHE | L | 84 | 29.580 | 22.525 | −0.099 | 1.00 | 55.52 | C |
| ATOM | 5984 | O | PHE | L | 84 | 28.532 | 22.610 | 0.553 | 1.00 | 56.71 | O |
| ATOM | 5985 | CB | PHE | L | 84 | 30.321 | 25.019 | −0.117 | 1.00 | 48.58 | C |
| ATOM | 5986 | CG | PHE | L | 84 | 31.024 | 26.059 | −0.943 | 1.00 | 48.75 | C |
| ATOM | 5987 | CD1 | PHE | L | 84 | 32.416 | 26.065 | −1.049 | 1.00 | 49.93 | C |
| ATOM | 5988 | CD2 | PHE | L | 84 | 30.299 | 26.991 | −1.680 | 1.00 | 50.42 | C |
| ATOM | 5989 | CE1 | PHE | L | 84 | 33.068 | 26.995 | −1.857 | 1.00 | 49.13 | C |
| ATOM | 5990 | CE2 | PHE | L | 84 | 30.953 | 27.910 | −2.503 | 1.00 | 51.88 | C |
| ATOM | 5991 | CZ | PHE | L | 84 | 32.333 | 27.902 | −2.583 | 1.00 | 48.58 | C |
| ATOM | 5992 | N | ALA | L | 85 | 30.255 | 21.364 | −0.254 | 1.00 | 51.11 | N |
| ATOM | 5993 | CA | ALA | L | 85 | 29.882 | 20.091 | 0.366 | 1.00 | 49.42 | C |
| ATOM | 5994 | C | ALA | L | 85 | 31.048 | 19.100 | 0.284 | 1.00 | 52.28 | C |
| ATOM | 5995 | O | ALA | L | 85 | 32.154 | 19.460 | −0.123 | 1.00 | 50.91 | O |
| ATOM | 5996 | CB | ALA | L | 85 | 28.659 | 19.500 | −0.351 | 1.00 | 49.99 | C |
| ATOM | 5997 | N | VAL | L | 86 | 30.785 | 17.838 | 0.666 | 1.00 | 48.77 | N |
| ATOM | 5998 | CA | VAL | L | 86 | 31.790 | 16.787 | 0.590 | 1.00 | 46.99 | C |
| ATOM | 5999 | C | VAL | L | 86 | 31.569 | 15.972 | −0.682 | 1.00 | 50.28 | C |
| ATOM | 6000 | O | VAL | L | 86 | 30.429 | 15.794 | −1.118 | 1.00 | 48.85 | O |
| ATOM | 6001 | CB | VAL | L | 86 | 31.868 | 15.940 | 1.871 | 1.00 | 47.72 | C |
| ATOM | 6002 | CG1 | VAL | L | 86 | 33.019 | 14.947 | 1.796 | 1.00 | 46.53 | C |
| ATOM | 6003 | CG2 | VAL | L | 86 | 32.019 | 16.841 | 3.092 | 1.00 | 46.57 | C |
| ATOM | 6004 | N | TYR | L | 87 | 32.673 | 15.540 | −1.300 | 1.00 | 46.90 | N |
| ATOM | 6005 | CA | TYR | L | 87 | 32.645 | 14.800 | −2.541 | 1.00 | 46.45 | C |
| ATOM | 6006 | C | TYR | L | 87 | 33.435 | 13.540 | −2.397 | 1.00 | 54.18 | C |
| ATOM | 6007 | O | TYR | L | 87 | 34.634 | 13.582 | −2.062 | 1.00 | 55.29 | O |
| ATOM | 6008 | CB | TYR | L | 87 | 33.207 | 15.653 | −3.679 | 1.00 | 46.51 | C |
| ATOM | 6009 | CG | TYR | L | 87 | 32.341 | 16.844 | −4.008 | 1.00 | 48.00 | C |
| ATOM | 6010 | CD1 | TYR | L | 87 | 31.309 | 16.745 | −4.934 | 1.00 | 47.70 | C |
| ATOM | 6011 | CD2 | TYR | L | 87 | 32.538 | 18.069 | −3.379 | 1.00 | 50.58 | C |
| ATOM | 6012 | CE1 | TYR | L | 87 | 30.501 | 17.835 | −5.229 | 1.00 | 48.16 | C |
| ATOM | 6013 | CE2 | TYR | L | 87 | 31.715 | 19.158 | −3.644 | 1.00 | 50.45 | C |
| ATOM | 6014 | CZ | TYR | L | 87 | 30.704 | 19.039 | −4.575 | 1.00 | 52.38 | C |
| ATOM | 6015 | OH | TYR | L | 87 | 29.915 | 20.116 | −4.855 | 1.00 | 50.93 | O |
| ATOM | 6016 | N | TYR | L | 88 | 32.775 | 12.403 | −2.668 | 1.00 | 49.42 | N |
| ATOM | 6017 | CA | TYR | L | 88 | 33.418 | 11.091 | −2.596 | 1.00 | 48.12 | C |
| ATOM | 6018 | C | TYR | L | 88 | 33.500 | 10.462 | −3.980 | 1.00 | 53.17 | C |
| ATOM | 6019 | O | TYR | L | 88 | 32.557 | 10.566 | −4.754 | 1.00 | 52.26 | O |
| ATOM | 6020 | CB | TYR | L | 88 | 32.661 | 10.138 | −1.635 | 1.00 | 46.86 | C |
| ATOM | 6021 | CG | TYR | L | 88 | 32.447 | 10.663 | −0.229 | 1.00 | 46.16 | C |
| ATOM | 6022 | CD1 | TYR | L | 88 | 33.352 | 10.378 | 0.790 | 1.00 | 47.49 | C |
| ATOM | 6023 | CD2 | TYR | L | 88 | 31.291 | 11.373 | 0.105 | 1.00 | 46.71 | C |
| ATOM | 6024 | CE1 | TYR | L | 88 | 33.153 | 10.853 | 2.093 | 1.00 | 46.28 | C |
| ATOM | 6025 | CE2 | TYR | L | 88 | 31.070 | 11.828 | 1.405 | 1.00 | 47.66 | C |
| ATOM | 6026 | CZ | TYR | L | 88 | 32.004 | 11.563 | 2.395 | 1.00 | 54.38 | C |
| ATOM | 6027 | OH | TYR | L | 88 | 31.783 | 12.045 | 3.660 | 1.00 | 62.00 | O |
| ATOM | 6028 | N | CYS | L | 89 | 34.624 | 9.827 | −4.298 | 1.00 | 53.10 | N |
| ATOM | 6029 | CA | CYS | L | 89 | 34.724 | 9.087 | −5.543 | 1.00 | 54.58 | C |
| ATOM | 6030 | C | CYS | L | 89 | 34.578 | 7.629 | −5.170 | 1.00 | 57.92 | C |
| ATOM | 6031 | O | CYS | L | 89 | 34.694 | 7.280 | −3.985 | 1.00 | 57.49 | O |
| ATOM | 6032 | CB | CYS | L | 89 | 35.998 | 9.382 | −6.333 | 1.00 | 56.37 | C |
| ATOM | 6033 | SG | CYS | L | 89 | 37.547 | 8.992 | −5.478 | 1.00 | 61.65 | S |
| ATOM | 6034 | N | GLN | L | 90 | 34.213 | 6.790 | −6.146 | 1.00 | 52.95 | N |
| ATOM | 6035 | CA | GLN | L | 90 | 33.928 | 5.385 | −5.889 | 1.00 | 51.28 | C |
| ATOM | 6036 | C | GLN | L | 90 | 34.458 | 4.509 | −7.003 | 1.00 | 54.42 | C |
| ATOM | 6037 | O | GLN | L | 90 | 34.506 | 4.941 | −8.147 | 1.00 | 53.41 | O |
| ATOM | 6038 | CB | GLN | L | 90 | 32.404 | 5.208 | −5.676 | 1.00 | 51.68 | C |
| ATOM | 6039 | CG | GLN | L | 90 | 31.880 | 3.783 | −5.473 | 1.00 | 48.00 | C |

TABLE1-continued

Three-dimensional crystal coordinate for anti-TcdB antibody beziotoxumab
Fab –C. difficile toxin B (TcdB$^{(1834-2101)}$) complex.

| | | | | | | | | | | |
|---|---|---|---|---|---|---|---|---|---|---|
| ATOM | 6040 | CD | GLN | L | 90 | 31.042 | 3.298 | −6.627 | 1.00 | 60.53 | C |
| ATOM | 6041 | OE1 | GLN | L | 90 | 29.946 | 3.767 | −6.847 | 1.00 | 55.93 | O |
| ATOM | 6042 | NE2 | GLN | L | 90 | 31.511 | 2.335 | −7.389 | 1.00 | 61.01 | N |
| ATOM | 6043 | N | GLN | L | 91 | 34.868 | 3.273 | −6.657 | 1.00 | 52.25 | N |
| ATOM | 6044 | CA | GLN | L | 91 | 35.339 | 2.259 | −7.600 | 1.00 | 51.01 | C |
| ATOM | 6045 | C | GLN | L | 91 | 34.766 | 0.873 | −7.345 | 1.00 | 54.19 | C |
| ATOM | 6046 | O | GLN | L | 91 | 34.031 | 0.662 | −6.383 | 1.00 | 52.08 | O |
| ATOM | 6047 | CB | GLN | L | 91 | 36.864 | 2.210 | −7.691 | 1.00 | 51.63 | C |
| ATOM | 6048 | CG | GLN | L | 91 | 37.381 | 2.922 | −8.928 | 1.00 | 70.35 | C |
| ATOM | 6049 | CD | GLN | L | 91 | 36.970 | 2.247 | −10.216 | 1.00 | 87.04 | C |
| ATOM | 6050 | OE1 | GLN | L | 91 | 36.722 | 1.040 | −10.252 | 1.00 | 77.33 | O |
| ATOM | 6051 | NE2 | GLN | L | 91 | 36.990 | 2.980 | −11.330 | 1.00 | 81.15 | N |
| ATOM | 6052 | N | TYR | L | 92 | 35.120 | −0.071 | −8.247 | 1.00 | 52.42 | N |
| ATOM | 6053 | CA | TYR | L | 92 | 34.729 | −1.489 | −8.319 | 1.00 | 51.01 | C |
| ATOM | 6054 | C | TYR | L | 92 | 35.730 | −2.301 | −9.241 | 1.00 | 57.90 | C |
| ATOM | 6055 | O | TYR | L | 92 | 35.980 | −1.927 | −10.389 | 1.00 | 59.31 | O |
| ATOM | 6056 | CB | TYR | L | 92 | 33.270 | −1.602 | −8.827 | 1.00 | 49.73 | C |
| ATOM | 6057 | CG | TYR | L | 92 | 32.686 | −2.994 | −8.747 | 1.00 | 48.18 | C |
| ATOM | 6058 | CD2 | TYR | L | 92 | 31.835 | −3.355 | −7.711 | 1.00 | 48.49 | C |
| ATOM | 6059 | CD1 | TYR | L | 92 | 32.980 | −3.951 | −9.712 | 1.00 | 49.10 | C |
| ATOM | 6060 | CE2 | TYR | L | 92 | 31.315 | −4.639 | −7.623 | 1.00 | 48.85 | C |
| ATOM | 6061 | CE1 | TYR | L | 92 | 32.451 | −5.229 | −9.647 | 1.00 | 47.70 | C |
| ATOM | 6062 | CZ | TYR | L | 92 | 31.617 | −5.568 | −8.603 | 1.00 | 55.08 | C |
| ATOM | 6063 | OH | TYR | L | 92 | 31.097 | −6.826 | −8.569 | 1.00 | 55.99 | O |
| ATOM | 6064 | N | GLY | L | 93 | 36.266 | −3.407 | −8.747 | 1.00 | 55.44 | N |
| ATOM | 6065 | CA | GLY | L | 93 | 36.050 | −3.802 | −7.376 | 1.00 | 56.50 | C |
| ATOM | 6066 | C | GLY | L | 93 | 36.167 | −5.245 | −6.957 | 1.00 | 61.87 | C |
| ATOM | 6067 | O | GLY | L | 93 | 36.490 | −5.482 | −5.790 | 1.00 | 62.75 | O |
| ATOM | 6068 | N | SER | L | 94 | 35.865 | −6.216 | −7.843 | 1.00 | 57.50 | N |
| ATOM | 6069 | CA | SER | L | 94 | 35.790 | −7.629 | −7.439 | 1.00 | 58.30 | C |
| ATOM | 6070 | C | SER | L | 94 | 34.799 | −7.801 | −6.209 | 1.00 | 63.67 | C |
| ATOM | 6071 | O | SER | L | 94 | 35.018 | −8.574 | −5.276 | 1.00 | 62.03 | O |
| ATOM | 6072 | CB | SER | L | 94 | 37.171 | −8.268 | −7.238 | 1.00 | 63.34 | C |
| ATOM | 6073 | OG | SER | L | 94 | 37.803 | −7.919 | −6.016 | 1.00 | 74.98 | O |
| ATOM | 6074 | N | SER | L | 95 | 33.743 | −6.960 | −6.222 | 1.00 | 62.49 | N |
| ATOM | 6075 | CA | SER | L | 95 | 32.524 | −6.925 | −5.419 | 1.00 | 62.73 | C |
| ATOM | 6076 | C | SER | L | 95 | 32.588 | −6.930 | −3.907 | 1.00 | 68.77 | C |
| ATOM | 6077 | O | SER | L | 95 | 31.933 | −7.816 | −3.363 | 1.00 | 70.24 | O |
| ATOM | 6078 | CB | SER | L | 95 | 31.658 | −8.127 | −5.804 | 1.00 | 65.58 | C |
| ATOM | 6079 | OG | SER | L | 95 | 32.314 | −9.366 | −5.573 | 1.00 | 65.96 | O |
| ATOM | 6080 | N | THR | L | 96 | 33.013 | −5.899 | −3.167 | 1.00 | 65.02 | N |
| ATOM | 6081 | CA | THR | L | 96 | 33.897 | −4.742 | −3.157 | 1.00 | 63.37 | C |
| ATOM | 6082 | C | THR | L | 96 | 33.537 | −3.604 | −4.104 | 1.00 | 61.52 | C |
| ATOM | 6083 | O | THR | L | 96 | 33.762 | −3.627 | −5.301 | 1.00 | 58.95 | O |
| ATOM | 6084 | CB | THR | L | 96 | 35.338 | −5.114 | −3.269 | 1.00 | 76.49 | C |
| ATOM | 6085 | OG1 | THR | L | 96 | 35.611 | −6.082 | −2.253 | 1.00 | 72.74 | O |
| ATOM | 6086 | CG2 | THR | L | 96 | 36.257 | −3.900 | −3.077 | 1.00 | 79.55 | C |
| ATOM | 6087 | N | TRP | L | 97 | 32.998 | −2.577 | −3.444 | 1.00 | 55.52 | N |
| ATOM | 6088 | CA | TRP | L | 97 | 32.676 | −1.235 | −3.847 | 1.00 | 53.96 | C |
| ATOM | 6089 | C | TRP | L | 97 | 33.539 | −0.471 | −2.840 | 1.00 | 59.28 | C |
| ATOM | 6090 | O | TRP | L | 97 | 33.444 | −0.707 | −1.636 | 1.00 | 58.38 | O |
| ATOM | 6091 | CB | TRP | L | 97 | 31.186 | −0.907 | −3.612 | 1.00 | 51.91 | C |
| ATOM | 6092 | CG | TRP | L | 97 | 30.251 | −1.234 | −4.755 | 1.00 | 52.42 | C |
| ATOM | 6093 | CD1 | TRP | L | 97 | 29.757 | −0.364 | −5.684 | 1.00 | 55.14 | C |
| ATOM | 6094 | CD2 | TRP | L | 97 | 29.642 | −2.507 | −5.039 | 1.00 | 51.58 | C |
| ATOM | 6095 | NE1 | TRP | L | 97 | 28.927 | −1.027 | −6.561 | 1.00 | 53.62 | N |
| ATOM | 6096 | CE2 | TRP | L | 97 | 28.819 | −2.336 | −6.172 | 1.00 | 55.11 | C |
| ATOM | 6097 | CE3 | TRP | L | 97 | 29.719 | −3.776 | −4.453 | 1.00 | 52.39 | C |
| ATOM | 6098 | CZ2 | TRP | L | 97 | 28.097 | −3.394 | −6.738 | 1.00 | 54.57 | C |
| ATOM | 6099 | CZ3 | TRP | L | 97 | 28.968 | −4.809 | −4.987 | 1.00 | 53.24 | C |
| ATOM | 6100 | CH2 | TRP | L | 97 | 28.180 | −4.619 | −6.125 | 1.00 | 53.75 | C |
| ATOM | 6101 | N | THR | L | 98 | 34.454 | 0.356 | −3.331 | 1.00 | 58.53 | N |
| ATOM | 6102 | CA | THR | L | 98 | 35.350 | 1.178 | −2.509 | 1.00 | 58.24 | C |
| ATOM | 6103 | C | THR | L | 98 | 34.928 | 2.640 | −2.670 | 1.00 | 59.16 | C |
| ATOM | 6104 | O | THR | L | 98 | 34.515 | 3.033 | −3.761 | 1.00 | 56.95 | O |
| ATOM | 6105 | CB | THR | L | 98 | 36.823 | 0.923 | −2.950 | 1.00 | 67.87 | C |
| ATOM | 6106 | OG1 | THR | L | 98 | 37.243 | −0.329 | −2.415 | 1.00 | 75.61 | O |
| ATOM | 6107 | CG2 | THR | L | 98 | 37.796 | 1.991 | −2.483 | 1.00 | 63.71 | C |
| ATOM | 6108 | N | PHE | L | 99 | 35.071 | 3.436 | −1.600 | 1.00 | 55.69 | N |
| ATOM | 6109 | CA | PHE | L | 99 | 34.848 | 4.894 | −1.601 | 1.00 | 55.39 | C |
| ATOM | 6110 | C | PHE | L | 99 | 36.157 | 5.627 | −1.260 | 1.00 | 61.67 | C |
| ATOM | 6111 | O | PHE | L | 99 | 37.070 | 5.062 | −0.657 | 1.00 | 62.56 | O |
| ATOM | 6112 | CB | PHE | L | 99 | 33.772 | 5.301 | −0.575 | 1.00 | 56.15 | C |
| ATOM | 6113 | CG | PHE | L | 99 | 32.356 | 5.021 | −0.993 | 1.00 | 57.66 | C |
| ATOM | 6114 | CD1 | PHE | L | 99 | 31.639 | 5.946 | −1.745 | 1.00 | 61.30 | C |
| ATOM | 6115 | CD2 | PHE | L | 99 | 31.736 | 3.829 | −0.646 | 1.00 | 59.26 | C |
| ATOM | 6116 | CE1 | PHE | L | 99 | 30.337 | 5.667 | −2.167 | 1.00 | 61.55 | C |

TABLE 1-continued

Three-dimensional crystal coordinate for anti-TcdB antibody beziotoxumab
Fab –C. difficile toxin B (TcdB$^{(1834-2101)}$) complex.

| ATOM | 6117 | CE2 | PHE | L | 99 | 30.420 | 3.566 | −1.035 | 1.00 | 61.41 | C |
|---|---|---|---|---|---|---|---|---|---|---|---|
| ATOM | 6118 | CZ | PHE | L | 99 | 29.745 | 4.470 | −1.821 | 1.00 | 59.96 | C |
| ATOM | 6119 | N | GLY | L | 100 | 36.228 | 6.879 | −1.669 | 1.00 | 58.51 | N |
| ATOM | 6120 | CA | GLY | L | 100 | 37.328 | 7.773 | −1.347 | 1.00 | 57.64 | C |
| ATOM | 6121 | C | GLY | L | 100 | 37.012 | 8.406 | −0.008 | 1.00 | 59.94 | C |
| ATOM | 6122 | O | GLY | L | 100 | 35.862 | 8.343 | 0.458 | 1.00 | 59.83 | O |
| ATOM | 6123 | N | GLN | L | 101 | 38.018 | 9.007 | 0.638 | 1.00 | 55.17 | N |
| ATOM | 6124 | CA | GLN | L | 101 | 37.828 | 9.576 | 1.975 | 1.00 | 54.34 | C |
| ATOM | 6125 | C | GLN | L | 101 | 37.092 | 10.927 | 1.967 | 1.00 | 57.93 | C |
| ATOM | 6126 | O | GLN | L | 101 | 36.678 | 11.406 | 3.024 | 1.00 | 59.17 | O |
| ATOM | 6127 | CB | GLN | L | 101 | 39.156 | 9.631 | 2.746 | 1.00 | 55.71 | C |
| ATOM | 6128 | CG | GLN | L | 101 | 40.066 | 10.835 | 2.445 | 1.00 | 69.37 | C |
| ATOM | 6129 | CD | GLN | L | 101 | 40.745 | 10.860 | 1.083 | 1.00 | 79.91 | C |
| ATOM | 6130 | OE1 | GLN | L | 101 | 41.001 | 9.825 | 0.414 | 1.00 | 76.02 | O |
| ATOM | 6131 | NE2 | GLN | L | 101 | 41.092 | 12.072 | 0.677 | 1.00 | 51.71 | N |
| ATOM | 6132 | N | GLY | L | 102 | 36.887 | 11.493 | 0.781 | 1.00 | 53.60 | N |
| ATOM | 6133 | CA | GLY | L | 102 | 36.197 | 12.764 | 0.601 | 1.00 | 52.06 | C |
| ATOM | 6134 | C | GLY | L | 102 | 37.118 | 13.941 | 0.396 | 1.00 | 54.52 | C |
| ATOM | 6135 | O | GLY | L | 102 | 38.318 | 13.874 | 0.689 | 1.00 | 55.03 | O |
| ATOM | 6136 | N | THR | L | 103 | 36.539 | 15.030 | −0.118 | 1.00 | 48.87 | N |
| ATOM | 6137 | CA | THR | L | 103 | 37.187 | 16.321 | −0.301 | 1.00 | 47.59 | C |
| ATOM | 6138 | C | THR | L | 103 | 36.106 | 17.320 | 0.097 | 1.00 | 51.08 | C |
| ATOM | 6139 | O | THR | L | 103 | 35.051 | 17.356 | −0.543 | 1.00 | 51.06 | O |
| ATOM | 6140 | CB | THR | L | 103 | 37.731 | 16.519 | −1.759 | 1.00 | 54.47 | C |
| ATOM | 6141 | OG1 | THR | L | 103 | 38.829 | 15.659 | −2.004 | 1.00 | 56.80 | O |
| ATOM | 6142 | CG2 | THR | L | 103 | 38.198 | 17.941 | −2.042 | 1.00 | 52.92 | C |
| ATOM | 6143 | N | LYS | L | 104 | 36.342 | 18.092 | 1.173 | 1.00 | 48.45 | N |
| ATOM | 6144 | CA | LYS | L | 104 | 35.405 | 19.139 | 1.604 | 1.00 | 49.14 | C |
| ATOM | 6145 | C | LYS | L | 104 | 35.707 | 20.417 | 0.783 | 1.00 | 56.09 | C |
| ATOM | 6146 | O | LYS | L | 104 | 36.872 | 20.814 | 0.653 | 1.00 | 56.77 | O |
| ATOM | 6147 | CB | LYS | L | 104 | 35.524 | 19.421 | 3.111 | 1.00 | 49.79 | C |
| ATOM | 6148 | CG | LYS | L | 104 | 34.578 | 20.497 | 3.628 | 1.00 | 53.51 | C |
| ATOM | 6149 | CD | LYS | L | 104 | 34.998 | 20.975 | 5.009 | 1.00 | 65.37 | C |
| ATOM | 6150 | CE | LYS | L | 104 | 34.237 | 22.203 | 5.439 | 1.00 | 77.53 | C |
| ATOM | 6151 | NZ | LYS | L | 104 | 34.367 | 22.442 | 6.903 | 1.00 | 85.83 | N |
| ATOM | 6152 | N | VAL | L | 105 | 34.657 | 21.030 | 0.206 | 1.00 | 51.55 | N |
| ATOM | 6153 | CA | VAL | L | 105 | 34.817 | 22.240 | −0.560 | 1.00 | 50.08 | C |
| ATOM | 6154 | C | VAL | L | 105 | 34.325 | 23.349 | 0.354 | 1.00 | 56.27 | C |
| ATOM | 6155 | O | VAL | L | 105 | 33.128 | 23.490 | 0.610 | 1.00 | 57.68 | O |
| ATOM | 6156 | CB | VAL | L | 105 | 34.200 | 22.205 | −1.982 | 1.00 | 51.60 | C |
| ATOM | 6157 | CG1 | VAL | L | 105 | 34.517 | 23.495 | −2.727 | 1.00 | 50.16 | C |
| ATOM | 6158 | CG2 | VAL | L | 105 | 34.712 | 21.007 | −2.777 | 1.00 | 50.96 | C |
| ATOM | 6159 | N | GLU | L | 106 | 35.289 | 24.029 | 0.951 | 1.00 | 53.19 | N |
| ATOM | 6160 | CA | GLU | L | 106 | 35.137 | 25.089 | 1.935 | 1.00 | 53.75 | C |
| ATOM | 6161 | C | GLU | L | 106 | 35.138 | 26.450 | 1.235 | 1.00 | 59.78 | C |
| ATOM | 6162 | O | GLU | L | 106 | 35.749 | 26.602 | 0.163 | 1.00 | 60.52 | O |
| ATOM | 6163 | CB | GLU | L | 106 | 36.325 | 24.984 | 2.907 | 1.00 | 55.46 | C |
| ATOM | 6164 | CG | GLU | L | 106 | 36.236 | 25.818 | 4.165 | 1.00 | 69.29 | C |
| ATOM | 6165 | CD | GLU | L | 106 | 37.569 | 26.417 | 4.571 | 1.00 | 92.80 | C |
| ATOM | 6166 | OE1 | GLU | L | 106 | 38.069 | 27.281 | 3.816 | 1.00 | 90.35 | O |
| ATOM | 6167 | OE2 | GLU | L | 106 | 38.120 | 26.034 | 5.631 | 1.00 | 85.01 | O |
| ATOM | 6168 | N | ILE | L | 107 | 34.468 | 27.449 | 1.850 | 1.00 | 54.66 | N |
| ATOM | 6169 | CA | ILE | L | 107 | 34.381 | 28.797 | 1.289 | 1.00 | 53.47 | C |
| ATOM | 6170 | C | ILE | L | 107 | 35.627 | 29.621 | 1.705 | 1.00 | 58.84 | C |
| ATOM | 6171 | O | ILE | L | 107 | 35.802 | 29.881 | 2.900 | 1.00 | 60.31 | O |
| ATOM | 6172 | CB | ILE | L | 107 | 33.045 | 29.486 | 1.693 | 1.00 | 55.76 | C |
| ATOM | 6173 | CG1 | ILE | L | 107 | 31.830 | 28.524 | 1.565 | 1.00 | 55.93 | C |
| ATOM | 6174 | CG2 | ILE | L | 107 | 32.832 | 30.759 | 0.881 | 1.00 | 55.85 | C |
| ATOM | 6175 | CD1 | ILE | L | 107 | 30.660 | 28.734 | 2.503 | 1.00 | 59.96 | C |
| ATOM | 6176 | N | LYS | L | 108 | 36.505 | 30.002 | 0.732 | 1.00 | 52.76 | N |
| ATOM | 6177 | CA | LYS | L | 108 | 37.670 | 30.847 | 1.026 | 1.00 | 50.95 | C |
| ATOM | 6178 | C | LYS | L | 108 | 37.155 | 32.242 | 1.343 | 1.00 | 55.85 | C |
| ATOM | 6179 | O | LYS | L | 108 | 36.216 | 32.733 | 0.682 | 1.00 | 58.35 | O |
| ATOM | 6180 | CB | LYS | L | 108 | 38.701 | 30.928 | −0.132 | 1.00 | 50.65 | C |
| ATOM | 6181 | N | ARG | L | 109 | 37.748 | 32.858 | 2.395 | 1.00 | 47.76 | N |
| ATOM | 6182 | CA | ARG | L | 109 | 37.473 | 34.210 | 2.850 | 1.00 | 44.54 | C |
| ATOM | 6183 | C | ARG | L | 109 | 38.727 | 34.797 | 3.502 | 1.00 | 46.41 | C |
| ATOM | 6184 | O | ARG | L | 109 | 39.704 | 34.090 | 3.717 | 1.00 | 46.17 | O |
| ATOM | 6185 | CB | ARG | L | 109 | 36.228 | 34.252 | 3.760 | 1.00 | 37.33 | C |
| ATOM | 6186 | CG | ARG | L | 109 | 36.454 | 33.695 | 5.118 | 1.00 | 37.37 | C |
| ATOM | 6187 | CD | ARG | L | 109 | 35.762 | 34.516 | 6.178 | 1.00 | 51.21 | C |
| ATOM | 6188 | NE | ARG | L | 109 | 36.459 | 35.764 | 6.484 | 1.00 | 49.17 | N |
| ATOM | 6189 | CZ | ARG | L | 109 | 35.906 | 36.781 | 7.130 | 1.00 | 73.40 | C |
| ATOM | 6190 | NH1 | ARG | L | 109 | 34.639 | 36.715 | 7.530 | 1.00 | 73.01 | N |
| ATOM | 6191 | NH2 | ARG | L | 109 | 36.601 | 37.888 | 7.351 | 1.00 | 58.92 | N |
| ATOM | 6192 | N | THR | L | 110 | 38.714 | 36.098 | 3.792 | 1.00 | 42.08 | N |
| ATOM | 6193 | CA | THR | L | 110 | 39.865 | 36.737 | 4.425 | 1.00 | 42.16 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 6194 | C | THR | L | 110 | 40.116 | 36.211 | 5.827 | 1.00 | 49.30 | C |
|---|---|---|---|---|---|---|---|---|---|---|---|
| ATOM | 6195 | O | THR | L | 110 | 39.178 | 35.827 | 6.524 | 1.00 | 51.84 | O |
| ATOM | 6196 | CB | THR | L | 110 | 39.701 | 38.264 | 4.454 | 1.00 | 45.02 | C |
| ATOM | 6197 | OG1 | THR | L | 110 | 38.435 | 38.626 | 5.031 | 1.00 | 53.95 | O |
| ATOM | 6198 | CG2 | THR | L | 110 | 39.876 | 38.890 | 3.103 | 1.00 | 33.32 | C |
| ATOM | 6199 | N | VAL | L | 111 | 41.379 | 36.209 | 6.249 | 1.00 | 45.46 | N |
| ATOM | 6200 | CA | VAL | L | 111 | 41.744 | 35.860 | 7.618 | 1.00 | 45.14 | C |
| ATOM | 6201 | C | VAL | L | 111 | 40.958 | 36.770 | 8.562 | 1.00 | 52.19 | C |
| ATOM | 6202 | O | VAL | L | 111 | 40.797 | 37.963 | 8.287 | 1.00 | 53.24 | O |
| ATOM | 6203 | CB | VAL | L | 111 | 43.278 | 35.944 | 7.864 | 1.00 | 47.80 | C |
| ATOM | 6204 | CG1 | VAL | L | 111 | 43.639 | 35.869 | 9.351 | 1.00 | 47.21 | C |
| ATOM | 6205 | CG2 | VAL | L | 111 | 44.013 | 34.860 | 7.074 | 1.00 | 47.70 | C |
| ATOM | 6206 | N | ALA | L | 112 | 40.362 | 36.159 | 9.590 | 1.00 | 50.55 | N |
| ATOM | 6207 | CA | ALA | L | 112 | 39.587 | 36.781 | 10.657 | 1.00 | 50.77 | C |
| ATOM | 6208 | C | ALA | L | 112 | 40.098 | 36.152 | 11.944 | 1.00 | 58.85 | C |
| ATOM | 6209 | O | ALA | L | 112 | 40.272 | 34.934 | 12.008 | 1.00 | 60.33 | O |
| ATOM | 6210 | CB | ALA | L | 112 | 38.113 | 36.495 | 10.482 | 1.00 | 51.01 | C |
| ATOM | 6211 | N | ALA | L | 113 | 40.402 | 36.979 | 12.947 | 1.00 | 56.14 | N |
| ATOM | 6212 | CA | ALA | L | 113 | 40.918 | 36.481 | 14.210 | 1.00 | 56.12 | C |
| ATOM | 6213 | C | ALA | L | 113 | 39.779 | 36.156 | 15.171 | 1.00 | 61.89 | C |
| ATOM | 6214 | O | ALA | L | 113 | 38.732 | 36.819 | 15.143 | 1.00 | 62.14 | O |
| ATOM | 6215 | CB | ALA | L | 113 | 41.852 | 37.503 | 14.826 | 1.00 | 56.91 | C |
| ATOM | 6216 | N | PRO | L | 114 | 39.935 | 35.129 | 16.026 | 1.00 | 59.20 | N |
| ATOM | 6217 | CA | PRO | L | 114 | 38.862 | 34.830 | 16.975 | 1.00 | 59.32 | C |
| ATOM | 6218 | C | PRO | L | 114 | 38.744 | 35.866 | 18.083 | 1.00 | 64.01 | C |
| ATOM | 6219 | O | PRO | L | 114 | 39.744 | 36.462 | 18.472 | 1.00 | 65.36 | O |
| ATOM | 6220 | CB | PRO | L | 114 | 39.265 | 33.463 | 17.552 | 1.00 | 60.92 | C |
| ATOM | 6221 | CG | PRO | L | 114 | 40.737 | 33.412 | 17.439 | 1.00 | 65.13 | C |
| ATOM | 6222 | CD | PRO | L | 114 | 41.086 | 34.220 | 16.207 | 1.00 | 60.79 | C |
| ATOM | 6223 | N | SER | L | 115 | 37.523 | 36.082 | 18.586 | 1.00 | 58.84 | N |
| ATOM | 6224 | CA | SER | L | 115 | 37.285 | 36.890 | 19.767 | 1.00 | 57.60 | C |
| ATOM | 6225 | C | SER | L | 115 | 37.285 | 35.768 | 20.816 | 1.00 | 64.02 | C |
| ATOM | 6226 | O | SER | L | 115 | 36.490 | 34.834 | 20.689 | 1.00 | 65.48 | O |
| ATOM | 6227 | CB | SER | L | 115 | 35.920 | 37.569 | 19.714 | 1.00 | 60.35 | C |
| ATOM | 6228 | OG | SER | L | 115 | 35.370 | 37.672 | 18.409 | 1.00 | 76.28 | O |
| ATOM | 6229 | N | VAL | L | 116 | 38.241 | 35.770 | 21.759 | 1.00 | 59.89 | N |
| ATOM | 6230 | CA | VAL | L | 116 | 38.339 | 34.716 | 22.785 | 1.00 | 58.69 | C |
| ATOM | 6231 | C | VAL | L | 116 | 37.552 | 35.119 | 24.060 | 1.00 | 65.01 | C |
| ATOM | 6232 | O | VAL | L | 116 | 37.503 | 36.308 | 24.393 | 1.00 | 65.19 | O |
| ATOM | 6233 | CB | VAL | L | 116 | 39.809 | 34.315 | 23.065 | 1.00 | 60.42 | C |
| ATOM | 6234 | CG1 | VAL | L | 116 | 39.906 | 33.133 | 24.040 | 1.00 | 59.87 | C |
| ATOM | 6235 | CG2 | VAL | L | 116 | 40.522 | 33.987 | 21.766 | 1.00 | 59.72 | C |
| ATOM | 6236 | N | PHE | L | 117 | 36.895 | 34.137 | 24.730 | 1.00 | 61.99 | N |
| ATOM | 6237 | CA | PHE | L | 117 | 36.113 | 34.313 | 25.965 | 1.00 | 61.54 | C |
| ATOM | 6238 | C | PHE | L | 117 | 36.270 | 33.084 | 26.852 | 1.00 | 69.02 | C |
| ATOM | 6239 | O | PHE | L | 117 | 36.144 | 31.967 | 26.356 | 1.00 | 69.59 | O |
| ATOM | 6240 | CB | PHE | L | 117 | 34.618 | 34.513 | 25.668 | 1.00 | 62.32 | C |
| ATOM | 6241 | CG | PHE | L | 117 | 34.258 | 35.682 | 24.788 | 1.00 | 63.82 | C |
| ATOM | 6242 | CD1 | PHE | L | 117 | 34.038 | 36.946 | 25.332 | 1.00 | 66.98 | C |
| ATOM | 6243 | CD2 | PHE | L | 117 | 34.120 | 35.522 | 23.412 | 1.00 | 66.25 | C |
| ATOM | 6244 | CE1 | PHE | L | 117 | 33.685 | 38.036 | 24.512 | 1.00 | 67.50 | C |
| ATOM | 6245 | CE2 | PHE | L | 117 | 33.754 | 36.604 | 22.595 | 1.00 | 68.57 | C |
| ATOM | 6246 | CZ | PHE | L | 117 | 33.536 | 37.854 | 23.153 | 1.00 | 66.42 | C |
| ATOM | 6247 | N | ILE | L | 118 | 36.535 | 33.282 | 28.160 | 1.00 | 67.17 | N |
| ATOM | 6248 | CA | ILE | L | 118 | 36.626 | 32.198 | 29.153 | 1.00 | 66.92 | C |
| ATOM | 6249 | C | ILE | L | 118 | 35.419 | 32.326 | 30.105 | 1.00 | 73.10 | C |
| ATOM | 6250 | O | ILE | L | 118 | 35.011 | 33.460 | 30.443 | 1.00 | 73.63 | O |
| ATOM | 6251 | CB | ILE | L | 118 | 38.004 | 32.082 | 29.904 | 1.00 | 68.99 | C |
| ATOM | 6252 | CG1 | ILE | L | 118 | 38.122 | 30.707 | 30.649 | 1.00 | 67.89 | C |
| ATOM | 6253 | CG2 | ILE | L | 118 | 38.245 | 33.282 | 30.860 | 1.00 | 69.25 | C |
| ATOM | 6254 | CD1 | ILE | L | 118 | 39.422 | 30.373 | 31.285 | 1.00 | 61.13 | C |
| ATOM | 6255 | N | PHE | L | 119 | 34.823 | 31.165 | 30.483 | 1.00 | 68.58 | N |
| ATOM | 6256 | CA | PHE | L | 119 | 33.676 | 31.092 | 31.391 | 1.00 | 67.30 | C |
| ATOM | 6257 | C | PHE | L | 119 | 33.994 | 30.148 | 32.542 | 1.00 | 74.85 | C |
| ATOM | 6258 | O | PHE | L | 119 | 34.381 | 28.995 | 32.310 | 1.00 | 75.06 | O |
| ATOM | 6259 | CB | PHE | L | 119 | 32.390 | 30.659 | 30.674 | 1.00 | 67.22 | C |
| ATOM | 6260 | CG | PHE | L | 119 | 31.981 | 31.537 | 29.520 | 1.00 | 67.50 | C |
| ATOM | 6261 | CD2 | PHE | L | 119 | 31.054 | 32.555 | 29.696 | 1.00 | 69.53 | C |
| ATOM | 6262 | CD1 | PHE | L | 119 | 32.496 | 31.326 | 28.245 | 1.00 | 69.24 | C |
| ATOM | 6263 | CE2 | PHE | L | 119 | 30.659 | 33.356 | 28.618 | 1.00 | 71.50 | C |
| ATOM | 6264 | CE1 | PHE | L | 119 | 32.098 | 32.124 | 27.169 | 1.00 | 69.39 | C |
| ATOM | 6265 | CZ | PHE | L | 119 | 31.189 | 33.136 | 27.365 | 1.00 | 68.80 | C |
| ATOM | 6266 | N | PRO | L | 120 | 33.865 | 30.633 | 33.797 | 1.00 | 73.31 | N |
| ATOM | 6267 | CA | PRO | L | 120 | 34.137 | 29.755 | 34.954 | 1.00 | 72.78 | C |
| ATOM | 6268 | C | PRO | L | 120 | 32.928 | 28.867 | 35.263 | 1.00 | 74.68 | C |
| ATOM | 6269 | O | PRO | L | 120 | 31.816 | 29.215 | 34.837 | 1.00 | 73.74 | O |
| ATOM | 6270 | CB | PRO | L | 120 | 34.398 | 30.751 | 36.100 | 1.00 | 74.41 | C |

TABLE 1-continued

Three-dimensional crystal coordinate for anti-TcdB antibody beziotoxumab Fab –C. difficile toxin B (TcdB$^{(1834-2101)}$) complex.

| ATOM | 6271 | CG | PRO | L | 120 | 34.267 | 32.159 | 35.466 | 1.00 | 79.17 | C |
|---|---|---|---|---|---|---|---|---|---|---|---|
| ATOM | 6272 | CD | PRO | L | 120 | 33.447 | 31.979 | 34.244 | 1.00 | 74.70 | C |
| ATOM | 6273 | N | PRO | L | 121 | 33.088 | 27.750 | 36.017 | 1.00 | 71.34 | N |
| ATOM | 6274 | CA | PRO | L | 121 | 31.911 | 26.924 | 36.350 | 1.00 | 71.54 | C |
| ATOM | 6275 | C | PRO | L | 121 | 30.891 | 27.680 | 37.203 | 1.00 | 76.06 | C |
| ATOM | 6276 | O | PRO | L | 121 | 31.289 | 28.337 | 38.162 | 1.00 | 76.73 | O |
| ATOM | 6277 | CB | PRO | L | 121 | 32.512 | 25.733 | 37.114 | 1.00 | 73.31 | C |
| ATOM | 6278 | CG | PRO | L | 121 | 33.830 | 26.170 | 37.566 | 1.00 | 77.43 | C |
| ATOM | 6279 | CD | PRO | L | 121 | 34.327 | 27.183 | 36.595 | 1.00 | 73.00 | C |
| ATOM | 6280 | N | SER | L | 122 | 29.588 | 27.609 | 36.854 | 1.00 | 72.64 | N |
| ATOM | 6281 | CA | SER | L | 122 | 28.512 | 28.278 | 37.609 | 1.00 | 72.35 | C |
| ATOM | 6282 | C | SER | L | 122 | 28.426 | 27.776 | 39.064 | 1.00 | 78.30 | C |
| ATOM | 6283 | O | SER | L | 122 | 28.969 | 26.703 | 39.381 | 1.00 | 78.38 | O |
| ATOM | 6284 | CB | SER | L | 122 | 27.169 | 28.109 | 36.908 | 1.00 | 73.53 | C |
| ATOM | 6285 | OG | SER | L | 122 | 26.877 | 26.741 | 36.688 | 1.00 | 78.62 | O |
| ATOM | 6286 | N | ASP | L | 123 | 27.792 | 28.569 | 39.954 | 1.00 | 76.42 | N |
| ATOM | 6287 | CA | ASP | L | 123 | 27.646 | 28.187 | 41.367 | 1.00 | 77.78 | C |
| ATOM | 6288 | C | ASP | L | 123 | 26.754 | 26.951 | 41.481 | 1.00 | 81.47 | C |
| ATOM | 6289 | O | ASP | L | 123 | 27.108 | 26.014 | 42.216 | 1.00 | 80.21 | O |
| ATOM | 6290 | CB | ASP | L | 123 | 27.128 | 29.361 | 42.237 | 1.00 | 80.90 | C |
| ATOM | 6291 | CG | ASP | L | 123 | 28.090 | 30.548 | 42.363 | 1.00 | 95.62 | C |
| ATOM | 6292 | OD1 | ASP | L | 123 | 29.288 | 30.320 | 42.718 | 1.00 | 95.52 | O |
| ATOM | 6293 | OD2 | ASP | L | 123 | 27.644 | 31.705 | 42.126 | 1.00 | 101.07 | O |
| ATOM | 6294 | N | GLU | L | 124 | 25.642 | 26.920 | 40.674 | 1.00 | 78.02 | N |
| ATOM | 6295 | CA | GLU | L | 124 | 24.687 | 25.799 | 40.572 | 1.00 | 77.43 | C |
| ATOM | 6296 | C | GLU | L | 124 | 25.445 | 24.494 | 40.286 | 1.00 | 82.94 | C |
| ATOM | 6297 | O | GLU | L | 124 | 25.236 | 23.494 | 40.982 | 1.00 | 83.57 | O |
| ATOM | 6298 | CB | GLU | L | 124 | 23.656 | 26.015 | 39.449 | 1.00 | 78.47 | C |
| ATOM | 6299 | CG | GLU | L | 124 | 23.003 | 27.386 | 39.352 | 1.00 | 90.29 | C |
| ATOM | 6300 | CD | GLU | L | 124 | 22.039 | 27.576 | 38.186 | 1.00 | 118.02 | C |
| ATOM | 6301 | OE1 | GLU | L | 124 | 21.899 | 28.732 | 37.720 | 1.00 | 98.07 | O |
| ATOM | 6302 | OE2 | GLU | L | 124 | 21.431 | 26.575 | 37.731 | 1.00 | 116.60 | O |
| ATOM | 6303 | N | GLN | L | 125 | 26.335 | 24.520 | 39.268 | 1.00 | 79.97 | N |
| ATOM | 6304 | CA | GLN | L | 125 | 27.137 | 23.378 | 38.839 | 1.00 | 80.57 | C |
| ATOM | 6305 | C | GLN | L | 125 | 28.133 | 22.949 | 39.893 | 1.00 | 88.33 | C |
| ATOM | 6306 | O | GLN | L | 125 | 28.387 | 21.753 | 40.028 | 1.00 | 88.50 | O |
| ATOM | 6307 | CB | GLN | L | 125 | 27.856 | 23.670 | 37.512 | 1.00 | 81.51 | C |
| ATOM | 6308 | CG | GLN | L | 125 | 28.297 | 22.401 | 36.775 | 1.00 | 77.62 | C |
| ATOM | 6309 | CD | GLN | L | 125 | 29.499 | 22.586 | 35.903 | 1.00 | 91.87 | C |
| ATOM | 6310 | OE1 | GLN | L | 125 | 29.854 | 23.697 | 35.476 | 1.00 | 86.35 | O |
| ATOM | 6311 | NE2 | GLN | L | 125 | 30.141 | 21.477 | 35.611 | 1.00 | 87.92 | N |
| ATOM | 6312 | N | LEU | L | 126 | 28.698 | 23.912 | 40.631 | 1.00 | 87.53 | N |
| ATOM | 6313 | CA | LEU | L | 126 | 29.676 | 23.619 | 41.672 | 1.00 | 89.11 | C |
| ATOM | 6314 | C | LEU | L | 126 | 29.075 | 22.930 | 42.906 | 1.00 | 96.71 | C |
| ATOM | 6315 | O | LEU | L | 126 | 29.806 | 22.209 | 43.595 | 1.00 | 96.87 | O |
| ATOM | 6316 | CB | LEU | L | 126 | 30.468 | 24.866 | 42.054 | 1.00 | 89.02 | C |
| ATOM | 6317 | CG | LEU | L | 126 | 31.702 | 25.099 | 41.201 | 1.00 | 93.32 | C |
| ATOM | 6318 | CD1 | LEU | L | 126 | 32.208 | 26.514 | 41.370 | 1.00 | 93.61 | C |
| ATOM | 6319 | CD2 | LEU | L | 126 | 32.802 | 24.052 | 41.497 | 1.00 | 94.35 | C |
| ATOM | 6320 | N | LYS | L | 127 | 27.743 | 23.115 | 43.153 | 1.00 | 94.65 | N |
| ATOM | 6321 | CA | LYS | L | 127 | 27.000 | 22.466 | 44.242 | 1.00 | 94.86 | C |
| ATOM | 6322 | C | LYS | L | 127 | 27.098 | 20.937 | 44.038 | 1.00 | 99.68 | C |
| ATOM | 6323 | O | LYS | L | 127 | 27.425 | 20.217 | 44.989 | 1.00 | 100.08 | O |
| ATOM | 6324 | CB | LYS | L | 127 | 25.541 | 22.955 | 44.298 | 1.00 | 97.29 | C |
| ATOM | 6325 | N | SER | L | 128 | 26.900 | 20.460 | 42.773 | 1.00 | 95.10 | N |
| ATOM | 6326 | CA | SER | L | 128 | 27.112 | 19.056 | 42.393 | 1.00 | 93.55 | C |
| ATOM | 6327 | C | SER | L | 128 | 28.635 | 18.920 | 42.235 | 1.00 | 95.39 | C |
| ATOM | 6328 | O | SER | L | 128 | 29.312 | 19.908 | 41.961 | 1.00 | 94.76 | O |
| ATOM | 6329 | CB | SER | L | 128 | 26.376 | 18.717 | 41.102 | 1.00 | 95.82 | C |
| ATOM | 6330 | OG | SER | L | 128 | 26.686 | 19.627 | 40.060 | 1.00 | 103.80 | O |
| ATOM | 6331 | N | GLY | L | 129 | 29.171 | 17.732 | 42.461 | 1.00 | 91.14 | N |
| ATOM | 6332 | CA | GLY | L | 129 | 30.618 | 17.505 | 42.453 | 1.00 | 90.50 | C |
| ATOM | 6333 | C | GLY | L | 129 | 31.427 | 17.658 | 41.175 | 1.00 | 91.89 | C |
| ATOM | 6334 | O | GLY | L | 129 | 32.459 | 16.987 | 41.047 | 1.00 | 91.73 | O |
| ATOM | 6335 | N | THR | L | 130 | 31.008 | 18.555 | 40.240 | 1.00 | 86.17 | N |
| ATOM | 6336 | CA | THR | L | 130 | 31.707 | 18.765 | 38.962 | 1.00 | 85.19 | C |
| ATOM | 6337 | C | THR | L | 130 | 31.799 | 20.260 | 38.577 | 1.00 | 87.71 | C |
| ATOM | 6338 | O | THR | L | 130 | 30.885 | 21.047 | 38.852 | 1.00 | 84.98 | O |
| ATOM | 6339 | CB | THR | L | 130 | 31.084 | 17.869 | 37.851 | 1.00 | 87.99 | C |
| ATOM | 6340 | OG1 | THR | L | 130 | 31.478 | 16.516 | 38.095 | 1.00 | 86.75 | O |
| ATOM | 6341 | CG2 | THR | L | 130 | 31.515 | 18.260 | 36.424 | 1.00 | 84.49 | C |
| ATOM | 6342 | N | ALA | L | 131 | 32.943 | 20.611 | 37.930 | 1.00 | 85.24 | N |
| ATOM | 6343 | CA | ALA | L | 131 | 33.313 | 21.927 | 37.405 | 1.00 | 84.94 | C |
| ATOM | 6344 | C | ALA | L | 131 | 33.669 | 21.853 | 35.912 | 1.00 | 86.98 | C |
| ATOM | 6345 | O | ALA | L | 131 | 34.554 | 21.089 | 35.509 | 1.00 | 86.62 | O |
| ATOM | 6346 | CB | ALA | L | 131 | 34.485 | 22.493 | 38.191 | 1.00 | 85.84 | C |
| ATOM | 6347 | N | SER | L | 132 | 32.964 | 22.661 | 35.103 | 1.00 | 81.96 | N |

TABLE 1-continued

Three-dimensional crystal coordinate for anti-TcdB antibody beziotoxumab Fab –C. *difficile* toxin B (TcdB$^{(1834-2101)}$) complex.

| ATOM | 6348 | CA | SER | L | 132 | 33.152 | 22.766 | 33.660 | 1.00 | 80.65 | C |
|------|------|-----|-----|---|-----|--------|--------|--------|------|-------|---|
| ATOM | 6349 | C | SER | L | 132 | 33.587 | 24.181 | 33.293 | 1.00 | 81.93 | C |
| ATOM | 6350 | O | SER | L | 132 | 32.836 | 25.149 | 33.488 | 1.00 | 81.18 | O |
| ATOM | 6351 | CB | SER | L | 132 | 31.885 | 22.362 | 32.909 | 1.00 | 83.31 | C |
| ATOM | 6352 | OG | SER | L | 132 | 31.622 | 20.975 | 33.063 | 1.00 | 90.07 | O |
| ATOM | 6353 | N | VAL | L | 133 | 34.828 | 24.296 | 32.804 | 1.00 | 76.88 | N |
| ATOM | 6354 | CA | VAL | L | 133 | 35.428 | 25.570 | 32.381 | 1.00 | 75.61 | C |
| ATOM | 6355 | C | VAL | L | 133 | 35.349 | 25.619 | 30.867 | 1.00 | 75.70 | C |
| ATOM | 6356 | O | VAL | L | 133 | 35.781 | 24.674 | 30.201 | 1.00 | 73.90 | O |
| ATOM | 6357 | CB | VAL | L | 133 | 36.881 | 25.770 | 32.885 | 1.00 | 79.61 | C |
| ATOM | 6358 | CG1 | VAL | L | 133 | 37.239 | 27.240 | 32.881 | 1.00 | 79.33 | C |
| ATOM | 6359 | CG2 | VAL | L | 133 | 37.088 | 25.179 | 34.278 | 1.00 | 79.43 | C |
| ATOM | 6360 | N | VAL | L | 134 | 34.779 | 26.708 | 30.329 | 1.00 | 71.56 | N |
| ATOM | 6361 | CA | VAL | L | 134 | 34.542 | 26.863 | 28.891 | 1.00 | 71.54 | C |
| ATOM | 6362 | C | VAL | L | 134 | 35.356 | 28.001 | 28.232 | 1.00 | 74.84 | C |
| ATOM | 6363 | O | VAL | L | 134 | 35.228 | 29.166 | 28.608 | 1.00 | 72.97 | O |
| ATOM | 6364 | CB | VAL | L | 134 | 33.022 | 27.018 | 28.602 | 1.00 | 75.58 | C |
| ATOM | 6365 | CG1 | VAL | L | 134 | 32.738 | 27.052 | 27.105 | 1.00 | 75.54 | C |
| ATOM | 6366 | CG2 | VAL | L | 134 | 32.216 | 25.909 | 29.263 | 1.00 | 75.67 | C |
| ATOM | 6367 | N | CYS | L | 135 | 36.106 | 27.652 | 27.173 | 1.00 | 72.40 | N |
| ATOM | 6368 | CA | CYS | L | 135 | 36.882 | 28.582 | 26.348 | 1.00 | 72.41 | C |
| ATOM | 6369 | C | CYS | L | 135 | 36.209 | 28.709 | 24.964 | 1.00 | 71.88 | C |
| ATOM | 6370 | O | CYS | L | 135 | 36.159 | 27.725 | 24.224 | 1.00 | 70.42 | O |
| ATOM | 6371 | CB | CYS | L | 135 | 38.321 | 28.096 | 26.227 | 1.00 | 73.93 | C |
| ATOM | 6372 | SG | CYS | L | 135 | 39.449 | 29.274 | 25.462 | 1.00 | 78.93 | S |
| ATOM | 6373 | N | LEU | L | 136 | 35.667 | 29.910 | 24.638 | 1.00 | 65.53 | N |
| ATOM | 6374 | CA | LEU | L | 136 | 34.990 | 30.221 | 23.370 | 1.00 | 63.25 | C |
| ATOM | 6375 | C | LEU | L | 136 | 35.875 | 31.025 | 22.403 | 1.00 | 67.07 | C |
| ATOM | 6376 | O | LEU | L | 136 | 36.407 | 32.053 | 22.795 | 1.00 | 68.54 | O |
| ATOM | 6377 | CB | LEU | L | 136 | 33.655 | 30.961 | 23.612 | 1.00 | 61.80 | C |
| ATOM | 6378 | CG | LEU | L | 136 | 32.977 | 31.578 | 22.385 | 1.00 | 64.05 | C |
| ATOM | 6379 | CD1 | LEU | L | 136 | 32.459 | 30.516 | 21.438 | 1.00 | 64.16 | C |
| ATOM | 6380 | CD2 | LEU | L | 136 | 31.852 | 32.496 | 22.780 | 1.00 | 62.75 | C |
| ATOM | 6381 | N | LEU | L | 137 | 35.981 | 30.568 | 21.131 | 1.00 | 61.13 | N |
| ATOM | 6382 | CA | LEU | L | 137 | 36.694 | 31.204 | 20.000 | 1.00 | 58.54 | C |
| ATOM | 6383 | C | LEU | L | 137 | 35.601 | 31.640 | 19.002 | 1.00 | 63.94 | C |
| ATOM | 6384 | O | LEU | L | 137 | 35.121 | 30.835 | 18.212 | 1.00 | 63.46 | O |
| ATOM | 6385 | CB | LEU | L | 137 | 37.705 | 30.244 | 19.328 | 1.00 | 56.45 | C |
| ATOM | 6386 | CG | LEU | L | 137 | 38.990 | 29.933 | 20.074 | 1.00 | 58.54 | C |
| ATOM | 6387 | CD1 | LEU | L | 137 | 38.732 | 29.079 | 21.322 | 1.00 | 59.18 | C |
| ATOM | 6388 | CD2 | LEU | L | 137 | 39.969 | 29.228 | 19.166 | 1.00 | 56.50 | C |
| ATOM | 6389 | N | ASN | L | 138 | 35.133 | 32.881 | 19.119 | 1.00 | 62.13 | N |
| ATOM | 6390 | CA | ASN | L | 138 | 34.027 | 33.362 | 18.295 | 1.00 | 61.99 | C |
| ATOM | 6391 | C | ASN | L | 138 | 34.486 | 33.835 | 16.902 | 1.00 | 64.53 | C |
| ATOM | 6392 | O | ASN | L | 138 | 35.542 | 34.444 | 16.758 | 1.00 | 64.06 | O |
| ATOM | 6393 | CB | ASN | L | 138 | 33.210 | 34.429 | 19.048 | 1.00 | 58.89 | C |
| ATOM | 6394 | CG | ASN | L | 138 | 31.957 | 34.831 | 18.347 | 1.00 | 89.15 | C |
| ATOM | 6395 | OD1 | ASN | L | 138 | 30.934 | 34.147 | 18.432 | 1.00 | 85.10 | O |
| ATOM | 6396 | ND2 | ASN | L | 138 | 32.018 | 35.949 | 17.629 | 1.00 | 87.54 | N |
| ATOM | 6397 | N | ASN | L | 139 | 33.672 | 33.505 | 15.894 | 1.00 | 59.08 | N |
| ATOM | 6398 | CA | ASN | L | 139 | 33.766 | 33.815 | 14.473 | 1.00 | 57.59 | C |
| ATOM | 6399 | C | ASN | L | 139 | 35.188 | 34.063 | 13.930 | 1.00 | 61.44 | C |
| ATOM | 6400 | O | ASN | L | 139 | 35.537 | 35.206 | 13.628 | 1.00 | 64.18 | O |
| ATOM | 6401 | CB | ASN | L | 139 | 32.831 | 34.977 | 14.140 | 1.00 | 49.62 | C |
| ATOM | 6402 | CG | ASN | L | 139 | 31.380 | 34.612 | 14.292 | 1.00 | 87.20 | C |
| ATOM | 6403 | OD1 | ASN | L | 139 | 30.615 | 35.295 | 14.986 | 1.00 | 83.45 | O |
| ATOM | 6404 | ND2 | ASN | L | 139 | 30.979 | 33.489 | 13.689 | 1.00 | 89.23 | N |
| ATOM | 6405 | N | PHE | L | 140 | 35.981 | 32.986 | 13.761 | 1.00 | 54.00 | N |
| ATOM | 6406 | CA | PHE | L | 140 | 37.337 | 33.057 | 13.202 | 1.00 | 52.69 | C |
| ATOM | 6407 | C | PHE | L | 140 | 37.452 | 32.350 | 11.832 | 1.00 | 53.51 | C |
| ATOM | 6408 | O | PHE | L | 140 | 36.538 | 31.630 | 11.440 | 1.00 | 51.52 | O |
| ATOM | 6409 | CB | PHE | L | 140 | 38.365 | 32.482 | 14.194 | 1.00 | 54.20 | C |
| ATOM | 6410 | CG | PHE | L | 140 | 38.276 | 30.989 | 14.439 | 1.00 | 55.05 | C |
| ATOM | 6411 | CD1 | PHE | L | 140 | 38.970 | 30.092 | 13.629 | 1.00 | 56.99 | C |
| ATOM | 6412 | CD2 | PHE | L | 140 | 37.518 | 30.483 | 15.496 | 1.00 | 56.38 | C |
| ATOM | 6413 | CE1 | PHE | L | 140 | 38.879 | 28.714 | 13.848 | 1.00 | 57.68 | C |
| ATOM | 6414 | CE2 | PHE | L | 140 | 37.409 | 29.107 | 15.709 | 1.00 | 58.67 | C |
| ATOM | 6415 | CZ | PHE | L | 140 | 38.113 | 28.233 | 14.902 | 1.00 | 57.15 | C |
| ATOM | 6416 | N | TYR | L | 141 | 38.591 | 32.548 | 11.129 | 1.00 | 48.76 | N |
| ATOM | 6417 | CA | TYR | L | 141 | 38.924 | 31.944 | 9.834 | 1.00 | 47.65 | C |
| ATOM | 6418 | C | TYR | L | 141 | 40.451 | 32.072 | 9.520 | 1.00 | 53.69 | C |
| ATOM | 6419 | O | TYR | L | 141 | 41.002 | 33.164 | 9.672 | 1.00 | 52.37 | O |
| ATOM | 6420 | CB | TYR | L | 141 | 38.080 | 32.542 | 8.680 | 1.00 | 47.33 | C |
| ATOM | 6421 | CG | TYR | L | 141 | 38.353 | 31.826 | 7.378 | 1.00 | 48.55 | C |
| ATOM | 6422 | CD2 | TYR | L | 141 | 37.524 | 30.800 | 6.938 | 1.00 | 48.58 | C |
| ATOM | 6423 | CD1 | TYR | L | 141 | 39.510 | 32.090 | 6.641 | 1.00 | 50.45 | C |
| ATOM | 6424 | CE2 | TYR | L | 141 | 37.801 | 30.099 | 5.763 | 1.00 | 49.74 | C |

TABLE 1-continued

Three-dimensional crystal coordinate for anti-TcdB antibody beziotoxumab
Fab –C. difficile toxin B (TcdB$^{(1834-2101)}$) complex.

| ATOM | 6425 | CE1 | TYR | L | 141 | 39.815 | 31.371 | 5.486 | 1.00 | 50.02 | C |
|------|------|-----|-----|---|-----|--------|--------|-------|------|-------|---|
| ATOM | 6426 | CZ  | TYR | L | 141 | 38.952 | 30.384 | 5.041 | 1.00 | 59.17 | C |
| ATOM | 6427 | OH  | TYR | L | 141 | 39.231 | 29.697 | 3.879 | 1.00 | 63.42 | O |
| ATOM | 6428 | N   | PRO | L | 142 | 41.159 | 31.033 | 9.012 | 1.00 | 52.88 | N |
| ATOM | 6429 | CA  | PRO | L | 142 | 40.727 | 29.652 | 8.740 | 1.00 | 53.77 | C |
| ATOM | 6430 | C   | PRO | L | 142 | 40.507 | 28.821 | 9.992 | 1.00 | 60.99 | C |
| ATOM | 6431 | O   | PRO | L | 142 | 40.750 | 29.309 | 11.105 | 1.00 | 61.31 | O |
| ATOM | 6432 | CB  | PRO | L | 142 | 41.862 | 29.106 | 7.858 | 1.00 | 55.31 | C |
| ATOM | 6433 | CG  | PRO | L | 142 | 43.063 | 29.848 | 8.288 | 1.00 | 58.47 | C |
| ATOM | 6434 | CD  | PRO | L | 142 | 42.588 | 31.220 | 8.676 | 1.00 | 54.53 | C |
| ATOM | 6435 | N   | ARG | L | 143 | 40.048 | 27.556 | 9.780 | 1.00 | 58.33 | N |
| ATOM | 6436 | CA  | ARG | L | 143 | 39.730 | 26.553 | 10.793 | 1.00 | 58.12 | C |
| ATOM | 6437 | C   | ARG | L | 143 | 40.911 | 26.213 | 11.779 | 1.00 | 63.25 | C |
| ATOM | 6438 | O   | ARG | L | 143 | 40.651 | 25.835 | 12.932 | 1.00 | 65.09 | O |
| ATOM | 6439 | CB  | ARG | L | 143 | 39.182 | 25.310 | 10.078 | 1.00 | 56.67 | C |
| ATOM | 6440 | CG  | ARG | L | 143 | 38.974 | 24.065 | 10.911 | 1.00 | 61.75 | C |
| ATOM | 6441 | CD  | ARG | L | 143 | 37.871 | 24.138 | 11.935 | 1.00 | 66.61 | C |
| ATOM | 6442 | NE  | ARG | L | 143 | 37.641 | 22.796 | 12.470 | 1.00 | 90.33 | N |
| ATOM | 6443 | CZ  | ARG | L | 143 | 36.819 | 21.888 | 11.936 | 1.00 | 103.98 | C |
| ATOM | 6444 | NH1 | ARG | L | 143 | 36.714 | 20.680 | 12.478 | 1.00 | 97.32 | N |
| ATOM | 6445 | NH2 | ARG | L | 143 | 36.090 | 22.187 | 10.859 | 1.00 | 71.31 | N |
| ATOM | 6446 | N   | GLU | L | 144 | 42.175 | 26.351 | 11.351 | 1.00 | 58.55 | N |
| ATOM | 6447 | CA  | GLU | L | 144 | 43.381 | 26.129 | 12.156 | 1.00 | 58.32 | C |
| ATOM | 6448 | C   | GLU | L | 144 | 43.510 | 27.059 | 13.365 | 1.00 | 63.84 | C |
| ATOM | 6449 | O   | GLU | L | 144 | 43.740 | 28.264 | 13.223 | 1.00 | 65.20 | O |
| ATOM | 6450 | CB  | GLU | L | 144 | 44.667 | 26.311 | 11.311 | 1.00 | 59.58 | C |
| ATOM | 6451 | CG  | GLU | L | 144 | 44.652 | 25.088 | 10.185 | 1.00 | 80.90 | C |
| ATOM | 6452 | CD  | GLU | L | 144 | 43.946 | 25.512 | 8.901 | 1.00 | 108.16 | C |
| ATOM | 6453 | OE1 | GLU | L | 144 | 44.386 | 26.511 | 8.288 | 1.00 | 111.55 | O |
| ATOM | 6454 | OE2 | GLU | L | 144 | 42.965 | 24.844 | 8.500 | 1.00 | 97.11 | O |
| ATOM | 6455 | N   | ALA | L | 145 | 43.316 | 26.471 | 14.551 | 1.00 | 59.89 | N |
| ATOM | 6456 | CA  | ALA | L | 145 | 43.367 | 27.082 | 15.872 | 1.00 | 59.59 | C |
| ATOM | 6457 | C   | ALA | L | 145 | 43.900 | 26.065 | 16.927 | 1.00 | 65.63 | C |
| ATOM | 6458 | O   | ALA | L | 145 | 43.481 | 24.900 | 16.916 | 1.00 | 68.15 | O |
| ATOM | 6459 | CB  | ALA | L | 145 | 41.973 | 27.557 | 16.258 | 1.00 | 60.04 | C |
| ATOM | 6460 | N   | LYS | L | 146 | 44.823 | 26.495 | 17.818 | 1.00 | 60.77 | N |
| ATOM | 6461 | CA  | LYS | L | 146 | 45.359 | 25.664 | 18.911 | 1.00 | 61.02 | C |
| ATOM | 6462 | C   | LYS | L | 146 | 44.835 | 26.219 | 20.223 | 1.00 | 69.89 | C |
| ATOM | 6463 | O   | LYS | L | 146 | 45.037 | 27.410 | 20.477 | 1.00 | 72.34 | O |
| ATOM | 6464 | CB  | LYS | L | 146 | 46.897 | 25.631 | 18.923 | 1.00 | 62.47 | C |
| ATOM | 6465 | N   | VAL | L | 147 | 44.094 | 25.399 | 21.018 | 1.00 | 66.58 | N |
| ATOM | 6466 | CA  | VAL | L | 147 | 43.565 | 25.827 | 22.320 | 1.00 | 66.61 | C |
| ATOM | 6467 | C   | VAL | L | 147 | 44.218 | 24.989 | 23.394 | 1.00 | 71.65 | C |
| ATOM | 6468 | O   | VAL | L | 147 | 44.062 | 23.769 | 23.424 | 1.00 | 71.89 | O |
| ATOM | 6469 | CB  | VAL | L | 147 | 42.025 | 25.819 | 22.435 | 1.00 | 71.09 | C |
| ATOM | 6470 | CG1 | VAL | L | 147 | 41.561 | 26.298 | 23.823 | 1.00 | 71.14 | C |
| ATOM | 6471 | CG2 | VAL | L | 147 | 41.406 | 26.666 | 21.339 | 1.00 | 71.13 | C |
| ATOM | 6472 | N   | GLN | L | 148 | 45.002 | 25.640 | 24.240 | 1.00 | 68.80 | N |
| ATOM | 6473 | CA  | GLN | L | 148 | 45.698 | 24.969 | 25.322 | 1.00 | 68.07 | C |
| ATOM | 6474 | C   | GLN | L | 148 | 45.065 | 25.358 | 26.655 | 1.00 | 71.74 | C |
| ATOM | 6475 | O   | GLN | L | 148 | 44.704 | 26.525 | 26.825 | 1.00 | 71.96 | O |
| ATOM | 6476 | CB  | GLN | L | 148 | 47.178 | 25.337 | 25.290 | 1.00 | 69.15 | C |
| ATOM | 6477 | CG  | GLN | L | 148 | 48.060 | 24.129 | 25.578 | 1.00 | 85.40 | C |
| ATOM | 6478 | CD  | GLN | L | 148 | 49.078 | 23.920 | 24.496 | 1.00 | 93.41 | C |
| ATOM | 6479 | OE1 | GLN | L | 148 | 50.023 | 24.702 | 24.350 | 1.00 | 82.71 | O |
| ATOM | 6480 | NE2 | GLN | L | 148 | 48.964 | 22.806 | 23.780 | 1.00 | 81.20 | N |
| ATOM | 6481 | N   | TRP | L | 149 | 44.865 | 24.374 | 27.577 | 1.00 | 66.93 | N |
| ATOM | 6482 | CA  | TRP | L | 149 | 44.334 | 24.671 | 28.914 | 1.00 | 65.84 | C |
| ATOM | 6483 | C   | TRP | L | 149 | 45.504 | 24.662 | 29.898 | 1.00 | 75.51 | C |
| ATOM | 6484 | O   | TRP | L | 149 | 46.372 | 23.784 | 29.813 | 1.00 | 77.24 | O |
| ATOM | 6485 | CB  | TRP | L | 149 | 43.231 | 23.703 | 29.349 | 1.00 | 62.25 | C |
| ATOM | 6486 | CG  | TRP | L | 149 | 41.878 | 24.015 | 28.790 | 1.00 | 61.15 | C |
| ATOM | 6487 | CD1 | TRP | L | 149 | 41.256 | 23.377 | 27.762 | 1.00 | 63.75 | C |
| ATOM | 6488 | CD2 | TRP | L | 149 | 40.966 | 25.024 | 29.247 | 1.00 | 60.31 | C |
| ATOM | 6489 | NE1 | TRP | L | 149 | 40.025 | 23.950 | 27.523 | 1.00 | 62.82 | N |
| ATOM | 6490 | CE2 | TRP | L | 149 | 39.816 | 24.952 | 28.430 | 1.00 | 64.12 | C |
| ATOM | 6491 | CE3 | TRP | L | 149 | 41.015 | 26.003 | 30.255 | 1.00 | 61.11 | C |
| ATOM | 6492 | CZ2 | TRP | L | 149 | 38.704 | 25.789 | 28.620 | 1.00 | 63.31 | C |
| ATOM | 6493 | CZ3 | TRP | L | 149 | 39.926 | 26.854 | 30.420 | 1.00 | 62.19 | C |
| ATOM | 6494 | CH2 | TRP | L | 149 | 38.796 | 26.756 | 29.597 | 1.00 | 62.87 | C |
| ATOM | 6495 | N   | LYS | L | 150 | 45.577 | 25.692 | 30.753 | 1.00 | 73.64 | N |
| ATOM | 6496 | CA  | LYS | L | 150 | 46.625 | 25.848 | 31.747 | 1.00 | 75.01 | C |
| ATOM | 6497 | C   | LYS | L | 150 | 45.983 | 26.150 | 33.104 | 1.00 | 84.34 | C |
| ATOM | 6498 | O   | LYS | L | 150 | 45.171 | 27.072 | 33.224 | 1.00 | 82.82 | O |
| ATOM | 6499 | CB  | LYS | L | 150 | 47.666 | 26.902 | 31.312 | 1.00 | 76.93 | C |
| ATOM | 6500 | N   | VAL | L | 151 | 46.277 | 25.297 | 34.103 | 1.00 | 86.19 | N |
| ATOM | 6501 | CA  | VAL | L | 151 | 45.734 | 25.411 | 35.463 | 1.00 | 88.08 | C |

TABLE 1-continued

Three-dimensional crystal coordinate for anti-TcdB antibody beziotoxumab Fab –C. *difficile* toxin B (TcdB$^{(1834-2101)}$) complex.

| ATOM | 6502 | C | VAL | L | 151 | 46.928 | 25.646 | 36.381 | 1.00 | 94.72 | C |
| --- | --- | --- | --- | --- | --- | --- | --- | --- | --- | --- | --- |
| ATOM | 6503 | O | VAL | L | 151 | 47.722 | 24.722 | 36.615 | 1.00 | 94.87 | O |
| ATOM | 6504 | CB | VAL | L | 151 | 44.905 | 24.152 | 35.844 | 1.00 | 92.46 | C |
| ATOM | 6505 | CG1 | VAL | L | 151 | 44.449 | 24.211 | 37.290 | 1.00 | 92.43 | C |
| ATOM | 6506 | CG2 | VAL | L | 151 | 43.707 | 23.980 | 34.919 | 1.00 | 92.04 | C |
| ATOM | 6507 | N | ASP | L | 152 | 47.075 | 26.901 | 36.854 | 1.00 | 92.52 | N |
| ATOM | 6508 | CA | ASP | L | 152 | 48.215 | 27.376 | 37.648 | 1.00 | 93.32 | C |
| ATOM | 6509 | C | ASP | L | 152 | 49.523 | 27.118 | 36.861 | 1.00 | 99.60 | C |
| ATOM | 6510 | O | ASP | L | 152 | 50.429 | 26.443 | 37.360 | 1.00 | 100.41 | O |
| ATOM | 6511 | CB | ASP | L | 152 | 48.243 | 26.784 | 39.086 | 1.00 | 94.73 | C |
| ATOM | 6512 | CG | ASP | L | 152 | 47.239 | 27.377 | 40.064 | 1.00 | 103.42 | C |
| ATOM | 6513 | OD1 | ASP | L | 152 | 46.815 | 28.539 | 39.857 | 1.00 | 104.73 | O |
| ATOM | 6514 | OD2 | ASP | L | 152 | 46.931 | 26.708 | 41.073 | 1.00 | 106.13 | O |
| ATOM | 6515 | N | ASN | L | 153 | 49.562 | 27.597 | 35.584 | 1.00 | 95.63 | N |
| ATOM | 6516 | CA | ASN | L | 153 | 50.672 | 27.505 | 34.611 | 1.00 | 95.12 | C |
| ATOM | 6517 | C | ASN | L | 153 | 51.069 | 26.058 | 34.203 | 1.00 | 96.90 | C |
| ATOM | 6518 | O | ASN | L | 153 | 52.105 | 25.875 | 33.550 | 1.00 | 96.75 | O |
| ATOM | 6519 | CB | ASN | L | 153 | 51.911 | 28.296 | 35.076 | 1.00 | 99.06 | C |
| ATOM | 6520 | CG | ASN | L | 153 | 51.607 | 29.642 | 35.707 | 1.00 | 135.84 | C |
| ATOM | 6521 | OD1 | ASN | L | 153 | 50.819 | 30.450 | 35.190 | 1.00 | 133.75 | O |
| ATOM | 6522 | ND2 | ASN | L | 153 | 52.236 | 29.908 | 36.846 | 1.00 | 128.26 | N |
| ATOM | 6523 | N | ALA | L | 154 | 50.232 | 25.053 | 34.538 | 1.00 | 91.39 | N |
| ATOM | 6524 | CA | ALA | L | 154 | 50.463 | 23.653 | 34.172 | 1.00 | 90.55 | C |
| ATOM | 6525 | C | ALA | L | 154 | 49.586 | 23.272 | 32.958 | 1.00 | 93.26 | C |
| ATOM | 6526 | O | ALA | L | 154 | 48.363 | 23.463 | 33.010 | 1.00 | 92.03 | O |
| ATOM | 6527 | CB | ALA | L | 154 | 50.149 | 22.750 | 35.357 | 1.00 | 91.22 | C |
| ATOM | 6528 | N | LEU | L | 155 | 50.208 | 22.759 | 31.864 | 1.00 | 89.26 | N |
| ATOM | 6529 | CA | LEU | L | 155 | 49.478 | 22.357 | 30.651 | 1.00 | 89.27 | C |
| ATOM | 6530 | C | LEU | L | 155 | 48.638 | 21.103 | 30.877 | 1.00 | 91.14 | C |
| ATOM | 6531 | O | LEU | L | 155 | 49.164 | 20.060 | 31.283 | 1.00 | 90.21 | O |
| ATOM | 6532 | CB | LEU | L | 155 | 50.362 | 22.220 | 29.381 | 1.00 | 89.99 | C |
| ATOM | 6533 | CG | LEU | L | 155 | 51.872 | 21.934 | 29.545 | 1.00 | 96.37 | C |
| ATOM | 6534 | CD1 | LEU | L | 155 | 52.155 | 20.439 | 29.678 | 1.00 | 97.09 | C |
| ATOM | 6535 | CD2 | LEU | L | 155 | 52.663 | 22.487 | 28.367 | 1.00 | 99.85 | C |
| ATOM | 6536 | N | GLN | L | 156 | 47.321 | 21.228 | 30.625 | 1.00 | 86.37 | N |
| ATOM | 6537 | CA | GLN | L | 156 | 46.323 | 20.176 | 30.788 | 1.00 | 85.57 | C |
| ATOM | 6538 | C | GLN | L | 156 | 46.213 | 19.278 | 29.573 | 1.00 | 90.15 | C |
| ATOM | 6539 | O | GLN | L | 156 | 46.221 | 19.776 | 28.442 | 1.00 | 90.24 | O |
| ATOM | 6540 | CB | GLN | L | 156 | 44.941 | 20.778 | 31.119 | 1.00 | 86.60 | C |
| ATOM | 6541 | CG | GLN | L | 156 | 44.898 | 21.673 | 32.354 | 1.00 | 95.54 | C |
| ATOM | 6542 | CD | GLN | L | 156 | 45.453 | 21.015 | 33.601 | 1.00 | 105.17 | C |
| ATOM | 6543 | OE1 | GLN | L | 156 | 44.798 | 20.200 | 34.256 | 1.00 | 91.50 | O |
| ATOM | 6544 | NE2 | GLN | L | 156 | 46.682 | 21.355 | 33.952 | 1.00 | 103.98 | N |
| ATOM | 6545 | N | SER | L | 157 | 46.074 | 17.953 | 29.814 | 1.00 | 87.33 | N |
| ATOM | 6546 | CA | SER | L | 157 | 45.891 | 16.949 | 28.764 | 1.00 | 87.63 | C |
| ATOM | 6547 | C | SER | L | 157 | 44.895 | 15.839 | 29.163 | 1.00 | 92.20 | C |
| ATOM | 6548 | O | SER | L | 157 | 44.918 | 15.366 | 30.302 | 1.00 | 92.53 | O |
| ATOM | 6549 | CB | SER | L | 157 | 47.226 | 16.378 | 28.293 | 1.00 | 90.25 | C |
| ATOM | 6550 | OG | SER | L | 157 | 47.550 | 15.160 | 28.942 | 1.00 | 99.31 | O |
| ATOM | 6551 | N | GLY | L | 158 | 44.043 | 15.458 | 28.204 | 1.00 | 87.36 | N |
| ATOM | 6552 | CA | GLY | L | 158 | 43.039 | 14.414 | 28.339 | 1.00 | 86.13 | C |
| ATOM | 6553 | C | GLY | L | 158 | 41.899 | 14.739 | 29.279 | 1.00 | 88.60 | C |
| ATOM | 6554 | O | GLY | L | 158 | 41.338 | 13.830 | 29.898 | 1.00 | 89.48 | O |
| ATOM | 6555 | N | ASN | L | 159 | 41.544 | 16.033 | 29.395 | 1.00 | 82.21 | N |
| ATOM | 6556 | CA | ASN | L | 159 | 40.457 | 16.487 | 30.264 | 1.00 | 80.42 | C |
| ATOM | 6557 | C | ASN | L | 159 | 39.609 | 17.600 | 29.633 | 1.00 | 80.71 | C |
| ATOM | 6558 | O | ASN | L | 159 | 38.851 | 18.284 | 30.337 | 1.00 | 80.62 | O |
| ATOM | 6559 | CB | ASN | L | 159 | 40.988 | 16.873 | 31.642 | 1.00 | 80.58 | C |
| ATOM | 6560 | CG | ASN | L | 159 | 41.974 | 18.008 | 31.680 | 1.00 | 105.23 | C |
| ATOM | 6561 | OD1 | ASN | L | 159 | 42.472 | 18.514 | 30.658 | 1.00 | 108.47 | O |
| ATOM | 6562 | ND2 | ASN | L | 159 | 42.281 | 18.435 | 32.887 | 1.00 | 91.62 | N |
| ATOM | 6563 | N | SER | L | 160 | 39.735 | 17.760 | 28.292 | 1.00 | 74.34 | N |
| ATOM | 6564 | CA | SER | L | 160 | 38.981 | 18.733 | 27.491 | 1.00 | 72.39 | C |
| ATOM | 6565 | C | SER | L | 160 | 38.424 | 18.138 | 26.192 | 1.00 | 72.37 | C |
| ATOM | 6566 | O | SER | L | 160 | 38.905 | 17.104 | 25.707 | 1.00 | 71.75 | O |
| ATOM | 6567 | CB | SER | L | 160 | 39.780 | 20.009 | 27.225 | 1.00 | 74.18 | C |
| ATOM | 6568 | OG | SER | L | 160 | 41.057 | 19.746 | 26.673 | 1.00 | 78.48 | O |
| ATOM | 6569 | N | GLN | L | 161 | 37.376 | 18.780 | 25.664 | 1.00 | 65.76 | N |
| ATOM | 6570 | CA | GLN | L | 161 | 36.709 | 18.374 | 24.443 | 1.00 | 64.69 | C |
| ATOM | 6571 | C | GLN | L | 161 | 36.374 | 19.603 | 23.605 | 1.00 | 68.02 | C |
| ATOM | 6572 | O | GLN | L | 161 | 35.634 | 20.476 | 24.086 | 1.00 | 67.59 | O |
| ATOM | 6573 | CB | GLN | L | 161 | 35.413 | 17.620 | 24.772 | 1.00 | 66.06 | C |
| ATOM | 6574 | CG | GLN | L | 161 | 35.575 | 16.176 | 25.233 | 1.00 | 78.85 | C |
| ATOM | 6575 | CD | GLN | L | 161 | 34.253 | 15.519 | 25.626 | 1.00 | 86.84 | C |
| ATOM | 6576 | OE1 | GLN | L | 161 | 33.383 | 16.063 | 26.345 | 1.00 | 88.62 | O |
| ATOM | 6577 | NE2 | GLN | L | 161 | 34.106 | 14.293 | 25.204 | 1.00 | 56.79 | N |
| ATOM | 6578 | N | GLU | L | 162 | 36.890 | 19.672 | 22.348 | 1.00 | 64.13 | N |

TABLE 1-continued

Three-dimensional crystal coordinate for anti-TcdB antibody beziotoxumab Fab –C. *difficile* toxin B (TcdB$^{(1834-2101)}$) complex.

| ATOM | 6579 | CA | GLU | L | 162 | 36.531 | 20.798 | 21.469 | 1.00 | 63.97 | C |
|------|------|------|------|---|-----|--------|--------|--------|------|--------|---|
| ATOM | 6580 | C | GLU | L | 162 | 35.373 | 20.413 | 20.515 | 1.00 | 65.63 | C |
| ATOM | 6581 | O | GLU | L | 162 | 35.184 | 19.237 | 20.179 | 1.00 | 65.14 | O |
| ATOM | 6582 | CB | GLU | L | 162 | 37.708 | 21.503 | 20.719 | 1.00 | 65.51 | C |
| ATOM | 6583 | CG | GLU | L | 162 | 39.087 | 20.877 | 20.806 | 1.00 | 78.12 | C |
| ATOM | 6584 | CD | GLU | L | 162 | 40.205 | 21.828 | 21.196 | 1.00 | 97.55 | C |
| ATOM | 6585 | OE1 | GLU | L | 162 | 40.525 | 21.907 | 22.410 | 1.00 | 75.69 | O |
| ATOM | 6586 | OE2 | GLU | L | 162 | 40.801 | 22.443 | 20.278 | 1.00 | 91.57 | O |
| ATOM | 6587 | N | SER | L | 163 | 34.574 | 21.428 | 20.143 | 1.00 | 59.67 | N |
| ATOM | 6588 | CA | SER | L | 163 | 33.427 | 21.323 | 19.265 | 1.00 | 58.35 | C |
| ATOM | 6589 | C | SER | L | 163 | 33.446 | 22.533 | 18.333 | 1.00 | 62.33 | C |
| ATOM | 6590 | O | SER | L | 163 | 33.529 | 23.665 | 18.793 | 1.00 | 62.41 | O |
| ATOM | 6591 | CB | SER | L | 163 | 32.145 | 21.272 | 20.083 | 1.00 | 59.35 | C |
| ATOM | 6592 | OG | SER | L | 163 | 31.008 | 21.198 | 19.244 | 1.00 | 68.85 | O |
| ATOM | 6593 | N | VAL | L | 164 | 33.395 | 22.278 | 17.023 | 1.00 | 58.13 | N |
| ATOM | 6594 | CA | VAL | L | 164 | 33.441 | 23.290 | 15.968 | 1.00 | 56.99 | C |
| ATOM | 6595 | C | VAL | L | 164 | 32.115 | 23.374 | 15.275 | 1.00 | 60.00 | C |
| ATOM | 6596 | O | VAL | L | 164 | 31.530 | 22.345 | 14.953 | 1.00 | 57.45 | O |
| ATOM | 6597 | CB | VAL | L | 164 | 34.532 | 23.007 | 14.897 | 1.00 | 59.72 | C |
| ATOM | 6598 | CG1 | VAL | L | 164 | 34.982 | 24.303 | 14.233 | 1.00 | 58.79 | C |
| ATOM | 6599 | CG2 | VAL | L | 164 | 35.719 | 22.244 | 15.478 | 1.00 | 59.49 | C |
| ATOM | 6600 | N | THR | L | 165 | 31.684 | 24.604 | 14.961 | 1.00 | 57.98 | N |
| ATOM | 6601 | CA | THR | L | 165 | 30.462 | 24.823 | 14.188 | 1.00 | 57.39 | C |
| ATOM | 6602 | C | THR | L | 165 | 30.814 | 24.650 | 12.712 | 1.00 | 63.01 | C |
| ATOM | 6603 | O | THR | L | 165 | 31.996 | 24.662 | 12.334 | 1.00 | 63.28 | O |
| ATOM | 6604 | CB | THR | L | 165 | 29.933 | 26.246 | 14.398 | 1.00 | 56.50 | C |
| ATOM | 6605 | OG1 | THR | L | 165 | 30.989 | 27.196 | 14.161 | 1.00 | 46.64 | O |
| ATOM | 6606 | CG2 | THR | L | 165 | 29.275 | 26.447 | 15.769 | 1.00 | 51.68 | C |
| ATOM | 6607 | N | GLU | L | 166 | 29.792 | 24.497 | 11.869 | 1.00 | 59.94 | N |
| ATOM | 6608 | CA | GLU | L | 166 | 30.023 | 24.450 | 10.432 | 1.00 | 59.28 | C |
| ATOM | 6609 | C | GLU | L | 166 | 30.223 | 25.916 | 9.982 | 1.00 | 63.81 | C |
| ATOM | 6610 | O | GLU | L | 166 | 29.886 | 26.842 | 10.740 | 1.00 | 65.09 | O |
| ATOM | 6611 | CB | GLU | L | 166 | 28.900 | 23.706 | 9.676 | 1.00 | 60.17 | C |
| ATOM | 6612 | CG | GLU | L | 166 | 29.029 | 22.185 | 9.754 | 1.00 | 71.55 | C |
| ATOM | 6613 | CD | GLU | L | 166 | 30.397 | 21.572 | 9.476 | 1.00 | 95.22 | C |
| ATOM | 6614 | OE1 | GLU | L | 166 | 30.916 | 21.753 | 8.349 | 1.00 | 94.17 | O |
| ATOM | 6615 | OE2 | GLU | L | 166 | 30.971 | 20.950 | 10.401 | 1.00 | 84.82 | O |
| ATOM | 6616 | N | GLN | L | 167 | 30.867 | 26.122 | 8.826 | 1.00 | 57.91 | N |
| ATOM | 6617 | CA | GLN | L | 167 | 31.153 | 27.428 | 8.270 | 1.00 | 57.24 | C |
| ATOM | 6618 | C | GLN | L | 167 | 29.868 | 28.259 | 8.232 | 1.00 | 64.32 | C |
| ATOM | 6619 | O | GLN | L | 167 | 28.850 | 27.781 | 7.726 | 1.00 | 65.01 | O |
| ATOM | 6620 | CB | GLN | L | 167 | 31.754 | 27.253 | 6.880 | 1.00 | 58.43 | C |
| ATOM | 6621 | CG | GLN | L | 167 | 32.611 | 28.409 | 6.456 | 1.00 | 62.33 | C |
| ATOM | 6622 | CD | GLN | L | 167 | 33.500 | 28.083 | 5.304 | 1.00 | 70.92 | C |
| ATOM | 6623 | OE1 | GLN | L | 167 | 33.163 | 27.294 | 4.411 | 1.00 | 70.04 | O |
| ATOM | 6624 | NE2 | GLN | L | 167 | 34.638 | 28.735 | 5.276 | 1.00 | 56.46 | N |
| ATOM | 6625 | N | ASP | L | 168 | 29.892 | 29.456 | 8.857 | 1.00 | 62.97 | N |
| ATOM | 6626 | CA | ASP | L | 168 | 28.745 | 30.366 | 8.980 | 1.00 | 64.01 | C |
| ATOM | 6627 | C | ASP | L | 168 | 28.143 | 30.791 | 7.651 | 1.00 | 69.44 | C |
| ATOM | 6628 | O | ASP | L | 168 | 28.868 | 31.127 | 6.715 | 1.00 | 68.58 | O |
| ATOM | 6629 | CB | ASP | L | 168 | 29.097 | 31.603 | 9.828 | 1.00 | 67.18 | C |
| ATOM | 6630 | CG | ASP | L | 168 | 27.874 | 32.314 | 10.377 | 1.00 | 84.60 | C |
| ATOM | 6631 | OD1 | ASP | L | 168 | 27.349 | 31.873 | 11.423 | 1.00 | 85.64 | O |
| ATOM | 6632 | OD2 | ASP | L | 168 | 27.409 | 33.274 | 9.731 | 1.00 | 94.21 | O |
| ATOM | 6633 | N | SER | L | 169 | 26.804 | 30.789 | 7.580 | 1.00 | 68.72 | N |
| ATOM | 6634 | CA | SER | L | 169 | 26.028 | 31.162 | 6.386 | 1.00 | 68.98 | C |
| ATOM | 6635 | C | SER | L | 169 | 26.210 | 32.635 | 5.998 | 1.00 | 74.28 | C |
| ATOM | 6636 | O | SER | L | 169 | 26.133 | 32.961 | 4.810 | 1.00 | 75.65 | O |
| ATOM | 6637 | CB | SER | L | 169 | 24.544 | 30.864 | 6.600 | 1.00 | 72.06 | C |
| ATOM | 6638 | OG | SER | L | 169 | 24.014 | 31.563 | 7.716 | 1.00 | 79.90 | O |
| ATOM | 6639 | N | LYS | L | 170 | 26.447 | 33.521 | 6.993 | 1.00 | 69.06 | N |
| ATOM | 6640 | CA | LYS | L | 170 | 26.590 | 34.959 | 6.766 | 1.00 | 68.01 | C |
| ATOM | 6641 | C | LYS | L | 170 | 28.036 | 35.398 | 6.444 | 1.00 | 70.53 | C |
| ATOM | 6642 | O | LYS | L | 170 | 28.290 | 35.953 | 5.361 | 1.00 | 69.20 | O |
| ATOM | 6643 | CB | LYS | L | 170 | 26.018 | 35.740 | 7.964 | 1.00 | 69.82 | C |
| ATOM | 6644 | CG | LYS | L | 170 | 25.252 | 37.003 | 7.601 | 1.00 | 89.35 | C |
| ATOM | 6645 | CD | LYS | L | 170 | 25.014 | 37.897 | 8.834 | 1.00 | 105.68 | C |
| ATOM | 6646 | CE | LYS | L | 170 | 23.554 | 38.034 | 9.238 | 1.00 | 115.69 | C |
| ATOM | 6647 | NZ | LYS | L | 170 | 23.380 | 38.840 | 10.481 | 1.00 | 115.76 | N |
| ATOM | 6648 | N | ASP | L | 171 | 28.980 | 35.126 | 7.381 | 1.00 | 65.54 | N |
| ATOM | 6649 | CA | ASP | L | 171 | 30.363 | 35.579 | 7.291 | 1.00 | 64.86 | C |
| ATOM | 6650 | C | ASP | L | 171 | 31.420 | 34.504 | 7.003 | 1.00 | 67.49 | C |
| ATOM | 6651 | O | ASP | L | 171 | 32.613 | 34.819 | 7.063 | 1.00 | 67.85 | O |
| ATOM | 6652 | CB | ASP | L | 171 | 30.738 | 36.352 | 8.557 | 1.00 | 67.16 | C |
| ATOM | 6653 | CG | ASP | L | 171 | 30.360 | 35.679 | 9.851 | 1.00 | 85.42 | C |
| ATOM | 6654 | OD2 | ASP | L | 171 | 31.253 | 35.444 | 10.669 | 1.00 | 85.04 | O |
| ATOM | 6655 | OD1 | ASP | L | 171 | 29.148 | 35.505 | 10.100 | 1.00 | 100.48 | O |

TABLE 1-continued

Three-dimensional crystal coordinate for anti-TcdB antibody beziotoxumab Fab –C. difficile toxin B (TcdB$^{(1834-2101)}$) complex.

| ATOM | 6656 | N   | SER | L | 172 | 31.001 | 33.271 | 6.640  | 1.00 | 61.23 | N |
| ---- | ---- | --- | --- | - | --- | ------ | ------ | ------ | ---- | ----- | - |
| ATOM | 6657 | CA  | SER | L | 172 | 31.872 | 32.127 | 6.302  | 1.00 | 59.37 | C |
| ATOM | 6658 | C   | SER | L | 172 | 32.965 | 31.821 | 7.367  | 1.00 | 61.12 | C |
| ATOM | 6659 | O   | SER | L | 172 | 34.056 | 31.361 | 7.031  | 1.00 | 62.37 | O |
| ATOM | 6660 | CB  | SER | L | 172 | 32.480 | 32.284 | 4.909  | 1.00 | 60.47 | C |
| ATOM | 6661 | OG  | SER | L | 172 | 31.459 | 32.266 | 3.932  | 1.00 | 66.32 | O |
| ATOM | 6662 | N   | THR | L | 173 | 32.642 | 32.022 | 8.637  | 1.00 | 54.69 | N |
| ATOM | 6663 | CA  | THR | L | 173 | 33.574 | 31.765 | 9.728  | 1.00 | 54.01 | C |
| ATOM | 6664 | C   | THR | L | 173 | 33.192 | 30.540 | 10.562 | 1.00 | 56.92 | C |
| ATOM | 6665 | O   | THR | L | 173 | 32.078 | 30.013 | 10.469 | 1.00 | 55.45 | O |
| ATOM | 6666 | CB  | THR | L | 173 | 33.674 | 32.974 | 10.658 | 1.00 | 61.06 | C |
| ATOM | 6667 | OG1 | THR | L | 173 | 32.410 | 33.181 | 11.283 | 1.00 | 59.29 | O |
| ATOM | 6668 | CG2 | THR | L | 173 | 34.183 | 34.220 | 9.963  | 1.00 | 63.26 | C |
| ATOM | 6669 | N   | TYR | L | 174 | 34.132 | 30.137 | 11.423 | 1.00 | 52.48 | N |
| ATOM | 6670 | CA  | TYR | L | 174 | 34.006 | 29.055 | 12.369 | 1.00 | 51.10 | C |
| ATOM | 6671 | C   | TYR | L | 174 | 34.004 | 29.575 | 13.798 | 1.00 | 57.34 | C |
| ATOM | 6672 | O   | TYR | L | 174 | 34.627 | 30.588 | 14.112 | 1.00 | 56.59 | O |
| ATOM | 6673 | CB  | TYR | L | 174 | 35.175 | 28.089 | 12.220 | 1.00 | 51.51 | C |
| ATOM | 6674 | CG  | TYR | L | 174 | 35.269 | 27.466 | 10.848 | 1.00 | 54.89 | C |
| ATOM | 6675 | CD1 | TYR | L | 174 | 34.445 | 26.399 | 10.485 | 1.00 | 55.67 | C |
| ATOM | 6676 | CD2 | TYR | L | 174 | 36.186 | 27.938 | 9.905  | 1.00 | 56.65 | C |
| ATOM | 6677 | CE1 | TYR | L | 174 | 34.510 | 25.836 | 9.213  | 1.00 | 54.47 | C |
| ATOM | 6678 | CE2 | TYR | L | 174 | 36.278 | 27.361 | 8.636  | 1.00 | 57.88 | C |
| ATOM | 6679 | CZ  | TYR | L | 174 | 35.437 | 26.311 | 8.297  | 1.00 | 63.76 | C |
| ATOM | 6680 | OH  | TYR | L | 174 | 35.524 | 25.753 | 7.051  | 1.00 | 65.23 | O |
| ATOM | 6681 | N   | SER | L | 175 | 33.314 | 28.852 | 14.667 | 1.00 | 55.37 | N |
| ATOM | 6682 | CA  | SER | L | 175 | 33.340 | 29.086 | 16.087 | 1.00 | 55.59 | C |
| ATOM | 6683 | C   | SER | L | 175 | 33.726 | 27.755 | 16.738 | 1.00 | 61.60 | C |
| ATOM | 6684 | O   | SER | L | 175 | 33.520 | 26.688 | 16.139 | 1.00 | 63.06 | O |
| ATOM | 6685 | CB  | SER | L | 175 | 32.030 | 29.666 | 16.578 | 1.00 | 59.50 | C |
| ATOM | 6686 | OG  | SER | L | 175 | 31.867 | 30.923 | 15.942 | 1.00 | 71.72 | O |
| ATOM | 6687 | N   | LEU | L | 176 | 34.389 | 27.819 | 17.888 | 1.00 | 56.69 | N |
| ATOM | 6688 | CA  | LEU | L | 176 | 34.893 | 26.653 | 18.586 | 1.00 | 56.83 | C |
| ATOM | 6689 | C   | LEU | L | 176 | 34.714 | 26.847 | 20.097 | 1.00 | 64.13 | C |
| ATOM | 6690 | O   | LEU | L | 176 | 34.899 | 27.953 | 20.603 | 1.00 | 65.40 | O |
| ATOM | 6691 | CB  | LEU | L | 176 | 36.380 | 26.445 | 18.211 | 1.00 | 56.22 | C |
| ATOM | 6692 | CG  | LEU | L | 176 | 37.113 | 25.219 | 18.761 | 1.00 | 59.69 | C |
| ATOM | 6693 | CD1 | LEU | L | 176 | 38.055 | 24.649 | 17.727 | 1.00 | 58.56 | C |
| ATOM | 6694 | CD2 | LEU | L | 176 | 37.904 | 25.565 | 19.994 | 1.00 | 61.88 | C |
| ATOM | 6695 | N   | SER | L | 177 | 34.337 | 25.770 | 20.804 | 1.00 | 59.19 | N |
| ATOM | 6696 | CA  | SER | L | 177 | 34.184 | 25.756 | 22.240 | 0.47 | 57.90 | C |
| ATOM | 6697 | C   | SER | L | 177 | 35.048 | 24.617 | 22.711 | 1.00 | 64.77 | C |
| ATOM | 6698 | O   | SER | L | 177 | 34.929 | 23.531 | 22.162 | 1.00 | 65.82 | O |
| ATOM | 6699 | CB  | SER | L | 177 | 32.725 | 25.521 | 22.624 | 0.47 | 58.20 | C |
| ATOM | 6700 | OG  | SER | L | 177 | 32.306 | 24.179 | 22.439 | 0.47 | 59.83 | O |
| ATOM | 6701 | N   | SER | L | 178 | 35.985 | 24.868 | 23.646 | 1.00 | 63.06 | N |
| ATOM | 6702 | CA  | SER | L | 178 | 36.840 | 23.834 | 24.250 | 1.00 | 63.78 | C |
| ATOM | 6703 | C   | SER | L | 178 | 36.444 | 23.760 | 25.730 | 1.00 | 70.61 | C |
| ATOM | 6704 | O   | SER | L | 178 | 36.601 | 24.751 | 26.450 | 1.00 | 70.86 | O |
| ATOM | 6705 | CB  | SER | L | 178 | 38.323 | 24.165 | 24.099 | 1.00 | 67.03 | C |
| ATOM | 6706 | OG  | SER | L | 178 | 39.135 | 23.202 | 24.755 | 1.00 | 75.97 | O |
| ATOM | 6707 | N   | THR | L | 179 | 35.860 | 22.624 | 26.165 | 1.00 | 68.28 | N |
| ATOM | 6708 | CA  | THR | L | 179 | 35.390 | 22.481 | 27.544 | 1.00 | 68.58 | C |
| ATOM | 6709 | C   | THR | L | 179 | 36.324 | 21.636 | 28.394 | 1.00 | 74.31 | C |
| ATOM | 6710 | O   | THR | L | 179 | 36.544 | 20.464 | 28.088 | 1.00 | 74.82 | O |
| ATOM | 6711 | CB  | THR | L | 179 | 33.941 | 21.978 | 27.591 | 1.00 | 74.00 | C |
| ATOM | 6712 | OG1 | THR | L | 179 | 33.116 | 22.819 | 26.785 | 1.00 | 74.89 | O |
| ATOM | 6713 | CG2 | THR | L | 179 | 33.376 | 21.957 | 28.997 | 1.00 | 73.26 | C |
| ATOM | 6714 | N   | LEU | L | 180 | 36.849 | 22.239 | 29.487 | 1.00 | 71.04 | N |
| ATOM | 6715 | CA  | LEU | L | 180 | 37.696 | 21.574 | 30.487 | 1.00 | 70.68 | C |
| ATOM | 6716 | C   | LEU | L | 180 | 36.765 | 21.022 | 31.598 | 1.00 | 76.45 | C |
| ATOM | 6717 | O   | LEU | L | 180 | 35.972 | 21.782 | 32.175 | 1.00 | 76.08 | O |
| ATOM | 6718 | CB  | LEU | L | 180 | 38.713 | 22.569 | 31.075 | 1.00 | 69.83 | C |
| ATOM | 6719 | CG  | LEU | L | 180 | 39.694 | 22.003 | 32.091 | 1.00 | 73.24 | C |
| ATOM | 6720 | CD1 | LEU | L | 180 | 40.910 | 21.399 | 31.413 | 1.00 | 73.44 | C |
| ATOM | 6721 | CD2 | LEU | L | 180 | 40.150 | 23.076 | 33.023 | 1.00 | 73.41 | C |
| ATOM | 6722 | N   | THR | L | 181 | 36.825 | 19.709 | 31.859 | 1.00 | 74.49 | N |
| ATOM | 6723 | CA  | THR | L | 181 | 35.957 | 19.127 | 32.889 | 1.00 | 75.84 | C |
| ATOM | 6724 | C   | THR | L | 181 | 36.817 | 18.530 | 34.015 | 1.00 | 82.31 | C |
| ATOM | 6725 | O   | THR | L | 181 | 37.712 | 17.690 | 33.793 | 1.00 | 81.08 | O |
| ATOM | 6726 | CB  | THR | L | 181 | 34.873 | 18.171 | 32.302 | 1.00 | 84.12 | C |
| ATOM | 6727 | OG1 | THR | L | 181 | 34.028 | 18.904 | 31.398 | 1.00 | 82.99 | O |
| ATOM | 6728 | CG2 | THR | L | 181 | 33.977 | 17.545 | 33.394 | 1.00 | 80.55 | C |
| ATOM | 6729 | N   | LEU | L | 182 | 36.530 | 19.024 | 35.224 | 1.00 | 81.49 | N |
| ATOM | 6730 | CA  | LEU | L | 182 | 37.198 | 18.664 | 36.465 | 1.00 | 83.11 | C |
| ATOM | 6731 | C   | LEU | L | 182 | 36.185 | 18.368 | 37.572 | 1.00 | 88.76 | C |
| ATOM | 6732 | O   | LEU | L | 182 | 35.103 | 18.973 | 37.606 | 1.00 | 88.11 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 6733 | CB | LEU | L | 182 | 38.048 | 19.857 | 36.934 | 1.00 | 83.59 | C |
|---|---|---|---|---|---|---|---|---|---|---|---|
| ATOM | 6734 | CG | LEU | L | 182 | 39.349 | 20.147 | 36.213 | 1.00 | 88.49 | C |
| ATOM | 6735 | CD1 | LEU | L | 182 | 39.821 | 21.554 | 36.530 | 1.00 | 88.95 | C |
| ATOM | 6736 | CD2 | LEU | L | 182 | 40.416 | 19.130 | 36.569 | 1.00 | 90.02 | C |
| ATOM | 6737 | N | SER | L | 183 | 36.580 | 17.492 | 38.523 | 1.00 | 85.90 | N |
| ATOM | 6738 | CA | SER | L | 183 | 35.787 | 17.194 | 39.720 | 1.00 | 85.74 | C |
| ATOM | 6739 | C | SER | L | 183 | 35.922 | 18.398 | 40.676 | 1.00 | 88.65 | C |
| ATOM | 6740 | O | SER | L | 183 | 37.036 | 18.926 | 40.810 | 1.00 | 87.92 | O |
| ATOM | 6741 | CB | SER | L | 183 | 36.305 | 15.931 | 40.404 | 1.00 | 89.15 | C |
| ATOM | 6742 | OG | SER | L | 183 | 37.600 | 16.126 | 40.948 | 1.00 | 97.89 | O |
| ATOM | 6743 | N | LYS | L | 184 | 34.804 | 18.830 | 41.334 | 1.00 | 84.92 | N |
| ATOM | 6744 | CA | LYS | L | 184 | 34.775 | 19.950 | 42.303 | 1.00 | 84.70 | C |
| ATOM | 6745 | C | LYS | L | 184 | 36.019 | 19.944 | 43.207 | 1.00 | 89.80 | C |
| ATOM | 6746 | O | LYS | L | 184 | 36.568 | 21.004 | 43.474 | 1.00 | 88.98 | O |
| ATOM | 6747 | CB | LYS | L | 184 | 33.483 | 19.935 | 43.146 | 1.00 | 86.54 | C |
| ATOM | 6748 | CG | LYS | L | 184 | 33.275 | 21.171 | 44.019 | 1.00 | 90.47 | C |
| ATOM | 6749 | CD | LYS | L | 184 | 32.385 | 20.869 | 45.217 | 1.00 | 98.25 | C |
| ATOM | 6750 | CE | LYS | L | 184 | 32.277 | 22.059 | 46.141 | 1.00 | 107.40 | C |
| ATOM | 6751 | NZ | LYS | L | 184 | 31.204 | 21.892 | 47.157 | 1.00 | 114.82 | N |
| ATOM | 6752 | N | ALA | L | 185 | 36.498 | 18.738 | 43.598 | 1.00 | 87.88 | N |
| ATOM | 6753 | CA | ALA | L | 185 | 37.692 | 18.496 | 44.411 | 1.00 | 88.22 | C |
| ATOM | 6754 | C | ALA | L | 185 | 38.924 | 19.155 | 43.788 | 1.00 | 93.04 | C |
| ATOM | 6755 | O | ALA | L | 185 | 39.465 | 20.084 | 44.387 | 1.00 | 93.34 | O |
| ATOM | 6756 | CB | ALA | L | 185 | 37.921 | 16.996 | 44.566 | 1.00 | 89.04 | C |
| ATOM | 6757 | N | ASP | L | 186 | 39.314 | 18.718 | 42.559 | 1.00 | 89.22 | N |
| ATOM | 6758 | CA | ASP | L | 186 | 40.457 | 19.218 | 41.787 | 1.00 | 88.68 | C |
| ATOM | 6759 | C | ASP | L | 186 | 40.335 | 20.693 | 41.368 | 1.00 | 91.99 | C |
| ATOM | 6760 | O | ASP | L | 186 | 41.352 | 21.380 | 41.239 | 1.00 | 91.21 | O |
| ATOM | 6761 | CB | ASP | L | 186 | 40.716 | 18.321 | 40.582 | 1.00 | 90.38 | C |
| ATOM | 6762 | CG | ASP | L | 186 | 41.163 | 16.932 | 40.969 | 1.00 | 100.56 | C |
| ATOM | 6763 | OD2 | ASP | L | 186 | 42.379 | 16.666 | 40.906 | 1.00 | 108.13 | O |
| ATOM | 6764 | OD1 | ASP | L | 186 | 40.300 | 16.120 | 41.357 | 1.00 | 100.27 | O |
| ATOM | 6765 | N | TYR | L | 187 | 39.103 | 21.181 | 41.181 | 1.00 | 88.60 | N |
| ATOM | 6766 | CA | TYR | L | 187 | 38.869 | 22.583 | 40.856 | 1.00 | 88.50 | C |
| ATOM | 6767 | C | TYR | L | 187 | 39.218 | 23.501 | 42.046 | 1.00 | 94.44 | C |
| ATOM | 6768 | O | TYR | L | 187 | 39.849 | 24.539 | 41.825 | 1.00 | 94.88 | O |
| ATOM | 6769 | CB | TYR | L | 187 | 37.430 | 22.815 | 40.373 | 1.00 | 88.86 | C |
| ATOM | 6770 | CG | TYR | L | 187 | 37.092 | 24.268 | 40.121 | 1.00 | 89.12 | C |
| ATOM | 6771 | CD1 | TYR | L | 187 | 37.641 | 24.956 | 39.044 | 1.00 | 90.63 | C |
| ATOM | 6772 | CD2 | TYR | L | 187 | 36.219 | 24.954 | 40.957 | 1.00 | 89.71 | C |
| ATOM | 6773 | CE1 | TYR | L | 187 | 37.342 | 26.300 | 38.816 | 1.00 | 90.87 | C |
| ATOM | 6774 | CE2 | TYR | L | 187 | 35.898 | 26.291 | 40.729 | 1.00 | 90.40 | C |
| ATOM | 6775 | CZ | TYR | L | 187 | 36.470 | 26.964 | 39.664 | 1.00 | 96.75 | C |
| ATOM | 6776 | OH | TYR | L | 187 | 36.116 | 28.268 | 39.426 | 1.00 | 96.71 | O |
| ATOM | 6777 | N | GLU | L | 188 | 38.820 | 23.119 | 43.299 | 1.00 | 91.05 | N |
| ATOM | 6778 | CA | GLU | L | 188 | 39.104 | 23.879 | 44.540 | 1.00 | 90.43 | C |
| ATOM | 6779 | C | GLU | L | 188 | 40.627 | 23.928 | 44.857 | 1.00 | 94.06 | C |
| ATOM | 6780 | O | GLU | L | 188 | 41.096 | 24.889 | 45.486 | 1.00 | 94.03 | O |
| ATOM | 6781 | CB | GLU | L | 188 | 38.358 | 23.308 | 45.763 | 1.00 | 91.70 | C |
| ATOM | 6782 | CG | GLU | L | 188 | 36.874 | 23.019 | 45.595 | 1.00 | 104.35 | C |
| ATOM | 6783 | CD | GLU | L | 188 | 35.883 | 24.140 | 45.834 | 1.00 | 132.32 | C |
| ATOM | 6784 | OE1 | GLU | L | 188 | 35.971 | 25.179 | 45.139 | 1.00 | 141.21 | O |
| ATOM | 6785 | OE2 | GLU | L | 188 | 34.963 | 23.940 | 46.661 | 1.00 | 122.04 | O |
| ATOM | 6786 | N | LYS | L | 189 | 41.381 | 22.883 | 44.411 | 1.00 | 88.77 | N |
| ATOM | 6787 | CA | LYS | L | 189 | 42.826 | 22.697 | 44.588 | 1.00 | 88.33 | C |
| ATOM | 6788 | C | LYS | L | 189 | 43.727 | 23.766 | 43.910 | 1.00 | 93.69 | C |
| ATOM | 6789 | O | LYS | L | 189 | 44.915 | 23.850 | 44.249 | 1.00 | 94.47 | O |
| ATOM | 6790 | CB | LYS | L | 189 | 43.236 | 21.305 | 44.058 | 1.00 | 90.35 | C |
| ATOM | 6791 | CG | LYS | L | 189 | 43.104 | 20.156 | 45.042 | 1.00 | 102.70 | C |
| ATOM | 6792 | CD | LYS | L | 189 | 43.736 | 18.882 | 44.466 | 1.00 | 111.79 | C |
| ATOM | 6793 | CE | LYS | L | 189 | 43.605 | 17.686 | 45.383 | 1.00 | 122.00 | C |
| ATOM | 6794 | NZ | LYS | L | 189 | 44.211 | 16.461 | 44.790 | 1.00 | 125.69 | N |
| ATOM | 6795 | N | HIS | L | 190 | 43.197 | 24.525 | 42.916 | 1.00 | 89.21 | N |
| ATOM | 6796 | CA | HIS | L | 190 | 43.964 | 25.506 | 42.130 | 1.00 | 87.90 | C |
| ATOM | 6797 | C | HIS | L | 190 | 43.277 | 26.872 | 41.997 | 1.00 | 91.03 | C |
| ATOM | 6798 | O | HIS | L | 190 | 42.061 | 26.942 | 42.179 | 1.00 | 89.21 | O |
| ATOM | 6799 | CB | HIS | L | 190 | 44.269 | 24.921 | 40.756 | 1.00 | 87.99 | C |
| ATOM | 6800 | CG | HIS | L | 190 | 45.067 | 23.667 | 40.819 | 1.00 | 90.88 | C |
| ATOM | 6801 | ND1 | HIS | L | 190 | 44.455 | 22.429 | 40.900 | 1.00 | 92.40 | N |
| ATOM | 6802 | CD2 | HIS | L | 190 | 46.409 | 23.498 | 40.836 | 1.00 | 93.03 | C |
| ATOM | 6803 | CE1 | HIS | L | 190 | 45.438 | 21.546 | 40.949 | 1.00 | 92.25 | C |
| ATOM | 6804 | NE2 | HIS | L | 190 | 46.634 | 22.141 | 40.913 | 1.00 | 92.79 | N |
| ATOM | 6805 | N | LYS | L | 191 | 44.055 | 27.949 | 41.658 | 1.00 | 88.42 | N |
| ATOM | 6806 | CA | LYS | L | 191 | 43.571 | 29.350 | 41.564 | 1.00 | 88.55 | C |
| ATOM | 6807 | C | LYS | L | 191 | 43.393 | 29.927 | 40.143 | 1.00 | 91.01 | C |
| ATOM | 6808 | O | LYS | L | 191 | 42.311 | 30.446 | 39.837 | 1.00 | 89.46 | O |
| ATOM | 6809 | CB | LYS | L | 191 | 44.477 | 30.300 | 42.381 | 1.00 | 91.03 | C |

TABLE 1-continued

Three-dimensional crystal coordinate for anti-TcdB antibody beziotoxumab
Fab –C. difficile toxin B (TcdB$^{(1834-2101)}$) complex.

| ATOM | 6810 | N   | VAL | L | 192 | 44.469 | 29.897 | 39.319 | 1.00 | 87.27 | N |
|------|------|-----|-----|---|-----|--------|--------|--------|------|-------|---|
| ATOM | 6811 | CA  | VAL | L | 192 | 44.497 | 30.447 | 37.955 | 1.00 | 87.31 | C |
| ATOM | 6812 | C   | VAL | L | 192 | 44.122 | 29.416 | 36.882 | 1.00 | 89.67 | C |
| ATOM | 6813 | O   | VAL | L | 192 | 44.802 | 28.398 | 36.704 | 1.00 | 88.82 | O |
| ATOM | 6814 | CB  | VAL | L | 192 | 45.819 | 31.167 | 37.574 | 1.00 | 91.79 | C |
| ATOM | 6815 | CG1 | VAL | L | 192 | 45.552 | 32.298 | 36.577 | 1.00 | 91.61 | C |
| ATOM | 6816 | CG2 | VAL | L | 192 | 46.564 | 31.688 | 38.804 | 1.00 | 91.76 | C |
| ATOM | 6817 | N   | TYR | L | 193 | 43.051 | 29.726 | 36.143 | 1.00 | 84.51 | N |
| ATOM | 6818 | CA  | TYR | L | 193 | 42.518 | 28.905 | 35.067 | 1.00 | 83.32 | C |
| ATOM | 6819 | C   | TYR | L | 193 | 42.607 | 29.684 | 33.768 | 1.00 | 83.43 | C |
| ATOM | 6820 | O   | TYR | L | 193 | 41.948 | 30.711 | 33.633 | 1.00 | 83.97 | O |
| ATOM | 6821 | CB  | TYR | L | 193 | 41.069 | 28.489 | 35.396 | 1.00 | 85.28 | C |
| ATOM | 6822 | CG  | TYR | L | 193 | 41.000 | 27.402 | 36.446 | 1.00 | 87.51 | C |
| ATOM | 6823 | CD1 | TYR | L | 193 | 41.078 | 26.059 | 36.091 | 1.00 | 89.43 | C |
| ATOM | 6824 | CD2 | TYR | L | 193 | 40.925 | 27.717 | 37.799 | 1.00 | 88.78 | C |
| ATOM | 6825 | CE1 | TYR | L | 193 | 41.059 | 25.054 | 37.054 | 1.00 | 90.87 | C |
| ATOM | 6826 | CE2 | TYR | L | 193 | 40.929 | 26.719 | 38.775 | 1.00 | 90.10 | C |
| ATOM | 6827 | CZ  | TYR | L | 193 | 41.005 | 25.388 | 38.398 | 1.00 | 97.03 | C |
| ATOM | 6828 | OH  | TYR | L | 193 | 40.988 | 24.393 | 39.346 | 1.00 | 94.97 | O |
| ATOM | 6829 | N   | ALA | L | 194 | 43.436 | 29.225 | 32.823 | 1.00 | 76.24 | N |
| ATOM | 6830 | CA  | ALA | L | 194 | 43.638 | 29.950 | 31.574 | 1.00 | 74.87 | C |
| ATOM | 6831 | C   | ALA | L | 194 | 43.592 | 29.118 | 30.311 | 1.00 | 77.60 | C |
| ATOM | 6832 | O   | ALA | L | 194 | 44.122 | 28.010 | 30.283 | 1.00 | 76.42 | O |
| ATOM | 6833 | CB  | ALA | L | 194 | 44.975 | 30.670 | 31.628 | 1.00 | 75.47 | C |
| ATOM | 6834 | N   | CYS | L | 195 | 43.039 | 29.685 | 29.229 | 1.00 | 74.49 | N |
| ATOM | 6835 | CA  | CYS | L | 195 | 43.133 | 29.033 | 27.926 | 1.00 | 73.76 | C |
| ATOM | 6836 | C   | CYS | L | 195 | 43.949 | 29.918 | 26.993 | 1.00 | 72.69 | C |
| ATOM | 6837 | O   | CYS | L | 195 | 43.788 | 31.137 | 27.015 | 1.00 | 71.87 | O |
| ATOM | 6838 | CB  | CYS | L | 195 | 41.788 | 28.608 | 27.331 | 1.00 | 74.99 | C |
| ATOM | 6839 | SG  | CYS | L | 195 | 40.642 | 29.965 | 26.973 | 1.00 | 79.53 | S |
| ATOM | 6840 | N   | GLU | L | 196 | 44.894 | 29.312 | 26.268 | 1.00 | 66.50 | N |
| ATOM | 6841 | CA  | GLU | L | 196 | 45.809 | 29.993 | 25.354 | 1.00 | 64.97 | C |
| ATOM | 6842 | C   | GLU | L | 196 | 45.545 | 29.616 | 23.874 | 1.00 | 69.19 | C |
| ATOM | 6843 | O   | GLU | L | 196 | 45.994 | 28.557 | 23.386 | 1.00 | 70.03 | O |
| ATOM | 6844 | CB  | GLU | L | 196 | 47.272 | 29.732 | 25.770 | 1.00 | 65.61 | C |
| ATOM | 6845 | CG  | GLU | L | 196 | 48.291 | 30.513 | 24.967 | 1.00 | 70.23 | C |
| ATOM | 6846 | CD  | GLU | L | 196 | 49.729 | 30.195 | 25.306 | 1.00 | 87.02 | C |
| ATOM | 6847 | OE1 | GLU | L | 196 | 50.232 | 30.733 | 26.318 | 1.00 | 89.05 | O |
| ATOM | 6848 | OE2 | GLU | L | 196 | 50.367 | 29.442 | 24.538 | 1.00 | 80.82 | O |
| ATOM | 6849 | N   | VAL | L | 197 | 44.834 | 30.532 | 23.169 | 1.00 | 63.00 | N |
| ATOM | 6850 | CA  | VAL | L | 197 | 44.465 | 30.465 | 21.746 | 1.00 | 61.71 | C |
| ATOM | 6851 | C   | VAL | L | 197 | 45.635 | 30.879 | 20.822 | 1.00 | 65.36 | C |
| ATOM | 6852 | O   | VAL | L | 197 | 46.303 | 31.881 | 21.067 | 1.00 | 64.58 | O |
| ATOM | 6853 | CB  | VAL | L | 197 | 43.191 | 31.298 | 21.501 | 1.00 | 65.41 | C |
| ATOM | 6854 | CG1 | VAL | L | 197 | 42.908 | 31.516 | 20.011 | 1.00 | 65.24 | C |
| ATOM | 6855 | CG2 | VAL | L | 197 | 41.999 | 30.651 | 22.192 | 1.00 | 65.11 | C |
| ATOM | 6856 | N   | THR | L | 198 | 45.881 | 30.091 | 19.772 | 1.00 | 62.72 | N |
| ATOM | 6857 | CA  | THR | L | 198 | 46.946 | 30.335 | 18.786 | 1.00 | 61.95 | C |
| ATOM | 6858 | C   | THR | L | 198 | 46.322 | 30.320 | 17.366 | 1.00 | 62.72 | C |
| ATOM | 6859 | O   | THR | L | 198 | 46.108 | 29.252 | 16.797 | 1.00 | 63.42 | O |
| ATOM | 6860 | CB  | THR | L | 198 | 48.081 | 29.297 | 18.993 | 1.00 | 68.37 | C |
| ATOM | 6861 | OG1 | THR | L | 198 | 48.479 | 29.287 | 20.370 | 1.00 | 77.57 | O |
| ATOM | 6862 | CG2 | THR | L | 198 | 49.280 | 29.543 | 18.098 | 1.00 | 58.19 | C |
| ATOM | 6863 | N   | HIS | L | 199 | 45.986 | 31.495 | 16.832 | 1.00 | 56.20 | N |
| ATOM | 6864 | CA  | HIS | L | 199 | 45.416 | 31.629 | 15.487 | 1.00 | 55.38 | C |
| ATOM | 6865 | C   | HIS | L | 199 | 46.292 | 32.576 | 14.649 | 1.00 | 59.30 | C |
| ATOM | 6866 | O   | HIS | L | 199 | 46.936 | 33.471 | 15.211 | 1.00 | 60.85 | O |
| ATOM | 6867 | CB  | HIS | L | 199 | 43.962 | 32.126 | 15.548 | 1.00 | 55.61 | C |
| ATOM | 6868 | CG  | HIS | L | 199 | 43.226 | 32.059 | 14.237 | 1.00 | 58.46 | C |
| ATOM | 6869 | ND1 | HIS | L | 199 | 43.284 | 33.092 | 13.323 | 1.00 | 59.86 | N |
| ATOM | 6870 | CD2 | HIS | L | 199 | 42.440 | 31.079 | 13.732 | 1.00 | 59.81 | C |
| ATOM | 6871 | CE1 | HIS | L | 199 | 42.550 | 32.703 | 12.290 | 1.00 | 59.11 | C |
| ATOM | 6872 | NE2 | HIS | L | 199 | 42.007 | 31.506 | 12.500 | 1.00 | 59.41 | N |
| ATOM | 6873 | N   | GLN | L | 200 | 46.323 | 32.376 | 13.317 | 1.00 | 53.39 | N |
| ATOM | 6874 | CA  | GLN | L | 200 | 47.107 | 33.205 | 12.387 | 1.00 | 52.53 | C |
| ATOM | 6875 | C   | GLN | L | 200 | 46.552 | 34.624 | 12.195 | 1.00 | 58.56 | C |
| ATOM | 6876 | O   | GLN | L | 200 | 47.176 | 35.429 | 11.520 | 1.00 | 58.57 | O |
| ATOM | 6877 | CB  | GLN | L | 200 | 47.308 | 32.506 | 11.026 | 1.00 | 53.01 | C |
| ATOM | 6878 | CG  | GLN | L | 200 | 46.074 | 32.440 | 10.133 | 1.00 | 53.61 | C |
| ATOM | 6879 | CD  | GLN | L | 200 | 46.193 | 31.319 | 9.157  | 1.00 | 69.13 | C |
| ATOM | 6880 | OE1 | GLN | L | 200 | 46.434 | 31.529 | 7.976  | 1.00 | 62.32 | O |
| ATOM | 6881 | NE2 | GLN | L | 200 | 46.057 | 30.098 | 9.639  | 1.00 | 74.77 | N |
| ATOM | 6882 | N   | GLY | L | 201 | 45.391 | 34.908 | 12.768 | 1.00 | 56.22 | N |
| ATOM | 6883 | CA  | GLY | L | 201 | 44.786 | 36.231 | 12.714 | 1.00 | 56.08 | C |
| ATOM | 6884 | C   | GLY | L | 201 | 45.251 | 37.074 | 13.875 | 1.00 | 60.60 | C |
| ATOM | 6885 | O   | GLY | L | 201 | 45.046 | 38.280 | 13.862 | 1.00 | 62.27 | O |
| ATOM | 6886 | N   | LEU | L | 202 | 45.879 | 36.440 | 14.883 | 1.00 | 57.20 | N |

TABLE 1-continued

Three-dimensional crystal coordinate for anti-TcdB antibody beziotoxumab Fab –C. *difficile* toxin B (TcdB$^{(1834-2101)}$) complex.

| ATOM | 6887 | CA | LEU | L | 202 | 46.376 | 37.063 | 16.111 | 1.00 | 57.43 | C |
|------|------|-----|-----|---|-----|--------|--------|--------|------|-------|---|
| ATOM | 6888 | C | LEU | L | 202 | 47.876 | 37.279 | 16.089 | 1.00 | 62.50 | C |
| ATOM | 6889 | O | LEU | L | 202 | 48.618 | 36.377 | 15.686 | 1.00 | 62.55 | O |
| ATOM | 6890 | CB | LEU | L | 202 | 45.999 | 36.208 | 17.343 | 1.00 | 57.78 | C |
| ATOM | 6891 | CG | LEU | L | 202 | 44.521 | 35.941 | 17.611 | 1.00 | 61.52 | C |
| ATOM | 6892 | CD1 | LEU | L | 202 | 44.356 | 34.819 | 18.621 | 1.00 | 61.78 | C |
| ATOM | 6893 | CD2 | LEU | L | 202 | 43.811 | 37.184 | 18.072 | 1.00 | 60.94 | C |
| ATOM | 6894 | N | SER | L | 203 | 48.306 | 38.471 | 16.575 | 1.00 | 60.60 | N |
| ATOM | 6895 | CA | SER | L | 203 | 49.695 | 38.960 | 16.672 | 1.00 | 61.89 | C |
| ATOM | 6896 | C | SER | L | 203 | 50.625 | 38.065 | 17.466 | 1.00 | 70.21 | C |
| ATOM | 6897 | O | SER | L | 203 | 51.813 | 37.935 | 17.126 | 1.00 | 71.14 | O |
| ATOM | 6898 | CB | SER | L | 203 | 49.746 | 40.375 | 17.234 | 1.00 | 65.21 | C |
| ATOM | 6899 | OG | SER | L | 203 | 48.744 | 40.591 | 18.212 | 1.00 | 77.85 | O |
| ATOM | 6900 | N | SER | L | 204 | 50.085 | 37.455 | 18.530 | 1.00 | 68.60 | N |
| ATOM | 6901 | CA | SER | L | 204 | 50.792 | 36.522 | 19.415 | 1.00 | 69.23 | C |
| ATOM | 6902 | C | SER | L | 204 | 49.734 | 35.634 | 20.114 | 1.00 | 73.37 | C |
| ATOM | 6903 | O | SER | L | 204 | 48.568 | 36.051 | 20.130 | 1.00 | 72.30 | O |
| ATOM | 6904 | CB | SER | L | 204 | 51.635 | 37.296 | 20.444 | 1.00 | 72.60 | C |
| ATOM | 6905 | OG | SER | L | 204 | 50.879 | 37.764 | 21.553 | 1.00 | 79.45 | O |
| ATOM | 6906 | N | PRO | L | 205 | 50.080 | 34.468 | 20.753 | 1.00 | 69.87 | N |
| ATOM | 6907 | CA | PRO | L | 205 | 49.038 | 33.695 | 21.467 | 1.00 | 69.21 | C |
| ATOM | 6908 | C | PRO | L | 205 | 48.295 | 34.542 | 22.492 | 1.00 | 73.08 | C |
| ATOM | 6909 | O | PRO | L | 205 | 48.921 | 35.281 | 23.257 | 1.00 | 73.09 | O |
| ATOM | 6910 | CB | PRO | L | 205 | 49.798 | 32.530 | 22.113 | 1.00 | 70.39 | C |
| ATOM | 6911 | CG | PRO | L | 205 | 51.226 | 32.887 | 22.016 | 1.00 | 74.78 | C |
| ATOM | 6912 | CD | PRO | L | 205 | 51.386 | 33.785 | 20.831 | 1.00 | 70.76 | C |
| ATOM | 6913 | N | VAL | L | 206 | 46.957 | 34.516 | 22.408 | 1.00 | 69.29 | N |
| ATOM | 6914 | CA | VAL | L | 206 | 46.039 | 35.257 | 23.264 | 1.00 | 69.12 | C |
| ATOM | 6915 | C | VAL | L | 206 | 45.644 | 34.349 | 24.433 | 1.00 | 75.87 | C |
| ATOM | 6916 | O | VAL | L | 206 | 45.257 | 33.198 | 24.216 | 1.00 | 76.61 | O |
| ATOM | 6917 | CB | VAL | L | 206 | 44.820 | 35.762 | 22.436 | 1.00 | 72.39 | C |
| ATOM | 6918 | CG1 | VAL | L | 206 | 43.641 | 36.155 | 23.317 | 1.00 | 72.28 | C |
| ATOM | 6919 | CG2 | VAL | L | 206 | 45.213 | 36.917 | 21.535 | 1.00 | 72.10 | C |
| ATOM | 6920 | N | THR | L | 207 | 45.784 | 34.860 | 25.668 | 1.00 | 72.53 | N |
| ATOM | 6921 | CA | THR | L | 207 | 45.426 | 34.143 | 26.888 | 1.00 | 71.57 | C |
| ATOM | 6922 | C | THR | L | 207 | 44.321 | 34.901 | 27.615 | 1.00 | 77.35 | C |
| ATOM | 6923 | O | THR | L | 207 | 44.395 | 36.117 | 27.836 | 1.00 | 78.07 | O |
| ATOM | 6924 | CB | THR | L | 207 | 46.656 | 33.864 | 27.755 | 1.00 | 71.78 | C |
| ATOM | 6925 | OG1 | THR | L | 207 | 47.646 | 33.197 | 26.968 | 1.00 | 72.44 | O |
| ATOM | 6926 | CG2 | THR | L | 207 | 46.334 | 33.032 | 28.987 | 1.00 | 67.86 | C |
| ATOM | 6927 | N | LYS | L | 208 | 43.276 | 34.169 | 27.944 | 1.00 | 73.65 | N |
| ATOM | 6928 | CA | LYS | L | 208 | 42.134 | 34.683 | 28.672 | 1.00 | 72.94 | C |
| ATOM | 6929 | C | LYS | L | 208 | 42.028 | 33.790 | 29.892 | 1.00 | 79.06 | C |
| ATOM | 6930 | O | LYS | L | 208 | 42.079 | 32.552 | 29.787 | 1.00 | 77.91 | O |
| ATOM | 6931 | CB | LYS | L | 208 | 40.859 | 34.722 | 27.806 | 1.00 | 72.93 | C |
| ATOM | 6932 | CG | LYS | L | 208 | 40.998 | 35.673 | 26.614 | 1.00 | 74.54 | C |
| ATOM | 6933 | CD | LYS | L | 208 | 39.909 | 36.710 | 26.593 | 1.00 | 83.24 | C |
| ATOM | 6934 | CE | LYS | L | 208 | 40.299 | 37.919 | 25.792 | 1.00 | 92.83 | C |
| ATOM | 6935 | NZ | LYS | L | 208 | 39.329 | 39.026 | 25.995 | 1.00 | 101.06 | N |
| ATOM | 6936 | N | SER | L | 209 | 42.039 | 34.434 | 31.064 | 1.00 | 77.32 | N |
| ATOM | 6937 | CA | SER | L | 209 | 42.032 | 33.708 | 32.317 | 1.00 | 77.31 | C |
| ATOM | 6938 | C | SER | L | 209 | 41.144 | 34.309 | 33.392 | 1.00 | 80.63 | C |
| ATOM | 6939 | O | SER | L | 209 | 40.551 | 35.377 | 33.229 | 1.00 | 79.17 | O |
| ATOM | 6940 | CB | SER | L | 209 | 43.460 | 33.533 | 32.830 | 1.00 | 81.70 | C |
| ATOM | 6941 | OG | SER | L | 209 | 43.857 | 34.513 | 33.775 | 1.00 | 95.27 | O |
| ATOM | 6942 | N | PHE | L | 210 | 41.071 | 33.586 | 34.506 | 1.00 | 79.14 | N |
| ATOM | 6943 | CA | PHE | L | 210 | 40.348 | 33.941 | 35.716 | 1.00 | 79.97 | C |
| ATOM | 6944 | C | PHE | L | 210 | 41.005 | 33.288 | 36.949 | 1.00 | 84.05 | C |
| ATOM | 6945 | O | PHE | L | 210 | 41.834 | 32.373 | 36.838 | 1.00 | 81.01 | O |
| ATOM | 6946 | CB | PHE | L | 210 | 38.829 | 33.612 | 35.614 | 1.00 | 82.01 | C |
| ATOM | 6947 | CG | PHE | L | 210 | 38.447 | 32.145 | 35.703 | 1.00 | 84.12 | C |
| ATOM | 6948 | CD1 | PHE | L | 210 | 38.337 | 31.509 | 36.937 | 1.00 | 87.68 | C |
| ATOM | 6949 | CD2 | PHE | L | 210 | 38.152 | 31.416 | 34.559 | 1.00 | 86.61 | C |
| ATOM | 6950 | CE1 | PHE | L | 210 | 37.985 | 30.162 | 37.017 | 1.00 | 88.82 | C |
| ATOM | 6951 | CE2 | PHE | L | 210 | 37.793 | 30.076 | 34.643 | 1.00 | 89.57 | C |
| ATOM | 6952 | CZ | PHE | L | 210 | 37.704 | 29.458 | 35.870 | 1.00 | 87.97 | C |
| ATOM | 6953 | N | ASN | L | 211 | 40.619 | 33.805 | 38.115 | 1.00 | 83.58 | N |
| ATOM | 6954 | CA | ASN | L | 211 | 40.987 | 33.364 | 39.448 | 1.00 | 84.77 | C |
| ATOM | 6955 | C | ASN | L | 211 | 39.637 | 33.266 | 40.144 | 1.00 | 92.29 | C |
| ATOM | 6956 | O | ASN | L | 211 | 38.712 | 33.998 | 39.770 | 1.00 | 92.16 | O |
| ATOM | 6957 | CB | ASN | L | 211 | 41.881 | 34.400 | 40.125 | 1.00 | 87.58 | C |
| ATOM | 6958 | CG | ASN | L | 211 | 43.122 | 34.753 | 39.327 | 1.00 | 121.75 | C |
| ATOM | 6959 | OD1 | ASN | L | 211 | 44.135 | 34.041 | 39.342 | 1.00 | 117.29 | O |
| ATOM | 6960 | ND2 | ASN | L | 211 | 43.061 | 35.857 | 38.596 | 1.00 | 114.95 | N |
| ATOM | 6961 | N | ARG | L | 212 | 39.500 | 32.355 | 41.119 | 1.00 | 91.14 | N |
| ATOM | 6962 | CA | ARG | L | 212 | 38.229 | 32.101 | 41.816 | 1.00 | 91.19 | C |
| ATOM | 6963 | C | ARG | L | 212 | 37.691 | 33.253 | 42.736 | 1.00 | 95.54 | C |

TABLE 1-continued

Three-dimensional crystal coordinate for anti-TcdB antibody beziotoxumab Fab –C. difficile toxin B (TcdB$^{(1834-2101)}$) complex.

| ATOM | 6964 | O | ARG | L | 212 | 37.631 | 33.105 | 43.954 | 1.00 | 95.00 | O |
|------|------|------|-----|---|-----|--------|--------|--------|------|--------|---|
| ATOM | 6965 | CB | ARG | L | 212 | 38.334 | 30.797 | 42.584 | 1.00 | 90.86 | C |
| ATOM | 6966 | CG | ARG | L | 212 | 38.161 | 29.595 | 41.676 | 1.00 | 98.37 | C |
| ATOM | 6967 | CD | ARG | L | 212 | 39.366 | 28.677 | 41.671 | 1.00 | 105.60 | C |
| ATOM | 6968 | NE | ARG | L | 212 | 39.908 | 28.394 | 43.007 | 1.00 | 110.08 | N |
| ATOM | 6969 | CZ | ARG | L | 212 | 39.338 | 27.611 | 43.920 | 1.00 | 114.15 | C |
| ATOM | 6970 | NH1 | ARG | L | 212 | 38.151 | 27.065 | 43.687 | 1.00 | 100.69 | N |
| ATOM | 6971 | NH2 | ARG | L | 212 | 39.926 | 27.413 | 45.092 | 1.00 | 91.15 | N |
| ATOM | 6972 | N | GLY | L | 213 | 37.213 | 34.333 | 42.113 | 1.00 | 92.58 | N |
| ATOM | 6973 | CA | GLY | L | 213 | 36.641 | 35.501 | 42.776 | 1.00 | 106.58 | C |
| ATOM | 6974 | C | GLY | L | 213 | 35.954 | 36.431 | 41.797 | 1.00 | 108.15 | C |
| ATOM | 6975 | O | GLY | L | 213 | 36.505 | 36.749 | 40.742 | 1.00 | 68.79 | O |
| TER | 6976 | | GLY | L | 213 | | | | | | |
| ATOM | 6977 | N | GLU | M | 1 | 20.740 | −42.473 | 42.489 | 1.00 | 109.36 | N |
| ATOM | 6978 | CA | GLU | M | 1 | 20.894 | −42.340 | 41.041 | 1.00 | 109.00 | C |
| ATOM | 6979 | C | GLU | M | 1 | 22.082 | −41.418 | 40.663 | 1.00 | 110.75 | C |
| ATOM | 6980 | O | GLU | M | 1 | 22.995 | −41.225 | 41.478 | 1.00 | 110.89 | O |
| ATOM | 6981 | CB | GLU | M | 1 | 19.562 | −41.916 | 40.364 | 1.00 | 110.65 | C |
| ATOM | 6982 | CG | GLU | M | 1 | 18.878 | −40.704 | 40.988 | 1.00 | 124.03 | C |
| ATOM | 6983 | CD | GLU | M | 1 | 18.721 | −39.477 | 40.106 | 1.00 | 146.85 | C |
| ATOM | 6984 | OE1 | GLU | M | 1 | 18.381 | −39.639 | 38.911 | 1.00 | 130.26 | O |
| ATOM | 6985 | OE2 | GLU | M | 1 | 18.897 | −38.348 | 40.622 | 1.00 | 144.32 | O |
| ATOM | 6986 | N | ILE | M | 2 | 22.075 | −40.890 | 39.418 | 1.00 | 104.17 | N |
| ATOM | 6987 | CA | ILE | M | 2 | 23.096 | −40.011 | 38.833 | 1.00 | 102.39 | C |
| ATOM | 6988 | C | ILE | M | 2 | 22.924 | −38.593 | 39.388 | 1.00 | 101.87 | C |
| ATOM | 6989 | O | ILE | M | 2 | 21.828 | −38.036 | 39.306 | 1.00 | 101.66 | O |
| ATOM | 6990 | CB | ILE | M | 2 | 23.049 | −40.023 | 37.271 | 1.00 | 105.84 | C |
| ATOM | 6991 | CG1 | ILE | M | 2 | 22.426 | −41.327 | 36.666 | 1.00 | 106.84 | C |
| ATOM | 6992 | CG2 | ILE | M | 2 | 24.415 | −39.748 | 36.686 | 1.00 | 105.75 | C |
| ATOM | 6993 | CD1 | ILE | M | 2 | 20.802 | −41.332 | 36.520 | 1.00 | 112.23 | C |
| ATOM | 6994 | N | VAL | M | 3 | 23.979 | −38.019 | 39.992 | 1.00 | 94.99 | N |
| ATOM | 6995 | CA | VAL | M | 3 | 23.877 | −36.670 | 40.569 | 1.00 | 93.13 | C |
| ATOM | 6996 | C | VAL | M | 3 | 24.926 | −35.747 | 39.967 | 1.00 | 92.30 | C |
| ATOM | 6997 | O | VAL | M | 3 | 26.121 | −36.038 | 40.031 | 1.00 | 92.23 | O |
| ATOM | 6998 | CB | VAL | M | 3 | 23.869 | −36.648 | 42.127 | 1.00 | 96.75 | C |
| ATOM | 6999 | CG1 | VAL | M | 3 | 23.683 | −35.229 | 42.662 | 1.00 | 96.56 | C |
| ATOM | 7000 | CG2 | VAL | M | 3 | 22.787 | −37.567 | 42.690 | 1.00 | 96.39 | C |
| ATOM | 7001 | N | LEU | M | 4 | 24.465 | −34.641 | 39.382 | 1.00 | 85.62 | N |
| ATOM | 7002 | CA | LEU | M | 4 | 25.331 | −33.664 | 38.742 | 1.00 | 84.86 | C |
| ATOM | 7003 | C | LEU | M | 4 | 25.594 | −32.477 | 39.653 | 1.00 | 87.43 | C |
| ATOM | 7004 | O | LEU | M | 4 | 24.681 | −31.715 | 39.991 | 1.00 | 86.43 | O |
| ATOM | 7005 | CB | LEU | M | 4 | 24.788 | −33.226 | 37.360 | 1.00 | 84.52 | C |
| ATOM | 7006 | CG | LEU | M | 4 | 24.569 | −34.326 | 36.315 | 1.00 | 87.66 | C |
| ATOM | 7007 | CD1 | LEU | M | 4 | 23.701 | −33.832 | 35.212 | 1.00 | 87.30 | C |
| ATOM | 7008 | CD2 | LEU | M | 4 | 25.873 | −34.819 | 35.745 | 1.00 | 88.72 | C |
| ATOM | 7009 | N | THR | M | 5 | 26.859 | −32.349 | 40.059 | 1.00 | 83.10 | N |
| ATOM | 7010 | CA | THR | M | 5 | 27.340 | −31.305 | 40.949 | 1.00 | 81.92 | C |
| ATOM | 7011 | C | THR | M | 5 | 28.238 | −30.375 | 40.162 | 1.00 | 83.23 | C |
| ATOM | 7012 | O | THR | M | 5 | 29.279 | −30.802 | 39.668 | 1.00 | 82.46 | O |
| ATOM | 7013 | CB | THR | M | 5 | 27.950 | −31.929 | 42.242 | 1.00 | 90.79 | C |
| ATOM | 7014 | OG1 | THR | M | 5 | 28.160 | −33.344 | 42.068 | 1.00 | 87.12 | O |
| ATOM | 7015 | CG2 | THR | M | 5 | 27.038 | −31.741 | 43.460 | 1.00 | 89.36 | C |
| ATOM | 7016 | N | GLN | M | 6 | 27.782 | −29.130 | 39.965 | 1.00 | 79.61 | N |
| ATOM | 7017 | CA | GLN | M | 6 | 28.488 | −28.077 | 39.222 | 1.00 | 79.93 | C |
| ATOM | 7018 | C | GLN | M | 6 | 29.291 | −27.158 | 40.139 | 1.00 | 88.34 | C |
| ATOM | 7019 | O | GLN | M | 6 | 28.852 | −26.842 | 41.237 | 1.00 | 89.23 | O |
| ATOM | 7020 | CB | GLN | M | 6 | 27.507 | −27.208 | 38.428 | 1.00 | 80.47 | C |
| ATOM | 7021 | CG | GLN | M | 6 | 26.898 | −27.886 | 37.222 | 1.00 | 73.52 | C |
| ATOM | 7022 | CD | GLN | M | 6 | 26.157 | −26.885 | 36.386 | 1.00 | 85.55 | C |
| ATOM | 7023 | OE1 | GLN | M | 6 | 24.924 | −26.881 | 36.349 | 1.00 | 71.00 | O |
| ATOM | 7024 | NE2 | GLN | M | 6 | 26.900 | −26.001 | 35.703 | 1.00 | 82.93 | N |
| ATOM | 7025 | N | SER | M | 7 | 30.441 | −26.683 | 39.666 | 1.00 | 86.67 | N |
| ATOM | 7026 | CA | SER | M | 7 | 31.301 | −25.768 | 40.419 | 1.00 | 86.03 | C |
| ATOM | 7027 | C | SER | M | 7 | 31.875 | −24.703 | 39.471 | 1.00 | 88.67 | C |
| ATOM | 7028 | O | SER | M | 7 | 32.178 | −25.039 | 38.325 | 1.00 | 87.56 | O |
| ATOM | 7029 | CB | SER | M | 7 | 32.409 | −26.532 | 41.138 | 1.00 | 89.10 | C |
| ATOM | 7030 | OG | SER | M | 7 | 33.219 | −27.271 | 40.239 | 1.00 | 97.65 | O |
| ATOM | 7031 | N | PRO | M | 8 | 31.963 | −23.407 | 39.848 | 1.00 | 84.59 | N |
| ATOM | 7032 | CA | PRO | M | 8 | 31.736 | −22.823 | 41.183 | 1.00 | 83.77 | C |
| ATOM | 7033 | C | PRO | M | 8 | 30.297 | −22.861 | 41.722 | 1.00 | 86.46 | C |
| ATOM | 7034 | O | PRO | M | 8 | 29.979 | −23.612 | 42.641 | 1.00 | 86.52 | O |
| ATOM | 7035 | CB | PRO | M | 8 | 32.264 | −21.379 | 41.032 | 1.00 | 85.25 | C |
| ATOM | 7036 | CG | PRO | M | 8 | 32.282 | −21.095 | 39.562 | 1.00 | 89.48 | C |
| ATOM | 7037 | CD | PRO | M | 8 | 32.549 | −22.417 | 38.914 | 1.00 | 85.51 | C |
| ATOM | 7038 | N | GLY | M | 9 | 29.467 | −22.013 | 41.172 | 1.00 | 81.88 | N |
| ATOM | 7039 | CA | GLY | M | 9 | 28.107 | −21.764 | 41.604 | 1.00 | 81.92 | C |
| ATOM | 7040 | C | GLY | M | 9 | 27.873 | −20.336 | 41.188 | 1.00 | 86.70 | C |

TABLE 1-continued

Three-dimensional crystal coordinate for anti-TcdB antibody beziotoxumab Fab –C. difficile toxin B (TcdB$^{(1834-2101)}$) complex.

| ATOM | 7041 | O | GLY | M | 9 | 26.759 | −19.958 | 40.804 | 1.00 | 87.35 | O |
|------|------|-----|-----|---|----|--------|---------|--------|------|-------|---|
| ATOM | 7042 | N | THR | M | 10 | 28.987 | −19.550 | 41.235 | 1.00 | 81.97 | N |
| ATOM | 7043 | CA | THR | M | 10 | 29.142 | −18.172 | 40.765 | 1.00 | 80.78 | C |
| ATOM | 7044 | C | THR | M | 10 | 30.556 | −17.945 | 40.274 | 1.00 | 82.37 | C |
| ATOM | 7045 | O | THR | M | 10 | 31.530 | −18.253 | 40.963 | 1.00 | 81.25 | O |
| ATOM | 7046 | CB | THR | M | 10 | 28.692 | −17.101 | 41.751 | 1.00 | 84.97 | C |
| ATOM | 7047 | OG1 | THR | M | 10 | 27.620 | −17.596 | 42.554 | 1.00 | 85.61 | O |
| ATOM | 7048 | CG2 | THR | M | 10 | 28.283 | −15.803 | 41.036 | 1.00 | 80.10 | C |
| ATOM | 7049 | N | LEU | M | 11 | 30.649 | −17.396 | 39.078 | 1.00 | 78.41 | N |
| ATOM | 7050 | CA | LEU | M | 11 | 31.906 | −17.126 | 38.427 | 1.00 | 78.49 | C |
| ATOM | 7051 | C | LEU | M | 11 | 31.871 | −15.684 | 37.998 | 1.00 | 82.50 | C |
| ATOM | 7052 | O | LEU | M | 11 | 31.060 | −15.311 | 37.151 | 1.00 | 82.45 | O |
| ATOM | 7053 | CB | LEU | M | 11 | 32.051 | −18.065 | 37.221 | 1.00 | 78.77 | C |
| ATOM | 7054 | CG | LEU | M | 11 | 33.402 | −18.148 | 36.517 | 1.00 | 83.66 | C |
| ATOM | 7055 | CD1 | LEU | M | 11 | 34.494 | −18.604 | 37.457 | 1.00 | 83.97 | C |
| ATOM | 7056 | CD2 | LEU | M | 11 | 33.331 | −19.128 | 35.359 | 1.00 | 86.96 | C |
| ATOM | 7057 | N | SER | M | 12 | 32.690 | −14.857 | 38.658 | 1.00 | 78.46 | N |
| ATOM | 7058 | CA | SER | M | 12 | 32.800 | −13.428 | 38.382 | 1.00 | 77.03 | C |
| ATOM | 7059 | C | SER | M | 12 | 34.056 | −13.203 | 37.538 | 1.00 | 79.52 | C |
| ATOM | 7060 | O | SER | M | 12 | 35.163 | −13.492 | 37.979 | 1.00 | 78.87 | O |
| ATOM | 7061 | CB | SER | M | 12 | 32.841 | −12.626 | 39.682 | 1.00 | 76.93 | C |
| ATOM | 7062 | OG | SER | M | 12 | 31.699 | −12.921 | 40.468 | 1.00 | 74.57 | O |
| ATOM | 7063 | N | LEU | M | 13 | 33.860 | −12.809 | 36.288 | 1.00 | 76.26 | N |
| ATOM | 7064 | CA | LEU | M | 13 | 34.912 | −12.540 | 35.306 | 1.00 | 76.96 | C |
| ATOM | 7065 | C | LEU | M | 13 | 34.506 | −11.316 | 34.491 | 1.00 | 81.23 | C |
| ATOM | 7066 | O | LEU | M | 13 | 33.327 | −10.994 | 34.404 | 1.00 | 80.24 | O |
| ATOM | 7067 | CB | LEU | M | 13 | 35.123 | −13.736 | 34.351 | 1.00 | 77.35 | C |
| ATOM | 7068 | CG | LEU | M | 13 | 35.281 | −15.155 | 34.935 | 1.00 | 82.36 | C |
| ATOM | 7069 | CD1 | LEU | M | 13 | 35.102 | −16.175 | 33.868 | 1.00 | 82.17 | C |
| ATOM | 7070 | CD2 | LEU | M | 13 | 36.642 | −15.367 | 35.587 | 1.00 | 85.57 | C |
| ATOM | 7071 | N | SER | M | 14 | 35.466 | −10.635 | 33.901 | 1.00 | 80.06 | N |
| ATOM | 7072 | CA | SER | M | 14 | 35.195 | −9.433 | 33.110 | 1.00 | 81.06 | C |
| ATOM | 7073 | C | SER | M | 14 | 34.999 | −9.777 | 31.620 | 1.00 | 86.39 | C |
| ATOM | 7074 | O | SER | M | 14 | 35.542 | −10.790 | 31.171 | 1.00 | 86.28 | O |
| ATOM | 7075 | CB | SER | M | 14 | 36.325 | −8.413 | 33.297 | 1.00 | 85.12 | C |
| ATOM | 7076 | OG | SER | M | 14 | 37.486 | −8.974 | 33.888 | 1.00 | 94.25 | O |
| ATOM | 7077 | N | PRO | M | 15 | 34.253 | −8.964 | 30.824 | 1.00 | 83.07 | N |
| ATOM | 7078 | CA | PRO | M | 15 | 34.113 | −9.276 | 29.386 | 1.00 | 83.23 | C |
| ATOM | 7079 | C | PRO | M | 15 | 35.468 | −9.398 | 28.662 | 1.00 | 88.88 | C |
| ATOM | 7080 | O | PRO | M | 15 | 36.391 | −8.635 | 28.939 | 1.00 | 89.33 | O |
| ATOM | 7081 | CB | PRO | M | 15 | 33.279 | −8.103 | 28.853 | 1.00 | 84.83 | C |
| ATOM | 7082 | CG | PRO | M | 15 | 32.551 | −7.575 | 30.047 | 1.00 | 88.71 | C |
| ATOM | 7083 | CD | PRO | M | 15 | 33.524 | −7.724 | 31.172 | 1.00 | 84.26 | C |
| ATOM | 7084 | N | GLY | M | 16 | 35.583 | −10.383 | 27.780 | 1.00 | 85.84 | N |
| ATOM | 7085 | CA | GLY | M | 16 | 36.804 | −10.697 | 27.037 | 1.00 | 84.99 | C |
| ATOM | 7086 | C | GLY | M | 16 | 37.590 | −11.846 | 27.642 | 1.00 | 87.67 | C |
| ATOM | 7087 | O | GLY | M | 16 | 38.390 | −12.479 | 26.948 | 1.00 | 88.13 | O |
| ATOM | 7088 | N | GLU | M | 17 | 37.347 | −12.135 | 28.933 | 1.00 | 82.44 | N |
| ATOM | 7089 | CA | GLU | M | 17 | 38.010 | −13.193 | 29.694 | 1.00 | 81.88 | C |
| ATOM | 7090 | C | GLU | M | 17 | 37.535 | −14.604 | 29.354 | 1.00 | 85.81 | C |
| ATOM | 7091 | O | GLU | M | 17 | 36.434 | −14.793 | 28.828 | 1.00 | 86.69 | O |
| ATOM | 7092 | CB | GLU | M | 17 | 37.814 | −12.941 | 31.183 | 1.00 | 83.34 | C |
| ATOM | 7093 | CG | GLU | M | 17 | 39.102 | −12.767 | 31.963 | 1.00 | 94.74 | C |
| ATOM | 7094 | CD | GLU | M | 17 | 38.880 | −12.867 | 33.457 | 1.00 | 114.57 | C |
| ATOM | 7095 | OE1 | GLU | M | 17 | 38.532 | −11.839 | 34.083 | 1.00 | 101.36 | O |
| ATOM | 7096 | OE2 | GLU | M | 17 | 39.055 | −13.980 | 34.004 | 1.00 | 112.29 | O |
| ATOM | 7097 | N | ARG | M | 18 | 38.368 | −15.605 | 29.656 | 1.00 | 80.93 | N |
| ATOM | 7098 | CA | ARG | M | 18 | 38.037 | −17.010 | 29.429 | 1.00 | 78.92 | C |
| ATOM | 7099 | C | ARG | M | 18 | 37.277 | −17.586 | 30.621 | 1.00 | 80.23 | C |
| ATOM | 7100 | O | ARG | M | 18 | 37.731 | −17.475 | 31.763 | 1.00 | 79.01 | O |
| ATOM | 7101 | CB | ARG | M | 18 | 39.298 | −17.844 | 29.144 | 1.00 | 76.78 | C |
| ATOM | 7102 | CG | ARG | M | 18 | 38.983 | −19.069 | 28.314 | 1.00 | 87.41 | C |
| ATOM | 7103 | CD | ARG | M | 18 | 40.215 | −19.764 | 27.796 | 1.00 | 90.67 | C |
| ATOM | 7104 | NE | ARG | M | 18 | 40.612 | −20.835 | 28.705 | 1.00 | 95.47 | N |
| ATOM | 7105 | CZ | ARG | M | 18 | 40.715 | −22.114 | 28.360 | 1.00 | 102.41 | C |
| ATOM | 7106 | NH1 | ARG | M | 18 | 40.452 | −22.496 | 27.115 | 1.00 | 85.39 | N |
| ATOM | 7107 | NH2 | ARG | M | 18 | 41.079 | −23.024 | 29.260 | 1.00 | 81.19 | N |
| ATOM | 7108 | N | ALA | M | 19 | 36.122 | −18.218 | 30.348 | 1.00 | 75.55 | N |
| ATOM | 7109 | CA | ALA | M | 19 | 35.290 | −18.874 | 31.367 | 1.00 | 73.77 | C |
| ATOM | 7110 | C | ALA | M | 19 | 35.384 | −20.372 | 31.248 | 1.00 | 75.13 | C |
| ATOM | 7111 | O | ALA | M | 19 | 35.306 | −20.900 | 30.142 | 1.00 | 73.92 | O |
| ATOM | 7112 | CB | ALA | M | 19 | 33.843 | −18.438 | 31.237 | 1.00 | 74.13 | C |
| ATOM | 7113 | N | THR | M | 20 | 35.570 | −21.043 | 32.390 | 1.00 | 71.16 | N |
| ATOM | 7114 | CA | THR | M | 20 | 35.669 | −22.494 | 32.534 | 1.00 | 71.02 | C |
| ATOM | 7115 | C | THR | M | 20 | 34.705 | −22.906 | 33.647 | 1.00 | 76.77 | C |
| ATOM | 7116 | O | THR | M | 20 | 34.902 | −22.528 | 34.809 | 1.00 | 75.13 | O |
| ATOM | 7117 | CB | THR | M | 20 | 37.132 | −22.911 | 32.780 | 1.00 | 75.37 | C |

TABLE 1-continued

Three-dimensional crystal coordinate for anti-TcdB antibody beziotoxumab Fab – *C. difficile* toxin B (TcdB$^{(1834\text{-}2101)}$) complex.

| | | | | | | | | | | |
|---|---|---|---|---|---|---|---|---|---|---|
| ATOM | 7118 | OG1 | THR | M | 20 | 37.850 | −22.813 | 31.551 | 1.00 | 80.96 O |
| ATOM | 7119 | CG2 | THR | M | 20 | 37.271 | −24.330 | 33.334 | 1.00 | 69.67 C |
| ATOM | 7120 | N | LEU | M | 21 | 33.634 | −23.640 | 33.262 | 1.00 | 75.20 N |
| ATOM | 7121 | CA | LEU | M | 21 | 32.557 | −24.138 | 34.135 | 1.00 | 74.83 C |
| ATOM | 7122 | C | LEU | M | 21 | 32.681 | −25.641 | 34.233 | 1.00 | 80.69 C |
| ATOM | 7123 | O | LEU | M | 21 | 32.894 | −26.292 | 33.218 | 1.00 | 79.75 O |
| ATOM | 7124 | CB | LEU | M | 21 | 31.185 | −23.804 | 33.532 | 1.00 | 74.33 C |
| ATOM | 7125 | CG | LEU | M | 21 | 30.684 | −22.369 | 33.601 | 1.00 | 78.00 C |
| ATOM | 7126 | CD1 | LEU | M | 21 | 31.184 | −21.528 | 32.423 | 1.00 | 77.70 C |
| ATOM | 7127 | CD2 | LEU | M | 21 | 29.221 | −22.364 | 33.517 | 1.00 | 80.33 C |
| ATOM | 7128 | N | SER | M | 22 | 32.538 | −26.191 | 35.439 | 1.00 | 80.99 N |
| ATOM | 7129 | CA | SER | M | 22 | 32.667 | −27.623 | 35.717 | 1.00 | 82.67 C |
| ATOM | 7130 | C | SER | M | 22 | 31.338 | −28.302 | 36.025 | 1.00 | 87.87 C |
| ATOM | 7131 | O | SER | M | 22 | 30.410 | −27.663 | 36.527 | 1.00 | 88.94 O |
| ATOM | 7132 | CB | SER | M | 22 | 33.648 | −27.856 | 36.868 | 1.00 | 89.27 C |
| ATOM | 7133 | OG | SER | M | 22 | 33.588 | −29.174 | 37.401 | 1.00 | 102.72 O |
| ATOM | 7134 | N | CYS | M | 23 | 31.280 | −29.613 | 35.735 | 1.00 | 83.37 N |
| ATOM | 7135 | CA | CYS | M | 23 | 30.162 | −30.518 | 35.950 | 1.00 | 82.62 C |
| ATOM | 7136 | C | CYS | M | 23 | 30.785 | −31.848 | 36.327 | 1.00 | 87.91 C |
| ATOM | 7137 | O | CYS | M | 23 | 31.514 | −32.439 | 35.527 | 1.00 | 87.54 O |
| ATOM | 7138 | CB | CYS | M | 23 | 29.308 | −30.634 | 34.687 | 1.00 | 82.16 C |
| ATOM | 7139 | SG | CYS | M | 23 | 27.815 | −31.662 | 34.863 | 1.00 | 85.53 S |
| ATOM | 7140 | N | ARG | M | 24 | 30.571 | −32.268 | 37.573 | 1.00 | 85.90 N |
| ATOM | 7141 | CA | ARG | M | 24 | 31.072 | −33.541 | 38.065 | 1.00 | 86.95 C |
| ATOM | 7142 | C | ARG | M | 24 | 29.880 | −34.451 | 38.363 | 1.00 | 91.30 C |
| ATOM | 7143 | O | ARG | M | 24 | 28.900 | −34.018 | 38.978 | 1.00 | 91.04 O |
| ATOM | 7144 | CB | ARG | M | 24 | 32.003 | −33.369 | 39.287 | 1.00 | 90.73 C |
| ATOM | 7145 | CG | ARG | M | 24 | 32.861 | −34.612 | 39.563 | 1.00 | 108.13 C |
| ATOM | 7146 | CD | ARG | M | 24 | 33.897 | −34.399 | 40.647 | 1.00 | 125.63 C |
| ATOM | 7147 | NE | ARG | M | 24 | 35.236 | −34.156 | 40.104 | 1.00 | 139.68 N |
| ATOM | 7148 | CZ | ARG | M | 24 | 36.340 | −34.053 | 40.841 | 1.00 | 159.27 C |
| ATOM | 7149 | NH1 | ARG | M | 24 | 36.281 | −34.186 | 42.162 | 1.00 | 149.63 N |
| ATOM | 7150 | NH2 | ARG | M | 24 | 37.514 | −33.830 | 40.262 | 1.00 | 146.24 N |
| ATOM | 7151 | N | ALA | M | 25 | 29.948 | −35.688 | 37.871 | 1.00 | 87.65 N |
| ATOM | 7152 | CA | ALA | M | 25 | 28.905 | −36.686 | 38.036 | 1.00 | 87.67 C |
| ATOM | 7153 | C | ALA | M | 25 | 29.232 | −37.618 | 39.186 | 1.00 | 93.12 C |
| ATOM | 7154 | O | ALA | M | 25 | 30.407 | −37.929 | 39.416 | 1.00 | 93.27 O |
| ATOM | 7155 | CB | ALA | M | 25 | 28.741 | −37.472 | 36.746 | 1.00 | 88.44 C |
| ATOM | 7156 | N | SER | M | 26 | 28.180 | −38.076 | 39.895 | 1.00 | 90.49 N |
| ATOM | 7157 | CA | SER | M | 26 | 28.241 | −38.985 | 41.044 | 1.00 | 90.94 C |
| ATOM | 7158 | C | SER | M | 26 | 28.793 | −40.370 | 40.665 | 1.00 | 96.44 C |
| ATOM | 7159 | O | SER | M | 26 | 29.290 | −41.097 | 41.528 | 1.00 | 97.79 O |
| ATOM | 7160 | CB | SER | M | 26 | 26.859 | −39.122 | 41.680 | 1.00 | 94.58 C |
| ATOM | 7161 | OG | SER | M | 26 | 25.973 | −39.820 | 40.823 | 1.00 | 105.57 O |
| ATOM | 7162 | N | GLN | M | 27 | 28.683 | −40.726 | 39.379 | 1.00 | 92.34 N |
| ATOM | 7163 | CA | GLN | M | 27 | 29.154 | −41.977 | 38.785 | 1.00 | 92.48 C |
| ATOM | 7164 | C | GLN | M | 27 | 29.487 | −41.729 | 37.315 | 1.00 | 96.55 C |
| ATOM | 7165 | O | GLN | M | 27 | 29.010 | −40.749 | 36.747 | 1.00 | 96.64 O |
| ATOM | 7166 | CB | GLN | M | 27 | 28.104 | −43.100 | 38.933 | 1.00 | 93.91 C |
| ATOM | 7167 | CG | GLN | M | 27 | 26.775 | −42.841 | 38.222 | 1.00 | 105.35 C |
| ATOM | 7168 | CD | GLN | M | 27 | 25.645 | −43.622 | 38.834 | 1.00 | 117.21 C |
| ATOM | 7169 | OE1 | GLN | M | 27 | 25.306 | −44.710 | 38.378 | 1.00 | 108.04 O |
| ATOM | 7170 | NE2 | GLN | M | 27 | 25.036 | −43.079 | 39.880 | 1.00 | 111.22 N |
| ATOM | 7171 | N | SER | M | 28 | 30.305 | −42.605 | 36.702 | 1.00 | 92.47 N |
| ATOM | 7172 | CA | SER | M | 28 | 30.691 | −42.520 | 35.285 | 1.00 | 91.75 C |
| ATOM | 7173 | C | SER | M | 28 | 29.432 | −42.507 | 34.384 | 1.00 | 93.80 C |
| ATOM | 7174 | O | SER | M | 28 | 28.473 | −43.244 | 34.656 | 1.00 | 92.75 O |
| ATOM | 7175 | CB | SER | M | 28 | 31.626 | −43.668 | 34.916 | 1.00 | 95.68 C |
| ATOM | 7176 | OG | SER | M | 28 | 32.129 | −43.505 | 33.600 | 1.00 | 104.65 O |
| ATOM | 7177 | N | VAL | M | 29 | 29.431 | −41.640 | 33.336 | 1.00 | 88.62 N |
| ATOM | 7178 | CA | VAL | M | 29 | 28.316 | −41.348 | 32.413 | 1.00 | 87.06 C |
| ATOM | 7179 | C | VAL | M | 29 | 28.757 | −41.371 | 30.939 | 1.00 | 89.62 C |
| ATOM | 7180 | O | VAL | M | 29 | 29.913 | −41.040 | 30.657 | 1.00 | 91.46 O |
| ATOM | 7181 | CB | VAL | M | 29 | 27.770 | −39.946 | 32.825 | 1.00 | 90.78 C |
| ATOM | 7182 | CG1 | VAL | M | 29 | 27.088 | −39.189 | 31.687 | 1.00 | 90.47 C |
| ATOM | 7183 | CG2 | VAL | M | 29 | 26.854 | −40.057 | 34.028 | 1.00 | 90.85 C |
| ATOM | 7184 | N | SER | M | 30 | 27.840 | −41.723 | 29.996 | 1.00 | 82.54 N |
| ATOM | 7185 | CA | SER | M | 30 | 28.143 | −41.671 | 28.558 | 1.00 | 81.04 C |
| ATOM | 7186 | C | SER | M | 30 | 28.281 | −40.209 | 28.120 | 1.00 | 84.28 C |
| ATOM | 7187 | O | SER | M | 30 | 27.524 | −39.344 | 28.578 | 1.00 | 84.52 O |
| ATOM | 7188 | CB | SER | M | 30 | 27.065 | −42.357 | 27.730 | 1.00 | 83.64 C |
| ATOM | 7189 | OG | SER | M | 30 | 27.444 | −42.384 | 26.362 | 1.00 | 92.12 O |
| ATOM | 7190 | N | SER | M | 31 | 29.264 | −39.931 | 27.248 | 1.00 | 79.14 N |
| ATOM | 7191 | CA | SER | M | 31 | 29.500 | −38.583 | 26.737 | 1.00 | 77.74 C |
| ATOM | 7192 | C | SER | M | 31 | 28.386 | −38.183 | 25.803 | 1.00 | 77.68 C |
| ATOM | 7193 | O | SER | M | 31 | 28.145 | −36.996 | 25.638 | 1.00 | 76.29 O |
| ATOM | 7194 | CB | SER | M | 31 | 30.842 | −38.504 | 26.025 | 1.00 | 82.29 C |

TABLE 1-continued

Three-dimensional crystal coordinate for anti-TcdB antibody beziotoxumab
Fab –*C. difficile* toxin B (TcdB$^{(1834-2101)}$) complex.

| ATOM | 7195 | OG | SER | M | 31 | 31.888 | −38.523 | 26.981 | 1.00 | 93.98 | O |
|---|---|---|---|---|---|---|---|---|---|---|---|
| ATOM | 7196 | N | SER | M | 32 | 27.669 | −39.179 | 25.243 | 1.00 | 72.18 | N |
| ATOM | 7197 | CA | SER | M | 32 | 26.556 | −39.007 | 24.313 | 1.00 | 70.62 | C |
| ATOM | 7198 | C | SER | M | 32 | 25.391 | −38.279 | 24.976 | 1.00 | 74.12 | C |
| ATOM | 7199 | O | SER | M | 32 | 24.716 | −37.458 | 24.345 | 1.00 | 74.35 | O |
| ATOM | 7200 | CB | SER | M | 32 | 26.092 | −40.365 | 23.817 | 1.00 | 71.76 | C |
| ATOM | 7201 | OG | SER | M | 32 | 27.183 | −41.134 | 23.340 | 1.00 | 82.23 | O |
| ATOM | 7202 | N | TYR | M | 33 | 25.172 | −38.583 | 26.261 | 1.00 | 68.78 | N |
| ATOM | 7203 | CA | TYR | M | 33 | 24.057 | −38.086 | 27.042 | 1.00 | 67.33 | C |
| ATOM | 7204 | C | TYR | M | 33 | 24.363 | −36.821 | 27.836 | 1.00 | 72.06 | C |
| ATOM | 7205 | O | TYR | M | 33 | 23.474 | −36.329 | 28.539 | 1.00 | 74.01 | O |
| ATOM | 7206 | CB | TYR | M | 33 | 23.508 | −39.216 | 27.932 | 1.00 | 66.94 | C |
| ATOM | 7207 | CG | TYR | M | 33 | 22.923 | −40.346 | 27.106 | 1.00 | 65.96 | C |
| ATOM | 7208 | CD1 | TYR | M | 33 | 21.877 | −40.117 | 26.215 | 1.00 | 67.44 | C |
| ATOM | 7209 | CD2 | TYR | M | 33 | 23.452 | −41.629 | 27.169 | 1.00 | 66.30 | C |
| ATOM | 7210 | CE1 | TYR | M | 33 | 21.359 | −41.141 | 25.418 | 1.00 | 66.28 | C |
| ATOM | 7211 | CE2 | TYR | M | 33 | 22.928 | −42.667 | 26.389 | 1.00 | 67.39 | C |
| ATOM | 7212 | CZ | TYR | M | 33 | 21.884 | −42.414 | 25.508 | 1.00 | 70.35 | C |
| ATOM | 7213 | OH | TYR | M | 33 | 21.386 | −43.403 | 24.696 | 1.00 | 67.62 | O |
| ATOM | 7214 | N | LEU | M | 34 | 25.569 | −36.242 | 27.665 | 1.00 | 66.30 | N |
| ATOM | 7215 | CA | LEU | M | 34 | 25.909 | −34.993 | 28.341 | 1.00 | 64.95 | C |
| ATOM | 7216 | C | LEU | M | 34 | 25.600 | −33.755 | 27.518 | 1.00 | 67.28 | C |
| ATOM | 7217 | O | LEU | M | 34 | 26.126 | −33.592 | 26.413 | 1.00 | 67.41 | O |
| ATOM | 7218 | CB | LEU | M | 34 | 27.343 | −34.922 | 28.877 | 1.00 | 64.67 | C |
| ATOM | 7219 | CG | LEU | M | 34 | 27.445 | −33.857 | 29.982 | 1.00 | 69.67 | C |
| ATOM | 7220 | CD1 | LEU | M | 34 | 27.533 | −34.465 | 31.363 | 1.00 | 70.32 | C |
| ATOM | 7221 | CD2 | LEU | M | 34 | 28.417 | −32.760 | 29.655 | 1.00 | 70.92 | C |
| ATOM | 7222 | N | ALA | M | 35 | 24.794 | −32.850 | 28.104 | 1.00 | 62.26 | N |
| ATOM | 7223 | CA | ALA | M | 35 | 24.406 | −31.586 | 27.493 | 1.00 | 61.37 | C |
| ATOM | 7224 | C | ALA | M | 35 | 24.572 | −30.371 | 28.420 | 1.00 | 63.32 | C |
| ATOM | 7225 | O | ALA | M | 35 | 24.545 | −30.506 | 29.636 | 1.00 | 59.47 | O |
| ATOM | 7226 | CB | ALA | M | 35 | 22.975 | −31.671 | 26.986 | 1.00 | 62.09 | C |
| ATOM | 7227 | N | TRP | M | 36 | 24.738 | −29.184 | 27.820 | 1.00 | 62.83 | N |
| ATOM | 7228 | CA | TRP | M | 36 | 24.858 | −27.918 | 28.532 | 1.00 | 63.95 | C |
| ATOM | 7229 | C | TRP | M | 36 | 23.815 | −26.964 | 27.992 | 1.00 | 66.63 | C |
| ATOM | 7230 | O | TRP | M | 36 | 23.664 | −26.840 | 26.772 | 1.00 | 66.49 | O |
| ATOM | 7231 | CB | TRP | M | 36 | 26.257 | −27.286 | 28.352 | 1.00 | 63.84 | C |
| ATOM | 7232 | CG | TRP | M | 36 | 27.366 | −27.990 | 29.077 | 1.00 | 65.37 | C |
| ATOM | 7233 | CD1 | TRP | M | 36 | 28.124 | −29.030 | 28.617 | 1.00 | 68.23 | C |
| ATOM | 7234 | CD2 | TRP | M | 36 | 27.873 | −27.669 | 30.373 | 1.00 | 65.65 | C |
| ATOM | 7235 | NE1 | TRP | M | 36 | 29.059 | −29.390 | 29.560 | 1.00 | 67.59 | N |
| ATOM | 7236 | CE2 | TRP | M | 36 | 28.917 | −28.579 | 30.655 | 1.00 | 69.44 | C |
| ATOM | 7237 | CE3 | TRP | M | 36 | 27.548 | −26.697 | 31.331 | 1.00 | 67.29 | C |
| ATOM | 7238 | CZ2 | TRP | M | 36 | 29.632 | −28.546 | 31.854 | 1.00 | 69.05 | C |
| ATOM | 7239 | CZ3 | TRP | M | 36 | 28.264 | −26.666 | 32.521 | 1.00 | 68.79 | C |
| ATOM | 7240 | CH2 | TRP | M | 36 | 29.284 | −27.586 | 32.775 | 1.00 | 69.23 | C |
| ATOM | 7241 | N | TYR | M | 37 | 23.111 | −26.276 | 28.909 | 1.00 | 60.69 | N |
| ATOM | 7242 | CA | TYR | M | 37 | 22.075 | −25.287 | 28.605. | 1.00 | 58.76 | C |
| ATOM | 7243 | C | TYR | M | 37 | 22.449 | −23.955 | 29.180 | 1.00 | 61.41 | C |
| ATOM | 7244 | O | TYR | M | 37 | 23.062 | −23.900 | 30.242 | 1.00 | 60.35 | O |
| ATOM | 7245 | CB | TYR | M | 37 | 20.709 | −25.702 | 29.195 | 1.00 | 59.06 | C |
| ATOM | 7246 | CG | TYR | M | 37 | 20.238 | −27.059 | 28.719 | 1.00 | 58.30 | C |
| ATOM | 7247 | CD2 | TYR | M | 37 | 19.422 | −27.183 | 27.592 | 1.00 | 57.96 | C |
| ATOM | 7248 | CD1 | TYR | M | 37 | 20.657 | −28.224 | 29.353 | 1.00 | 59.41 | C |
| ATOM | 7249 | CE2 | TYR | M | 37 | 19.033 | −28.433 | 27.120 | 1.00 | 58.14 | C |
| ATOM | 7250 | CE1 | TYR | M | 37 | 20.304 | −29.477 | 28.870 | 1.00 | 59.20 | C |
| ATOM | 7251 | CZ | TYR | M | 37 | 19.496 | −29.578 | 27.753 | 1.00 | 62.82 | C |
| ATOM | 7252 | OH | TYR | M | 37 | 19.139 | −30.822 | 27.323 | 1.00 | 60.93 | O |
| ATOM | 7253 | N | GLN | M | 38 | 22.046 | −22.882 | 28.496 | 1.00 | 58.94 | N |
| ATOM | 7254 | CA | GLN | M | 38 | 22.215 | −21.498 | 28.924 | 1.00 | 59.80 | C |
| ATOM | 7255 | C | GLN | M | 38 | 20.827 | −20.924 | 29.230 | 1.00 | 65.13 | C |
| ATOM | 7256 | O | GLN | M | 38 | 19.893 | −21.131 | 28.457 | 1.00 | 65.70 | O |
| ATOM | 7257 | CB | GLN | M | 38 | 22.885 | −20.658 | 27.816 | 1.00 | 61.01 | C |
| ATOM | 7258 | CG | GLN | M | 38 | 23.111 | −19.180 | 28.215 | 1.00 | 67.64 | C |
| ATOM | 7259 | CD | GLN | M | 38 | 23.550 | −18.316 | 27.063 | 1.00 | 81.27 | C |
| ATOM | 7260 | OE1 | GLN | M | 38 | 22.874 | −18.197 | 26.040 | 1.00 | 71.43 | O |
| ATOM | 7261 | NE2 | GLN | M | 38 | 24.696 | −17.676 | 27.202 | 1.00 | 79.70 | N |
| ATOM | 7262 | N | GLN | M | 39 | 20.699 | −20.177 | 30.315 | 1.00 | 62.04 | N |
| ATOM | 7263 | CA | GLN | M | 39 | 19.432 | −19.548 | 30.640 | 1.00 | 62.53 | C |
| ATOM | 7264 | C | GLN | M | 39 | 19.651 | −18.102 | 31.015 | 1.00 | 69.37 | C |
| ATOM | 7265 | O | GLN | M | 39 | 20.153 | −17.829 | 32.108 | 1.00 | 68.00 | O |
| ATOM | 7266 | CB | GLN | M | 39 | 18.715 | −20.312 | 31.759 | 1.00 | 63.51 | C |
| ATOM | 7267 | CG | GLN | M | 39 | 17.304 | −19.797 | 31.997 | 1.00 | 71.07 | C |
| ATOM | 7268 | CD | GLN | M | 39 | 16.590 | −20.538 | 33.082 | 1.00 | 81.21 | C |
| ATOM | 7269 | OE1 | GLN | M | 39 | 17.176 | −20.945 | 34.083 | 1.00 | 81.20 | O |
| ATOM | 7270 | NE2 | GLN | M | 39 | 15.301 | −20.691 | 32.931 | 1.00 | 66.53 | N |
| ATOM | 7271 | N | LYS | M | 40 | 19.283 | −17.167 | 30.118 | 1.00 | 69.29 | N |

TABLE 1-continued

Three-dimensional crystal coordinate for anti-TcdB antibody beziotoxumab Fab –C. *difficile* toxin B (TcdB$^{(1834-2101)}$) complex.

| ATOM | 7272 | CA | LYS | M | 40 | 19.391 | −15.727 | 30.416 | 1.00 | 70.48 | C |
|---|---|---|---|---|---|---|---|---|---|---|---|
| ATOM | 7273 | C | LYS | M | 40 | 18.316 | −15.373 | 31.466 | 1.00 | 80.16 | C |
| ATOM | 7274 | O | LYS | M | 40 | 17.333 | −16.102 | 31.558 | 1.00 | 79.45 | O |
| ATOM | 7275 | CB | LYS | M | 40 | 19.245 | −14.875 | 29.151 | 1.00 | 71.41 | C |
| ATOM | 7276 | N | PRO | M | 41 | 18.464 | −14.334 | 32.315 | 1.00 | 81.41 | N |
| ATOM | 7277 | CA | PRO | M | 41 | 17.404 | −14.074 | 33.327 | 1.00 | 81.36 | C |
| ATOM | 7278 | C | PRO | M | 41 | 16.034 | −13.764 | 32.721 | 1.00 | 85.30 | C |
| ATOM | 7279 | O | PRO | M | 41 | 15.933 | −13.013 | 31.743 | 1.00 | 86.00 | O |
| ATOM | 7280 | CB | PRO | M | 41 | 17.951 | −12.902 | 34.144 | 1.00 | 83.24 | C |
| ATOM | 7281 | CG | PRO | M | 41 | 19.424 | −12.833 | 33.805 | 1.00 | 88.66 | C |
| ATOM | 7282 | CD | PRO | M | 41 | 19.563 | −13.345 | 32.405 | 1.00 | 84.09 | C |
| ATOM | 7283 | N | GLY | M | 42 | 15.004 | −14.405 | 33.271 | 1.00 | 80.78 | N |
| ATOM | 7284 | CA | GLY | M | 42 | 13.616 | −14.258 | 32.825 | 1.00 | 79.73 | C |
| ATOM | 7285 | C | GLY | M | 42 | 13.315 | −14.797 | 31.433 | 1.00 | 80.94 | C |
| ATOM | 7286 | O | GLY | M | 42 | 12.350 | −14.366 | 30.791 | 1.00 | 80.00 | O |
| ATOM | 7287 | N | GLN | M | 43 | 14.152 | −15.744 | 30.953 | 1.00 | 74.70 | N |
| ATOM | 7288 | CA | GLN | M | 43 | 14.050 | −16.366 | 29.642 | 1.00 | 72.84 | C |
| ATOM | 7289 | C | GLN | M | 43 | 14.106 | −17.884 | 29.775 | 1.00 | 73.41 | C |
| ATOM | 7290 | O | GLN | M | 43 | 14.475 | −18.402 | 30.842 | 1.00 | 71.73 | O |
| ATOM | 7291 | CB | GLN | M | 43 | 15.177 | −15.862 | 28.726 | 1.00 | 74.66 | C |
| ATOM | 7292 | CG | GLN | M | 43 | 15.061 | −14.377 | 28.371 | 1.00 | 94.33 | C |
| ATOM | 7293 | CD | GLN | M | 43 | 15.837 | −14.035 | 27.134 | 1.00 | 112.28 | C |
| ATOM | 7294 | OE1 | GLN | M | 43 | 15.523 | −14.487 | 26.024 | 1.00 | 105.82 | O |
| ATOM | 7295 | NE2 | GLN | M | 43 | 16.858 | −13.208 | 27.298 | 1.00 | 106.17 | N |
| ATOM | 7296 | N | ALA | M | 44 | 13.718 | −18.597 | 28.699 | 1.00 | 67.78 | N |
| ATOM | 7297 | CA | ALA | M | 44 | 13.729 | −20.058 | 28.677 | 1.00 | 66.34 | C |
| ATOM | 7298 | C | ALA | M | 44 | 15.157 | −20.602 | 28.496 | 1.00 | 67.41 | C |
| ATOM | 7299 | O | ALA | M | 44 | 15.981 | −19.931 | 27.842 | 1.00 | 68.14 | O |
| ATOM | 7300 | CB | ALA | M | 44 | 12.846 | −20.561 | 27.542 | 1.00 | 66.87 | C |
| ATOM | 7301 | N | PRO | M | 45 | 15.464 | −21.828 | 29.003 | 1.00 | 60.38 | N |
| ATOM | 7302 | CA | PRO | M | 45 | 16.788 | −22.408 | 28.727 | 1.00 | 60.40 | C |
| ATOM | 7303 | C | PRO | M | 45 | 16.963 | −22.671 | 27.225 | 1.00 | 66.02 | C |
| ATOM | 7304 | O | PRO | M | 45 | 15.979 | −22.804 | 26.496 | 1.00 | 66.24 | O |
| ATOM | 7305 | CB | PRO | M | 45 | 16.760 | −23.740 | 29.496 | 1.00 | 61.47 | C |
| ATOM | 7306 | CG | PRO | M | 45 | 15.613 | −23.644 | 30.457 | 1.00 | 63.87 | C |
| ATOM | 7307 | CD | PRO | M | 45 | 14.626 | −22.772 | 29.775 | 1.00 | 59.92 | C |
| ATOM | 7308 | N | ARG | M | 46 | 18.210 | −22.704 | 26.757 | 1.00 | 63.55 | N |
| ATOM | 7309 | CA | ARG | M | 46 | 18.527 | −23.038 | 25.370 | 1.00 | 63.30 | C |
| ATOM | 7310 | C | ARG | M | 46 | 19.717 | −23.975 | 25.340 | 1.00 | 69.04 | C |
| ATOM | 7311 | O | ARG | M | 46 | 20.611 | −23.844 | 26.175 | 1.00 | 68.87 | O |
| ATOM | 7312 | CB | ARG | M | 46 | 18.703 | −21.813 | 24.453 | 1.00 | 61.48 | C |
| ATOM | 7313 | CG | ARG | M | 46 | 19.934 | −20.978 | 24.678 | 1.00 | 66.93 | C |
| ATOM | 7314 | CD | ARG | M | 46 | 20.127 | −19.978 | 23.558 | 1.00 | 88.00 | C |
| ATOM | 7315 | NE | ARG | M | 46 | 21.432 | −19.312 | 23.674 | 1.00 | 113.15 | N |
| ATOM | 7316 | CZ | ARG | M | 46 | 22.121 | −18.792 | 22.658 | 1.00 | 127.37 | C |
| ATOM | 7317 | NH1 | ARG | M | 46 | 21.639 | −18.844 | 21.422 | 1.00 | 119.94 | N |
| ATOM | 7318 | NH2 | ARG | M | 46 | 23.307 | −18.231 | 22.870 | 1.00 | 104.31 | N |
| ATOM | 7319 | N | LEU | M | 47 | 19.700 | −24.957 | 24.426 | 1.00 | 66.83 | N |
| ATOM | 7320 | CA | LEU | M | 47 | 20.792 | −25.922 | 24.290 | 1.00 | 65.69 | C |
| ATOM | 7321 | C | LEU | M | 47 | 21.985 | −25.221 | 23.670 | 1.00 | 68.82 | C |
| ATOM | 7322 | O | LEU | M | 47 | 21.826 | −24.437 | 22.722 | 1.00 | 67.73 | O |
| ATOM | 7323 | CB | LEU | M | 47 | 20.368 | −27.144 | 23.434 | 1.00 | 64.63 | C |
| ATOM | 7324 | CG | LEU | M | 47 | 21.343 | −28.316 | 23.330 | 1.00 | 67.32 | C |
| ATOM | 7325 | CD1 | LEU | M | 47 | 21.457 | −29.051 | 24.608 | 1.00 | 66.65 | C |
| ATOM | 7326 | CD2 | LEU | M | 47 | 20.917 | −29.279 | 22.281 | 1.00 | 69.38 | C |
| ATOM | 7327 | N | LEU | M | 48 | 23.173 | −25.476 | 24.262 | 1.00 | 65.41 | N |
| ATOM | 7328 | CA | LEU | M | 48 | 24.474 | −24.996 | 23.789 | 1.00 | 64.24 | C |
| ATOM | 7329 | C | LEU | M | 48 | 25.269 | −26.180 | 23.229 | 1.00 | 66.69 | C |
| ATOM | 7330 | O | LEU | M | 48 | 25.742 | −26.112 | 22.104 | 1.00 | 66.83 | O |
| ATOM | 7331 | CB | LEU | M | 48 | 25.307 | −24.361 | 24.919 | 1.00 | 63.52 | C |
| ATOM | 7332 | CG | LEU | M | 48 | 24.856 | −23.079 | 25.550 | 1.00 | 67.40 | C |
| ATOM | 7333 | CD1 | LEU | M | 48 | 25.853 | −22.665 | 26.570 | 1.00 | 67.89 | C |
| ATOM | 7334 | CD2 | LEU | M | 48 | 24.640 | −21.970 | 24.520 | 1.00 | 67.64 | C |
| ATOM | 7335 | N | ILE | M | 49 | 25.457 | −27.234 | 24.045 | 1.00 | 62.19 | N |
| ATOM | 7336 | CA | ILE | M | 49 | 26.294 | −28.379 | 23.715 | 1.00 | 62.09 | C |
| ATOM | 7337 | C | ILE | M | 49 | 25.569 | −29.680 | 23.952 | 1.00 | 64.66 | C |
| ATOM | 7338 | O | ILE | M | 49 | 25.011 | −29.851 | 25.022 | 1.00 | 64.62 | O |
| ATOM | 7339 | CB | ILE | M | 49 | 27.587 | −28.307 | 24.600 | 1.00 | 65.60 | C |
| ATOM | 7340 | CG1 | ILE | M | 49 | 28.419 | −27.019 | 24.352 | 1.00 | 66.16 | C |
| ATOM | 7341 | CG2 | ILE | M | 49 | 28.457 | −29.557 | 24.488 | 1.00 | 66.81 | C |
| ATOM | 7342 | CD1 | ILE | M | 49 | 29.009 | −26.809 | 22.916 | 1.00 | 78.14 | C |
| ATOM | 7343 | N | TYR | M | 50 | 25.595 | −30.594 | 22.982 | 1.00 | 60.35 | N |
| ATOM | 7344 | CA | TYR | M | 50 | 25.025 | −31.930 | 23.121 | 1.00 | 61.08 | C |
| ATOM | 7345 | C | TYR | M | 50 | 26.135 | −32.954 | 22.891 | 1.00 | 68.46 | C |
| ATOM | 7346 | O | TYR | M | 50 | 27.111 | −32.645 | 22.212 | 1.00 | 68.72 | O |
| ATOM | 7347 | CB | TYR | M | 50 | 23.861 | −32.173 | 22.144 | 1.00 | 62.02 | C |
| ATOM | 7348 | CG | TYR | M | 50 | 24.236 | −32.136 | 20.680 | 1.00 | 63.07 | C |

TABLE 1-continued

Three-dimensional crystal coordinate for anti-TcdB antibody beziotoxumab Fab – *C. difficile* toxin B (TcdB$^{(1834-2101)}$) complex.

| ATOM | 7349 | CD2 | TYR | M | 50 | 24.495 | −33.312 | 19.973 | 1.00 | 63.14 | C |
|---|---|---|---|---|---|---|---|---|---|---|---|
| ATOM | 7350 | CD1 | TYR | M | 50 | 24.231 | −30.937 | 19.972 | 1.00 | 65.35 | C |
| ATOM | 7351 | CE2 | TYR | M | 50 | 24.797 | −33.285 | 18.611 | 1.00 | 64.05 | C |
| ATOM | 7352 | CE1 | TYR | M | 50 | 24.550 | −30.896 | 18.615 | 1.00 | 66.04 | C |
| ATOM | 7353 | CZ | TYR | M | 50 | 24.837 | −32.071 | 17.939 | 1.00 | 71.13 | C |
| ATOM | 7354 | OH | TYR | M | 50 | 25.156 | −32.016 | 16.608 | 1.00 | 71.44 | O |
| ATOM | 7355 | N | GLY | M | 51 | 25.998 | −34.150 | 23.450 | 1.00 | 66.09 | N |
| ATOM | 7356 | CA | GLY | M | 51 | 26.990 | −35.204 | 23.260 | 1.00 | 66.23 | C |
| ATOM | 7357 | C | GLY | M | 51 | 28.375 | −34.847 | 23.753 | 1.00 | 72.07 | C |
| ATOM | 7358 | O | GLY | M | 51 | 29.378 | −35.301 | 23.186 | 1.00 | 74.10 | O |
| ATOM | 7359 | N | ALA | M | 52 | 28.414 | −34.029 | 24.835 | 1.00 | 66.83 | N |
| ATOM | 7360 | CA | ALA | M | 52 | 29.562 | −33.518 | 25.599 | 1.00 | 65.45 | C |
| ATOM | 7361 | C | ALA | M | 52 | 30.403 | −32.476 | 24.889 | 1.00 | 68.60 | C |
| ATOM | 7362 | O | ALA | M | 52 | 30.818 | −31.533 | 25.550 | 1.00 | 68.68 | O |
| ATOM | 7363 | CB | ALA | M | 52 | 30.447 | −34.647 | 26.101 | 1.00 | 65.65 | C |
| ATOM | 7364 | N | SER | M | 53 | 30.642 | −32.618 | 23.569 | 1.00 | 64.94 | N |
| ATOM | 7365 | CA | SER | M | 53 | 31.508 | −31.728 | 22.777 | 1.00 | 64.13 | C |
| ATOM | 7366 | C | SER | M | 53 | 30.864 | −31.058 | 21.558 | 1.00 | 68.66 | C |
| ATOM | 7367 | O | SER | M | 53 | 31.438 | −30.089 | 21.039 | 1.00 | 68.95 | O |
| ATOM | 7368 | CB | SER | M | 53 | 32.735 | −32.496 | 22.310 | 1.00 | 65.66 | C |
| ATOM | 7369 | OG | SER | M | 53 | 32.358 | −33.470 | 21.352 | 1.00 | 73.06 | O |
| ATOM | 7370 | N | SER | M | 54 | 29.723 | −31.601 | 21.067 | 1.00 | 63.93 | N |
| ATOM | 7371 | CA | SER | M | 54 | 29.054 | −31.101 | 19.873 | 1.00 | 62.92 | C |
| ATOM | 7372 | C | SER | M | 54 | 28.269 | −29.882 | 20.204 | 1.00 | 66.55 | C |
| ATOM | 7373 | O | SER | M | 54 | 27.649 | −29.798 | 21.252 | 1.00 | 65.89 | O |
| ATOM | 7374 | CB | SER | M | 54 | 28.177 | −32.165 | 19.224 | 1.00 | 68.35 | C |
| ATOM | 7375 | OG | SER | M | 54 | 28.833 | −33.418 | 19.075 | 1.00 | 82.57 | O |
| ATOM | 7376 | N | ARG | M | 55 | 28.333 | −28.915 | 19.324 | 1.00 | 64.56 | N |
| ATOM | 7377 | CA | ARG | M | 55 | 27.726 | −27.617 | 19.487 | 1.00 | 64.93 | C |
| ATOM | 7378 | C | ARG | M | 55 | 26.354 | −27.598 | 18.822 | 1.00 | 70.90 | C |
| ATOM | 7379 | O | ARG | M | 55 | 26.241 | −27.952 | 17.644 | 1.00 | 70.44 | O |
| ATOM | 7380 | CB | ARG | M | 55 | 28.680 | −26.606 | 18.836 | 1.00 | 67.13 | C |
| ATOM | 7381 | CG | ARG | M | 55 | 28.663 | −25.200 | 19.396 | 1.00 | 82.33 | C |
| ATOM | 7382 | CD | ARG | M | 55 | 30.041 | −24.553 | 19.425 | 1.00 | 88.94 | C |
| ATOM | 7383 | NE | ARG | M | 55 | 30.782 | −24.688 | 18.170 | 1.00 | 92.83 | N |
| ATOM | 7384 | CZ | ARG | M | 55 | 32.090 | −24.920 | 18.087 | 1.00 | 99.82 | C |
| ATOM | 7385 | NH1 | ARG | M | 55 | 32.828 | −25.034 | 19.191 | 1.00 | 64.11 | N |
| ATOM | 7386 | NH2 | ARG | M | 55 | 32.671 | −25.047 | 16.903 | 1.00 | 97.18 | N |
| ATOM | 7387 | N | ALA | M | 56 | 25.305 | −27.190 | 19.579 | 1.00 | 69.63 | N |
| ATOM | 7388 | CA | ALA | M | 56 | 23.921 | −27.068 | 19.085 | 1.00 | 69.91 | C |
| ATOM | 7389 | C | ALA | M | 56 | 23.833 | −26.026 | 17.960 | 1.00 | 74.64 | C |
| ATOM | 7390 | O | ALA | M | 56 | 24.743 | −25.210 | 17.818 | 1.00 | 74.16 | O |
| ATOM | 7391 | CB | ALA | M | 56 | 22.986 | −26.700 | 20.221 | 1.00 | 70.53 | C |
| ATOM | 7392 | N | THR | M | 57 | 22.772 | −26.078 | 17.139 | 1.00 | 72.67 | N |
| ATOM | 7393 | CA | THR | M | 57 | 22.611 | −25.182 | 15.987 | 1.00 | 73.42 | C |
| ATOM | 7394 | C | THR | M | 57 | 22.650 | −23.688 | 16.372 | 1.00 | 77.88 | C |
| ATOM | 7395 | O | THR | M | 57 | 21.976 | −23.272 | 17.320 | 1.00 | 76.09 | O |
| ATOM | 7396 | CB | THR | M | 57 | 21.354 | −25.533 | 15.162 | 1.00 | 85.42 | C |
| ATOM | 7397 | OG1 | THR | M | 57 | 21.072 | −26.929 | 15.232 | 1.00 | 85.01 | O |
| ATOM | 7398 | CG2 | THR | M | 57 | 21.495 | −25.128 | 13.707 | 1.00 | 87.10 | C |
| ATOM | 7399 | N | GLY | M | 58 | 23.455 | −22.922 | 15.635 | 1.00 | 75.65 | N |
| ATOM | 7400 | CA | GLY | M | 58 | 23.606 | −21.481 | 15.829 | 1.00 | 76.07 | C |
| ATOM | 7401 | C | GLY | M | 58 | 24.333 | −21.066 | 17.098 | 1.00 | 79.99 | C |
| ATOM | 7402 | O | GLY | M | 58 | 24.191 | −19.928 | 17.565 | 1.00 | 79.15 | O |
| ATOM | 7403 | N | ILE | M | 59 | 25.135 | −21.971 | 17.659 | 1.00 | 75.67 | N |
| ATOM | 7404 | CA | ILE | M | 59 | 25.881 | −21.658 | 18.864 | 1.00 | 74.60 | C |
| ATOM | 7405 | C | ILE | M | 59 | 27.306 | −21.219 | 18.486 | 1.00 | 80.18 | C |
| ATOM | 7406 | O | ILE | M | 59 | 28.073 | −22.015 | 17.917 | 1.00 | 80.89 | O |
| ATOM | 7407 | CB | ILE | M | 59 | 25.811 | −22.792 | 19.942 | 1.00 | 76.66 | C |
| ATOM | 7408 | CG1 | ILE | M | 59 | 24.359 | −23.070 | 20.414 | 1.00 | 77.27 | C |
| ATOM | 7409 | CG2 | ILE | M | 59 | 26.735 | −22.546 | 21.124 | 1.00 | 75.40 | C |
| ATOM | 7410 | CD1 | ILE | M | 59 | 23.491 | −21.867 | 20.865 | 1.00 | 83.72 | C |
| ATOM | 7411 | N | PRO | M | 60 | 27.647 | −19.944 | 18.820 | 1.00 | 75.11 | N |
| ATOM | 7412 | CA | PRO | M | 60 | 29.003 | −19.412 | 18.570 | 1.00 | 74.06 | C |
| ATOM | 7413 | C | PRO | M | 60 | 30.178 | −20.318 | 18.935 | 1.00 | 79.41 | C |
| ATOM | 7414 | O | PRO | M | 60 | 30.122 | −21.040 | 19.939 | 1.00 | 78.74 | O |
| ATOM | 7415 | CB | PRO | M | 60 | 29.038 | −18.177 | 19.453 | 1.00 | 75.24 | C |
| ATOM | 7416 | CG | PRO | M | 60 | 27.658 | −17.723 | 19.516 | 1.00 | 79.74 | C |
| ATOM | 7417 | CD | PRO | M | 60 | 26.796 | −18.937 | 19.484 | 1.00 | 75.90 | C |
| ATOM | 7418 | N | ASP | M | 61 | 31.272 | −20.222 | 18.142 | 1.00 | 77.58 | N |
| ATOM | 7419 | CA | ASP | M | 61 | 32.505 | −21.011 | 18.313 | 1.00 | 78.06 | C |
| ATOM | 7420 | C | ASP | M | 61 | 33.205 | −20.792 | 19.662 | 1.00 | 78.50 | C |
| ATOM | 7421 | O | ASP | M | 61 | 34.031 | −21.630 | 20.051 | 1.00 | 78.43 | O |
| ATOM | 7422 | CB | ASP | M | 61 | 33.501 | −20.766 | 17.163 | 1.00 | 81.37 | C |
| ATOM | 7423 | CG | ASP | M | 61 | 32.893 | −20.787 | 15.777 | 1.00 | 105.70 | C |
| ATOM | 7424 | OD1 | ASP | M | 61 | 32.153 | −19.827 | 15.438 | 1.00 | 108.63 | O |
| ATOM | 7425 | OD2 | ASP | M | 61 | 33.183 | −21.745 | 15.011 | 1.00 | 115.01 | O |

TABLE 1-continued

Three-dimensional crystal coordinate for anti-TcdB antibody beziotoxumab Fab –*C. difficile* toxin B (TcdB$^{(1834-2101)}$) complex.

| ATOM | 7426 | N | ARG | M | 62 | 32.902 | −19.674 | 20.368 | 1.00 | 71.40 | N |
|------|------|------|-----|---|----|--------|---------|--------|------|-------|---|
| ATOM | 7427 | CA | ARG | M | 62 | 33.510 | −19.403 | 21.678 | 1.00 | 70.23 | C |
| ATOM | 7428 | C | ARG | M | 62 | 33.081 | −20.443 | 22.724 | 1.00 | 73.27 | C |
| ATOM | 7429 | O | ARG | M | 62 | 33.832 | −20.757 | 23.660 | 1.00 | 72.55 | O |
| ATOM | 7430 | CB | ARG | M | 62 | 33.285 | −17.965 | 22.140 | 1.00 | 68.39 | C |
| ATOM | 7431 | CG | ARG | M | 62 | 31.837 | −17.555 | 22.329 | 1.00 | 73.40 | C |
| ATOM | 7432 | CD | ARG | M | 62 | 31.787 | −16.068 | 22.516 | 1.00 | 72.20 | C |
| ATOM | 7433 | NE | ARG | M | 62 | 30.453 | −15.592 | 22.853 | 1.00 | 77.05 | N |
| ATOM | 7434 | CZ | ARG | M | 62 | 29.561 | −15.168 | 21.964 | 1.00 | 85.17 | C |
| ATOM | 7435 | NH1 | ARG | M | 62 | 29.849 | −15.171 | 20.671 | 1.00 | 58.18 | N |
| ATOM | 7436 | NH2 | ARG | M | 62 | 28.372 | −14.740 | 22.363 | 1.00 | 79.51 | N |
| ATOM | 7437 | N | PHE | M | 63 | 31.894 | −21.033 | 22.499 | 1.00 | 69.13 | N |
| ATOM | 7438 | CA | PHE | M | 63 | 31.357 | −22.104 | 23.324 | 1.00 | 67.88 | C |
| ATOM | 7439 | C | PHE | M | 63 | 31.983 | −23.433 | 22.873 | 1.00 | 70.49 | C |
| ATOM | 7440 | O | PHE | M | 63 | 31.870 | −23.819 | 21.706 | 1.00 | 70.37 | O |
| ATOM | 7441 | CB | PHE | M | 63 | 29.813 | −22.129 | 23.265 | 1.00 | 69.11 | C |
| ATOM | 7442 | CG | PHE | M | 63 | 29.136 | −20.946 | 23.916 | 1.00 | 69.80 | C |
| ATOM | 7443 | CD1 | PHE | M | 63 | 29.073 | −20.835 | 25.304 | 1.00 | 72.17 | C |
| ATOM | 7444 | CD2 | PHE | M | 63 | 28.534 | −19.959 | 23.145 | 1.00 | 71.35 | C |
| ATOM | 7445 | CE1 | PHE | M | 63 | 28.437 | −19.743 | 25.907 | 1.00 | 73.18 | C |
| ATOM | 7446 | CE2 | PHE | M | 63 | 27.891 | −18.869 | 23.749 | 1.00 | 74.57 | C |
| ATOM | 7447 | CZ | PHE | M | 63 | 27.842 | −18.771 | 25.123 | 1.00 | 72.57 | C |
| ATOM | 7448 | N | SER | M | 64 | 32.682 | −24.100 | 23.798 | 1.00 | 65.48 | N |
| ATOM | 7449 | CA | SER | M | 64 | 33.350 | −25.374 | 23.577 | 1.00 | 64.30 | C |
| ATOM | 7450 | C | SER | M | 64 | 33.031 | −26.306 | 24.760 | 1.00 | 65.76 | C |
| ATOM | 7451 | O | SER | M | 64 | 32.982 | −25.856 | 25.911 | 1.00 | 64.40 | O |
| ATOM | 7452 | CB | SER | M | 64 | 34.853 | −25.140 | 23.409 | 1.00 | 68.68 | C |
| ATOM | 7453 | OG | SER | M | 64 | 35.675 | −26.196 | 23.881 | 1.00 | 81.78 | O |
| ATOM | 7454 | N | GLY | M | 65 | 32.772 | −27.571 | 24.449 | 1.00 | 61.73 | N |
| ATOM | 7455 | CA | GLY | M | 65 | 32.459 | −28.592 | 25.440 | 1.00 | 62.24 | C |
| ATOM | 7456 | C | GLY | M | 65 | 33.457 | −29.733 | 25.406 | 1.00 | 68.95 | C |
| ATOM | 7457 | O | GLY | M | 65 | 33.890 | −30.149 | 24.324 | 1.00 | 68.18 | O |
| ATOM | 7458 | N | SER | M | 66 | 33.832 | −30.249 | 26.596 | 1.00 | 67.02 | N |
| ATOM | 7459 | CA | SER | M | 66 | 34.822 | −31.327 | 26.729 | 1.00 | 66.91 | C |
| ATOM | 7460 | C | SER | M | 66 | 34.628 | −32.113 | 28.002 | 1.00 | 70.38 | C |
| ATOM | 7461 | O | SER | M | 66 | 33.875 | −31.684 | 28.886 | 1.00 | 71.07 | O |
| ATOM | 7462 | CB | SER | M | 66 | 36.235 | −30.751 | 26.717 | 1.00 | 72.37 | C |
| ATOM | 7463 | OG | SER | M | 66 | 36.354 | −29.700 | 27.665 | 1.00 | 87.21 | O |
| ATOM | 7464 | N | GLY | M | 67 | 35.320 | −33.249 | 28.082 | 1.00 | 65.26 | N |
| ATOM | 7465 | CA | GLY | M | 67 | 35.294 | −34.144 | 29.230 | 1.00 | 64.70 | C |
| ATOM | 7466 | C | GLY | M | 67 | 34.866 | −35.555 | 28.890 | 1.00 | 69.17 | C |
| ATOM | 7467 | O | GLY | M | 67 | 34.442 | −35.818 | 27.759 | 1.00 | 67.77 | O |
| ATOM | 7468 | N | SER | M | 68 | 35.000 | −36.475 | 29.874 | 1.00 | 67.72 | N |
| ATOM | 7469 | CA | SER | M | 68 | 34.604 | −37.891 | 29.823 | 1.00 | 69.00 | C |
| ATOM | 7470 | C | SER | M | 68 | 34.502 | −38.469 | 31.243 | 1.00 | 78.38 | C |
| ATOM | 7471 | O | SER | M | 68 | 35.014 | −37.869 | 32.197 | 1.00 | 79.74 | O |
| ATOM | 7472 | CB | SER | M | 68 | 35.590 | −38.714 | 29.004 | 1.00 | 72.16 | C |
| ATOM | 7473 | OG | SER | M | 68 | 36.660 | −39.192 | 29.806 | 1.00 | 83.70 | O |
| ATOM | 7474 | N | GLY | M | 69 | 33.865 | −39.630 | 31.362 | 1.00 | 77.07 | N |
| ATOM | 7475 | CA | GLY | M | 69 | 33.696 | −40.323 | 32.635 | 1.00 | 77.99 | C |
| ATOM | 7476 | C | GLY | M | 69 | 32.801 | −39.606 | 33.624 | 1.00 | 84.14 | C |
| ATOM | 7477 | O | GLY | M | 69 | 31.578 | −39.728 | 33.544 | 1.00 | 84.30 | O |
| ATOM | 7478 | N | THR | M | 70 | 33.408 | −38.845 | 34.556 | 1.00 | 81.77 | N |
| ATOM | 7479 | CA | THR | M | 70 | 32.685 | −38.104 | 35.598 | 1.00 | 82.14 | C |
| ATOM | 7480 | C | THR | M | 70 | 32.899 | −36.598 | 35.509 | 1.00 | 86.96 | C |
| ATOM | 7481 | O | THR | M | 70 | 32.051 | −35.852 | 35.994 | 1.00 | 86.99 | O |
| ATOM | 7482 | CB | THR | M | 70 | 33.048 | −38.608 | 37.017 | 1.00 | 90.39 | C |
| ATOM | 7483 | OG1 | THR | M | 70 | 34.455 | −38.482 | 37.236 | 1.00 | 90.99 | O |
| ATOM | 7484 | CG2 | THR | M | 70 | 32.612 | −40.039 | 37.265 | 1.00 | 88.15 | C |
| ATOM | 7485 | N | ASP | M | 71 | 34.029 | −36.143 | 34.932 | 1.00 | 83.69 | N |
| ATOM | 7486 | CA | ASP | M | 71 | 34.342 | −34.706 | 34.861 | 1.00 | 83.48 | C |
| ATOM | 7487 | C | ASP | M | 71 | 34.156 | −34.108 | 33.490 | 1.00 | 83.76 | C |
| ATOM | 7488 | O | ASP | M | 71 | 34.835 | −34.512 | 32.540 | 1.00 | 83.82 | O |
| ATOM | 7489 | CB | ASP | M | 71 | 35.752 | −34.408 | 35.401 | 1.00 | 86.12 | C |
| ATOM | 7490 | CG | ASP | M | 71 | 35.899 | −34.609 | 36.899 | 1.00 | 105.25 | C |
| ATOM | 7491 | OD1 | ASP | M | 71 | 35.437 | −35.667 | 37.414 | 1.00 | 107.33 | O |
| ATOM | 7492 | OD2 | ASP | M | 71 | 36.500 | −33.733 | 37.558 | 1.00 | 113.57 | O |
| ATOM | 7493 | N | PHE | M | 72 | 33.248 | −33.117 | 33.404 | 1.00 | 76.78 | N |
| ATOM | 7494 | CA | PHE | M | 72 | 32.891 | −32.395 | 32.177 | 1.00 | 74.75 | C |
| ATOM | 7495 | C | PHE | M | 72 | 33.106 | −30.889 | 32.348 | 1.00 | 77.36 | C |
| ATOM | 7496 | O | PHE | M | 72 | 33.150 | −30.400 | 33.480 | 1.00 | 77.58 | O |
| ATOM | 7497 | CB | PHE | M | 72 | 31.460 | −32.746 | 31.733 | 1.00 | 75.70 | C |
| ATOM | 7498 | CG | PHE | M | 72 | 31.277 | −34.212 | 31.390 | 1.00 | 76.10 | C |
| ATOM | 7499 | CD1 | PHE | M | 72 | 31.524 | −34.681 | 30.100 | 1.00 | 78.31 | C |
| ATOM | 7500 | CD2 | PHE | M | 72 | 30.893 | −35.130 | 32.364 | 1.00 | 76.94 | C |
| ATOM | 7501 | CE1 | PHE | M | 72 | 31.377 | −36.044 | 29.786 | 1.00 | 78.91 | C |
| ATOM | 7502 | CE2 | PHE | M | 72 | 30.743 | −36.493 | 32.049 | 1.00 | 79.38 | C |

TABLE 1-continued

Three-dimensional crystal coordinate for anti-TcdB antibody beziotoxumab Fab –*C. difficile* toxin B (TcdB$^{(1834-2101)}$) complex.

| ATOM | 7503 | CZ  | PHE | M | 72 | 30.991 | −36.941 | 30.764 | 1.00 | 77.55  | C |
|------|------|-----|-----|---|----|--------|---------|--------|------|--------|---|
| ATOM | 7504 | N   | THR | M | 73 | 33.318 | −30.168 | 31.238 | 1.00 | 72.05  | N |
| ATOM | 7505 | CA  | THR | M | 73 | 33.657 | −28.745 | 31.268 | 1.00 | 71.23  | C |
| ATOM | 7506 | C   | THR | M | 73 | 33.076 | −27.965 | 30.093 | 1.00 | 73.10  | C |
| ATOM | 7507 | O   | THR | M | 73 | 33.247 | −28.350 | 28.927 | 1.00 | 74.43  | O |
| ATOM | 7508 | CB  | THR | M | 73 | 35.220 | −28.582 | 31.240 | 1.00 | 83.28  | C |
| ATOM | 7509 | OG1 | THR | M | 73 | 35.840 | −29.422 | 32.217 | 1.00 | 85.83  | O |
| ATOM | 7510 | CG2 | THR | M | 73 | 35.702 | −27.122 | 31.410 | 1.00 | 79.56  | C |
| ATOM | 7511 | N   | LEU | M | 74 | 32.477 | −26.823 | 30.402 | 1.00 | 66.05  | N |
| ATOM | 7512 | CA  | LEU | M | 74 | 32.018 | −25.897 | 29.393 | 1.00 | 65.83  | C |
| ATOM | 7513 | C   | LEU | M | 74 | 33.012 | −24.728 | 29.416 | 1.00 | 74.78  | C |
| ATOM | 7514 | O   | LEU | M | 74 | 33.320 | −24.185 | 30.493 | 1.00 | 74.90  | O |
| ATOM | 7515 | CB  | LEU | M | 74 | 30.592 | −25.391 | 29.671 | 1.00 | 64.90  | C |
| ATOM | 7516 | CG  | LEU | M | 74 | 30.035 | −24.377 | 28.657 | 1.00 | 67.42  | C |
| ATOM | 7517 | CD1 | LEU | M | 74 | 29.501 | −25.065 | 27.412 | 1.00 | 67.03  | C |
| ATOM | 7518 | CD2 | LEU | M | 74 | 28.974 | −23.548 | 29.265 | 1.00 | 67.92  | C |
| ATOM | 7519 | N   | THR | M | 75 | 33.494 | −24.337 | 28.225 | 1.00 | 72.63  | N |
| ATOM | 7520 | CA  | THR | M | 75 | 34.451 | −23.258 | 28.070 | 1.00 | 73.13  | C |
| ATOM | 7521 | C   | THR | M | 75 | 33.885 | −22.149 | 27.189 | 1.00 | 79.12  | C |
| ATOM | 7522 | O   | THR | M | 75 | 33.246 | −22.427 | 26.178 | 1.00 | 78.73  | O |
| ATOM | 7523 | CB  | THR | M | 75 | 35.770 | −23.822 | 27.515 | 1.00 | 83.40  | C |
| ATOM | 7524 | OG1 | THR | M | 75 | 36.109 | −25.026 | 28.211 | 1.00 | 80.36  | O |
| ATOM | 7525 | CG2 | THR | M | 75 | 36.912 | −22.840 | 27.620 | 1.00 | 84.68  | C |
| ATOM | 7526 | N   | ILE | M | 76 | 34.114 | −20.894 | 27.586 | 1.00 | 77.31  | N |
| ATOM | 7527 | CA  | ILE | M | 76 | 33.754 | −19.704 | 26.805 | 1.00 | 77.62  | C |
| ATOM | 7528 | C   | ILE | M | 76 | 35.112 | −19.000 | 26.628 | 1.00 | 83.41  | C |
| ATOM | 7529 | O   | ILE | M | 76 | 35.613 | −18.424 | 27.594 | 1.00 | 84.55  | O |
| ATOM | 7530 | CB  | ILE | M | 76 | 32.644 | −18.804 | 27.464 | 1.00 | 79.80  | C |
| ATOM | 7531 | CG  | ILE | M | 76 | 31.408 | −19.636 | 27.871 | 1.00 | 80.15  | C |
| ATOM | 7532 | CG2 | ILE | M | 76 | 32.234 | −17.667 | 26.524 | 1.00 | 78.66  | C |
| ATOM | 7533 | CD1 | ILE | M | 76 | 30.645 | −19.159 | 29.081 | 1.00 | 89.91  | C |
| ATOM | 7534 | N   | SER | M | 77 | 35.766 | −19.175 | 25.457 | 1.00 | 78.88  | N |
| ATOM | 7535 | CA  | SER | M | 77 | 37.098 | −18.643 | 25.141 | 1.00 | 78.41  | C |
| ATOM | 7536 | C   | SER | M | 77 | 37.246 | −17.105 | 25.336 | 1.00 | 84.24  | C |
| ATOM | 7537 | O   | SER | M | 77 | 38.331 | −16.644 | 25.713 | 1.00 | 85.24  | O |
| ATOM | 7538 | CB  | SER | M | 77 | 37.534 | −19.071 | 23.739 | 1.00 | 80.83  | C |
| ATOM | 7539 | OG  | SER | M | 77 | 36.663 | −18.657 | 22.695 | 1.00 | 86.41  | O |
| ATOM | 7540 | N   | ARG | M | 78 | 36.162 | −16.328 | 25.102 | 1.00 | 80.06  | N |
| ATOM | 7541 | CA  | ARG | M | 78 | 36.112 | −14.873 | 25.253 | 1.00 | 79.61  | C |
| ATOM | 7542 | C   | ARG | M | 78 | 34.657 | −14.479 | 25.610 | 1.00 | 81.43  | C |
| ATOM | 7543 | O   | ARG | M | 78 | 33.754 | −14.637 | 24.779 | 1.00 | 81.65  | O |
| ATOM | 7544 | CB  | ARG | M | 78 | 36.630 | −14.179 | 23.962 | 1.00 | 82.68  | C |
| ATOM | 7545 | CG  | ARG | M | 78 | 36.221 | −12.712 | 23.795 | 1.00 | 103.04 | C |
| ATOM | 7546 | CD  | ARG | M | 78 | 36.926 | −12.046 | 22.633 | 1.00 | 118.91 | C |
| ATOM | 7547 | NE  | ARG | M | 78 | 37.655 | −10.869 | 23.093 | 1.00 | 131.41 | N |
| ATOM | 7548 | CZ  | ARG | M | 78 | 38.970 | −10.818 | 23.290 | 1.00 | 147.10 | C |
| ATOM | 7549 | NH1 | ARG | M | 78 | 39.730 | −11.880 | 23.039 | 1.00 | 131.62 | N |
| ATOM | 7550 | NH2 | ARG | M | 78 | 39.534 | −9.707  | 23.743 | 1.00 | 134.79 | N |
| ATOM | 7551 | N   | LEU | M | 79 | 34.433 | −13.989 | 26.849 | 1.00 | 74.82  | N |
| ATOM | 7552 | CA  | LEU | M | 79 | 33.093 | −13.619 | 27.294 | 1.00 | 73.39  | C |
| ATOM | 7553 | C   | LEU | M | 79 | 32.559 | −12.351 | 26.652 | 1.00 | 79.29  | C |
| ATOM | 7554 | O   | LEU | M | 79 | 33.186 | −11.299 | 26.732 | 1.00 | 79.90  | O |
| ATOM | 7555 | CB  | LEU | M | 79 | 33.009 | −13.518 | 28.807 | 1.00 | 72.74  | C |
| ATOM | 7556 | CG  | LEU | M | 79 | 33.087 | −14.813 | 29.545 | 1.00 | 76.92  | C |
| ATOM | 7557 | CD1 | LEU | M | 79 | 33.608 | −14.585 | 30.913 | 1.00 | 76.88  | C |
| ATOM | 7558 | CD2 | LEU | M | 79 | 31.737 | −15.468 | 29.616 | 1.00 | 80.60  | C |
| ATOM | 7559 | N   | GLU | M | 80 | 31.404 | −12.459 | 25.994 | 1.00 | 75.97  | N |
| ATOM | 7560 | CA  | GLU | M | 80 | 30.729 | −11.323 | 25.388 | 1.00 | 75.43  | C |
| ATOM | 7561 | C   | GLU | M | 80 | 29.671 | −10.825 | 26.393 | 1.00 | 80.11  | C |
| ATOM | 7562 | O   | GLU | M | 80 | 29.446 | −11.514 | 27.391 | 1.00 | 79.20  | O |
| ATOM | 7563 | CB  | GLU | M | 80 | 30.103 | −11.724 | 24.049 | 1.00 | 76.92  | C |
| ATOM | 7564 | CG  | GLU | M | 80 | 31.105 | −12.053 | 22.948 | 1.00 | 89.29  | C |
| ATOM | 7565 | CD  | GLU | M | 80 | 32.147 | −11.004 | 22.595 | 1.00 | 112.97 | C |
| ATOM | 7566 | OE1 | GLU | M | 80 | 31.765 | −9.830  | 22.387 | 1.00 | 109.19 | O |
| ATOM | 7567 | OE2 | GLU | M | 80 | 33.342 | −11.370 | 22.485 | 1.00 | 103.26 | O |
| ATOM | 7568 | N   | PRO | M | 81 | 29.039 | −9.633  | 26.213 | 1.00 | 79.04  | N |
| ATOM | 7569 | CA  | PRO | M | 81 | 28.042 | −9.172  | 27.206 | 1.00 | 79.27  | C |
| ATOM | 7570 | C   | PRO | M | 81 | 26.859 | −10.129 | 27.376 | 1.00 | 82.31  | C |
| ATOM | 7571 | O   | PRO | M | 81 | 26.402 | −10.387 | 28.501 | 1.00 | 81.62  | O |
| ATOM | 7572 | CB  | PRO | M | 81 | 27.593 | −7.812  | 26.652 | 1.00 | 81.01  | C |
| ATOM | 7573 | CG  | PRO | M | 81 | 28.692 | −7.390  | 25.755 | 1.00 | 85.20  | C |
| ATOM | 7574 | CD  | PRO | M | 81 | 29.187 | −8.643  | 25.129 | 1.00 | 80.93  | C |
| ATOM | 7575 | N   | GLU | M | 82 | 26.406 | −10.693 | 26.244 | 1.00 | 77.78  | N |
| ATOM | 7576 | CA  | GLU | M | 82 | 25.287 | −11.627 | 26.155 | 1.00 | 76.94  | C |
| ATOM | 7577 | C   | GLU | M | 82 | 25.509 | −12.931 | 26.961 | 1.00 | 81.09  | C |
| ATOM | 7578 | O   | GLU | M | 82 | 24.539 | −13.481 | 27.489 | 1.00 | 82.66  | O |
| ATOM | 7579 | CB  | GLU | M | 82 | 24.918 | −11.907 | 24.682 | 1.00 | 78.06  | C |

TABLE 1-continued

Three-dimensional crystal coordinate for anti-TcdB antibody beziotoxumab Fab –C. difficile toxin B (TcdB$^{(1834-2101)}$) complex.

| ATOM | 7580 | CG  | GLU | M | 82 | 26.090 | −12.192 | 23.736 | 1.00 | 93.22  | C |
|------|------|-----|-----|---|----|--------|---------|--------|------|--------|---|
| ATOM | 7581 | CD  | GLU | M | 82 | 26.707 | −11.041 | 22.946 | 1.00 | 118.73 | C |
| ATOM | 7582 | OE1 | GLU | M | 82 | 26.514 | −9.862  | 23.327 | 1.00 | 119.68 | O |
| ATOM | 7583 | OE2 | GLU | M | 82 | 27.421 | −11.329 | 21.957 | 1.00 | 109.26 | O |
| ATOM | 7584 | N   | ASP | M | 83 | 26.787 | −13.350 | 27.134 | 1.00 | 75.07  | N |
| ATOM | 7585 | CA  | ASP | M | 83 | 27.232 | −14.582 | 27.800 | 1.00 | 73.43  | C |
| ATOM | 7586 | C   | ASP | M | 83 | 27.043 | −14.634 | 29.333 | 1.00 | 73.97  | C |
| ATOM | 7587 | O   | ASP | M | 83 | 27.217 | −15.699 | 29.948 | 1.00 | 71.12  | O |
| ATOM | 7588 | CB  | ASP | M | 83 | 28.697 | −14.879 | 27.431 | 1.00 | 75.05  | C |
| ATOM | 7589 | CG  | ASP | M | 83 | 28.931 | −15.115 | 25.951 | 1.00 | 80.44  | C |
| ATOM | 7590 | OD1 | ASP | M | 83 | 27.931 | −15.248 | 25.198 | 1.00 | 80.35  | O |
| ATOM | 7591 | OD2 | ASP | M | 83 | 30.107 | −15.174 | 25.543 | 1.00 | 84.90  | O |
| ATOM | 7592 | N   | PHE | M | 84 | 26.674 | −13.511 | 29.950 | 1.00 | 70.75  | N |
| ATOM | 7593 | CA  | PHE | M | 84 | 26.452 | −13.518 | 31.393 | 1.00 | 70.42  | C |
| ATOM | 7594 | C   | PHE | M | 84 | 25.029 | −14.040 | 31.680 | 1.00 | 74.12  | C |
| ATOM | 7595 | O   | PHE | M | 84 | 24.043 | −13.377 | 31.336 | 1.00 | 73.72  | O |
| ATOM | 7596 | CB  | PHE | M | 84 | 26.783 | −12.151 | 31.994 | 1.00 | 71.76  | C |
| ATOM | 7597 | CG  | PHE | M | 84 | 28.268 | −11.844 | 31.856 | 1.00 | 73.47  | C |
| ATOM | 7598 | CD1 | PHE | M | 84 | 29.187 | −12.319 | 32.791 | 1.00 | 76.09  | C |
| ATOM | 7599 | CD2 | PHE | M | 84 | 28.756 | −11.131 | 30.758 | 1.00 | 75.48  | C |
| ATOM | 7600 | CE1 | PHE | M | 84 | 30.563 | −12.067 | 32.642 | 1.00 | 76.58  | C |
| ATOM | 7601 | CE2 | PHE | M | 84 | 30.139 | −10.887 | 30.609 | 1.00 | 77.83  | C |
| ATOM | 7602 | CZ  | PHE | M | 84 | 31.027 | −11.363 | 31.546 | 1.00 | 75.79  | C |
| ATOM | 7603 | N   | ALA | M | 85 | 24.944 | −15.304 | 32.192 | 1.00 | 69.37  | N |
| ATOM | 7604 | CA  | ALA | M | 85 | 23.707 | −16.048 | 32.468 | 1.00 | 67.88  | C |
| ATOM | 7605 | C   | ALA | M | 85 | 23.960 | −17.285 | 33.328 | 1.00 | 71.82  | C |
| ATOM | 7606 | O   | ALA | M | 85 | 25.060 | −17.460 | 33.841 | 1.00 | 72.58  | O |
| ATOM | 7607 | CB  | ALA | M | 85 | 23.059 | −16.465 | 31.155 | 1.00 | 68.31  | C |
| ATOM | 7608 | N   | VAL | M | 86 | 22.939 | −18.141 | 33.499 | 1.00 | 67.12  | N |
| ATOM | 7609 | CA  | VAL | M | 86 | 23.061 | −19.380 | 34.270 | 1.00 | 65.87  | C |
| ATOM | 7610 | C   | VAL | M | 86 | 23.286 | −20.530 | 33.302 | 1.00 | 68.16  | C |
| ATOM | 7611 | O   | VAL | M | 86 | 22.768 | −20.511 | 32.176 | 1.00 | 68.43  | O |
| ATOM | 7612 | CB  | VAL | M | 86 | 21.883 | −19.620 | 35.262 | 1.00 | 68.92  | C |
| ATOM | 7613 | CG1 | VAL | M | 86 | 22.117 | −20.865 | 36.126 | 1.00 | 68.05  | C |
| ATOM | 7614 | CG2 | VAL | M | 86 | 21.670 | −18.392 | 36.144 | 1.00 | 68.69  | C |
| ATOM | 7615 | N   | TYR | M | 87 | 24.100 | −21.501 | 33.728 | 1.00 | 61.59  | N |
| ATOM | 7616 | CA  | TYR | M | 87 | 24.458 | −22.629 | 32.911 | 1.00 | 60.36  | C |
| ATOM | 7617 | C   | TYR | M | 87 | 24.204 | −23.894 | 33.661 | 1.00 | 66.95  | C |
| ATOM | 7618 | O   | TYR | M | 87 | 24.751 | −24.092 | 34.754 | 1.00 | 66.24  | O |
| ATOM | 7619 | CB  | TYR | M | 87 | 25.937 | −22.537 | 32.486 | 1.00 | 60.29  | C |
| ATOM | 7620 | CG  | TYR | M | 87 | 26.233 | −21.385 | 31.551 | 1.00 | 60.16  | C |
| ATOM | 7621 | CD2 | TYR | M | 87 | 26.116 | −21.533 | 30.172 | 1.00 | 60.97  | C |
| ATOM | 7622 | CD1 | TYR | M | 87 | 26.593 | −20.135 | 32.044 | 1.00 | 61.22  | C |
| ATOM | 7623 | CE2 | TYR | M | 87 | 26.361 | −20.466 | 29.304 | 1.00 | 62.18  | C |
| ATOM | 7624 | CE1 | TYR | M | 87 | 26.812 | −19.053 | 31.186 | 1.00 | 61.78  | C |
| ATOM | 7625 | CZ  | TYR | M | 87 | 26.708 | −19.225 | 29.814 | 1.00 | 70.43  | C |
| ATOM | 7626 | OH  | TYR | M | 87 | 26.951 | −18.177 | 28.950 | 1.00 | 72.32  | O |
| ATOM | 7627 | N   | TYR | M | 88 | 23.381 | −24.776 | 33.060 | 1.00 | 65.88  | N |
| ATOM | 7628 | CA  | TYR | M | 88 | 23.042 | −26.073 | 33.648 | 1.00 | 65.44  | C |
| ATOM | 7629 | C   | TYR | M | 88 | 23.606 | −27.197 | 32.796 | 1.00 | 74.16  | C |
| ATOM | 7630 | O   | TYR | M | 88 | 23.556 | −27.119 | 31.567 | 1.00 | 74.12  | O |
| ATOM | 7631 | CB  | TYR | M | 88 | 21.517 | −26.263 | 33.795 | 1.00 | 64.37  | C |
| ATOM | 7632 | CG  | TYR | M | 88 | 20.796 | −25.190 | 34.575 | 1.00 | 63.82  | C |
| ATOM | 7633 | CD1 | TYR | M | 88 | 20.561 | −25.330 | 35.937 | 1.00 | 65.49  | C |
| ATOM | 7634 | CD2 | TYR | M | 88 | 20.268 | −24.078 | 33.937 | 1.00 | 64.05  | C |
| ATOM | 7635 | CE1 | TYR | M | 88 | 19.888 | −24.345 | 36.662 | 1.00 | 65.46  | C |
| ATOM | 7636 | CE2 | TYR | M | 88 | 19.589 | −23.093 | 34.645 | 1.00 | 64.61  | C |
| ATOM | 7637 | CZ  | TYR | M | 88 | 19.400 | −23.226 | 36.011 | 1.00 | 69.56  | C |
| ATOM | 7638 | OH  | TYR | M | 88 | 18.750 | −22.238 | 36.719 | 1.00 | 67.73  | O |
| ATOM | 7639 | N   | CYS | M | 89 | 24.161 | −28.228 | 33.438 | 1.00 | 73.84  | N |
| ATOM | 7640 | CA  | CYS | M | 89 | 24.590 | −29.389 | 32.708 | 1.00 | 76.04  | C |
| ATOM | 7641 | C   | CYS | M | 89 | 23.500 | −30.431 | 32.919 | 1.00 | 76.09  | C |
| ATOM | 7642 | O   | CYS | M | 89 | 22.698 | −30.279 | 33.832 | 1.00 | 74.76  | O |
| ATOM | 7643 | CB  | CYS | M | 89 | 25.991 | −29.875 | 33.085 | 1.00 | 79.22  | C |
| ATOM | 7644 | SG  | CYS | M | 89 | 26.200 | −30.375 | 34.816 | 1.00 | 85.08  | S |
| ATOM | 7645 | N   | GLN | M | 90 | 23.336 | −31.352 | 31.976 | 1.00 | 70.36  | N |
| ATOM | 7646 | CA  | GLN | M | 90 | 22.272 | −32.326 | 32.019 | 1.00 | 68.74  | C |
| ATOM | 7647 | C   | GLN | M | 90 | 22.819 | −33.665 | 31.630 | 1.00 | 73.99  | C |
| ATOM | 7648 | O   | GLN | M | 90 | 23.790 | −33.735 | 30.891 | 1.00 | 74.39  | O |
| ATOM | 7649 | CB  | GLN | M | 90 | 21.168 | −31.878 | 31.043 | 1.00 | 69.40  | C |
| ATOM | 7650 | CG  | GLN | M | 90 | 19.965 | −32.818 | 30.858 | 1.00 | 64.98  | C |
| ATOM | 7651 | CD  | GLN | M | 90 | 20.035 | −33.587 | 29.551 | 1.00 | 67.33  | C |
| ATOM | 7652 | OE1 | GLN | M | 90 | 20.030 | −33.021 | 28.456 | 1.00 | 61.54  | O |
| ATOM | 7653 | NE2 | GLN | M | 90 | 20.081 | −34.900 | 29.627 | 1.00 | 47.33  | N |
| ATOM | 7654 | N   | GLN | M | 91 | 22.179 | −34.734 | 32.093 | 1.00 | 71.53  | N |
| ATOM | 7655 | CA  | GLN | M | 91 | 22.531 | −36.110 | 31.746 | 1.00 | 71.32  | C |
| ATOM | 7656 | C   | GLN | M | 91 | 21.244 | −36.989 | 31.682 | 1.00 | 73.57  | C |

TABLE 1-continued

Three-dimensional crystal coordinate for anti-TcdB antibody beziotoxumab Fab –C. difficile toxin B (TcdB$^{(1834-2101)}$) complex.

| ATOM | 7657 | O | GLN | M | 91 | 20.224 | −36.630 | 32.262 | 1.00 | 72.54 | O |
|---|---|---|---|---|---|---|---|---|---|---|---|
| ATOM | 7658 | CB | GLN | M | 91 | 23.573 | −36.649 | 32.752 | 1.00 | 72.69 | C |
| ATOM | 7659 | CG | GLN | M | 91 | 23.878 | −38.138 | 32.669 | 1.00 | 97.58 | C |
| ATOM | 7660 | CD | GLN | M | 91 | 23.012 | −39.018 | 33.561 | 1.00 | 135.20 | C |
| ATOM | 7661 | OE1 | GLN | M | 91 | 23.164 | −40.247 | 33.577 | 1.00 | 137.74 | O |
| ATOM | 7662 | NE2 | GLN | M | 91 | 22.093 | −38.434 | 34.337 | 1.00 | 126.45 | N |
| ATOM | 7663 | N | TYR | M | 92 | 21.297 | −38.100 | 30.941 | 1.00 | 69.01 | N |
| ATOM | 7664 | CA | TYR | M | 92 | 20.250 | −39.110 | 30.871 | 1.00 | 68.58 | C |
| ATOM | 7665 | C | TYR | M | 92 | 20.888 | −40.433 | 31.256 | 1.00 | 74.67 | C |
| ATOM | 7666 | O | TYR | M | 92 | 22.040 | −40.692 | 30.910 | 1.00 | 74.91 | O |
| ATOM | 7667 | CB | TYR | M | 92 | 19.615 | −39.214 | 29.464 | 1.00 | 68.96 | C |
| ATOM | 7668 | CG | TYR | M | 92 | 18.699 | −40.415 | 29.302 | 1.00 | 68.08 | C |
| ATOM | 7669 | CD1 | TYR | M | 92 | 17.406 | −40.407 | 29.820 | 1.00 | 69.50 | C |
| ATOM | 7670 | CD2 | TYR | M | 92 | 19.144 | −41.574 | 28.679 | 1.00 | 68.06 | C |
| ATOM | 7671 | CE1 | TYR | M | 92 | 16.568 | −41.512 | 29.693 | 1.00 | 68.53 | C |
| ATOM | 7672 | CE2 | TYR | M | 92 | 18.312 | −42.682 | 28.535 | 1.00 | 68.69 | C |
| ATOM | 7673 | CZ | TYR | M | 92 | 17.026 | −42.646 | 29.044 | 1.00 | 76.90 | C |
| ATOM | 7674 | OH | TYR | M | 92 | 16.216 | −43.745 | 28.913 | 1.00 | 81.18 | O |
| ATOM | 7675 | N | GLY | M | 93 | 20.120 | −41.264 | 31.935 | 1.00 | 73.23 | N |
| ATOM | 7676 | CA | GLY | M | 93 | 20.536 | −42.586 | 32.384 | 1.00 | 74.06 | C |
| ATOM | 7677 | C | GLY | M | 93 | 19.415 | −43.253 | 33.153 | 1.00 | 81.29 | C |
| ATOM | 7678 | O | GLY | M | 93 | 18.614 | −42.563 | 33.805 | 1.00 | 81.98 | O |
| ATOM | 7679 | N | SER | M | 94 | 19.344 | −44.598 | 33.073 | 1.00 | 78.50 | N |
| ATOM | 7680 | CA | SER | M | 94 | 18.331 | −45.424 | 33.739 | 1.00 | 78.75 | C |
| ATOM | 7681 | C | SER | M | 94 | 16.920 | −44.780 | 33.670 | 1.00 | 83.47 | C |
| ATOM | 7682 | O | SER | M | 94 | 16.310 | −44.441 | 34.692 | 1.00 | 84.21 | O |
| ATOM | 7683 | CB | SER | M | 94 | 18.755 | −45.796 | 35.164 | 1.00 | 81.92 | C |
| ATOM | 7684 | OG | SER | M | 94 | 19.016 | −44.666 | 35.983 | 1.00 | 91.80 | O |
| ATOM | 7685 | N | SER | M | 95 | 16.461 | −44.541 | 32.427 | 1.00 | 78.65 | N |
| ATOM | 7686 | CA | SER | M | 95 | 15.143 | −44.000 | 32.065 | 1.00 | 77.45 | C |
| ATOM | 7687 | C | SER | M | 95 | 14.805 | −42.604 | 32.657 | 1.00 | 79.83 | C |
| ATOM | 7688 | O | SER | M | 95 | 13.643 | −42.179 | 32.555 | 1.00 | 80.57 | O |
| ATOM | 7689 | CB | SER | M | 95 | 14.044 | −45.010 | 32.397 | 1.00 | 79.36 | C |
| ATOM | 7690 | OG | SER | M | 95 | 14.403 | −46.313 | 31.960 | 1.00 | 85.33 | O |
| ATOM | 7691 | N | THR | M | 96 | 15.802 | −41.873 | 33.239 | 1.00 | 72.62 | N |
| ATOM | 7692 | CA | THR | M | 96 | 15.531 | −40.543 | 33.805 | 1.00 | 70.71 | C |
| ATOM | 7693 | C | THR | M | 96 | 16.577 | −39.505 | 33.370 | 1.00 | 72.02 | C |
| ATOM | 7694 | O | THR | M | 96 | 17.734 | −39.859 | 33.151 | 1.00 | 69.84 | O |
| ATOM | 7695 | CB | THR | M | 96 | 15.322 | −40.575 | 35.353 | 1.00 | 75.36 | C |
| ATOM | 7696 | OG1 | THR | M | 96 | 16.562 | −40.515 | 36.039 | 1.00 | 79.81 | O |
| ATOM | 7697 | CG2 | THR | M | 96 | 14.540 | −41.797 | 35.852 | 1.00 | 72.56 | C |
| ATOM | 7698 | N | TRP | M | 97 | 16.144 | −38.221 | 33.252 | 1.00 | 69.30 | N |
| ATOM | 7699 | CA | TRP | M | 97 | 16.927 | −37.020 | 32.893 | 1.00 | 69.28 | C |
| ATOM | 7700 | C | TRP | M | 97 | 17.254 | −36.203 | 34.169 | 1.00 | 74.52 | C |
| ATOM | 7701 | O | TRP | M | 97 | 16.347 | −35.841 | 34.920 | 1.00 | 74.72 | O |
| ATOM | 7702 | CB | TRP | M | 97 | 16.139 | −36.106 | 31.936 | 1.00 | 68.02 | C |
| ATOM | 7703 | CG | TRP | M | 97 | 16.170 | −36.479 | 30.486 | 1.00 | 69.44 | C |
| ATOM | 7704 | CD1 | TRP | M | 97 | 16.850 | −35.838 | 29.493 | 1.00 | 72.45 | C |
| ATOM | 7705 | CD2 | TRP | M | 97 | 15.391 | −37.499 | 29.844 | 1.00 | 69.35 | C |
| ATOM | 7706 | NE1 | TRP | M | 97 | 16.599 | −36.442 | 28.281 | 1.00 | 71.60 | N |
| ATOM | 7707 | CE2 | TRP | M | 97 | 15.696 | −37.456 | 28.467 | 1.00 | 72.93 | C |
| ATOM | 7708 | CE3 | TRP | M | 97 | 14.488 | −38.471 | 30.302 | 1.00 | 70.69 | C |
| ATOM | 7709 | CZ2 | TRP | M | 97 | 15.117 | −38.335 | 27.546 | 1.00 | 72.21 | C |
| ATOM | 7710 | CZ3 | TRP | M | 97 | 13.925 | −39.350 | 29.388 | 1.00 | 71.77 | C |
| ATOM | 7711 | CH2 | TRP | M | 97 | 14.244 | −39.280 | 28.031 | 1.00 | 72.23 | C |
| ATOM | 7712 | N | THR | M | 98 | 18.539 | −35.870 | 34.378 | 1.00 | 71.29 | N |
| ATOM | 7713 | CA | THR | M | 98 | 19.022 | −35.128 | 35.546 | 1.00 | 70.49 | C |
| ATOM | 7714 | C | THR | M | 98 | 19.715 | −33.835 | 35.135 | 1.00 | 73.37 | C |
| ATOM | 7715 | O | THR | M | 98 | 20.435 | −33.820 | 34.141 | 1.00 | 73.23 | O |
| ATOM | 7716 | CB | THR | M | 98 | 19.926 | −36.048 | 36.384 | 1.00 | 77.65 | C |
| ATOM | 7717 | OG1 | THR | M | 98 | 19.269 | −37.311 | 36.530 | 1.00 | 77.30 | O |
| ATOM | 7718 | CG2 | THR | M | 98 | 20.263 | −35.469 | 37.757 | 1.00 | 77.49 | C |
| ATOM | 7719 | N | PHE | M | 99 | 19.502 | −32.763 | 35.911 | 1.00 | 69.52 | N |
| ATOM | 7720 | CA | PHE | M | 99 | 20.119 | −31.458 | 35.691 | 1.00 | 69.85 | C |
| ATOM | 7721 | C | PHE | M | 99 | 21.062 | −31.098 | 36.840 | 1.00 | 75.69 | C |
| ATOM | 7722 | O | PHE | M | 99 | 20.946 | −31.638 | 37.946 | 1.00 | 76.62 | O |
| ATOM | 7723 | CB | PHE | M | 99 | 19.051 | −30.363 | 35.554 | 1.00 | 71.64 | C |
| ATOM | 7724 | CG | PHE | M | 99 | 18.306 | −30.357 | 34.241 | 1.00 | 72.97 | C |
| ATOM | 7725 | CD2 | PHE | M | 99 | 18.681 | −29.496 | 33.215 | 1.00 | 74.82 | C |
| ATOM | 7726 | CD1 | PHE | M | 99 | 17.217 | −31.200 | 34.035 | 1.00 | 75.20 | C |
| ATOM | 7727 | CE2 | PHE | M | 99 | 17.994 | −29.495 | 32.001 | 1.00 | 77.60 | C |
| ATOM | 7728 | CE1 | PHE | M | 99 | 16.521 | −31.188 | 32.825 | 1.00 | 75.89 | C |
| ATOM | 7729 | CZ | PHE | M | 99 | 16.909 | −30.330 | 31.818 | 1.00 | 75.60 | C |
| ATOM | 7730 | N | GLY | M | 100 | 22.003 | −30.200 | 36.550 | 1.00 | 71.75 | N |
| ATOM | 7731 | CA | GLY | M | 100 | 22.944 | −29.648 | 37.516 | 1.00 | 70.80 | C |
| ATOM | 7732 | C | GLY | M | 100 | 22.253 | −28.474 | 38.173 | 1.00 | 74.33 | C |
| ATOM | 7733 | O | GLY | M | 100 | 21.235 | −27.986 | 37.648 | 1.00 | 74.17 | O |

TABLE 1-continued

Three-dimensional crystal coordinate for anti-TcdB antibody beziotoxumab Fab –*C. difficile* toxin B (TcdB$^{(1834-2101)}$) complex.

| | | | | | | | | | | |
|---|---|---|---|---|---|---|---|---|---|---|
| ATOM | 7734 | N | GLN | M | 101 | 22.781 | −28.009 | 39.321 | 1.00 | 69.25 | N |
| ATOM | 7735 | CA | GLN | M | 101 | 22.138 | −26.919 | 40.050 | 1.00 | 68.83 | C |
| ATOM | 7736 | C | GLN | M | 101 | 22.396 | −25.512 | 39.430 | 1.00 | 73.59 | C |
| ATOM | 7737 | O | GLN | M | 101 | 21.750 | −24.534 | 39.825 | 1.00 | 73.35 | O |
| ATOM | 7738 | CB | GLN | M | 101 | 22.495 | −26.982 | 41.538 | 1.00 | 70.35 | C |
| ATOM | 7739 | CG | GLN | M | 101 | 23.844 | −26.355 | 41.937 | 1.00 | 103.67 | C |
| ATOM | 7740 | CD | GLN | M | 101 | 25.100 | −27.087 | 41.502 | 1.00 | 124.67 | C |
| ATOM | 7741 | OE1 | GLN | M | 101 | 25.134 | −28.318 | 41.293 | 1.00 | 118.07 | O |
| ATOM | 7742 | NE2 | GLN | M | 101 | 26.179 | −26.320 | 41.417 | 1.00 | 116.30 | N |
| ATOM | 7743 | N | GLY | M | 102 | 23.300 | −25.442 | 38.453 | 1.00 | 70.28 | N |
| ATOM | 7744 | CA | GLY | M | 102 | 23.651 | −24.210 | 37.766 | 1.00 | 69.62 | C |
| ATOM | 7745 | C | GLY | M | 102 | 24.940 | −23.567 | 38.242 | 1.00 | 73.46 | C |
| ATOM | 7746 | O | GLY | M | 102 | 25.466 | −23.889 | 39.314 | 1.00 | 71.71 | O |
| ATOM | 7747 | N | THR | M | 103 | 25.458 | −22.647 | 37.415 | 1.00 | 70.36 | N |
| ATOM | 7748 | CA | THR | M | 103 | 26.619 | −21.804 | 37.673 | 1.00 | 69.17 | C |
| ATOM | 7749 | C | THR | M | 103 | 26.247 | −20.437 | 37.064 | 1.00 | 71.30 | C |
| ATOM | 7750 | O | THR | M | 103 | 26.026 | −20.359 | 35.847 | 1.00 | 70.58 | O |
| ATOM | 7751 | CB | THR | M | 103 | 27.943 | −22.405 | 37.075 | 1.00 | 73.24 | C |
| ATOM | 7752 | OG1 | THR | M | 103 | 28.313 | −23.605 | 37.762 | 1.00 | 71.98 | O |
| ATOM | 7753 | CG2 | THR | M | 103 | 29.137 | −21.410 | 37.135 | 1.00 | 71.51 | C |
| ATOM | 7754 | N | LYS | M | 104 | 26.136 | −19.376 | 37.906 | 1.00 | 66.33 | N |
| ATOM | 7755 | CA | LYS | M | 104 | 25.878 | −18.028 | 37.383 | 1.00 | 65.48 | C |
| ATOM | 7756 | C | LYS | M | 104 | 27.226 | −17.445 | 36.887 | 1.00 | 69.38 | C |
| ATOM | 7757 | O | LYS | M | 104 | 28.290 | −17.746 | 37.448 | 1.00 | 67.87 | O |
| ATOM | 7758 | CB | LYS | M | 104 | 25.194 | −17.099 | 38.416 | 1.00 | 66.47 | C |
| ATOM | 7759 | N | VAL | M | 105 | 27.185 | −16.713 | 35.777 | 1.00 | 66.76 | N |
| ATOM | 7760 | CA | VAL | M | 105 | 28.370 | −16.056 | 35.251 | 1.00 | 67.67 | C |
| ATOM | 7761 | C | VAL | M | 105 | 28.093 | −14.574 | 35.377 | 1.00 | 76.97 | C |
| ATOM | 7762 | O | VAL | M | 105 | 27.282 | −14.006 | 34.638 | 1.00 | 78.29 | O |
| ATOM | 7763 | CB | VAL | M | 105 | 28.837 | −16.513 | 33.853 | 1.00 | 70.84 | C |
| ATOM | 7764 | CG1 | VAL | M | 105 | 30.141 | −15.815 | 33.470 | 1.00 | 70.79 | C |
| ATOM | 7765 | CG2 | VAL | M | 105 | 29.032 | −18.027 | 33.828 | 1.00 | 70.35 | C |
| ATOM | 7766 | N | GLU | M | 106 | 28.667 | −14.000 | 36.427 | 1.00 | 74.45 | N |
| ATOM | 7767 | CA | GLU | M | 106 | 28.500 | −12.622 | 36.841 | 1.00 | 74.93 | C |
| ATOM | 7768 | C | GLU | M | 106 | 29.615 | −11.743 | 36.250 | 1.00 | 78.42 | C |
| ATOM | 7769 | O | GLU | M | 106 | 30.712 | −12.246 | 35.990 | 1.00 | 78.99 | O |
| ATOM | 7770 | CB | GLU | M | 106 | 28.543 | −12.604 | 38.373 | 1.00 | 76.65 | C |
| ATOM | 7771 | CG | GLU | M | 106 | 28.117 | −11.300 | 39.012 | 1.00 | 87.72 | C |
| ATOM | 7772 | CD | GLU | M | 106 | 28.956 | −10.966 | 40.221 | 1.00 | 120.65 | C |
| ATOM | 7773 | OE1 | GLU | M | 106 | 30.166 | −10.692 | 40.046 | 1.00 | 116.45 | O |
| ATOM | 7774 | OE2 | GLU | M | 106 | 28.414 | −11.024 | 41.347 | 1.00 | 122.66 | O |
| ATOM | 7775 | N | ILE | M | 107 | 29.339 | −10.435 | 36.060 | 1.00 | 72.75 | N |
| ATOM | 7776 | CA | ILE | M | 107 | 30.301 | −9.489 | 35.500 | 1.00 | 71.74 | C |
| ATOM | 7777 | C | ILE | M | 107 | 31.189 | −8.954 | 36.605 | 1.00 | 75.97 | C |
| ATOM | 7778 | O | ILE | M | 107 | 30.676 | −8.246 | 37.472 | 1.00 | 75.84 | O |
| ATOM | 7779 | CB | ILE | M | 107 | 29.597 | −8.338 | 34.702 | 1.00 | 74.40 | C |
| ATOM | 7780 | CG1 | ILE | M | 107 | 28.476 | −8.889 | 33.775 | 1.00 | 75.02 | C |
| ATOM | 7781 | CG2 | ILE | M | 107 | 30.611 | −7.533 | 33.893 | 1.00 | 73.58 | C |
| ATOM | 7782 | CD1 | ILE | M | 107 | 27.262 | −8.003 | 33.477 | 1.00 | 80.17 | C |
| ATOM | 7783 | N | LYS | M | 108 | 32.516 | −9.297 | 36.600 | 1.00 | 72.99 | N |
| ATOM | 7784 | CA | LYS | M | 108 | 33.474 | −8.745 | 37.579 | 1.00 | 72.40 | C |
| ATOM | 7785 | C | LYS | M | 108 | 33.681 | −7.266 | 37.237 | 1.00 | 76.18 | C |
| ATOM | 7786 | O | LYS | M | 108 | 33.777 | −6.893 | 36.062 | 1.00 | 77.54 | O |
| ATOM | 7787 | CB | LYS | M | 108 | 34.830 | −9.482 | 37.626 | 1.00 | 74.35 | C |
| ATOM | 7788 | CG | LYS | M | 108 | 35.739 | −8.997 | 38.772 | 1.00 | 81.96 | C |
| ATOM | 7789 | CD | LYS | M | 108 | 36.424 | −10.131 | 39.539 | 1.00 | 90.23 | C |
| ATOM | 7790 | CE | LYS | M | 108 | 35.729 | −10.422 | 40.854 | 1.00 | 97.68 | C |
| ATOM | 7791 | NZ | LYS | M | 108 | 36.243 | −11.664 | 41.498 | 1.00 | 99.88 | N |
| ATOM | 7792 | N | ARG | M | 109 | 33.666 | −6.427 | 38.260 | 1.00 | 70.31 | N |
| ATOM | 7793 | CA | ARG | M | 109 | 33.884 | −4.991 | 38.137 | 1.00 | 68.59 | C |
| ATOM | 7794 | C | ARG | M | 109 | 34.538 | −4.513 | 39.446 | 1.00 | 73.22 | C |
| ATOM | 7795 | O | ARG | M | 109 | 34.675 | −5.291 | 40.410 | 1.00 | 71.26 | O |
| ATOM | 7796 | CB | ARG | M | 109 | 32.580 | −4.238 | 37.789 | 1.00 | 64.34 | C |
| ATOM | 7797 | CG | ARG | M | 109 | 31.578 | −4.172 | 38.922 | 1.00 | 66.86 | C |
| ATOM | 7798 | CD | ARG | M | 109 | 30.890 | −2.834 | 39.003 | 1.00 | 63.66 | C |
| ATOM | 7799 | NE | ARG | M | 109 | 31.745 | −1.805 | 39.577 | 1.00 | 71.48 | N |
| ATOM | 7800 | CZ | ARG | M | 109 | 31.515 | −0.502 | 39.483 | 1.00 | 90.80 | C |
| ATOM | 7801 | NH1 | ARG | M | 109 | 30.459 | −0.054 | 38.811 | 1.00 | 77.20 | N |
| ATOM | 7802 | NH2 | ARG | M | 109 | 32.347 | 0.368 | 40.041 | 1.00 | 81.07 | N |
| ATOM | 7803 | N | THR | M | 110 | 34.985 | −3.257 | 39.465 | 1.00 | 71.75 | N |
| ATOM | 7804 | CA | THR | M | 110 | 35.607 | −2.700 | 40.657 | 1.00 | 72.07 | C |
| ATOM | 7805 | C | THR | M | 110 | 34.622 | −2.633 | 41.810 | 1.00 | 76.56 | C |
| ATOM | 7806 | O | THR | M | 110 | 33.421 | −2.436 | 41.603 | 1.00 | 75.40 | O |
| ATOM | 7807 | CB | THR | M | 110 | 36.228 | −1.331 | 40.393 | 1.00 | 79.36 | C |
| ATOM | 7808 | OG1 | THR | M | 110 | 35.264 | −0.463 | 39.787 | 1.00 | 81.03 | O |
| ATOM | 7809 | CG2 | THR | M | 110 | 37.486 | −1.422 | 39.554 | 1.00 | 75.55 | C |
| ATOM | 7810 | N | VAL | M | 111 | 35.130 | −2.822 | 43.031 | 1.00 | 73.53 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 7811 | CA | VAL | M | 111 | 34.311 | −2.714 | 44.221 | 1.00 | 72.69 | C |
|---|---|---|---|---|---|---|---|---|---|---|---|
| ATOM | 7812 | C | VAL | M | 111 | 33.716 | −1.292 | 44.201 | 1.00 | 78.73 | C |
| ATOM | 7813 | O | VAL | M | 111 | 34.392 | −0.319 | 43.806 | 1.00 | 78.21 | O |
| ATOM | 7814 | CB | VAL | M | 111 | 35.136 | −3.026 | 45.484 | 1.00 | 75.37 | C |
| ATOM | 7815 | CG1 | VAL | M | 111 | 34.418 | −2.565 | 46.744 | 1.00 | 74.82 | C |
| ATOM | 7816 | CG2 | VAL | M | 111 | 35.486 | −4.512 | 45.569 | 1.00 | 74.57 | C |
| ATOM | 7817 | N | ALA | M | 112 | 32.408 | −1.229 | 44.478 | 1.00 | 76.54 | N |
| ATOM | 7818 | CA | ALA | M | 112 | 31.595 | −0.019 | 44.560 | 1.00 | 76.55 | C |
| ATOM | 7819 | C | ALA | M | 112 | 30.810 | −0.153 | 45.849 | 1.00 | 83.30 | C |
| ATOM | 7820 | O | ALA | M | 112 | 30.269 | −1.223 | 46.138 | 1.00 | 84.71 | O |
| ATOM | 7821 | CB | ALA | M | 112 | 30.651 | 0.075 | 43.367 | 1.00 | 76.93 | C |
| ATOM | 7822 | N | ALA | M | 113 | 30.802 | 0.897 | 46.660 | 1.00 | 79.51 | N |
| ATOM | 7823 | CA | ALA | M | 113 | 30.112 | 0.868 | 47.936 | 1.00 | 78.03 | C |
| ATOM | 7824 | C | ALA | M | 113 | 28.659 | 1.336 | 47.764 | 1.00 | 80.12 | C |
| ATOM | 7825 | O | ALA | M | 113 | 28.365 | 2.190 | 46.906 | 1.00 | 79.06 | O |
| ATOM | 7826 | CB | ALA | M | 113 | 30.849 | 1.737 | 48.936 | 1.00 | 78.65 | C |
| ATOM | 7827 | N | PRO | M | 114 | 27.722 | 0.774 | 48.555 | 1.00 | 76.20 | N |
| ATOM | 7828 | CA | PRO | M | 114 | 26.328 | 1.211 | 48.421 | 1.00 | 75.42 | C |
| ATOM | 7829 | C | PRO | M | 114 | 26.092 | 2.609 | 48.981 | 1.00 | 79.26 | C |
| ATOM | 7830 | O | PRO | M | 114 | 26.776 | 3.026 | 49.923 | 1.00 | 80.78 | O |
| ATOM | 7831 | CB | PRO | M | 114 | 25.555 | 0.170 | 49.241 | 1.00 | 76.78 | C |
| ATOM | 7832 | CG | PRO | M | 114 | 26.523 | −0.330 | 50.253 | 1.00 | 81.40 | C |
| ATOM | 7833 | CD | PRO | M | 114 | 27.878 | −0.253 | 49.614 | 1.00 | 77.61 | C |
| ATOM | 7834 | N | SER | M | 115 | 25.123 | 3.325 | 48.400 | 1.00 | 73.02 | N |
| ATOM | 7835 | CA | SER | M | 115 | 24.641 | 4.596 | 48.928 | 1.00 | 71.66 | C |
| ATOM | 7836 | C | SER | M | 115 | 23.456 | 4.079 | 49.745 | 1.00 | 74.29 | C |
| ATOM | 7837 | O | SER | M | 115 | 22.580 | 3.428 | 49.172 | 1.00 | 74.33 | O |
| ATOM | 7838 | CB | SER | M | 115 | 24.141 | 5.526 | 47.820 | 1.00 | 74.11 | C |
| ATOM | 7839 | OG | SER | M | 115 | 24.658 | 5.224 | 46.533 | 1.00 | 84.18 | O |
| ATOM | 7840 | N | VAL | M | 116 | 23.484 | 4.240 | 51.080 | 1.00 | 68.90 | N |
| ATOM | 7841 | CA | VAL | M | 116 | 22.415 | 3.725 | 51.956 | 1.00 | 67.19 | C |
| ATOM | 7842 | C | VAL | M | 116 | 21.334 | 4.802 | 52.198 | 1.00 | 72.40 | C |
| ATOM | 7843 | O | VAL | M | 116 | 21.662 | 5.987 | 52.267 | 1.00 | 73.57 | O |
| ATOM | 7844 | CB | VAL | M | 116 | 22.998 | 3.098 | 53.266 | 1.00 | 69.08 | C |
| ATOM | 7845 | CG1 | VAL | M | 116 | 21.910 | 2.466 | 54.125 | 1.00 | 68.56 | C |
| ATOM | 7846 | CG2 | VAL | M | 116 | 24.087 | 2.071 | 52.939 | 1.00 | 68.16 | C |
| ATOM | 7847 | N | PHE | M | 117 | 20.044 | 4.392 | 52.259 | 1.00 | 68.71 | N |
| ATOM | 7848 | CA | PHE | M | 117 | 18.884 | 5.272 | 52.506 | 1.00 | 68.31 | C |
| ATOM | 7849 | C | PHE | M | 117 | 17.840 | 4.537 | 53.344 | 1.00 | 72.63 | C |
| ATOM | 7850 | O | PHE | M | 117 | 17.534 | 3.392 | 53.037 | 1.00 | 73.06 | O |
| ATOM | 7851 | CB | PHE | M | 117 | 18.210 | 5.727 | 51.193 | 1.00 | 69.76 | C |
| ATOM | 7852 | CG | PHE | M | 117 | 19.079 | 6.469 | 50.214 | 1.00 | 71.83 | C |
| ATOM | 7853 | CD1 | PHE | M | 117 | 19.190 | 7.851 | 50.270 | 1.00 | 76.07 | C |
| ATOM | 7854 | CD2 | PHE | M | 117 | 19.761 | 5.789 | 49.206 | 1.00 | 74.95 | C |
| ATOM | 7855 | CE1 | PHE | M | 117 | 19.986 | 8.545 | 49.344 | 1.00 | 77.44 | C |
| ATOM | 7856 | CE2 | PHE | M | 117 | 20.556 | 6.479 | 48.282 | 1.00 | 78.21 | C |
| ATOM | 7857 | CZ | PHE | M | 117 | 20.664 | 7.855 | 48.359 | 1.00 | 76.29 | C |
| ATOM | 7858 | N | ILE | M | 118 | 17.289 | 5.188 | 54.387 | 1.00 | 68.60 | N |
| ATOM | 7859 | CA | ILE | M | 118 | 16.218 | 4.641 | 55.229 | 1.00 | 68.31 | C |
| ATOM | 7860 | C | ILE | M | 118 | 14.925 | 5.442 | 54.985 | 1.00 | 74.55 | C |
| ATOM | 7861 | O | ILE | M | 118 | 14.982 | 6.668 | 54.804 | 1.00 | 75.09 | O |
| ATOM | 7862 | CB | ILE | M | 118 | 16.587 | 4.506 | 56.739 | 1.00 | 71.06 | C |
| ATOM | 7863 | CG1 | ILE | M | 118 | 15.573 | 3.581 | 57.498 | 1.00 | 70.31 | C |
| ATOM | 7864 | CG2 | ILE | M | 118 | 16.745 | 5.899 | 57.407 | 1.00 | 72.55 | C |
| ATOM | 7865 | CD1 | ILE | M | 118 | 15.887 | 3.222 | 58.910 | 1.00 | 70.07 | C |
| ATOM | 7866 | N | PHE | M | 119 | 13.771 | 4.737 | 54.947 | 1.00 | 71.64 | N |
| ATOM | 7867 | CA | PHE | M | 119 | 12.454 | 5.329 | 54.736 | 1.00 | 71.38 | C |
| ATOM | 7868 | C | PHE | M | 119 | 11.512 | 4.897 | 55.856 | 1.00 | 78.77 | C |
| ATOM | 7869 | O | PHE | M | 119 | 11.369 | 3.695 | 56.120 | 1.00 | 79.48 | O |
| ATOM | 7870 | CB | PHE | M | 119 | 11.871 | 4.968 | 53.360 | 1.00 | 72.44 | C |
| ATOM | 7871 | CG | PHE | M | 119 | 12.731 | 5.365 | 52.183 | 1.00 | 73.57 | C |
| ATOM | 7872 | CD1 | PHE | M | 119 | 12.650 | 6.644 | 51.641 | 1.00 | 76.47 | C |
| ATOM | 7873 | CD2 | PHE | M | 119 | 13.628 | 4.460 | 51.612 | 1.00 | 74.60 | C |
| ATOM | 7874 | CE1 | PHE | M | 119 | 13.460 | 7.020 | 50.552 | 1.00 | 76.76 | C |
| ATOM | 7875 | CE2 | PHE | M | 119 | 14.439 | 4.837 | 50.529 | 1.00 | 77.12 | C |
| ATOM | 7876 | CZ | PHE | M | 119 | 14.342 | 6.113 | 49.998 | 1.00 | 75.24 | C |
| ATOM | 7877 | N | PRO | M | 120 | 10.886 | 5.870 | 56.549 | 1.00 | 76.16 | N |
| ATOM | 7878 | CA | PRO | M | 120 | 9.947 | 5.522 | 57.628 | 1.00 | 76.00 | C |
| ATOM | 7879 | C | PRO | M | 120 | 8.555 | 5.166 | 57.075 | 1.00 | 78.32 | C |
| ATOM | 7880 | O | PRO | M | 120 | 8.249 | 5.549 | 55.934 | 1.00 | 76.57 | O |
| ATOM | 7881 | CB | PRO | M | 120 | 9.895 | 6.814 | 58.469 | 1.00 | 77.89 | C |
| ATOM | 7882 | CG | PRO | M | 120 | 10.853 | 7.800 | 57.793 | 1.00 | 82.08 | C |
| ATOM | 7883 | CD | PRO | M | 120 | 10.977 | 7.332 | 56.392 | 1.00 | 77.83 | C |
| ATOM | 7884 | N | PRO | M | 121 | 7.681 | 4.472 | 57.856 | 1.00 | 75.39 | N |
| ATOM | 7885 | CA | PRO | M | 121 | 6.330 | 4.171 | 57.346 | 1.00 | 76.10 | C |
| ATOM | 7886 | C | PRO | M | 121 | 5.493 | 5.433 | 57.101 | 1.00 | 84.80 | C |
| ATOM | 7887 | O | PRO | M | 121 | 5.467 | 6.307 | 57.962 | 1.00 | 85.61 | O |

TABLE 1-continued

Three-dimensional crystal coordinate for anti-TcdB antibody beziotoxumab
Fab –*C. difficile* toxin B (TcdB$^{(1834-2101)}$) complex.

| ATOM | 7888 | CB | PRO | M | 121 | 5.708 | 3.296 | 58.448 | 1.00 | 77.23 | C |
|---|---|---|---|---|---|---|---|---|---|---|---|
| ATOM | 7889 | CG | PRO | M | 121 | 6.483 | 3.564 | 59.639 | 1.00 | 81.02 | C |
| ATOM | 7890 | CD | PRO | M | 121 | 7.872 | 3.924 | 59.214 | 1.00 | 76.61 | C |
| ATOM | 7891 | N | SER | M | 122 | 4.810 | 5.530 | 55.938 | 1.00 | 84.30 | N |
| ATOM | 7892 | CA | SER | M | 122 | 3.952 | 6.675 | 55.594 | 1.00 | 85.59 | C |
| ATOM | 7893 | C | SER | M | 122 | 2.778 | 6.837 | 56.583 | 1.00 | 93.22 | C |
| ATOM | 7894 | O | SER | M | 122 | 2.452 | 5.884 | 57.311 | 1.00 | 92.20 | O |
| ATOM | 7895 | CB | SER | M | 122 | 3.429 | 6.554 | 54.164 | 1.00 | 88.65 | C |
| ATOM | 7896 | OG | SER | M | 122 | 2.751 | 5.323 | 53.983 | 1.00 | 98.43 | O |
| ATOM | 7897 | N | ASP | M | 123 | 2.171 | 8.054 | 56.634 | 1.00 | 92.40 | N |
| ATOM | 7898 | CA | ASP | M | 123 | 1.040 | 8.316 | 57.526 | 1.00 | 93.40 | C |
| ATOM | 7899 | C | ASP | M | 123 | −0.174 | 7.486 | 57.099 | 1.00 | 98.68 | C |
| ATOM | 7900 | O | ASP | M | 123 | −0.824 | 6.877 | 57.963 | 1.00 | 97.76 | O |
| ATOM | 7901 | CB | ASP | M | 123 | 0.710 | 9.815 | 57.611 | 1.00 | 95.72 | C |
| ATOM | 7902 | CG | ASP | M | 123 | 1.765 | 10.678 | 58.294 | 1.00 | 106.59 | C |
| ATOM | 7903 | OD1 | ASP | M | 123 | 2.206 | 10.317 | 59.418 | 1.00 | 105.62 | O |
| ATOM | 7904 | OD2 | ASP | M | 123 | 2.094 | 11.745 | 57.745 | 1.00 | 115.47 | O |
| ATOM | 7905 | N | GLU | M | 124 | −0.410 | 7.392 | 55.754 | 1.00 | 96.41 | N |
| ATOM | 7906 | CA | GLU | M | 124 | −1.479 | 6.585 | 55.143 | 1.00 | 96.83 | C |
| ATOM | 7907 | C | GLU | M | 124 | −1.400 | 5.135 | 55.652 | 1.00 | 100.75 | C |
| ATOM | 7908 | O | GLU | M | 124 | −2.416 | 4.576 | 56.075 | 1.00 | 101.26 | O |
| ATOM | 7909 | CB | GLU | M | 124 | −1.369 | 6.539 | 53.603 | 1.00 | 98.53 | C |
| ATOM | 7910 | CG | GLU | M | 124 | −1.117 | 7.841 | 52.865 | 1.00 | 113.72 | C |
| ATOM | 7911 | CD | GLU | M | 124 | −1.021 | 7.679 | 51.352 | 1.00 | 143.08 | C |
| ATOM | 7912 | OE1 | GLU | M | 124 | −0.250 | 8.447 | 50.730 | 1.00 | 148.48 | O |
| ATOM | 7913 | OE2 | GLU | M | 124 | −1.721 | 6.803 | 50.785 | 1.00 | 128.78 | O |
| ATOM | 7914 | N | GLN | M | 125 | −0.185 | 4.535 | 55.602 | 1.00 | 95.87 | N |
| ATOM | 7915 | CA | GLN | M | 125 | 0.077 | 3.163 | 56.028 | 1.00 | 94.83 | C |
| ATOM | 7916 | C | GLN | M | 125 | −0.131 | 2.980 | 57.511 | 1.00 | 97.86 | C |
| ATOM | 7917 | O | GLN | M | 125 | −0.597 | 1.921 | 57.927 | 1.00 | 96.81 | O |
| ATOM | 7918 | CB | GLN | M | 125 | 1.489 | 2.721 | 55.629 | 1.00 | 95.88 | C |
| ATOM | 7919 | CG | GLN | M | 125 | 1.641 | 1.210 | 55.603 | 1.00 | 99.10 | C |
| ATOM | 7920 | CD | GLN | M | 125 | 3.037 | 0.731 | 55.850 | 1.00 | 110.83 | C |
| ATOM | 7921 | OE1 | GLN | M | 125 | 4.038 | 1.453 | 55.670 | 1.00 | 100.61 | O |
| ATOM | 7922 | NE2 | GLN | M | 125 | 3.117 | −0.528 | 56.253 | 1.00 | 104.86 | N |
| ATOM | 7923 | N | LEU | M | 126 | 0.219 | 3.999 | 58.305 | 1.00 | 95.29 | N |
| ATOM | 7924 | CA | LEU | M | 126 | 0.082 | 3.941 | 59.753 | 1.00 | 95.51 | C |
| ATOM | 7925 | C | LEU | M | 126 | −1.379 | 3.980 | 60.227 | 1.00 | 100.64 | C |
| ATOM | 7926 | O | LEU | M | 126 | −1.661 | 3.461 | 61.312 | 1.00 | 99.93 | O |
| ATOM | 7927 | CB | LEU | M | 126 | 0.941 | 5.010 | 60.430 | 1.00 | 95.44 | C |
| ATOM | 7928 | CG | LEU | M | 126 | 2.375 | 4.577 | 60.709 | 1.00 | 100.13 | C |
| ATOM | 7929 | CD1 | LEU | M | 126 | 3.252 | 5.763 | 61.016 | 1.00 | 100.47 | C |
| ATOM | 7930 | CD2 | LEU | M | 126 | 2.433 | 3.542 | 61.827 | 1.00 | 102.38 | C |
| ATOM | 7931 | N | LYS | M | 127 | −2.310 | 4.544 | 59.399 | 1.00 | 97.62 | N |
| ATOM | 7932 | CA | LYS | M | 127 | −3.759 | 4.589 | 59.668 | 1.00 | 96.98 | C |
| ATOM | 7933 | C | LYS | M | 127 | −4.268 | 3.135 | 59.787 | 1.00 | 100.53 | C |
| ATOM | 7934 | O | LYS | M | 127 | −4.966 | 2.807 | 60.755 | 1.00 | 100.35 | O |
| ATOM | 7935 | CB | LYS | M | 127 | −4.511 | 5.384 | 58.583 | 1.00 | 98.80 | C |
| ATOM | 7936 | N | SER | M | 128 | −3.841 | 2.250 | 58.849 | 1.00 | 96.28 | N |
| ATOM | 7937 | CA | SER | M | 128 | −4.102 | 0.808 | 58.925 | 1.00 | 95.84 | C |
| ATOM | 7938 | C | SER | M | 128 | −3.079 | 0.270 | 59.955 | 1.00 | 99.50 | C |
| ATOM | 7939 | O | SER | M | 128 | −2.019 | 0.875 | 60.134 | 1.00 | 100.36 | O |
| ATOM | 7940 | CB | SER | M | 128 | −3.925 | 0.146 | 57.561 | 1.00 | 99.00 | C |
| ATOM | 7941 | OG | SER | M | 128 | −2.672 | 0.452 | 56.971 | 1.00 | 107.09 | O |
| ATOM | 7942 | N | GLY | M | 129 | −3.409 | −0.805 | 60.653 | 1.00 | 94.41 | N |
| ATOM | 7943 | CA | GLY | M | 129 | −2.570 | −1.331 | 61.731 | 1.00 | 93.97 | C |
| ATOM | 7944 | C | GLY | M | 129 | −1.195 | −1.910 | 61.433 | 1.00 | 97.27 | C |
| ATOM | 7945 | O | GLY | M | 129 | −0.747 | −2.781 | 62.186 | 1.00 | 96.78 | O |
| ATOM | 7946 | N | THR | M | 130 | −0.488 | −1.419 | 60.371 | 1.00 | 92.89 | N |
| ATOM | 7947 | CA | THR | M | 130 | 0.847 | −1.919 | 59.984 | 1.00 | 91.42 | C |
| ATOM | 7948 | C | THR | M | 130 | 1.822 | −0.779 | 59.597 | 1.00 | 92.85 | C |
| ATOM | 7949 | O | THR | M | 130 | 1.417 | 0.234 | 59.021 | 1.00 | 91.01 | O |
| ATOM | 7950 | CB | THR | M | 130 | 0.710 | −3.022 | 58.898 | 1.00 | 90.13 | C |
| ATOM | 7951 | OG1 | THR | M | 130 | 0.220 | −4.208 | 59.535 | 1.00 | 83.52 | O |
| ATOM | 7952 | CG2 | THR | M | 130 | 2.028 | −3.342 | 58.173 | 1.00 | 84.47 | C |
| ATOM | 7953 | N | ALA | M | 131 | 3.118 | −0.985 | 59.948 | 1.00 | 89.07 | N |
| ATOM | 7954 | CA | ALA | M | 131 | 4.281 | −0.122 | 59.694 | 1.00 | 88.19 | C |
| ATOM | 7955 | C | ALA | M | 131 | 5.389 | −0.889 | 58.953 | 1.00 | 89.81 | C |
| ATOM | 7956 | O | ALA | M | 131 | 5.852 | −1.941 | 59.409 | 1.00 | 88.35 | O |
| ATOM | 7957 | CB | ALA | M | 131 | 4.827 | 0.431 | 61.000 | 1.00 | 88.88 | C |
| ATOM | 7958 | N | SER | M | 132 | 5.799 | −0.346 | 57.802 | 1.00 | 85.66 | N |
| ATOM | 7959 | CA | SER | M | 132 | 6.844 | −0.895 | 56.945 | 1.00 | 84.62 | C |
| ATOM | 7960 | C | SER | M | 132 | 8.003 | 0.094 | 56.828 | 1.00 | 83.81 | C |
| ATOM | 7961 | O | SER | M | 132 | 7.846 | 1.200 | 56.294 | 1.00 | 82.31 | O |
| ATOM | 7962 | CB | SER | M | 132 | 6.290 | −1.265 | 55.566 | 1.00 | 89.81 | C |
| ATOM | 7963 | OG | SER | M | 132 | 5.374 | −2.348 | 55.639 | 1.00 | 101.31 | O |
| ATOM | 7964 | N | VAL | M | 133 | 9.155 | −0.303 | 57.375 | 1.00 | 78.33 | N |

TABLE 1-continued

Three-dimensional crystal coordinate for anti-TcdB antibody beziotoxumab Fab –*C. difficile* toxin B (TcdB$^{(1834-2101)}$) complex.

| ATOM | 7965 | CA | VAL | M | 133 | 10.387 | 0.485 | 57.357 | 1.00 | 76.97 | C |
|------|------|-----|-----|---|-----|--------|--------|--------|------|-------|---|
| ATOM | 7966 | C | VAL | M | 133 | 11.276 | −0.083 | 56.255 | 1.00 | 78.70 | C |
| ATOM | 7967 | O | VAL | M | 133 | 11.515 | −1.287 | 56.226 | 1.00 | 76.34 | O |
| ATOM | 7968 | CB | VAL | M | 133 | 11.114 | 0.519 | 58.723 | 1.00 | 79.88 | C |
| ATOM | 7969 | CG1 | VAL | M | 133 | 12.047 | 1.715 | 58.787 | 1.00 | 79.44 | C |
| ATOM | 7970 | CG2 | VAL | M | 133 | 10.127 | 0.539 | 59.891 | 1.00 | 79.19 | C |
| ATOM | 7971 | N | VAL | M | 134 | 11.748 | 0.781 | 55.349 | 1.00 | 75.97 | N |
| ATOM | 7972 | CA | VAL | M | 134 | 12.537 | 0.374 | 54.180 | 1.00 | 75.62 | C |
| ATOM | 7973 | C | VAL | M | 134 | 13.994 | 0.895 | 54.179 | 1.00 | 79.01 | C |
| ATOM | 7974 | O | VAL | M | 134 | 14.226 | 2.100 | 54.197 | 1.00 | 77.94 | O |
| ATOM | 7975 | CB | VAL | M | 134 | 11.797 | 0.767 | 52.861 | 1.00 | 78.66 | C |
| ATOM | 7976 | CG1 | VAL | M | 134 | 12.534 | 0.251 | 51.625 | 1.00 | 77.85 | C |
| ATOM | 7977 | CG2 | VAL | M | 134 | 10.347 | 0.288 | 52.868 | 1.00 | 78.15 | C |
| ATOM | 7978 | N | CYS | M | 135 | 14.950 | −0.026 | 54.042 | 1.00 | 76.33 | N |
| ATOM | 7979 | CA | CYS | M | 135 | 16.384 | 0.249 | 53.937 | 1.00 | 76.75 | C |
| ATOM | 7980 | C | CYS | M | 135 | 16.858 | −0.042 | 52.493 | 1.00 | 76.94 | C |
| ATOM | 7981 | O | CYS | M | 135 | 16.818 | −1.194 | 52.064 | 1.00 | 76.37 | O |
| ATOM | 7982 | CB | CYS | M | 135 | 17.154 | −0.584 | 54.957 | 1.00 | 78.31 | C |
| ATOM | 7983 | SG | CYS | M | 135 | 18.895 | −0.133 | 55.131 | 1.00 | 82.90 | S |
| ATOM | 7984 | N | LEU | M | 136 | 17.282 | 1.005 | 51.747 | 1.00 | 71.06 | N |
| ATOM | 7985 | CA | LEU | M | 136 | 17.770 | 0.929 | 50.358 | 1.00 | 69.29 | C |
| ATOM | 7986 | C | LEU | M | 136 | 19.306 | 1.002 | 50.262 | 1.00 | 73.49 | C |
| ATOM | 7987 | O | LEU | M | 136 | 19.906 | 1.929 | 50.811 | 1.00 | 73.15 | O |
| ATOM | 7988 | CB | LEU | M | 136 | 17.133 | 2.027 | 49.466 | 1.00 | 68.10 | C |
| ATOM | 7989 | CG | LEU | M | 136 | 17.769 | 2.238 | 48.080 | 1.00 | 71.48 | C |
| ATOM | 7990 | CD1 | LEU | M | 136 | 17.524 | 1.038 | 47.158 | 1.00 | 71.63 | C |
| ATOM | 7991 | CD2 | LEU | M | 136 | 17.281 | 3.514 | 47.440 | 1.00 | 72.61 | C |
| ATOM | 7992 | N | LEU | M | 137 | 19.918 | 0.034 | 49.520 | 1.00 | 68.88 | N |
| ATOM | 7993 | CA | LEU | M | 137 | 21.364 | −0.067 | 49.220 | 1.00 | 66.96 | C |
| ATOM | 7994 | C | LEU | M | 137 | 21.500 | 0.180 | 47.700 | 1.00 | 72.11 | C |
| ATOM | 7995 | O | LEU | M | 137 | 21.305 | −0.733 | 46.901 | 1.00 | 71.80 | O |
| ATOM | 7996 | CB | LEU | M | 137 | 21.929 | −1.456 | 49.612 | 1.00 | 65.00 | C |
| ATOM | 7997 | CG | LEU | M | 137 | 22.134 | −1.749 | 51.090 | 1.00 | 66.10 | C |
| ATOM | 7998 | CD1 | LEU | M | 137 | 20.816 | −1.898 | 51.829 | 1.00 | 64.63 | C |
| ATOM | 7999 | CD2 | LEU | M | 137 | 22.952 | −2.996 | 51.262 | 1.00 | 65.13 | C |
| ATOM | 8000 | N | ASN | M | 138 | 21.738 | 1.433 | 47.306 | 1.00 | 69.09 | N |
| ATOM | 8001 | CA | ASN | M | 138 | 21.787 | 1.793 | 45.893 | 1.00 | 69.48 | C |
| ATOM | 8002 | C | ASN | M | 138 | 23.155 | 1.494 | 45.243 | 1.00 | 76.72 | C |
| ATOM | 8003 | O | ASN | M | 138 | 24.209 | 1.688 | 45.856 | 1.00 | 77.63 | O |
| ATOM | 8004 | CB | ASN | M | 138 | 21.340 | 3.247 | 45.687 | 1.00 | 67.60 | C |
| ATOM | 8005 | CG | ASN | M | 138 | 21.177 | 3.637 | 44.250 | 1.00 | 99.03 | C |
| ATOM | 8006 | OD1 | ASN | M | 138 | 20.156 | 3.363 | 43.618 | 1.00 | 89.53 | O |
| ATOM | 8007 | ND2 | ASN | M | 138 | 22.196 | 4.278 | 43.694 | 1.00 | 99.70 | N |
| ATOM | 8008 | N | ASN | M | 139 | 23.097 | 0.981 | 44.001 | 1.00 | 73.16 | N |
| ATOM | 8009 | CA | ASN | M | 139 | 24.176 | 0.623 | 43.079 | 1.00 | 71.78 | C |
| ATOM | 8010 | C | ASN | M | 139 | 25.526 | 0.249 | 43.736 | 1.00 | 71.84 | C |
| ATOM | 8011 | O | ASN | M | 139 | 26.491 | 1.016 | 43.672 | 1.00 | 71.48 | O |
| ATOM | 8012 | CB | ASN | M | 139 | 24.354 | 1.726 | 42.040 | 1.00 | 74.26 | C |
| ATOM | 8013 | CG | ASN | M | 139 | 23.185 | 1.859 | 41.106 | 1.00 | 106.94 | C |
| ATOM | 8014 | OD1 | ASN | M | 139 | 22.626 | 2.944 | 40.935 | 1.00 | 102.43 | O |
| ATOM | 8015 | ND2 | ASN | M | 139 | 22.773 | 0.752 | 40.500 | 1.00 | 106.65 | N |
| ATOM | 8016 | N | PHE | M | 140 | 25.592 | −0.957 | 44.320 | 1.00 | 66.60 | N |
| ATOM | 8017 | CA | PHE | M | 140 | 26.805 | −1.503 | 44.938 | 1.00 | 65.79 | C |
| ATOM | 8018 | C | PHE | M | 140 | 27.355 | −2.728 | 44.177 | 1.00 | 70.66 | C |
| ATOM | 8019 | O | PHE | M | 140 | 26.679 | −3.270 | 43.312 | 1.00 | 68.97 | O |
| ATOM | 8020 | CB | PHE | M | 140 | 26.546 | −1.857 | 46.408 | 1.00 | 67.59 | C |
| ATOM | 8021 | CG | PHE | M | 140 | 25.604 | −3.013 | 46.657 | 1.00 | 69.36 | C |
| ATOM | 8022 | CD1 | PHE | M | 140 | 26.077 | −4.314 | 46.718 | 1.00 | 73.26 | C |
| ATOM | 8023 | CD2 | PHE | M | 140 | 24.253 | −2.796 | 46.864 | 1.00 | 71.82 | C |
| ATOM | 8024 | CE1 | PHE | M | 140 | 25.207 | −5.384 | 46.931 | 1.00 | 74.74 | C |
| ATOM | 8025 | CE2 | PHE | M | 140 | 23.383 | −3.869 | 47.079 | 1.00 | 75.24 | C |
| ATOM | 8026 | CZ | PHE | M | 140 | 23.871 | −5.155 | 47.133 | 1.00 | 73.84 | C |
| ATOM | 8027 | N | TYR | M | 141 | 28.572 | −3.176 | 44.536 | 1.00 | 70.90 | N |
| ATOM | 8028 | CA | TYR | M | 141 | 29.267 | −4.343 | 43.975 | 1.00 | 72.34 | C |
| ATOM | 8029 | C | TYR | M | 141 | 30.456 | −4.802 | 44.873 | 1.00 | 75.79 | C |
| ATOM | 8030 | O | TYR | M | 141 | 31.255 | −3.949 | 45.259 | 1.00 | 75.05 | O |
| ATOM | 8031 | CB | TYR | M | 141 | 29.767 | −4.082 | 42.531 | 1.00 | 75.09 | C |
| ATOM | 8032 | CG | TYR | M | 141 | 30.396 | −5.321 | 41.951 | 1.00 | 78.94 | C |
| ATOM | 8033 | CD1 | TYR | M | 141 | 29.631 | −6.255 | 41.259 | 1.00 | 81.70 | C |
| ATOM | 8034 | CD2 | TYR | M | 141 | 31.738 | −5.615 | 42.178 | 1.00 | 80.12 | C |
| ATOM | 8035 | CE1 | TYR | M | 141 | 30.181 | −7.457 | 40.825 | 1.00 | 84.27 | C |
| ATOM | 8036 | CE2 | TYR | M | 141 | 32.295 | −6.818 | 41.761 | 1.00 | 81.26 | C |
| ATOM | 8037 | CZ | TYR | M | 141 | 31.519 | −7.726 | 41.064 | 1.00 | 89.64 | C |

TABLE 1-continued

Three-dimensional crystal coordinate for anti-TcdB antibody beziotoxumab
Fab –*C. difficile* toxin B (TcdB$^{(1834\text{-}2101)}$) complex.

| ATOM | 8038 | OH | TYR | M | 141 | 32.081 | −8.904 | 40.650 | 1.00 | 90.24 | O |
| ATOM | 8039 | N | PRO | M | 142 | 30.659 | −6.119 | 45.172 | 1.00 | 72.48 | N |
| ATOM | 8040 | CA | PRO | M | 142 | 29.855 | −7.300 | 44.795 | 1.00 | 72.32 | C |
| ATOM | 8041 | C | PRO | M | 142 | 28.531 | −7.401 | 45.531 | 1.00 | 76.51 | C |
| ATOM | 8042 | O | PRO | M | 142 | 28.262 | −6.566 | 46.399 | 1.00 | 75.57 | O |
| ATOM | 8043 | CB | PRO | M | 142 | 30.798 | −8.472 | 45.097 | 1.00 | 73.69 | C |
| ATOM | 8044 | CG | PRO | M | 142 | 31.643 | −7.994 | 46.205 | 1.00 | 77.85 | C |
| ATOM | 8045 | CD | PRO | M | 142 | 31.824 | −6.514 | 45.990 | 1.00 | 73.65 | C |
| ATOM | 8046 | N | ARG | M | 143 | 27.679 | −8.416 | 45.158 | 1.00 | 73.22 | N |
| ATOM | 8047 | CA | ARG | M | 143 | 26.337 | −8.669 | 45.737 | 1.00 | 71.94 | C |
| ATOM | 8048 | C | ARG | M | 143 | 26.355 | −8.838 | 47.280 | 1.00 | 74.95 | C |
| ATOM | 8049 | O | ARG | M | 143 | 25.393 | −8.413 | 47.933 | 1.00 | 74.63 | O |
| ATOM | 8050 | CB | ARG | M | 143 | 25.600 | −9.847 | 45.045 | 1.00 | 67.15 | C |
| ATOM | 8051 | N | GLU | M | 144 | 27.460 | −9.391 | 47.856 | 1.00 | 70.59 | N |
| ATOM | 8052 | CA | GLU | M | 144 | 27.602 | −9.617 | 49.303 | 1.00 | 70.76 | C |
| ATOM | 8053 | C | GLU | M | 144 | 27.456 | −8.331 | 50.134 | 1.00 | 74.61 | C |
| ATOM | 8054 | O | GLU | M | 144 | 28.291 | −7.414 | 50.088 | 1.00 | 73.94 | O |
| ATOM | 8055 | CB | GLU | M | 144 | 28.885 | −10.377 | 49.667 | 1.00 | 72.34 | C |
| ATOM | 8056 | CG | GLU | M | 144 | 29.018 | −11.737 | 49.006 | 1.00 | 84.65 | C |
| ATOM | 8057 | CD | GLU | M | 144 | 29.595 | −11.704 | 47.600 | 1.00 | 110.96 | C |
| ATOM | 8058 | OE1 | GLU | M | 144 | 30.748 | −11.237 | 47.433 | 1.00 | 100.79 | O |
| ATOM | 8059 | OE2 | GLU | M | 144 | 28.890 | −12.156 | 46.667 | 1.00 | 101.82 | O |
| ATOM | 8060 | N | ALA | M | 145 | 26.337 | −8.285 | 50.865 | 1.00 | 71.23 | N |
| ATOM | 8061 | CA | ALA | M | 145 | 25.909 | −7.195 | 51.734 | 1.00 | 71.02 | C |
| ATOM | 8062 | C | ALA | M | 145 | 25.105 | −7.757 | 52.935 | 1.00 | 76.17 | C |
| ATOM | 8063 | O | ALA | M | 145 | 24.260 | −8.638 | 52.747 | 1.00 | 75.30 | O |
| ATOM | 8064 | CB | ALA | M | 145 | 25.056 | −6.209 | 50.941 | 1.00 | 71.13 | C |
| ATOM | 8065 | N | LYS | M | 146 | 25.408 | −7.281 | 54.166 | 1.00 | 74.50 | N |
| ATOM | 8066 | CA | LYS | M | 146 | 24.698 | −7.673 | 55.393 | 1.00 | 75.21 | C |
| ATOM | 8067 | C | LYS | M | 146 | 23.890 | −6.468 | 55.846 | 1.00 | 79.39 | C |
| ATOM | 8068 | O | LYS | M | 146 | 24.462 | −5.394 | 56.032 | 1.00 | 79.23 | O |
| ATOM | 8069 | CB | LYS | M | 146 | 25.646 | −8.147 | 56.526 | 1.00 | 77.49 | C |
| ATOM | 8070 | N | VAL | M | 147 | 22.558 | −6.623 | 55.955 | 1.00 | 75.21 | N |
| ATOM | 8071 | CA | VAL | M | 147 | 21.666 | −5.548 | 56.404 | 1.00 | 74.51 | C |
| ATOM | 8072 | C | VAL | M | 147 | 21.040 | −5.999 | 57.701 | 1.00 | 78.78 | C |
| ATOM | 8073 | O | VAL | M | 147 | 20.322 | −7.003 | 57.744 | 1.00 | 78.63 | O |
| ATOM | 8074 | CB | VAL | M | 147 | 20.624 | −5.086 | 55.354 | 1.00 | 77.72 | C |
| ATOM | 8075 | CG1 | VAL | M | 147 | 19.755 | −3.962 | 55.896 | 1.00 | 77.14 | C |
| ATOM | 8076 | CG2 | VAL | M | 147 | 21.302 | −4.647 | 54.065 | 1.00 | 77.31 | C |
| ATOM | 8077 | N | GLN | M | 148 | 21.370 | −5.289 | 58.770 | 1.00 | 75.74 | N |
| ATOM | 8078 | CA | GLN | M | 148 | 20.863 | −5.597 | 60.094 | 1.00 | 75.59 | C |
| ATOM | 8079 | C | GLN | M | 148 | 19.880 | −4.508 | 60.512 | 1.00 | 79.57 | C |
| ATOM | 8080 | O | GLN | M | 148 | 20.116 | −3.336 | 60.222 | 1.00 | 78.89 | O |
| ATOM | 8081 | CB | GLN | M | 148 | 22.024 | −5.716 | 61.079 | 1.00 | 76.79 | C |
| ATOM | 8082 | CG | GLN | M | 148 | 21.846 | −6.828 | 62.086 | 1.00 | 97.70 | C |
| ATOM | 8083 | CD | GLN | M | 148 | 22.937 | −7.862 | 61.990 | 1.00 | 125.40 | C |
| ATOM | 8084 | OE1 | GLN | M | 148 | 24.134 | −7.579 | 62.180 | 1.00 | 123.64 | O |
| ATOM | 8085 | NE2 | GLN | M | 148 | 22.544 | −9.085 | 61.663 | 1.00 | 120.34 | N |
| ATOM | 8086 | N | TRP | M | 149 | 18.745 | −4.897 | 61.114 | 1.00 | 75.92 | N |
| ATOM | 8087 | CA | TRP | M | 149 | 17.750 | −3.938 | 61.596 | 1.00 | 74.81 | C |
| ATOM | 8088 | C | TRP | M | 149 | 17.906 | −3.823 | 63.115 | 1.00 | 75.96 | C |
| ATOM | 8089 | O | TRP | M | 149 | 18.088 | −4.831 | 63.803 | 1.00 | 75.06 | O |
| ATOM | 8090 | CB | TRP | M | 149 | 16.322 | −4.340 | 61.192 | 1.00 | 73.45 | C |
| ATOM | 8091 | CG | TRP | M | 149 | 15.945 | −3.966 | 59.779 | 1.00 | 74.48 | C |
| ATOM | 8092 | CD1 | TRP | M | 149 | 15.859 | −4.803 | 58.702 | 1.00 | 77.23 | C |
| ATOM | 8093 | CD2 | TRP | M | 149 | 15.577 | −2.657 | 59.298 | 1.00 | 74.24 | C |
| ATOM | 8094 | NE1 | TRP | M | 149 | 15.497 | −4.094 | 57.574 | 1.00 | 76.30 | N |
| ATOM | 8095 | CE2 | TRP | M | 149 | 15.295 | −2.781 | 57.915 | 1.00 | 77.16 | C |
| ATOM | 8096 | CE3 | TRP | M | 149 | 15.461 | −1.389 | 59.905 | 1.00 | 75.42 | C |
| ATOM | 8097 | CZ2 | TRP | M | 149 | 14.871 | −1.699 | 57.137 | 1.00 | 75.91 | C |
| ATOM | 8098 | CZ3 | TRP | M | 149 | 15.065 | −0.310 | 59.121 | 1.00 | 76.68 | C |
| ATOM | 8099 | CH2 | TRP | M | 149 | 14.789 | −0.469 | 57.751 | 1.00 | 77.03 | C |
| ATOM | 8100 | N | LYS | M | 150 | 17.935 | −2.589 | 63.618 | 1.00 | 70.84 | N |
| ATOM | 8101 | CA | LYS | M | 150 | 18.075 | −2.291 | 65.040 | 1.00 | 69.24 | C |
| ATOM | 8102 | C | LYS | M | 150 | 16.986 | −1.289 | 65.450 | 1.00 | 71.88 | C |
| ATOM | 8103 | O | LYS | M | 150 | 16.830 | −0.235 | 64.824 | 1.00 | 70.62 | O |
| ATOM | 8104 | CB | LYS | M | 150 | 19.505 | −1.825 | 65.382 | 1.00 | 70.46 | C |
| ATOM | 8105 | N | VAL | M | 151 | 16.163 | −1.679 | 66.436 | 1.00 | 69.06 | N |
| ATOM | 8106 | CA | VAL | M | 151 | 15.047 | −0.869 | 66.948 | 1.00 | 69.24 | C |
| ATOM | 8107 | C | VAL | M | 151 | 15.367 | −0.560 | 68.410 | 1.00 | 72.09 | C |
| ATOM | 8108 | O | VAL | M | 151 | 15.292 | −1.457 | 69.262 | 1.00 | 71.91 | O |
| ATOM | 8109 | CB | VAL | M | 151 | 13.696 | −1.596 | 66.761 | 1.00 | 74.14 | C |
| ATOM | 8110 | CG1 | VAL | M | 151 | 12.561 | −0.821 | 67.400 | 1.00 | 74.59 | C |

TABLE 1-continued

Three-dimensional crystal coordinate for anti-TcdB antibody beziotoxumab
Fab –*C. difficile* toxin B (TcdB$^{(1834-2101)}$) complex.

| ATOM | 8111 | CG2 | VAL | M | 151 | 13.405 | −1.844 | 65.288 | 1.00 | 74.36 | C |
|---|---|---|---|---|---|---|---|---|---|---|---|
| ATOM | 8112 | N   | ASP | M | 152 | 15.784 | 0.701  | 68.681 | 1.00 | 67.71 | N |
| ATOM | 8113 | CA  | ASP | M | 152 | 16.269 | 1.176  | 69.976 | 1.00 | 67.55 | C |
| ATOM | 8114 | C   | ASP | M | 152 | 17.441 | 0.278  | 70.439 | 1.00 | 73.84 | C |
| ATOM | 8115 | O   | ASP | M | 152 | 17.386 | −0.331 | 71.516 | 1.00 | 72.41 | O |
| ATOM | 8116 | CB  | ASP | M | 152 | 15.149 | 1.287  | 71.032 | 1.00 | 69.36 | C |
| ATOM | 8117 | CG  | ASP | M | 152 | 14.206 | 2.469  | 70.884 | 1.00 | 78.91 | C |
| ATOM | 8118 | OD1 | ASP | M | 152 | 14.618 | 3.487  | 70.283 | 1.00 | 76.51 | O |
| ATOM | 8119 | OD2 | ASP | M | 152 | 13.077 | 2.403  | 71.436 | 1.00 | 86.40 | O |
| ATOM | 8120 | N   | ASN | M | 153 | 18.471 | 0.141  | 69.550 | 1.00 | 74.03 | N |
| ATOM | 8121 | CA  | ASN | M | 153 | 19.719 | −0.640 | 69.723 | 1.00 | 75.32 | C |
| ATOM | 8122 | C   | ASN | M | 153 | 19.517 | −2.176 | 69.904 | 1.00 | 81.40 | C |
| ATOM | 8123 | O   | ASN | M | 153 | 20.469 | −2.880 | 70.262 | 1.00 | 80.97 | O |
| ATOM | 8124 | CB  | ASN | M | 153 | 20.597 | −0.073 | 70.875 | 1.00 | 77.65 | C |
| ATOM | 8125 | CG  | ASN | M | 153 | 20.659 | 1.431  | 70.959 | 1.00 | 102.77 | C |
| ATOM | 8126 | OD1 | ASN | M | 153 | 20.869 | 2.128  | 69.966 | 1.00 | 94.59 | O |
| ATOM | 8127 | ND2 | ASN | M | 153 | 20.469 | 1.966  | 72.156 | 1.00 | 98.76 | N |
| ATOM | 8128 | N   | ALA | M | 154 | 18.298 | −2.692 | 69.637 | 1.00 | 79.85 | N |
| ATOM | 8129 | CA  | ALA | M | 154 | 17.985 | −4.126 | 69.732 | 1.00 | 80.08 | C |
| ATOM | 8130 | C   | ALA | M | 154 | 17.988 | −4.753 | 68.322 | 1.00 | 83.48 | C |
| ATOM | 8131 | O   | ALA | M | 154 | 17.270 | −4.255 | 67.445 | 1.00 | 81.98 | O |
| ATOM | 8132 | CB  | ALA | M | 154 | 16.628 | −4.324 | 70.403 | 1.00 | 80.67 | C |
| ATOM | 8133 | N   | LEU | M | 155 | 18.818 | −5.819 | 68.095 | 1.00 | 80.27 | N |
| ATOM | 8134 | CA  | LEU | M | 155 | 18.895 | −6.491 | 66.784 | 1.00 | 80.17 | C |
| ATOM | 8135 | C   | LEU | M | 155 | 17.621 | −7.287 | 66.477 | 1.00 | 86.53 | C |
| ATOM | 8136 | O   | LEU | M | 155 | 17.201 | −8.146 | 67.265 | 1.00 | 85.42 | O |
| ATOM | 8137 | CB  | LEU | M | 155 | 20.156 | −7.356 | 66.603 | 1.00 | 79.72 | C |
| ATOM | 8138 | N   | GLN | M | 156 | 16.996 | −6.956 | 65.336 | 1.00 | 85.05 | N |
| ATOM | 8139 | CA  | GLN | M | 156 | 15.763 | −7.562 | 64.836 | 1.00 | 85.54 | C |
| ATOM | 8140 | C   | GLN | M | 156 | 16.022 | −8.836 | 64.023 | 1.00 | 91.85 | C |
| ATOM | 8141 | O   | GLN | M | 156 | 16.954 | −8.883 | 63.219 | 1.00 | 91.33 | O |
| ATOM | 8142 | CB  | GLN | M | 156 | 14.965 | −6.558 | 63.981 | 1.00 | 86.58 | C |
| ATOM | 8143 | CG  | GLN | M | 156 | 14.616 | −5.240 | 64.678 | 1.00 | 92.61 | C |
| ATOM | 8144 | CD  | GLN | M | 156 | 13.900 | −5.417 | 65.993 | 1.00 | 99.30 | C |
| ATOM | 8145 | OE1 | GLN | M | 156 | 12.698 | −5.667 | 66.037 | 1.00 | 91.94 | O |
| ATOM | 8146 | NE2 | GLN | M | 156 | 14.626 | −5.283 | 67.096 | 1.00 | 90.14 | N |
| ATOM | 8147 | N   | SER | M | 157 | 15.166 | −9.858 | 64.224 | 1.00 | 89.42 | N |
| ATOM | 8148 | CA  | SER | M | 157 | 15.219 | −11.141 | 63.521 | 1.00 | 88.49 | C |
| ATOM | 8149 | C   | SER | M | 157 | 13.814 | −11.699 | 63.178 | 1.00 | 89.03 | C |
| ATOM | 8150 | O   | SER | M | 157 | 12.900 | −11.642 | 64.005 | 1.00 | 88.12 | O |
| ATOM | 8151 | CB  | SER | M | 157 | 16.049 | −12.157 | 64.304 | 1.00 | 92.49 | C |
| ATOM | 8152 | OG  | SER | M | 157 | 15.253 | −12.999 | 65.123 | 1.00 | 103.25 | O |
| ATOM | 8153 | N   | GLY | M | 158 | 13.686 | −12.226 | 61.961 | 1.00 | 83.87 | N |
| ATOM | 8154 | CA  | GLY | M | 158 | 12.475 | −12.840 | 61.428 | 1.00 | 82.91 | C |
| ATOM | 8155 | C   | GLY | M | 158 | 11.331 | −11.885 | 61.168 | 1.00 | 85.06 | C |
| ATOM | 8156 | O   | GLY | M | 158 | 10.166 | −12.284 | 61.269 | 1.00 | 84.31 | O |
| ATOM | 8157 | N   | ASN | M | 159 | 11.650 | −10.620 | 60.834 | 1.00 | 80.28 | N |
| ATOM | 8158 | CA  | ASN | M | 159 | 10.639 | −9.589 | 60.587 | 1.00 | 79.42 | C |
| ATOM | 8159 | C   | ASN | M | 159 | 11.006 | −8.667 | 59.428 | 1.00 | 83.39 | C |
| ATOM | 8160 | O   | ASN | M | 159 | 10.422 | −7.581 | 59.284 | 1.00 | 82.20 | O |
| ATOM | 8161 | CB  | ASN | M | 159 | 10.315 | −8.807 | 61.867 | 1.00 | 77.63 | C |
| ATOM | 8162 | CG  | ASN | M | 159 | 11.455 | −8.036 | 62.489 | 1.00 | 95.96 | C |
| ATOM | 8163 | OD1 | ASN | M | 159 | 12.632 | −8.137 | 62.100 | 1.00 | 97.06 | O |
| ATOM | 8164 | ND2 | ASN | M | 159 | 11.116 | −7.230 | 63.480 | 1.00 | 81.54 | N |
| ATOM | 8165 | N   | SER | M | 160 | 11.961 | −9.124 | 58.583 | 1.00 | 80.32 | N |
| ATOM | 8166 | CA  | SER | M | 160 | 12.403 | −8.408 | 57.377 | 1.00 | 79.64 | C |
| ATOM | 8167 | C   | SER | M | 160 | 12.543 | −9.323 | 56.147 | 1.00 | 81.25 | C |
| ATOM | 8168 | O   | SER | M | 160 | 12.659 | −10.547 | 56.274 | 1.00 | 79.81 | O |
| ATOM | 8169 | CB  | SER | M | 160 | 13.679 | −7.599 | 57.624 | 1.00 | 82.15 | C |
| ATOM | 8170 | OG  | SER | M | 160 | 14.703 | −8.371 | 58.225 | 1.00 | 89.12 | O |
| ATOM | 8171 | N   | GLN | M | 161 | 12.491 | −8.711 | 54.962 | 1.00 | 76.55 | N |
| ATOM | 8172 | CA  | GLN | M | 161 | 12.604 | −9.402 | 53.694 | 1.00 | 75.90 | C |
| ATOM | 8173 | C   | GLN | M | 161 | 13.447 | −8.588 | 52.722 | 1.00 | 76.47 | C |
| ATOM | 8174 | O   | GLN | M | 161 | 13.089 | −7.445 | 52.420 | 1.00 | 74.44 | O |
| ATOM | 8175 | CB  | GLN | M | 161 | 11.206 | −9.613 | 53.092 | 1.00 | 77.70 | C |
| ATOM | 8176 | CG  | GLN | M | 161 | 10.408 | −10.800 | 53.664 | 1.00 | 85.75 | C |
| ATOM | 8177 | CD  | GLN | M | 161 | 9.097  | −10.975 | 52.920 | 1.00 | 96.85 | C |
| ATOM | 8178 | OE1 | GLN | M | 161 | 8.247  | −10.068 | 52.878 | 1.00 | 87.82 | O |
| ATOM | 8179 | NE2 | GLN | M | 161 | 8.928  | −12.124 | 52.270 | 1.00 | 90.29 | N |
| ATOM | 8180 | N   | GLU | M | 162 | 14.546 | −9.177 | 52.202 | 1.00 | 72.61 | N |
| ATOM | 8181 | CA  | GLU | M | 162 | 15.369 | −8.469 | 51.209 | 1.00 | 72.24 | C |
| ATOM | 8182 | C   | GLU | M | 162 | 15.013 | −8.899 | 49.751 | 1.00 | 75.88 | C |
| ATOM | 8183 | O   | GLU | M | 162 | 14.512 | −9.995 | 49.510 | 1.00 | 74.49 | O |

TABLE 1-continued

Three-dimensional crystal coordinate for anti-TcdB antibody beziotoxumab Fab –C. difficile toxin B (TcdB$^{(1834-2101)}$) complex.

| ATOM | 8184 | CB | GLU | M | 162 | 16.909 | −8.486 | 51.468 | 1.00 | 73.26 | C |
|------|------|-----|-----|---|-----|--------|--------|--------|------|--------|---|
| ATOM | 8185 | CG | GLU | M | 162 | 17.432 | −9.348 | 52.607 | 1.00 | 81.65 | C |
| ATOM | 8186 | CD | GLU | M | 162 | 18.368 | −8.648 | 53.577 | 1.00 | 104.38 | C |
| ATOM | 8187 | OE1 | GLU | M | 162 | 17.885 | −8.167 | 54.630 | 1.00 | 109.82 | O |
| ATOM | 8188 | OE2 | GLU | M | 162 | 19.592 | −8.632 | 53.314 | 1.00 | 89.31 | O |
| ATOM | 8189 | N | SER | M | 163 | 15.218 | −7.973 | 48.810 | 1.00 | 73.21 | N |
| ATOM | 8190 | CA | SER | M | 163 | 14.956 | −8.117 | 47.379 | 1.00 | 73.00 | C |
| ATOM | 8191 | C | SER | M | 163 | 16.108 | −7.441 | 46.614 | 1.00 | 77.13 | C |
| ATOM | 8192 | O | SER | M | 163 | 16.427 | −6.280 | 46.870 | 1.00 | 75.05 | O |
| ATOM | 8193 | CB | SER | M | 163 | 13.618 | −7.477 | 47.014 | 1.00 | 75.67 | C |
| ATOM | 8194 | OG | SER | M | 163 | 13.373 | −7.512 | 45.619 | 1.00 | 77.74 | O |
| ATOM | 8195 | N | VAL | M | 164 | 16.744 | −8.198 | 45.705 | 1.00 | 75.65 | N |
| ATOM | 8196 | CA | VAL | M | 164 | 17.899 | −7.770 | 44.915 | 1.00 | 75.67 | C |
| ATOM | 8197 | C | VAL | M | 164 | 17.531 | −7.612 | 43.469 | 1.00 | 81.03 | C |
| ATOM | 8198 | O | VAL | M | 164 | 16.840 | −8.473 | 42.923 | 1.00 | 81.74 | O |
| ATOM | 8199 | CB | VAL | M | 164 | 19.081 | −8.768 | 45.013 | 1.00 | 79.45 | C |
| ATOM | 8200 | CG1 | VAL | M | 164 | 20.405 | −8.055 | 44.769 | 1.00 | 79.96 | C |
| ATOM | 8201 | CG2 | VAL | M | 164 | 19.107 | −9.504 | 46.346 | 1.00 | 79.05 | C |
| ATOM | 8202 | N | THR | M | 165 | 18.065 | −6.569 | 42.819 | 1.00 | 77.80 | N |
| ATOM | 8203 | CA | THR | M | 165 | 17.880 | −6.364 | 41.383 | 1.00 | 78.05 | C |
| ATOM | 8204 | C | THR | M | 165 | 18.891 | −7.246 | 40.641 | 1.00 | 83.27 | C |
| ATOM | 8205 | O | THR | M | 165 | 19.841 | −7.782 | 41.238 | 1.00 | 82.67 | O |
| ATOM | 8206 | CB | THR | M | 165 | 18.107 | −4.892 | 40.985 | 1.00 | 84.35 | C |
| ATOM | 8207 | OG1 | THR | M | 165 | 19.376 | −4.451 | 41.470 | 1.00 | 83.40 | O |
| ATOM | 8208 | CG2 | THR | M | 165 | 16.974 | −3.971 | 41.426 | 1.00 | 81.73 | C |
| ATOM | 8209 | N | GLU | M | 166 | 18.697 | −7.379 | 39.325 | 1.00 | 80.20 | N |
| ATOM | 8210 | CA | GLU | M | 166 | 19.663 | −8.097 | 38.497 | 1.00 | 79.16 | C |
| ATOM | 8211 | C | GLU | M | 166 | 20.824 | −7.122 | 38.236 | 1.00 | 81.68 | C |
| ATOM | 8212 | O | GLU | M | 166 | 20.639 | −5.900 | 38.404 | 1.00 | 81.79 | O |
| ATOM | 8213 | CB | GLU | M | 166 | 19.012 | −8.602 | 37.189 | 1.00 | 80.21 | C |
| ATOM | 8214 | CG | GLU | M | 166 | 18.112 | −9.824 | 37.369 | 1.00 | 89.57 | C |
| ATOM | 8215 | CD | GLU | M | 166 | 18.720 | −10.979 | 38.144 | 1.00 | 117.07 | C |
| ATOM | 8216 | OE1 | GLU | M | 166 | 19.762 | −11.518 | 37.705 | 1.00 | 118.90 | O |
| ATOM | 8217 | OE2 | GLU | M | 166 | 18.171 | −11.321 | 39.216 | 1.00 | 113.77 | O |
| ATOM | 8218 | N | GLN | M | 167 | 22.025 | −7.654 | 37.914 | 1.00 | 76.65 | N |
| ATOM | 8219 | CA | GLN | M | 167 | 23.227 | −6.845 | 37.650 | 1.00 | 75.46 | C |
| ATOM | 8220 | C | GLN | M | 167 | 22.906 | −5.799 | 36.591 | 1.00 | 78.85 | C |
| ATOM | 8221 | O | GLN | M | 167 | 22.365 | −6.163 | 35.550 | 1.00 | 79.01 | O |
| ATOM | 8222 | CB | GLN | M | 167 | 24.374 | −7.753 | 37.209 | 1.00 | 76.31 | C |
| ATOM | 8223 | CG | GLN | M | 167 | 25.740 | −7.157 | 37.463 | 1.00 | 87.41 | C |
| ATOM | 8224 | CD | GLN | M | 167 | 26.854 | −8.162 | 37.439 | 1.00 | 109.02 | C |
| ATOM | 8225 | OE1 | GLN | M | 167 | 26.831 | −9.140 | 36.689 | 1.00 | 103.33 | O |
| ATOM | 8226 | NE2 | GLN | M | 167 | 27.886 | −7.904 | 38.229 | 1.00 | 107.72 | N |
| ATOM | 8227 | N | ASP | M | 168 | 23.131 | −4.503 | 36.898 | 1.00 | 75.13 | N |
| ATOM | 8228 | CA | ASP | M | 168 | 22.818 | −3.365 | 36.020 | 1.00 | 75.07 | C |
| ATOM | 8229 | C | ASP | M | 168 | 23.487 | −3.432 | 34.655 | 1.00 | 78.28 | C |
| ATOM | 8230 | O | ASP | M | 168 | 24.676 | −3.753 | 34.558 | 1.00 | 77.47 | O |
| ATOM | 8231 | CB | ASP | M | 168 | 23.126 | −2.018 | 36.706 | 1.00 | 77.40 | C |
| ATOM | 8232 | CG | ASP | M | 168 | 22.395 | −0.849 | 36.064 | 1.00 | 90.00 | C |
| ATOM | 8233 | OD1 | ASP | M | 168 | 21.204 | −0.641 | 36.396 | 1.00 | 92.12 | O |
| ATOM | 8234 | OD2 | ASP | M | 168 | 22.993 | −0.175 | 35.191 | 1.00 | 91.26 | O |
| ATOM | 8235 | N | SER | M | 169 | 22.710 | −3.129 | 33.599 | 1.00 | 74.89 | N |
| ATOM | 8236 | CA | SER | M | 169 | 23.181 | −3.130 | 32.207 | 1.00 | 74.63 | C |
| ATOM | 8237 | C | SER | M | 169 | 24.286 | −2.073 | 31.931 | 1.00 | 78.65 | C |
| ATOM | 8238 | O | SER | M | 169 | 25.143 | −2.296 | 31.075 | 1.00 | 78.77 | O |
| ATOM | 8239 | CB | SER | M | 169 | 22.011 | −2.908 | 31.256 | 1.00 | 78.13 | C |
| ATOM | 8240 | OG | SER | M | 169 | 21.372 | −1.663 | 31.498 | 1.00 | 91.08 | O |
| ATOM | 8241 | N | LYS | M | 170 | 24.259 | −0.936 | 32.652 | 1.00 | 74.32 | N |
| ATOM | 8242 | CA | LYS | M | 170 | 25.207 | 0.162 | 32.468 | 1.00 | 73.05 | C |
| ATOM | 8243 | C | LYS | M | 170 | 26.489 | 0.023 | 33.309 | 1.00 | 76.92 | C |
| ATOM | 8244 | O | LYS | M | 170 | 27.592 | −0.017 | 32.744 | 1.00 | 76.15 | O |
| ATOM | 8245 | CB | LYS | M | 170 | 24.510 | 1.523 | 32.725 | 1.00 | 73.88 | C |
| ATOM | 8246 | CG | LYS | M | 170 | 24.981 | 2.646 | 31.814 | 1.00 | 75.65 | C |
| ATOM | 8247 | CD | LYS | M | 170 | 24.488 | 4.010 | 32.303 | 1.00 | 88.07 | C |
| ATOM | 8248 | CE | LYS | M | 170 | 25.502 | 5.081 | 31.980 | 1.00 | 105.62 | C |
| ATOM | 8249 | NZ | LYS | M | 170 | 25.377 | 6.264 | 32.879 | 1.00 | 118.17 | N |
| ATOM | 8250 | N | ASP | M | 171 | 26.339 | −0.046 | 34.658 | 1.00 | 73.20 | N |
| ATOM | 8251 | CA | ASP | M | 171 | 27.446 | −0.036 | 35.606 | 1.00 | 71.75 | C |
| ATOM | 8252 | C | ASP | M | 171 | 27.722 | −1.353 | 36.315 | 1.00 | 74.36 | C |
| ATOM | 8253 | O | ASP | M | 171 | 28.573 | −1.369 | 37.202 | 1.00 | 75.03 | O |
| ATOM | 8254 | CB | ASP | M | 171 | 27.254 | 1.098 | 36.630 | 1.00 | 73.51 | C |
| ATOM | 8255 | CG | ASP | M | 171 | 25.875 | 1.181 | 37.266 | 1.00 | 85.40 | C |
| ATOM | 8256 | OD2 | ASP | M | 171 | 25.789 | 1.092 | 38.503 | 1.00 | 83.18 | O |

TABLE1-continued

Three-dimensional crystal coordinate for anti-TcdB antibody beziotoxumab Fab –C. difficile toxin B (TcdB$^{(1834-2101)}$) complex.

| ATOM | 8257 | OD1 | ASP | M | 171 | 24.897 | 1.456 | 36.533 | 1.00 | 96.40 | O |
|---|---|---|---|---|---|---|---|---|---|---|---|
| ATOM | 8258 | N | SER | M | 172 | 27.080 | −2.459 | 35.897 | 1.00 | 69.88 | N |
| ATOM | 8259 | CA | SER | M | 172 | 27.257 | −3.817 | 36.453 | 1.00 | 69.38 | C |
| ATOM | 8260 | C | SER | M | 172 | 27.110 | −3.911 | 37.985 | 1.00 | 74.38 | C |
| ATOM | 8261 | O | SER | M | 172 | 27.750 | −4.747 | 38.633 | 1.00 | 73.95 | O |
| ATOM | 8262 | CB | SER | M | 172 | 28.577 | −4.433 | 35.992 | 1.00 | 70.82 | C |
| ATOM | 8263 | OG | SER | M | 172 | 28.579 | −4.608 | 34.586 | 1.00 | 74.37 | O |
| ATOM | 8264 | N | THR | M | 173 | 26.219 | −3.100 | 38.549 | 1.00 | 72.80 | N |
| ATOM | 8265 | CA | THR | M | 173 | 25.975 | −3.097 | 39.983 | 1.00 | 74.02 | C |
| ATOM | 8266 | C | THR | M | 173 | 24.619 | −3.700 | 40.366 | 1.00 | 80.73 | C |
| ATOM | 8267 | O | THR | M | 173 | 23.730 | −3.890 | 39.526 | 1.00 | 79.35 | O |
| ATOM | 8268 | CB | THR | M | 173 | 26.059 | −1.678 | 40.541 | 1.00 | 83.15 | C |
| ATOM | 8269 | OG1 | THR | M | 173 | 24.988 | −0.909 | 39.992 | 1.00 | 86.55 | O |
| ATOM | 8270 | CG2 | THR | M | 173 | 27.427 | −1.027 | 40.337 | 1.00 | 78.18 | C |
| ATOM | 8271 | N | TYR | M | 174 | 24.469 | −3.929 | 41.677 | 1.00 | 79.72 | N |
| ATOM | 8272 | CA | TYR | M | 174 | 23.267 | −4.430 | 42.325 | 1.00 | 79.86 | C |
| ATOM | 8273 | C | TYR | M | 174 | 22.652 | −3.378 | 43.230 | 1.00 | 81.16 | C |
| ATOM | 8274 | O | TYR | M | 174 | 23.349 | −2.530 | 43.788 | 1.00 | 81.48 | O |
| ATOM | 8275 | CB | TYR | M | 174 | 23.600 | −5.643 | 43.190 | 1.00 | 81.77 | C |
| ATOM | 8276 | CG | TYR | M | 174 | 24.181 | −6.782 | 42.406 | 1.00 | 85.33 | C |
| ATOM | 8277 | CD1 | TYR | M | 174 | 23.364 | −7.631 | 41.661 | 1.00 | 88.14 | C |
| ATOM | 8278 | CD2 | TYR | M | 174 | 25.548 | −7.025 | 42.411 | 1.00 | 86.18 | C |
| ATOM | 8279 | CE1 | TYR | M | 174 | 23.899 | −8.687 | 40.928 | 1.00 | 88.53 | C |
| ATOM | 8280 | CE2 | TYR | M | 174 | 26.090 | −8.092 | 41.707 | 1.00 | 87.38 | C |
| ATOM | 8281 | CZ | TYR | M | 174 | 25.259 | −8.923 | 40.968 | 1.00 | 93.52 | C |
| ATOM | 8282 | OH | TYR | M | 174 | 25.775 | −9.973 | 40.262 | 1.00 | 93.26 | O |
| ATOM | 8283 | N | SER | M | 175 | 21.341 | −3.468 | 43.399 | 1.00 | 74.13 | N |
| ATOM | 8284 | CA | SER | M | 175 | 20.604 | −2.668 | 44.350 | 1.00 | 72.10 | C |
| ATOM | 8285 | C | SER | M | 175 | 19.813 | −3.665 | 45.207 | 1.00 | 76.01 | C |
| ATOM | 8286 | O | SER | M | 175 | 19.541 | −4.787 | 44.763 | 1.00 | 76.50 | O |
| ATOM | 8287 | CB | SER | M | 175 | 19.764 | −1.602 | 43.665 | 1.00 | 72.12 | C |
| ATOM | 8288 | OG | SER | M | 175 | 20.660 | −0.739 | 42.982 | 1.00 | 76.36 | O |
| ATOM | 8289 | N | LEU | M | 176 | 19.559 | −3.308 | 46.464 | 1.00 | 70.96 | N |
| ATOM | 8290 | CA | LEU | M | 176 | 18.881 | −4.162 | 47.430 | 1.00 | 69.48 | C |
| ATOM | 8291 | C | LEU | M | 176 | 17.965 | −3.313 | 48.302 | 1.00 | 72.59 | C |
| ATOM | 8292 | O | LEU | M | 176 | 18.314 | −2.184 | 48.659 | 1.00 | 71.26 | O |
| ATOM | 8293 | CB | LEU | M | 176 | 19.946 | −4.902 | 48.274 | 1.00 | 69.33 | C |
| ATOM | 8294 | CG | LEU | M | 176 | 19.488 | −5.927 | 49.307 | 1.00 | 73.25 | C |
| ATOM | 8295 | CD1 | LEU | M | 176 | 20.415 | −7.101 | 49.346 | 1.00 | 72.91 | C |
| ATOM | 8296 | CD2 | LEU | M | 176 | 19.430 | −5.317 | 50.684 | 1.00 | 75.90 | C |
| ATOM | 8297 | N | SER | M | 177 | 16.786 | −3.859 | 48.631 | 1.00 | 70.00 | N |
| ATOM | 8298 | CA | SER | M | 177 | 15.806 | −3.228 | 49.505 | 0.47 | 69.16 | C |
| ATOM | 8299 | C | SER | M | 177 | 15.523 | −4.252 | 50.577 | 1.00 | 75.37 | C |
| ATOM | 8300 | O | SER | M | 177 | 15.239 | −5.393 | 50.229 | 1.00 | 76.80 | O |
| ATOM | 8301 | CB | SER | M | 177 | 14.530 | −2.884 | 48.737 | 0.47 | 69.51 | C |
| ATOM | 8302 | OG | SER | M | 177 | 13.723 | −4.021 | 48.466 | 0.47 | 72.01 | O |
| ATOM | 8303 | N | SER | M | 178 | 15.682 | −3.887 | 51.867 | 1.00 | 71.86 | N |
| ATOM | 8304 | CA | SER | M | 178 | 15.367 | −4.753 | 53.022 | 1.00 | 71.31 | C |
| ATOM | 8305 | C | SER | M | 178 | 14.196 | −4.105 | 53.760 | 1.00 | 76.37 | C |
| ATOM | 8306 | O | SER | M | 178 | 14.342 | −2.987 | 54.253 | 1.00 | 76.36 | O |
| ATOM | 8307 | CB | SER | M | 178 | 16.562 | −4.907 | 53.955 | 1.00 | 72.73 | C |
| ATOM | 8308 | OG | SER | M | 178 | 16.227 | −5.677 | 55.098 | 1.00 | 77.92 | O |
| ATOM | 8309 | N | THR | M | 179 | 13.019 | −4.764 | 53.775 | 1.00 | 73.37 | N |
| ATOM | 8310 | CA | THR | M | 179 | 11.818 | −4.204 | 54.400 | 1.00 | 72.66 | C |
| ATOM | 8311 | C | THR | M | 179 | 11.510 | −4.828 | 55.747 | 1.00 | 77.98 | C |
| ATOM | 8312 | O | THR | M | 179 | 11.276 | −6.035 | 55.821 | 1.00 | 77.34 | O |
| ATOM | 8313 | CB | THR | M | 179 | 10.617 | −4.264 | 53.445 | 1.00 | 72.27 | C |
| ATOM | 8314 | OG1 | THR | M | 179 | 10.973 | −3.681 | 52.189 | 1.00 | 70.75 | O |
| ATOM | 8315 | CG2 | THR | M | 179 | 9.399 | −3.564 | 54.001 | 1.00 | 68.20 | C |
| ATOM | 8316 | N | LEU | M | 180 | 11.477 | −3.980 | 56.806 | 1.00 | 76.59 | N |
| ATOM | 8317 | CA | LEU | M | 180 | 11.113 | −4.347 | 58.183 | 1.00 | 77.09 | C |
| ATOM | 8318 | C | LEU | M | 180 | 9.605 | −4.142 | 58.348 | 1.00 | 81.91 | C |
| ATOM | 8319 | O | LEU | M | 180 | 9.109 | −3.039 | 58.086 | 1.00 | 82.02 | O |
| ATOM | 8320 | CB | LEU | M | 180 | 11.879 | −3.485 | 59.199 | 1.00 | 77.03 | C |
| ATOM | 8321 | CG | LEU | M | 180 | 11.631 | −3.794 | 60.677 | 1.00 | 81.51 | C |
| ATOM | 8322 | CD1 | LEU | M | 180 | 12.533 | −4.910 | 61.162 | 1.00 | 82.20 | C |
| ATOM | 8323 | CD2 | LEU | M | 180 | 11.871 | −2.572 | 61.518 | 1.00 | 82.87 | C |
| ATOM | 8324 | N | THR | M | 181 | 8.867 | −5.200 | 58.743 | 1.00 | 78.07 | N |
| ATOM | 8325 | CA | THR | M | 181 | 7.414 | −5.079 | 58.893 | 1.00 | 77.34 | C |
| ATOM | 8326 | C | THR | M | 181 | 7.022 | −5.335 | 60.349 | 1.00 | 78.91 | C |
| ATOM | 8327 | O | THR | M | 181 | 7.338 | −6.372 | 60.938 | 1.00 | 76.84 | O |
| ATOM | 8328 | CB | THR | M | 181 | 6.626 | −5.903 | 57.825 | 1.00 | 84.14 | C |
| ATOM | 8329 | OG1 | THR | M | 181 | 6.972 | −5.447 | 56.501 | 1.00 | 76.93 | O |

TABLE 1-continued

Three-dimensional crystal coordinate for anti-TcdB antibody beziotoxumab Fab –C. *difficile* toxin B (TcdB$^{(1834-2101)}$) complex.

| ATOM | 8330 | CG2 | THR | M | 181 | 5.113 | −5.776 | 57.988 | 1.00 | 84.81 | C |
|---|---|---|---|---|---|---|---|---|---|---|---|
| ATOM | 8331 | N | LEU | M | 182 | 6.336 | −4.335 | 60.908 | 1.00 | 76.46 | N |
| ATOM | 8332 | CA | LEU | M | 182 | 5.858 | −4.285 | 62.283 | 1.00 | 77.01 | C |
| ATOM | 8333 | C | LEU | M | 182 | 4.404 | −3.853 | 62.345 | 1.00 | 82.00 | C |
| ATOM | 8334 | O | LEU | M | 182 | 3.955 | −3.068 | 61.495 | 1.00 | 79.44 | O |
| ATOM | 8335 | CB | LEU | M | 182 | 6.674 | −3.237 | 63.067 | 1.00 | 76.95 | C |
| ATOM | 8336 | CG | LEU | M | 182 | 8.082 | −3.591 | 63.484 | 1.00 | 81.00 | C |
| ATOM | 8337 | CD1 | LEU | M | 182 | 8.833 | −2.343 | 63.868 | 1.00 | 79.89 | C |
| ATOM | 8338 | CD2 | LEU | M | 182 | 8.069 | −4.592 | 64.636 | 1.00 | 84.88 | C |
| ATOM | 8339 | N | SER | M | 183 | 3.687 | −4.308 | 63.413 | 1.00 | 80.38 | N |
| ATOM | 8340 | CA | SER | M | 183 | 2.309 | −3.887 | 63.681 | 1.00 | 80.20 | C |
| ATOM | 8341 | C | SER | M | 183 | 2.368 | −2.454 | 64.258 | 1.00 | 84.38 | C |
| ATOM | 8342 | O | SER | M | 183 | 3.251 | −2.181 | 65.088 | 1.00 | 83.93 | O |
| ATOM | 8343 | CB | SER | M | 183 | 1.650 | −4.827 | 64.686 | 1.00 | 82.66 | C |
| ATOM | 8344 | OG | SER | M | 183 | 2.240 | −4.721 | 65.972 | 1.00 | 90.34 | O |
| ATOM | 8345 | N | LYS | M | 184 | 1.440 | −1.547 | 63.824 | 1.00 | 80.38 | N |
| ATOM | 8346 | CA | LYS | M | 184 | 1.333 | −0.153 | 64.316 | 1.00 | 80.10 | C |
| ATOM | 8347 | C | LYS | M | 184 | 1.579 | −0.057 | 65.848 | 1.00 | 82.17 | C |
| ATOM | 8348 | O | LYS | M | 184 | 2.252 | 0.867 | 66.293 | 1.00 | 81.53 | O |
| ATOM | 8349 | CB | LYS | M | 184 | −0.036 | 0.462 | 63.951 | 1.00 | 82.88 | C |
| ATOM | 8350 | CG | LYS | M | 184 | −0.154 | 1.959 | 64.242 | 1.00 | 97.25 | C |
| ATOM | 8351 | CD | LYS | M | 184 | −1.597 | 2.393 | 64.446 | 1.00 | 108.18 | C |
| ATOM | 8352 | CE | LYS | M | 184 | −1.677 | 3.849 | 64.848 | 1.00 | 118.26 | C |
| ATOM | 8353 | NZ | LYS | M | 184 | −3.059 | 4.385 | 64.750 | 1.00 | 124.68 | N |
| ATOM | 8354 | N | ALA | M | 185 | 1.097 | −1.061 | 66.617 | 1.00 | 77.26 | N |
| ATOM | 8355 | CA | ALA | M | 185 | 1.268 | −1.196 | 68.058 | 1.00 | 76.71 | C |
| ATOM | 8356 | C | ALA | M | 185 | 2.744 | −1.149 | 68.445 | 1.00 | 81.88 | C |
| ATOM | 8357 | O | ALA | M | 185 | 3.155 | −0.203 | 69.112 | 1.00 | 79.67 | O |
| ATOM | 8358 | CB | ALA | M | 185 | 0.638 | −2.502 | 68.529 | 1.00 | 77.30 | C |
| ATOM | 8359 | N | ASP | M | 186 | 3.546 | −2.136 | 67.963 | 1.00 | 82.05 | N |
| ATOM | 8360 | CA | ASP | M | 186 | 4.991 | −2.294 | 68.206 | 1.00 | 82.73 | C |
| ATOM | 8361 | C | ASP | M | 186 | 5.842 | −1.164 | 67.634 | 1.00 | 86.05 | C |
| ATOM | 8362 | O | ASP | M | 186 | 6.894 | −0.856 | 68.199 | 1.00 | 85.77 | O |
| ATOM | 8363 | CB | ASP | M | 186 | 5.476 | −3.657 | 67.706 | 1.00 | 85.45 | C |
| ATOM | 8364 | CG | ASP | M | 186 | 4.880 | −4.806 | 68.497 | 1.00 | 101.57 | C |
| ATOM | 8365 | OD2 | ASP | M | 186 | 5.578 | −5.333 | 69.388 | 1.00 | 110.59 | O |
| ATOM | 8366 | OD1 | ASP | M | 186 | 3.693 | −5.156 | 68.247 | 1.00 | 102.43 | O |
| ATOM | 8367 | N | TYR | M | 187 | 5.387 | −0.535 | 66.536 | 1.00 | 81.83 | N |
| ATOM | 8368 | CA | TYR | M | 187 | 6.080 | 0.611 | 65.961 | 1.00 | 81.55 | C |
| ATOM | 8369 | C | TYR | M | 187 | 6.015 | 1.844 | 66.900 | 1.00 | 90.03 | C |
| ATOM | 8370 | O | TYR | M | 187 | 7.043 | 2.508 | 67.080 | 1.00 | 90.58 | O |
| ATOM | 8371 | CB | TYR | M | 187 | 5.552 | 0.945 | 64.566 | 1.00 | 80.86 | C |
| ATOM | 8372 | CG | TYR | M | 187 | 6.166 | 2.192 | 63.967 | 1.00 | 80.88 | C |
| ATOM | 8373 | CD1 | TYR | M | 187 | 7.494 | 2.213 | 63.555 | 1.00 | 82.25 | C |
| ATOM | 8374 | CD2 | TYR | M | 187 | 5.417 | 3.351 | 63.804 | 1.00 | 82.03 | C |
| ATOM | 8375 | CE1 | TYR | M | 187 | 8.067 | 3.363 | 63.007 | 1.00 | 82.87 | C |
| ATOM | 8376 | CE2 | TYR | M | 187 | 5.974 | 4.504 | 63.246 | 1.00 | 83.17 | C |
| ATOM | 8377 | CZ | TYR | M | 187 | 7.305 | 4.511 | 62.862 | 1.00 | 90.63 | C |
| ATOM | 8378 | OH | TYR | M | 187 | 7.848 | 5.639 | 62.284 | 1.00 | 92.21 | O |
| ATOM | 8379 | N | GLU | M | 188 | 4.817 | 2.137 | 67.502 | 1.00 | 87.70 | N |
| ATOM | 8380 | CA | GLU | M | 188 | 4.605 | 3.263 | 68.441 | 1.00 | 87.70 | C |
| ATOM | 8381 | C | GLU | M | 188 | 5.419 | 3.090 | 69.753 | 1.00 | 92.05 | C |
| ATOM | 8382 | O | GLU | M | 188 | 5.784 | 4.086 | 70.383 | 1.00 | 91.36 | O |
| ATOM | 8383 | CB | GLU | M | 188 | 3.110 | 3.457 | 68.791 | 1.00 | 89.12 | C |
| ATOM | 8384 | CG | GLU | M | 188 | 2.115 | 3.466 | 67.640 | 1.00 | 99.23 | C |
| ATOM | 8385 | CD | GLU | M | 188 | 1.855 | 4.772 | 66.918 | 1.00 | 114.10 | C |
| ATOM | 8386 | OE1 | GLU | M | 188 | 2.826 | 5.368 | 66.395 | 1.00 | 97.56 | O |
| ATOM | 8387 | OE2 | GLU | M | 188 | 0.665 | 5.146 | 66.790 | 1.00 | 104.41 | O |
| ATOM | 8388 | N | LYS | M | 189 | 5.682 | 1.822 | 70.150 | 1.00 | 89.49 | N |
| ATOM | 8389 | CA | LYS | M | 189 | 6.424 | 1.394 | 71.348 | 1.00 | 89.59 | C |
| ATOM | 8390 | C | LYS | M | 189 | 7.918 | 1.822 | 71.401 | 1.00 | 93.70 | C |
| ATOM | 8391 | O | LYS | M | 189 | 8.518 | 1.761 | 72.481 | 1.00 | 92.71 | O |
| ATOM | 8392 | CB | LYS | M | 189 | 6.355 | −0.147 | 71.479 | 1.00 | 91.83 | C |
| ATOM | 8393 | CG | LYS | M | 189 | 5.128 | −0.688 | 72.200 | 1.00 | 99.98 | C |
| ATOM | 8394 | CD | LYS | M | 189 | 5.277 | −2.187 | 72.448 | 1.00 | 107.51 | C |
| ATOM | 8395 | CE | LYS | M | 189 | 4.078 | −2.798 | 73.133 | 1.00 | 112.80 | C |
| ATOM | 8396 | NZ | LYS | M | 189 | 4.245 | −4.260 | 73.346 | 1.00 | 116.11 | N |
| ATOM | 8397 | N | HIS | M | 190 | 8.530 | 2.182 | 70.243 | 1.00 | 90.56 | N |
| ATOM | 8398 | CA | HIS | M | 190 | 9.959 | 2.516 | 70.145 | 1.00 | 90.84 | C |
| ATOM | 8399 | C | HIS | M | 190 | 10.242 | 3.813 | 69.381 | 1.00 | 93.35 | C |
| ATOM | 8400 | O | HIS | M | 190 | 9.390 | 4.238 | 68.604 | 1.00 | 92.79 | O |
| ATOM | 8401 | CB | HIS | M | 190 | 10.710 | 1.339 | 69.514 | 1.00 | 92.43 | C |
| ATOM | 8402 | CG | HIS | M | 190 | 10.601 | 0.079 | 70.310 | 1.00 | 96.72 | C |
| ATOM | 8403 | ND1 | HIS | M | 190 | 9.571 | −0.820 | 70.094 | 1.00 | 98.94 | N |
| ATOM | 8404 | CD2 | HIS | M | 190 | 11.372 | −0.370 | 71.331 | 1.00 | 99.19 | C |
| ATOM | 8405 | CE1 | HIS | M | 190 | 9.751 | −1.792 | 70.978 | 1.00 | 98.82 | C |
| ATOM | 8406 | NE2 | HIS | M | 190 | 10.824 | −1.564 | 71.746 | 1.00 | 99.18 | N |

TABLE 1-continued

Three-dimensional crystal coordinate for anti-TcdB antibody beziotoxumab Fab –C. difficile toxin B (TcdB$^{(1834-2101)}$) complex.

| | | | | | | | | | | | |
|---|---|---|---|---|---|---|---|---|---|---|---|
| ATOM | 8407 | N | LYS | M | 191 | 11.455 | 4.418 | 69.577 | 1.00 | 88.84 | N |
| ATOM | 8408 | CA | LYS | M | 191 | 11.872 | 5.701 | 68.978 | 1.00 | 88.17 | C |
| ATOM | 8409 | C | LYS | M | 191 | 12.890 | 5.629 | 67.818 | 1.00 | 90.16 | C |
| ATOM | 8410 | O | LYS | M | 191 | 12.628 | 6.200 | 66.755 | 1.00 | 88.77 | O |
| ATOM | 8411 | CB | LYS | M | 191 | 12.418 | 6.653 | 70.064 | 1.00 | 90.84 | C |
| ATOM | 8412 | N | VAL | M | 192 | 14.069 | 4.997 | 68.050 | 1.00 | 86.13 | N |
| ATOM | 8413 | CA | VAL | M | 192 | 15.173 | 4.887 | 67.074 | 1.00 | 85.38 | C |
| ATOM | 8414 | C | VAL | M | 192 | 15.081 | 3.627 | 66.208 | 1.00 | 85.70 | C |
| ATOM | 8415 | O | VAL | M | 192 | 15.131 | 2.499 | 66.711 | 1.00 | 84.40 | O |
| ATOM | 8416 | CB | VAL | M | 192 | 16.599 | 5.027 | 67.686 | 1.00 | 89.46 | C |
| ATOM | 8417 | CG1 | VAL | M | 192 | 17.566 | 5.648 | 66.679 | 1.00 | 88.94 | C |
| ATOM | 8418 | CG2 | VAL | M | 192 | 16.587 | 5.822 | 68.993 | 1.00 | 89.50 | C |
| ATOM | 8419 | N | TYR | M | 193 | 14.993 | 3.848 | 64.896 | 1.00 | 80.82 | N |
| ATOM | 8420 | CA | TYR | M | 193 | 14.904 | 2.804 | 63.883 | 1.00 | 80.16 | C |
| ATOM | 8421 | C | TYR | M | 193 | 16.122 | 2.908 | 62.977 | 1.00 | 81.15 | C |
| ATOM | 8422 | O | TYR | M | 193 | 16.270 | 3.902 | 62.275 | 1.00 | 80.57 | O |
| ATOM | 8423 | CB | TYR | M | 193 | 13.571 | 2.935 | 63.104 | 1.00 | 81.30 | C |
| ATOM | 8424 | CG | TYR | M | 193 | 12.379 | 2.450 | 63.905 | 1.00 | 83.20 | C |
| ATOM | 8425 | CD1 | TYR | M | 193 | 12.007 | 1.109 | 63.895 | 1.00 | 85.19 | C |
| ATOM | 8426 | CD2 | TYR | M | 193 | 11.670 | 3.315 | 64.734 | 1.00 | 83.80 | C |
| ATOM | 8427 | CE1 | TYR | M | 193 | 10.942 | 0.646 | 64.667 | 1.00 | 86.34 | C |
| ATOM | 8428 | CE2 | TYR | M | 193 | 10.613 | 2.858 | 65.527 | 1.00 | 84.39 | C |
| ATOM | 8429 | CZ | TYR | M | 193 | 10.259 | 1.519 | 65.497 | 1.00 | 91.59 | C |
| ATOM | 8430 | OH | TYR | M | 193 | 9.208 | 1.058 | 66.253 | 1.00 | 92.88 | O |
| ATOM | 8431 | N | ALA | M | 194 | 17.012 | 1.909 | 63.022 | 1.00 | 76.20 | N |
| ATOM | 8432 | CA | ALA | M | 194 | 18.242 | 1.953 | 62.241 | 1.00 | 76.13 | C |
| ATOM | 8433 | C | ALA | M | 194 | 18.580 | 0.700 | 61.454 | 1.00 | 80.10 | C |
| ATOM | 8434 | O | ALA | M | 194 | 18.419 | −0.408 | 61.966 | 1.00 | 79.57 | O |
| ATOM | 8435 | CB | ALA | M | 194 | 19.400 | 2.266 | 63.163 | 1.00 | 76.80 | C |
| ATOM | 8436 | N | CYS | M | 195 | 19.133 | 0.877 | 60.239 | 1.00 | 76.36 | N |
| ATOM | 8437 | CA | CYS | M | 195 | 19.657 | −0.264 | 59.501 | 1.00 | 77.21 | C |
| ATOM | 8438 | C | CYS | M | 195 | 21.161 | −0.133 | 59.365 | 1.00 | 77.47 | C |
| ATOM | 8439 | O | CYS | M | 195 | 21.646 | 0.962 | 59.123 | 1.00 | 75.83 | O |
| ATOM | 8440 | CB | CYS | M | 195 | 18.952 | −0.543 | 58.170 | 1.00 | 78.77 | C |
| ATOM | 8441 | SG | CYS | M | 195 | 19.064 | 0.788 | 56.940 | 1.00 | 83.19 | S |
| ATOM | 8442 | N | GLU | M | 196 | 21.893 | −1.223 | 59.653 | 1.00 | 73.16 | N |
| ATOM | 8443 | CA | GLU | M | 196 | 23.347 | −1.278 | 59.638 | 1.00 | 73.13 | C |
| ATOM | 8444 | C | GLU | M | 196 | 23.889 | −2.174 | 58.486 | 1.00 | 78.56 | C |
| ATOM | 8445 | O | GLU | M | 196 | 23.933 | −3.413 | 58.593 | 1.00 | 75.88 | O |
| ATOM | 8446 | CB | GLU | M | 196 | 23.870 | −1.697 | 61.019 | 1.00 | 74.26 | C |
| ATOM | 8447 | CG | GLU | M | 196 | 25.377 | −1.655 | 61.141 | 1.00 | 88.40 | C |
| ATOM | 8448 | CD | GLU | M | 196 | 25.902 | −2.174 | 62.463 | 1.00 | 116.07 | C |
| ATOM | 8449 | OE1 | GLU | M | 196 | 25.830 | −1.424 | 63.463 | 1.00 | 127.43 | O |
| ATOM | 8450 | OE2 | GLU | M | 196 | 26.391 | −3.327 | 62.500 | 1.00 | 102.98 | O |
| ATOM | 8451 | N | VAL | M | 197 | 24.318 | −1.498 | 57.392 | 1.00 | 77.68 | N |
| ATOM | 8452 | CA | VAL | M | 197 | 24.886 | −2.060 | 56.161 | 1.00 | 78.35 | C |
| ATOM | 8453 | C | VAL | M | 197 | 26.372 | −2.438 | 56.350 | 1.00 | 87.18 | C |
| ATOM | 8454 | O | VAL | M | 197 | 27.148 | −1.648 | 56.883 | 1.00 | 88.16 | O |
| ATOM | 8455 | CB | VAL | M | 197 | 24.638 | −1.095 | 54.972 | 1.00 | 80.86 | C |
| ATOM | 8456 | CG1 | VAL | M | 197 | 25.433 | −1.484 | 53.735 | 1.00 | 79.86 | C |
| ATOM | 8457 | CG2 | VAL | M | 197 | 23.156 | −1.018 | 54.649 | 1.00 | 80.79 | C |
| ATOM | 8458 | N | THR | M | 198 | 26.752 | −3.653 | 55.919 | 1.00 | 85.19 | N |
| ATOM | 8459 | CA | THR | M | 198 | 28.116 | −4.180 | 56.009 | 1.00 | 85.28 | C |
| ATOM | 8460 | C | THR | M | 198 | 28.553 | −4.647 | 54.588 | 1.00 | 91.68 | C |
| ATOM | 8461 | O | THR | M | 198 | 28.238 | −5.764 | 54.158 | 1.00 | 90.48 | O |
| ATOM | 8462 | CB | THR | M | 198 | 28.178 | −5.285 | 57.086 | 1.00 | 85.80 | C |
| ATOM | 8463 | OG1 | THR | M | 198 | 27.590 | −4.821 | 58.303 | 1.00 | 79.89 | O |
| ATOM | 8464 | CG2 | THR | M | 198 | 29.575 | −5.797 | 57.329 | 1.00 | 83.55 | C |
| ATOM | 8465 | N | HIS | M | 199 | 29.238 | −3.765 | 53.857 | 1.00 | 90.30 | N |
| ATOM | 8466 | CA | HIS | M | 199 | 29.733 | −4.057 | 52.519 | 1.00 | 91.19 | C |
| ATOM | 8467 | C | HIS | M | 199 | 31.251 | −3.869 | 52.502 | 1.00 | 98.18 | C |
| ATOM | 8468 | O | HIS | M | 199 | 31.774 | −3.056 | 53.272 | 1.00 | 99.31 | O |
| ATOM | 8469 | CB | HIS | M | 199 | 29.032 | −3.166 | 51.467 | 1.00 | 91.81 | C |
| ATOM | 8470 | CG | HIS | M | 199 | 29.314 | −3.570 | 50.051 | 1.00 | 94.54 | C |
| ATOM | 8471 | ND1 | HIS | M | 199 | 30.418 | −3.095 | 49.381 | 1.00 | 95.70 | N |
| ATOM | 8472 | CD2 | HIS | M | 199 | 28.633 | −4.408 | 49.237 | 1.00 | 95.27 | C |
| ATOM | 8473 | CE1 | HIS | M | 199 | 30.386 | −3.665 | 48.193 | 1.00 | 94.63 | C |
| ATOM | 8474 | NE2 | HIS | M | 199 | 29.321 | −4.452 | 48.057 | 1.00 | 94.88 | N |
| ATOM | 8475 | N | GLN | M | 200 | 31.957 | −4.611 | 51.630 | 1.00 | 95.69 | N |
| ATOM | 8476 | CA | GLN | M | 200 | 33.419 | −4.524 | 51.513 | 1.00 | 96.16 | C |
| ATOM | 8477 | C | GLN | M | 200 | 33.918 | −3.227 | 50.841 | 1.00 | 101.29 | C |
| ATOM | 8478 | O | GLN | M | 200 | 35.127 | −3.002 | 50.789 | 1.00 | 101.98 | O |
| ATOM | 8479 | CB | GLN | M | 200 | 34.016 | −5.760 | 50.830 | 1.00 | 97.38 | C |
| ATOM | 8480 | CG | GLN | M | 200 | 33.751 | −5.854 | 49.341 | 1.00 | 110.20 | C |
| ATOM | 8481 | CD | GLN | M | 200 | 33.833 | −7.283 | 48.899 | 1.00 | 124.96 | C |
| ATOM | 8482 | OE1 | GLN | M | 200 | 34.806 | −7.684 | 48.249 | 1.00 | 113.48 | O |
| ATOM | 8483 | NE2 | GLN | M | 200 | 32.813 | −8.088 | 49.263 | 1.00 | 118.64 | N |

TABLE 1-continued

Three-dimensional crystal coordinate for anti-TcdB antibody beziotoxumab Fab –C. difficile toxin B (TcdB$^{(1834-2101)}$) complex.

| ATOM | 8484 | N | GLY | M | 201 | 32.994 | −2.403 | 50.353 | 1.00 | 96.85 | N |
|---|---|---|---|---|---|---|---|---|---|---|---|
| ATOM | 8485 | CA | GLY | M | 201 | 33.309 | −1.118 | 49.748 | 1.00 | 96.28 | C |
| ATOM | 8486 | C | GLY | M | 201 | 33.341 | −0.025 | 50.783 | 1.00 | 99.10 | C |
| ATOM | 8487 | O | GLY | M | 201 | 33.828 | 1.076 | 50.510 | 1.00 | 98.75 | O |
| ATOM | 8488 | N | LEU | M | 202 | 32.802 | −0.332 | 51.981 | 1.00 | 94.47 | N |
| ATOM | 8489 | CA | LEU | M | 202 | 32.707 | 0.572 | 53.127 | 1.00 | 93.54 | C |
| ATOM | 8490 | C | LEU | M | 202 | 33.778 | 0.250 | 54.170 | 1.00 | 99.77 | C |
| ATOM | 8491 | O | LEU | M | 202 | 33.980 | −0.922 | 54.515 | 1.00 | 99.08 | O |
| ATOM | 8492 | CB | LEU | M | 202 | 31.317 | 0.489 | 53.769 | 1.00 | 92.62 | C |
| ATOM | 8493 | CG | LEU | M | 202 | 30.102 | 0.801 | 52.886 | 1.00 | 95.87 | C |
| ATOM | 8494 | CD1 | LEU | M | 202 | 28.827 | 0.332 | 53.536 | 1.00 | 95.22 | C |
| ATOM | 8495 | CD2 | LEU | M | 202 | 30.014 | 2.268 | 52.548 | 1.00 | 97.28 | C |
| ATOM | 8496 | N | SER | M | 203 | 34.457 | 1.300 | 54.677 | 1.00 | 97.91 | N |
| ATOM | 8497 | CA | SER | M | 203 | 35.544 | 1.239 | 55.674 | 1.00 | 98.07 | C |
| ATOM | 8498 | C | SER | M | 203 | 35.146 | 0.515 | 56.974 | 1.00 | 101.20 | C |
| ATOM | 8499 | O | SER | M | 203 | 35.944 | −0.235 | 57.547 | 1.00 | 100.69 | O |
| ATOM | 8500 | CB | SER | M | 203 | 36.049 | 2.650 | 55.977 | 1.00 | 102.44 | C |
| ATOM | 8501 | OG | SER | M | 203 | 35.008 | 3.618 | 55.940 | 1.00 | 111.49 | O |
| ATOM | 8502 | N | SER | M | 204 | 33.891 | 0.741 | 57.410 | 1.00 | 96.40 | N |
| ATOM | 8503 | CA | SER | M | 204 | 33.280 | 0.167 | 58.604 | 1.00 | 95.18 | C |
| ATOM | 8504 | C | SER | M | 204 | 31.741 | 0.141 | 58.397 | 1.00 | 97.04 | C |
| ATOM | 8505 | O | SER | M | 204 | 31.247 | 0.888 | 57.531 | 1.00 | 95.97 | O |
| ATOM | 8506 | CB | SER | M | 204 | 33.655 | 0.996 | 59.835 | 1.00 | 97.87 | C |
| ATOM | 8507 | OG | SER | M | 204 | 32.832 | 2.141 | 59.998 | 1.00 | 106.11 | O |
| ATOM | 8508 | N | PRO | M | 205 | 30.966 | −0.681 | 59.169 | 1.00 | 92.29 | N |
| ATOM | 8509 | CA | PRO | M | 205 | 29.508 | −0.685 | 58.984 | 1.00 | 91.17 | C |
| ATOM | 8510 | C | PRO | M | 205 | 28.892 | 0.713 | 59.032 | 1.00 | 93.41 | C |
| ATOM | 8511 | O | PRO | M | 205 | 29.209 | 1.515 | 59.915 | 1.00 | 94.96 | O |
| ATOM | 8512 | CB | PRO | M | 205 | 28.991 | −1.605 | 60.106 | 1.00 | 92.71 | C |
| ATOM | 8513 | CG | PRO | M | 205 | 30.111 | −1.780 | 61.040 | 1.00 | 97.74 | C |
| ATOM | 8514 | CD | PRO | M | 205 | 31.364 | −1.633 | 60.231 | 1.00 | 93.61 | C |
| ATOM | 8515 | N | VAL | M | 206 | 28.085 | 1.016 | 58.009 | 1.00 | 86.05 | N |
| ATOM | 8516 | CA | VAL | M | 206 | 27.356 | 2.272 | 57.818 | 1.00 | 84.00 | C |
| ATOM | 8517 | C | VAL | M | 206 | 25.959 | 2.113 | 58.402 | 1.00 | 86.35 | C |
| ATOM | 8518 | O | VAL | M | 206 | 25.280 | 1.136 | 58.094 | 1.00 | 86.65 | O |
| ATOM | 8519 | CB | VAL | M | 206 | 27.340 | 2.681 | 56.317 | 1.00 | 86.76 | C |
| ATOM | 8520 | CG1 | VAL | M | 206 | 26.262 | 3.715 | 55.995 | 1.00 | 85.55 | C |
| ATOM | 8521 | CG2 | VAL | M | 206 | 28.716 | 3.185 | 55.891 | 1.00 | 86.96 | C |
| ATOM | 8522 | N | THR | M | 207 | 25.545 | 3.055 | 59.262 | 1.00 | 81.12 | N |
| ATOM | 8523 | CA | THR | M | 207 | 24.225 | 3.062 | 59.888 | 1.00 | 79.79 | C |
| ATOM | 8524 | C | THR | M | 207 | 23.446 | 4.316 | 59.455 | 1.00 | 82.19 | C |
| ATOM | 8525 | O | THR | M | 207 | 23.958 | 5.430 | 59.589 | 1.00 | 82.00 | O |
| ATOM | 8526 | CB | THR | M | 207 | 24.346 | 2.864 | 61.420 | 1.00 | 82.94 | C |
| ATOM | 8527 | OG1 | THR | M | 207 | 25.113 | 1.682 | 61.693 | 1.00 | 82.62 | O |
| ATOM | 8528 | CG2 | THR | M | 207 | 22.993 | 2.781 | 62.112 | 1.00 | 76.15 | C |
| ATOM | 8529 | N | LYS | M | 208 | 22.241 | 4.113 | 58.879 | 1.00 | 77.66 | N |
| ATOM | 8530 | CA | LYS | M | 208 | 21.312 | 5.161 | 58.442 | 1.00 | 76.95 | C |
| ATOM | 8531 | C | LYS | M | 208 | 20.026 | 4.989 | 59.294 | 1.00 | 82.75 | C |
| ATOM | 8532 | O | LYS | M | 208 | 19.426 | 3.917 | 59.288 | 1.00 | 82.97 | O |
| ATOM | 8533 | CB | LYS | M | 208 | 21.064 | 5.081 | 56.920 | 1.00 | 77.87 | C |
| ATOM | 8534 | N | SER | M | 209 | 19.676 | 5.999 | 60.115 | 1.00 | 80.38 | N |
| ATOM | 8535 | CA | SER | M | 209 | 18.553 | 5.916 | 61.047 | 1.00 | 80.44 | C |
| ATOM | 8536 | C | SER | M | 209 | 17.607 | 7.124 | 61.061 | 1.00 | 86.58 | C |
| ATOM | 8537 | O | SER | M | 209 | 17.839 | 8.132 | 60.392 | 1.00 | 85.89 | O |
| ATOM | 8538 | CB | SER | M | 209 | 19.072 | 5.645 | 62.460 | 1.00 | 83.66 | C |
| ATOM | 8539 | OG | SER | M | 209 | 19.221 | 6.807 | 63.260 | 1.00 | 91.69 | O |
| ATOM | 8540 | N | PHE | M | 210 | 16.533 | 6.989 | 61.851 | 1.00 | 85.72 | N |
| ATOM | 8541 | CA | PHE | M | 210 | 15.513 | 7.991 | 62.102 | 1.00 | 86.96 | C |
| ATOM | 8542 | C | PHE | M | 210 | 14.885 | 7.788 | 63.493 | 1.00 | 91.32 | C |
| ATOM | 8543 | O | PHE | M | 210 | 15.051 | 6.739 | 64.133 | 1.00 | 91.33 | O |
| ATOM | 8544 | CB | PHE | M | 210 | 14.438 | 8.033 | 60.981 | 1.00 | 89.64 | C |
| ATOM | 8545 | CG | PHE | M | 210 | 13.435 | 6.892 | 60.947 | 1.00 | 92.29 | C |
| ATOM | 8546 | CD1 | PHE | M | 210 | 12.318 | 6.893 | 61.783 | 1.00 | 95.74 | C |
| ATOM | 8547 | CD2 | PHE | M | 210 | 13.584 | 5.842 | 60.053 | 1.00 | 94.61 | C |
| ATOM | 8548 | CE1 | PHE | M | 210 | 11.400 | 5.829 | 61.761 | 1.00 | 96.33 | C |
| ATOM | 8549 | CE2 | PHE | M | 210 | 12.658 | 4.791 | 60.024 | 1.00 | 97.19 | C |
| ATOM | 8550 | CZ | PHE | M | 210 | 11.571 | 4.793 | 60.873 | 1.00 | 94.96 | C |
| ATOM | 8551 | N | ASN | M | 211 | 14.174 | 8.823 | 63.940 | 1.00 | 87.36 | N |
| ATOM | 8552 | CA | ASN | M | 211 | 13.408 | 8.906 | 65.171 | 1.00 | 87.32 | C |
| ATOM | 8553 | C | ASN | M | 211 | 12.069 | 9.441 | 64.695 | 1.00 | 91.87 | C |
| ATOM | 8554 | O | ASN | M | 211 | 12.043 | 10.165 | 63.693 | 1.00 | 92.50 | O |
| ATOM | 8555 | CB | ASN | M | 211 | 14.077 | 9.873 | 66.150 | 1.00 | 90.21 | C |
| ATOM | 8556 | CG | ASN | M | 211 | 15.525 | 9.545 | 66.447 | 1.00 | 118.86 | C |
| ATOM | 8557 | OD1 | ASN | M | 211 | 15.831 | 8.688 | 67.282 | 1.00 | 116.71 | O |
| ATOM | 8558 | ND2 | ASN | M | 211 | 16.449 | 10.211 | 65.760 | 1.00 | 108.60 | N |
| ATOM | 8559 | N | ARG | M | 212 | 10.965 | 9.093 | 65.366 | 1.00 | 87.97 | N |
| ATOM | 8560 | CA | ARG | M | 212 | 9.620 | 9.498 | 64.941 | 1.00 | 87.97 | C |

TABLE 1-continued

Three-dimensional crystal coordinate for anti-TcdB antibody beziotoxumab
Fab –C. difficile toxin B (TcdB$^{(1834-2101)}$) complex.

| ATOM | 8561 | C | ARG | M | 212 | 9.273 | 11.032 | 65.069 | 1.00 | 93.22 | C |
|---|---|---|---|---|---|---|---|---|---|---|---|
| ATOM | 8562 | O | ARG | M | 212 | 8.432 | 11.418 | 65.892 | 1.00 | 93.64 | O |
| ATOM | 8563 | CB | ARG | M | 212 | 8.598 | 8.646 | 65.684 | 1.00 | 86.47 | C |
| ATOM | 8564 | CG | ARG | M | 212 | 8.447 | 7.264 | 65.091 | 1.00 | 88.28 | C |
| ATOM | 8565 | CD | ARG | M | 212 | 8.770 | 6.172 | 66.083 | 1.00 | 87.21 | C |
| ATOM | 8566 | NE | ARG | M | 212 | 8.171 | 6.368 | 67.410 | 1.00 | 91.76 | N |
| ATOM | 8567 | CZ | ARG | M | 212 | 6.881 | 6.214 | 67.705 | 1.00 | 100.71 | C |
| ATOM | 8568 | NH1 | ARG | M | 212 | 6.004 | 5.920 | 66.751 | 1.00 | 95.66 | N |
| ATOM | 8569 | NH2 | ARG | M | 212 | 6.451 | 6.403 | 68.946 | 1.00 | 72.84 | N |
| ATOM | 8570 | N | GLY | M | 213 | 9.873 | 11.860 | 64.209 | 1.00 | 88.76 | N |
| ATOM | 8571 | CA | GLY | M | 213 | 9.658 | 13.303 | 64.188 | 1.00 | 101.30 | C |
| ATOM | 8572 | C | GLY | M | 213 | 10.587 | 14.045 | 63.245 | 1.00 | 112.67 | C |
| ATOM | 8573 | O | GLY | M | 213 | 11.803 | 13.830 | 63.256 | 1.00 | 65.19 | O |
| TER | 8574 | | GLY | M | 213 | | | | | | |
| HETATM | 8575 | O | HOH | W | 1 | 26.307 | −31.997 | −2.011 | 1.00 | 48.73 | O |
| HETATM | 8576 | O | HOH | W | 2 | 22.526 | −3.989 | −23.853 | 1.00 | 48.16 | O |
| HETATM | 8577 | O | HOH | W | 3 | 14.644 | −7.119 | −27.035 | 1.00 | 66.79 | O |
| HETATM | 8578 | O | HOH | W | 4 | 19.424 | −39.800 | −5.896 | 1.00 | 52.99 | O |
| HETATM | 8579 | O | HOH | W | 5 | 23.260 | 15.691 | −1.224 | 1.00 | 50.95 | O |
| HETATM | 8580 | O | HOH | W | 6 | 18.764 | 2.750 | 35.487 | 1.00 | 42.29 | O |
| HETATM | 8581 | O | HOH | W | 7 | 25.977 | 0.281 | −32.052 | 1.00 | 45.46 | O |
| HETATM | 8582 | O | HOH | W | 8 | 18.861 | −2.190 | 37.149 | 1.00 | 46.78 | O |
| HETATM | 8583 | O | HOH | W | 9 | 31.231 | 15.144 | −17.678 | 1.00 | 48.84 | O |
| HETATM | 8584 | O | HOH | W | 10 | 9.450 | −45.171 | 15.010 | 1.00 | 52.02 | O |
| HETATM | 8585 | O | HOH | W | 11 | 3.958 | −31.748 | 11.822 | 1.00 | 58.88 | O |
| HETATM | 8586 | O | HOH | W | 12 | −10.876 | −63.982 | 33.588 | 1.00 | 59.28 | O |
| HETATM | 8587 | O | HOH | W | 13 | −8.867 | −60.172 | 31.826 | 1.00 | 45.54 | O |
| HETATM | 8588 | O | HOH | W | 14 | 15.215 | −23.239 | 21.830 | 1.00 | 56.03 | O |
| END | | | | | | | | | | | |

Example 8

Binding Analysis of Toxin Fragments to Bezlotoxumab (Sandwich Assay Format)

Binding of TcdB and TcdB fragments to the antibodies was studied by surface plasmon resonance using ProteOn XPR36 instrument (BioRad, Hercules, Calif., USA). Bezlotoxumab was immobilized to the sensor chip surface using an antibody capture method. Briefly, a ProteOn GLC Sensor chip was docked to the system, and after standard cleaning according to the manufacturer's recommendations, a mixture of 1xEDC+sNHS was injected over the chip to activate the chip surface. A 25 mg/mL solution of Goat anti-Human IgG F(ab')$_2$ (ThermoScientific, Rockford, Ill., USA) in ProteOn immobilization buffer (10 mM Sodium Acetate, pH 5.5) was injected over 2 min. 1 M Ethanolamine HCl was then injected over 5 mins to block any unoccupied reactive sites on the chip surface. Twenty mg/mL Bezlotoxumab in ProteOn Running Buffer (PBS pH 7.4, 0.005% Tween-20) was injected over 2 mins. Toxins fragments were diluted at various concentrations in ProteOn Running Buffer (PBS pH 7.4, 0.005% Tween-20) and injected in horizontal orientation for 4 min (flow rate 25 ml/min). Association and dissociation were measured over time as changes in the refractive index. Data analyses were carried out using the ProteOn instrument software and data were fitted using a two site heterogeneous ligand model to determine $k_{on}$, $k_{off}$ and $K_d$.

TABLE 2

Binding of toxin B fragments to bezlotoxumab

| Toxin Fragment | High affinity binding site | | | Low affinity binding site | | |
|---|---|---|---|---|---|---|
| | $k_{on}^a$ (M$^{-1}$·sec$^{-1}$) | $k_{off}$ (sec$^{-1}$) | $K_d$' (pM) | $k_{on}$ (M$^{-1}$·sec$^{-1}$) | $k_{off}$ (sec$^{-1}$) | $K_d$' (pM) |
| TcdB | 1.52 × 10$^6$ ± 0.45 × 10$^6$ | 2.83 × 10$^{-5}$ ± 0.11 × 10$^{-5}$ | 19 ± 5 | 1.57 × 10$^7$ ± 0.14 × 10$^7$ | 5.59 × 10$^{-3}$ ± 4.36 × 10$^{-3}$ | 370 + 310 |
| B1 | 3.64 × 10$^6$ ± 0.11 × 10$^6$ | 1.41 × 10$^{-4}$ ± 0.06 × 10$^{-4}$ | 41 ± 13 | 2.09 × 10$^7$ ± 0.11 × 10$^7$ | 1.37 × 10$^{-2}$ ± 0.07 × 10$^{-2}$ | 660 ± 35 |
| B2 | 3.73 × 10$^6$ ± 0.11 × 10$^6$ | 1.61 × 10$^{-4}$ ± 0.28 × 10$^{-4}$ | 46 ± 21 | 1.35 × 10$^7$ ± 0.13 × 10$^7$ | 1.10 × 10$^{-2}$ ± 0.18 × 10$^{-2}$ | 810 ± 56 |
| B3 | N/M$^b$ | N/M | N/M | 3.25 × 10$^6$ ± 1.52 × 10$^6$ | 3.03 × 10$^{-2}$ ± 0.36 × 10$^{-2}$ | 11,000 ± 6,000 |
| B4 | N/M | N/M | N/M | N/M | N/M | N/M |

The present invention is not to be limited in scope by the specific embodiments described herein. Indeed, the scope of the present invention includes embodiments specifically set forth herein and other embodiments not specifically set forth herein; the embodiments specifically set forth herein are not necessarily intended to be exhaustive. Various modifications of the invention in addition to those described herein will become apparent to those skilled in the art from the foregoing description. Such modifications are intended to fall within the scope of the claims.

Patents, patent applications, publications, product descriptions, and protocols are cited throughout this application, the disclosures of which are incorporated herein by reference in their entireties for all purposes.

We claim:

1. An isolated crystal comprising a bezlotoxumab Fab fragment complexed to a polypeptide comprising SEQ ID NO: 14, wherein said polypeptide is *C. difficile* toxin B amino acids 1834-2101 and wherein the crystal is characterized by:

space group: P21; and unit cell dimensions: a=79.413 Å, b=134.659 Å, c=102.579 Å, α=γ=90°, β=112.559°.

2. The crystal of claim 1, wherein said polypeptide is characterized by structure coordinates comprising a root mean square deviation (RMSD) of conserved residue backbone atoms of less than about 2.0 angstroms when superimposed on backbone atoms described by structural coordinates of Table 1.

3. A method for producing a crystalline complex of claim 1 comprising incubating a first solution comprising 10 mg/ml of the complex, 5 mM phosphate, pH 7.4, 68.5 mM sodium chloride, 1.35 mM potassium chloride and 2.2% polyethylene glycol 4000 in a sealed container in close proximity to a second solution comprising 4.4 polyethylene glycol 4000.

4. The method of claim 3 wherein the first solution is in the form of a drop which is hanging or sitting on a surface.

\* \* \* \* \*